(12) United States Patent
Glunz et al.

(10) Patent No.: US 10,112,929 B2
(45) Date of Patent: Oct. 30, 2018

(54) LACTAMS AS INHIBITORS OF ROCK

(71) Applicant: BRISTOL-MYERS SQUIBB COMPANY, Princeton, NJ (US)

(72) Inventors: Peter W. Glunz, Yardley, PA (US); Doree F. Sitkoff, Dresher, PA (US); Mandar Shrikrishna Bodas, Bangalore (IN); Navnath Dnyanoba Yadav, Bangalore (IN); Sharanabasappa Patil, Raichur (IN); Prasanna Savanor Maddu Rao, Shimoga (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/554,741

(22) PCT Filed: Mar. 8, 2016

(86) PCT No.: PCT/US2016/021328
§ 371 (c)(1),
(2) Date: Aug. 31, 2017

(87) PCT Pub. No.: WO2016/144936
PCT Pub. Date: Sep. 15, 2016

(65) Prior Publication Data
US 2018/0044326 A1 Feb. 15, 2018

Related U.S. Application Data

(60) Provisional application No. 62/130,104, filed on Mar. 9, 2015.

(51) Int. Cl.
| | | |
|---|---|---|
| A61K 31/506 | (2006.01) | |
| C07D 403/14 | (2006.01) | |
| C07D 403/10 | (2006.01) | |
| C07D 417/14 | (2006.01) | |
| C07D 405/14 | (2006.01) | |
| C07D 471/04 | (2006.01) | |
| C07D 401/14 | (2006.01) | |

(52) U.S. Cl.
CPC ......... *C07D 403/14* (2013.01); *C07D 401/14* (2013.01); *C07D 403/10* (2013.01); *C07D 405/14* (2013.01); *C07D 417/14* (2013.01); *C07D 471/04* (2013.01)

(58) Field of Classification Search
CPC .......................... C07D 403/04; C07D 403/14
See application file for complete search history.

(56) References Cited

U.S. PATENT DOCUMENTS

| | | | |
|---|---|---|---|
| 2007/0142369 A1 | 6/2007 | van Heek et al. | |
| 2007/0191336 A1 | 8/2007 | Flynn et al. | |
| 2008/0146571 A1 | 6/2008 | Augeri et al. | |
| 2018/0000788 A1* | 1/2018 | Glunz | A61K 31/4178 |

FOREIGN PATENT DOCUMENTS

| | | | |
|---|---|---|---|
| CN | 103952009 A | 7/2014 | |
| DE | 102004058061 A1 | 6/2006 | |
| EP | 0548680 A1 | 6/1993 | |
| EP | 0581095 A2 | 2/1994 | |
| JP | 2012-0566903 A | 3/2012 | |
| KR | 20140006707 A | 1/2014 | |
| WO | WO2000/59285 A2 | 10/2000 | |
| WO | WO2003/103669 A1 | 12/2003 | |
| WO | WO2004/050643 A2 | 6/2004 | |
| WO | WO2004/089303 A2 | 10/2004 | |
| WO | WO2004/089308 A2 | 10/2004 | |
| WO | WO2004/110994 A1 | 12/2004 | |
| WO | WO-2004110994-cA1 * | 12/2004 | ......... C07D 207/273 |
| WO | WO2005/003099 A2 | 1/2005 | |
| WO | WO2005/070925 A1 | 8/2005 | |
| WO | WO2005/074643 A2 | 8/2005 | |
| WO | WO2005/090300 A1 | 9/2005 | |
| WO | WO2006/000912 A2 | 1/2006 | |
| WO | WO2006/002099 A2 | 1/2006 | |
| WO | WO2006/063113 A2 | 6/2006 | |
| WO | WO2006/089909 A1 | 8/2006 | |
| WO | WO2007/005668 A2 | 1/2007 | |

(Continued)

OTHER PUBLICATIONS

Z. Wang et al., 19 Drug Discovery Today, 145-150 (2014).*

(Continued)

*Primary Examiner* — Alexander R Pagano
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

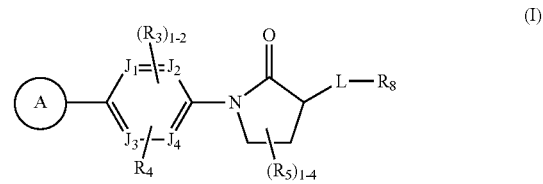

14 Claims, No Drawings
Specification includes a Sequence Listing.

(56) References Cited

FOREIGN PATENT DOCUMENTS

| | | |
|---|---|---|
| WO | WO2007/075702 A2 | 7/2007 |
| WO | WO2010/022033 A2 | 2/2010 |
| WO | WO2010/135536 A2 | 11/2010 |
| WO | WO2011/143129 A1 | 11/2011 |
| WO | WO2012/006202 A1 | 1/2012 |
| WO | WO2012/098132 A1 | 7/2012 |
| WO | WO2014/078611 A1 | 5/2014 |
| WO | WO2014/113620 A2 | 7/2014 |
| WO | WO2014/134388 A1 | 9/2014 |
| WO | WO2014/134391 A1 | 9/2014 |
| WO | WO2015/002915 A1 | 1/2015 |
| WO | WO2015/002926 A1 | 1/2015 |
| WO | WO2015/099196 A1 | 7/2015 |
| WO | WO2015/107053 A1 | 7/2015 |
| WO | WO2015/112441 A1 | 7/2015 |
| WO | WO2015/154022 A1 | 10/2015 |
| WO | WO2015/154039 A2 | 10/2015 |
| WO | WO2016/010950 A1 | 1/2016 |
| WO | WO2016/028971 A1 | 2/2016 |
| WO | WO2016/112236 A1 | 7/2016 |
| WO | WO2016/144936 A1 | 9/2016 |
| WO | WO2017/123860 A1 | 7/2017 |

OTHER PUBLICATIONS

U.K. Marelli et al., 3 Frontiers in Oncology, 1-12 (2013).*
P. Pan et al., 18 Drug Discovery Today, 1323-1333 (2013).*
A. Salminen et al., 371 Biochemical and Biophysical Research Communications, 587-590 (2008).*
Y. Liu et al., 1490 Brain Research, 43-51 (2013).*
L. Huang et al., 277 Neuroscience, 383-391 (2014).*
Zhang, Xiao-Chun et al., "Facile synthesis and photochromic properties of diarylethene-containing terpyridine and its transition metal ($Zn^{2+}/Co^{2+}/Ru^{2+}$)complexes", Journal of Physical Organic Chemistry, vol. 25(9), pp. 754-759 (2012).

* cited by examiner

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: labeled with fluorescein isothiocyanate

<400> SEQUENCE: 1

Ala His Ala Ala Lys Arg Arg Arg Leu Ser Ser Leu Arg Ala
1               5                   10

LACTAMS AS INHIBITORS OF ROCK

CROSS-REFERENCE TO RELATED APPLICATIONS

This application is a 371 application of PCT/US2016/021328 filed Mar. 8, 2016, which claims priority to U.S. Provisional Application Ser. No. 62/130,104, filed Mar. 9, 2015, the entire content of which is fully incorporated herein by reference.

FIELD OF THE INVENTION

The present invention relates to novel lactam derivatives, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, U.S. Publication No. 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel lactam derivatives including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

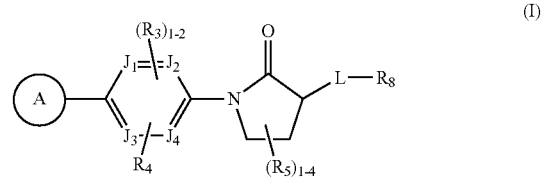

or stereoisomers, tautomers, pharmaceutically acceptable salts, solvates, or prodrugs thereof, wherein
Ring A is independently selected from

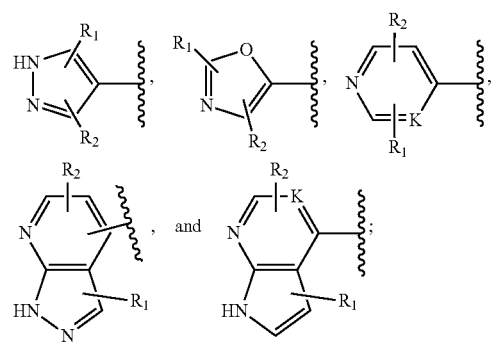

$J_1$, $J_2$, $J_3$, and $J_4$ are independently selected from N, $CR_3$ and $CR_4$; provided no more than two of $J_1$, $J_2$, $J_3$, and $J_4$ are N;
K is independently selected from N, $CR_1$ and $CR_2$;
L is independently selected from O and $NR_6(CR_7R_7)_m$;
$R_1$ is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

R₂ is independently selected from H, F, Cl, Br, —(CH₂)ᵣORᵦ, (CH₂)ᵣS(O)ₚR_c, —(CH₂)ᵣC(=O)Rᵦ, —(CH₂)ᵣNRₐRₐ, —(CH₂)ᵣCN, —(CH₂)ᵣC(=O)NRₐRₐ, —(CH₂)ᵣNRₐC(=O)Rᵦ, —(CH₂)ᵣNRₐC(=O)NRₐRₐ, —(CH₂)ᵣNRₐC(=O)ORᵦ, —(CH₂)ᵣOC(=O)NRₐRₐ, —(CH₂)ᵣC(=O)ORᵦ, —(CH₂)ᵣS(O)ₚNRₐRₐ, —(CH₂)ᵣNRₐS(O)ₚNRₐRₐ, —(CH₂)ᵣNRₐS(O)ₚR_c, (CH₂)ᵣ—C₃₋₆ carbocyclyl substituted with 0-3 R_e, and —(CH₂)ᵣ-heterocyclyl substituted with 0-3 R_e;

R₃ is independently selected from H, F, Cl, Br, CN, C₁₋₄ alkyl substituted with 0-3 R_e, —(CH₂)ᵣORᵦ, (CH₂)ᵣS(O)ₚR_c, —(CH₂)ᵣC(=O)Rᵦ, —(CH₂)ᵣNRₐRₐ, —(CH₂)ᵣC(=O)NRₐRₐ, —(CH₂)ᵣC(=O)(CH₂)ᵣNRₐRₐ, —(CH₂)ᵣCN, —(CH₂)ᵣNRₐC(=O)Rᵦ, —(CH₂)ᵣNRₐC(=O)ORᵦ, —(CH₂)ᵣOC(=O)NRₐRₐ, —(CH₂)ᵣNRₐC(=O)NRₐRₐ, —(CH₂)ᵣC(=O)ORᵦ, —(CH₂)ᵣS(O)ₚNRₐRₐ, —(CH₂)ᵣNRₐS(O)ₚNRₐRₐ, —(CH₂)ᵣNRₐS(O)ₚR_c, (CH₂)ᵣ—C₃₋₆ carbocyclyl substituted with 0-3 R_e, and —(CH₂)ᵣ-heterocyclyl substituted with 0-3 R_e;

R₄ is independently selected from H, F, Cl, Br, OH, CN, OC₁₋₄ alkyl substituted with 0-3 R_e, NRₐRₐ, and C₁₋₄ alkyl substituted with 0-3 R_e;

R₅ is independently selected from H, =O, C₁₋₄alkyl substituted with 0-4 R_e, —(CH₂)ᵣORᵦ, (CH₂)ᵣS(O)ₚR_c, —(CH₂)ᵣC(=O)Rᵦ, —(CH₂)ᵣNRₐRₐ, —(CH₂)ᵣCN, —(CH₂)ᵣC(=O)NRₐRₐ, —(CH₂)ᵣNRₐC(=O)Rᵦ, —(CH₂)ᵣNRₐC(=O)NRₐRₐ, —(CH₂)ᵣNRₐC(=O)ORᵦ, —(CH₂)ᵣOC(=O)NRₐRₐ, —(CH₂)ᵣC(=O)ORᵦ, —(CH₂)ᵣS(O)ₚNRₐRₐ, —(CH₂)ᵣNRₐS(O)ₚNRₐRₐ, —(CH₂)ᵣNRₐS(O)ₚR_c, (CH₂)ᵣ—C₃₋₆ carbocyclyl substituted with 0-3 R_e, and —(CH₂)ᵣ-heterocyclyl substituted with 0-3 R_e;

R₆ is independently selected from H and C₁₋₄alkyl substituted with 0-4 R_e;

R₇ is independently selected from H, C₁₋₄alkyl substituted with 0-4 R_e, —(CH₂)ᵣORᵦ, —(CH₂)ᵣS(O)ₚR_c, —(CH₂)ᵣC(=O)Rᵦ, —(CH₂)ᵣNRₐRₐ, —(CH₂)ᵣC(=O)NRₐRₐ, —(CH₂)ᵣC(=O)(CH₂)ᵣNRₐRₐ, —(CH₂)ᵣNRₐC(=O)Rᵦ, —(CH₂)ᵣNRₐC(=O)ORᵦ, —(CH₂)ᵣOC(=O)NRₐRₐ, —(CH₂)ᵣNRₐC(=O)NRₐRₐ, —(CH₂)ᵣC(=O)ORᵦ, —(CH₂)ᵣS(O)ₚNRₐRₐ, —(CH₂)ᵣNRₐS(O)ₚNRₐRₐ, —(CH₂)ᵣNRₐS(O)ₚR_c, (CH₂)ᵣ—C₃₋₆ carbocyclyl substituted with 0-3 R_e, and —(CH₂)ᵣ-heterocyclyl substituted with 0-3 R_e; alternatively, R₇ and R₇ form =O;

R₈ is independently selected from C₃₋₆ cycloalkyl, heterocyclyl, aryl and heteroaryl, each substituted with 0-5 R₉; alternatively, when m is zero, R₈ and R₆ together with the nitrogen atom to which they are both attached form a heterocyclic ring substituted with 0-5 R₉;

R₉ is independently selected from H, =O, F, Cl, Br, C₁₋₄alkyl, C₂₋₄alkenyl, C₂₋₄alkynyl, nitro, —(CR_dR_d)ᵣS(O)ₚR_c, —(CR_dR_d)ᵣS(O)ₚNRₐRₐ, —(CR_dR_d)ᵣNRₐS(O)ₚR_c, —(CR_dR_d)ᵣORᵦ, —(CR_dR_d)ᵣCN, —(CR_dR_d)ᵣNRₐRₐ, —(CR_dR_d)ᵣNRₐC(=O)Rᵦ, —(CR_dR_d)ᵣNRₐC(=O)NRₐRₐ, —(CR_dR_d)ᵣNRₐC(=O)ORᵦ, —(CR_dR_d)ᵣC(=O)ORᵦ, —(CR_dR_d)ᵣC(=O)NRₐRₐ, —(CR_dR_d)ᵣC(=O)Rᵦ, —(CR_dR_d)ᵣOC(=O)Rᵦ, —(CR_dR_d)ᵣOC(=O)NRₐRₐ, —(CR_dR_d)ᵣ-cycloalkyl, —(CR_dR_d)ᵣ-heterocyclyl, —(CR_dR_d)ᵣ-aryl, and —(CR_dR_d)ᵣ-heteroaryl, wherein said alkyl, cycloalkyl, heterocyclyl, aryl, or heteroaryl is substituted with 0-4 R_e;

Rₐ, at each occurrence, is independently selected from H, C₁₋₆ alkyl substituted with 0-5 R_e, C₂₋₆ alkenyl substituted with 0-5 R_e, C₂₋₆ alkynyl substituted with 0-5 R_e, —(CH₂)ᵣ—C₃₋₁₀carbocyclyl substituted with 0-5 R_e, and —(CH₂)ᵣ-heterocyclyl substituted with 0-5 R_e; or Rₐ and Rₐ together with the nitrogen atom to which they are both attached form a heterocyclic ring substituted with 0-5 R_e;

Rᵦ, at each occurrence, is independently selected from H, C₁₋₆ alkyl substituted with 0-5 R_e, C₂₋₆ alkenyl substituted with 0-5 R_e, C₂₋₆ alkynyl substituted with 0-5 R_e, —(CH₂)ᵣ—C₃₋₁₀carbocyclyl substituted with 0-5 R_e, and —(CH₂)ᵣ-heterocyclyl substituted with 0-5 R_e;

R_c, at each occurrence, is independently selected from C₁₋₆ alkyl substituted with 0-5 R_e, C₂₋₆alkenyl substituted with 0-5 R_e, C₂₋₆alkynyl substituted with 0-5 R_e, C₃₋₆carbocyclyl, and heterocyclyl;

R_d, at each occurrence, is independently selected from H and C₁₋₄alkyl substituted with 0-5 R_e;

R_e, at each occurrence, is independently selected from C₁₋₆ alkyl substituted with 0-5 R_f, C₂₋₆ alkenyl, C₂₋₆ alkynyl, —(CH₂)ᵣ—C₃₋₆ cycloalkyl, —(CH₂)ᵣ—C₄₋₆ heterocyclyl, —(CH₂)ᵣ-aryl, —(CH₂)ᵣ-heteroaryl, F, Cl, Br, CN, NO₂, =O, CO₂H, —(CH₂)ᵣOR_f, S(O)ₚR_f, C(=O)NR_fR_f, NR_fC(=O)R_d, S(O)ₚNR_fR_f, NR_fS(O)ₚR_d, NR_fC(=O)OR_d, OC(=O)NR_fR_f, and —(CH₂)ᵣNR_fR_f;

R_f, at each occurrence, is independently selected from H, F, Cl, Br, CN, OH, C₁₋₅alkyl, C₃₋₆ cycloalkyl, and phenyl; or R_f and R_f together with the nitrogen atom to which they are both attached form a heterocyclic ring optionally substituted with C₁₋₄alkyl;

m is independently selected from zero, 1, and 2;

p, at each occurrence, is independently selected from zero, 1, and 2; and r, at each occurrence, is independently selected from zero, 1, 2, 3, and 4.

In another aspect, the present invention provides compounds of Formula (I) or stereoisomers, tautomers, pharmaceutically acceptable salts, solvates, or prodrugs thereof, wherein Ring A is independently selected from

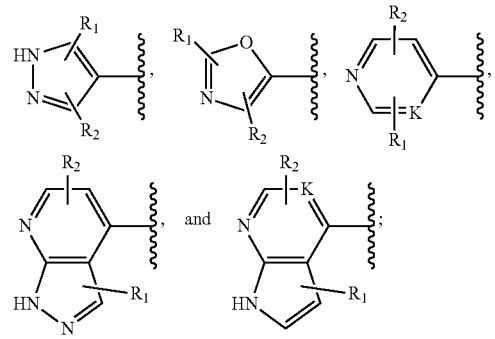

J₁, J₂, J₃, and J₄ are independently selected from N, CR₃ and CR₄; provided no more than two of J₁, J₂, J₃, and J₄ are N;

K is independently selected from N, CR₁ and CR₂;

L is independently selected from O, NR₆(CR₇R₇)ₘ, and (CR₇R₇)ₙ;

R₁ is independently selected from H, F, Cl, Br, OH, CN, NRₐRₐ, —OC₁₋₄ alkyl substituted with 0-3 R_e, and C₁₋₄ alkyl substituted with 0-3 R_e;

R₂ is independently selected from H, —(CH₂)ᵣORᵦ, (CH₂)ᵣS(O)ₚR_c, —(CH₂)ᵣC(=O)Rᵦ, —(CH₂)ᵣNRₐRₐ, —(CH₂)ᵣCN, —(CH₂)ᵣC(=O)NRₐRₐ, —(CH₂)ᵣNRₐC(=O)Rᵦ, —(CH₂)ᵣNRₐC(=O)NRₐRₐ, —(CH₂)ᵣNRₐC(=O)ORᵦ, —(CH₂)ᵣOC(=O)NRₐRₐ, —(CH₂)ᵣC(=O)ORᵦ, —(CH₂)ᵣS(O)ₚNRₐRₐ, —(CH₂)ᵣNRₐS(O)ₚNRₐRₐ, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_3$ is independently selected from H, F, Cl, Br, CN, C$_{1-4}$ alkyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H, F, Cl, Br, OH, CN, OC$_{1-4}$ alkyl substituted with 0-3 R$_e$, NR$_a$R$_a$, and C$_{1-4}$ alkyl substituted with 0-3 R$_e$;

R$_5$ is independently selected from H, =O, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_6$ is independently selected from H and C$_{1-4}$alkyl substituted with 0-4 R$_e$;

R$_7$ is independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$; alternatively, R$_7$ and R$_7$ form =O;

R$_8$ is independently selected from aryl and heteroaryl, each substituted with 0-5 R$_9$;

alternatively, R$_8$ and R$_6$ together with the nitrogen atom to which they are both attached form a heterocyclic ring substituted with 0-5 R$_9$ when m is zero;

R$_9$ is independently selected from F, Cl, Br, C$_{1-4}$alkyl, C$_{2-4}$alkenyl, C$_{2-4}$alkynyl, nitro, —(CR$_d$R$_d$)$_r$S(O)$_p$R$_c$, —(CR$_d$R$_d$)$_r$S(O)$_p$NR$_a$R$_a$, —(CR$_d$R$_d$)$_r$NR$_a$S(O)$_p$R$_c$, —(CR$_d$R$_d$)$_r$OR$_b$, —(CR$_d$R$_d$)$_r$CN, —(CR$_d$R$_d$)$_r$NR$_a$R$_a$, —(CR$_d$R$_d$)$_r$NR$_a$C(=O)R$_b$, —(CR$_d$R$_d$)$_r$NR$_a$C(=O)NR$_a$R$_a$, —(CR$_d$R$_d$)$_r$NR$_a$C(=O)OR$_b$, —(CR$_d$R$_d$)$_r$C(=O)OR$_b$, —(CR$_d$R$_d$)$_r$C(=O)NR$_a$R$_a$, —(CR$_d$R$_d$)$_r$C(=O)R$_b$, —(CR$_d$R$_d$)$_r$OC(=O)R$_b$, —(CR$_d$R$_d$)$_r$OC(=O)NR$_a$R$_a$, —(CR$_d$R$_d$)$_r$-cycloalkyl, —(CR$_d$R$_d$)$_r$-heterocyclyl, —(CR$_d$R$_d$)$_r$-aryl, and —(CR$_d$R$_d$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$, at each occurrence, is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

m is independently selected from zero, 1, and 2;

n is independently selected from zero, 1, 2, and 3;

p, at each occurrence, is independently selected from zero, 1, and 2;

r, at each occurrence, is independently selected from zero, 1, 2, 3, and 4; and provided R$_9$ is not a substituted piperazine.

In another aspect, the present invention provides compounds of Formula (I) or stereoisomers, tautomers, pharmaceutically acceptable salts, solvates, or prodrugs thereof, wherein L is independently selected from O, NR$_6$(CR$_7$R$_7$)$_m$, and (CR$_7$R$_7$)$_n$;

R$_1$ is independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R$_2$ is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$NR$_a$S(O)$_p$NR$_a$R$_a$, and —(CH$_2$)$_r$NR$_a$S(O)$_p$R$_c$;

R$_3$ is independently selected from H, F, Cl, Br, CN, C$_{1-4}$ alkyl substituted with 0-3 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H, F, Cl, Br, OH, CN, and C$_{1-4}$ alkyl substituted with 0-3 R$_e$;

R$_5$ is independently selected from H, =O, C$_{1-4}$alkyl substituted with 0-4 R$_e$, —(CH$_2$)$_r$OR$_b$, C(=O)R$_b$, and —C(=O)OR$_b$;

R$_6$ is independently selected from H and C$_{1-4}$alkyl substituted with 0-4 R$_e$;

R$_7$ is independently selected from H, C$_{1-4}$alkyl substituted with 0-4 R$_e$, —(CH$_2$)$_r$OR$_b$, —(CH$_2$)$_r$C(=O)R$_b$, —(CH$_2$)$_r$NR$_a$C(=O)R$_b$, —(CH$_2$)$_r$C(=O)OR$_b$, (CH$_2$)$_r$—C$_{3-6}$ carbocyclyl substituted with 0-3 R$_e$, and —(CH$_2$)$_r$-heterocyclyl substituted with 0-3 R$_e$;

$R_8$ is independently selected from

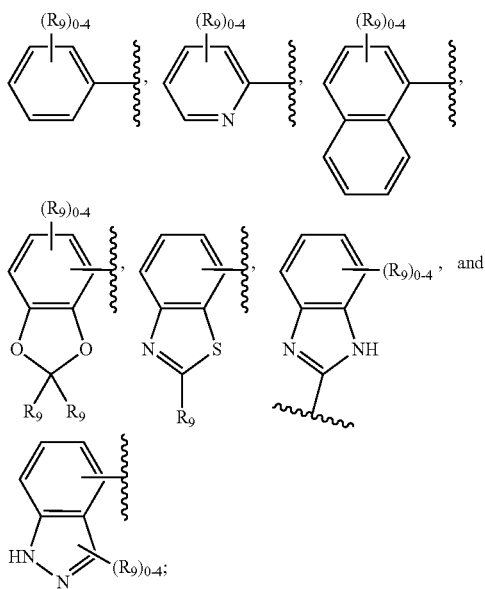

$R_9$ is independently selected from F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rNR_aC(=O)OR_b$, $-(CHR_d)_rC(=O)OR_b$, $-(CHR_d)_rC(=O)NR_aR_a$, $-(CHR_d)_rOC(=O)NR_aR_a$, $-(CHR_d)_rC(=O)R_b$, $-(CHR_d)_rOC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r$-$C_{3-6}$ cycloalkyl, $-(CH_2)_r$-$C_{4-6}$ heterocyclyl, $-(CH_2)_r$-aryl, $-(CH_2)_r$-heteroaryl, F, Cl, Br, CN, $NO_2$, =O, $CO_2H$, $-(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)$ $OR_d$, $OC(=O)NR_fR_f$ and $-(CH_2)_rNR_fR_f$;

$R_f$ at each occurrence, is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

m is independently selected from zero, 1, and 2;

n is independently selected from zero, 1, 2, and 3;

p, at each occurrence, is independently selected from zero, 1, and 2;

r, at each occurrence, is independently selected from zero, 1, 2, 3, and 4; and provided $R_9$ is not a substituted piperazine.

In another aspect, the present invention provides compounds of Formula (I) or stereoisomers, tautomers, pharmaceutically acceptable salts, solvates, or prodrugs thereof, wherein L is independently selected from O and $NR_6(CR_7R_7)_m$;

$R_1$ is independently selected from H, F, Cl, Br, OH, CN, $NR_aR_a$, $-OC_{1-4}$ alkyl substituted with 0-3 $R_e$, and $C_{1-4}$ alkyl substituted with 0-3 $R_e$;

$R_2$ is independently selected from H, F, Cl, Br, $-(CH_2)_rOR_b$, $(CH_2)_rS(O)_pR_c$, $-(CH_2)_rC(=O)R_b$, $-(CH_2)_rNR_aR_a$, $-(CH_2)_rCN$, $-(CH_2)_rNR_aC(=O)$ $OR_b$, $-(CH_2)_rOC(=O)NR_aR_a$, $-(CH_2)_rC(=O)OR_b$, $-(CH_2)_rNR_aS(O)_pNR_aR_a$, and $-(CH_2)_rNR_aS(O)_pR_c$;

$R_3$ is independently selected from H, F, Cl, Br, CN, $C_{1-4}$ alkyl substituted with 0-3 $R_e$, $-(CH_2)_rOR_b$, $-(CH_2)_rS$ $(O)_pR_c$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_r$-$C_{3-6}$ carbocyclyl substituted with 0-3 $R_e$, and $-(CH_2)_r$-heterocyclyl substituted with 0-3 $R_e$;

$R_4$ is independently selected from H, F, Cl, Br, OH, CN, and $C_{1-4}$ alkyl substituted with 0-3 $R_e$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_6$ is independently selected from H and $C_{1-4}$alkyl substituted with 0-4 $R_e$;

$R_7$ is independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, $(CH_2)_r$-$C_{3-6}$ carbocyclyl substituted with 0-3 $R_e$, and $-(CH_2)_r$-heterocyclyl substituted with 0-3 $R_e$;

$R_8$ is independently selected from

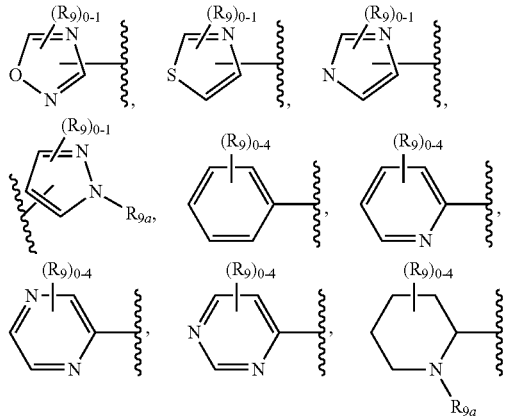

-continued

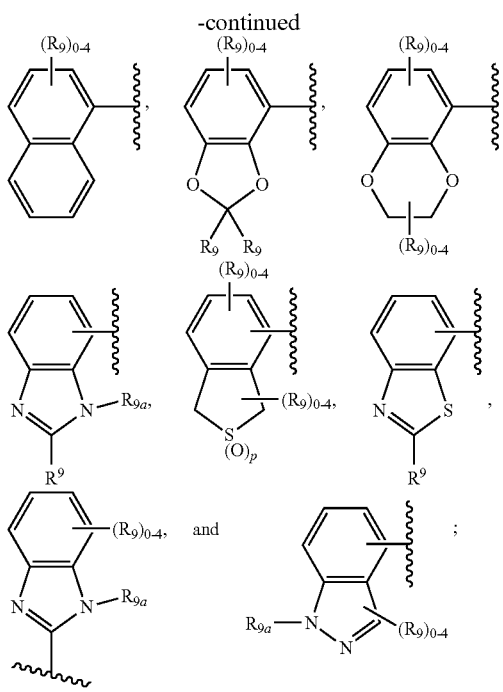

R$_9$ is independently selected from H, =O, F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$NR$_a$C(=O)OR$_b$, —(CHR$_d$)$_r$C(=O)OR$_b$, —(CHR$_d$)$_r$C(=O)NR$_a$R$_a$, —(CHR$_d$)$_r$OC(=O)NR$_a$R$_a$, —(CHR$_d$)$_r$C(=O)R$_b$, —(CHR$_d$)$_r$OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

R$_{9a}$ is independently selected from H, C$_{1-4}$ alkyl, —S(O)$_p$R$_c$, —S(O)$_p$NR$_a$R$_a$, —C(=O)OR$_b$, —(CH$_2$)$_r$C(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (II):

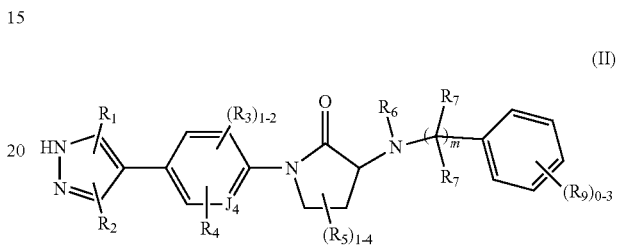

(II)

or stereoisomers, tautomers, pharmaceutically acceptable salts, solvates, or prodrugs thereof, wherein J$_4$ is independently selected from N and CH;

R$_1$ is independently selected from H, F, Cl, Br, CN, NR$_a$R$_a$, and C$_{1-4}$alkyl substituted with 0-4 R$_e$;

R$_2$ is independently selected from H, F, Cl, Br, OH, CN, NR$_a$R$_a$, and C$_{1-4}$alkyl substituted with 0-4 R$_e$;

R$_3$ is independently selected from H, F, Cl, Br, CN, C$_{1-4}$ alkyl substituted with 0-3 R$_e$, and —(CH$_2$)$_r$OR$_b$;

R$_4$ is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is independently selected from H, =O, C$_{1-4}$alkyl substituted with 0-4 R$_e$, —(CH$_2$)$_r$OR$_b$, C(=O)R$_b$, and —C(=O)OR$_b$;

R$_6$ is independently selected from H and C$_{1-4}$alkyl substituted with 0-4 R$_e$;

R$_7$ is independently selected from H, C$_{1-4}$alkyl substituted with 0-4 R$_e$, and —(CH$_2$)$_r$OR$_b$; alternatively, R$_7$ and R$_7$ form =O;

R$_9$ is independently selected from F, Cl, Br, C$_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CHR$_d$)$_r$NR$_a$C(=O)OR$_b$, —(CHR$_d$)$_r$C(=O)OR$_b$, —(CHR$_d$)$_r$C(=O)NR$_a$R$_a$, —(CHR$_d$)$_r$OC(=O)NR$_a$R$_a$, —(CH$_2$)$_r$C(=O)R$_b$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

m is independently selected from zero, 1, and 2;

p, at each occurrence, is independently selected from zero, 1, and 2; and r, at each occurrence, is independently selected from zero, 1, 2, 3, and 4.

In another aspect, the present invention provides compounds of Formula (II) or stereoisomers, tautomers, pharmaceutically acceptable salts, solvates, or prodrugs thereof, wherein J$_4$ is independently selected from N and CR$_4$;

R$_1$ is independently selected from H, F, Cl, Br, CN, NR$_a$R$_a$, and C$_{1-4}$alkyl substituted with 0-4 R$_e$;

R$_2$ is independently selected from H, F, Cl, Br, OH, CN, NR$_a$R$_a$, and C$_{1-4}$alkyl substituted with 0-4 R$_e$;

R$_3$ is independently selected from H, F, Cl, Br, CN, C$_{1-4}$ alkyl substituted with 0-3 R$_e$, —(CH$_2$)$_r$OR$_b$, —NR$_a$R$_a$, C(=O)NR$_a$R$_a$, and C$_{3-6}$ cycloalkyl substituted with 0-3 R$_e$;

R$_4$ is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is independently selected from H, =O, C$_{1-4}$alkyl substituted with 0-4 R$_e$, —(CH$_2$)$_r$OR$_b$, C(=O)R$_b$, and —C(=O)OR$_b$;

R$_6$ is independently selected from H and C$_{1-4}$alkyl substituted with 0-4 R$_e$;

R$_7$ is independently selected from H, C$_{1-4}$alkyl substituted with 0-4 R$_e$, and —(CH$_2$)$_r$OR$_b$; alternatively, R$_7$ and R$_7$ form =O;

R$_9$ is independently selected from F, Cl, Br, C$_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$C(=O)OR$_b$, —(CH$_2$)$_r$C(=O)NR$_a$R$_a$, —(CH$_2$)$_r$OC(=O)NR$_a$R$_a$, —(CH$_2$)$_r$C(=O)R$_b$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

m is independently selected from zero, 1, and 2;

p, at each occurrence, is independently selected from zero, 1, and 2; and r, at each occurrence, is independently selected from zero, 1, 2, 3, and 4.

In another aspect, the present invention provides compounds of Formula (III):

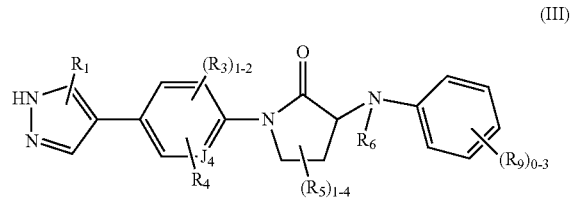

(III)

or stereoisomers, tautomers, pharmaceutically acceptable salts, solvates, or prodrugs thereof, wherein J$_4$ is independently selected from N and CH;

R$_1$ is independently selected from H, F, Cl, Br, CN, NR$_a$R$_a$, and C$_{1-4}$alkyl substituted with 0-4 R$_e$;

R$_3$ is independently selected from H, F, Cl, Br, CN, C$_{1-4}$ alkyl substituted with 0-3 R$_e$, and —(CH$_2$)$_r$OR$_b$;

R$_4$ is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is independently selected from H, =O, C$_{1-4}$alkyl substituted with 0-4 R$_e$, —(CH$_2$)$_r$OR$_b$, C(=O)R$_b$, and —C(=O)OR$_b$;

R$_6$ is independently selected from H and C$_{1-4}$alkyl substituted with 0-4 R$_e$;

R$_9$ is independently selected from F, Cl, Br, C$_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CHR$_d$)$_r$NR$_a$C(=O)OR$_b$, —(CHR$_d$)$_r$C(=O)OR$_b$, —(CHR$_d$)$_r$C(=O)NR$_a$R$_a$, —(CHR$_d$)$_r$OC(=O)NR$_a$R$_a$, —(CH$_2$)$_r$C(=O)R$_b$, —(CH$_2$)$_r$OC(=O)R$_b$, —(CH$_2$)$_r$C(=O)NR$_a$R$_a$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r OR_f$, $S(O)_p R_f$, $S(O)_p NR_f R_f$, and —$(CH_2)_r NR_f R_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (III) or stereoisomers, tautomers, pharmaceutically acceptable salts, solvates, or prodrugs thereof, wherein $J_4$ is independently selected from N and $CR_4$;
$R_1$ is independently selected from H, F, Cl, Br, CN, $NR_a R_a$, and $C_{1-4}$alkyl substituted with 0-4 $R_e$;
$R_3$ is independently selected from H, F, Cl, Br, CN, $C_{1-4}$ alkyl substituted with 0-3 $R_e$, —$(CH_2)_r OR_b$, —$NR_a R_a$, C(=O)$NR_a R_a$, and $C_{3-6}$ cycloalkyl substituted with 0-3 $R_e$;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$ is independently selected from H, =O, $C_{1-4}$alkyl substituted with 0-4 $R_e$, —$(CH_2)_r OR_b$, C(=O)$R_b$, and —C(=O)$OR_b$;
$R_6$ is independently selected from H and $C_{1-4}$alkyl substituted with 0-4 $R_e$;
$R_9$ is independently selected from F, Cl, Br, $C_{1-4}$ alkyl, nitro, —$(CH_2)_r S(O)_p R_c$, —$(CH_2)_r S(O)_r NR_a R_a$, —$(CH_2)_r NR_a S(O)_p R_c$, —$(CH_2)_r OR_b$, —$(CH_2)_r CN$, —$(CH_2)_r NR_a R_a$, —$(CH_2)_r NR_a C(=O)R_b$, —$(CH_2)_r NR_a C(=O)NR_a R_a$, —$(CH_2)_r NR_a C(=O)OR_b$, —$(CH_2)_r C(=O)OR_b$, —$(CH_2)_r C(=O)NR_a R_a$, —$(CH_2)_r OC(=O)NR_a R_a$, —$(CH_2)_r C(=O)R_b$, —$(CH_2)_r OC(=O)R_b$, —$(CH_2)_r C(=O)NR_a R_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r OR_f$, $S(O)_p R_f$, $S(O)_p NR_f R_f$, and —$(CH_2)_r NR_f R_f$;

$R_f$ at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (III) or stereoisomers, tautomers, pharmaceutically acceptable salts, solvates, or prodrugs thereof, wherein $R_1$ is independently selected from H;
$R_3$ is independently selected from H, F, Cl, $C_{1-4}$ alkyl, and —$OC_{1-3}$ alkyl;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$ is independently selected from H, =O, $C_{1-4}$alkyl substituted with 0-4 $R_e$, —$OR_b$, C(=O)$R_b$, and —C(=O)$OR_b$;
$R_6$ is independently selected from H and $C_{1-4}$alkyl substituted with 0-3 $R_e$;
$R_9$ is independently selected from F, Cl, $C_{1-4}$ alkyl substituted with 0-3 $R_e$, —$OR_b$, and heterocyclyl substituted with 0-3 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;
r, at each occurrence, is independently selected from zero, 1, 2, and 3; and
other variables are as defined in Formula (III) above.

In another aspect, the present invention provides compounds of Formula (III) or stereoisomers, tautomers, pharmaceutically acceptable salts, solvates, or prodrugs thereof, wherein $R_1$ is independently selected from H and $C_{1-4}$alkyl;
$R_3$ is independently selected from H, F, Cl, CN, $C_{1-3}$ alkyl substituted with 0-3 $R_e$, —$OC_{1-3}$ alkyl substituted with 0-3 $R_e$, $NR_a R_a$, C(=O)$NR_a R_a$, and $C_{3-6}$ cycloalkyl;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$ is independently selected from H, =O, $C_{1-4}$alkyl substituted with 0-4 $R_e$, —$(CH_2)_r OR_b$, C(=O)$R_b$, and —C(=O)$OR_b$;
$R_6$ is H;
$R_9$ is independently selected from F, Cl, $C_{1-4}$ alkyl, —$OR_b$, CN, $S(O)_p NR_a R_a$, $NHS(O)_p R_c$, $NR_a R_a$, C(=O)$NR_a R_a$, $NR_a C(=O)R_b$, $C_{3-6}$ cycloalkyl, and heterocyclyl, wherein said alkyl, cycloalkyl, or heterocyclyl is substituted with 0-4 $R_e$;

$R_a$, at each occurrence, is independently selected from H and $C_{1-6}$ alkyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{3-6}$ cycloalkyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

r, at each occurrence, is independently selected from zero, 1, 2, and 3 and other variables are as defined in Formula (III) above.

In another aspect, the present invention provides compounds of Formula (IV):

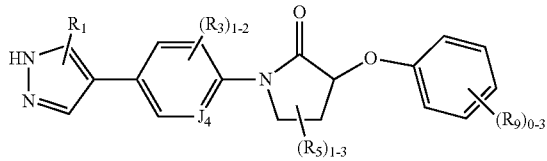

(IV)

or stereoisomers, tautomers, pharmaceutically acceptable salts, solvates, or prodrugs thereof, wherein $J_4$ is independently selected from N and CH;

$R_1$ is independently selected from H, F, Cl, Br, CN, $NR_aR_a$, and $C_{1-4}$alkyl substituted with 0-4 $R_e$;

$R_3$ is independently selected from H, F, CN, $C_{1-4}$ alkyl substituted with 0-3 $R_e$, and —$OR_b$;

$R_5$ is independently selected from H, =O, $C_{1-4}$alkyl substituted with 0-4 $R_e$, —$(CH_2)_rOR_b$, $C(=O)R_b$, and —$C(=O)OR_b$;

$R_9$ is independently selected from F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (IV) or stereoisomers, tautomers, pharmaceutically acceptable salts, solvates, or prodrugs thereof, wherein $J_4$ is independently selected from N and $CR_4$;

$R_1$ is independently selected from H, F, Cl, Br, CN, $NR_aR_a$, and $C_{1-4}$alkyl substituted with 0-4 $R_e$;

$R_3$ is independently selected from H, F, CN, $C_{1-4}$ alkyl substituted with 0-3 $R_e$, and —$OR_b$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_rOR_b$, $C(=O)R_b$, and —$C(=O)OR_b$;

$R_9$ is independently selected from F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (V):

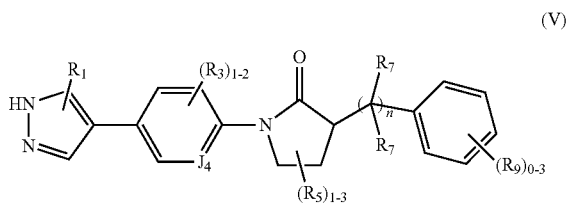

(V)

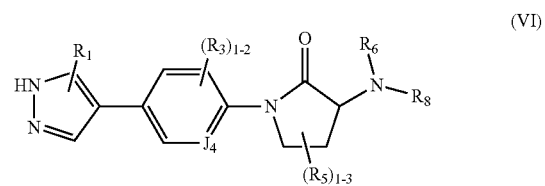

(VI)

or stereoisomers, tautomers, pharmaceutically acceptable salts, solvates, or prodrugs thereof, wherein $J_4$ is independently selected from N and CH;

$R_1$ is independently selected from H, F, Cl, Br, CN, $NR_aR_a$, and $C_{1-4}$alkyl substituted with 0-4 $R_e$;

$R_3$ is independently selected from H, F, CN, $C_{1-4}$ alkyl substituted with 0-3 $R_e$, and $-OR_b$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_7$ is independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, $(CH_2)_r-C_{3-6}$ carbocyclyl substituted with 0-3 $R_e$, and $-(CH_2)_r$-heterocyclyl substituted with 0-3 $R_e$;

$R_9$ is independently selected from F, Cl, Br, $C_{1-4}$ alkyl, $-S(O)_pR_c$, $-S(O)_pNR_aR_a$, $-OR_b$, CN, $-NR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, =O, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

n is independently selected from zero, 1, and 2;

p, at each occurrence, is independently selected from zero, 1, and 2; and r, at each occurrence, is independently selected from zero, 1, 2, 3, and 4.

In another aspect, the present invention provides compounds of Formula (VI):

or stereoisomers, tautomers, pharmaceutically acceptable salts, solvates, or prodrugs thereof, wherein $J_4$ is independently selected from N and CH;

$R_1$ is independently selected from H, F, Cl, Br, CN, $NR_aR_a$, and $C_{1-4}$alkyl substituted with 0-4 $R_e$;

$R_3$ is independently selected from H, F, CN, $C_{1-4}$ alkyl substituted with 0-3 $R_e$, and $-OR_b$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_6$ and $R_8$ together with the nitrogen atom to which they are both attached form a heterocyclic ring substituted with 0-5 $R_9$;

$R_9$ is independently selected from F, Cl, Br, $C_{1-4}$ alkyl, nitro, $-S(O)_pR_c$, $-S(O)_pNR_aR_a$, $-OR_b$, $-NR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, =O, $CO_2H$, $-(CH_2)_rOR_f$, $S(O)_pR_f$, $S(O)_pNR_fR_f$, and $-(CH_2)_rNR_fR_f$;

$R_f$ at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (VI) or stereoisomers, tautomers, pharmaceutically acceptable salts, solvates, or prodrugs thereof, wherein $J_4$ is independently selected from N and $CR_4$;

$R_1$ is independently selected from H, F, Cl, Br, CN, $NR_aR_a$, and $C_{1-4}$alkyl substituted with 0-4 $R_e$;

$R_3$ is independently selected from H, F, CN, $C_{1-4}$ alkyl substituted with 0-3 $R_e$, and —$OR_b$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_rOR_b$, $C(=O)R_b$, and —$C(=O)OR_b$;

$R_6$ and $R_8$ together with the nitrogen atom to which they are both attached form a heterocyclic ring substituted with 0-5 $R_9$;

$R_9$ is independently selected from H, =O, F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (VI) or stereoisomers, tautomers, pharmaceutically acceptable salts, solvates, or prodrugs thereof, wherein $R_6$ and $R_8$ together with the nitrogen atom to which they are both attached form a heterocyclic ring substituted with 0-5 $R_9$, wherein the heterocyclic ring is selected from

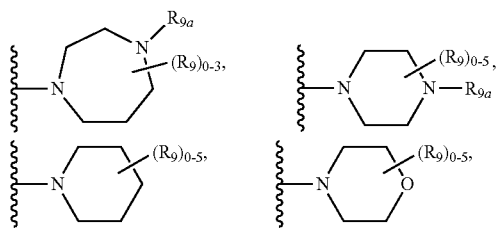

-continued

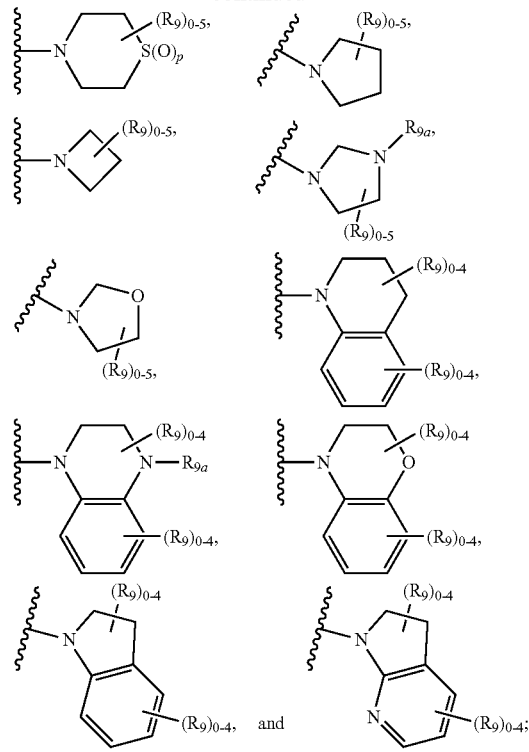

$R_9$ is independently selected from H, =O, F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_{9a}$ is independently selected from H, $C_{1-4}$ alkyl, —$S(O)_pR_c$, —$S(O)_pNR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2;

r, at each occurrence, is independently selected from zero, 1, 2, 3, and 4; and other variables are as defined in Formula (VI) above.

In another aspect, the present invention provides compounds of Formula (VII):

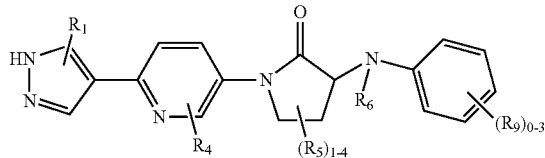

(VII)

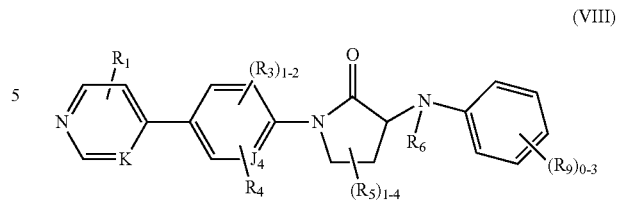

(VIII)

or stereoisomers, tautomers, pharmaceutically acceptable salts, solvates, or prodrugs thereof, wherein
$R_1$ is independently selected from H, F, Cl, Br, CN, $NR_aR_a$, and $C_{1-4}$alkyl substituted with 0-4 $R_e$;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$ is independently selected from H, =O, $C_{1-4}$alkyl substituted with 0-4 $R_e$, —$(CH_2)_rOR_b$, C(=O)$R_b$, and —C(=O)$OR_b$;
$R_6$ is independently selected from H and $C_{1-4}$alkyl substituted with 0-4 $R_e$;
$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rC(=O)OR_b$, —$(CH_2)_rC(=O)NR_aR_a$, —$(CH_2)_rOC(=O)NR_aR_a$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;
$R_f$ at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;
p, at each occurrence, is independently selected from zero, 1, and 2; and
r, at each occurrence, is independently selected from zero, 1, 2, 3, and 4.

In another aspect, the present invention provides compounds of Formula (VIII):

or stereoisomers, tautomers, pharmaceutically acceptable salts, solvates, or prodrugs thereof, wherein
$J_4$ is independently selected from N and $CR_4$;
K is independently selected from N and $CR_1$;
$R_1$ is independently selected from H, F, Cl, Br, CN, $NR_aR_a$, and $C_{1-4}$alkyl substituted with 0-4 $R_e$;
$R_3$ is independently selected from H, F, Cl, Br, CN, $C_{1-4}$ alkyl substituted with 0-3 $R_e$, and —$(CH_2)_rOR_b$;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$ is independently selected from H, =O, $C_{1-4}$alkyl substituted with 0-4 $R_e$, —$(CH_2)_rOR_b$, C(=O)$R_b$, and —C(=O)$OR_b$;
$R_6$ is independently selected from H and $C_{1-4}$alkyl substituted with 0-4 $R_e$;
$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rC(=O)OR_b$, —$(CH_2)_rC(=O)NR_aR_a$, —$(CH_2)_rOC(=O)NR_aR_a$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;
$R_f$ at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;
p, at each occurrence, is independently selected from zero, 1, and 2; and r, at each occurrence, is independently selected from zero, 1, 2, 3, and 4.

In another aspect, the present invention provides compounds of Formula (IX):

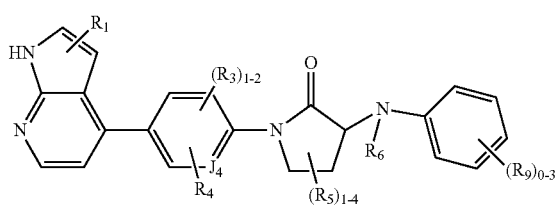

(IX)

or stereoisomers, tautomers, pharmaceutically acceptable salts, solvates, or prodrugs thereof, wherein $J_4$ is independently selected from N and $CR_4$;

$R_1$ is independently selected from H, F, Cl, Br, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, and $—(CH_2)_rOR_b$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, $—(CH_2)_rOR_b$, $C(=O)R_b$, and $—C(=O)OR_b$;

$R_6$ is independently selected from H and $C_{1-4}$alkyl substituted with 0-4 $R_e$;

$R_9$ is independently selected from F, Cl, Br, $C_{1-4}$ alkyl, nitro, $—(CH_2)_rS(O)_pR_c$, $—(CH_2)_rS(O)_pNR_aR_a$, $—(CH_2)_rNR_aS(O)_pR_c$, $—(CH_2)_rOR_b$, $—(CH_2)_rCN$, $—(CH_2)_rNR_aR_a$, $—(CH_2)_rNR_aC(=O)R_b$, $—(CH_2)_rNR_aC(=O)NR_aR_a$, $—(CH_2)_rNR_aC(=O)OR_b$, $—(CH_2)_rC(=O)OR_b$, $—(CH_2)_rC(=O)NR_aR_a$, $—(CH_2)_rOC(=O)NR_aR_a$, $—(CH_2)_rC(=O)R_b$, $—(CH_2)_rOC(=O)R_b$, $—(CH_2)_rC(=O)NR_aR_a$, $—(CH_2)_r$-cycloalkyl, $—(CH_2)_r$-heterocyclyl, $—(CH_2)_r$-aryl, and $—(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $—(CH_2)_r$—$C_{3-10}$cycloalkyl substituted with 0-5 $R_e$, $—(CH_2)_r$-aryl substituted with 0-5 $R_e$, and $—(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $—(CH_2)_r$—$C_{3-10}$carbocyclyl substituted with 0-5 $R_e$, and $—(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $—(CH_2)_r$—$C_{3-6}$ cycloalkyl, $—(CH_2)_r$—$C_{4-6}$ heterocyclyl, F, Cl, Br, CN, $NO_2$, =O, $CO_2H$, $—(CH_2)_rOR_f$, $S(O)_pR_f$, $S(O)_pNR_fR_f$, and $—(CH_2)_rNR_fR_f$;

$R_f$ at each occurrence, is independently selected from H, F, Cl, Br, CN, OH, $C_{1-5}$ alkyl, $C_{3-6}$ cycloalkyl, and phenyl;

or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (X):

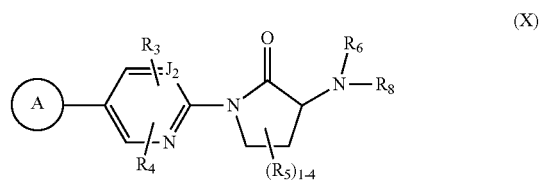

(X)

or stereoisomers, tautomers, pharmaceutically acceptable salts, solvates, or prodrugs thereof, wherein $J_2$ is independently selected from N, $CR_3$ and $CR_4$;

Ring A is independently selected from

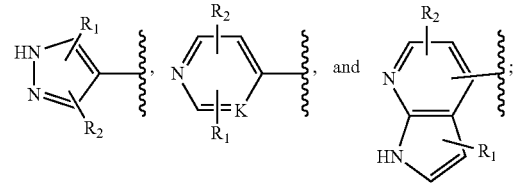

K is independently selected from N, $CR_1$, and $CR_2$;

$R_1$ is independently selected from H, F, Cl, Br, CN, $NR_aR_a$, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, $—(CH_2)_rOR_b$, $—NR_aR_a$, $C(=O)NR_aR_a$, and $C_{3-6}$ cycloalkyl substituted with 0-3 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, $—(CH_2)_rOR_b$, $C(=O)R_b$, and $—C(=O)OR_b$;

$R_6$ is H;

$R_8$ is independently selected from

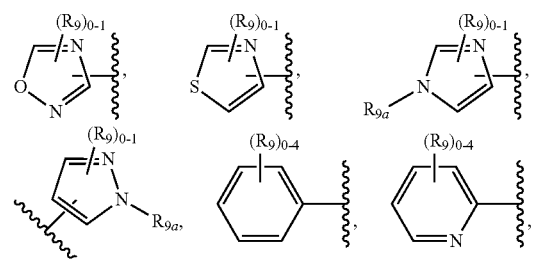

-continued

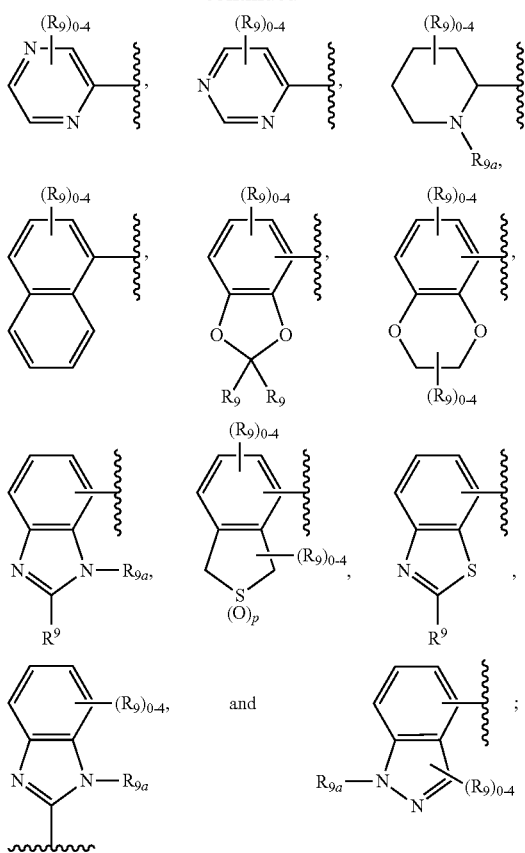

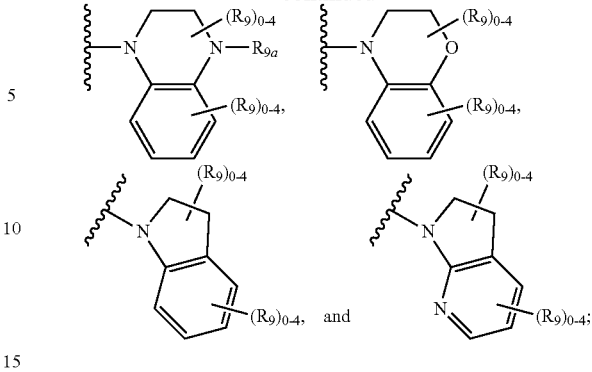

or $R_6$ and $R_8$ together with the nitrogen atom to which they are both attached form a heterocyclic ring substituted with 0-5 $R_9$, wherein the heterocyclic ring is selected from

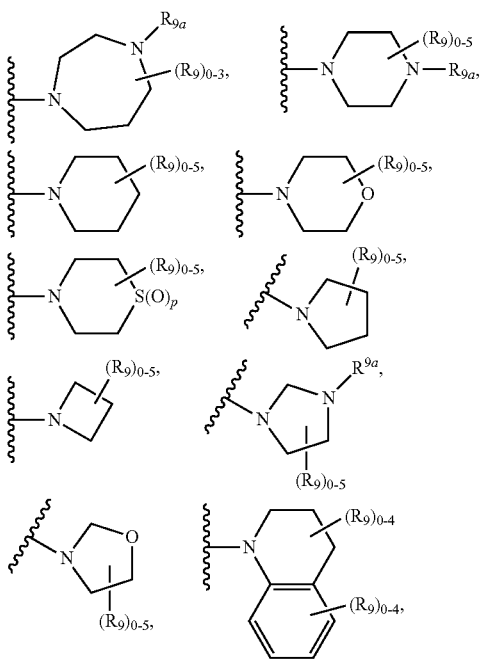

$R_9$ is independently selected from H, F, Cl, $C_{1-4}$ alkyl, —$OR_b$, CN, $S(O)_pNR_aR_a$, $NHS(O)_pR_c$, $NR_aR_a$, $C(=O)NR_aR_a$, $NR_aC(=O)R_b$, $C_{3-6}$ cycloalkyl, and heterocyclyl, wherein said alkyl, cycloalkyl, or heterocyclyl is substituted with 0-4 $R_e$;

$R_{9a}$ is independently selected from H, $C_{1-4}$ alkyl, —$S(O)_pR_c$, —$S(O)_pNR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H and $C_{1-6}$ alkyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl; and r, at each occurrence, is independently selected from zero, 1, 2, and 3.

In another aspect, the present invention provides compounds of Formula (X) or stereoisomers, tautomers, pharmaceutically acceptable salts, solvates, or prodrugs thereof, wherein $J_2$ is N; and other variables are as defined in Formula (X) above.

In another aspect, the present invention provides compounds of Formula (X) or stereoisomers, tautomers, pharmaceutically acceptable salts, solvates, or prodrugs thereof, wherein $J_2$ is $CR_3$ or $CR_4$; and other variables are as defined in Formula (X) above.

In another aspect, the present invention provides compounds of Formula (XI):

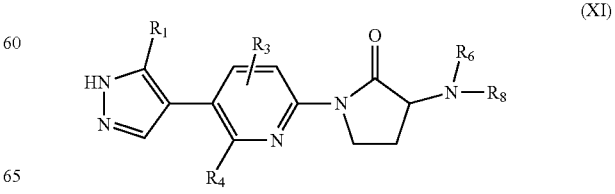

(XI)

R₄ (XI) or stereoisomers, tautomers, pharmaceutically acceptable salts, solvates, or prodrugs thereof, wherein $R_1$ is independently selected from H and $C_{1-4}$alkyl;

$R_3$ is independently selected from H, F, Me, and Et;

$R_4$ is independently selected from H, OMe, Me Et, and NHMe;

$R_6$ is H;

$R_8$ is independently selected from

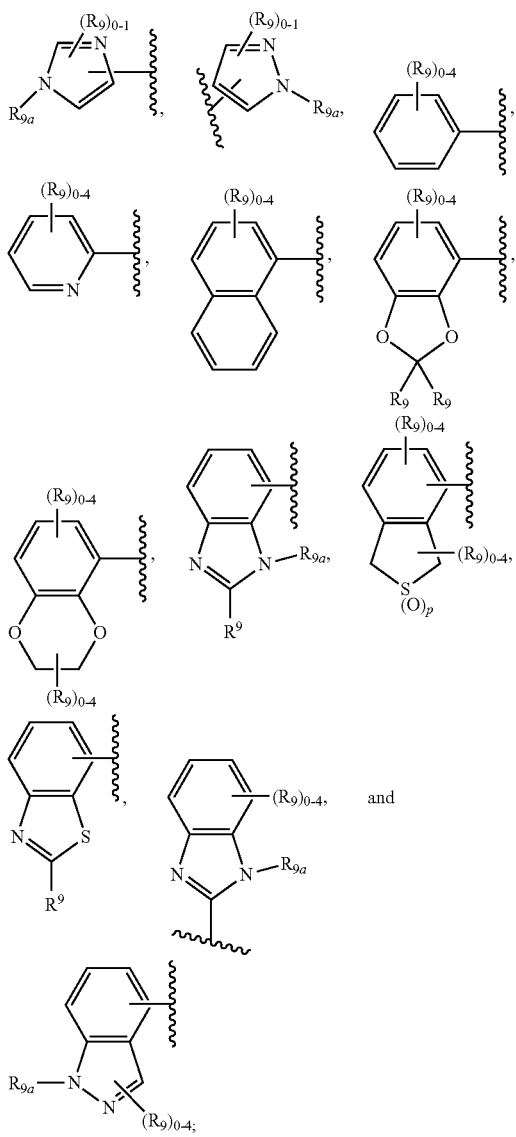

alternatively, $R_6$ and $R_8$ together with the nitrogen atom to which they are both attached form a heterocyclic ring selected from

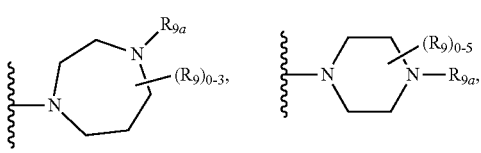

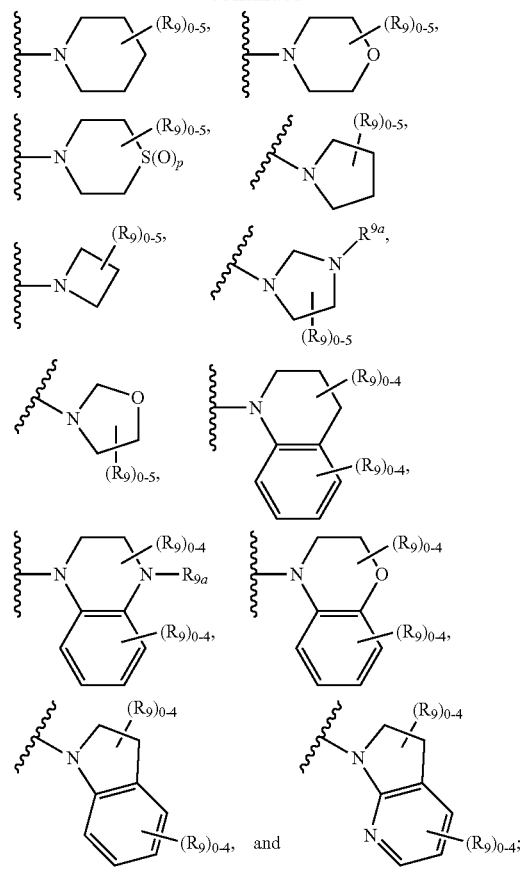

$R_9$ is independently selected from =O, F, Cl, $C_{1-4}$ alkyl, —$OR_b$, CN, $S(O)_pNR_aR_a$, $NHS(O)_pR_c$, $NR_aR_a$, C(=O)$NR_aR_a$, $NR_aC(=O)R_b$, $C_{3-6}$ cycloalkyl, aryl, and heterocyclyl, wherein said alkyl, cycloalkyl, aryl, or heterocyclyl is substituted with 0-4 $R_e$;

$R_{9a}$ is independently selected from H, $C_{1-4}$ alkyl, —$S(O)_pR_c$, —$S(O)_pNR_aR_a$, —C(=O)$OR_b$, —(CH$_2$)$_r$C(=O)$R_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_a$, at each occurrence, is independently selected from H and $C_{1-6}$ alkyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —(CH$_2$)$_r$—$C_{3-6}$ cycloalkyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$;

$R_e$, at each occurrence, is independently selected from $C_{1-6}$ alkyl substituted with 0-5 $R_f$, F, Cl, Br, CN, NO$_2$, =O, CO$_2$H, OH, and O$C_{1-4}$alkyl; and r, at each occurrence, is independently selected from zero, 1, 2, and 3.

In another aspect, the present invention provides compounds of Formula (XII):

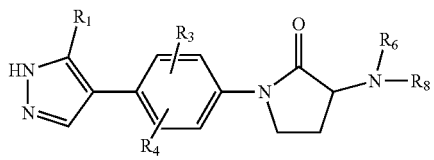

(XII)

or stereoisomers, tautomers, pharmaceutically acceptable salts, solvates, or prodrugs thereof, wherein $R_1$ is independently selected from H and $C_{1-4}$alkyl;

$R_3$ is independently selected from H, F, Cl, Br, CN, —$(CH_2)_rOR_b$, $NR^aR^a$, $C(O)NR^aR^a$, cyclopropyl, and $C_{1-4}$ alkyl substituted with 0-3 $R_e$;

$R_4$ is independently selected from H, F, Cl, OMe, Me, and Et;

$R_6$ is H;

$R_8$ is independently selected from

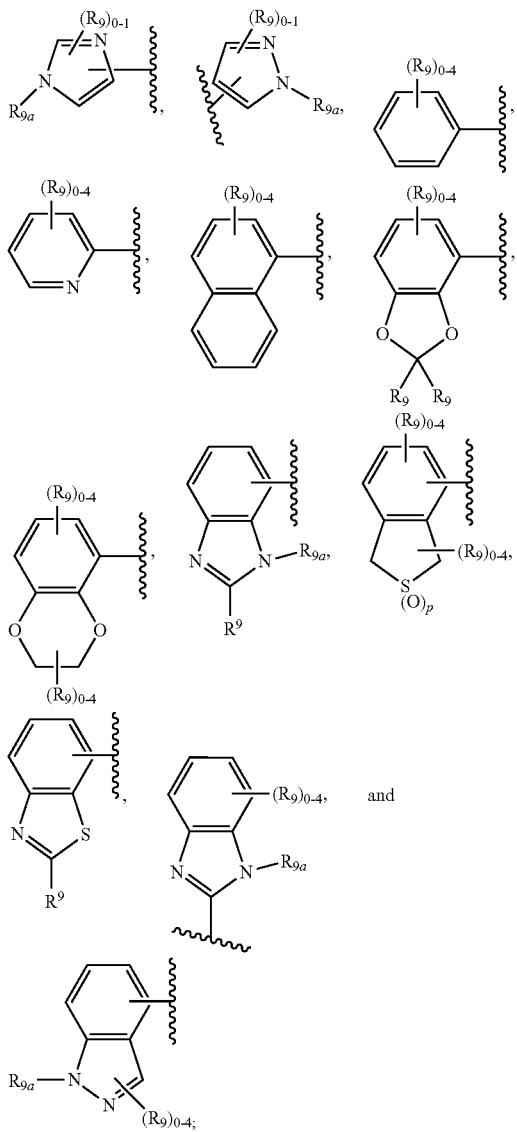

alternatively, $R_6$ and $R_8$ together with the nitrogen atom to which they are both attached form a heterocyclic ring selected from

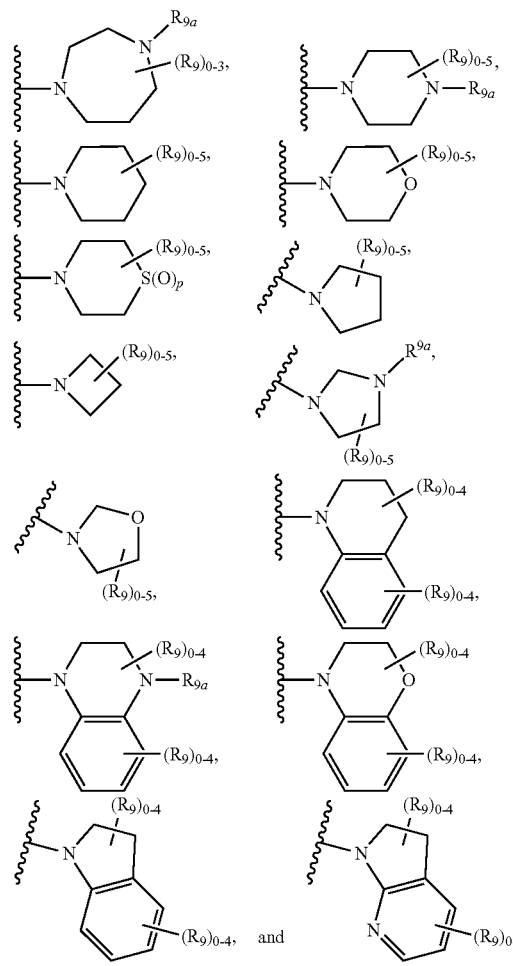

$R_9$ is independently selected from F, Cl, $C_{1-4}$ alkyl, —$OR_b$, CN, $S(O)_pNR_aR_a$, $NHS(O)_pR_c$, $NR_aR_a$, $C(=O)NR_aR_a$, $NR_aC(=O)R_b$, $C_{3-6}$ cycloalkyl, and heterocyclyl, wherein said alkyl, cycloalkyl, or heterocyclyl is substituted with 0-4 $R_e$;

$R_{9a}$ is independently selected from H, $C_{1-4}$ alkyl, —$S(O)_pR_c$, —$S(O)_pNR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H and $C_{1-6}$ alkyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, $OC_{1-4}$alkyl, and $NR_fRf$;

$R_f$, at each occurrence, is independently selected from H and $C_{1-4}$alkyl; and r, at each occurrence, is independently selected from zero, 1, 2, and 3.

In another aspect, the present invention provides a compound selected from any subset list of compounds exemplified in the present application.

In another aspect, the present invention provides a compound selected from the list below:
1-(4-(1H-pyrazol-4-yl)phenyl)-3-((3-fluoro-2-methoxyphenyl)amino)pyrrolidin-2-one (1); 1-(4-(1H-pyrazol-4-yl)phenyl)-3-(m-tolylamino)pyrrolidin-2-one (2); 1-(4-(1H-pyrazol-4-yl)phenyl)-3-((3-fluoro-5-methoxyphenyl)amino)pyrrolidin-2-one (3); 1-(4-(1H-pyrazol-4-yl)phenyl)-3-((4-fluoro-3-methoxyphenyl)amino)pyrrolidin-2-one (4); 1-(4-(1H-pyrazol-4-yl)phenyl)-3-((5-fluoro-2-methoxyphenyl)amino)pyrrolidin-2-one (5); 1-(4-(1H-pyrazol-4-yl)phenyl)-3-((3-ethoxyphenyl)amino)pyrrolidin-2-one (6); 1-(4-(1H-pyrazol-4-yl)phenyl)-3-((3-(difluoromethoxy)phenyl)amino)pyrrolidin-2-one (7); 1-(4-(1H-pyrazol-4-yl)phenyl)-3-((3-(trifluoromethoxy)phenyl)amino)pyrrolidin-2-one (8); 1-(4-(1H-pyrazol-4-yl)phenyl)-3-(pyridin-3-ylamino)pyrrolidin-2-one (9); 1-(4-(1H-pyrazol-4-yl)phenyl)-3-((3-isopropoxyphenyl)amino)pyrrolidin-2-one (10); 1-(4-(1H-pyrazol-4-yl)phenyl)-3-((3-(cyclopropylmethoxy)phenyl)amino)pyrrolidin-2-one (11); 1-(4-(1H-pyrazol-4-yl)phenyl)-3-((2-hydroxyethyl)(3-methoxyphenyl)amino)pyrrolidin-2-one (12); 1-(4-(1H-pyrazol-4-yl)phenyl)-3-((3-fluoro-4-methoxyphenyl)amino) pyrrolidin-2-one (13); 1-(4-(1H-pyrazol-4-yl)phenyl)-3-((3-fluoro-4-methoxyphenyl) amino)pyrrolidin-2-one (14); 1-(4-(1H-pyrazol-4-yl)phenyl)-3-((3-fluoro-2-methoxyphenyl)amino)pyrrolidin-2-one (15); 1-(4-(1H-pyrazol-4-yl)phenyl)-3-((3-fluoro-2-methoxyphenyl)amino)pyrrolidin-2-one (16); 1-(4-(1H-pyrazol-4-yl)phenyl)-3-((4-fluoro-3-methoxyphenyl)amino) pyrrolidin-2-one (17); 1-(4-(1H-pyrazol-4-yl)phenyl)-3-((4-fluoro-3-methoxyphenyl)amino)pyrrolidin-2-one (18); 1-(4-(1H-pyrazol-4-yl)phenyl)-3-((2-fluoro-4-methoxyphenyl)amino)pyrrolidin-2-one (19); 1-(4-(1H-pyrazol-4-yl)phenyl)-3-((2-fluoro-4-methoxyphenyl)amino)pyrrolidin-2-one (20); 1-(4-(1H-pyrazol-4-yl)phenyl)-3-((3,5-dimethoxyphenyl)amino)pyrrolidin-2-one (21); 1-(4-(1H-pyrazol-4-yl)phenyl)-3-((3,5-dimethoxyphenyl)amino) pyrrolidin-2-one (22); 1-(4-(1H-pyrazol-4-yl)phenyl)-3-((2,3-difluorophenyl)amino)pyrrolidin-2-one (23); 1-(4-(1H-pyrazol-4-yl)phenyl)-3-((2,4-difluorophenyl)amino) pyrrolidin-2-one (24); 1-(4-(1H-pyrazol-4-yl)phenyl)-3-((2,4-difluorophenyl)amino)pyrrolidin-2-one (25); 1-(4-(1H-pyrazol-4-yl)phenyl)-3-((3-fluoro-5-methoxyphenyl)amino) pyrrolidin-2-one as enantiomer-1 (26); 1-(4-(1H-pyrazol-4-yl)phenyl)-3-((3-fluoro-5-methoxyphenyl)amino) pyrrolidin-2-one as enantiomer-II (27); 1-(4-(1H-pyrazol-4-yl)phenyl)-3-((3-methoxyphenyl)amino)pyrrolidin-2-one (28); 1-(4-(1H-pyrazol-4-yl)phenyl)-3-((3-methoxyphenyl) amino)pyrrolidin-2-one (29); 1-(4-(1H-pyrazol-4-yl)phenyl)-3-((3-methoxyphenyl)(methyl)amino)pyrrolidin-2-one (30); 1-(4-(1H-pyrazol-4-yl)phenyl)-3-((3-methoxyphenyl)(methyl)amino)pyrrolidin-2-one (31); 1-(3-(difluoromethoxy)-4-(1H-pyrazol-4-yl)phenyl)-3-((3-fluoro-2-methoxyphenyl)amino)pyrrolidin-2-one (32); 1-(3-(difluoromethoxy)-4-(1H-pyrazol-4-yl)phenyl)-3-((3-fluoro-2-methoxyphenyl)amino) pyrrolidin-2-one (33); 1-(3-ethoxy-4-(1H-pyrazol-4-yl)phenyl)-3-((3-methoxyphenyl) amino)pyrrolidin-2-one (34); 1-(3-ethoxy-4-(1H-pyrazol-4-yl)phenyl)-3-((3-methoxyphenyl)amino)pyrrolidin-2-one (35); 1-(3-ethoxy-4-(1H-pyrazol-4-yl)phenyl)-3-((3-fluoro-5-methoxyphenyl)amino)pyrrolidin-2-one (36); 1-(3-ethoxy-4-(1H-pyrazol-4-yl)phenyl)-3-((3-fluoro-5-methoxyphenyl)amino)pyrrolidin-2-one (37); 1-(3-ethoxy-4-(1H-pyrazol-4-yl)phenyl)-3-((4-fluoro-3-methoxyphenyl)amino)pyrrolidin-2-one (38); 1-(3-ethoxy-4-(1H-pyrazol-4-yl)phenyl)-3-((4-fluoro-3-methoxyphenyl)amino) pyrrolidin-2-one (39); 1-(3-ethoxy-4-(1H-pyrazol-4-yl)phenyl)-3-((2-fluoro-5-methoxyphenyl) amino)pyrrolidin-2-one (40); 1-(3-ethoxy-4-(1H-pyrazol-4-yl)phenyl)-3-((2-fluoro-5-methoxyphenyl)amino)pyrrolidin-2-one (41); 1-(4-(1H-pyrazol-4-yl)phenyl)-3-(5-methoxyindolin-1-yl) pyrrolidin-2-one (42); 1-(3-fluoro-4-(1H-pyrazol-4-yl)phenyl)-3-(phenylamino)pyrrolidin-2-one (43); 1-(3-fluoro-4-(1H-pyrazol-4-yl)phenyl)-3-(phenylamino)pyrrolidin-2-one (44); 1-(3-fluoro-4-(1H-pyrazol-4-yl)phenyl)-3-((3-methoxyphenyl)amino)pyrrolidin-2-one (45); 1-(3-fluoro-4-(1H-pyrazol-4-yl)phenyl)-3-((3-methoxyphenyl)amino) pyrrolidin-2-one (46); 1-(3-fluoro-4-(1H-pyrazol-4-yl)phenyl)-3-((3-fluorophenyl)amino)pyrrolidin-2-one (47); 1-(3-fluoro-4-(1H-pyrazol-4-yl)phenyl)-3-((3-fluorophenyl)amino)pyrrolidin-2-one (48); 1-(3-fluoro-4-(1H-pyrazol-4-yl)phenyl)-3-((3-fluoro-5-methoxyphenyl)amino)pyrrolidin-2-one (49); 1-(3-fluoro-4-(1H-pyrazol-4-yl)phenyl)-3-((3-fluoro-5-methoxyphenyl)amino)pyrrolidin-2-one (50); 1-(4-(1H-pyrazol-4-yl)phenyl)-3-(7-methoxyindolin-1-yl) pyrrolidin-2-one (51); 1-(4-(1H-pyrazol-4-yl)phenyl)-3-(7-methoxyindolin-1-yl)pyrrolidin-2-one (52); 1-(4-(1H-pyrazol-4-yl)phenyl)-3-((2,2-difluorobenzo[d][1,3]dioxol-5-yl) amino)pyrrolidin-2-one (53); 1-(4-(1H-pyrazol-4-yl)phenyl)-3-((2,2-difluorobenzo[d][1,3]dioxol-5-yl)amino) pyrrolidin-2-one (54); 3-((1H-benzo[d]imidazol-2-yl)amino)-1-(4-(1H-pyrazol-4-yl)phenyl)pyrrolidin-2-one (55); 3-((1H-benzo[d]imidazol-2-yl)amino)-1-(4-(1H-pyrazol-4-yl)phenyl) pyrrolidin-2-one (56); 1-(4-(1H-pyrazol-4-yl)phenyl)-3-(benzylamino)pyrrolidin-2-one (57); 1-(4-(1H-pyrazol-4-yl)phenyl)-3-(phenylamino)pyrrolidin-2-one (58); 1-(4-(1H-pyrazol-4-yl)phenyl)-3-(phenethylamino) pyrrolidin-2-one, 2 TFA (59); 1-(4-(1H-pyrazol-4-yl)phenyl)-3-(((R)-1-(3-methoxyphenyl)ethyl)amino)pyrrolidin-2-one, TFA (60); 1-(4-(1H-pyrazol-4-yl)phenyl)-3-((3-fluorobenzyl)amino)pyrrolidin-2-one, TFA (61); 1-(4-(1H-pyrazol-4-yl)phenyl)-3-((3-fluorophenyl)amino)pyrrolidin-2-one (62); 1-(4-(1H-pyrazol-4-yl)phenyl)-3-((3-methoxyphenyl)amino)pyrrolidin-2-one (63); 1-(4-(1H-pyrazol-4-yl)phenyl)-3-phenoxypyrrolidin-2-one (64); N-(1-(4-(1H-pyrazol-4-yl)phenyl)-2-oxopyrrolidin-3-yl)-3-methoxybenzamide (65); 3-((3-(difluoromethoxy)phenyl)amino)-1-(3-methoxy-4-(1H-pyrazol-4-yl)phenyl)pyrrolidin-2-one (66); 1-(3-methoxy-4-(1H-pyrazol-4-yl)phenyl)-3-(phenylamino)pyrrolidin-2-one (67); 1-(3-methoxy-4-(1H-pyrazol-4-yl)phenyl)-3-((3-methoxyphenyl)amino) pyrrolidin-2-one (68); 3-((3-(difluoromethoxy)phenyl)amino)-1-(3-methoxy-4-(1H-pyrazol-4-yl)phenyl) pyrrolidin-2-one (69); 1-(3-methoxy-4-(1H-pyrazol-4-yl)phenyl)-3-((3-(trifluoromethoxy)phenyl) amino)pyrrolidin-2-one (70); 3-((3-isopropoxyphenyl)amino)-1-(3-methoxy-4-(1H-pyrazol-4-yl)phenyl)pyrrolidin-2-one, TFA (71); 3-((3-fluorophenyl)amino)-1-(3-methoxy-4-(1H-pyrazol-4-yl)phenyl)pyrrolidin-2-one (72); N-(3-((1-(3-methoxy-4-(1H-pyrazol-4-yl)phenyl)-2-oxopyrrolidin-3-yl)amino)phenyl)methanesulfonamide (73); 1-(3-methoxy-4-(1H-pyrazol-4-yl)phenyl)-3-((3-methoxyphenyl)amino) pyrrolidin-2-one (74); 1-(3-methoxy-4-(1H-pyrazol-4-yl)phenyl)-3-((3-methoxyphenyl)amino)pyrrolidin-2-one (75); 1-(4-(2-aminopyridin-4-yl)phenyl)-3-((3-methoxyphenyl) amino)pyrrolidin-2-one (76); 1-(4-(2-aminopyridin-4-yl)phenyl)-3-((3-methoxyphenyl)amino)pyrrolidin-2-one (77); 1-(4-(2-aminopyrimidin-4-yl)phenyl)-3-((3-methoxyphenyl)amino)pyrrolidin-2-one (78); 1-(4-(2-aminopyrimidin-4-yl)phenyl)-3-((3-methoxyphenyl)amino)pyrrolidin-2-one (79); 1-(4-(1H-pyrrolo[2,3-b]pyridin-4-yl)phenyl)-3-((3-methoxyphenyl)amino) pyrrolidin-2-one (80); 1-(4-(1H-pyrrolo[2,3-b]pyridin-4-yl)phenyl)-3-((3-methoxyphenyl)amino)pyrrolidin-2-one (81); 1-(5-(1H-pyrazol-4-yl)pyridin-2-yl)-3-((3-fluoro-5-methoxyphenyl)amino)pyrrolidin-2-one (82); 1-(5-(1H-pyrazol-4-yl)pyridin-2-yl)-3-((4-fluoro-3-methoxyphenyl)amino)pyrrolidin-2-one (83); 1-(5-(1H-pyrazol-4-yl)pyridin-2-yl)-3-((4-fluoro-3-methoxyphenyl)amino)pyrrolidin-2-one (84); 1-(5-(1H-pyrazol-4-yl)pyridin-2-yl)-3-((3-methoxyphenyl)amino)pyrrolidin-2-one (85); 1-(5-(1H-pyrazol-4-yl)pyridin-2-yl)-3-((3-methoxyphenyl)amino)pyrrolidin-2-one (86); 1-(5-(1H-pyrazol-4-yl)pyridin-2-yl)-3-((3-fluoro-5-methoxyphenyl)amino)pyrrolidin-2-one (87); 1-(5-(1H-pyrazol-4-yl)pyridin-2-yl)-3-((3-fluoro-5-methoxyphenyl) amino)pyrrolidin-2-one (88); 1-(5-(1H-pyrazol-4-yl)pyridin-2-yl)-3-((3-fluoro-2-methoxyphenyl)amino) pyrrolidin-2-one (89); 1-(5-(1H-pyrazol-4-yl)pyridin-2-yl)-3-((3-fluoro-2-methoxyphenyl)amino)pyrrolidin-2-one (90); 1-(4-(1H-pyrazol-4-yl)phenyl)-3-(3-fluorobenzyl)pyrrolidin-2-one (91); 1-(4-(1H-pyrazol-4-yl)phenyl)-3-benzylpyrrolidin-2-one (92); 1-(4-(1H-pyrazol-4-yl)phenyl)-3-(3-methoxybenzyl)pyrrolidin-2-one (93); 1-(4-(1H-pyrazol-4-yl)phenyl)-3-(2,6-difluorobenzyl)pyrrolidin-2-one (94); 1-(4-(1H-pyrazol-4-yl)phenyl)-3-(2-chlorobenzyl)pyrrolidin-2-one (95); 1-(4-(1H-pyrazol-4-yl)phenyl)-3-(2-fluorobenzyl)pyrrolidin-2-one (96); 3-((1-(4-(1H-pyrazol-4-yl)phenyl)-2-oxopyrrolidin-3-yl)methyl)benzonitrile (97); 1-(4-(1H-pyrazol-4-yl)phenyl)-3-(4-fluorobenzyl)pyrrolidin-2-one (98); 1-(4-(1H-pyrazol-4-yl)phenyl)-3-(3-methoxyphenethyl)pyrrolidin-2-one (99); 1-(4-(1H-pyrazol-4-yl)phenyl)-3-(2-chlorophenethyl)pyrrolidin-2-one (100); 1-(4-(1H-pyrazol-4-yl)phenyl)-3-phenylpyrrolidin-2-one (101); 1-(4-(1H-pyrazol-4-yl)phenyl)-3-(3-fluorophenyl)pyrrolidin-2-one (102); 1-(4-(1H-pyrazol-4-yl)phenyl)-3-(3-methoxyphenyl)pyrrolidin-2-one (103); 1-(4-(1H-pyrazol-4-yl)phenyl)-3-(2-fluorophenyl)pyrrolidin-2-one (104); 1-(4-(1H-pyrazol-4-yl)phenyl)-3-(2-chlorophenyl)pyrrolidin-2-one (105); 1-[3-(difluoromethoxy)-4-(1H-pyrazol-4-yl)phenyl]-3-[(4-fluoro-3-methoxyphenyl)amino]pyrrolidin-2-one (106); 1-[3-(difluoromethoxy)-4-(1H-pyrazol-4-yl)phenyl]-3-[(4-fluoro-3-methoxyphenyl)amino]pyrrolidin-2-one (107); 1-(4-(1H-pyrazol-4-yl)phenyl)-3-(3-methoxyphenoxy)pyrrolidin-2-one, TFA (108); 1-(4-(1H-pyrazol-4-yl)phenyl)-3-(m-tolyloxy)pyrrolidin-2-one (109); 1-(4-(1H-pyrazol-4-yl)phenyl)-3-(2-chlorophenoxy) pyrrolidin-2-one (110); 1-(4-(1H-pyrazol-4-yl)phenyl)-3-(2-fluoro-5-methoxyphenoxy) pyrrolidin-2-one (111); 1-(4-(1H-pyrazol-4-yl)phenyl)-3-(3-fluoro-5-methoxyphenoxy) pyrrolidin-2-one (112); 1-(4-(1H-pyrazol-4-yl)phenyl)-3-(3-aminophenoxy)pyrrolidin-2-one, TFA (113); 1-(3-(difluoromethoxy)-4-(1H-pyrazol-4-yl)phenyl)-3-((3-methoxyphenyl)amino)pyrrolidin-2-one (114); 1-(4-(1H-pyrazol-4-yl)phenyl)-3-((2-methylbenzo[d]thiazol-6-yl)amino) pyrrolidin-2-one (115); 2-((1-(4-(1H-pyrazol-4-yl)phenyl)-2-oxopyrrolidin-3-yl)amino)isonicotinonitrile (116); 3-((3-methoxy-2-methylphenyl)amino)-1-(6-methoxy-5-(1H-pyrazol-4-yl)pyridin-2-yl)pyrrolidin-2-one (117); 1-(3'-fluoro-2-methoxy-[3,4'-bipyridin]-6-yl)-3-((3-methoxyphenyl)amino) pyrrolidin-2-one (118); 3-((3-methoxyphenyl)amino)-1-(6-methyl-5-(1H-pyrrolo[2,3-b]pyridin-4-yl)pyridin-2-yl)pyrrolidin-2-one (119); 3-((3-methoxyphenyl)amino)-1-(6-methyl-5-(1H-pyrrolo[2,3-b]pyridin-4-yl)pyridin-2-yl)pyrrolidin-2-one (120); 1-(3'-fluoro-2-methyl-[3,4'-bipyridin]-6-yl)-3-((3-methoxyphenyl)amino)pyrrolidin-2-one (121); 1-(5-(2-aminopyrimidin-4-yl)-6-methylpyridin-2-yl)-3-((3-methoxyphenyl)amino) pyrrolidin-2-one (122); 1-(5-(1H-indazol-5-yl)-6-methoxypyridin-2-yl)-3-(3-methoxyphenoxy)pyrrolidin-2-one (123); 1-(5-(1H-indazol-6-yl)-6-methoxypyridin-2-yl)-3-(3-methoxyphenoxy) pyrrolidin-2-one (124); 1-(5-(1H-indazol-6-yl)-6-methoxypyridin-2-yl)-3-(3-methoxyphenoxy)pyrrolidin-2-one (125); 1-(2'-fluoro-2-methoxy-[3,4'-bipyridin]-6-yl)-3-((3-methoxyphenyl)amino)pyrrolidin-2-one (127); 1-(6-methoxy-5-(1H-pyrrolo[2,3-b]pyridin-4-yl)pyridin-2-yl)-3-((3-methoxyphenyl)amino) pyrrolidin-2-one (128); 1-(6-methoxy-5-(3-methyl-1H-pyrazol-4-yl)pyridin-2-yl)-3-((3-methoxyphenyl)amino)pyrrolidin-2-one (129); 5-(3-((3-methoxyphenyl)amino)-2-oxopyrrolidin-1-yl)-2-(1H-pyrazol-4-yl)benzamide (130); 1-(4-methoxy-5-(1H-pyrazol-4-yl)pyrimidin-2-yl)-3-((3-methoxyphenyl)amino) pyrrolidin-2-one (132); (3R,4S)-1-(4-(1H-pyrazol-4-yl)phenyl)-4-(hydroxymethyl)-3-((3-methoxyphenyl)amino) pyrrolidin-2-one (133); 1-[6-methoxy-5-(1H-pyrazol-4-yl)pyrazin-2-yl]-3-[(3-methoxyphenyl)amino]pyrrolidin-2-one (134); 3-((2-fluoro-6-methoxyphenyl)amino)-1-(3-methoxy-4-(1H-pyrazol-4-yl)phenyl)pyrrolidin-2-one (135); 3-((2-fluoro-6-methoxyphenyl)amino)-1-(3-methoxy-4-(1H-pyrazol-4-yl)phenyl)pyrrolidin-2-one (136); 3-((3-fluoro-5-methoxyphenyl)amino)-1-(3-methoxy-4-(1H-pyrazol-4-yl)phenyl)pyrrolidin-2-one (137); 3-((3-fluoro-5-methoxyphenyl)amino)-1-(3-methoxy-4-(1H-pyrazol-4-yl)phenyl) pyrrolidin-2-one (138); 3-((3,5-dimethoxyphenyl)amino)-1-(3-methoxy-4-(1H-pyrazol-4-yl)phenyl)pyrrolidin-2-one (139); 3-((3,5-dimethoxyphenyl)amino)-1-(3-methoxy-4-(1H-pyrazol-4-yl)phenyl)pyrrolidin-2-one (140); 3-((3-fluoro-4-methoxyphenyl)amino)-1-(3-methoxy-4-(1H-pyrazol-4-yl)phenyl)pyrrolidin-2-one (141); 3-((3-fluoro-4-methoxyphenyl)amino)-1-(3-methoxy-4-(1H-pyrazol-4-yl)phenyl)pyrrolidin-2-one (142); 3-((4-fluoro-2-methoxyphenyl)amino)-1-(3-methoxy-4-(1H-pyrazol-4-yl)phenyl) pyrrolidin-2-one (143); 3-((4-fluoro-2-methoxyphenyl)amino)-1-(3-methoxy-4-(1H-pyrazol-4-yl)phenyl)pyrrolidin-2-one (144); 3-((3,5-difluorophenyl)amino)-1-(3-methoxy-4-(1H-pyrazol-4-yl)phenyl) pyrrolidin-2-one (145); 3-((3,5-difluorophenyl) amino)-1-(3-methoxy-4-(1H-pyrazol-4-yl)phenyl)pyrrolidin-2-one (146); 3-((2-fluoro-5-methoxyphenyl)amino)-1-(3-methoxy-4-(1H-pyrazol-4-yl)phenyl)pyrrolidin-2-one (147); 3-((5-fluoro-2-methoxyphenyl)amino)-1-(3-methoxy-4-(1H-pyrazol-4-yl)phenyl) pyrrolidin-2-one (148); 3-((2-fluoro-5-methoxyphenyl)amino)-1-(3-methoxy-4-(1H-pyrazol-4-yl)phenyl)pyrrolidin-2-one (149); 3-((3-fluoro-2-methoxyphenyl)amino)-1-(3-methoxy-4-(1H-pyrazol-4-yl)phenyl)pyrrolidin-2-one (150); 3-((3-fluoro-2-methoxyphenyl)amino)-1-(3-methoxy-4-(1H-pyrazol-4-yl)phenyl)pyrrolidin-2-one (151); 3-((2-fluoro-4-methoxyphenyl)amino)-1-(3-methoxy-4-(1H-pyrazol-4-yl)phenyl) pyrrolidin-2-one (152); 3-((2-fluoro-4-methoxyphenyl)amino)-1-(3-methoxy-4-(1H-pyrazol-4-yl)phenyl)pyrrolidin-2-one (153); 3-((4-fluoro-3-methoxyphenyl)amino)-1-(3-methoxy-4-(1H-pyrazol-4-yl)phenyl)pyrrolidin-2-one (154); 3-((4-fluoro-3-methoxyphenyl)amino)-1-(3-methoxy-4-(1H-pyrazol-4-yl)phenyl)pyrrolidin-2-one (155); 1-(3-chloro-4-(1H-pyrazol-4-yl)phenyl)-3-((3-fluoro-4-methoxyphenyl)amino)pyrrolidin-2-one (156); 1-(3-chloro-4-(1H-pyrazol-4-yl)phenyl)-3-((3-fluoro-4-methoxyphenyl) amino)pyrrolidin-2-one (157); 1-(3-chloro-4-(1H-pyrazol-4-yl)phenyl)-3-((3-fluoro-5-methoxyphenyl)

amino)pyrrolidin-2-one (158); 1-(3-chloro-4-(1H-pyrazol-4-yl)phenyl)-3-((3-fluoro-5-methoxyphenyl)amino)pyrrolidin-2-one (159); 1-(3-chloro-4-(1H-pyrazol-4-yl)phenyl)-3-((4-fluoro-3-methoxyphenyl)amino)pyrrolidin-2-one Ena-I (160); 1-(3-chloro-4-(1H-pyrazol-4-yl)phenyl)-3-((4-fluoro-3-methoxyphenyl)amino)pyrrolidin-2-one Ena-II (161); 1-(2-chloro-4-(1H-pyrazol-4-yl)phenyl)-3-((4-fluoro-3-methoxyphenyl) amino)pyrrolidin-2-one (162); 1-(2-chloro-4-(1H-pyrazol-4-yl)phenyl)-3-((4-fluoro-3-methoxyphenyl)amino)pyrrolidin-2-one (163); 1-(3-chloro-4-(1H-pyrazol-4-yl)phenyl)-3-((3-methoxyphenyl)amino)pyrrolidin-2-one (164); 1-(3-chloro-4-(1H-pyrazol-4-yl)phenyl)-3-((3-methoxyphenyl)amino)pyrrolidin-2-one (165); 1-(2-chloro-4-(1H-pyrazol-4-yl)phenyl)-3-((3-methoxyphenyl)amino)pyrrolidin-2-one (166); 1-(2-chloro-4-(1H-pyrazol-4-yl)phenyl)-3-((3-methoxyphenyl)amino)pyrrolidin-2-one (167); 1-(2-chloro-4-(1H-pyrazol-4-yl)phenyl)-3-((3-fluoro-5-methoxyphenyl)amino)pyrrolidin-2-one (168); 1-(2-chloro-4-(1H-pyrazol-4-yl)phenyl)-3-((3-fluoro-5-methoxyphenyl)amino) pyrrolidin-2-one (169); 1-(6-methoxy-5-(1H-pyrazol-4-yl)pyridin-2-yl)-3-(3-methoxyphenoxy)pyrrolidin-2-one (170); 1-(6-methoxy-5-(1H-pyrazol-4-yl)pyridin-2-yl)-3-(3-methoxyphenoxy)pyrrolidin-2-one (171); 3-(3-fluoro-5-methoxyphenoxy)-1-(6-methoxy-5-(1H-pyrazol-4-yl)pyridin-2-yl)pyrrolidin-2-one (172); 3-(3-fluoro-5-methoxyphenoxy)-1-(6-methoxy-5-(1H-pyrazol-4-yl)pyridin-2-yl)pyrrolidin-2-one (173); 1-(3-(difluoromethyl)-4-(1H-pyrazol-4-yl)phenyl)-3-((3-methoxyphenyl)amino) pyrrolidin-2-one (175); 1-(3-(difluoromethyl)-4-(1H-pyrazol-4-yl)phenyl)-3-((3-methoxyphenyl)amino)pyrrolidin-2-one (176); 1-(3-(difluoromethyl)-4-(1H-pyrazol-4-yl)phenyl)-3-((3-fluoro-5-methoxyphenyl)amino)pyrrolidin-2-one (177); 1-(3-(difluoromethyl)-4-(1H-pyrazol-4-yl)phenyl)-3-((3-fluoro-5-methoxyphenyl)amino) pyrrolidin-2-one (178); 1-(3-(difluoromethyl)-4-(1H-pyrazol-4-yl)phenyl)-3-((4-fluoro-3-methoxyphenyl)amino)pyrrolidin-2-one (179); 1-(3-(difluoromethyl)-4-(1H-pyrazol-4-yl)phenyl)-3-((4-fluoro-3-methoxyphenyl)amino)pyrrolidin-2-one (180); 3-((4-fluoro-3-methoxyphenyl)amino)-1-(3-(methoxymethyl)-4-(1H-pyrazol-4-yl)phenyl)pyrrolidin-2-one (181); 3-((4-fluoro-3-methoxyphenyl)amino)-1-(3-(methoxymethyl)-4-(1H-pyrazol-4-yl)phenyl)pyrrolidin-2-one (182); 1-(3-(methoxymethyl)-4-(1H-pyrazol-4-yl)phenyl)-3-((3-methoxyphenyl)amino)pyrrolidin-2-one (183); 1-(3-(methoxymethyl)-4-(1H-pyrazol-4-yl)phenyl)-3-((3-methoxyphenyl)amino)pyrrolidin-2-one (184); 3-((3-fluoro-5-methoxyphenyl)amino)-1-(3-(methoxymethyl)-4-(1H-pyrazol-4-yl)phenyl)pyrrolidin-2-one (185); 3-((3-fluoro-5-methoxyphenyl)amino)-1-(3-(methoxymethyl)-4-(1H-pyrazol-4-yl)phenyl)pyrrolidin-2-one (186); 1-(3-(hydroxymethyl)-4-(1H-pyrazol-4-yl)phenyl)-3-((3-methoxyphenyl)amino)pyrrolidin-2-one (187); 3-((3-methoxyphenyl)amino)-1-(6-methyl-5-(1H-pyrazol-4-yl)pyridin-2-yl)pyrrolidin-2-one (188); 3-((3-methoxyphenyl)amino)-1-(6-methyl-5-(1H-pyrazol-4-yl)pyridin-2-yl)pyrrolidin-2-one (189); 3-((3-cyclopropylmethoxy)phenyl)amino)-1-(6-methyl-5-(1H-pyrazol-4-yl)pyridin-2-yl)pyrrolidin-2-one (190); 3-((3-cyclopropylmethoxy)phenyl)amino)-1-(6-methyl-5-(1H-pyrazol-4-yl)pyridin-2-yl)pyrrolidin-2-one (191); 3-((3-fluoro-5-methoxyphenyl)amino)-1-(6-methyl-5-(1H-pyrazol-4-yl)pyridin-2-yl)pyrrolidin-2-one (192); 3-((3-fluoro-5-methoxyphenyl)amino)-1-(6-methyl-5-(1H-pyrazol-4-yl)pyridin-2-yl)pyrrolidin-2-one (193); 3-((4-fluoro-3-methoxyphenyl)amino)-1-(6-methyl-5-(1H-pyrazol-4-yl)pyridin-2-yl)pyrrolidin-2-one (194); 3-((4-fluoro-3-methoxyphenyl)amino)-1-(6-methyl-5-(1H-pyrazol-4-yl)pyridin-2-yl)pyrrolidin-2-one (195); 1-(6-methoxy-5-(1H-pyrazol-4-yl)pyridin-2-yl)-3-((3-methoxyphenyl)amino)pyrrolidin-2-one (196); 1-(6-methoxy-5-(1H-pyrazol-4-yl)pyridin-2-yl)-3-((3-methoxyphenyl)amino)pyrrolidin-2-one (197); 3-((3-fluoro-5-methoxyphenyl)amino)-1-(6-methoxy-5-(1H-pyrazol-4-yl)pyridin-2-yl)pyrrolidin-2-one (198); 3-((3-fluoro-5-methoxyphenyl)amino)-1-(6-methoxy-5-(1H-pyrazol-4-yl)pyridin-2-yl)pyrrolidin-2-one (199); 3-((3-methoxyphenyl)amino)-1-(4-methyl-5-(1H-pyrazol-4-yl)pyridin-2-yl)pyrrolidin-2-one (200); 3-((3-(difluoromethoxy) phenyl)amino)-1-(6-methyl-5-(1H-pyrazol-4-yl)pyridin-2-yl)pyrrolidin-2-one (201); 3-((3-(difluoromethoxy)phenyl)amino)-1-(6-methyl-5-(1H-pyrazol-4-yl)pyridin-2-yl)pyrrolidin-2-one (202); 1-(4-ethyl-5-(1H-pyrazol-4-yl)pyridin-2-yl)-3-((3-methoxyphenyl)amino)pyrrolidin-2-one (203); 1-(4-ethyl-5-(1H-pyrazol-4-yl)pyridin-2-yl)-3-((3-methoxyphenyl)amino)pyrrolidin-2-one (204); 3-((3-(cyclopropylmethoxy)phenyl)amino)-1-(6-methoxy-5-(1H-pyrazol-4-yl)pyridin-2-yl)pyrrolidin-2-one (205); 3-((3-(cyclopropylmethoxy)phenyl)amino)-1-(4-methyl-5-(1H-pyrazol-4-yl)pyridin-2-yl)pyrrolidin-2-one (206); 3-((4-fluoro-3-methoxyphenyl)amino)-1-(6-methoxy-5-(1H-pyrazol-4-yl)pyridin-2-yl)pyrrolidin-2-one (207); 3-((4-fluoro-3-methoxyphenyl)amino)-1-(6-methoxy-5-(1H-pyrazol-4-yl)pyridin-2-yl)pyrrolidin-2-one (208); 3-((4-fluoro-3-methoxyphenyl)amino)-1-(4-methyl-5-(1H-pyrazol-4-yl)pyridin-2-yl)pyrrolidin-2-one (209); 1-(4-ethyl-5-(1H-pyrazol-4-yl)pyridin-2-yl)-3-((4-fluoro-3-methoxyphenyl) amino)pyrrolidin-2-one (210); 3-((3-(cyclopropylmethoxy)-4-fluorophenyl)amino)-1-(6-ethyl-5-(1H-pyrazol-4-yl)pyridin-2-yl)pyrrolidin-2-one (211); 3-((3-(cyclopropylmethoxy)-4-fluorophenyl)amino)-1-(6-ethyl-5-(1H-pyrazol-4-yl)pyridin-2-yl)pyrrolidin-2-one (212); 3-((3-(cyclopropylmethoxy)-4-fluorophenyl)amino)-1-(4-ethyl-5-(1H-pyrazol-4-yl)pyridin-2-yl)pyrrolidin-2-one (213); 3-((3-(cyclopropylmethoxy)phenyl)amino)-1-(6-methoxy-5-(1H-pyrazol-4-yl)pyridin-2-yl)pyrrolidin-2-one (214); 3-((3-(cyclopropylmethoxy)phenyl)amino)-1-(6-methoxy-5-(1H-pyrazol-4-yl)pyridin-2-yl)pyrrolidin-2-one (215); 3-((3-(cyclopropylmethoxy)-4-fluorophenyl)amino)-1-(6-methoxy-5-(1H-pyrazol-4-yl)pyridin-2-yl)pyrrolidin-2-one (216); 3-((3-(cyclopropylmethoxy)-4-fluorophenyl)amino)-1-(6-methoxy-5-(1H-pyrazol-4-yl)pyridin-2-yl)pyrrolidin-2-one (217); 3-((3-ethoxyphenyl)amino)-1-(6-methoxy-5-(1H-pyrazol-4-yl)pyridin-2-yl)pyrrolidin-2-one (218); 3-((3-ethoxyphenyl)amino)-1-(6-methoxy-5-(1H-pyrazol-4-yl)pyridin-2-yl)pyrrolidin-2-one (219); 3-((3-(difluoromethoxy)phenyl)amino)-1-(6-methoxy-5-(1H-pyrazol-4-yl)pyridin-2-yl)pyrrolidin-2-one (220); 3-((3-(difluoromethoxy)phenyl)amino)-1-(6-methoxy-5-(1H-pyrazol-4-yl)pyridin-2-yl)pyrrolidin-2-one (221); 1-(4-(1H-pyrazol-4-yl)phenyl)-3-((6-methoxypyridin-2-yl)amino) pyrrolidin-2-one (223); 3-((2-fluorophenyl)amino)-1-(6-methoxy-5-(1H-pyrazol-4-yl)pyridin-2-yl)pyrrolidin-2-one (224); 3-(2H-benzo[b][1,4]oxazin-4(3H)-yl)-1-(6-methoxy-5-(1H-pyrazol-4-yl)pyridin-2-yl)pyrrolidin-2-one (225); 1-(4-(1H-pyrazol-4-yl)phenyl)-3-(pyrazin-2-ylamino)pyrrolidin-2-one (226); 1-(4-(1H-pyrazol-4-yl)phenyl)-3-(pyrimidin-5-ylamino)pyrrolidin-2-one (227); 3-(3,4-dihydroquinoxalin-1 (2H)-yl)-1-(6-methoxy-5-(1H-pyrazol-4-yl)pyridin-2-yl)pyrrolidin-2-one (228); 3-(2H-benzo[b][1,4]oxazin-4(3H)-yl)-1-(6-methoxy-5-(1H-pyrazol-4-yl)pyridin-2-yl)pyrrolidin-2-one (229); 3-(2H-benzo[b][1,4]oxazin-4(3H)-yl)-1-(6-methoxy-5-(1H-pyrazol-4-yl)pyridin-2-yl)pyrrolidin-2-one (230); 1-(4-(1H-pyrazol-4-yl)

phenyl)-3-((3-(difluoromethoxy)phenyl)amino)pyrrolidin-2-one (231); 1-(4-(1H-pyrazol-4-yl)phenyl)-3-((3-(difluoromethoxy)phenyl)amino)pyrrolidin-2-one (232); 1-(4-(1H-pyrazol-4-yl)phenyl)-3-((3-(cyclopropylmethoxy)phenyl)amino)pyrrolidin-2-one (233); 1-(4-(1H-pyrazol-4-yl)phenyl)-3-((3-(cyclopropylmethoxy)phenyl)amino)pyrrolidin-2-one (235); 1-(4-(1H-pyrazol-4-yl)phenyl)-3-((3-(2,2-difluoroethoxy)phenyl) amino)pyrrolidin-2-one (237); 1-(4-(1H-pyrazol-4-yl)phenyl)-3-((3-(2,2-difluoroethoxy) phenyl)amino)pyrrolidin-2-one (238); 1-(4-(1H-pyrazol-4-yl)phenyl)-3-((2-fluoro-5-methoxyphenyl)amino)pyrrolidin-2-one (239); 1-(4-(1H-pyrazol-4-yl)phenyl)-3-((2-fluoro-5-methoxyphenyl)amino)pyrrolidin-2-one (240); 1-(3-ethyl-4-(1H-pyrazol-4-yl)phenyl)-3-((4-fluoro-3-methoxyphenyl)amino)pyrrolidin-2-one (241); 1-(3-ethyl-4-(1H-pyrazol-4-yl)phenyl)-3-((4-fluoro-3-methoxyphenyl)amino)pyrrolidin-2-one (242); 1-(3-ethyl-4-(1H-pyrazol-4-yl)phenyl)-3-((3-methoxyphenyl)amino)pyrrolidin-2-one (243); 1-(3-ethyl-4-(1H-pyrazol-4-yl)phenyl)-3-((3-methoxyphenyl)amino)pyrrolidin-2-one (244); 1-(3-ethyl-4-(1H-pyrazol-4-yl)phenyl)-3-((3-fluoro-5-methoxyphenyl)amino) pyrrolidin-2-one (245); 1-(3-ethyl-4-(1H-pyrazol-4-yl)phenyl)-3-((3-fluoro-5-methoxyphenyl)amino)pyrrolidin-2-one (246); 3-((3-(cyclopropylmethoxy)phenyl)amino)-1-(3-ethyl-4-(1H-pyrazol-4-yl)phenyl)pyrrolidin-2-one (247); 3-((3-(cyclopropylmethoxy)phenyl)amino)-1-(3-ethyl-4-(1H-pyrazol-4-yl)phenyl)pyrrolidin-2-one (248); 3-((3-ethoxyphenyl)amino)-1-(3-methoxy-4-(1H-pyrazol-4-yl)phenyl) pyrrolidin-2-one (249); 3-((3-ethoxyphenyl)amino)-1-(3-methoxy-4-(1H-pyrazol-4-yl)phenyl)pyrrolidin-2-one (250); 3-((3-fluoro-5-methoxyphenyl)amino)-1-(6-(methylamino)-5-(1H-pyrazol-4-yl)pyridin-2-yl) pyrrolidin-2-one (251); 3-((3-fluoro-5-methoxyphenyl)amino)-1-(6-(methylamino)-5-(1H-pyrazol-4-yl)pyridin-2-yl)pyrrolidin-2-one (252); 3-((3-methoxyphenyl)amino)-1-(6-(methylamino)-5-(1H-pyrazol-4-yl)pyridin-2-yl)pyrrolidin-2-one (253); 3-((3-methoxyphenyl)amino)-1-(6-(methylamino)-5-(1H-pyrazol-4-yl)pyridin-2-yl)pyrrolidin-2-one (254); 3-(benzo[d][1,3]dioxol-5-ylamino)-1-(6-methoxy-5-(1H-pyrazol-4-yl)pyridin-2-yl)pyrrolidin-2-one (255); 3-((2,3-dihydrobenzo[b][1,4]dioxin-6-yl)amino)-1-(6-methoxy-5-(1H-pyrazol-4-yl)pyridin-2-yl)pyrrolidin-2-one (256); 3-((1-(6-methoxy-5-(1H-pyrazol-4-yl)pyridin-2-yl)-2-oxopyrrolidin-3-yl)amino)benzonitrile (257); 3-((1-(6-methoxy-5-(1H-pyrazol-4-yl)pyridin-2-yl)-2-oxopyrrolidin-3-yl)amino)benzamide (258); 3-(benzo[d]thiazol-6-ylamino)-1-(6-methoxy-5-(1H-pyrazol-4-yl)pyridin-2-yl)pyrrolidin-2-one (259); N-(3-((1-(6-methoxy-5-(1H-pyrazol-4-yl)pyridin-2-yl)-2-oxopyrrolidin-3-yl)amino)phenyl) acetamide (260); 3-((2-chloro-5-methoxyphenyl)amino)-1-(6-methoxy-5-(1H-pyrazol-4-yl)pyridin-2-yl) pyrrolidin-2-one (261); 1-(6-methoxy-5-(1H-pyrazol-4-yl)pyridin-2-yl)-3-((3-(oxazol-5-yl)phenyl)amino)pyrrolidin-2-one (262); 3-((2,2-dioxido-1,3-dihydrobenzo[c]thiophen-5-yl)amino)-1-(6-methoxy-5-(1H-pyrazol-4-yl)pyridin-2-yl)pyrrolidin-2-one (263); 1-(6-methoxy-5-(1H-pyrazol-4-yl)pyridin-2-yl)-3-((3-(morpholinosulfonyl)phenyl)amino) pyrrolidin-2-one (264); N-(3-((1-(6-methoxy-5-(1H-pyrazol-4-yl)pyridin-2-yl)-2-oxopyrrolidin-3-yl)amino) phenyl)methanesulfonamide (265); 3-((3-(1H-tetrazol-5-yl)phenyl)amino)-1-(6-methoxy-5-(1H-pyrazol-4-yl)pyridin-2-yl)pyrrolidin-2-one (266); 3-((3-isopropoxyphenyl)amino)-1-(6-methoxy-5-(1H-pyrazol-4-yl)pyridin-2-yl)pyrrolidin-2-one (267); 3-((1-(6-methoxy-5-(1H-pyrazol-4-yl)pyridin-2-yl)-2-oxopyrrolidin-3-yl)amino) benzenesulfonamide (268); 3-((4-(tert-butyl)thiazol-2-yl)amino)-1-(6-methoxy-5-(1H-pyrazol-4-yl)pyridin-2-yl) pyrrolidin-2-one (269); 3-((1,3-dimethyl-1H-pyrazol-5-yl)amino)-1-(6-methoxy-5-(1H-pyrazol-4-yl)pyridin-2-yl) pyrrolidin-2-one (270); 3-((1,5-dimethyl-1H-pyrazol-3-yl)amino)-1-(6-methoxy-5-(1H-pyrazol-4-yl)pyridin-2-yl) pyrrolidin-2-one (271); 3-((1-isopropyl-1H-pyrazol-4-yl)amino)-1-(6-methoxy-5-(1H-pyrazol-4-yl)pyridin-2-yl) pyrrolidin-2-one (272); 1-(6-methoxy-5-(1H-pyrazol-4-yl)pyridin-2-yl)-3-morpholinopyrrolidine-2-one (273); 1-(6-methoxy-5-(1H-pyrazol-4-yl)pyridin-2-yl)-3-((R)-3-methylmorpholino) pyrrolidin-2-one (274); 3-(2,6-dimethylmorpholino)-1-(6-methoxy-5-(1H-pyrazol-4-yl)pyridin-2-yl)pyrrolidin-2-one (275); 3-(4-(dimethylamino)piperidin-1-yl)-1-(6-methoxy-5-(1H-pyrazol-4-yl)pyridin-2-yl)pyrrolidin-2-one (276); 3-(3,4-dihydroisoquinolin-2(1H)-yl)-1-(6-methoxy-5-(1H-pyrazol-4-yl)pyridin-2-yl)pyrrolidin-2-one (277); 3-(3,3-dimethylpiperidin-1-yl)-1-(6-methoxy-5-(1H-pyrazol-4-yl)pyridin-2-yl)pyrrolidin-2-one (278); 1-(6-methoxy-5-(1H-pyrazol-4-yl)pyridin-2-yl)-3-(methyl(1-methylpiperidin-4-yl)amino)pyrrolidin-2-one (279); 3-(1,1-dioxidothiomorpholin)-1-(6-methoxy-5-(1H-pyrazol-4-yl)pyridin-2-yl)pyrrolidin-2-one (280); 3-(2,3-dihydro-1H-pyrrolo[2,3-b]pyridin-1-yl)-1-(6-methoxy-5-(1H-pyrazol-4-yl)pyridin-2-yl)pyrrolidin-2-one (281); 3-(4,4-difluoropiperidin-1-yl)-1-(6-methoxy-5-(1H-pyrazol-4-yl)pyridin-2-yl)pyrrolidin-2-one hydrochloride (282); 3-(3-fluoropiperidin-1-yl)-1-(6-methoxy-5-(1H-pyrazol-4-yl)pyridin-2-yl)pyrrolidin-2-one hydrochloride (283); 3,3-difluoro-1'-(6-methoxy-5-(1H-pyrazol-4-yl)pyridin-2-yl)-[1,3'-bipyrrolidin]-2'-one hydrochloride (284); 1-(6-methoxy-5-(1H-pyrazol-4-yl)pyridin-2-yl)-3-(4-(trifluoromethyl)piperidin-1-yl)pyrrolidin-2-one hydrochloride (285); 1-(6-methoxy-5-(1H-pyrazol-4-yl)pyridin-2-yl)-3-(4-(methylsulfonyl)piperazin-1-yl)pyrrolidin-2-one (286); 1-(6-methoxy-5-(1H-pyrazol-4-yl)pyridin-2-yl)-3-(4-(4-methoxyphenyl)piperazin-1-yl)pyrrolidin-2-one dihydrochloride (287); 3-(4-(4-hydroxyphenyl)piperazin-1-yl)-1-(6-methoxy-5-(1H-pyrazol-4-yl)pyridin-2-yl)pyrrolidin-2-one (288); 3-(4-(hydroxymethyl)piperidin-1-yl)-1-(6-methoxy-5-(1H-pyrazol-4-yl)pyridin-2-yl)pyrrolidin-2-one (289); (3S)-3-fluoro-1'-(6-methoxy-5-(1H-pyrazol-4-yl)pyridin-2-yl)-[1,3'-bipyrrolidin]-2'-one hydrochloride (290); 1-(6-methoxy-5-(1H-pyrazol-4-yl)pyridin-2-yl)-3-(4-methoxypiperidin-1-yl)pyrrolidin-2-one hydrochloride (291); 1-(1-(6-methoxy-5-(1H-pyrazol-4-yl)pyridin-2-yl)-2-oxopyrrolidin-3-yl)piperidin-4-one hydrochloride hydrate (292); (3R)-3-(dimethylamino)-1'-(6-methoxy-5-(1H-pyrazol-4-yl)pyridin-2-yl)-[1,3'-bipyrrolidin]-2'-one (293); N-((3S)-1'-(6-methoxy-5-(1H-pyrazol-4-yl)pyridin-2-yl)-2'-oxo-[1,3'-bipyrrolidin]-3-yl) acetamide (294); (3S)-3-hydroxy-1'-(6-methoxy-5-(1H-pyrazol-4-yl)pyridin-2-yl)-[1,3'-bipyrrolidin]-2'-one (295); 3-(4-fluoropiperidin-1-yl)-1-(6-methoxy-5-(1H-pyrazol-4-yl)pyridin-2-yl)pyrrolidin-2-one hydrochloride (296); 1-(6-(1H-pyrazol-4-yl)pyridin-3-yl)-3-((3-methoxyphenyl) amino)pyrrolidin-2-one (297); 1-(6-(1H-pyrazol-4-yl)pyridin-3-yl)-3-((3-methoxyphenyl)amino)pyrrolidin-2-one (298); 1-(6-(1H-pyrazol-4-yl)pyridin-3-yl)-3-((4-fluoro-3-methoxyphenyl)amino)pyrrolidin-2-one (299); 1-(6-(1H-pyrazol-4-yl)pyridin-3-yl)-3-((4-fluoro-3-methoxyphenyl)amino) pyrrolidin-2-one (300); 1-(6-(1H-pyrazol-4-yl)pyridin-3-yl)-3-((3-fluoro-5-methoxyphenyl)amino) pyrrolidin-2-one (301); 1-(6-(1H-pyrazol-4-yl)pyridin-3-yl)-3-((3-fluoro-5-methoxyphenyl)amino)pyrrolidin-2-one (302); 1-(5-(1H-pyrazol-4-yl)pyridin-2-yl)-3-((2-fluoro-5-methoxyphenyl)amino)pyrrolidin-2-one (303); 1-(5-(1H-pyrazol-4-yl)pyridin-2-yl)-3-((2-fluoro-5-methoxyphenyl)amino)pyrrolidin-2-one (304); 1-(2,3-difluoro-4-(1H- pyrazol-4-yl)phenyl)-3-((3-methoxyphenyl)amino) pyrrolidin-2-one (305); 1-(2,3-difluoro-4-(1H-pyrazol-4-yl)phenyl)-3-((3-methoxyphenyl)amino)pyrrolidin-2-one (306); 1-(2,3-difluoro-4-(1H-pyrazol-4-yl)phenyl)-3-((4-fluoro-3-methoxyphenyl)amino) pyrrolidin-2-one (307); 1-(2,3-difluoro-4-(1H-pyrazol-4-yl)phenyl)-3-((4-fluoro-3-methoxyphenyl)amino)pyrrolidin-2-one (308); 1-(2,3-difluoro-4-(1H-pyrazol-4-yl)phenyl)-3-((3-fluoro-5-methoxyphenyl)amino)pyrrolidin-2-one (309); 1-(2,3-difluoro-4-(1H-pyrazol-4-yl)phenyl)-3-((3-fluoro-5-methoxyphenyl) amino)pyrrolidin-2-one (310); 1-(3,5-difluoro-4-(1H-pyrazol-4-yl)phenyl)-3-((3-methoxyphenyl)amino) pyrrolidin-2-one (311); 1-(3,5-difluoro-4-(1H-pyrazol-4-yl)phenyl)-3-((3-methoxyphenyl)amino) pyrrolidin-2-one (312); 1-(6-ethyl-5-(1H-pyrazol-4-yl)pyridin-2-yl)-3-((3-methoxyphenyl)amino)pyrrolidin-2-one (313); 1-(6-ethyl-5-(1H-pyrazol-4-yl)pyridin-2-yl)-3-((3-methoxyphenyl) amino)pyrrolidin-2-one (314); 1-(6-ethyl-5-(1H-pyrazol-4-yl)pyridin-2-yl)-3-((3-fluoro-5-methoxyphenyl)amino) pyrrolidin-2-one (315); 1-(6-ethyl-5-(1H-pyrazol-4-yl) pyridin-2-yl)-3-((3-fluoro-5-methoxyphenyl)amino) pyrrolidin-2-one (316); 1-(6-ethyl-5-(1H-pyrazol-4-yl) pyridin-2-yl)-3-((4-fluoro-3-methoxyphenyl)amino) pyrrolidin-2-one (317); 1-(6-ethyl-5-(1H-pyrazol-4-yl)pyridin-2-yl)-3-((4-fluoro-3-methoxyphenyl)amino)pyrrolidin-2-one (318); 1-(5-(1H-pyrazol-4-yl)pyridin-2-yl)-3-((3-(cyclopropylmethoxy)phenyl)amino)pyrrolidin-2-one (319); 1-(5-(1H-pyrazol-4-yl)pyridin-2-yl)-3-((3-(cyclopropylmethoxy)phenyl)amino)pyrrolidin-2-one (320); 1-(5-(1H-pyrazol-4-yl)pyridin-2-yl)-3-((3-(difluoromethoxy)phenyl) amino)pyrrolidin-2-one (321); 1-(5-(1H-pyrazol-4-yl) pyridin-2-yl)-3-((3-(difluoromethoxy)phenyl)amino) pyrrolidin-2-one (322); (3S,4R)-1-(4-(1H-pyrazol-4-yl)phenyl)-4-(hydroxymethyl)-3-((3-methoxyphenyl)amino)pyrrolidin-2-one (323); 2-((1-(4-(1H-pyrazol-4-yl)phenyl)-2-oxopyrrolidin-3-yl)amino)-4-methoxybenzamide (324); 1-(4-(1H-pyrazol-4-yl)phenyl)-3-((3-methoxy-2-methylphenyl)amino)pyrrolidin-2-one (325); 1-(4-(1H-pyrazol-4-yl)phenyl)-3-((3-methoxy-2-methylphenyl)amino)pyrrolidin-2-one (326); 1-(4-(1H-pyrazol-4-yl)phenyl)-2-oxopyrrolidin-3-yl 2-amino-4-methoxybenzoate (327); 1-(2-fluoro-4-(1H-pyrazol-4-yl)phenyl)-3-((3-methoxyphenyl)amino)pyrrolidin-2-one (328); 1-(2-fluoro-4-(1H-pyrazol-4-yl)phenyl)-3-((3-methoxyphenyl)amino)pyrrolidin-2-one (329); 3-((4-fluoro-3-methoxyphenyl)amino)-1-(2-fluoro-4-(1H-pyrazol-4-yl)phenyl) pyrrolidin-2-one (330); 3-((4-fluoro-3-methoxyphenyl)amino)-1-(2-fluoro-4-(1H-pyrazol-4-yl)phenyl)pyrrolidin-2-one (331); 3-((4-fluoro-3-methoxyphenyl)amino)-1-(3-fluoro-4-(1H-pyrazol-4-yl)phenyl)pyrrolidin-2-one (332); 3-((4-fluoro-3-methoxyphenyl)amino)-1-(3-fluoro-4-(1H-pyrazol-4-yl)phenyl)pyrrolidin-2-one (333); 1-(3-fluoro-4-(1H-pyrazol-4-yl)phenyl)-3-((2-fluoro-5-methoxyphenyl)amino) pyrrolidin-2-one (334); 1-(3-fluoro-4-(1H-pyrazol-4-yl)phenyl)-3-((2-fluoro-5-methoxyphenyl)amino)pyrrolidin-2-one (335); 3-((3-fluoro-2-methoxyphenyl)amino)-1-(3-fluoro-4-(1H-pyrazol-4-yl)phenyl)pyrrolidin-2-one (336); 3-((3-fluoro-2-methoxyphenyl)amino)-1-(3-fluoro-4-(1H-pyrazol-4-yl)phenyl)pyrrolidin-2-one (337); 1-(2-fluoro-4-(1H-pyrazol-4-yl)phenyl)-3-((3-fluoro-5-methoxyphenyl) amino)pyrrolidin-2-one (338); 1-(2-fluoro-4-(1H-pyrazol-4-yl)phenyl)-3-((3-fluoro-5-methoxyphenyl)amino) pyrrolidin-2-one (339); 1-(2-fluoro-4-(1H-pyrazol-4-yl)phenyl)-3-((2-fluoro-5-methoxyphenyl)amino)pyrrolidin-2-one (340); 1-(2-fluoro-4-(1H-pyrazol-4-yl)phenyl)-3-((2-fluoro-5-methoxyphenyl)amino)pyrrolidin-2-one (341); 3-((3-fluoro-2-methoxyphenyl)amino)-1-(2-fluoro-4-(1H-pyrazol-4-yl)phenyl)pyrrolidin-2-one (342); 3-((3-fluoro-2-methoxyphenyl)amino)-1-(2-fluoro-4-(1H-pyrazol-4-yl)phenyl)pyrrolidin-2-one (343); 1-(2-fluoro-4-(1H-pyrazol-4-yl)phenyl)-3-((3-fluoro-4-methoxyphenyl)amino) pyrrolidin-2-one (344); 1-(2-fluoro-4-(1H-pyrazol-4-yl)phenyl)-3-((3-fluoro-4-methoxyphenyl)amino)pyrrolidin-2-one (345); 1-(3-(2-(dimethylamino)ethoxy)-4-(1H-pyrazol-4-yl)phenyl)-3-((4-fluoro-3-methoxyphenyl) amino) pyrrolidin-2-one (346); 1-(3-(2-(dimethylamino)ethoxy)-4-(1H-pyrazol-4-yl)phenyl)-3-((3-methoxyphenyl)amino) pyrrolidin-2-one (347); 1-(4-(1H-pyrazol-4-yl)-3-(2,2,2-trifluoro-1-hydroxyethyl)phenyl)-3-((3-methoxyphenyl) amino)pyrrolidin-2-one (348); 1-(2,5-difluoro-4-(1H-pyrazol-4-yl)phenyl)-3-((4-fluoro-3-methoxyphenyl)amino) pyrrolidin-2-one (349); 1-(2,5-difluoro-4-(1H-pyrazol-4-yl)phenyl)-3-((4-fluoro-3-methoxyphenyl)amino)pyrrolidin-2-one (350); 1-(2,5-difluoro-4-(1H-pyrazol-4-yl)phenyl)-3-((3-fluoro-5-methoxyphenyl)amino)pyrrolidin-2-one (351); 1-(2,5-difluoro-4-(1H-pyrazol-4-yl)phenyl)-3-((3-fluoro-5-methoxyphenyl)amino)pyrrolidin-2-one (352); 1-(2,5-difluoro-4-(1H-pyrazol-4-yl)phenyl)-3-((3-methoxyphenyl) amino)pyrrolidin-2-one (353); 1-(2,5-difluoro-4-(1H-pyrazol-4-yl)phenyl)-3-((3-methoxyphenyl)amino) pyrrolidin-2-one (354); 3-((3-(difluoromethoxy)phenyl) amino)-1-(3-fluoro-4-(1H-pyrazol-4-yl)phenyl)pyrrolidin-2-one (355); 3-((3-(difluoromethoxy)phenyl)amino)-1-(3-fluoro-4-(1H-pyrazol-4-yl)phenyl)pyrrolidin-2-one (356); 1-(3-fluoro-5-(1H-pyrazol-4-yl)pyridin-2-yl)-3-((3-methoxyphenyl)amino)pyrrolidin-2-one (357); 1-(3-fluoro-5-(1H-pyrazol-4-yl)pyridin-2-yl)-3-((3-methoxyphenyl) amino)pyrrolidin-2-one (358); 1-(3-fluoro-5-(1H-pyrazol-4-yl)pyridin-2-yl)-3-((3-fluoro-5-methoxyphenyl)amino) pyrrolidin-2-one (359); 1-(3-fluoro-5-(1H-pyrazol-4-yl)pyridin-2-yl)-3-((3-fluoro-5-methoxyphenyl) amino) pyrrolidin-2-one (360); 3-((3-(cyclopropylmethoxy)phenyl)amino)-1-(3-fluoro-4-(1H-pyrazol-4-yl)phenyl)pyrrolidin-2-one (361); 3-((3-(cyclopropylmethoxy)phenyl) amino)-1-(3-fluoro-4-(1H-pyrazol-4-yl)phenyl)pyrrolidin-2-one (362); 1-(3-cyclopropyl-4-(1H-pyrazol-4-yl)phenyl)-3-((3-methoxyphenyl)amino)pyrrolidin-2-one (363); 3-((2-fluoro-5-methoxyphenyl)amino)-1-(3-methyl-4-(1H-pyrazol-4-yl)phenyl)pyrrolidin-2-one, Enantiomer-II (364); 3-((3-fluoro-4-methoxyphenyl)amino)-1-(3-methyl-4-(1H-pyrazol-4-yl)phenyl)pyrrolidin-2-one (365); 3-((3,5-dimethoxyphenyl) amino)-1-(3-methyl-4-(1H-pyrazol-4-yl)phenyl)pyrrolidin-2-one (366); 1-(4-(1H-pyrazol-4-yl)-3-(trifluoromethyl)phenyl)-3-((3-methoxyphenyl)amino)pyrrolidin-2-one (367); 1-(4-(1H-pyrazol-4-yl)-3-(trifluoromethyl)phenyl)-3-((3-methoxyphenyl)amino)pyrrolidin-2-one (368); 1-(4-(1H-pyrazol-4-yl)-3-(trifluoromethyl)phenyl)-3-((3-fluoro-5-methoxyphenyl) amino)pyrrolidin-2-one (369); 1-(4-(1H-pyrazol-4-yl)-3-(trifluoromethyl)phenyl)-3-((3-fluoro-5-methoxyphenyl)amino)pyrrolidin-2-one (370); 1-(4-(1H-pyrazol-4-yl)-3-(trifluoromethyl)phenyl)-3-((4-fluoro-3-methoxyphenyl)amino)pyrrolidin-2-one (371); 1-(4-(1H-pyrazol-4-yl)-3-(trifluoromethyl)phenyl)-3-((4-fluoro-3-methoxyphenyl)amino) pyrrolidin-2-one (372); 1-(4-(1H-pyrazol-4-yl)-3-(trifluoromethyl)phenyl)-3-((2-fluoro-5-methoxyphenyl)amino)pyrrolidin-2-one (373); 5-(3-((3-fluoro-5-methoxyphenyl)amino)-2-oxopyrrolidin-1-yl)-2-(1H-pyrazol-4-yl)benzonitrile (374); 5-(3-((3-fluoro-5-methoxyphenyl)amino)-2-oxopyrrolidin-1-yl)-2-(1H-pyrazol-4-yl)benzonitrile (375); 5-(3-((3-fluoro-2-methoxyphenyl)amino)-2-oxopyrrolidin-1-yl)-2-(1H-pyrazol-4-yl)benzonitrile (376); 5-(3-((3-methoxyphenyl) amino)-2-oxopyrrolidin-1-yl)-2-(1H-pyrazol-4-yl) benzonitrile (377); 5-(3-((3-methoxyphenyl)amino)-2- oxopyrrolidin-1-yl)-2-(1H-pyrazol-4-yl)benzonitrile (378); 5-(3-((4-fluoro-3-methoxyphenyl)amino)-2-oxopyrrolidin-1-yl)-2-(1H-pyrazol-4-yl)benzonitrile (379); 5-(3-((4-fluoro-3-methoxyphenyl)amino)-2-oxopyrrolidin-1-yl)-2-(1H-pyrazol-4-yl)benzonitrile (380); (R)-1-(4-(1H-pyrazol-4-yl)phenyl)-3-((2,4-dimethoxyphenyl)amino)pyrrolidin-2-one (384); (R)-1-(4-(1H-pyrazol-4-yl)phenyl)-3-((2,3-dimethoxyphenyl)amino)pyrrolidin-2-one (385); (R)-1-(4-(1H-pyrazol-4-yl)phenyl)-3-(benzo[d][1,3]dioxol-4-ylamino)pyrrolidin-2-one (386); (R)-3-((1-(4-(1H-pyrazol-4-yl)phenyl)-2-oxopyrrolidin-3-yl)amino) benzonitrile (387); 3-((1-(4-(1H-pyrazol-4-yl)phenyl)-2-oxopyrrolidin-3-yl)amino) benzamide (388); (R)-1-(4-(1H-pyrazol-4-yl)phenyl)-3-((3,4-dimethoxyphenyl)amino) pyrrolidin-2-one (389); (R)-1-(4-(1H-pyrazol-4-yl)phenyl)-3-((3-(dimethylamino)phenyl) amino)pyrrolidin-2-one (390); N-(3-((1-(4-(1H-pyrazol-4-yl)phenyl)-2-oxopyrrolidin-3-yl)amino)phenyl)acetamide (391); (R)-1-(4-(1H-pyrazol-4-yl)phenyl)-3-((2,2-dioxido-1,3-dihydrobenzo[c]thiophen-5-yl)amino) pyrrolidin-2-one (392); (R)-1-(4-(1H-pyrazol-4-yl)phenyl)-3-(indolin-1-yl)pyrrolidin-2-one (393); (R)-1-(4-(1H-pyrazol-4-yl)phenyl)-3-(3,4-dihydroquinolin-1 (2H)-yl) pyrrolidin-2-one (394); (R)-1-(4-(1H-pyrazol-4-yl)phenyl)-3-((2,4-dimethoxyphenyl)amino)pyrrolidin-2-one (395); and (R)-1-(4-(1H-pyrazol-4-yl)phenyl)-3-(benzo[d][1,3]dioxol-5-ylamino)pyrrolidin-2-one (396).

In another embodiment, the compounds of the present invention have ROCK $IC_{50}$ values ≤10 μM.

In another embodiment, the compounds of the present invention have ROCK $IC_{50}$ values ≤1 μM.

In another embodiment, the compounds of the present invention have ROCK $IC_{50}$ values ≤0.1 μM.

In another embodiment, the compounds of the present invention have ROCK $IC_{50}$ values ≤0.05 μM.

In another embodiment, the compounds of the present invention have ROCK $IC_{50}$ values ≤0.01 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6\text{-}10}$ aryl" refers to phenyl and naphthyl. Unless otherwise specified, "aryl", "$C_6$ or $C_{10}$ aryl" or "$C_{6\text{-}10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent within the definition of the substitution of the heterocyclic ring). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocyclyl" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent within the definition of the substitution of the heterocyclic ring). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988); and
e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^{2}H$" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^{1}H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate Burgess reagent 1-methoxy-N-triethylammoniosulfonyl-methanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-benziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5 S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5 S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(tricyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperazine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(O)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
PyBOP benzotriazol-1-yl-oxytripyrrolidinophosphonium hexafluorophosphate
SEM-Cl 2-(trimethysilyl)ethoxymethyl chloride
2nd generation XPhos precatalyst Chloro(2-dicyclohexylphosphino-2',4',6'-triisopropyl-1,1' biphenyl)[2-(2'-amino-1,1'-biphenyl)]palladium(II), THF adduct
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
T3P® propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM $MgCl_2$, 0.015% Brij-35, 4 mM DTT, 5 μM ATP and 1.5 μM peptide substrate (FITC-AHA-AKRRRLSSLRA-OH (SEQ ID NO: 1)). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative Examples were tested in the ROCK assay described above and found having ROCK inhibitory activity. Table A below lists the ROCK $IC_{50}$ value ranges measured for the examples: A=0-10 nM; B=10.01-100 nM; C=100.01-2200 nM.

TABLE A

| Example No. | ROCK2 $IC_{50}$ (nM) |
| --- | --- |
| 1 | A |
| 2 | B |

TABLE A-continued

| Example No. | ROCK2 IC$_{50}$ (nM) |
|---|---|
| 3 | A |
| 4 | A |
| 5 | B |
| 6 | A |
| 7 | A |
| 8 | B |
| 9 | B |
| 10 | B |
| 11 | A |
| 12 | B |
| 13 | C |
| 14 | C |
| 15 | A |
| 16 | C |
| 17 | B |
| 18 | A |
| 19 | C |
| 20 | C |
| 21 | C |
| 22 | C |
| 23 | A |
| 24 | B |
| 25 | B |
| 26 | A |
| 27 | A |
| 28 | A |
| 29 | A |
| 30 | B |
| 31 | C |
| 32 | C |
| 33 | B |
| 34 | A |
| 35 | B |
| 36 | A |
| 37 | C |
| 38 | B |
| 39 | B |
| 40 | C |
| 41 | C |
| 42 | B |
| 43 | A |
| 44 | A |
| 45 | A |
| 46 | A |
| 47 | A |
| 48 | B |
| 49 | A |
| 50 | A |
| 51 | B |
| 52 | C |
| 53 | C |
| 54 | C |
| 55 | C |
| 56 | B |
| 57 | C |
| 58 | B |
| 59 | C |
| 60 | C |
| 61 | C |
| 62 | A |
| 63 | A |
| 64 | B |
| 65 | C |
| 66 | A |
| 67 | A |
| 68 | A |
| 69 | B |
| 70 | C |
| 71 | B |
| 72 | A |
| 73 | B |
| 74 | A |
| 75 | A |
| 76 | C |
| 77 | B |
| 78 | B |
| 79 | B |
| 80 | C |

TABLE A-continued

| Example No. | ROCK2 IC$_{50}$ (nM) |
|---|---|
| 81 | B |
| 82 | A |
| 83 | B |
| 84 | B |
| 85 | A |
| 86 | A |
| 87 | B |
| 88 | A |
| 89 | A |
| 90 | C |
| 91 | C |
| 92 | C |
| 93 | C |
| 94 | C |
| 95 | C |
| 96 | B |
| 97 | C |
| 98 | C |
| 99 | B |
| 100 | C |
| 101 | B |
| 102 | C |
| 103 | A |
| 104 | B |
| 105 | B |
| 106 | B |
| 107 | B |
| 108 | B |
| 109 | C |
| 110 | B |
| 111 | B |
| 112 | C |
| 113 | B |
| 114 | B |
| 115 | C |
| 116 | B |
| 117 | A |
| 118 | A |
| 119 | C |
| 120 | B |
| 121 | C |
| 122 | B |
| 123 | C |
| 124 | C |
| 125 | C |
| 127 | B |
| 128 | B |
| 129 | A |
| 130 | C |
| 132 | B |
| 133 | A |
| 134 | A |
| 135 | B |
| 136 | B |
| 137 | A |
| 138 | A |
| 139 | C |
| 140 | C |
| 141 | C |
| 142 | C |
| 143 | C |
| 144 | C |
| 145 | B |
| 146 | A |
| 147 | B |
| 148 | B |
| 149 | B |
| 150 | C |
| 151 | A |
| 152 | C |
| 153 | C |
| 154 | C |
| 155 | A |
| 156 | C |
| 157 | C |
| 158 | C |
| 159 | C |
| 160 | B |

TABLE A-continued

| Example No. | ROCK2 IC$_{50}$ (nM) |
|---|---|
| 161 | A |
| 162 | C |
| 163 | C |
| 164 | A |
| 165 | B |
| 166 | C |
| 167 | C |
| 168 | C |
| 169 | C |
| 170 | B |
| 171 | A |
| 172 | B |
| 173 | A |
| 175 | C |
| 176 | B |
| 177 | C |
| 178 | B |
| 179 | B |
| 180 | C |
| 181 | C |
| 182 | C |
| 183 | C |
| 184 | B |
| 185 | C |
| 186 | B |
| 187 | C |
| 188 | B |
| 189 | A |
| 190 | B |
| 191 | B |
| 192 | B |
| 193 | A |
| 194 | B |
| 195 | B |
| 196 | A |
| 197 | A |
| 198 | A |
| 199 | A |
| 200 | C |
| 201 | B |
| 202 | B |
| 203 | C |
| 204 | C |
| 205 | A |
| 206 | C |
| 207 | A |
| 208 | A |
| 209 | C |
| 210 | C |
| 211 | B |
| 212 | C |
| 213 | C |
| 214 | A |
| 215 | A |
| 216 | A |
| 217 | B |
| 218 | A |
| 219 | A |
| 220 | A |
| 221 | A |
| 223 | B |
| 224 | A |
| 225 | A |
| 226 | B |
| 227 | B |
| 228 | A |
| 229 | B |
| 230 | A |
| 231 | B |
| 232 | A |
| 233 | B |
| 235 | A |
| 237 | A |
| 238 | B |
| 239 | B |
| 240 | B |
| 241 | B |
| 242 | B |
| 243 | B |
| 244 | A |
| 245 | B |
| 246 | A |
| 247 | B |
| 248 | C |
| 249 | B |
| 250 | A |
| 251 | B |
| 252 | A |
| 253 | B |
| 254 | B |
| 255 | A |
| 256 | B |
| 257 | A |
| 258 | A |
| 259 | A |
| 260 | A |
| 261 | B |
| 262 | B |
| 263 | C |
| 264 | B |
| 265 | B |
| 266 | B |
| 267 | B |
| 268 | A |
| 269 | C |
| 270 | B |
| 271 | C |
| 272 | C |
| 273 | B |
| 274 | B |
| 275 | C |
| 276 | C |
| 277 | C |
| 278 | C |
| 279 | C |
| 280 | B |
| 281 | B |
| 282 | B |
| 283 | B |
| 284 | C |
| 285 | C |
| 286 | C |
| 287 | C |
| 288 | C |
| 289 | B |
| 290 | C |
| 291 | C |
| 292 | B |
| 293 | C |
| 294 | C |
| 295 | C |
| 296 | B |
| 297 | B |
| 298 | B |
| 299 | B |
| 300 | B |
| 301 | B |
| 302 | A |
| 303 | B |
| 304 | B |
| 305 | B |
| 306 | A |
| 307 | B |
| 308 | B |
| 309 | B |
| 310 | A |
| 311 | A |
| 312 | A |
| 313 | A |
| 314 | A |
| 315 | B |
| 316 | A |
| 317 | A |
| 318 | B |
| 319 | B |
| 320 | C |

TABLE A-continued

| Example No. | ROCK2 IC$_{50}$ (nM) |
|---|---|
| 321 | C |
| 322 | B |
| 323 | A |
| 324 | C |
| 325 | B |
| 326 | B |
| 327 | C |
| 328 | B |
| 329 | B |
| 330 | B |
| 331 | B |
| 332 | A |
| 333 | A |
| 334 | B |
| 335 | B |
| 336 | A |
| 337 | C |
| 338 | B |
| 339 | B |
| 340 | C |
| 341 | B |
| 342 | C |
| 343 | C |
| 344 | C |
| 345 | C |
| 346 | C |
| 347 | C |
| 348 | C |
| 349 | B |
| 350 | C |
| 351 | B |
| 352 | A |
| 353 | B |
| 354 | B |
| 355 | B |
| 356 | B |
| 357 | C |
| 358 | C |
| 359 | C |
| 360 | C |
| 361 | A |
| 362 | B |
| 363 | B |
| 364 | B |
| 365 | C |
| 366 | C |
| 367 | C |
| 368 | C |
| 369 | C |
| 370 | B |
| 371 | C |
| 372 | C |
| 373 | C |
| 374 | C |
| 375 | B |
| 376 | C |
| 377 | C |
| 378 | B |
| 379 | C |
| 380 | C |
| 383 | A |
| 384 | C |
| 385 | C |
| 386 | C |
| 387 | B |
| 388 | A |
| 389 | C |
| 390 | C |
| 391 | B |
| 392 | C |
| 393 | B |
| 394 | B |
| 395 | C |
| 396 | B |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. In one embodiment, the compounds or compositions of the invention can be used in the methods of treatment in combination with other ROCK inhibitors, including, but not limited to, Y27632, Wf536, Fasudil, H-1152P, and/or CID5056270. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example, as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, Fourth Edition, Wiley-Interscience (2006)).

Scheme 1

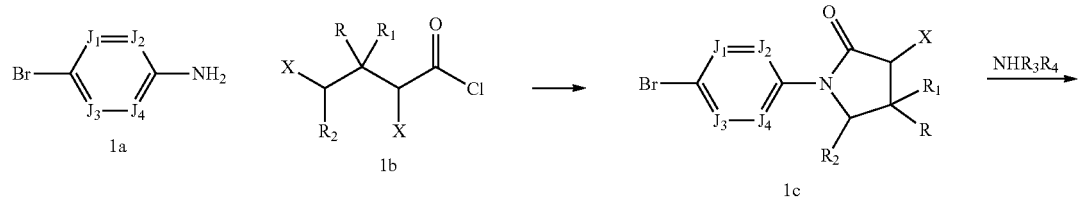

-continued

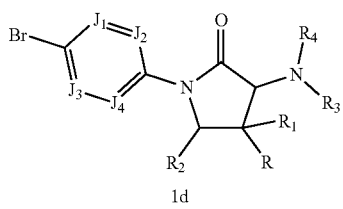
1d

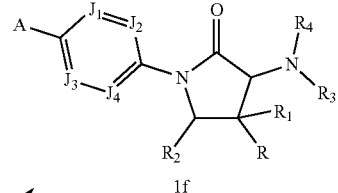
1f

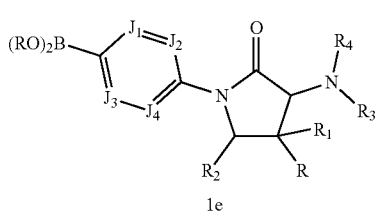
1e

Scheme 1 shows the synthesis of compound 1f from aniline 1a and dihalobutyryl chloride 1b (either commercially available or prepared via known methods). Treatment of these two reactants under basic conditions affords halolactam 1c. Alternatively, 1c is prepared via a two-step sequence in which 1a and 1b are coupled under basic conditions to form an amide, followed by cyclization under basic conditions using sodium hydride. Treatment of 1c with a substituted amine affords aminolactam 1d. Intermediate 1d is transformed to 1f via Pd-catalyzed coupling with an appropriate heteroaryl boronic acid or ester. Alternatively, aryl halide 1d is converted to boronic acid/ester 1e, which is coupled under Pd-catalyzed conditions with a heteroaryl halide to afford 1f.

Scheme 2

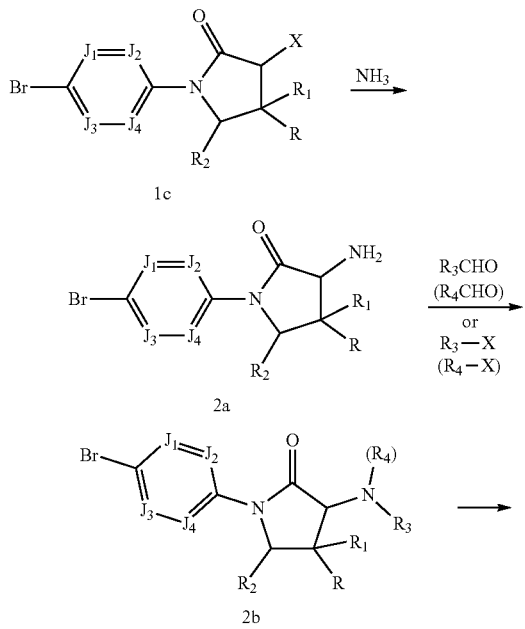

-continued

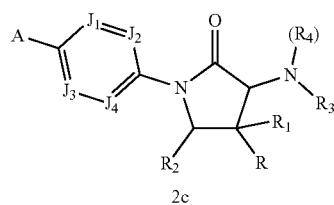
2c

Scheme 2 shows the preparation of 2c from halo-substituted lactam 1c. Reaction of 1c with ammonia affords amine 2a. 2a is converted to 2b by alkylation either via reductive amination with an appropriate aldehyde and a reducing agent such as sodium triacetoxyborohydride, or treatment with a base such as $Cs_2CO_3$ and an electrophile. Either of these alkylation steps can be repeated to afford a disubstituted amine. Pd-catalyzed coupling with an appropriate heteroaryl boronic acid or ester affords compound 2c.

Scheme 3

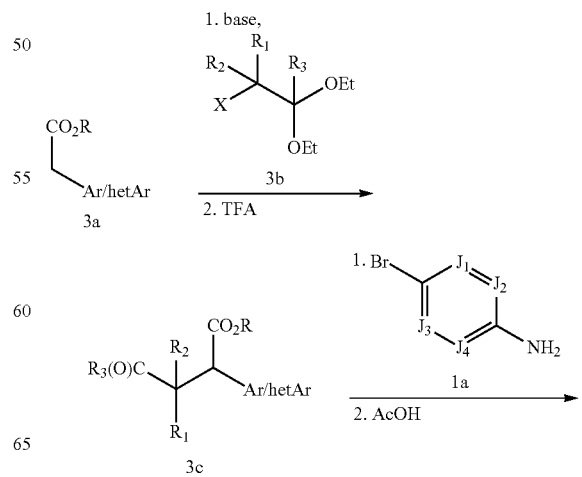

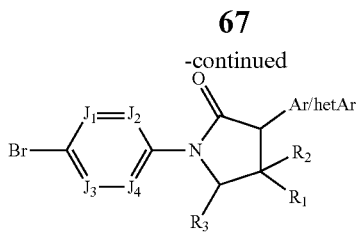

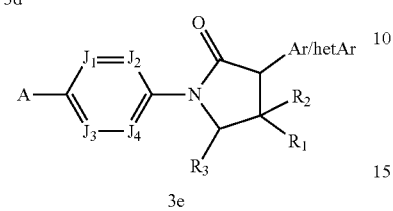

Scheme 3 shows the synthesis of lactam 3e from ester 3a. Reaction of 3a with haloacetal/haloketal 3b in the presence of a base such as KHMDS, followed by treatment with acid affords intermediate 3c. Reductive amination of aniline/amine heterocycle 1a with ketone/aldehyde 3c using a reducing agent such as sodium triacetoxyborohydride affords an amine that is cyclized under acidic conditions to afford lactam 3d. Pd-catalyzed coupling with an appropriate heteroaryl boronic acid or ester affords compound 3e.

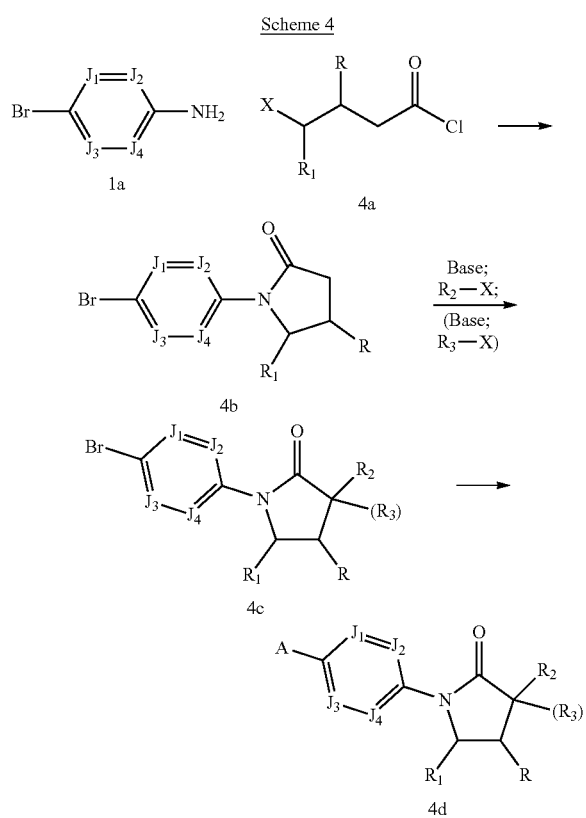

Scheme 4 shows the synthesis of compound 4d from aniline 1a and halobutyryl chloride 4a (either commercially available or prepared via known methods). Treatment of these two reactants under basic conditions affords halolactam 4b. Alternatively, 4b is prepared via a two-step sequence in which 1a and 4a are coupled under basic conditions to form an amide, followed by cyclization under basic conditions using sodium hydride. Lactam 4b is alkylated by treatment with a strong base such as LiHMDS, followed by addition of an electrophile. This sequence can be repeated to introduce a second electrophile. Pd-catalyzed coupling with an appropriate heteroaryl boronic acid or ester affords compound 4d.

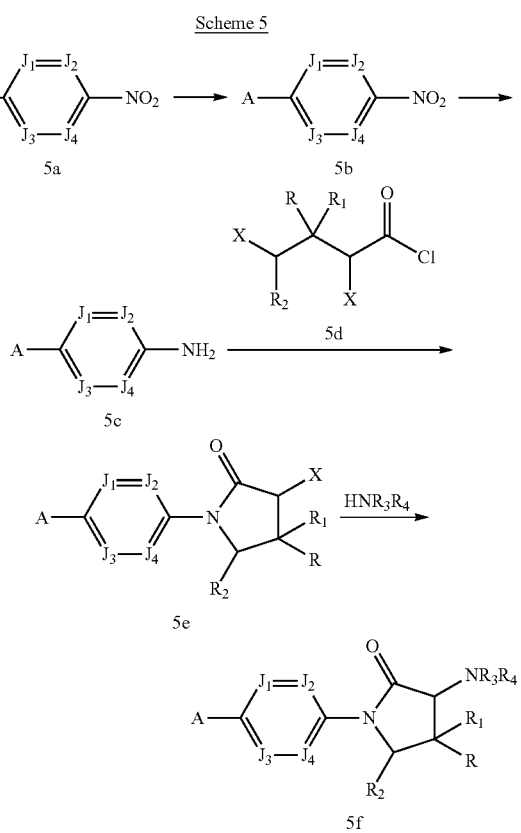

Scheme 5 shows the synthesis of compound 5f from the nitro starting material 5a. Pd-catalyzed coupling with an appropriate heteroaryl boronic acid or ester affords compound 5b. Reduction of the nitro functionality of 5b using a reagent such as Zn or H2/Pd—C affords aniline 5c. Treatment of aniline 5c with halobutyryl chloride 5d under basic conditions affords halolactam 5e. Alternatively, 5e is prepared via a two-step sequence in which 5c and 5d are coupled under basic conditions to form an amide, followed by cyclization under basic conditions using sodium hydride. Displacement of the halo functionality with an amine affords compound 5f.

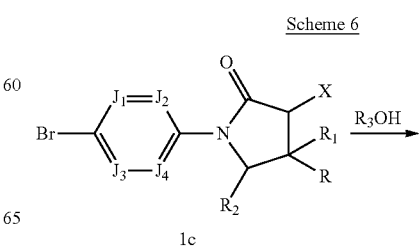

-continued

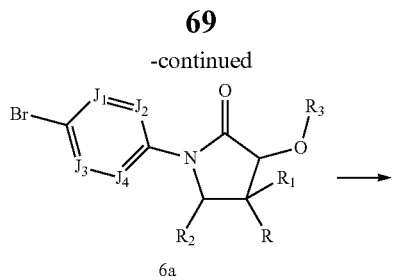
6a

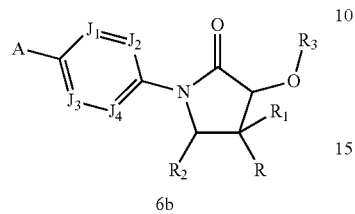
6b

Scheme 6 shows the synthesis of compound 6b from halolactam 1c. Treatment of 1c with an alcohol in the presence of a base such as NaH affords ether 6a. Pd-catalyzed coupling with an appropriate heteroaryl boronic acid or ester affords compound 6b.

Scheme 7

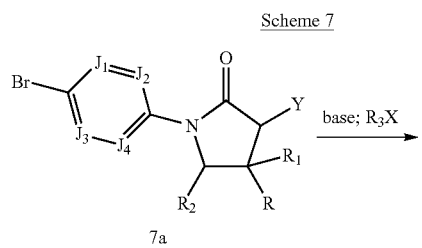
7a base; R₃X →

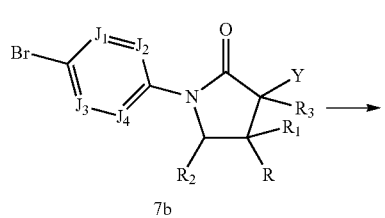
7b

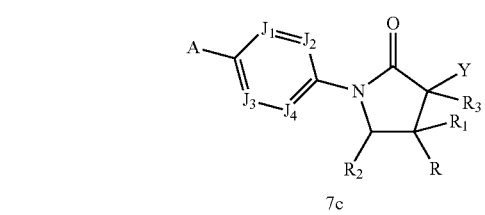
7c

Y = alkyl, aryl, heteroaryl, OR', NR'R''

Scheme 7 shows the synthesis of compound 7c from compound 7a, which itself is prepared according to the schemes above. Treatment of 7a with a base such as LiHMDS or LDA, followed by treatment with an electrophile affords intermediate 7b. Pd-catalyzed coupling with an appropriate heteroaryl boronic acid or ester affords compound 7c.

Scheme 8

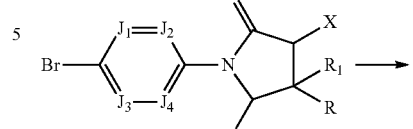
1c

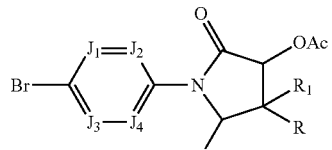
8a

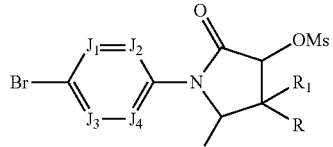
8b

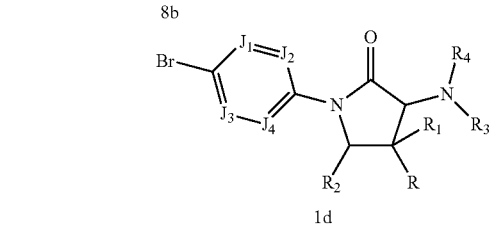
1d

Scheme 8 shows the synthesis of compound 1d from intermediate 1c. 1c is treated with an acetate salt such as potassium acetate to afford 8a. Next, the acetate is cleaved via either hydrolysis with hydroxide or displacement with an alkoxide, such as NaOMe or NaOEt, to afford the alcohol intermediate. This in turn can be converted to mesylate 8b by treatment with MsCl or Ms₂O and a base, such as TEA or pyridine. Treatment of mesylate 8b with an amine affords intermediate 1d. This compound is further elaborated to compounds such as 1f as outlined above.

Purification of intermediates and final products was carried out via either normal or reverse phase chromatography. Normal phase chromatography was carried out using pre-packed SiO₂ cartridges eluting with either gradients of hexanes and EtOAc or DCM and MeOH unless otherwise indicated. Reverse phase preparative HPLC was carried out using C18 columns eluting with gradients of Solvent A (90% H₂O, 10% MeOH, 0.1% TFA) and Solvent B (10% H₂O, 90% MeOH, 0.1% TFA, UV 220 nm) or with gradients of Solvent A (90% H₂O, 10% ACN, 0.1% TFA) and Solvent B (10% H₂O, 90% ACN, 0.1% TFA, UV 220 nm) or with gradients of Solvent A (98% H₂O, 2% ACN, 0.05% TFA) and Solvent B (98% ACN, 2% H₂O, 0.05% TFA, UV 220 nm) (or) SunFire Prep C18 OBD 5µ 30×100 mm, 25 min gradient from 0-100% B. A=H₂O/ACN/TFA 90:10:0.1. B=ACN/H₂O/TFA 90:10:0.1 (or) Waters XBridge C18, 19×200 mm, 5-µm particles; Guard Column: Waters XBridge C18, 19×10 mm, 5-µm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method A: SunFire C18 column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method B: XBridge Phenyl column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method C: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 4 minutes, then a 1-minute hold at 100% B; Flow: 1.1 mL/min.

Method D: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 4 minutes, then a 1-minute hold at 100% B; Flow: 1.1 mL/min.

Method E: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 3 minutes, then a 1-minute hold at 100% B; Flow: 1.1 mL/min.

Method F: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min.

Method G: SunFire C18 column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method H: XBridge Phenyl column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method I: SunFire C18 column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method J: XBridge Phenyl column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method K: SunFire C18 column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method L: XBridge Phenyl column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method M: SunFire C18 column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method N: XBridge Phenyl column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

SFC and Chiral Purity Methods

Method I: CHIRALPAK® AD-H (250×4.6 mm), 5.0-μm particles; % $CO_2$: 60%, % Co-solvent: 40% [0.2% DEA in IPA: $CH_3CN$ (1:1)], Total Flow: 4.0 g/min, Back Pressure: 100 bars, Temperature: 25° C., UV: 218 nm.

Method II: CHIRALPAK® OD-H (250×4.6 mm), 5.0-μm particles; % $CO_2$: 60%, % Co-solvent: 40% [0.2% DEA in IPA:$CH_3CN$ (1:1)], Total Flow: 4.0 g/min, Back Pressure: 104 bars, Temperature: 24.9° C., UV: 287 nm.

Method III: CHIRALPAK® OJ-H (250×4.6 mm), 5.0-μm particles; % $CO_2$: 60%, % Co-solvent: 30% (0.3% DEA in methanol), Total Flow: 4.0 g/min, Back Pressure: 101 bars, Temperature: 23.6° C., UV: 272 nm.

Method IV: CHIRALPAK® AS-H (250×4.6 mm), 5.0-μm particles; % $CO_2$: 60%, % Co-solvent: 40% (0.3% DEA in methanol), Total Flow: 4.0 g/min, Back Pressure: 102 bars, Temperature: 25.4° C., UV: 272 nm.

Method V: CHIRALCEL® OJ-H (250×4.6 mm), 5.0-μm particles; % $CO_2$: 60%, % Co-solvent: 40% (0.2% DEA in methanol), Total Flow: 4.0 g/min, Back Pressure: 102 bars, Temperature: 24.6° C., UV: 272 nm.

Method VI: Lux Cellulose-2 (250×4.6 mm), 5.0-μm particles; % $CO_2$: 60%, % Co-solvent: 35% (0.2% DEA in methanol), Total Flow: 3.0 g/min, Back Pressure: 101 bars, Temperature: 23.6° C., UV: 260 nm.

Method VII: CHIRALCEL® AS-H (250×4.6 mm), 5.0-μm particles; % $CO_2$: 60%, % Co-solvent: 40% (0.2% DEA in methanol), Total Flow: 4.0 g/min, Back Pressure: 101 bars, Temperature: 24.4° C., UV: 270 nm.

Method VIII: CHIRALPAK® I (250×4.6 mm), 5.0-μm particles; % $CO_2$: 60%, % Co-solvent: 40% (0.2% DEA in methanol), Total Flow: 4.0 g/min, Back Pressure: 101 bars, Temperature: 24.4° C., UV: 270 nm.

Method IX: CHIRALPAK® IF (250×4.6 mm), 5μ, Mobile Phase: 0.2% DEA in EtOH, Flow: 1.0 ml/min.

Method X: Lux Amylose 2 (250×4.6 mm), 5μ, Mobile Phase: 0.2% DEA in n-hexane:ethanol: 5:95, Flow: 1.0 ml/min.

Method XI: CHIRALCEL® OD-H (250×4.6 mm), 5μ, Mobile Phase: 0.2% DEA in n-hexane:ethanol: 70:30, Flow: 1.0 ml/min.

Method XII: CHIRALPAK® (250×4.6 mm), 5 t, Mobile Phase: 0.1% DEA in MeOH, Flow: 1.0 ml/min.

Intermediate 1

3-Bromo-1-(4-bromophenyl) pyrrolidin-2-one

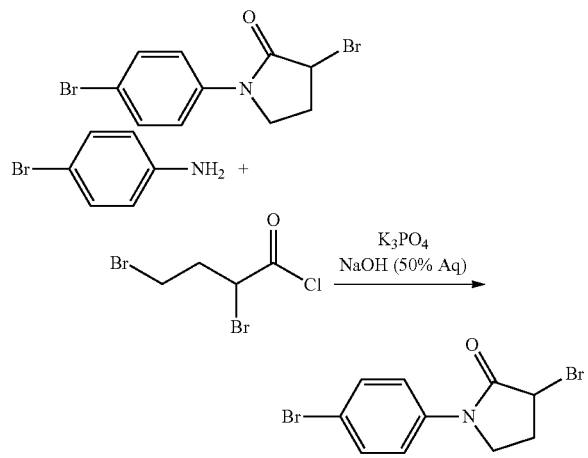

To a suspension of 4-bromoaniline (2.0 g, 11.6 mmol) and potassium phosphate, tribasic (1.013 g, 5.81 mmol) in acetonitrile (100 mL) was added 2,4-dibromobutyryl chloride (1.54 mL, 11.6 mmol) at 0° C. The mixture was brought to rt and stirred for 50 min. Aqueous NaOH solution (40%) (3 mL, 11.63 mmol) was added, and the mixture was stirred 4 h at rt. Reaction mixture was filtered through CELITE® and rinsed with acetonitrile, then the filtrate was concentrated to give a brown solid. The product was purified by flash chromatography (0-40% EtOAc/Hex gradient) to obtain Intermediate 1 (3.5 g, 74% yield) as a brown solid. MS(ESI) m/z: 319.9 (M+H)$^+$; $^1$H NMR (300 MHz, DMSO-d$_6$) δ ppm 7.56-7.71 (m, 4H) 4.90 (dd, J=7.20, 3.75 Hz, 1H) 3.81-3.99 (m, 2H) 2.76 (dq, J=14.43, 7.26 Hz, 1H) 2.33 (ddt, J=14.32, 7.02, 3.61, 3.61 Hz, 1H).

Intermediate 2 tert-Butyl 4-(4-(3-bromo-2-oxopyrrolidin-1-yl)phenyl)-1H-pyrazole-1-carboxylate

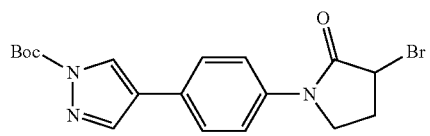 [SMILES: CC(C)(C)OC(=O)n1cc(-c2ccc(N3CCC(Br)C3=O)cc2)cn1]

Intermediate 2A

Preparation of tert-butyl 4-(4-nitrophenyl)-1H-pyrazole-1-carboxylate

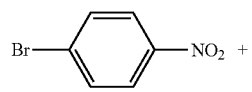

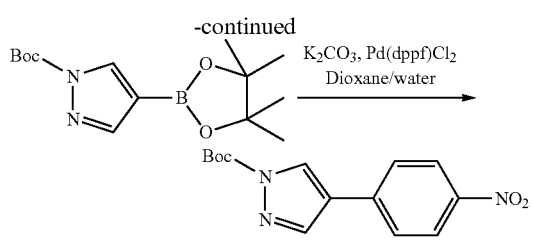

To a solution of 1-bromo-4-nitrobenzene (5.0 g, 24.8 mmol), K$_2$CO$_3$ (10.26 g, 74.3 mmol) in dioxane (20 mL) and water (2 mL), the reaction mixture was purged with nitrogen for 10 min and then was charged with tert-butyl 4-(4,4,5,5-tetramethyl-1,3,2-dioxaborolan-2-yl)-1H-pyrazole-1-carboxylate (8.01 g, 27.2 mmol) and PdCl$_2$(dppf) (1.08 g, 1.48 mmol), again purged with nitrogen for 5 min and heated at 80° C. for 3 h. The reaction mixture was cooled to rt and then diluted with ethyl acetate, washed with brine solution, dried over Na$_2$SO$_4$, filtered and concentrated. The residue was purified by flash chromatography (0-25% EtOAc/Hex gradient) to obtain Intermediate 2a (4.8 g, 67% yield) as a yellow solid. MS(ESI) m/z: 231.0 [M+H-(t-Bu)]; $^1$H NMR (300 MHz, DMSO-d$_6$) δ ppm 9.01 (s, 1H) 8.47 (s, 1H) 8.26 (d, J=8.92 Hz, 2H) 8.07 (d, J=8.97 Hz, 2H) 1.62 (s, 9H).

Intermediate 2B

Preparation of tert-butyl 4-(4-aminophenyl)-1H-pyrazole-1-carboxylate

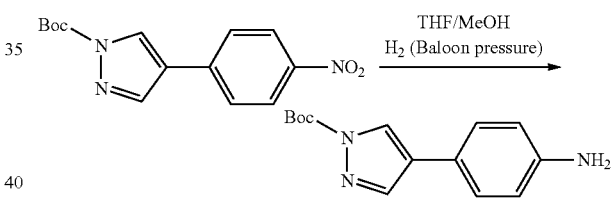

A solution of Intermediate 2A (2.7 g, 9.33 mmol) in ethanol (80 mL) and THF (20 mL) was purged with nitrogen for 5 min and then charged with 10% Pd/C (4.97 g, 4.67 mmol) and stirred at rt under hydrogen (Balloon) for 4 h. The reaction mixture was filtered through CELITE®, which was rinsed with methanol (2×20 mL). The filtrate was concentrated to give Intermediate 2b (2.15 g, 89% yield) as an off-white solid. MS(ESI) m/z: 261.1 (M+H)$^+$; $^1$H NMR (300 MHz, DMSO-d$_6$) δ ppm 8.41 (s, 1H) 8.11 (s, 1H) 7.38 (d, J=8.45 Hz, 2H) 6.58 (d, J=8.50 Hz, 2H) 5.19 (s, 2H) 1.59 (s, 9H).

Intermediate 2

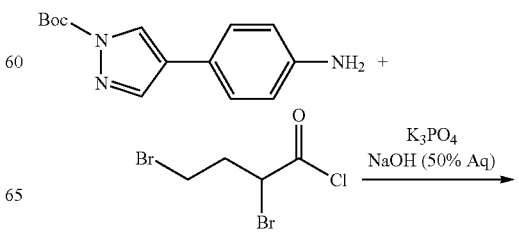

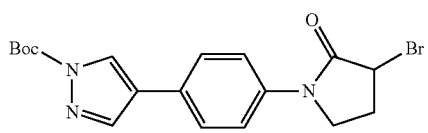

To a suspension of Intermediate 2B (1.6 g, 6.2 mmol) and potassium phosphate, tribasic (0.537 g, 3.1 mmol) in acetonitrile (100 mL) at 0° C., was added 2,4-dibromobutyryl chloride (0.816 mL, 6.2 mmol). The reaction mixture was brought to rt and stirred for 50 min. Aqueous NaOH (40%) (3 mL, 6.17 mmol) was added, and the mixture was stirred 30 min at rt. The reaction mixture was filtered through CELITE®, which was rinsed with acetonitrile. The filtrate was concentrated to give Intermediate 2 (2.1 g, 84% yield) as a yellow solid. MS(ESI) m/z: 406.1 (M+H)$^+$; $^1$H NMR (300 MHz, DMSO-$d_6$) δ ppm 8.73 (s, 1H) 8.31 (s, 1H) 7.77-7.84 (m, 2H) 7.69-7.76 (m, 2H) 4.91 (dd, J=7.22, 3.73 Hz, 1H) 3.87-4.03 (m, 2H) 2.71-2.88 (m, 1H) 2.28-2.45 (m, 1H) 1.61 (s, 9H).

Intermediate 3

3-Amino-1-(4-bromophenyl)pyrrolidin-2-one

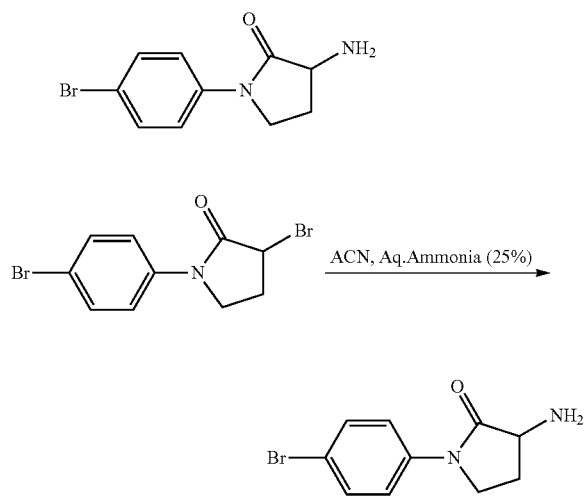

To a solution of Intermediate 1 (1.02 g, 3.20 mmol) in acetonitrile, was added aqueous ammonia (25%) (10 mL). The mixture was heated at 45° C. in a sealed tube for 14 h. The reaction mixture was cooled, purged with nitrogen for 15 min and portioned between water and DCM. The combined DCM layers were washed with water and brine, dried over Na$_2$SO$_4$, and concentrated. The solid was dissolved in DCM and precipitated by adding hexanes. The precipitate was collected by filtration and dried under vacuum to obtain Intermediate 3 (0.5 g, 57% yield) as an off-white solid. MS(ESI) m/z: 257.0 (M+H)$^+$; $^1$H NMR (300 MHz, DMSO-$d_6$) δ ppm 7.64-7.72 (m, 2H) 7.52-7.60 (m, 2H) 3.65-3.74 (m, 2H) 3.53 (dd, J=10.20, 8.31 Hz, 1H) 2.35 (dddd, J=12.13, 8.45, 6.04, 2.46 Hz, 1H) 1.95 (br. s., 2H) 1.64-1.82 (m, 1H).

Intermediate 4

3-Bromo-1-(4-bromo-3-methoxyphenyl)pyrrolidin-2-one

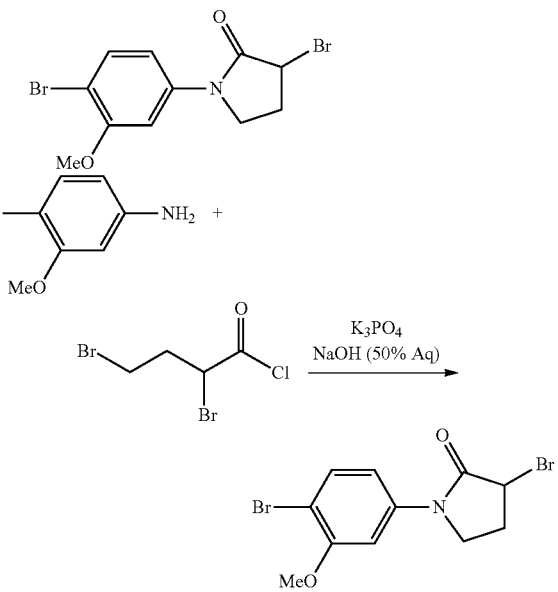

To a suspension of 4-bromo-3-methoxyaniline (2.5 g, 12.4 mmol) and potassium phosphate, tribasic (1.08 g, 6.19 mmol) in acetonitrile (40 mL) at 0° C., was added 2,4-dibromobutyryl chloride (1.64 mL, 12.4 mmol). The mixture was brought to rt and stirred for 1 h. Aqueous NaOH (50%) (5 mL, 12.37 mmol) was added, and the mixture was stirred at rt for 4 h. The reaction mixture was filtered through CELITE®, which was rinsed with acetonitrile. The filtrate was concentrated. The product was purified by flash chromatography (0-50% EtOAc/Hex gradient) to obtain Intermediate 4 (3.5 g, 66% yield) as a pinkish colored solid. MS(ESI) m/z: 350.0 (M+H)$^+$; $^1$H NMR (300 MHz, chloroform-d) δ ppm 7.77 (d, J=2.27 Hz, 1H) 7.53 (d, J=8.69 Hz, 1H) 6.82 (dd, J=8.69, 2.27 Hz, 1H) 4.61 (dd, J=7.18, 3.40 Hz, 1H) 4.05 (dt, J=9.73, 7.22 Hz, 1H) 3.94 (s, 3H) 3.85 (ddd, J=10.01, 7.55, 2.83 Hz, 1H) 2.69-2.83 (m, 1H) 2.48 (ddt, J=14.35, 6.70, 3.26, 3.26 Hz, 1H).

Intermediate 5

3-((3-Methoxyphenyl)amino)-1-(4-(4,4,5,5-tetramethyl-1,3,2-dioxaborolan-2-yl)phenyl)pyrrolidin-2-one

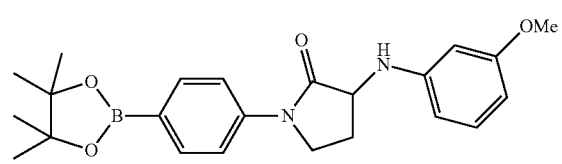 [SMILES: COc1cccc(NC2CCN(c3ccc(B4OC(C)(C)C(C)(C)O4)cc3)C2=O)c1]

Intermediate 5A

Preparation of 1-(4-bromophenyl)-3-((3-methoxyphenyl)amino)pyrrolidin-2-one

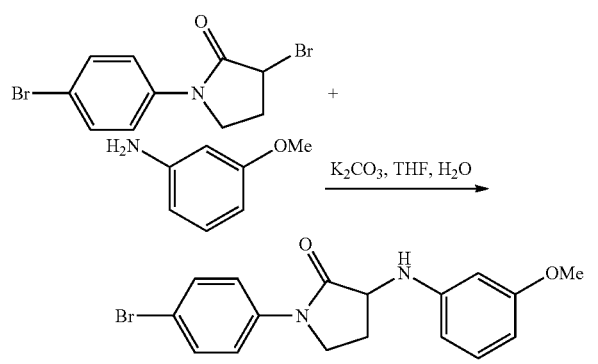

To a solution of Intermediate 1 (2.0 g, 6.3 mmol) in THF (10 mL), was added 3-methoxyaniline (1.16 g, 9.40 mmol), K$_2$CO$_3$ (1.73 g, 12.5 mmol) and water (1.0 mL). The mixture was stirred at 100° C. for 14 h. The reaction mixture was cooled to rt, then was diluted with ethyl acetate. The organic phase was washed with water and brine, dried over Na$_2$SO$_4$, and concentrated. The product was dissolved in DCM and precipitated by adding hexanes. The precipitate was collected by filtration, washed with hexane and dried to obtain Intermediate 5A (1.8 g, 70% yield) as a white solid. MS(ESI) m/z: 361.0 (M+H)$^+$; $^1$H NMR (300 MHz, DMSO-d$_6$) δ ppm 7.67-7.74 (m, 2H) 7.55-7.64 (m, 2H) 6.94-7.02 (m, 1H) 6.26-6.33 (m, 2H) 6.13-6.20 (m, 1H) 5.94 (d, J=7.55 Hz, 1H) 4.32-4.43 (m, 1H) 3.76-3.86 (m, 2H) 3.68 (s, 3H) 2.56-2.65 (m, 1H) 1.80-1.97 (m, 1H).

Intermediate 5

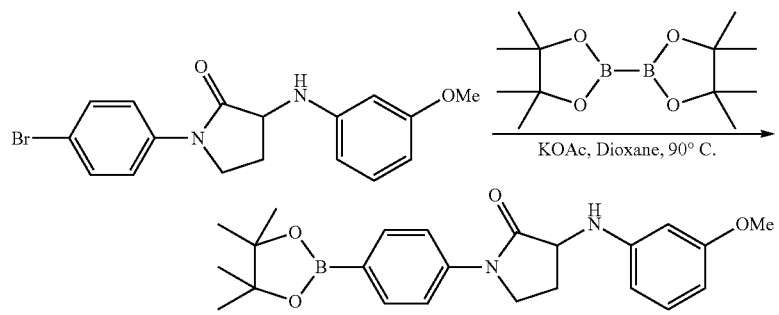

To a solution of Intermediate 5A (1.5 g, 4.15 mmol) in dioxane (20 mL) was added bis(pinacolato)diboron (1.26 g, 4.98 mmol) and potassium acetate (1.22 g, 12.5 mmol). The reaction mixture was purged with nitrogen for 10 min, and then was charged with PdCl$_2$(dppf)-CH$_2$Cl$_2$ adduct (0.203 g, 0.249 mmol) and heated at 100° C. for 14 h. The reaction was cooled to rt and concentrated. The residue was partitioned between ethyl acetate and water, and the aqueous phase was extracted with ethyl acetate. The combined organic phase was washed with brine, dried over Na$_2$SO$_4$, and concentrated. The residue was purified by flash chromatography (0-35% EtOAc/Hex gradient) to obtain Intermediate 5 (1.6 g, 78% yield) as a yellow solid. MS(ESI) m/z: 409.4 (M+H)$^+$; $^1$H NMR (300 MHz, DMSO-d$_6$) δ ppm 7.66-7.78 (m, 4H) 6.94-7.02 (m, 1H) 6.26-6.33 (m, 2H) 6.13-6.20 (m, 1H) 5.94 (d, J=7.18 Hz, 1H) 4.34-4.45 (m, 1H) 3.76-3.88 (m, 2H) 3.68 (s, 3H) 2.56-2.65 (m, 1H) 1.81-1.98 (m, 1H) 1.30 (s, 12H).

Intermediate 6

4-Bromo-3-(difluoromethoxy)aniline

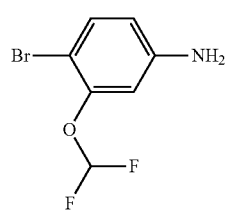 [SMILES: Nc1ccc(Br)c(OC(F)F)c1]

Intermediate 6A

Preparation of 2-bromo-5-nitrophenol

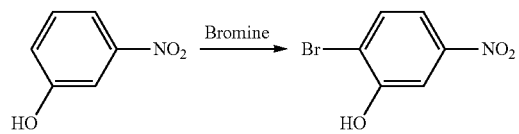 [SMILES: O=[N+]([O-])c1cccc(O)c1 ; O=[N+]([O-])c1ccc(Br)c(O)c1]

To a solution of 3-nitrophenol (1.00 g, 7.19 mmol) in acetic acid (10 mL) at rt, was added bromine (0.37 mL, 7.19 mmol), dropwise. The reaction mixture was heated at 120° C. for 1.5 h, then was cooled to rt and concentrated. The product was partitioned between water and EtOAc. The organic layer was dried with Na$_2$SO$_4$, filtered and concentrated. The crude product was purified by flash chromatography (0-8% EtOAc/pet. ether) to afford Intermediate 6A (0.86 g, 3.53 mmol, 49.1% yield) as a pale yellow solid. $^1$H NMR (300 MHz, CDCl$_3$) δ 7.89 (d, J=2.3 Hz, 1H), 7.76-7.64 (m, 2H), 5.91 (s, 1H).

Intermediate 6B

Preparation of 1-bromo-2-(difluoromethoxy)-4-nitrobenzene

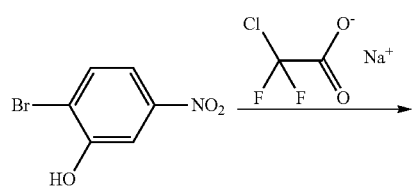

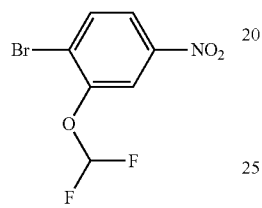

To a solution of Intermediate 6A (0.625 g, 2.87 mmol) and sodium 2-chloro-2,2-difluoroacetate (0.437 g, 2.87 mmol) in DMF (15 mL) and water (0.5 mL), was added sodium hydroxide (0.115 g, 2.87 mmol). The reaction mixture was heated at 120° C. for 1 h, then was cooled to rt and concentrated. The crude product was purified by flash chromatography (0-6% EtOAc/pet. ether) to afford Intermediate 6B (0.505 g, 1.88 mmol, 66% yield) as a pale yellow liquid. $^1$H NMR (300 MHz, CDCl$_3$) δ 8.12 (d, J=2.6 Hz, 1H), 8.06-7.96 (m, 1H), 7.85 (d, J=9.1 Hz, 1H), 6.95-6.39 (m, 1H).

Intermediate 6

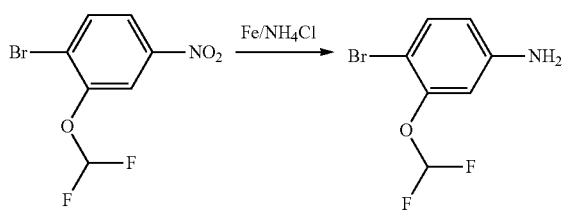 [SMILES: O=[N+]([O-])c1ccc(Br)c(OC(F)F)c1 ; Nc1ccc(Br)c(OC(F)F)c1]

A solution of Intermediate 6b (0.500 g, 1.87 mmol) in methanol (10 mL) was added to a mixture of iron (0.521 g, 9.33 mmol) and ammonium chloride (0.499 g, 9.33 mmol) in water (20 mL). The reaction mixture was heated at 80° C. for 3 h. The reaction mixture was cooled to rt and filtered through CELITE®. The filtrate was concentrated, then the crude product was diluted with water and extracted with EtOAc (2×). The combined organic phase was dried with Na$_2$SO$_4$, and concentrated to afford Intermediate 6 (0.419 g, 1.76 mmol, 94% yield) as a pale yellow liquid. LCMS: MS(ESI) m/z: 236.1 (M−H)$^+$; $^1$H NMR (300 MHz, CDCl$_3$) δ 7.36-7.25 (m, 1H), 6.77-6.21 (m, 3H), 3.81 (br. s., 2H).

Intermediate 7

Preparation of 3-bromo-1-(4-bromo-3-(difluoromethoxy)phenyl)pyrrolidin-2-one

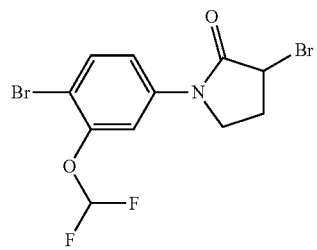 [SMILES: O=C1C(Br)CCN1c1ccc(Br)c(OC(F)F)c1]

Intermediate 7A

Preparation of 2,4-dibromo-N-(4-bromo-3-(difluoromethoxy)phenyl)butanamide

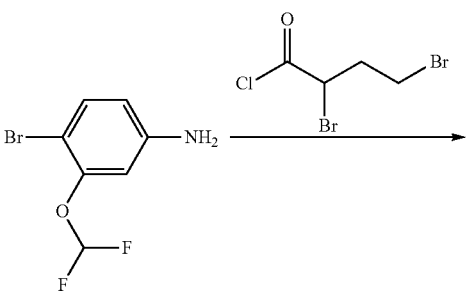

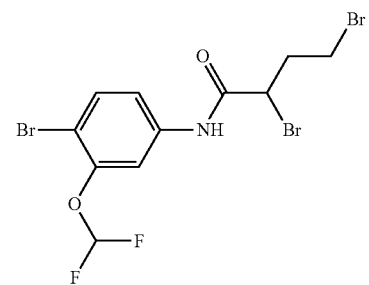

To a solution of Intermediate 6 (0.419 g, 1.76 mmol) in DCM (10 mL) at 0° C., was added 2,4-dibromobutanoyl chloride (0.233 mL, 1.76 mmol), dropwise over 5 min. The reaction mixture was allowed to warm to rt and stirred for 2 h. The reaction mixture was diluted with DCM and then washed with 1.5N HCl, 10% NaHCO$_3$ and brine. The organic phase was dried over Na$_2$SO$_4$, and concentrated to give Intermediate 7A (0.76 g, 1.63 mmol, 93% yield) as a pale yellow solid. LCMS: MS(ESI) m/z: 464.0 (M+H)$^+$; $^1$H NMR (300 MHz, DMSO-d$_6$) δ 10.83 (s, 1H), 7.78-7.65 (m, 2H), 7.53-6.97 (m, 2H), 4.72 (dd, J=7.9, 6.0 Hz, 1H), 4.48 (dd, J=8.7, 5.7 Hz, 1H), 3.76-3.47 (m, 2H), 2.40-2.34 (m, 1H).

Intermediate 7

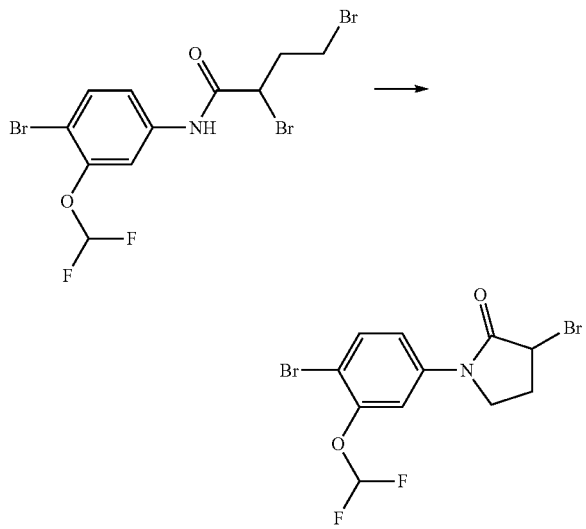

To a solution of Intermediate 7A (0.76 g, 1.63 mmol) in DCM (10 mL), was added dropwise a solution of sodium hydroxide (0.261 g, 6.52 mmol) in water (0.5 mL). The reaction mixture was stirred at rt for 5 h. The reaction mixture was poured into ice-cold water. The organic layer was separated. The aqueous layer was extracted with DCM (80 ml×2). The combined organic phase was dried with Na$_2$SO$_4$, filtered and concentrated to afford Intermediate 7 (0.354 g, 0.919 mmol, 56.4% yield) as a pale yellow semi-solid. LCMS: MS(ESI) m/z: 384.1 (M+H)$^+$; $^1$H NMR (300 MHz, DMSO-d$_6$) δ 7.86 (d, J=2.3 Hz, 1H), 7.81-7.73 (m, 1H), 7.56-7.01 (m, 2H), 4.92 (dd, J=7.2, 3.8 Hz, 1H), 4.02-3.84 (m, 2H), 2.77 (dq, J=14.4, 7.3 Hz, 1H), 2.35 (ddt, J=10.9, 7.1, 3.5 Hz, 1H).

Intermediate 8

Preparation of 4-bromo-3-ethoxy aniline

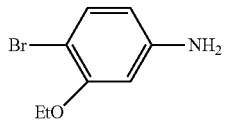

Intermediate 8A

Preparation of 1-bromo-2-ethoxy 4-nitrobenzene

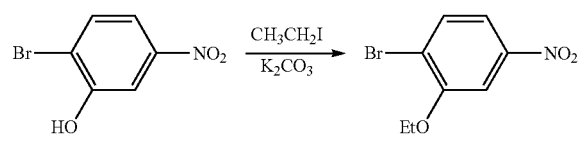

To a mixture of 2-bromo-5-nitrophenol (1.0 g, 4.59 mmol) and potassium carbonate (1.59 g, 11.5 mmol) in DMF (10 mL), was added iodomethane (1.79 g, 11.5 mmol). The reaction mixture was stirred at 70° C. for 4 h, then was cooled to rt. The mixture was diluted with water (100 mL) and extracted with EtOAc (2×75 mL). Combined organic extracts were washed with water and brine, dried over Na$_2$SO$_4$ and concentrated to give Intermediate 8A (1.10 g, 4.18 mmol, 91% yield). MS(ESI) m/z: 248.0 (M+H)$^+$; $^1$H NMR (300 MHz, DMSO-d$_6$) δ ppm 7.90 (d, J=8.6 Hz, 1H), 7.81 (d, J=2.5 Hz, 1H), 7.78-7.73 (m, 1H), 4.27 (q, J=7.0 Hz, 2H), 1.40 (t, J=7.0 Hz, 3H).

Intermediate 8

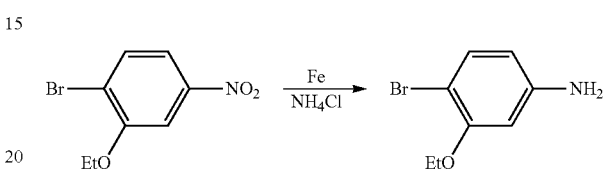

To a mixture of iron (0.851 g, 15.2 mmol) and ammonium chloride (0.815 g, 15.2 mmol) in water (30 mL), was added a solution of Intermediate 8A (0.61 g, 2.62 mmol, 86% yield) in methanol (15 mL). The reaction mixture was stirred at 80° C. for 3 h. The reaction mixture was cooled to rt, filtered through CELITE®, and the filtrate was concentrated. The residue obtained was dissolved in EtOAc (75 mL), washed with water and brine, dried over Na$_2$SO$_4$ and concentrated to give Intermediate 8 (0.61 g, 2.62 mmol, 86% yield). MS(ESI) m/z: 217.0 (M+H)$^+$; $^1$H NMR (300 MHz, DMSO-d$_6$) δ ppm 7.09 (d, J=8.5 Hz, 1H), 6.29 (d, J=2.4 Hz, 1H), 6.09 (dd, J=2.4, 8.5 Hz, 1H), 5.25 (s, 2H), 3.96 (q, J=7.0 Hz, 2H), 1.32 (t, J=7.0 Hz, 3H).

Intermediate 9

Preparation of 3-bromo-1-(5-bromopyridin-2-yl)pyrrolidin-2-one

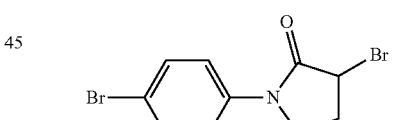

Intermediate 9A

Preparation of 2,4-dibromo-N-(5-bromopyridin-2-yl)butanamide

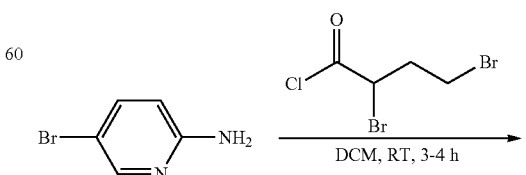

-continued

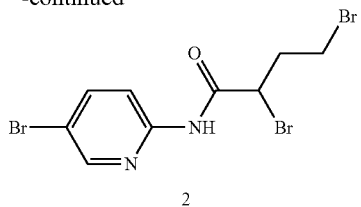

To a solution of 5-bromopyridin-2-amine (2 g, 11.56 mmol) in DCM (60 mL) at 0° C., was added 2,4-dibromobutanoyl chloride (0.764 mL, 5.78 mmol) dropwise over 20 min. The mixture was allowed to warm to rt and stir for 4 h. The reaction mixture was diluted with DCM, and then the organic phase was washed with 1.5N HCl solution, 10% NaHCO$_3$ and brine. The organic phase was dried with Na$_2$SO$_4$ and concentrated to afford Intermediate 9A (2.1 g, 5.24 mmol, 45% yield) as a pale yellow liquid. MS(ESI) m/z: 399.0 (M+H)$^+$; $^1$H NMR (300 MHz, DMSO-d$_6$) δ 11.20 (s, 1H), 8.49 (t, J=1.5 Hz, 1H), 8.06 (d, J=1.5 Hz, 2H), 4.97-4.89 (m, 1H), 4.48 (dd, J=8.7, 5.3 Hz, 1H), 3.70-3.58 (m, 2H), 2.40-2.34 (m, 1H).

Intermediate 9

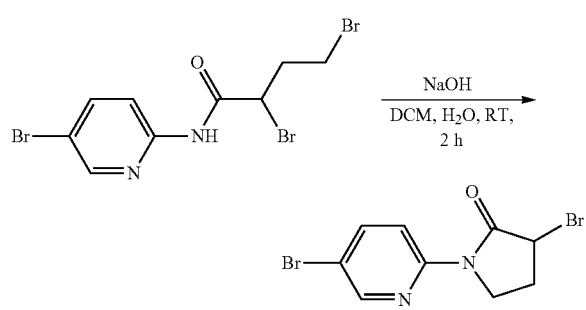

To a solution of Intermediate 9A (2.1 g, 5.24 mmol) in DCM (25 mL), was added a solution of sodium hydroxide (0.838 g, 20.95 mmol) in water (1.6 mL), dropwise. The reaction mixture was stirred at rt for 2 h, then was poured into ice-cold water. The organic layer was separated. The aqueous layer was extracted with DCM (2×100 ml). The combined organic phase was dried with Na$_2$SO$_4$ and concentrated. The crude product was purified by flash chromatography (0-12% EtOAc/pet. ether) to afford Intermediate 9 (1.17 g, 3.66 mmol, 70% yield) as a pale yellow solid. MS(ESI) m/z: 319.1 (M+H)$^+$; $^1$H NMR (300 MHz, DMSO-d$_6$) δ 8.59-8.54 (m, 1H), 8.29-8.22 (m, 1H), 8.11 (dd, J=8.9, 2.5 Hz, 1H), 4.97 (dd, J=7.2, 3.8 Hz, 1H), 4.11-3.93 (m, 2H), 2.82-2.68 (m, 1H), 2.38-2.26 (m, 1H).

Intermediate 10

Ethyl 4-((4-bromophenyl)amino)-2-(3-fluorophenyl)butanoate

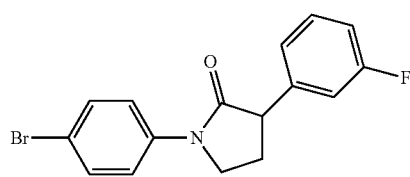 [SMILES: O=C1C(c2cccc(F)c2)CCN1c1ccc(Br)cc1]

Intermediate 10A

Preparation of ethyl 2-(3-fluorophenyl)-4-oxobutanoate

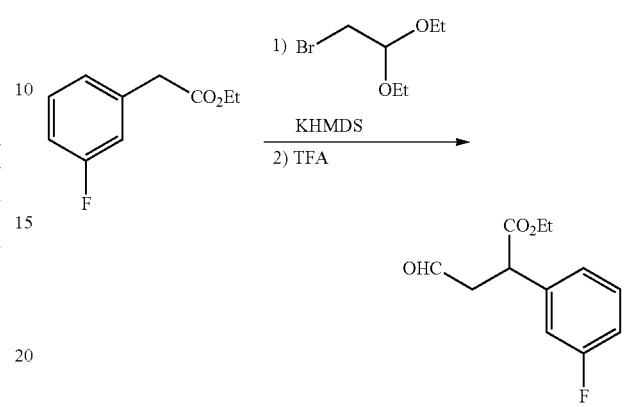

To a solution of ethyl 2-(3-fluorophenyl) acetate (2.0 g, 10.98 mmol) in THF (20 mL), was added potassium bis(trimethylsilyl) amide (1.0 M solution in THF; 12.1 mL, 12.1 mmol), dropwise. The reaction mixture was stirred at rt for 15 min, and then 2-bromo-1,1-diethoxyethane (2.38 g, 12.1 mmol) was added, dropwise. The mixture was heated at 45° C. for 1 h, then was cooled to 0° C. and was treated with saturated NH$_4$Cl solution (10 mL) and water (50 mL). The mixture was extracted with MTBE (3×50 mL). The combined organic phase was washed with water and brine, dried over Na$_2$SO$_4$ and concentrated. This product was taken up in water (7.5 mL) and was treated with a mixture of chloroform (25 mL) and TFA (25 mL) and was stirred at 0° C. to 10° C. for 2 h. The reaction mixture was poured into a mixture of 1M solution of K$_2$CO$_3$ (125 mL) and dichloromethane (200 mL). Solid K$_2$CO$_3$ was added until pH 7.5 was reached. The organic layer was separated, washed with water and brine, dried over Na$_2$SO$_4$ and concentrated. The crude product was purified by flash chromatography (10%-15% EtOAc/hexanes gradient) to give Intermediate 10A (0.95 g, 4.24 mmol, 39% yield). GCMS m/z=224; NMR (300 MHz, chloroform-d) δ ppm 9.78 (s, 1H), 7.35-7.26 (m, 1H), 7.12-6.94 (m, 3H), 4.23-4.04 (m, 3H), 3.40 (dd, J=9.8, 18.6 Hz, 1H), 2.83 (dd, J=4.7, 18.3 Hz, 1H), 1.23 (t, J=7.1 Hz, 3H).

Intermediate 10B

Preparation of ethyl 4-((4-bromophenyl)amino)-2-(3-fluorophenyl)butanoate

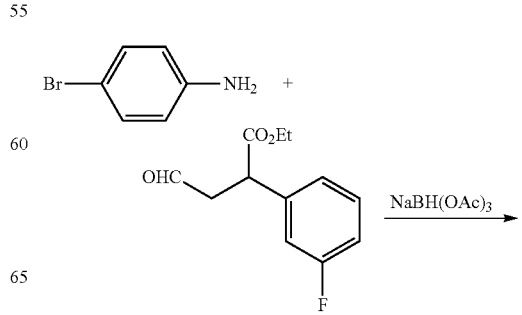

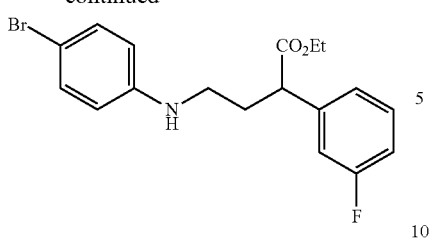

To a mixture of Intermediate 10A (0.20 g, 0.89 mmol) and 4-bromoaniline (0.153 g, 0.892 mmol) in 1,2-dichloroethane (10 mL), was added sodium triacetoxyborohydride (0.416 g, 1.962 mmol), followed by acetic acid (0.02 mL). The reaction mixture was stirred overnight at rt, then was basified with saturated aq. NaHCO$_3$ solution and extracted with dichloromethane (2×15 mL). Combined organic extracts were washed with water and brine, dried over Na$_2$SO$_4$ and concentrated. The crude product was purified by flash chromatography (10-15% EtOAc in hexane gradient) to give Intermediate 10B (0.185 g, 0.487 mmol, 55% yield). MS(ESI) m/z: 382.0 (M+H)$^+$; $^1$H NMR (300 MHz, chloroform-d) δ ppm 7.36-7.29 (m, 1H), 7.27-7.21 (m, 2H), 7.12-6.94 (m, 4H), 6.47-6.41 (m, 2H), 4.22-4.07 (m, 2H), 3.69 (t, J=7.5 Hz, 2H), 3.17-3.05 (m, 1H), 2.47-2.32 (m, 1H), 2.13-1.98 (m, 1H), 1.25-1.18 (m, 3H).

Intermediate 10: Preparation of ethyl 4-((4-bromophenyl)amino)-2-(3-fluorophenyl) butanoate

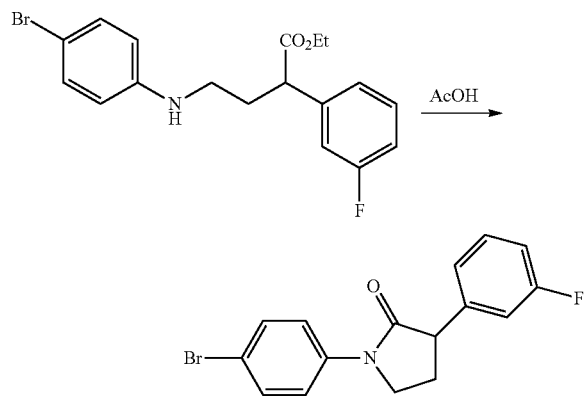

A solution of Intermediate 10B (100 mg, 0.263 mmol) in acetic acid (8 mL, 0.263 mmol) was stirred at 70° C. for 6 h. Reaction mixture was cooled to rt, then concentrated. The residue obtained was basified with saturated aqueous NaHCO$_3$ solution (5 mL) and extracted EtOAc (2×10 mL). Combined organic extracts were washed with water and brine, dried over Na$_2$SO$_4$ and concentrated. The crude was purified by flash chromatography (10-20% EtOAc in hexane gradient) to give Intermediate 10 (60 mg, 0.180 mmol, 68% yield). MS(ESI) m/z: 336.0 (M+H)$^+$; $^1$H NMR (400 MHz, chloroform-d) δ ppm 7.62-7.56 (m, 2H), 7.52-7.47 (m, 2H), 7.33 (dd, J=6.0, 7.9 Hz, 1H), 7.11 (dd, J=0.7, 7.7 Hz, 1H), 7.07-6.94 (m, 2H), 3.95-3.84 (m, 3H), 2.72-2.61 (m, 1H), 2.35-2.24 (m, 1H); $^{19}$F NMR (376 MHz, chloroform-d) δ ppm −112.37.

Intermediate 11

1-(4-Bromophenyl)-3-(3-fluorobenzyl)pyrrolidin-2-one

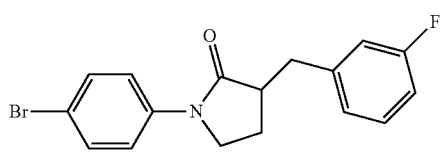 [SMILES: O=C1C(Cc2cccc(F)c2)CCN1c1ccc(Br)cc1]

Intermediate 11A

Preparation of N-(4-bromophenyl)-4-chlorobutanamide

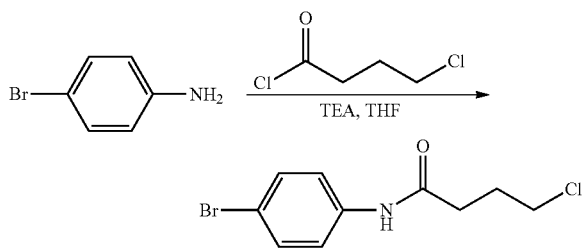

To a solution of 4-bromoaniline (2.5 g, 14.5 mmol) and triethylamine (3.04 mL, 21.8 mmol) in THF (50 mL) at 0° C., was added 4-chlorobutyryl chloride (1.96 mL, 17.4 mmol), dropwise. The reaction mixture was stirred at rt for 2 h, then was diluted with water (100 mL) and extracted with EtOAc (2×50 mL). Combined organic extracts were washed with water and brine, dried over Na$_2$SO$_4$ and concentrated to give Intermediate 11A (4.1 g, 13.9 mmol, 96% yield) as an off-white solid. MS(ESI) m/z: 278.0 (M+H)$^+$; $^1$H NMR (400 MHz, chloroform-d) δ ppm 7.48-7.38 (m, 4H), 7.15 (br. s., 1H), 3.71-3.59 (m, 2H), 2.61-2.52 (m, 2H), 2.27-2.08 (m, 2H).

Intermediate 11B

Preparation of 1-(4-bromophenyl)pyrrolidin-2-one

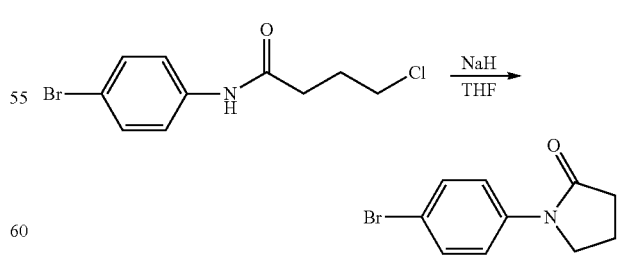

To a solution of Intermediate 11A (4.0 g, 14.5 mmol) in THF (75 mL) at 0° C., was added sodium hydride (60% suspension in mineral oil) (0.868 g, 21.70 mmol) and the reaction mixture was stirred at rt for 2 h. Reaction mixture was quenched with saturated aqueous NH$_4$Cl solution (100 mL), diluted with water (50 mL) and extracted with EtOAc (2×75 mL). Combined organic extracts were washed with water and brine, dried over Na₂SO₄ and concentrated. The crude product was triturated with hexane, and the precipitate was collected by filtration and dried to give Intermediate 11B (3.1 g, 12.9 mmol, 89% yield) as an off-white solid. MS(ESI) m/z: 241.9 (M+H)⁺; ¹H NMR (300 MHz, chloroform-d) δ ppm 7.59-7.45 (m, 4H), 3.86 (t, J=7.0 Hz, 2H), 2.67-2.59 (t, J=10.8 Hz, 2H), 2.25-2.13 (m, 2H).

Intermediate 11

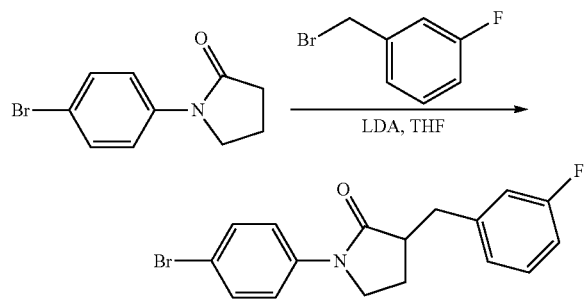

To a solution of Intermediate 11B (0.30 g, 1.25 mmol) in THF (12 mL) at −78° C., was added lithium diisopropylamide (2.0 M solution in THF; 1.37 mL, 2.75 mmol), dropwise. The reaction mixture was allowed to warm to −30° C. over a period of 30 min, then was cooled to −78° C. To this mixture was added a solution 1-(bromomethyl)-3-fluorobenzene (0.709 g, 3.75 mmol) in THF (3 mL), dropwise. The reaction mixture was allowed to warm to 15° C. over a period of 2 h, then was quenched with saturated aqueous NH₄Cl solution (20 mL). The mixture was diluted with water (20 mL) and extracted with EtOAc (2×30 mL). Combined organic extracts were washed with water and brine, dried over Na₂SO₄ and concentrated. The crude product was purified by flash chromatography (10-15% EtOAc in hexane gradient) to give Intermediate 11 (0.365 g, 1.05 mmol, 84% yield) as an off-white solid. MS(ESI) m/z: 349.9 (M+H)⁺; ¹H NMR (300 MHz, chloroform-d) δ ppm 7.57-7.44 (m, 4H), 7.28-7.24 (m, 1H), 7.05-6.88 (m, 3H), 3.77-3.55 (m, 2H), 3.29 (dd, J=3.9, 13.5 Hz, 1H), 2.99-2.72 (m, 2H), 2.28-2.11 (m, 1H), 1.95-1.74 (m, 1H).

Intermediate 12

Preparation of 1-(4-bromophenyl)-3-(3-methoxyphenethyl)pyrrolidin-2-one

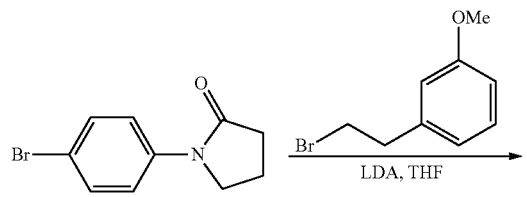

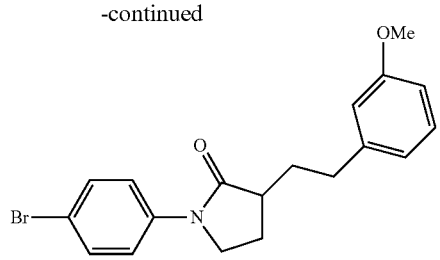

To a solution of Intermediate 11B (0.20 g, 0.833 mmol) in THF (10 mL) at −78° C. was added lithium diisopropylamide (2.0 M solution in THF) (0.625 mL, 1.25 mmol), dropwise. The reaction mixture was allowed to warm up to −45° C. over a period of 45 min, then was cooled to −78° C. To this mixture was added a solution of 1-(2-bromoethyl)-3-methoxybenzene (0.538 g, 2.499 mmol) in THF (3 mL), dropwise. The reaction mixture was stirred at −78° C. for 1 h and then allowed to warm up to rt and stir for 3 h. Reaction mixture was quenched with saturated aqueous NH₄Cl solution (10 mL), then was diluted with water (20 mL) and extracted with EtOAc (2×25 mL). The combined organic extracts were washed with water and brine, dried over Na₂SO₄ and concentrated. The crude product was purified by flash chromatography (10-15% EtOAc in hexane gradient) to give Intermediate 12 (0.11 g, 0.249 mmol, 30% yield) as a colorless oil. MS(ESI) m/z: 374.0 (M+H)⁺; ¹H NMR (400 MHz, chloroform-d) δ ppm 7.56-7.52 (m, 2H), 7.49-7.44 (m, 2H), 7.21 (t, J=7.8 Hz, 1H), 6.85-6.81 (m, 1H), 6.80-6.70 (m, 2H), 3.80 (s, 3H), 3.79-3.71 (m, 2H), 2.85-2.68 (m, 2H), 2.59 (dd, J=4.8, 8.8 Hz, 1H), 2.40-2.25 (m, 2H), 1.90-1.71 (m, 2H).

Intermediate 13

4-Bromo-3-cyclopropylaniline

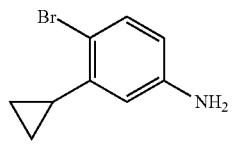 [SMILES: Nc1ccc(Br)c(C2CC2)c1]

Intermediate 13a

Preparation of 3-cyclopropylaniline

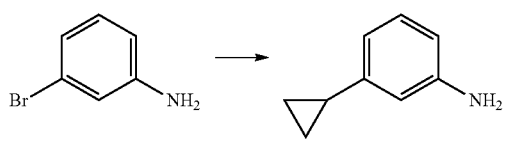 [SMILES: Nc1cccc(Br)c1 ; Nc1cccc(C2CC2)c1]

To a degassed solution of 3-bromoaniline (4.0 g, 23.3 mmol) in toluene (20 mL), were added cyclopropylboronic acid (3.99 g, 46.5 mmol), tricyclohexyl-phosphine (1.30 g, 4.65 mmol), potassium phosphate, dibasic (8.10 g, 46.5 mmol) and Pd (II) acetate (0.522 g, 2.33 mmol), at rt. The reaction was stirred under argon at 90° C. for 6 h. The reaction mixture was allowed to cool to rt, diluted with the DCM, washed with water, dried over sodium sulphate and concentrated to get the crude compound. The crude compound was purified by silica gel column chromatography using CombiFlash (silica gel 60-120, pet. ether/ethyl acetate as mobile phase 0-80%) to afford 3-cyclopropylaniline (2.0 g, 45%). MS(ESI) m/z: 135.1; $^1$H NMR (400 MHz, DMSO-$d_6$) δ 6.87 (t, J=7.72 Hz, 1H) 6.32 (ddd, J=7.91, 2.23, 0.97 Hz, 1H) 6.25-6.28 (m, 1H) 6.21-6.25 (m, 1H) 4.88 (s, 2H) 1.68-1.77 (m, 1H) 0.81-0.88 (m, 2H) 0.52-0.58 (m, 2H).

Intermediate 13b

Preparation of tert-butyl (3-cyclopropylphenyl)carbamate

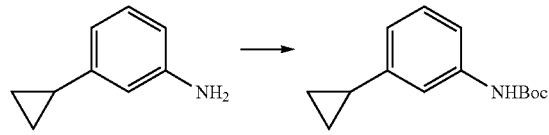 [SMILES: Nc1cccc(C2CC2)c1 ; CC(C)(C)OC(=O)Nc1cccc(C2CC2)c1]

To a solution of 3-cyclopropylaniline (2.0 g, 15.0 mmol) in DCM (20 mL), was added TEA (5.23 mL, 37.5 mmol) and BOC$_2$O (4.18 mL, 18.0 mmol). The reaction mixture was stirred for 4.5 h. The reaction mixture was diluted with DCM, washed with the water, dried over sodium sulphate and concentrated. The crude compound was purified by silica gel column chromatography using CombiFlash (silica gel 60-120, pet. ether/ethyl acetate as mobile phase 0-80%). Collected fractions were concentrated in vacuo to afford tert-butyl (3-cyclopropylphenyl)carbamate (1.8 g). $^1$H NMR (400 MHz, DMSO-$d_6$) δ 7.17-7.23 (m, 2H) 7.07-7.13 (m, 1H) 6.64-6.70 (m, 1H) 1.78-1.89 (m, 1H) 1.40-1.50 (s, 9H) 0.89-0.95 (m, 2H) 0.57-0.62 (m, 2H).

Intermediate 13c

Preparation of tert-butyl (4-bromo-3-cyclopropylphenyl)carbamate

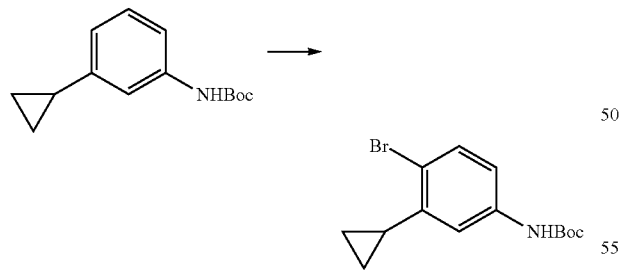

To a solution of tert-butyl (3-cyclopropylphenyl)carbamate (1.8 g, 7.72 mmol) in DMF (20 mL) was added 1-bromopyrrolidine-2,5-dione (1.37 g, 7.72 mmol) and the reaction mixture was stirred for 3 h. The reaction mixture was diluted with DCM, washed with the water, dried over sodium sulphate and concentrated. The crude compound was purified by purified by silica gel column chromatography using CombiFlash (silica gel 60-120, pet. ether/ethyl acetate as mobile phase 0-80%). Collected fractions were concentrated in vacuo to afford tert-butyl (4-bromo-3-cyclo-propylphenyl)carbamate (1.8 g). MS(ESI) m/z: 312.0; $^1$H NMR (400 MHz, DMSO-$d_6$) δ 9.34 (s, 1H) 7.42 (d, J=8.59 Hz, 1H) 7.23 (m, 1H) 7.12 (m, 1H) 1.46 (s, 9H) 0.99 (d, J=8.26 Hz, 2H) 0.57 (d, J=5.05 Hz, 2H).

Intermediate 13: Preparation of 4-bromo-3-cyclopropylaniline

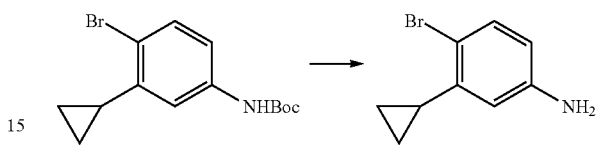

To a solution of tert-butyl (4-bromo-3-cyclopropylphenyl)carbamate (1.8 g, 7.72 mmol) in dioxane (20 mL), was added 3 M HCl solution (5 mL). The reaction mixture was stirred overnight. The reaction mixture was concentrated in vacuo, then partitioned between DCM and water. The organic layers were separated, washed with the water, dried over sodium sulphate and concentrated. The crude compound was purified by silica gel column chromatography using CombiFlash (silica gel 60-120, pet. ether/ethyl acetate as mobile phase 0-100%). Collected fractions were concentrated in vacuo to 4-bromo-3-cyclopropylaniline (1.0 g). MS(ESI) m/z: 212.2; $^1$H NMR (400 MHz, DMSO-$d_6$) δ 7.13 (d, J=8.47 Hz, 1H) 6.31 (dd, J=8.50, 2.73 Hz, 1H) 6.20 (d, J=2.70 Hz, 1H) 5.12 (br. s., 2H) 1.90-2.01 (m, 1H) 0.89-0.95 (m, 2H) 0.52-0.57 (m, 2H).

Intermediate 14

4-Bromo-3-(2-(dimethylamino)ethoxy)aniline

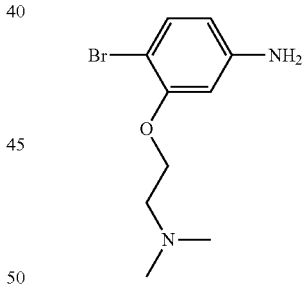

Intermediate 14a

Preparation of 2-(2-bromo-5-nitrophenoxy)-N,N-dimethylethanamine

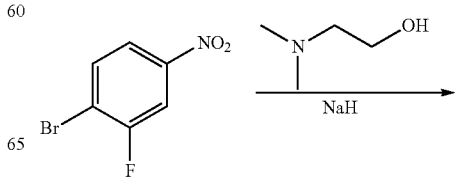

-continued

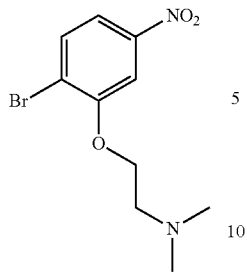

To a solution of 2-(dimethylamino)ethanol (2.5 g, 28.0 mmol) in DMF (2 mL), was added NaH (0.729 g, 30.4 mmol) and 1-bromo-2-fluoro-4-nitrobenzene (5.14 g, 23.4 mmol). The reaction mixture was stirred for 1 h. The reaction mixture was quenched with water and concentrated. The residue was partitioned between DCM and satd. aq. sodium bicarbonate solution. The organic layer was separated and the aqueous layer extracted with DCM (2×). The combine organic layers were washed with brine, dried over sodium sulphate and concentrated. The crude compound was purified by silica gel column chromatography using CombiFlash (0-100% ethyl acetate in pet. ether) to afford 2-(2-bromo-5-nitrophenoxy)-N,N-dimethylethanamine (2.8 g, 41%). $^1$H NMR (300 MHz, DMSO-d$_6$) δ ppm 1 7.86-7.90 (m, 1H) 7.77 (d, J=2.55 Hz, 1H) 7.74 (d, J=2.55 Hz, 1H) 4.30 (t, J=5.55 Hz, 2H) 2.71 (t, J=5.55 Hz, 2H) 2.26 (s, 6H).

Intermediate 14: Preparation of 4-bromo-3-(2-(dimethylamino)ethoxy)aniline

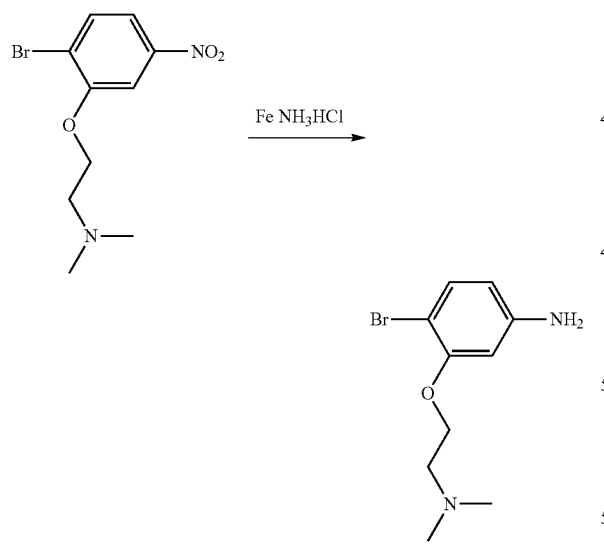

To a solution of 2-(2-bromo-5-nitrophenoxy)-N,N-dimethylethanamine (2.0 g, 6.92 mmol) in ethanol (35 mL), was added iron (3.86 g, 69.2 mmol). The reaction mixture was heated at 80° C. for 10 h. The reaction was cooled to rt and filtered through a pad of CELITE®. The filtrate was concentrated. The crude compound was purified by silica gel column chromatography using CombiFlash (2-20% methanol in chloroform) to afford 4-bromo-3-(2-(dimethylamino) ethoxy)aniline (1.2 g, 66%). $^1$H NMR (300 MHz, DMSO-d$_6$) δ ppm 7.14 (d, J=8.50 Hz, 1H), 6.33 (d, J=2.36 Hz, 1H), 6.16 (dd, J=8.52, 2.38 Hz, 1H) 5.34-5.40 (bs, 2H) 4.28-4.35 (m, 2H) 3.51 (t, J=4.77 Hz, 8H) 2.88 (s, 6H).

Intermediate 15

1-(5-Amino-2-chlorophenyl)-2,2,2-trifluoroethanol

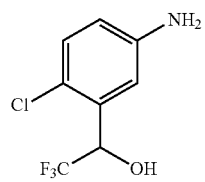

Intermediate 15a

Preparation of (1-(2-chloro-5-nitrophenyl)-2,2,2-trifluoroethoxy)trimethylsilane

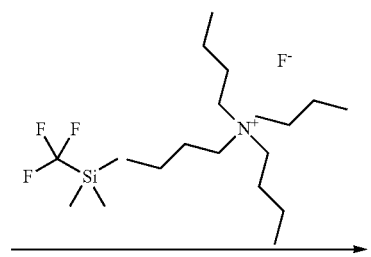

To a solution of 2-chloro-5-nitrobenzaldehyde (6 g, 32.3 mmol) and trimethyl(trifluoromethyl)silane (11.49 g, 81 mmol) in 10 ml THF at 0° C., was added tetrabutylammonium fluoride (1.691 g, 6.47 mmol). The reaction mixture was warmed up to rt and stirred for 4 hours. The reaction mixture was concentrated. The residue was dissolved in DCM and washed with water, followed by brine. The DCM layer was dried over Na$_2$SO$_4$, filtered and concentrated to get the crude (1-(2-chloro-5-nitrophenyl)-2,2,2-trifluoroethoxy)trimethylsilane, which was taken to the next step without further purification. $^1$H NMR (300 MHz, chloroform-d) δ ppm 8.59 (d, J=2.64 Hz, 1H) 8.21 (dd, J=8.81, 2.76 Hz, 1H) 7.60 (d, J=8.78 Hz, 1H) 7.28 (m, 1H) 5.56 (q, J=5.84 Hz, 1H) 0.22 (s, 9H).

Intermediate 15b

Preparation of
1-(2-chloro-5-nitrophenyl)-2,2,2-trifluoroethanol

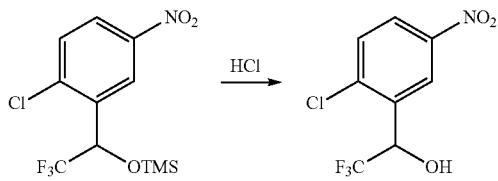

(1-(2-Chloro-5-nitrophenyl)-2,2,2-trifluoroethoxy)trimethylsilane (9 g, 27.5 mmol) was treated with 80 ml of 1N HCl in THF (75 mL) and stirred for 4 h. The reaction mixture was diluted with DCM, washed with water, dried over sodium sulphate and concentrated. The crude compound was purified by silica gel column chromatography using CombiFlash (20-60% ethyl acetate in pet. ether) to afford 1-(2-chloro-5-nitrophenyl)-2,2,2-trifluoroethanol (6.5 g, 85%). $^1$H NMR (400 MHz, chloroform-d) δ ppm 8.61 (d, J=2.64 Hz, 1H) 8.21 (dd, J=8.82, 2.73 Hz, 1H) 7.61 (d, J=8.85 Hz, 1H) 7.26 (s, 1H) 5.67 (q, J=5.98 Hz, 1H).

Intermediate 15: Preparation of
1-(5-amino-2-chlorophenyl)-2,2,2-trifluoroethanol

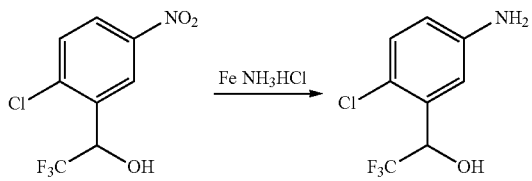 [SMILES: O=[N+]([O-])c1ccc(Cl)c(C(O)C(F)(F)F)c1 ; "Fe NH3HCl" ; Nc1ccc(Cl)c(C(O)C(F)(F)F)c1]

To a solution of 1-(2-chloro-5-nitrophenyl)-2,2,2-trifluoroethanol (3 g, 11.74 mmol) in ethanol (5 mL) and water (1 mL), were added iron (5.24 g, 94 mmol) and ammonium chloride (3.77 g, 70.4 mmol). The reaction mixture was heated at 80° C. for 2 h. The reaction mixture was cooled to RT, filtered through a pad of CELITE®. The filtrate was concentrated. The crude compound was purified by silica gel column chromatography (20-60% ethyl acetate in pet. ether) to afford 1-(5-amino-2-chlorophenyl)-2,2,2-trifluoroethanol (2.5 g, 94%). $^1$H NMR (300 MHz, DMSO-$d_6$) δ ppm 7.07 (d, J=8.59 Hz, 1H) 6.86-6.92 (m, 2H) 6.57 (dd, J=8.62, 2.81 Hz, 1H) 5.40 (s, 2H) 5.30 (dd, J=6.73, 5.64 Hz, 1H).

Intermediate 16

3-Bromo-1-(4-bromo-3-(difluoromethyl)phenyl) pyrrolidin-2-one

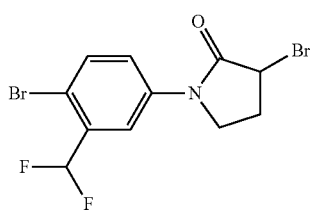 [SMILES: O=C1C(Br)CCN1c1ccc(Br)c(C(F)F)c1]

Intermediate 16a

Preparation of
1-bromo-2-(difluoromethyl)-4-nitrobenzene

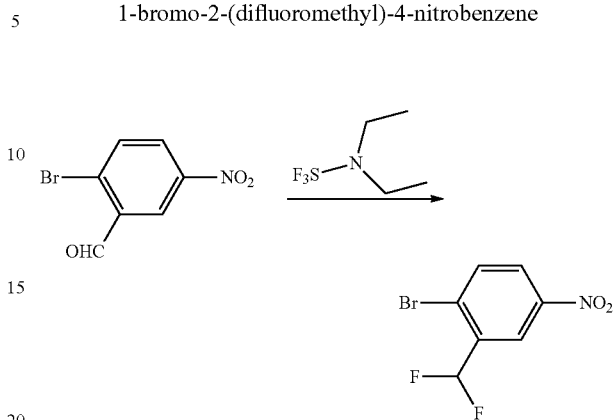

To a solution of 2-bromo-5-nitrobenzaldehyde (1.0 g, 4.35 mmol) in dichloromethane (50 mL) at 0° C., was added diethylaminosulfur trifluoride (3.45 mL, 26.1 mmol). The reaction mixture was stirred for overnight at rt. Reaction mixture was basified with 10% NaHCO$_3$ solution and extracted with dichloromethane (2×50 mL). Combined organic extracts were washed with water and brine, dried over Na$_2$SO$_4$ and concentrated. The crude product was purified by flash chromatography (eluting with 5-10% EtOAc in hexane) to afford 1-bromo-2-(difluoromethyl)-4-nitrobenzene (0.97 g, 89% yield) as a pale yellow oil. GCMS m/z: 253.0; $^1$H NMR (400 MHz, chloroform-d) δ ppm 8.52 (d, J=2.6 Hz, 1H), 8.21 (dd, J=2.7, 8.8 Hz, 1H), 7.84 (d, J=8.8 Hz, 1H), 7.08-6.79 (m, 1H); $^{19}$F NMR (376 MHz, chloroform-d) δ ppm −115.82.

Intermediate 16b

Preparation of 4-bromo-3-(difluoromethyl)aniline

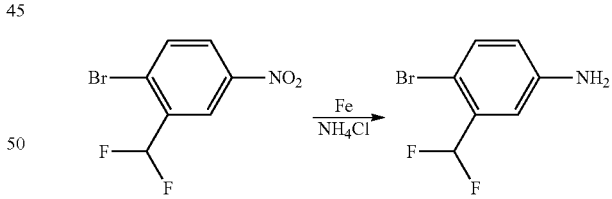

To a mixture of iron (1.33 g, 23.8 mmol) and ammonium chloride (1.274 g, 23.81 mmol) in water (40 mL), was added a solution of 1-bromo-2-(difluoromethyl)-4-nitrobenzene (1.2 g, 4.76 mmol) in methanol (20 mL). The reaction mixture was stirred at 75° C. for 3 h. Reaction mixture was cooled to RT, filtered through CELITE®, and the filtrate was concentrated. The residue obtained was dissolved in EtOAc (100 mL), washed with water and brine, dried over Na$_2$SO$_4$ and concentrated to give 4-bromo-3-(difluoromethyl) aniline (0.96 g, 90% yield) as a yellow solid. MS(ESI) m/z: 224.0 (M+H)$^+$; $^1$H NMR (400 MHz, DMSO-$d_6$) δ ppm 7.29 (d, J=8.6 Hz, 1H), 7.09-6.80 (m, 2H), 6.66-6.61 (m, 1H), 5.59 (s, 2H); $^{19}$F NMR (376 MHz, DMSO-$d_6$) δ ppm −113.95.

Intermediate 16: Preparation of 3-bromo-1-(4-bromo-3-(difluoromethyl)phenyl) pyrrolidin-2-one

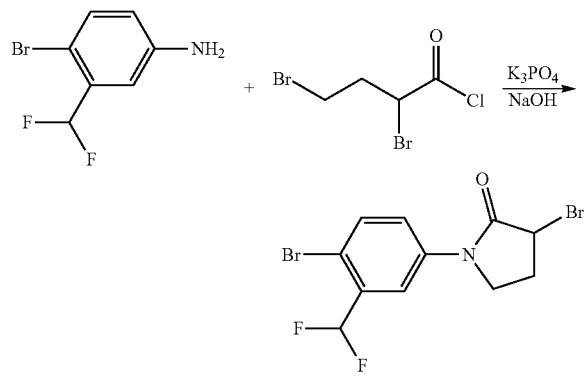

To a solution of 4-bromo-3-(difluoromethyl)aniline (0.4 g, 1.80 mmol) and potassium phosphate tribasic (0.191 g, 0.901 mmol) in acetonitrile (15 mL) at 0° C., was added 2,4-dibromobutanoyl chloride (0.571 g, 2.16 mmol) dropwise. The reaction mixture was stirred at rt for 1 h. Sodium hydroxide (0.4 g, 10.00 mmol) in water (0.8 mL, 50% solution) was added to the reaction mixture and stirred at rt for 3 h. The reaction mixture was filtered through CELITE®, rinsing with acetonitrile. The filtrate was concentrated. The crude product was purified by flash chromatography (eluting with 15-30% EtOAc in hexane to give 3-bromo-1-(4-bromo-3-(difluoromethyl)phenyl)pyrrolidin-2-one (0.58 g, 85% yield) as an off-white solid. MS(ESI) m/z: 369.9 (M+H)$^+$; $^1$H NMR (400 MHz, chloroform-d) δ ppm 7.92 (dd, J=8.8, 2.8 Hz, 1H), 7.77 (d, J=3.0 Hz, 1H), 7.62 (d, J=9.0 Hz, 1H), 7.05-6.75 (m, 1H), 4.59 (dd, J=7.0, 2.5 Hz, 1H), 4.12-4.04 (m, 1H), 3.89-3.83 (m, 1H), 2.82-2.70 (m, 1H), 2.54-2.45 (m, 1H); $^{19}$F NMR (376 MHz, chloroform-d) δ ppm −114.73.

Intermediate 17

3-Bromo-1-(4-bromo-3-(methoxymethyl)phenyl) pyrrolidin-2-one

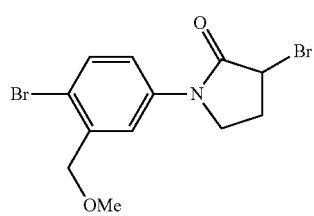 [SMILES: COCc1cc(N2CCC(Br)C2=O)ccc1Br]

Intermediate 17a

Preparation of (2-bromo-5-nitrophenyl)methanol

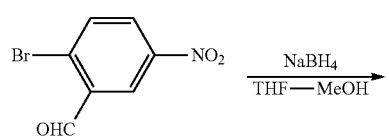

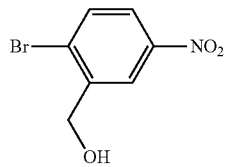

To a solution of 2-bromo-5-nitrobenzaldehyde (0.75 g, 3.26 mmol) in THF (10 mL) and methanol (10 mL) at 0° C., was added sodium borohydride (0.247 g, 6.52 mmol). The reaction mixture was stirred at rt for 1 h, then was diluted with 10% NaHCO$_3$ solution (50 mL) and water (50 mL) and extracted with EtOAc (2×50 mL). Combined organic extracts were washed with water and brine, dried over Na$_2$SO$_4$ and concentrated to give (2-bromo-5-nitrophenyl)methanol (0.7 g, 86% yield) as an off-white solid. MS(ESI) m/z: 231.9 (M+H)$^+$; $^1$H NMR (300 MHz, DMSO-d$_6$) δ ppm 8.31 (d, J=2.3 Hz, 1H), 8.05 (dd, J=8.7, 3.0 Hz, 1H), 7.89 (d, J=8.7 Hz, 1H), 5.84 (t, J=5.5 Hz, 1H), 4.58 (d, J=5.7 Hz, 2H).

Intermediate 17b

Preparation of 1-bromo-2-(methoxymethyl)-4-nitrobenzene

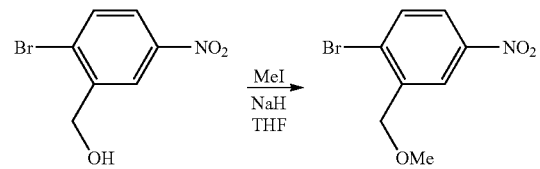 [SMILES: "MeI" ; O=[N+]([O-])c1ccc(Br)c(CO)c1 ; COCc1cc([N+](=O)[O-])ccc1Br]

To a solution of (2-bromo-5-nitrophenyl)methanol (0.7 g, 3.02 mmol) in THF (20 mL) at 0° C., was added sodium hydride (60% suspension in mineral oil, 0.241 g, 6.03 mmol). The reaction mixture was stirred at 10° C. for 30 min. Iodomethane (1.13 mL, 18.1 mmol) was added dropwise to the reaction mixture and the reaction stirred at rt for 2 h. The reaction mixture was quenched with water (20 mL) and extracted with EtOAc (2×25 mL). Combined organic extracts were washed with water and brine, dried over Na$_2$SO$_4$ and concentrated to give 1-bromo-2-(methoxymethyl)-4-nitrobenzene (0.71 g, 89% yield) as an off-white solid. MS(ESI) m/z: 245.8 (M+H)$^+$; $^1$H NMR (400 MHz, DMSO-d$_6$) δ ppm 8.23 (d, J=2.5 Hz, 1H), 8.08 (dd, J=8.5, 3.0 Hz, 1H), 7.94 (d, J=9.0 Hz, 1H), 4.54 (s, 2H), 3.45 (s, 3H).

Intermediate 17c

Preparation of 4-bromo-3-(methoxymethyl)aniline

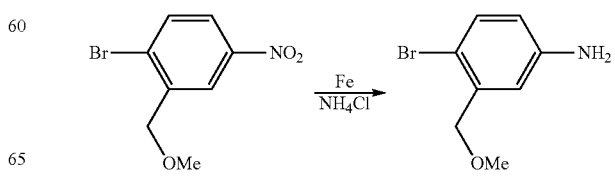

To a mixture of iron (0.806 g, 14.4 mmol) and ammonium chloride (0.772 g, 14.4 mmol) in water (30 mL), was added a solution of 1-bromo-2-(methoxymethyl)-4-nitrobenzene (0.71 g, 2.89 mmol) in methanol (20 mL). The reaction mixture was stirred at 75° C. for 4 h. Reaction mixture was cooled to rt, filtered through CELITE® and the filtrate was concentrated. The residue obtained was dissolved in EtOAc (75 mL), washed with water and brine, dried over Na$_2$SO$_4$ and concentrated to give 4-bromo-3-(methoxymethyl) aniline (0.605 g, 95% yield) as a pale brown oil. MS(ESI) m/z: 217.9 (M+H)$^+$; $^1$H NMR (400 MHz, DMSO-d$_6$) δ ppm 7.15 (d, J=8.5 Hz, 1H), 6.69 (d, J=2.5 Hz, 1H), 6.41 (dd, J=8.5, 3.0 Hz, 1H), 5.28 (s, 2H), 4.29 (s, 2H), 3.33 (s, 3H).

Intermediate 17: Preparation of 3-bromo-1-(4-bromo-3-(methoxymethyl)phenyl) pyrrolidin-2-one

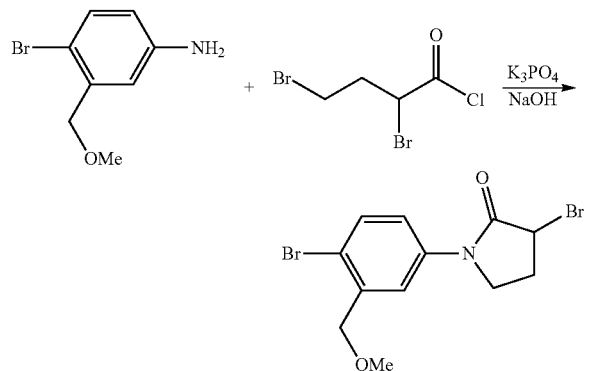

To a solution of 4-bromo-3-(methoxymethyl)aniline (0.6 g, 2.78 mmol) and potassium phosphate tribasic (0.295 g, 1.39 mmol) in acetonitrile (25 mL) at 0° C., was added 2,4-dibromobutyryl chloride (0.88 g, 3.33 mmol) dropwise. The reaction mixture was warmed to rt and stirred for 1 h. NaOH (0.6 g, 15.0 mmol) (in 1.2 mL water, 50% aqueous solution) was added to the reaction mixture, which was stirred at rt for 3 h. The reaction mixture was filtered, the solid was rinsed with acetonitrile, and the filtrate was concentrated. The crude product was purified by flash chromatography (eluting with 20-30% EtOAc in hexane) to give 3-bromo-1-(4-bromo-3-(methoxymethyl)phenyl) pyrrolidin-2-one (0.71 g, 70% yield) as a pale brown oil. MS(ESI) m/z: 363.8 (M+H)$^+$; $^1$H NMR (300 MHz, chloroform-d) δ ppm 7.69-7.64 (m, 1H), 7.63-7.60 (m, 1H), 7.57-7.53 (m, 1H), 4.59 (dd, J=6.8, 3.0 Hz, 1H), 4.52 (s, 2H), 4.12-4.01 (m, 1H), 3.90-3.79 (m, 1H), 3.50 (s, 3H), 2.80-2.67 (m, 1H), 2.55-2.41 (m, 1H).

Intermediate 18

Preparation of 3-bromo-1-(5-bromo-6-methylpyridin-2-yl)pyrrolidin-2-one

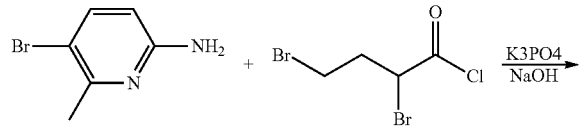

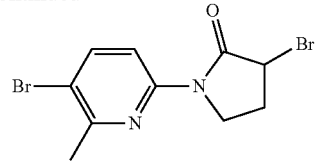

To a mixture of 5-bromo-6-methylpyridin-2-amine (0.5 g, 2.67 mmol) and potassium phosphate tribasic (0.284 g, 1.34 mmol) in acetonitrile (20 mL) at 0° C., was added 2,4-dibromobutyryl chloride (0.85 g, 3.21 mmol) dropwise. The reaction mixture was stirred at RT for 1 h. To this was added NaOH (0.5 g, 12.5 mmol) (in 1.0 mL water, 50% aqueous solution) and the mixture was stirred at rt for 3 h. The reaction mixture was filtered, the solid was rinsed with the acetonitrile, and the filtrate was concentrated. The crude product was purified by flash chromatography (eluting with 10-20% EtOAc in hexane to give 3-bromo-1-(5-bromo-6-methylpyridin-2-yl)pyrrolidin-2-one (0.725 g, 80% yield) as an off-white solid. MS(ESI) m/z: 334.8 (M+H)$^+$; $^1$H NMR (300 MHz, chloroform-d) δ ppm 8.05 (s, 2H), 4.95 (dd, J=7.0, 4.0 Hz, 1H), 4.10-3.95 (m, 2H), 2.80-2.67 (m, 1H), 2.55 (s, 3H), 2.35-2.26 (m, 1H).

Intermediate 19

3-Bromo-1-(5-bromo-6-methoxypyridin-2-yl)pyrrolidin-2-one

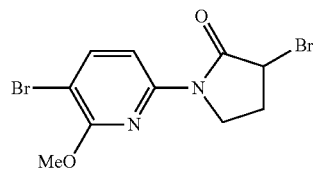 [SMILES: COc1nc(N2CCC(Br)C2=O)ccc1Br]

Intermediate 19a

Preparation of 5-bromo-6-methoxypyridin-2-amine

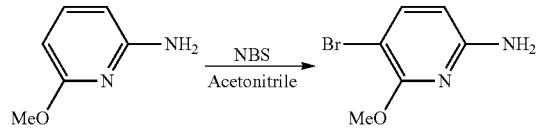

To a solution of 6-methoxypyridin-2-amine (10 g, 81 mmol) in acetonitrile (150 mL) was added N-bromosuccinimide (7.17 g, 40.3 mmol). The reaction mixture was stirred at rt for 90 min. Additional N-bromosuccinimide (7.17 g, 40.3 mmol) in acetonitrile (35 mL) was added, and the reaction mixture was stirred at RT for another 90 min. The reaction mixture was diluted with water (250 mL) and extracted with EtOAc (2×250 mL). Combined organic extracts were washed with water and brine, dried over Na$_2$SO$_4$ and concentrated. The crude product was purified by flash chromatography (eluting with 10-15% EtOAc in hexane) to give 5-bromo-6-methoxypyridin-2-amine (12.1 g, 74% yield) as an off-white solid. MS(ESI) m/z: 205.3

(M+H)⁺; ¹H NMR (300 MHz, chloroform-d) δ ppm 7.49 (d, J=8.0 Hz, 1H), 5.99 (d, J=8.0 Hz, 1H), 4.31 (br. s., 2H), 3.91 (s, 3H).

Intermediate 19: Preparation of 3-bromo-1-(5-bromo-6-methoxypyridin-2-yl)pyrrolidin-2-one

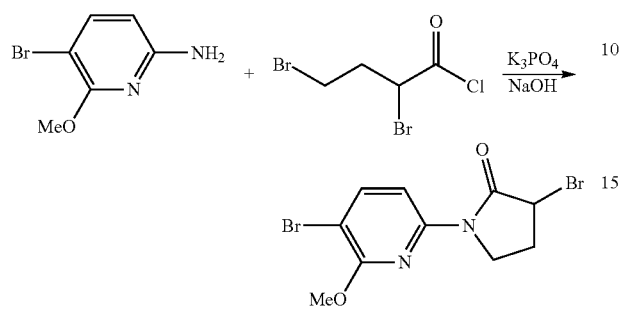

To a solution of 5-bromo-6-methoxypyridin-2-amine (2.5 g, 12.3 mmol) and potassium phosphate tribasic (1.31 g, 6.16 mmol) in acetonitrile (100 mL) at 0° C., was added 2,4-dibromobutanoyl chloride (3.91 g, 14.78 mmol) dropwise. The reaction mixture was stirred at rt for 1 h. Sodium hydroxide (2.5 g, 62.5 mmol) in water (5.0 mL) (50% solution) was added and the reaction mixture stirred at rt for 3 h. The reaction mixture was filtered, the solid was rinsed with acetonitrile, and the filtrate was concentrated. The crude product was purified by flash chromatography (eluting with 10-15% EtOAc in hexane) to give 3-bromo-1-(5-bromo-6-methoxypyridin-2-yl)pyrrolidin-2-one (3.55 g, 80% yield) as an off-white solid. MS(ESI) m/z: 350.8 (M+H)⁺; ¹H NMR (400 MHz, DMSO-d₆) δ ppm 8.05 (d, J=8.3 Hz, 1H), 7.80 (d, J=8.7 Hz, 1H), 4.96 (dd, J=6.8, 3.8 Hz, 1H), 4.17-4.09 (m, 1H), 4.08-4.01 (m, 1H), 3.94 (s, 3H), 2.83-2.70 (m, 1H), 2.35-2.26 (m, 1H).

Intermediate 20

3-Bromo-1-(4-bromophenyl)-4-(((tert-butyldimethylsilyl)oxy)methyl)pyrrolidin-2-one

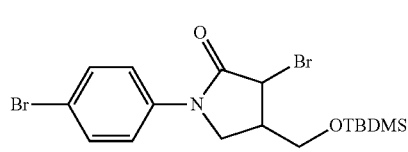 [SMILES: CC(C)(C)[Si](C)(C)OCC1CN(c2ccc(Br)cc2)C(=O)C1Br]

Intermediate 20a

Preparation of 1-(4-bromophenyl)-5-oxopyrrolidine-3-carboxylic acid

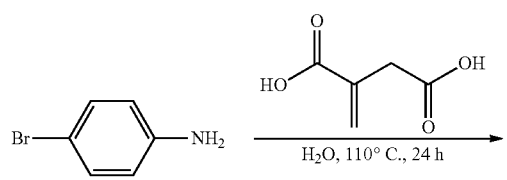

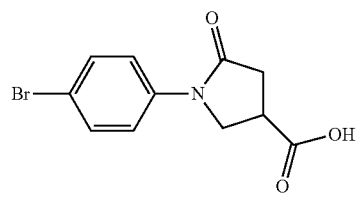

A mixture of 4-bromoaniline (10.0 g, 58.1 mmol) and 2-methylenesuccinic acid (8.32 g, 63.9 mmol) in water (250 mL) was heated at 110° C. for 24 h. The reaction mixture was cooled to 0° C. affording a pale yellow precipitate, which was stirred for 30 min. The suspension was filtered and the collected solid was washed with ether several times to afford 1-(4-bromophenyl)-5-oxopyrrolidine-3-carboxylic acid (15.78 g, 83% yield) as a white solid. MS(ESI) m/z: 283.8 (M+H)⁺; ¹H NMR (300 MHz, DMSO-d₆) δ ppm 12.80 (br. s., 1H) 7.39-7.78 (m, 4H) 3.91-4.11 (m, 2H) 3.34-3.42 (m, 1H) 2.58-2.90 (m, 2H).

Intermediate 20b

Preparation of methyl 1-(4-bromophenyl)-5-oxopyrrolidine-3-carboxylate

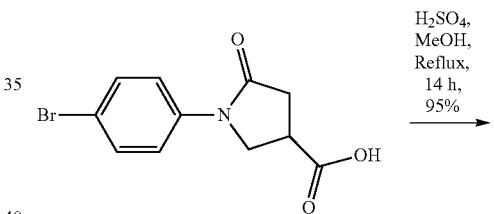

To a solution of 1-(4-bromophenyl)-5-oxopyrrolidine-3-carboxylic acid (15.5 g, 54.6 mmol) in methanol (350 mL), was added sulfuric acid (0.291 mL, 5.46 mmol) dropwise. The reaction mixture was heated at 70° C. overnight, then was evaporated. The crude product was basified with 10% NaHCO₃ and extracted with DCM. The combined organic extracts were washed with brine, dried over Na₂SO₄ and concentrated to afford methyl 1-(4-bromophenyl)-5-oxopyrrolidine-3-carboxylate (14.8 g, 49.7 mmol, 91% yield). MS(ESI) m/z: 299.9 (M+H)⁺; ¹H NMR (300 MHz, chloroform-d) δ ppm 7.46-7.56 (m, 4H) 3.97-4.23 (m, 2H) 3.80 (s, 3H) 3.27-3.46 (m, 1H) 2.80-3.07 (m, 2H).

Intermediate 20c

Preparation of 1-(4-bromophenyl)-4-(hydroxymethyl)pyrrolidin-2-one

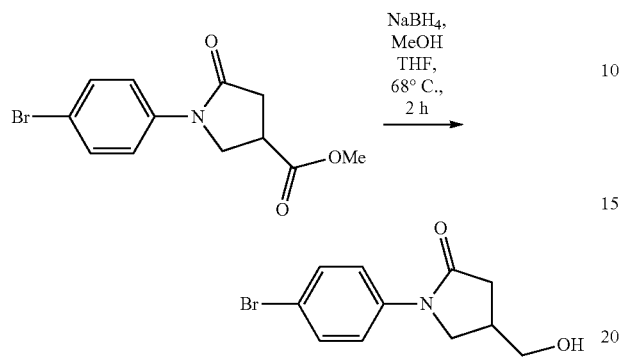

Methanol (25 mL) was added dropwise to a suspension of methyl 1-(4-bromophenyl)-5-oxopyrrolidine-3-carboxylate (6 g, 20.13 mmol) and NaBH$_4$ (1.14 g, 30.2 mmol) in refluxing THF (100 mL). The reaction mixture was refluxed for 3 h, then was cooled to rt and concentrated. The crude product which was purified by flash chromatography (0%-50% EtOAc in hexane). The collected fractions were concentrated to afford 1-(4-bromophenyl)-4-(hydroxymethyl)pyrrolidin-2-one (4.65 g, 78% yield). MS(ESI) m/z: 299.9 (M+H)$^+$; $^1$H NMR (400 MHz, chloroform-d) δ ppm 7.42-7.59 (m, 4H) 3.82-3.99 (m, 1H) 3.66-3.81 (m, 3H) 2.62-2.79 (m, 2H) 2.32-2.50 (m, 1H) 1.74 (t, J=4.52 Hz, 1H).

Intermediate 20d

Preparation of 1-(4-bromophenyl)-4-(((tert-butyldimethylsilyl)oxy) methyl)pyrrolidin-2-one

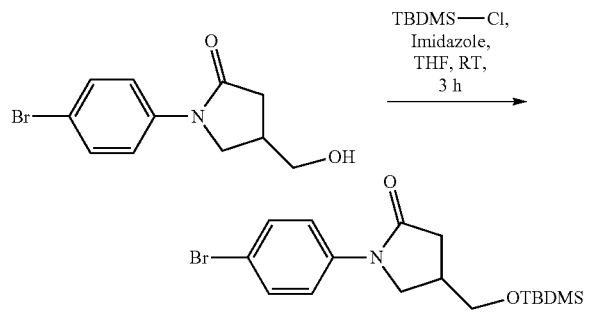

To a solution of 1-(4-bromophenyl)-4-(hydroxymethyl)pyrrolidin-2-one (4.50 g, 16.66 mmol) in DMF (75 mL) at 0° C., was added TBDMS-Cl (3.01 g, 20.0 mmol), followed by imidazole (1.70 g, 25.0 mmol). The reaction was stirred at 0° C. for 30 min and then allowed to warm to RT and stir overnight. Ice-cold water was added to the reaction mixture, and the aqueous was extracted with EtOAc (3×). The combined organic extracts were washed with brine, dried over Na$_2$SO$_4$ and concentrated to afford 1-(4-bromophenyl)-4-(((tert-butyldimethylsilyl)oxy)methyl)pyrrolidin-2-one (5.40 g, 84%). MS(ESI) m/z: 384.1 (M+H)$^+$; $^1$H NMR (300 MHz, DMSO-d$_6$) δ ppm 7.59-7.69 (m, 2H) 7.50-7.59 (m, 2H) 3.92 (dd, J=9.82, 7.93 Hz, 1H) 3.50-3.69 (m, 3H) 2.54-2.74 (m, 2H) 2.21-2.33 (m, 1H) 0.83 (s, 9H) 0.03 (d, J=3.40 Hz, 6H).

Intermediate 20: Preparation of 3-bromo-1-(4-bromophenyl)-4-(((tert-butyldimethylsilyl) oxy)methyl)pyrrolidin-2-one

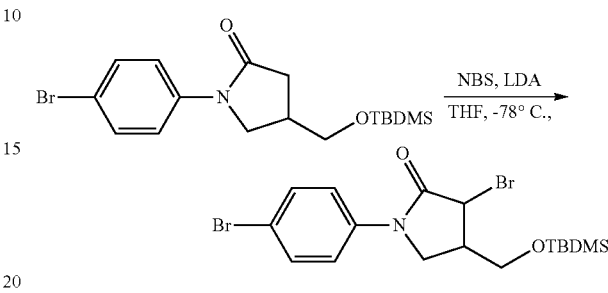

To a solution of 1-(4-bromophenyl)-4-(((tert-butyldimethylsilyl)oxy)methyl) pyrrolidin-2-one (1 g, 2.60 mmol) in THF (40 mL) at −78° C., was added dropwise 1M LiHMDS (5.72 mL, 5.72 mmol). After 5 min, NBS (0.556 g, 3.12 mmol) in THF (20 mL) was added dropwise and the reaction stirred at −78° C. for 1 hr. The reaction was quenched with sat. aq. NH$_4$Cl. The layers were separated and the aqueous phase extracted with EtOAC (3×). The combined organic extracts were washed with brine, dried over Na$_2$SO$_4$ and concentrated. The crude product was purified by flash chromatography (10%-35% EtOAc in hexane). Collected fractions were concentrated to afford 3-bromo-1-(4-bromophenyl)-4-(((tert-butyldimethylsilyl)oxy)methyl)pyrrolidin-2-one (0.352 g, 19% yield). MS(ESI) m/z: 384.1 (M+H)$^+$; $^1$H NMR (400 MHz, DMSO-d$_6$) δ ppm 7.64-7.72 (m, 2H) 7.56-7.63 (m, 2H) 4.71 (d, J=6.02 Hz, 1H) 4.06 (dd, J=10.04, 8.03 Hz, 1H) 3.73-3.86 (m, 2H) 3.61-3.68 (m, 1H) 2.79 (dt, J=7.78, 5.15 Hz, 1H) 0.84 (s, 9H) 0.06 (d, J=3.40 Hz, 6H).

Intermediate 21

1-(4-Bromophenyl)-2-oxopyrrolidin-3-yl methanesulfonate

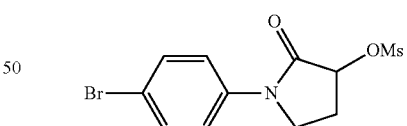

Intermediate 21a

Preparation of 1-(4-bromophenyl)-2-oxopyrrolidin-3-yl acetate

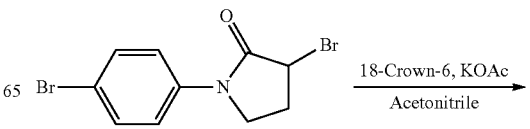

-continued

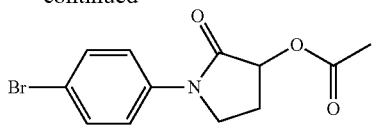

To a solution of 3-bromo-1-(4-bromophenyl)pyrrolidin-2-one (1.0 g, 3.13 mmol) in acetonitrile (12 mL), was added potassium acetate (1.23 g, 12.5 mmol) and 18-crown-6 (0.033 g, 0.125 mmol). The reaction mixture was heated at 85° C. overnight. Reaction mixture was cooled to rt, filtered through CELITE® bed, rinsing with acetonitrile. The filtrate was concentrated to give a brown solid, which was purified flash chromatography (100% hexane for 5 min, then 60% EtOAc/Hex for 25 min) to afford 1-(4-bromophenyl)-2-oxopyrrolidin-3-yl acetate (750 mg, 41%) as a white solid. MS(ESI) m/z: 300.0 (M+H)$^+$; $^1$H NMR (300 MHz, DMSO-d$_6$) δ ppm 7.64-7.71 (m, 2H) 7.55-7.63 (m, 2H) 5.49 (t, J=8.69 Hz, 1H) 3.75-3.89 (m, 1H) 2.54-2.62 (m, 1H) 2.11 (s, 3H) 2.04 (dd, J=12.46, 9.07 Hz, 1H).

Intermediate 21b

Preparation of 1-(4-bromophenyl)-3-hydroxypyrrolidin-2-one

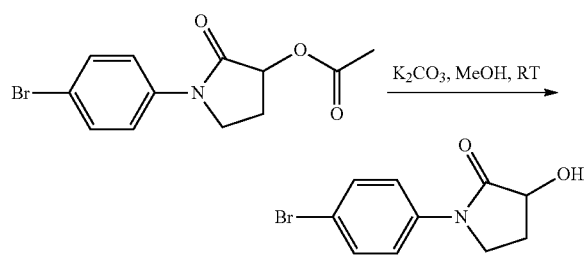

To a suspension of 1-(4-bromophenyl)-2-oxopyrrolidin-3-yl acetate (0.75 g, 2.52 mmol) in methanol (10 mL), was added K$_2$CO$_3$ (0.035 g, 0.252 mmol). The reaction mixture was stirred at rt overnight. Methanol was removed in vacuo to give yellow solid, which was suspended with acetone and stirred for 10 minutes. The mixture was filtered and the filtrate concentrated to afford 1-(4-bromophenyl)-3-hydroxypyrrolidin-2-one (620 mg, 96%) as a white solid. MS(ESI) m/z: 258.0 (M+H)$^+$; $^1$H NMR (300 MHz, DMSO-d$_6$) δ ppm 7.64-7.72 (m, 2H) 7.51-7.60 (m, 2H) 5.80 (s, 1H) 4.30 (dd, J=9.07, 8.31 Hz, 1H) 3.61-3.81 (m, 2H) 2.40 (dddd, J=12.13, 8.26, 6.42, 2.27 Hz, 1H) 1.84 (dq, J=12.46, 9.07 Hz, 1H).

Intermediate 21: Preparation of 1-(4-bromophenyl)-2-oxopyrrolidin-3-yl methanesulfonate

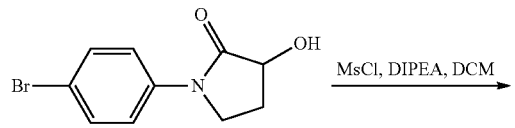

-continued

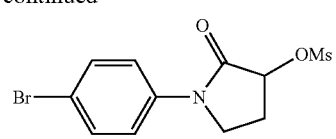

To a solution of 1-(4-bromophenyl)-3-hydroxypyrrolidin-2-one (200 mg, 0.781 mmol) in DCM (10 mL) was added DIPEA (0.409 mL, 2.34 mmol) and methanesulfonyl chloride (0.091 mL, 1.17 mmol) at 0° C. The reaction mixture was allowed to warm to RT and stir for 2 h. Reaction mixture was diluted with DCM and washed with 10% NaHCO$_3$ (aq), water and brine, dried over Na$_2$SO$_4$, filtered and concentrated to give 1-(4-bromophenyl)-2-oxopyrrolidin-3-yl methanesulfonate (270 mg, 98%) as a brown solid. MS(ESI) m/z: 332.0 (M+H)$^+$; $^1$H NMR (300 MHz, DMSO-d$_6$) δ ppm 7.65-7.73 (m, 2H) 7.54-7.65 (m, 2H) 5.46 (t, J=8.69 Hz, 1H) 3.74-3.92 (m, 2H) 3.35 (s, 3H) 2.69 (dddd, J=12.70, 8.64, 6.61, 2.27 Hz, 1H) 2.10-2.31 (m, 1H).

Intermediate 22

Preparation of 1-(4-bromophenyl)-3-((3-methoxyphenyl)amino)pyrrolidin-2-one

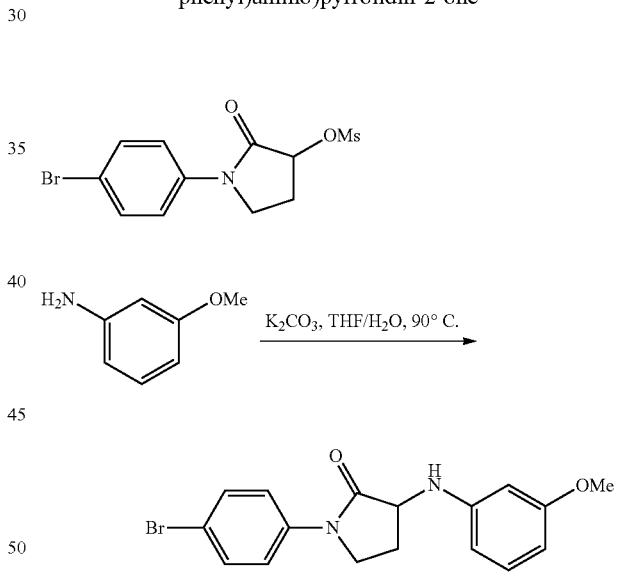

To a solution of 1-(4-bromophenyl)-2-oxopyrrolidin-3-yl methanesulfonate (100 mg, 0.299 mmol) in THF (5 mL), was added 3-methoxyaniline (55.3 mg, 0.449 mmol) and K$_2$CO$_3$ (83 mg, 0.60 mmol). The reaction mixture was heated at 90° C. overnight, then was cooled to rt and dilute with ethyl acetate. The ethyl acetate layer was washed with water and brine, dried over Na$_2$SO$_4$, filtered and concentrated to afford 1-(4-bromophenyl)-3-((3-methoxyphenyl)amino)pyrrolidin-2-one (160 mg, 76%) as a brown gummy mass. MS(ESI) m/z: 363.0 (M+H)$^+$; $^1$H NMR (400 MHz, DMSO-d$_6$) δ ppm 7.65-7.75 (m, 2H) 7.54-7.62 (m, 2H) 6.98 (t, J=8.03 Hz, 1H) 6.25-6.33 (m, 2H) 6.13-6.20 (m, 1H) 5.93 (d, J=7.53 Hz, 1H) 4.38 (dt, J=9.66, 7.72 Hz, 1H) 3.75-3.87 (m, 2H) 3.68 (s, 3H) 2.53-2.64 (m, 1H) 1.82-1.96 (m, 1H).

Intermediate 23

(S)-1-(4-Bromophenyl)-2-oxopyrrolidin-3-yl methanesulfonate

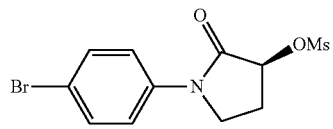 [SMILES: CS(=O)(=O)O[C@H]1CCN(c2ccc(Br)cc2)C1=O]

Intermediate 23a

Preparation of (S)-3-((tert-butyldiphenylsilyl)oxy)dihydrofuran-2(3H)-one

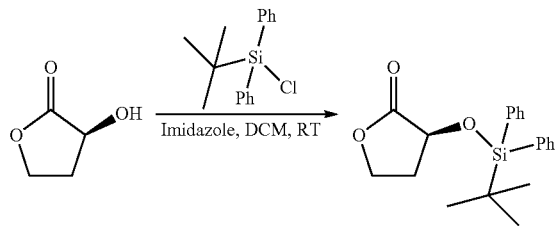 [SMILES: O=C1OCC[C@@H]1O ; CC(C)(C)[Si](Cl)(c1ccccc1)c1ccccc1 ; CC(C)(C)[Si](O[C@H]1CCOC1=O)(c1ccccc1)c1ccccc1]

To a solution of (S)-3-hydroxydihydrofuran-2(3H)-one (0.36 mL, 4.90 mmol) in DCM (10 mL), was added imidazole (0.834 g, 12.2 mmol). The mixture was cooled to 0° C., then tert-butylchlorodiphenylsilane (1.62 mL, 5.88 mmol) was added dropwise over 10 min. The mixture was warmed to rt and stirred for 24 h. DCM was evaporated and crude material purified by flash chromatography (gradient elution 0-12% EtOAc/hexane) to afford (S)-3-((tert-butyldiphenylsilyl)oxy)dihydrofuran-2(3H)-one (1.4 g, 84%) as a white solid. MS(ESI) m/z: 341.0 (M+H)$^+$; $^1$H NMR (300 MHz, CHCl$_3$-d) δ ppm 7.79-7.87 (m, 2H) 7.68-7.76 (m, 2H) 7.38-7.52 (m, 6H) 4.28-4.44 (m, 2H) 4.03 (td, J=9.48, 6.49 Hz, 1H) 2.14-2.31 (m, 2H) 1.12 (s, 9H); 100% ee (rt=3.53) [determined by chiral HPLC analysis, Column: CHIRALCEL® AD-H (250×4.6 mm), 5μ, Mobile Phase: 0.2% DEA n-hexane:ethanol: 70:30) Flow Rate: 1 ml/min]; $[α]^{25}_D$=−40.00 (c 0.1, MeOH).

Intermediate 23b

Preparation of (S)—N-(4-bromophenyl)-2-((tert-butyldiphenylsilyl)oxy)-4-hydroxybutanamide

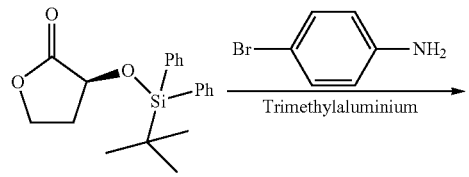

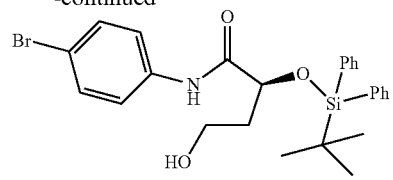

To a solution of 4-bromoaniline (0.303 g, 1.762 mmol) in DCM (20 mL) at rt, was added trimethylaluminum (1.101 mL, 2.203 mmol) dropwise. The reaction mixture stirred at RT for 40 min. A solution of (S)-3-((tert-butyldiphenylsilyl)oxy)dihydrofuran-2(3H)-one (0.500 g, 1.468 mmol) in DCM (12 mL) was added dropwise, and the reaction mixture stirred at rt for 16 hours. The reaction mixture was poured into a saturated solution of sodium potassium tartaric acid and stirred for 15 min. The layers were separated, and the aqueous layer was washed with DCM (3×20 mL). The combined organics were washed with 0.1M HCl (10 mL), brine, dried over Na$_2$SO$_4$ and evaporated to dryness. The crude material was purified by flash chromatography (gradient elution 0-35% EtOAc/hexanes) to afford (S)—N-(4-bromophenyl)-2-((tert-butyldiphenylsilyl)oxy)-4-hydroxybutanamide (0.72 g, 96%) as a white solid. MS(ESI) m/z: 510.2 (M+H)$^+$; $^1$H NMR (300 MHz, CDCl$_3$) δ ppm 8.64 (s, 1H) 7.61-7.71 (m, 4H) 7.33-7.50 (m, 10H) 4.43 (dd, J=7.08, 4.49 Hz, 1H) 3.56-3.75 (m, 2H) 2.28 (dd, J=7.25, 4.84 Hz, 1H) 1.86-2.08 (m, 2H) 1.19 (br. s., 9H); 100% ee (rt-18.83), [determined by chiral HPLC analysis, Column: Amylose A2 (250×4.6 mm), 5μ, Mobile Phase: 0.2% DEA n-hexane:ethanol: 70:30) Flow Rate: 1 ml/min]; $[α]^{25}_D$=−88.00 (c 0.1, MeOH).

Intermediate 23c

Preparation of (S)-1-(4-bromophenyl)-3-((tert-butyldiphenylsilyl)oxy)pyrrolidin-2-one

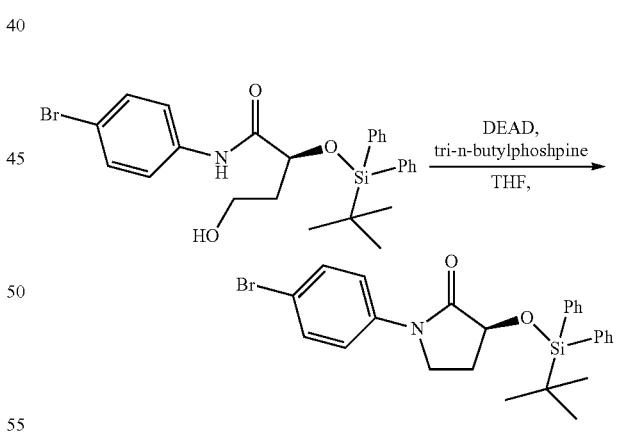

To a solution of di-tert-butyl azodicarboxylate (0.359 g, 1.561 mmol) in THF (10 mL) at 0° C., was added tri-n-butylphosphine (0.226 mL, 1.561 mmol) dropwise. The reaction mixture was allowed to warm to rt and stir for 20 min, then was cooled to 0° C. A solution of (S)—N-(4-bromophenyl)-2-((tert-butyldiphenylsilyl)oxy)-4-hydroxybutanamide (0.200 g, 0.390 mmol) in THF (5 mL) was added dropwise. The reaction mixture was allowed to warm to rt and stir for 45 min. The reaction mixture was poured into water and extracted with EtOAc (3×30 mL). The combined organics were washed with water (2×10 mL), brine, dried over MgSO₄ and evaporated. The residue was purified by flash chromatography (gradient elution 0-20% EtOAc/hexane) to afford (S)-1-(4-bromophenyl)-3-((tert-butyldiphenylsilyl)oxy)pyrrolidin-2-one (0.166 g, 86%) as a white solid. ¹H NMR (300 MHz, CDCl₃) δ ppm 7.85-7.92 (m, 2H) 7.72-7.79 (m, 2H) 7.54-7.62 (m, 2H) 7.38-7.51 (m, 8H) 4.44 (dd, J=9.16, 7.93 Hz, 1H) 3.62-3.73 (m, 1H) 3.53 (td, J=9.38, 6.78 Hz, 1H) 2.11-2.26 (m, 2H) 1.14 (br. s., 9H); 100% ee (rt=9.32) [determined by chiral HPLC analysis, CHIRALCEL® OJ-H (250×4.6 mm), 5μ, Mobile Phase: 0.2% DEA n-heptane:EtOH: 70:30) Flow Rate: 2 ml/min]; $[\alpha]^{24.7}_D$=−86.00 (c 0.1, MeOH).

Intermediate 23: Preparation of (S)-1-(4-bromophenyl)-3-hydroxypyrrolidin-2-one

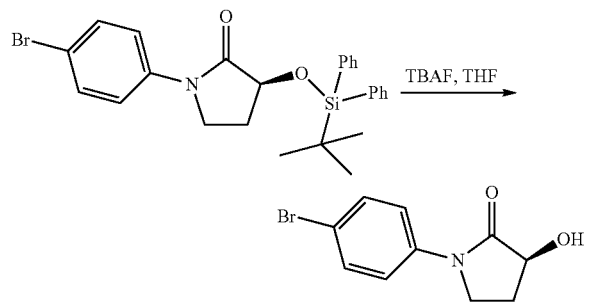

To a solution of (S)-1-(4-bromophenyl)-3-((tert-butyldiphenylsilyl)oxy) pyrrolidin-2-one (0.150 g, 0.303 mmol) in THF (5 mL) at 0° C. was added TBAF (1 M in THF, 0.607 mL, 0.607 mmol) dropwise. The reaction mixture stirred at rt for 3 h, then was poured into water and extracted with EtOAc (2×20 mL). The combined organics were dried over Na₂SO₄. The crude product was purified by flash chromatography (0-8% MeOH/DCM) to afford (S)-1-(4-bromophenyl)-3-hydroxypyrrolidin-2-one (0.065 g, 84%) as a white solid. MS(ESI) m/z: 258.0 (M+H)⁺; ¹H NMR (300 MHz, DMSO-d₆) δ ppm 7.65-7.71 (m, 2H) 7.53-7.61 (m, 2H) 5.78 (d, J=5.90 Hz, 1H) 4.24-4.36 (m, 1H) 3.61-3.79 (m, 2H) 2.34-2.46 (m, 1H) 1.84 (dq, J=12.33, 9.09 Hz, 1H); 99.69% ee (rt=3.55) [determined by chiral SFC analysis, Column: WHELK-O1® (R,R) (250×4.6 mm), 5μ, Mobile Phase: CO₂: 70% with % Co-solvent: 30% (0.2% DEA in methanol), Flow Rate: 3 ml/min, UV: 252 nm]; $[\alpha]^{25}_D$=−46.00 (c 0.1, MeOH).

Intermediate 24

(S)-1-(4-Bromophenyl)-2-oxopyrrolidin-3-yl methanesulfonate

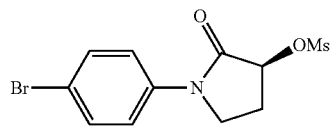

Intermediate 24a

Preparation of (R)-1-(4-bromophenyl)-3-hydroxypyrrolidin-2-one (Enantiomer 1), and (S)-1-(4-bromophenyl)-3-hydroxypyrrolidin-2-one (Enantiomer 2)

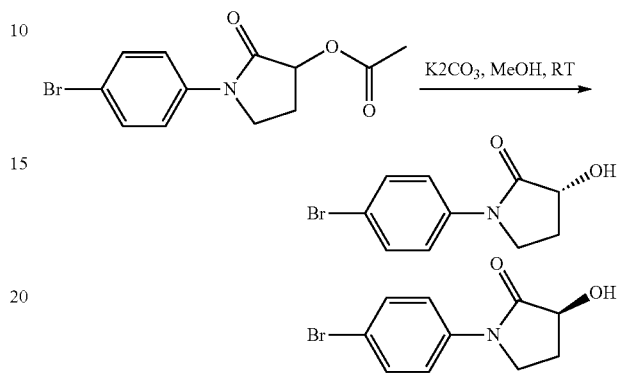

To a suspension of 1-(4-bromophenyl)-2-oxopyrrolidin-3-yl acetate (10.5 g, 35.2 mmol) in methanol (100 mL) was added K₂CO₃ (0.487 g, 3.52 mmol). The mixture stirred at RT for 3 h. Methanol was removed in vacuo to give yellow solid which was diluted with acetone and stirred at RT for 10 minutes. The precipitate formed were filtered, washed with acetone (2×). The filtrate was concentrated in vacuo to afford brown solid (9.0 g). The brown solid was crystallized using DCM and pet. ether, filtered, washed with pet. ether to give yellow solid (7.5 g). The yellow solid was subjected to chiral separation using Supercritical Fluid Chromatography (SFC) [Column: WHELK-O1® (R,R) (250×4.6 mm), 5μ, Co-solvent is 30% (0.25% DEA in methanol)] to give (R)-1-(4-bromophenyl)-3-hydroxypyrrolidin-2-one (Enantiomer 1) (yellow solid, 2.6 g); MS(ESI) m/z: 258.0 (M+H)⁺; ¹H NMR (300 MHz, DMSO-d₆) δ ppm 7.64-7.72 (m, 2H) 7.51-7.60 (m, 2H) 5.80 (s, 1H) 4.30 (dd, J=9.07, 8.31 Hz, 1H) 3.61-3.81 (m, 2H) 2.40 (dddd, J=12.13, 8.26, 6.42, 2.27 Hz, 1H) 1.84 (dq, J=12.46, 9.07 Hz, 1H); 99.52% ee (rt=2.87 [Column: WHELK-O1® (R,R) (250×4.6 mm), 5μ, Mobile Phase: 0.2% DEA in MeOH, CO₂ Flow Rate: 2.1 ml/min]; $[\alpha]^{24.7}_D$=+38.0 (c 0.1, MeOH) and (S)-1-(4-bromophenyl)-3-hydroxypyrrolidin-2-one (Enantiomer 2; stereochemistry confirmed with Intermediate 23) (yellow solid, 1.0 g); MS(ESI) m/z: 258.0 (M+H)⁺; ¹H NMR (300 MHz, DMSO-d₆) δ ppm 7.64-7.70 (m, 2H) 7.51-7.60 (m, 2H) 5.80 (s, 1H) 4.30 (dd, J=9.07, 8.31 Hz, 1H) 3.60-3.80 (m, 2H) 2.42 (dddd, J=12.13, 8.26, 6.42, 2.27 Hz, 1H) 1.81 (dq, J=12.46, 9.07 Hz, 1H); 98.2% ee (rt=3.3) [Column: WHELK-O1® (R,R) (250×4.6 mm), 5μ, Mobile Phase: 0.2% DEA in MeOH, CO₂ Flow Rate: 2.1 ml/min]; $[\alpha]^{24.8}_D$=−46.0 (c 0.1, MeOH).

Intermediate 24: (S)-1-(4-Bromophenyl)-2-oxopyrrolidin-3-yl methanesulfonate

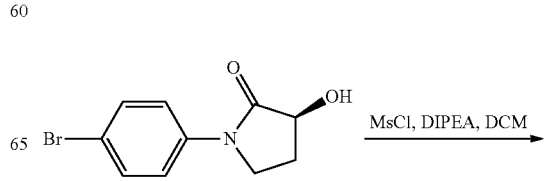

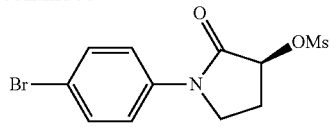

To a solution of 1-(4-bromophenyl)-3-hydroxypyrrolidin-2-one (150 mg, 0.586 mmol) in DCM (10 mL) was added DIPEA (0.307 mL, 1.76 mmol) at 0° C. Methanesulfonyl chloride (0.068 mL, 0.879 mmol) was added dropwise. The mixture was stirred at rt for 2 h. The reaction mixture was diluted with DCM and washed with 10% NaHCO$_3$ (aq), water and brine, dried over Na$_2$SO$_4$, filtered and concentrated to afford (R)-1-(4-bromophenyl)-2-oxopyrrolidin-3-yl methanesulfonate (190 mg, 97%) as a brown solid. MS(ESI) m/z: 336.0 (M+H)$^+$; $^1$H NMR (300 MHz, DMSO-d$_6$) δ ppm 7.65-7.73 (m, 2H) 7.54-7.65 (m, 2H) 5.46 (t, J=8.69 Hz, 1H) 3.74-3.92 (m, 2H) 3.35 (s, 3H) 2.69 (dddd, J=12.70, 8.64, 6.61, 2.27 Hz, 1H) 2.10-2.31 (m, 1H).

Example 1

1-(4-(1H-Pyrazol-4-yl)phenyl)-3-((3-fluoro-2-methoxyphenyl)amino)pyrrolidin-2-one

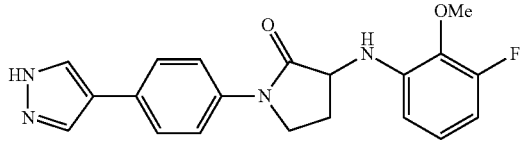 [SMILES: COc1c(F)cccc1NC1CCN(c2ccc(-c3cn[nH]c3)cc2)C1=O]

Example 1A

Preparation of 1-(4-bromophenyl)-3-((3-fluoro-2-methoxyphenyl)amino)pyrrolidin-2-one

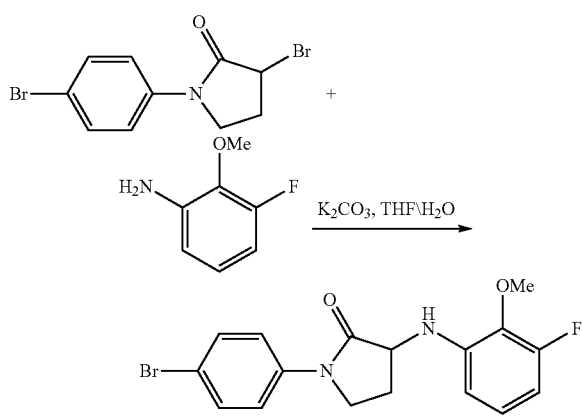

To a solution of Intermediate 1 (150 mg, 0.47 mmol) in THF (6.0 mL) was added 3-fluoro-2-methoxyaniline (100 mg, 0.705 mmol), K$_2$CO$_3$ (130 mg, 0.94 mmol) and water (0.60 mL). The mixture was stirred at 95° C. for 30 h, then was cooled to rt. The mixture was diluted with ethyl acetate, washed with brine solution, dried over Na$_2$SO$_4$, and concentrated. The product was purified by flash chromatography (0-35% EtOAc/Hex gradient) to obtain Example 1A (0.075 g, 36% yield) as an off-white solid. MS(ESI) m/z: 379.5 (M+H)$^+$; $^1$H NMR (300 MHz, DMSO-d$_6$) δ ppm 7.68-7.75 (m, 2H) 7.56-7.63 (m, 2H) 6.88 (td, J=8.22, 6.23 Hz, 1H) 6.59 (d, J=8.31 Hz, 2H) 6.47 (ddd, J=11.14, 8.31, 1.32 Hz, 1H) 5.63 (d, J=7.18 Hz, 1H) 3.78-3.83 (m, 5H) 2.54-2.65 (m, 1H) 1.97-2.13 (m, 1H).

Example 1

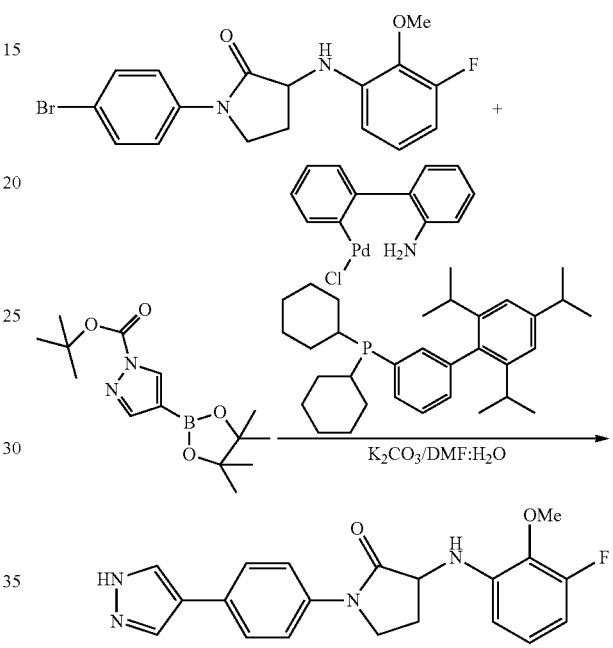

To a solution of Example 1A (75 mg, 0.198 mmol) in DMF (3 mL), were added K$_2$CO$_3$ (82 mg, 0.593 mmol) and water (0.5 mL). The mixture was purged with nitrogen for 10 min and then was charged with tert-butyl 4-(4,4,5,5-tetramethyl-1,3,2-dioxaborolan-2-yl)-1H-pyrazole-1-carboxylate (87 mg, 0.30 mmol) and 2nd generation XPhos precatalyst (9.3 mg, 0.012 mmol) and again was purged with nitrogen for 10 min. The mixture was heated at 90° C. for 14 h, then was cooled to rt and diluted with water. The mixture was extracted with ethyl acetate. The combined ethyl acetate layers were washed with water and brine, dried over Na$_2$SO$_4$, and concentrated. The residue was purified by preparative LC/MS to afford Example 1 (13 mg, 17% yield). MS(ESI) m/z: 367.2 (M+H)$^+$; $^1$H NMR (400 MHz, DMSO-d$_6$) δ ppm 12.92 (s, 1H) 8.18 (br. s., 1H) 7.92 (br. s., 1H) 7.69-7.74 (m, 2H) 7.62-7.67 (m, 2H) 6.90 (td, J=8.28, 6.21 Hz, 1H) 6.61 (d, J=8.41 Hz, 1H) 6.49 (ddd, J=11.06, 8.33, 1.32 Hz, 1H) 5.60 (d, J=7.03 Hz, 1H) 4.39-4.47 (m, 1H) 3.82-3.88 (m, 2H) 3.81 (s, 3H) 2.59-2.69 (m, 1H) 2.00-2.12 (m, 1H). $^{19}$F NMR (376 MHz, DMSO-d$_6$) δ ppm −133.173, HPLC RT=1.56 min, 95.47% (Method E), 1.55 min, 95.70% (Method F).

The following Examples in Table 1 were prepared using procedures similar to those used for the synthesis of Example 1.

TABLE 1

| Ex. | Structure and Name | LCMS (M + H)+ | HPLC Method, RT (min) & Purity | NMR |
|---|---|---|---|---|
| 2 | 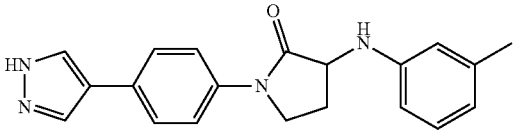<br>1-(4-(1H-pyrazol-4-yl)phenyl)-3-(m-tolylamino)pyrrolidin-2-one | 333.2 | C: 2.371, 96.45%<br>D: 2.432, 96.55% | $^1$H NMR (400 MHz, DMSO-d$_6$) δ ppm 12.98 (br. s, 1 H) 8.11 (br. s, 2 H) 7.67-7.72 (m, 2H) 7.61-7.65 (m, 2 H) 6.97 (t, J = 7.72 Hz, 1 H) 6.49-6.55 (m, 2 H) 6.40 (d, J = 7.34 Hz, 1 H) 4.35 (t, J = 8.4 Hz, 1 H) 3.80-3.86 (m, 2 H) 2.56-2.64 (m, 1 H) 2.21 (s, 3 H) 1.88 (dd, J = 12.08, 9.95 Hz, 1 H). |
| 3 | <br>1-(4-(1H-pyrazol-4-yl)phenyl)-3-((3-fluoro-5-methoxyphenyl)amino)pyrrolidin-2-one | 367.2 | C: 2.401, 98.85%<br>D: 2.402, 98.39% | $^1$H NMR (400 MHz, DMSO-d$_6$) δ ppm 8.04 (s, 2 H) 7.67-7.71 (m, 2 H) 7.61-7.65 (m, 2 H) 6.10-6.16 (m, 2 H) 5.99 (dt, J = 11.15, 2.20 Hz, 1 H) 4.40 (dd, J = 9.85, 8.35 Hz, 1 H) 3.79-3.85 (m, 2 H) 3.69 (s, 3 H) 2.60 (dtd, J = 14.31, 5.84, 5.84, 2.45 Hz, 1 H) 1.81-1.93 (m, 1 H). $^{19}$F NMR (376 MHz, DMSO-d$_6$) δ ppm −112.575. |
| 4 | 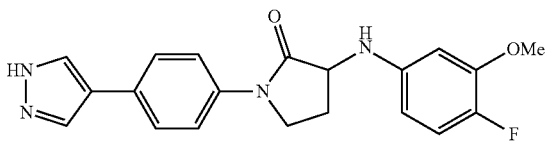<br>1-(4-(1H-pyrazol-4-yl)phenyl)-3-((4-fluoro-3-methoxyphenyl)amino)pyrrolidin-2-one | 367.2 | E: 1.327, 99.49%<br>F: 1.348, 99.46% | $^1$H NMR (400 MHz, DMSO-d$_6$) δ ppm 12.90 (s, 1 H) 8.18 (s, 1 H) 7.92 (s, 1 H) 7.67-7.73 (m, 2 H) 7.61-7.66 (m, 2 H) 6.92 (dd, J = 11.55, 8.78 Hz, 1 H) 6.54 (dd, J = 7.53, 2.64 Hz, 1 H) 6.22 (dt, J = 8.71, 3.08 Hz, 1 H) 5.84 (d, J = 6.84 Hz, 1 H) 4.31-4.40 (m, 1 H) 3.81-3.87 (m, 2 H) 3.78 (s, 3 H) 2.58-2.67 (m, 1 H) 1.89 (dq, J = 12.15, 9.38 Hz, 1 H). $^{19}$F NMR (376 MHz, DMSO-d$_6$) δ ppm −151.120. |
| 5 | 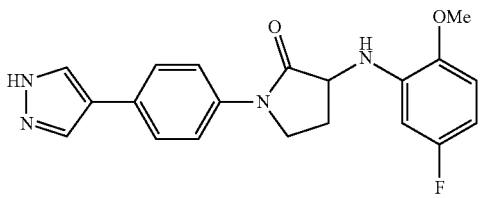<br>1-(4-(1H-pyrazol-4-yl)phenyl)-3-((5-fluoro-2-methoxyphenyl)amino)pyrrolidin-2-one | 367.2 | E: 1.576, 98.72%<br>F: 1.570, 95.19% | $^1$H NMR (400 MHz, DMSO-d$_6$) δ ppm 12.92 (br. s., 1 H) 8.18 (br. s., 1 H) 7.92 (br. s., 1 H) 7.69-7.74 (m, 2 H) 7.61-7.67 (m, 2 H) 6.81 (dd, J = 8.78, 5.33 Hz, 1 H) 6.57 (dd, J = 11.29, 2.95 Hz, 1 H) 6.36 (td, J = 8.67, 2.98 Hz, 1 H) 5.42 (dd, J = 6.37, 1.35 Hz, 1 H) 4.38 (ddd, J = 10.34, 8.08, 6.49 Hz, 1 H) 3.82-3.88 (m, 2 H) 3.80 (s, 3 H) 2.64-2.73 (m, 1 H) 1.94-2.06 (m, 1 H). $^{19}$F NMR (376 MHz, DMSO-d$_6$) δ ppm −122.306. |
| 6 | 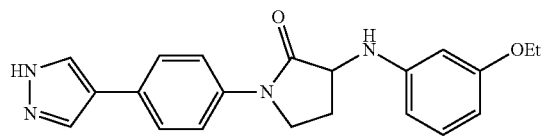<br>1-(4-1H-pyrazol-4-yl)phenyl)-3-((3-ethoxyphenyl)amino)pyrrolidin-2-one | 363.2 | E: 1.432, 96.30%<br>F: 1.499, 99.44% | $^1$H NMR (400 MHz, DMSO-d$_6$) δ ppm 12.92 (s, 1 H) 8.17 (s, 1 H) 7.92 (s, 1 H) 7.67-7.72 (m, 2 H) 7.60-7.66 (m, 2 H) 6.93-7.00 (m, 1 H) 6.25-6.32 (m, 2 H) 6.12-6.18 (m, 1 H) 5.91 (s, 1 H) 4.36 (dt, J = 9.49, 7.77 Hz, 1 H) 3.90-3.98 (m, 2 H) 3.79-3.86 (m, 2 H) 2.56-2.64 (m, 1 H) 1.88 (dq, J = 12.15, 9.42 Hz, 1 H) 1.30 (t, J = 7.2 Hz, 3 H). |
| 7 | 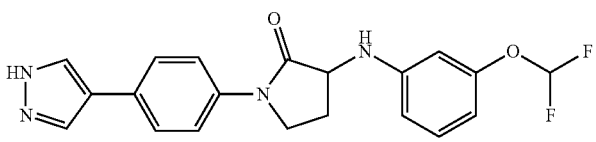<br>1-(4-(1H-pyrazol-4-yl)phenyl)-3-((3-(difluoromethoxy)-phenyl)amino)pyrrolidin-2-one | 385.2 | E: 1.479, 99.40%<br>F: 1.522, 99.33% | $^1$H NMR (400 MHz, DMSO-d$_6$) δ ppm 12.92 (br. s., 1 H) 8.18 (s, 1 H) 7.92 (s, 1 H) 7.67-7.72 (m, 2 H) 7.60-7.66 (m, 2 H) 6.93-7.34 (m, 2 H) 6.58 (dd, J = 8.25, 1.60 Hz, 1 H) 6.50 (t, J = 2.20 Hz, 1 H) 6.35 (dd, J = 7.97, 1.95 Hz, 1 H) 6.30 (s, 1 H) 4.42 (dt, J = 9.84, 7.82 Hz, 1 H) 3.80-3.87 (m, 2 H) 2.55-2.65 (m, 1 H) 1.83-1.95 (m, 1 H). $^{19}$F NMR (376 MHz, DMSO-d$_6$) δ ppm −80.903. |

US 10,112,929 B2

TABLE 1-continued

| Ex. | Structure and Name | LCMS (M + H)+ | HPLC Method, RT (min) & Purity | NMR |
|---|---|---|---|---|
| 8 | 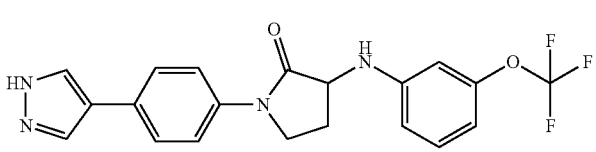<br>1(4-(1H-pyrazol-4-yl)phenyl)-3-((3-(trifluoromethoxy)-phenyl)amino)pyrrolidin-2-one | 403.2 | E: 1.697, 99.24%<br>F: 1.734, 99.29% | $^1$H NMR (400 MHz, DMSO-d$_6$) δ ppm 12.92 (br. s., 1 H) 8.18 (br. s., 1 H) 7.92 (br. s., 1 H) 7.67-7.72 (m, 2 H) 7.60-7.66 (m, 2 H) 7.18 (t, J = 8.16 Hz, 1 H) 6.72 (dd, J= 8.03, 1.88 Hz, 1 H) 6.66 (s, 1 H) 6.42-6.52 (m, 2 H) 4.45 (dt, J = 9.90, 7.85 Hz, 1 H) 3.80-3.87 (m, 2 H) 2.55-2.65 (m, 1 H) 1.90 (dq, J = 12.09, 9.52 Hz, 1 H).<br>$^{19}$F NMR (376 MHz, DMSO-d$_6$) δ ppm −56.330. |
| 9 | 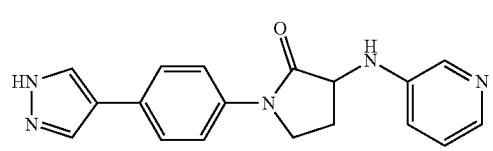<br>1-(4-(1H-pyrazol-4-yl)phenyl)-3-(pyridin-3-ylamino)pyrrolidin-2-one | 320.2 | E: 0.550, 100.0%<br>F: 0.869, 98.86% | $^1$H NMR (400 MHz, DMSO-d$_6$) δ ppm 12.95 (s, 1 H) 8.18 (s, 1 H) 8.09 (dd, J = 2.48, 1.04 Hz, 1 H) 7.92 (s, 1 H) 7.80 (dd, J = 4.02, 1.94 Hz, 1 H) 7.67-7.72 (m, 2 H) 7.61-7.66 (m, 2 H) 7.05-7.12 (m, 2 H) 6.22 (d, J = 7.34 Hz, 1 H) 4.46 (dt, J = 9.85, 7.91 Hz, 1 H) 3.81-3.87 (m, 2 H) 2.61 (dtt, J = 11.64, 5.78, 5.78, 2.99, 2.99 Hz, 1 H) 1.87-1.98 (m, 1 H). |
| 10 | 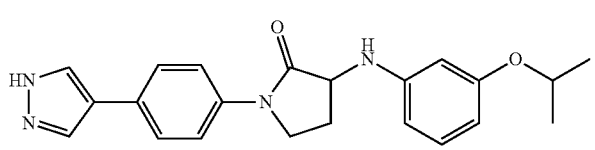<br>1-(4-(1H-pyrazol-4-yl)phenyl)-3-((3-isopropoxyphenyl)-amino)pyrrolidin-2-one | 377.3 | F: 1.545, 97.50%<br>F: 1.599, 97.25% | $^1$H NMR (400 MHz, DMSO-d$_6$) δ ppm 12.92 (br. s., 1 H) 8.17 (br. s., 1 H) 7.91 (br. s., 1 H) 7.60-7.72 (m, 4 H) 6.92-6.99 (m, 1 H) 6.24-6.30 (m, 2 H) 6.12-6.17 (m, 1 H) 5.88 (d, J = 6.96 Hz, 1 H) 4.50 (spt, J = 6.03 Hz, 1 H) 4.31-4.39 (m, 1 H) 3.77-3.87 (m, 2 H) 2.54-2.64 (m, 1 H) 1.88 (dq, J = 12.09, 9.42 Hz, 1 H) 1.24 (d, J = 6.00 Hz, 6 H). |
| 11 | 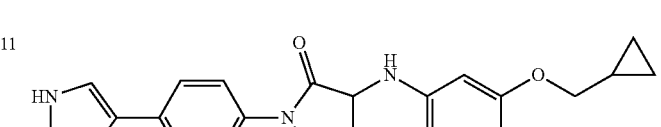<br>1-(4-1H-pyrazol-4-yl)phenyl)-3-((3-(cyclopropylmethoxy)phenyl)-amino)pyrrolidin-2-one | 389.3 | F: 1.572, 99.72%<br>F: 1.609, 96.92% | $^1$H NMR (400 MHz, DMSO-d$_6$) δ ppm 8.05 (s, 2 H) 7.67-7.72 (m, 2 H) 7.60-7.66 (m, 2 H) 6.96 (t, J = 8.25 Hz, 1 H) 6.26-6.31 (m, 2 H) 6.12-6.16 (m, 1 H) 4.36 (dd, J = 9.91, 8.28 Hz, 1 H) 3.79-3.85 (m, 2 H) 3.73 (s, 2 H) 2.55-2.64 (m, 1 H) 1.88 (dq, J = 12.13, 9.43 Hz, 1 H) 1.14-1.28 (m, 2 H) 0.51-0.58 (m, 2 H) 0.25-0.32 (m, 2 H). |
| 12 | 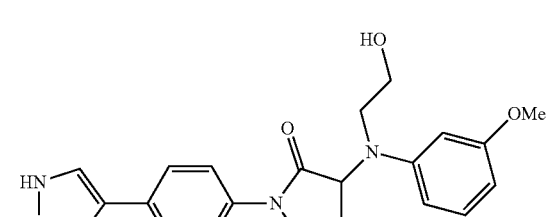<br>1-(4-(1H-pyrazol-4-yl)phenyl)-3-((2-hydroxyethyl)(3-methoxyphenyl)amino)pyrrolidin-2-one | 393.2 | E: 1.151, 98.75%<br>F: 1.225, 99.80% | $^1$H NMR (400 MHz, DMSO-d$_6$) δ ppm 12.92 (s, 1 H) 8.18 (s, 1 H) 7.92 (s, 1 H) 7.67-7.72 (m, 2 H) 7.61-7.66 (m, 2 H) 7.07 (t, J = 8.19 Hz, 1 H) 6.41 (dd, J = 8.28, 2.26 Hz, 1 H) 6.33 (t, J = 2.29 Hz, 1 H) 6.26 (dd, J = 8.00, 2.04 Hz, 1 H) 4.87 (dd, J = 10.45, 9.00 Hz, 1 H) 4.73 (t, J = 5.65 Hz, 1 H) 3.79-3.90 (m, 2 H) 3.69 (s, 3 H) 3.50-3.64 (m, 2 H) 3.37-3.45 (m, 1 H) 3.19-3.28 (m, 1 H) 2.37-2.46 (m, 1 H) 2.13-2.25 (m, 1 H). |

Example 13

1-(4-(1H-Pyrazol-4-yl)phenyl)-3-((3-fluoro-4-methoxyphenyl)amino)pyrrolidin-2-one (Enantiomer-1)

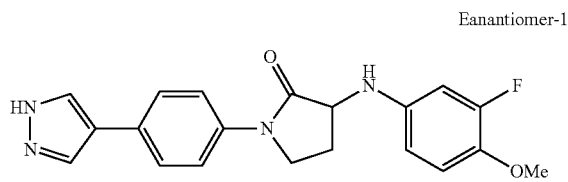 [SMILES: COc1ccc(NC2CCN(c3ccc(-c4cn[nH]c4)cc3)C2=O)cc1F]

Enantiomer-1

Example 13A

Preparation of 1-(4-bromophenyl)-3-((3-fluoro-4-methoxyphenyl)amino)pyrrolidin-2-one (Enantiomer-1), and

Example 13B 1-(4-bromophenyl)-3-((3-fluoro-4-methoxyphenyl)amino)pyrrolidin-2-one (Enantiomer-2)

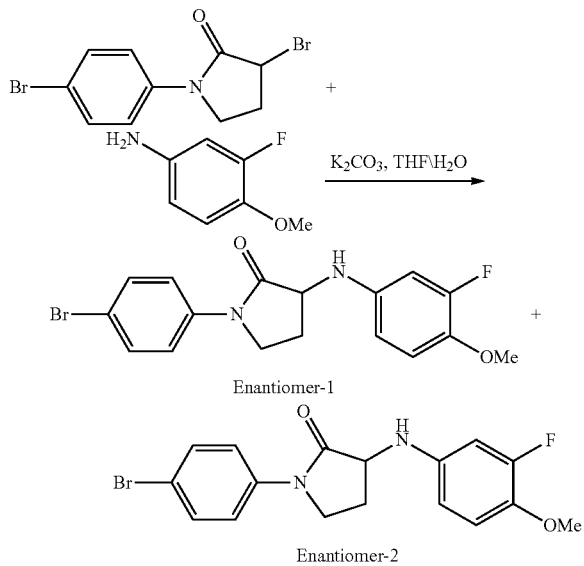

To a solution of 3-bromo-1-(4-bromophenyl)pyrrolidin-2-one (400 mg, 1.25 mmol) in THF (6 mL), were added 3-fluoro-4-methoxyaniline (265 mg, 1.88 mmol), $K_2CO_3$ (347 mg, 2.51 mmol) and water (0.6 mL). The mixture was stirred at 90° C. for 14 h. The reaction mixture was cooled, diluted with ethyl acetate, washed with brine, dried over $Na_2SO_4$, filtered and concentrated. The solid was dissolved in DCM and precipitated by adding hexanes. The precipitate was collected by filtration and dried. The solid was purified by Supercritical Fluid Chromatography (Column: CHIRALPAK® AS-H (250×21 mm), 5μ, Co-solvent is 45% methanol) to obtain Example 13A (150 mg, 31% yield) and Example 13B (160 mg, 30% yield) as brown solids.

Analytical data for Example 13A: MS(ESI) m/z: 381.0 $(M+H)^+$; $^1H$ NMR (400 MHz, DMSO-$d_6$) δ ppm 7.66-7.72 (m, 2H) 7.56-7.61 (m, 2H) 6.89-6.95 (m, 1H) 6.61 (dd, J=14.05, 3.01 Hz, 1H) 6.42-6.48 (m, 1H) 5.84 (d, J=7.03 Hz, 1H) 4.31 (dt, J=9.66, 7.72 Hz, 1H) 3.75-3.84 (m, 2H) 3.71 (s, 3H) 2.58 (dddd, J=12.17, 8.28, 6.15, 2.01 Hz, 1H) 1.86 (dq, J=12.30, 9.45 Hz, 1H), 100% ee with Chiral HPLC RT=7.72 min (Method IV), $[α]^{24.9}_D$=-26.0 (c 0.1, MeOH).

Analytical data for Example 13B: MS(ESI) m/z: 381.0 $(M+H)^+$; $^1H$ NMR (400 MHz, DMSO-$d_6$) δ ppm 7.65-7.72 (m, 2H) 7.55-7.62 (m, 2H) 6.89-6.96 (m, 1H) 6.61 (dd, J=14.31, 2.76 Hz, 1H) 6.45 (dt, J=8.91, 1.32 Hz, 1H) 5.84 (d, J=7.03 Hz, 1H) 4.31 (dt, J=9.79, 7.91 Hz, 1H) 3.74-3.85 (m, 2H) 3.71 (s, 3H) 2.54-2.63 (m, 1H) 1.80-1.92 (m, 1H), 100% ee with Chiral HPLC RT=13.28 min (Method IV), $[α]^{24.7}_D$=+24.0 (c 0.1, MeOH).

Example 13

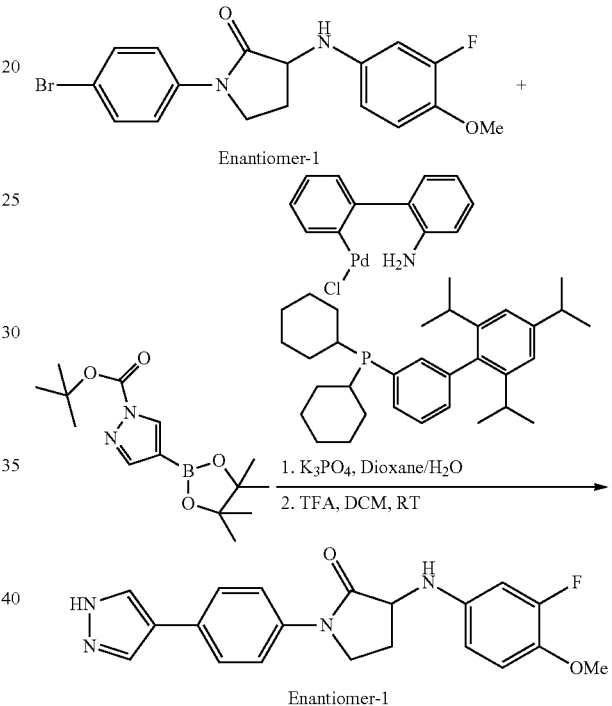

To a solution of Example 13A (160 mg, 0.42 mmol) in dioxane (10 mL), were added tert-butyl 4-(4,4,5,5-tetramethyl-1,3,2-dioxaborolan-2-yl)-1H-pyrazole-1-carboxylate (186 mg, 0.63 mmol), potassium phosphate tribasic (224 mg, 1.05 mmol) and water (1 mL). The reaction mixture was purged with nitrogen for 10 min, then was charged with 2nd generation XPhos precatalyst (19.9 mg, 0.025 mmol) and again purged with nitrogen for 10 min. The mixture was heated at 70° C. for 2 h. The reaction mixture was cooled and diluted with ethyl acetate. The solution was washed with water and brine, dried over $Na_2SO_4$, and concentrated. The solid was dissolved in DCM (10 mL) and charged with TFA (0.198 mL, 2.57 mmol) and stirred at rt for 3 h. The mixture was concentrated, and the residue was washed with hexanes and diethyl ether. The solid was purified by preparative LC/MS to afford Example 13 (6 mg, 3.0% yield) as an off-white solid. MS(ESI) m/z: 367.2 $(M+H)^+$; $^1H$ NMR (400 MHz, DMSO-$d_6$) δ ppm 12.92 (s, 1H) 8.15 (br. s., 1H) 7.99 (br. s., 1H) 7.67-7.72 (m, 2H) 7.60-7.65 (m, 2H) 6.90-6.96 (m, 1H) 6.62 (dd, J=14.18, 2.70 Hz, 1H) 6.47 (dd, J=8.88, 1.54 Hz, 1H) 5.84 (d, J=6.84 Hz, 1H) 4.30 (dt, J=9.63, 7.67 Hz, 1H) 3.82 (dd, J=9.63, 6.31 Hz, 2H) 3.72 (s, 3H) 2.60 (td, J=5.73, 3.04 Hz, 1H) 1.80-1.90 (m, 1H). $^{19}F$ NMR (376 MHz, DMSO-$d_6$) δ ppm -134.261, HPLC RT=1.395 min, 98.10% (Method E), HPLC RT=1.447 min, 97.07% (Method F), 100% ee with Chiral HPLC RT=8.37 min (Method V).

The following Examples in Table 2 were prepared using procedures similar to those used for the synthesis of Example 13.

TABLE 2

| Ex. | Structure and Name | LCMS (M + H)+ | HPLC Method, RT (min) & Purity | NMR |
|---|---|---|---|---|
| 14 | 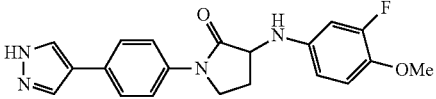 [SMILES: COc1ccc(NC2CCN(c3ccc(-c4cn[nH]c4)cc3)C2=O)cc1F]<br>Enantiomer-II<br>1-(4-(1H-pyrazol-4-yl)phenyl)-3-((3-fluoro-4-methoxyphenyl)amino)pyrrolidin-2-one (Enantiomer-2) | 367.2 | E: 1.395, 97.85%<br>F: 1.447, 96.73% | $^1$H NMR (400 MHz, DMSO-d$_6$) δ ppm 12.92 (s, 1 H) 8.15 (br. s., 1 H) 7.99 (br. s., 1 H) 7.67-7.72 (m, 2 H) 7.61-7.65 (m, 2 H) 6.93 (t, J = 9.38 Hz, 1 H) 6.62 (dd, J = 14.12, 2.70 Hz, 1 H) 6.47 (dd, J = 8.91, 1.57 Hz, 1 H) 5.84 (d, J = 6.65 Hz, 1 H) 4.26-4.34 (m, 1 H) 3.79-3.85 (m, 2 H) 3.72 (s, 3 H) 2.55-2.64 (m, 1 H) 1.80-1.91 (m, 1 H). $^{19}$F NMR (376 MHz, DMSO-d$_6$) δ ppm −134.261. 100% ee with Chiral HPLC RT = 9.6 min (Method V). |
| 15 | 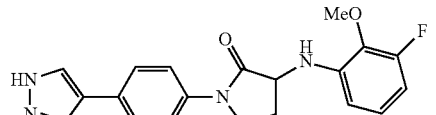<br>Enantiomer-I<br>1-(4-(1H-pyrazol-4-yl)phenyl)-3-((3-fluoro-2-methoxyphenyl)amino)pyrrolidin-2-one (Enantiomer-I) | 367.2 | A: 9.778, 99.39%<br>B: 9.195, 99.73% | $^1$H NMR (400 MHz, DMSO-d$_6$) δ ppm 12.91 (br. s., 1 H) 8.05 (s, 2 H) 7.68-7.73 (m, 2 H) 7.61-7.66 (m, 2 H) 6.86-6.93 (m, 1 H) 6.60 (d, J = 8.35 Hz, 1 H) 6.48 (ddd, J = 10.96, 8.36, 1.25 Hz, 1 H) 5.60 (d, J = 7.03 Hz, 1 H) 4.42 (dt, J = 10.07, 7.80 Hz, 1 H) 3.81-3.87 (m, 2 H) 3.79 (s, 3 H) 2.57-2.65 (m,1 H) 1.99-2.10 (m, 1 H). $^{19}$F NMR (376 MHz, DMSO-d$_6$) δ ppm −132.929, 100% ee with Chiral HPLC RT = 4.35 min (Method VII), [α]$^{25.0}_D$ = +10.0 (c 0.1, THF). |
| 16 | 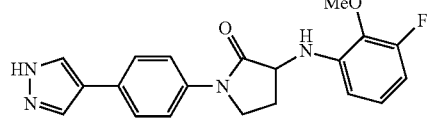<br>Enantiomer-II<br>1-(4-(1H-pyrazol-4-yl)phenyl)-3-((3-fluoro-2-methoxyphenyl)amino)pyrrolidin-2-one (Enantiomer-2) | 367.2 | A: 9.703, 99.48%<br>B: 9.172, 99.35% | $^1$H NMR (400 MHz, DMSO-d$_6$) δ ppm 12.91 (br. s., 1 H) 7.92 (s, 1 H) 7.72 (s, 1 H) 7.68-7.73 (m, 2 H) 7.61-7.66 (m, 2 H) 6.89 (td, J = 8.25, 6.15 Hz, 1 H) 6.60 (d, J = 8.41 Hz, 1 H) 6.48 (ddd, J = 11.00, 8.36, 1.29 Hz, 1 H) 5.60 (d, J = 7.03 Hz, 1 H) 4.38-4.46 (m, 1 H) 3.81-3.87 (m, 2 H) 3.80 (s, 3 H) 2.58-2.65 (m, 1 H) 1.98-2.10 (m, 1 H). $^{19}$F NMR (376 MHz, DMSO-d$_6$) δ ppm −132.930, 100% ee with Chiral HPLC RT =3.78 min (Method VII), [α]$^{24.9}_D$ = −12.0 (c 0.1, THF). |
| 17 | 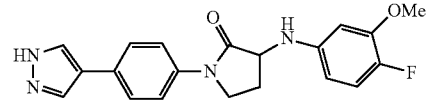 [SMILES: COc1cc(NC2CCN(c3ccc(-c4cn[nH]c4)cc3)C2=O)ccc1F]<br>Enantiomer-I<br>1-(4-(1H-pyrazol-4-yl)phenyl)-3-((4-fluoro-3-methoxyphenyl)amino)pyrrolidin-2-one (Enantiomer-1) | 367.2 | A: 8.891, 99.31%<br>B: 8.519, 99.35% | $^1$H NMR (400 MHz, DMSO-d$_6$) δ ppm 12.91 (br. s., 1 H) 8.16 (s, 1 H) 7.91 (s, 1 H) 7.67-7.72 (m, 2 H) 7.61-7.65 (m, 2 H) 6.91 (dd, J = 11.55, 8.78 Hz, 1 H) 6.53 (dd, J = 7.47, 2.70 Hz, 1 H) 6.20 (dt, J = 8.75, 3.06 Hz, 1 H) 5.85 (d, J = 6.96 Hz, 1 H) 4.31-4.38 (m, 1 H) 3.80-3.86 (m, 2 H) 3.76 (s, 3 H) 2.57-2.65 (m, 1 H) 1.82-1.93 (m, 1 H). $^{19}$F NMR (376 MHz, DMSO-d$_6$) δ ppm −150.915, 100% ee with Chiral HPLC RT = 6.73 min (Method V). [α]$^{25.0}_D$ = +20.0 (c 0.1, THF). |
| 18 | 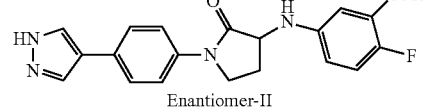<br>Enantiomer-II<br>1-(4-(1H-pyrazol-4-yl)phenyl)-3-((4-fluoro-3-methoxyphenyl)amino)pyrrolidin-2-one (Enantiomer-2) | 367.2 | A: 8.895, 99.73%<br>B: 8.513, 99.58% | $^1$H NMR (400 MHz, DMSO-d$_6$) δ ppm 12.91 (br. s., 1 H) 8.11 (s, 1 H) 7.99 (s, 1 H) 7.67-7.72 (m, 2 H) 7.60-7.66 (m, 2 H) 6.91 (dd, J = 11.51, 8.75 Hz, 1 H) 6.53 (dd, J = 7.62, 2.60 Hz, 1 H) 6.20 (dt, J = 8.66, 3.04 Hz, 1 H) 5.85 (d, J = 6.84 Hz, 1 H) 4.31-4.39 (m, 1 H) 3.80-3.86 (m, 2 H) 3.76 (s, 3 H) 2.57-2.66 (m, 1 H) 1.88 (dd, J = 12.20, 9.76 Hz, 1 H). $^{19}$F NMR (376 MHz, DMSO-d$_6$) δ ppm −150.915, 100% ee with Chiral HPLC RT = 7.97 min (Method V). [α]$^{24.9}_D$ = −12.0 (c 0.1,THF). |
| 19 | 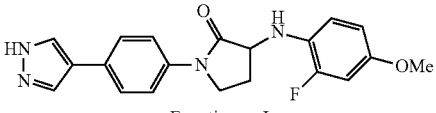<br>Enantiomer-I<br>1-(4-(1H-pyrazol-4-yl)phenyl)-3-((2-fluoro-4-methoxyphenyl)amino)pyrrolidin-2-one (Enantiomer-1) | 367.2 | E: 1.481, 98.93%<br>F: 1.444, 99.72% | $^1$H NMR (400 MHz. DMSO-d$_6$) δ ppm 12.92 (br. s., 1 H) 8.17 (br. s., 1 H) 7.91 (br. s., 1 H) 7.67-7.72 (m, 2 H) 7.60-7.66 (m, 2 H) 6.86 (t, J = 9.54 Hz, 1 H) 6.78 (dd, J = 13.36, 2.76 Hz, 1 H) 6.62 (dd, J = 8.75, 2.35 Hz, 1 H) 5.14-5.19 (m, 1 H) 4.30-4.38 (m, 2 H) 3.77-3.86 (m, 2 H) 3.68 (s, 3 H) 2.53-2.62 (m, 1 H) 1.95-2.07 (m, 1 H). $^{19}$F NMR (376 MHz, DMSO-d$_6$) δ ppm −131.048, 100% ee with Chiral HPLC RT = 5.11 min (Method V), [α]$^{24.8}_D$ = −32.0 (c 0.1, THF). |

TABLE 2-continued

| Ex. | Structure and Name | LCMS (M + H)+ | HPLC Method, RT (min) & Purity | NMR |
|---|---|---|---|---|
| 20 | 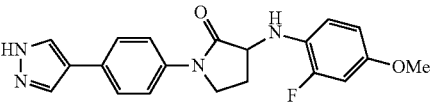 [SMILES: COc1ccc(NC2CCN(c3ccc(-c4cn[nH]c4)cc3)C2=O)c(F)c1]<br>Enantiomer-II<br>1-(4-(1H-pyrazol-4-yl)phenyl)-3-((2-fluoro-4-methoxyphenyl)amino)pyrrolidin-2-one<br>(Enantiomer-2) | 367.2 | A: 8.879, 99.43%<br>B: 8.610, 99.77% | $^1$H NMR (400 MHz, DMSO-$d_6$) δ ppm 12.92 (s, 1 H) 8.17 (s, 1 H) 7.91 (s, 1 H) 7.67-7.72 (m, 2 H) 7.60-7.66 (m, 2 H) 6.83-6.90 (m, 1 H) 6.78 (dd, J = 13.40, 2.79 Hz, 1 H) 6.62 (dd, J = 8.75, 1.79 Hz, 1 H) 5.17 (dd, J = 7.15, 1.76 Hz, 1 H) 4.34 (dt, J = 9.88, 7.89 Hz, 1 H) 3.77-3.86 (m, 2 H) 3.68 (s, 3 H) 2.53-2.62 (m, 1 H) 1.95-2.07 (m, 1 H). $^{19}$F NMR (376 MHz, DMSO-$d_6$) δ ppm −131.053, 100% ee with Chiral HPLC RT = 3.31 min (Method IV). $[α]^{24.8}_D$ = +4.0 (c 0.1, THF). |
| 21 | 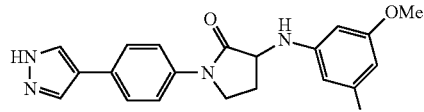<br>Enantiomer-I<br>1-(4-(1H-pyrazol-4-yl)phenyl)-3-((3,5-dimethoxyphenyl)amino)pyrrolidin-2-one<br>(Enantiomer-1) | 379.2 | A: 9.200, 99.76%<br>B: 8.437, 99.98% | $^1$H NMR (400 MHz, DMSO-$d_6$) δ ppm 12.92 (s, 1 H) 8.05 (s, 2 H) 7.66-7.72 (m, 2 H) 7.61-7.66 (m, 2 H) 5.89-5.96 (m, 3 H) 5.77 (t, J = 2.10 Hz, 1 H) 4.35 (dt, J = 9.55, 7.80 Hz, 1 H) 3.77-3.86 (m, 2 H) 3.66 (s, 6 H) 2.54-2.63 (m, 1 H) 1.81-1.93 (m, 1 H), 100% ee with Chiral HPLC RT = 5.36 min (Method VII), $[α]^{24.8}_D$ = +22.0 (c 0.1, THF). |
| 22 | 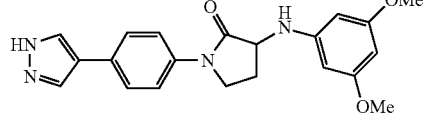<br>Enantiomer-II<br>1-(4-(1H-pyrazol-4-yl)phenyl)-3-((3,5-dimethoxyphenyl)amino)pyrrolidin-2-one<br>(Enantiomer-2) | 379.2 | A: 8.900, 99.73%<br>B: 8.434, 99.85% | $^1$H NMR (400 MHz, DMSO-$d_6$) δ ppm 12.92 (s, 1 H) 8.17 (br.s., 1 H) 7.91 (br. s., 1 H) 7.67-7.72 (m, 2 H) 7.61-7.66 (m, 2H) 5.89-5.96 (m, 3 H) 5.77 (t, J = 2.10 Hz, 1 H) 4.35 (dt, J = 9.55, 7.80 Hz, 1 H) 3.79-3.85 (m, 2 H) 3.66 (s, 6 H) 2.55-2.63 (m, 1 H) 1.81-1.93 (m, 1 H), 98.88% ee with Chiral HPLC RT = 3.99 min (Method VII), $[α]^{24.8}_D$ = −34.0 (c 0.1, THF). |
| 23 | 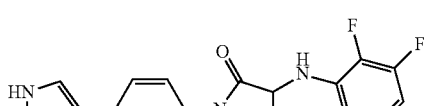<br>Enantiomer-II<br>1-(4-(1H-pyrazol-4-yl)phenyl)-3-((2,3-difluorophenyl)amino)pyrrolidin-2-one<br>(Enantiomer-2) | 355.2 | E: 1.590, 98.31%<br>F: 1.610, 97.93% | $^1$H NMR (400 MHz, DMSO-$d_6$) δ ppm 12.91 (s, 1 H) 8.16 (s, 1 H) 7.91 (br. s., 1 H) 7.67-7.72 (m, 2 H) 7.60-7.66 (m, 2 H) 6.91-6.99 (m, 1 H) 6.74 (t, J = 8.06 Hz, 1 H) 6.53-6.62 (m, 1 H) 6.08 (d, J = 1.69 Hz, 1 H) 4.50-4.58 (m, 1 H) 3.79-3.86 (m, 2 H) 2.54-2.59 (m, 1 H) 2.03-2.15 (m, 1 H). $^{19}$F NMR (376 MHz, DMSO-$d_6$) δ ppm −140.731 and −160.841, 98.80% ee with Chiral HPLC RT = 7.92 min (Method VII). |
| 24 | 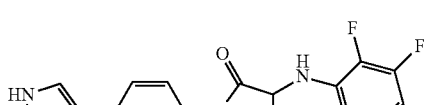<br>Enantiomer-I<br>1-(4-(1H-pyrazol-4-yl)phenyl)-3-((2,4-difluorophenyl)amino)pyrrolidin-2-one<br>(Enantiomer-1) | 355.2 | E: 1.567, 100.0%<br>F: 1.586, 97.49% | $^1$H NMR (400 MHz, DMSO-$d_6$) δ ppm 12.91 (s, 1 H) 8.17 (s, 1 H) 7.91 (s, 1 H) 7.67-7.72 (m, 2 H) 7.60-7.66 (m, 2 H) 7.11 (ddd, J = 11.87, 8.96, 2.70 Hz, 1 H) 6.84-6.96 (m, 2 H) 5.56 (dd, J = 7.72, 2.13 Hz, 1 H) 4.41-4.49 (m, 1 H) 3.79-3.86 (m, 2 H) 2.54-2.60 (m, 1 H) 1.99-2.11 (m, 1 H). $^{19}$F NMR (376 MHz, DMSO-$d_6$) δ ppm −126.595 and −129.746, 98.09% ee with Chiral HPLC RT = 7.00 min (Method VII). |
| 25 | 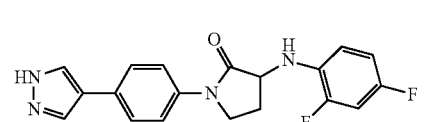<br>Enantiomer-II<br>1-(4-(1H-pyrazol-4-yl)phenyl)-3-((2,4-difluorophenyl)amino)pyrrolidin-2-one<br>(Enantiomer-2) | 355.2 | E: 1.545, 100.0%<br>F: 1.533, 100.0% | $^1$H NMR (400 MHz, DMSO-$d_6$) δ ppm 12.91 (s, 1 H) 8.17 (s,1 H) 7.91 (s, 1 H) 7.67-7.72 (m, 2 H) 7.60-7.66 (m, 2 H) 7.11 (ddd, J = 11.81, 9.15, 2.64 Hz, 1 H) 6.84-6.96 (m, 2 H) 5.56 (d, J = 7.22 Hz, 1 H) 4.40-4.49 (m, 1 H) 3.79-3.86 (m, 2 H)2.54-2.61 (m, 1 H) 1.99-2.11 (m, 1 H). $^{19}$F NMR (376 MHz, DMSO-$d_6$) δ ppm −126.590 and −129.746. 100% ee with Chiral HPLC RT = 3.29 min (Method VII). |

TABLE 2-continued

| Ex. | Structure and Name | LCMS (M + H)+ | HPLC Method, RT (min) & Purity | NMR |
|---|---|---|---|---|
| 26 | 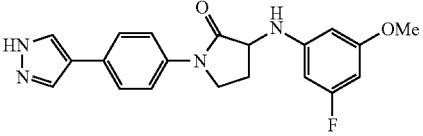 [SMILES: COc1cc(F)cc(NC2CCN(c3ccc(-c4cn[nH]c4)cc3)C2=O)c1]<br>Enantiomer-1<br>1-(4-(1H-pyrazol-4-yl)phenyl)-3-((3-fluoro-5-methoxyphenyl)amino)pyrrolidin-2-one as Enatiomer-1 | 367.2 | A: 9.35, 99.2%<br>B: 9.044, 99.4% | $^1$H NMR (400 MHz, DMSO-d$_6$) δ ppm 12.92 (s, 1 H) 8.04 (s, 2 H) 7.67-7.73 (m, 2 H) 7.62-7.66 (m, 2 H) 6.30 (d, J = 7.09 Hz, 1 H) 6.11-6.17 (m, 2 H) 6.00 (dt, J = 11.15, 2.17 Hz, 1 H) 4.41 (dt, J = 9.79, 7.81 Hz, 1 H) 3.78-3.89 (m, 2 H) 3.70 (s, 3 H) 2.55-2.65 (m, 1 H) 1.88 (dq, J = 12.16, 9.48 Hz, 1 H). $^{19}$F NMR (376 MHz, DMSO-d$_6$) δ ppm −112.814; 100% ee with Chiral HPLC RT = 5.59 min (Method III), [α]$^{25.2}_D$ = −22.4 (c 0.1, MeOH). |
| 27 | 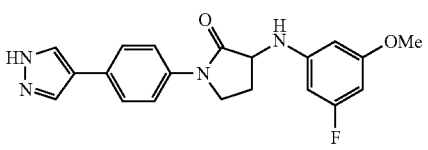 [SMILES: COc1cc(F)cc(NC2CCN(c3ccc(-c4cn[nH]c4)cc3)C2=O)c1]<br>Enantiomer-2<br>1-(4-(1H-pyrazol-4-yl)phenyl)-3-((3-fluoro-5-methoxyphenyl)amino)pyrrolidin-2-one as Enantiomer-II | 367.2 | A: 9.34, 95.2%<br>B: 9.01, 96.0% | $^1$H NMR (400 MHz, DMSO-d$_6$) δ ppm 12.93 (s, 1 H) 8.17 (s,1 H) 7.92 (s, 1 H) 7.67-7.73 (m, 2 H) 7.61-7.66 (m, 2 H) 6.30 (d, J = 7.28 Hz, 1 H) 6.11-6.18 (m, 2 H) 6.00 (dt, J = 11.11, 2.20 Hz, 1 H) 4.41 (dt, J = 9.74, 7.84 Hz, 1 H) 3.80-3.86 (m, 2 H) 3.70 (s, 3 H) 2.56-2.66 (m, 1 H) 1.82-1.94 (m, 1 H). $^{19}$F NMR (376 MHz, DMSO-d$_6$) δ ppm −112.564; 100% ee with Chiral HPLC RT = 8.83 min (Method III), [α]$^{25.1}_D$ = +16.0 (c 0.1, MeOH). |
| 28 | 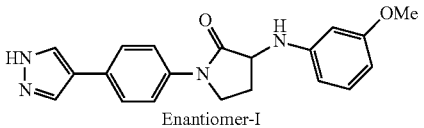<br>Enantiomer-I<br>1-(4-(1H-pyrazol-4-yl)phenyl)-3-((3-methoxyphenyl)amino)pyrrolidin-2-one | 349.2 | A: 8.738, 99.09%<br>B: 8.526, 99.44% | $^1$H NMR (400 MHz, DMSO-d$_6$) δ ppm 12.93 (s, 1 H) 8.05 (s, 2 H) 7.67-7.73 (m, 2 H) 7.61-7.66 (m, 2 H) 6.99 (t, J = 8.03 Hz,1 H) 6.28-6.35 (m, 2 H) 6.18 (ddd, J = 8.09, 2.26, 0.75 Hz, 1 H) 5.92 (d, J = 7.09 Hz, 1 H) 4.33-4.42 (m, 1 H) 3.81-3.87(m, 2 H) 3.69 (s, 3 H) 2.56-2.65 (m, 1 H) 1.90 (dq, J = 12.06, 9.45 Hz, 1 H), 97.54% ee with Chiral HPLC RT = 7.32 min (Method IV), [α]$^{25.0}_D$ = +4.0 (c 0.05, MeOH). |
| 29 | 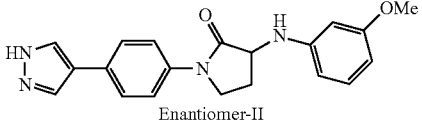<br>Enantiomer-II<br>1-(4-(1H-pyrazol-4-yl)phenyl)-3-((3-methoxyphenyl)amino)pyrrolidin-2-one | 349.2 | A: 8.481, 98.85%<br>B: 8.696, 98.54% | $^1$H NMR (400 MHz, DMSO-d$_6$) δ ppm 12.93 (s, 1 H) 8.12 (s, 1 H) 7.90 (s, 1 H) 7.68-7.74 (m, 2 H) 7.61-7.67 (m, 2 H) 6.99 (t, J = 8.00 Hz, 1 H) 6.28-6.34 (m, 2 H) 6.15-6.21 (m, 1 H) 5.94 (d, J = 7.03 Hz, 1 H) 4.37 (dt, J = 9.52, 7.82 Hz, 1 H)3.80-3.88 (m, 2 H) 3.69 (s, 3 H) 2.56-2.65 (m, 1 H) 1.89 (dq, J = 12.12, 9.51 Hz, 1 H), 100% ee with Chiral HPLC RT = 9.17 min (Method IV), [α]$^{24.8}_D$ = −16.0 (c 0.05, MeOH). |
| 30 | 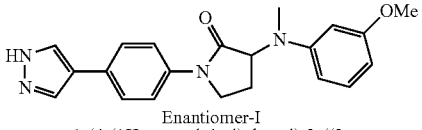<br>Enantiomer-I<br>1-(4-(1H-pyrazol-4-yl)phenyl)-3-((3-methoxyphenyl)(methyl)amino)pyrrolidin-2-one | 363.2 | A: 9.226, 99.16%<br>B: 8.980, 98.91% | $^1$H NMR (400 MHz, DMSO-d$_6$) δ ppm 12.92 (br. s., 1 H) 8.08 (s. 2 H) 7.67-7.73 (m, 2 H) 7.61-7.66 (m, 2 H) 7.09 (t, J = 8.22 Hz, 1 H) 6.46 (dd. J = 8.19, 2.05 Hz, 1 H) 6.38 (t, J = 2.31 Hz, 1 H) 6.28 (dd, J = 8.05, 2.01 Hz, 1 H) 4.98 (t, J = 9.63 Hz, 1 H) 3.79-3.87 (m, 2 H) 3.72 (s, 3 H) 2.78 (s, 3 H) 2.34-2.47 (m, 1 H) 2.05-2.17 (m, 1 H), 100% ee with Chiral HPLC RT = 4.78 min (Method V). |
| 31 | 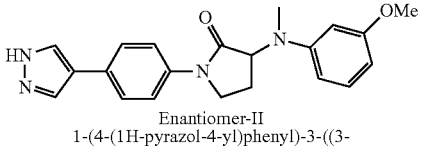<br>Enantiomer-II<br>1-(4-(1H-pyrazol-4-yl)phenyl)-3-((3-methoxyphenyl)(methyl)amino)pyrrolidin-2-one | 363.2 | A: 9.220, 97.77%<br>B: 8.977, 97.88% | $^1$H NMR (400 MHz, DMSO-d$_6$) δ ppm 12.91 (br. s., 1 H) 8.15 (s, 1 H) 8.03 (s, 1 H) 7.68-7.74 (m, 2 H) 7.62-7.67 (m, 2 H) 7.10 (t, J = 8.22 Hz, 1 H) 6.47 (dd, J = 8,22, 2.26 Hz, 1 H) 6.39 (t, J = 2.32 Hz, 1 H) 6.29 (dd, J = 8.06, 1.98 Hz, 1 H) 4.99 (dd, J = 10.20, 9.00 Hz, 1 H) 3.81-3.87 (m, 2 H) 3.73 (s, 3 H) 2.79 (s, 3 H) 2.36-2.45 (m, 1 H) 2.05-2.16 (m, 1 H), 100% ee with Chiral HPLC RT = 8.50 min (Method V). |
| 32 | 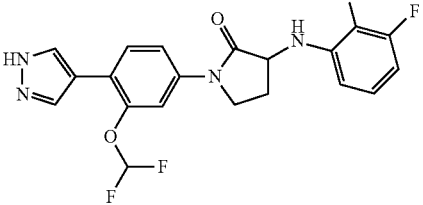<br>Enantiomer-I<br>1-(3-(difluoromethoxy)-4-(1H-pyrazol-4-yl)phenyl)-3-((3-fluoro-2-methoxyphenyl)amino)pyrrolidin-2-one | 433.0 | A: 16.50, 97.52%<br>B: 15.64, 96.50% | $^1$H NMR ($^1$H NMR (400 MHz, DMSO-d$_6$) δ 13.03 (br. s., 1 H), 8.16-7.89 (m, 2 H), 7.88-7.73 (m, 2 H), 7.55-7.46 (m, 1 H), 7.43-7.01 (m, 1 H), 6.89 (dt, J = 6.0, 8.3 Hz, 1 H), 6.62 (s, 1 H), 6.54-6.42 (m, 1 H), 5.63 (d, J = 7.0 Hz, 1 H), 4.52-4.42 (m, 1 H), 3.92-3.82 (m, 2 H), 3.80 (s, 3 H), 2.70-2.57 (m, 1 H), 2.14-1.99 (m, 1 H); $^{19}$F NMR (376 MHz, DMSO-d$_6$) δ−80.588, −132.920: 99.1% ee with Chiral HPLC RT = 10.97 min (Method IV). [α]$^{24.9}_D$ = −8.0 (c 0.1, MeOH). |

TABLE 2-continued

| Ex. | Structure and Name | LCMS (M + H)+ | HPLC Method, RT (min) & Purity | NMR |
|---|---|---|---|---|
| 33 | 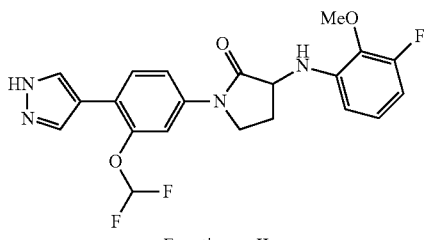<br>Enantiomer-II<br>1-(3-(difluoromethoxy)-4-(1H-pyrazol-4-yl)phenyl)-3-((3-fluoro-2-methoxyphenl)amino)pyrrolidin-2-one | 433.0 | A: 16.54, 98.12%<br>B: 15.67, 98.18% | $^1$H NMR $^1$H NMR ($^1$H NMR (400 MHz, DMSO-d$_6$) δ 13.03 (br. s., 1 H), 8.16-7.89 (m, 2 H), 7.88-7.73 (m, 2 H), 7.55-7.46 (m, 1 H), 7.43-7.01 (m, 1 H), 6.89 (dt, J = 6.0, 8.3 Hz, 1 H), 6.62 (s, 1 H), 6.54-6.42 (m, 1 H), 5.63 (d, J = 7.0 Hz, 1 H), 4.52-4.42 (m, 1 H), 3.92-3.82 (m, 2 H), 3.80 (s, 3 H), 2.70-2.57 (m, 1 H), 2.14-1.99 (m, 1 H); $^{19}$F NMR (376 MHz, DMSO-d$_6$) δ −80.588, −132.92; 99.1% ee with Chiral HPLC RT = 12.63 min (Method IV), $[α]^{25}_D$ = +8.0 (c 0.1, MeOH). |
| 34 | 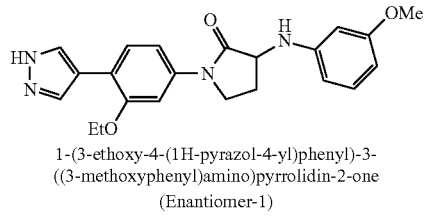<br>1-(3-ethoxy-4-(1H-pyrazol-4-yl)phenyl)-3-((3-methoxyphenyl)amino)pyrrolidin-2-one (Enantiomer-1) | 393.2 | A: 9.35, 98.99%<br>B: 9.05, 99.67% | $^1$H NMR (400 MHz, DMSO-d$_6$) δ ppm 12.84 (s, 1 H), 8.04 (br. s., 2 H), 7.67-7.59 (m, 2 H), 7.17 (dd, J = 1.7, 8.5 Hz, 1 H), 6.99 (t, J = 8.0 Hz, 1 H), 6.35-6.27 (m, 2 H), 6.20-6.15 (m, 1 H), 5.93 (d, J = 7.1 Hz, 1 H), 4.42-4.33 (m, 1 H), 4.11 (q, J = 7.0 Hz, 2 H), 3.90-3.79 (m, 2 H), 3.68 (s, 3 H), 2.65-2.55 (m, 1 H), 1.95-1.84 (m, 1 H), 1.44 (t, J = 6.9 Hz, 3 H); 99.52% ee with Chiral HPLC RT = 8.57 min (Method IV), $[α]^{24.9}_D$ = −4.0 (c 0.1, MeOH). |
| 35 | 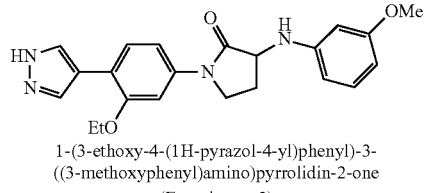<br>1-(3-ethoxy-4-(1H-pyrazol-4-yl)phenyl)-3-((3-methoxyphenyl)amino)pyrrolidin-2-one (Enantiomer-2) | 393.2 | A: 9.36, 98.16%<br>B: 9.05, 99.25% | $^1$H NMR (400 MHz, DMSO-d$_6$) δ ppm 12.84 (s. 1 H), 8.04 (br. s., 2 H), 7.66-7.59 (m, 2 H), 7.16 (dd, J = 1.7, 8.5 Hz, 1 H), 6.98 (t, J = 8.0 Hz, 1 H), 6.34-6.26 (m, 2 H), 6.17 (d, J = 8.1 Hz, 1 H), 5.93 (d, J = 6.9 Hz, 1 H), 4.43-4.34 (m, 1 H), 4.11 (q, J = 7.0 Hz, 2 H), 3.88-3.79 (m, 2 H), 3.68 (s, 3 H), 2.64-2.55 (m, 1 H), 1.96-1.82 (m, 1 H), 1.44 (t, J = 6.8 Hz, 3 H); 97.68% ee with Chiral HPLC RT = 12.32 min (Method IV), $[α]^{24.9}_D$ = +4.0 (c 0.1, MeOH). |
| 36 | 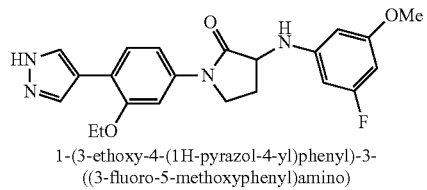<br>1-(3-ethoxy-4-(1H-pyrazol-4-yl)phenyl)-3-((3-fluoro-5-methoxyphenyl)amino)pyrrolidin-2-one (Enantiomer-1) | 411.0 | A: 9.85, 99.31%<br>B: 7.77, 94.80% | $^1$H NMR (400 MHz, DMSO-d$_6$) δ ppm 12.85 (s, 1 H), 8.12 (br.s., 1 H), 7.98 (br. s., 1 H), 7.66-7.58 (m, 2 H), 7.16 (dd, J = 2.0, 8.5 Hz, 1 H), 6.30 (d, J = 7.3 Hz, 1 H), 6.17-6.09 (m, 2 H), 6.03-5.97 (m, 1 H), 4.46-4.38 (m, 1 H), 4.11 (q, J = 6.9 Hz, 2 H), 3.89-3.78 (m, 2 H), 3.69 (s, 3 H), 2.64-2.55 (m, 1 H), 1.94-1.83 (m, 1 H), 1.44 (t, J = 6.9 Hz, 3 H); $^{19}$F NMR (376 MHz, DMSO-d$_6$) δ ppm −112.57; 100% ee with Chiral HPLC RT = 5.01 min (Method IV), $[α]^{24.9}_D$ = −20.0 (c 0.1, MeOH). |
| 37 | 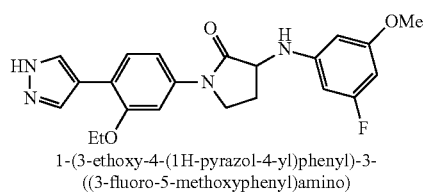<br>1-(3-ethoxy-4-(1H-pyrazol-4-yl)phenyl)-3-((3-fluoro-5-methoxyphenyl)amino)pyrrolidin-2-one (Enantiomer-2) | 411.0 | A: 9.86, 98.22%<br>B: 7.70, 95.54% | $^1$H NMR (400 MHz, DMSO-d$_6$) δ ppm 12.85 (s, 1 H), 8.05 (br.s., 2 H), 7.67-7.60 (m, 2 H), 7.17 (dd, J = 2.1, 8.5 Hz, 1 H), 6.30 (d, J = 7.1 Hz, 1 H), 6.18-6.11 (m, 2 H), 6.04-5.98 (m, 1 H), 4.47-4.38 (m, 1 H), 4.12 (q, J = 6.9 Hz, 2 H), 3.90-3.80 (m, 2 H), 3.70 (s, 3 H), 2.66-2.59 (m, 1 H), 1.93-1.83(m, 1 H), 1.45 (t, J = 6.9 Hz, 3 H); $^{19}$F NMR (376 MHz, DMSO-d$_6$) δ ppm −112.57; 98.66% ee with Chiral HPLC RT = 8.21 min (Method IV), $[α]^{24.9}_D$ = +20.0 (c 0.1, MeOH). |
| 38 | 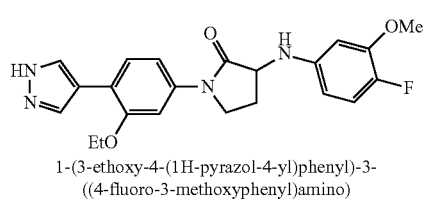<br>1-(3-ethoxy-4-(1H-pyrazol-4-yl)phenyl)-3-((4-fluoro-3-methoxyphenyl)amino)pyrrolidin-2-one (Enantiomer-1) | 411.5 | A: 9.22, 92.62%<br>B: 9.13, 97.75% | $^1$H NMR (400 MHz, DMSO-d$_6$) δ ppm 12.84 (s, 1 H), 8.11 (br.s., 1 H), 7.97 (br. s., 1 H), 7.66-7.58 (m, 2 H), 7.17 (dd, J = 2.0, 8.5 Hz, 1 H), 6.91 (dd, J = 8.8, 11.5 Hz, 1 H), 6.53 (dd, J = 2.5, 7.6 Hz, 1 H), 6.24-6.18 (m, 1 H), 5.85 (d, J = 7.0 Hz, 1 H), 4.41-4.32 (m, 1 H), 4.11 (q, J = 6.9 Hz, 2 H), 3.90-3.79 (m, 2 H), 3.77 (s, 3 H), 2.66-2.55 (m, 1 H), 1.96-1.83 (m, 1 H), 1.44 (t, J = 6.9 Hz, 3 H); $^{19}$F NMR (376 MHz, DMSO-d$_6$) δ ppm −150.89; 99.68% ee with Chiral HPLC RT = 7.18 min (Method IV), $[α]^{24.9}_D$ = −8.0 (c 0.1, MeOH). |

TABLE 2-continued

| Ex. | Structure and Name | LCMS (M + H)+ | HPLC Method, RT (min) & Purity | NMR |
|---|---|---|---|---|
| 39 | 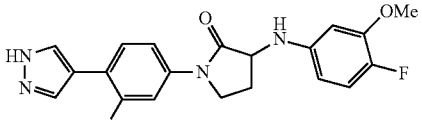<br>1-(3-ethoxy-4-(1H-pyrazol-4-yl)phenyl)-3-((4-fluoro-3-methoxyphenyl)amino)pyrrolidin-2-one (Enantiomer-2) | 411.3 | A: 9.19, 96.20%<br>B: 9.12, 93.68% | $^1$H NMR (400 MHz, DMSO-d$_6$) δ ppm 12.84 (s, 1 H), 8.05 (br.s., 2 H), 7.67-7.59 (m, 2 H), 7.18 (dd, J = 2.1, 8.5 Hz, 1 H), 6.92 (dd, J = 8.8, 11.5 Hz, 1 H), 6.54 (dd, J = 2.7, 7.6 Hz, 1 H), 6.24-6.19 (m, 1 H), 5.85 (d, J = 7.0 Hz, 1 H), 4.42-4.33 (m, 1 H), 4.11 (q, J = 6.9 Hz, 2 H), 3.90-3.80 (m, 2 H), 3.77 (s, 3 H), 2.66-2.57 (m, 1 H), 1.96-1.84 (m, 1 H), 1.45 (t, J = 7.0 Hz, 3 H). $^{19}$F NMR (376 MHz, DMSO-d$_6$) δ ppm −150.86; 98.42% ee with Chiral HPLC RT = 10.46 min (Method IV), [α]$^{24.9}_D$ = +4.0 (c 0.1, MeOH). |
| 40 | 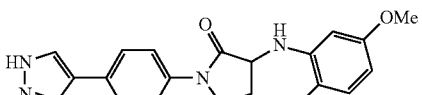<br>1-(3-ethoxy-4-(1H-pyrazol-4-yl)phenyl)-3-((2-fluoro-5-methoxyphenyl)amino)pyrrolidin-2-one (Enantiomer-1) | 411.0 | A: 9.69, 99.15%<br>B: 9.58, 99.50% | $^1$H NMR (400 MHz, DMSO-d$_6$) δ ppm 12.80 (br. s., 1 H), 8.04 (s, 2 H), 7.67-7.60 (m, 2 H), 7.16 (dd, J = 2.1, 8.5 Hz, 1 H), 6.95 (dd, J = 8.8, 11.6 Hz, 1 H), 6.46 (dd, J = 2.9, 7.5 Hz, 1 H), 6.18-6.10 (m, 1 H), 5.68 (dd. J = 2.1, 7.9 Hz, 1 H), 4.57-4.45 (m, 1 H), 4.10 (q, J = 7.1 Hz, 2 H), 3.91-3.77 (m, 2 H), 3.68 (s, 3 H), 2.60-2.53 (m, 1 H), 2.13-2.00 (m, 1 H), 1.44 (t, J = 6.9 Hz, 3 H); $^{19}$F NMR (376 MHz, DMSO-d$_6$) δ ppm −144.17; 99.18% ee with Chiral HPLC RT = 3.08 min (Method IV), [α]$^{24.9}_D$ = +30.0 (c 0.1, MeOH). |
| 41 | 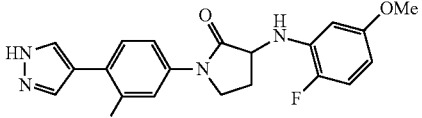<br>1-(3-ethoxy-4-(1H-pyrazol-4-yl)phenyl)-3-((2-fluoro-5-methoxyphenyl)amino)pyrrolidin-2-one (Enantiomer-2) | 411.0 | A: 9.67, 95.09%<br>B: 9.57, 95.39% | $^1$H NMR (400 MHz, DMSO-d$_6$) δ ppm 12.85 (s, 1 H), 8.04 (br. s., 2 H), 7.67-7.61 (m, 2 H), 7.17 (dd, J = 2.2, 8.5 Hz, 1 H), 6.96 (dd, J = 8.8, 11.7 Hz, 1 H), 6.47 (dd. J = 2.9, 7.7 Hz, 1 H), 6.18-6.10 (m, 1 H), 5.69-5.64 (m, 1 H), 4.54-4.46 (m, 1 H), 4.11 (q, J = 7.1 Hz, 2 H), 3.90-3.79 (m, 2 H), 3.69 (s, 3 H), 2.60-2.53 (m, 1 H), 2.12-2.02 (m, 1 H), 1.45 (t, J = 6.9 Hz, 3 H), $^{19}$F NMR (376 MHz, DMSO-d$_6$) δ ppm −144.17; 99.08% ee with Chiral HPLC RT = 5.37 min (Method IV), [α]$^{24.9}_D$ = −48.0 (c 0.1, MeOH). |
| 42 | 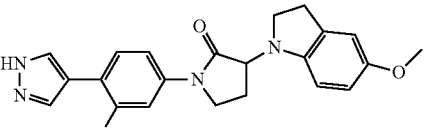<br>1-(4-(1H-pyrazol-4-yl)phenyl)-3-(5-methoxyindolin-1-yl)pyrrolidin-2-one | 375.2 | A: 8.105, 90.94%<br>B: 8.315, 88.87% | $^1$H NMR (400 MHz, DMSO-d$_6$) δ ppm 12.90 (br. s., 1 H) 8.16 (br. s., 1 H) 7.96 (br. s., 1 H) 7.66-7.70 (m, 2 H) 7.60-7.65 (m, 2 H) 6.73 (d, J = 2.57 Hz, 1 H) 6.57(m, 1 H) 6.45-6.49 (m, 1 H) 4.65 (t, J = 9.44 Hz, 1 H) 3.80-3.85 (m, 2 H) 3.65 (s, 3 H) 3.40-3.48 (m, 2 H) 2.88-2.93 (m, 3 H) 2.06-2.19 (m, 1 H); 99.24% ee with Chiral HPLC RT = 5.78 min (Method IV). [α]$^{20}_D$ = +12.0 (c 0.05, MeOH). |
| 43 | 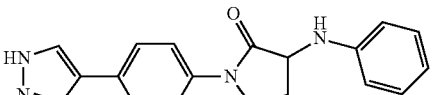<br>1-(3-fluoro-4-(1H-pyrazol-4-yl)phenyl)-3-(phenylamino)pyrrolidin-2-one | 337.2 | A: 8.905, 97.84%<br>B: 9.348, 99.45% | $^1$H NMR (400 MHz, DMSO-d$_6$) δ ppm 13.10 (s, 1 H) 8.15 (s, 1 H) 7.93 (s, 1 H) 7.73-7.80 (m, 2 H) 7.52 (dd, J = 8.63, 2.16 Hz, 1 H) 7.07-7.11 (m, 2 H) 6.71 (d, J = 7.72 Hz, 2 H) 6.58 (t, J = 7.28 Hz, 1 H) 5.91 (d, J = 7.15 Hz, 1 H) 4.37-4.45 (m, 1 H) 3.77-3.92 (m, 2 H) 2.56-2.64 (m, 1 H) 1.84-1.97 (m, 1 H); 99.10% ee with Chiral HPLC RT = 4.84 min (Method IV), [α]$^{20}_D$ = +4.8 (c 0.05, MeOH). |
| 44 | 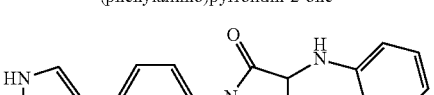<br>1-(3-fluoro-4-(1H-pyrazol-4-yl)phenyl)-3-(phenylamino)pyrrolidin-2-one | 337.2 | A: 8.907, 99.76%<br>B: 9.362, 99.37% | $^1$H NMR (400 MHz, DMSO-d$_6$) δ ppm 13.075 (s, 1 H) 8.145 (s, 1 H) 7.93 (s, 1 H) 7.73-7.80 (m, 2H) 7.52 (dd, J = 8.63, 2.10 Hz, 1 H) 7.09-7.12 (t, J = 7.91 Hz, 2 H) 6.71 (d, J = 7.72 Hz, 2 H) 6.58 (t, J = 7.31 Hz, 1 H) 5.91 (d, J = 7.09 Hz, 1 H) 4.35-4.45 (m, 1 H) 3.79-3.92 (m, 2 H) 2.58-2.64 (m, 1 H) 1.86-1.97 (m, 1 H); 98.10% ee with Chiral HPLC RT = 6.29 min (Method IV), [α]$^{20}_D$ = −12.0 (c 0.05, MeOH). |
| 45 | 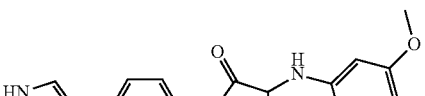<br>1-(3-fluoro-4-(1H-pyrazol-4-yl)phenyl)-3-((3-methoxyphenyl)amino)pyrrolidin-2-one | 367.0 | A: 8.857, 99.30%<br>B: 9.282, 99.21% | $^1$H NMR (400 MHz, DMSO-d$_6$) δ ppm 13.071 (s, 1 H) 8.15 (s, 1 H) 7.93 (s, 1 H) 7.72-7.80 (m, 2 H) 7.52 (dd, J = 8.69, 2.16 Hz, 1 H) 6.99 (t, J = 8.00 Hz, 1 H) 6.26-6.32 (m, 2 H) 6.17 (dd, J = 7.75, 1.98 Hz, 1 H) 5.94 (d, J = 7.28 Hz, 1 H) 4.36-4.45 (m, 1 H) 3.76-3.91 (m, 2 H) 3.68 (s, 3 H) 2.56-2.64 (m, 1 H) 1.82-1.96 (m, 1 H); 99.32% ee with Chiral HPLC RT = 5.27 min (Method IV), [α]$^{20}_D$ = −8.0 (c 0.05, MeOH). |

TABLE 2-continued

| Ex. | Structure and Name | LCMS (M + H)+ | HPLC Method, RT (min) & Purity | NMR |
|---|---|---|---|---|
| 46 | 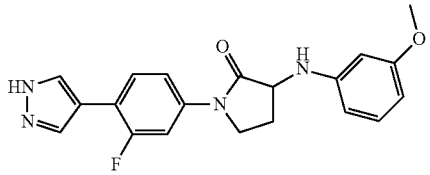 [SMILES: COc1cccc(NC2CCN(c3ccc(-c4cn[nH]c4)c(F)c3)C2=O)c1]

1-(3-fluoro-4-(1H-pyrazol-4-yl)phenyl)-3-((3-methoxyphenyl)amino)pyrrolidin-2-one | 367.0 | A: 8.859, 98.41% B: 9.287, 98.72% | $^1$H NMR (400 MHz, DMSO-d$_6$) δ ppm 13.08 (s, 1 H) 8.14 (s, 1 H) 7.93 (s, 1 H) 7.73-7.80 (m, 2 H) 7.52 (dd, J = 8.60, 2.20 Hz, 1 H) 6.99 (t, J = 8.00 Hz, 1 H) 6.27-6.33 (m, 2 H) 6.15-6.19 (m, 1 H) 5.94 (d, J = 7.34 Hz, 1 H) 4.37-4.45 (m, 1 H) 3.74-3.91 (m, 2 H) 3.68 (s, 3 H) 2.55-2.64 (m, 1 H) 1.84-1.96 (m, 1 H); 98.26% ee with Chiral HPLC RT = 6.71 min (Method IV), [α]$^{20}_D$ = +4.0 (c 0.05, MeOH). |
| 47 | 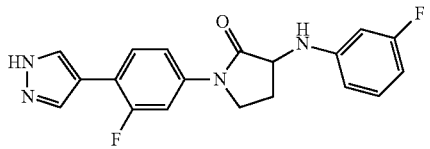 [SMILES: O=C1C(Nc2cccc(F)c2)CCN1c1ccc(-c2cn[nH]c2)c(F)c1]

1-(3-fluoro-4-(1H-pyrazol-4-yl)phenyl)-3-((3-fluorophenyl)amino)pyrrolidin-2-one | 355.0 | A: 9.287, 98.78% B: 9.748, 99.03% | $^1$H NMR (400 MHz, DMSO-d$_6$) δ ppm 13.07 (s, 1 H) 8.14 (br.s, 1 H) 7.93 (s, 1 H) 7.72-7.80 (m, 2 H) 7.52 (dd, J = 8.63, 2.16 Hz, 1 H) 7.04-7.13 (m, 1 H) 6.47-6.56 (m, 2 H) 6.28-6.38 (m, 2 H) 4.40-4.51 (m, 1 H) 3.77-3.92 (m, 2 H) 2.55-2.65 (m, 1 H) 1.84-1.96 (m, 1 H); 99.50% ee with Chiral HPLC RT = 4.01 min (Method IV), [α]$^{20}_D$ = -32.0 (c 0.05, MeOH). |
| 48 | 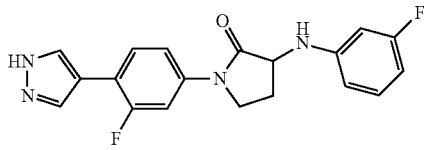 [SMILES: O=C1C(Nc2cccc(F)c2)CCN1c1ccc(-c2cn[nH]c2)c(F)c1]

1-(3-fluoro-4-(1H-pyrazol-4-yl)phenyl)-3-((3-fluorophenyl)amino)pyrrolidin-2-one | 355.2 | A: 9.328, 99.20% B: 9.816, 99.23% | $^1$H NMR (400 MHz, DMSO-d$_6$) δ ppm 13.07 (s, 1 H) 8.15 (br.s., 1 H) 7.93 (s, 1 H) 7.73-7.80 (m, 2 H) 7.52 (dd, J = 8.66, 2.20 Hz, 1 H) 7.05-7.13 (m, 1 H) 6.48-6.55 (m, 2 H) 6.30-6.37 (m, 2 H) 4.41-4.50 (m, 1 H) 3.76-3.92 (m, 2 H) 2.57-2.65 (m, 1 H) 1.84-1.96 (m, 1 H); $^{19}$F NMR (376 MHz, DMSO-d$_6$) δ ppm -113.332, -113.549; 97.26% ee with Chiral HPLC RT = 6.68 min (Method IV), [α]$^{20}_D$ = +12.0 (c 0.05, MeOH). |
| 49 | 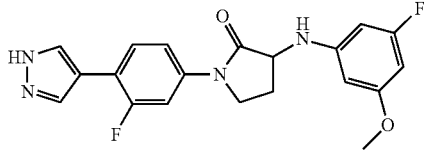 [SMILES: COc1cc(F)cc(NC2CCN(c3ccc(-c4cn[nH]c4)c(F)c3)C2=O)c1]

1-(3-fluoro-4-(1H-pyrazol-4-yl)phenyl)-3-((3-fluoro-5-methoxyphenyl)amino)pyrrolidin-2-one | 385.2 | A: 9.332, 99.34% B: 9.816, 99.46% | $^1$H NMR (400 MHz, DMSO-d$_6$) δ ppm 13.073 (s, 1 H) 8.15 (s, 1 H) 7.93 (s, 1 H) 7.72-7.80 (m, 2 H) 7.52 (dd, J = 8.69, 2.29 Hz, 1 H) 6.31 (d, J = 7.34 Hz, 1 H) 6.09-6.16 (m, 2 H) 5.97-6.01 (m, 1 H) 4.39-4.49 (m, 1H) 3.76-3.90 (m, 2H) 3.69 (s, 3 H) 2.57-2.64 (m, 2 H) 1.79-1.97 (m, 1 H); $^{19}$F NMR (376 MHz, DMSO-d$_6$) δ ppm -112.539, -113.550; 98.46% ee with Chiral HPLC RT = 4.18 min (Method IV), [α]$^{20}_D$ = -32.0 (c 0.05, MeOH). |
| 50 | 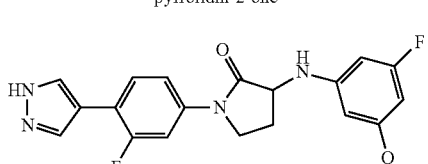

1-(3-fluoro-4-(1H-pyrazol-4-yl)phenyl)-3-((3-fluoro-5-methoxyphenyl)amino)pyrrolidin-2-one | 385.2 | A: 9.295, 98.79% B: 9.762, 98.93% | $^1$H NMR (400 MHz, DMSO-d$_6$) δ ppm 13.07 (br. s., 1 H) 8.15 (br. s., 1 H) 7.93 (br. s., 1 H) 7.69-7.81 (m, 2 H) 7.52 (dd, J = 8.56, 2.16 Hz, 1 H) 6.31 (d, J = 7.34 Hz, 1 H) 6.09-6.16 (m, 2 H) 5.99-6.01 (m, 1 H) 4.37-4.49 (m, 1 H) 3.74-3.91 (m, 2 H) 3.69 (s, 3 H) 2.56-2.64 (m, 1 H) 1.82-1.94 (m, 1 H); $^{19}$FNMR (376 MHz, DMSO-d$_6$) δ ppm -112.536, -113.549; 97.36% ee with Chiral HPLC RT = 6.58 min (Method IV), [α]$^{20}_D$ = +16.0 (c 0.05, MeOH). |
| 51 | 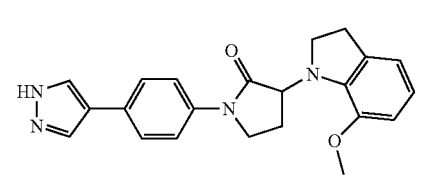 [SMILES: COc1cccc2c1N(C1CCN(c3ccc(-c4cn[nH]c4)cc3)C1=O)CC2]

1-(4-(1H-pyrazol-4-yl)phenyl)-3-(7-methoxyindolin-1-yl)pyrrolidin-2-one | 375.3 | C: 1.549, 97.01% D: 1.35, 100% | $^1$H NMR (400 MHz, DMSO-d$_6$) δ ppm 12.9 (s, 1 H) 8.15 (s, 1 H) 7.9 (s, 1 H) 7.65-7.70 (m, 1 H) 7.59-7.64 (m, 2 H) 6.68-6.75 (m, 2 H) 6.63 (d, J = 7.59 Hz, 1 H) 5.11-5.20 (m, 1 H) 3.76-3.85 (m, 2 H) 3.69 (s, 3 H) 3.51 (d, J = 1.32 Hz, 1 H) 3.25-3.30 (m, 1 H) 2.87-3.05 (m, 3 H) 2.07-2.28 (m, 1 H) 1.21-1.28 (m, 1 H); 92.04% ee with Chiral HPLC RT = 3.64 min (Method IV). |
| 52 | 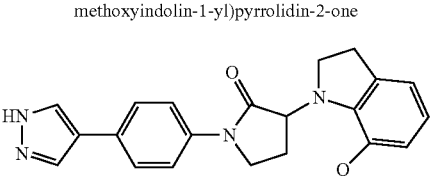

1-(4-(1H-pyrazol-4-yl)phenyl)-3-(7-methoxyindolin-1-yl)pyrrolidin-2-one | 375.3 | A: 8.370, 90.32% B: 8.399, 90.64% | $^1$H NMR (400 MHz, DMSO-d$_6$) δ ppm 12.9 (s, 1 H) 8.15 (s, 1 H) 7.9 (s, 1 H) 7.65-7.70 (m, 1 H) 7.59-7.64 (m, 2 H) 6.68-6.75 (m, 2 H) 6.63 (d, J = 7.59 Hz, 1 H) 5.11-5.20 (m, 1 H) 3.76-3.85 (m, 2 H) 3.69 (s, 3 H) 3.51 (d, J = 1.32 Hz, 1 H) 3.25-3.30 (m, 1 H) 2.87-3.05 (m, 3 H) 2.07-2.28 (m, 1 H) 1.21-1.28 (m, 1 H); 95.24% ee with Chiral HPLC RT = 4.41 min (Method IV); [α]$^{20}_D$ = -50.0 (c 0.05, MeOH). |

TABLE 2-continued

| Ex. | Structure and Name | LCMS (M + H)+ | HPLC Method, RT (min) & Purity | NMR |
|---|---|---|---|---|
| 53 | 1-(4-(1H-pyrazol-4-yl)phenyl)-3-((2,2-difluorobenzo[d][1,3]dioxol-5-yl)amino)pyrrolidin-2-one | 399.3 | A: 9.690, 95.30% B: 8.315, 92.21% | $^1$H NMR (400 MHz, DMSO-$d_6$) δ ppm 12.9 (s, 1 H) 8.20 (s, 1 H) 7.90 (s, 1H) 7.68-7.73 (m, 2 H) 7.61-7.66 (m, 2 H) 7.11 (d, J = 8.78 Hz, 1 H) 6.79 (d, J = 2.32 Hz, 1 H) 6.48 (dd, J = 8.78, 2.32 Hz, 1 H) 6.20 (d, J = 7.09 Hz, 1 H) 4.34-4.43 (m, 1 H) 3.76-3.89 (m, 2 H) 2.58-2.66 (m, 1 H) 1.82-1.95 (m, 1 H); 99.00% ee with Chiral HPLC RT = 5.08 min (Method IV); $[α]^{20}_D$ = −15.0 (c 0.05, MeOH). |
| 54 | 1-(4-(1H-pyrazol-4-yl)phenyl)-3-((2,2-difluorobenzo[d][1,3]dioxol-5-yl)amino)pyrrolidin-2-one | 399.2 | A: 9.690, 97.33% B: 9.920, 92.57% | $^1$H NMR (400 MHz, DMSO-$d_6$) δ ppm 12.9 (s, 1 H) 8.18 (s, 1 H) 7.92 (s, 1 H) 7.67-7.73 (m, 2H) 7.60-7.66 (m, 2 H) 7.11 (d, J = 8.72 Hz, 1 H) 6.79 (d, J = 2.26 Hz, 1 H) 6.48 (dd, J = 8.78, 2.26 Hz, 1 H) 6.20 (d, J = 7.09 Hz, 1 H) 4.33-4.43 (m, 1 H) 3.77-3.91 (m, 2 H) 2.66-2.69 (m, 1 H) 1.80-1.96 (m, 1 H); 97.74% ee with Chiral HPLC RT = 6.29 min (Method IV); $[α]^{20}_D$ = +32.0 (c 0.05, MeOH). |
| 55 | 3-((1H-benzo[d]imidazol-2-yl)amino)-1-(4-(1H-pyrazol-4-yl)phenyl)pyrrolidin-2-one | 359.2 | C: 1.026, 99.18% D: 0.86, 97.70% | $^1$H NMR (400 MHz, DMSO-$d_6$) δ ppm 12.93 (s, 1 H) 8.193 (s, 1 H) 7.93 (s, 1 H) 7.72-7.76 (m, 2 H) 7.65-7.71 (m, 2 H) 7.18 (d, J = 7.78 Hz, 1 H) 6.91-6.99 (m, 2 H) 6.81-6.87 (m, 1 H) 6.45 (s, 1 H) 5.49 (t, J = 10.04 Hz, 1 H) 4.04-4.12 (m, 1 H) 3.93-4.02 (m, 1 H) 3.14-3.19 (m, 1 H) 2.58-2.65 (m, 1 H) 2.41-2.47 (m, 1 H); 95.74% ee with Chiral HPLC RT = 6.29 min (Method IV). |
| 56 | 3-((1H-benzo[d]imidazol-2-yl)amino)-1-(4-(1H-pyrazol-4-yl)phenyl)pyrrolidin-2-one | 359.2 | C: 1.025, 99.08% D: 0.866, 97.54% | $^1$H NMR (400 MHz, DMSO-$d_6$) δ ppm 12.93 (s, 1 H) 8.193 (s, 1 H) 7.93 (s, 1 H) 7.71-7.76 (m, 2 H) 7.66-7.71 (m, 2 H) 7.18 (d, J = 7.72 Hz, 1 H) 6.89-6.99 (m, 2 H) 6.79-6.88 (m, 1 H) 6.45 (s, 2H) 5.49 (t, J = 10.04 Hz, 1 H) 4.04-4.12 (m, 1 H) 3.92-4.02 (m, 1 H) 2.58-2.65 (m, 1 H) 2.39-2.47 (m, 1 H); 66.10% ee with Chiral HPLC RT = 7.95 min (Method IV). |
| 106 | Enantiomer-I 1-[3-(difluoromethoxy)-4-(1H-pyrazol-4-yl)phenyl]-3-[(4-fluoro-3-methoxyphenyl)amino]pyrrolidin-2-one | 433.2 | A: 9.74, 99.3% B: 9.36, 98.9% | $^1$H NMR (400 MHz, DMSO-$d_6$) δ ppm 13.04 (br. s., 1 H), 8.02 (br. s., 2 H). 7.87-7.73 (m, 2 H), 7.49 (dd, J = 2.0, 8.5 Hz, 1 H), 7.22-7.04 (m, 1 H), 6.92 (dd, J = 9.0, 11.5 Hz, 1 H), 6.56-6.49 (m, 1 H), 6.24-6.16 (m, 1 H), 5.88 (d, J = 7.0 Hz, 1 H), 4.44-4.33 (m, 1 H), 3.91-3.80 (m, 2 H), 3.77 (s, 3 H), 2.69-2.57 (m, 1 H), 1.96-1.83 (m, 1 H); $^{19}$F NMR (376 MHz, DMSO-$d_6$) δ ppm −80.554, −150.833; 98.7% ee with Chiral HPLC RT = 6.33 min (Method IV); $[α]^{25.1}_D$ = +4.0 (c = 0.05, MeOH). |
| 107 | Enantiomer-II 1-[3-(difluoromethoxy)-4-(1H-pyrazol-4-yl)phenyl]-3-[(4-fluoro-3-methoxyphenyl)amino]pyrrolidin-2-one | 433.2 | A: 9.76, 99.2% B: 9.38, 99.0% | $^1$H NMR (400 MHz, DMSO-$d_6$) δ ppm 13.03 (br. s., 1 H), 7.97 (br. s., 2H), 7.86-7.73 (m, 2 H), 7.53-7.36 (m, 1 H), 7.25-6.82 (m, 2 H), 6.52 (dd, J = 2.5, 7.5 Hz, 1 H), 6.25-6.16 (m, 1 H), 5.88 (d, J = 6.5 Hz, 1 H), 4.44-4.34 (m, 1 H), 3.90-3.80 (m, 2 H), 3.77 (s, 3 H), 2.68-2.58 (m, 1 H), 1.95-1.82 (m, 1 H); $^{19}$F NMR (376 MHz, DMSO-$d_6$) δ ppm −80.555, −150.833; 96.7% ee with Chiral HPLC RT = 8.48 min (Method IV); $[α]^{25.1}_D$ = −8.0 (c = 0.05, MeOH). |
| 114 | Enantiomer-I 1-(3-(difluoromethoxy)-4-(1H-pyrazol-4-yl)phenyl)-3-((3-methoxyphenyl)amino)pyrrolidin-2-one | 415.2 | A: 9.76, 99.2% B: 9.37, 99.0% | $^1$H NMR (400 MHz, DMSO-$d_6$) δ ppm 13.04 (br. s., 1 H), 8.03 (br. s., 2 H), 7.89-7.71 (m, 2 H), 7.55-7.45 (m, 1 H), 7.44-6.94 (m, 2 H), 6.38-6.27 (m, 1 H), 6.19 (dd, J = 1.8, 7.8 Hz, 1 H), 5.95 (d, J = 7.5 Hz, 1 H), 4.41 (td, J = 7.7, 9.7 Hz, 1 H), 3.92-3.78 (m, 2 H), 3.69 (s, 3 H), 2.65-2.56 (m, 1 H), 1.97-1.86 (m, 1 H); $^{19}$F NMR (376 MHz, DMSO-$d_6$) δ ppm −80.540; $[α]^{25.1}_D$ = +2.0 (c = 0.1, MeOH). |

TABLE 2-continued

| Ex. | Structure and Name | LCMS (M + H)+ | HPLC Method, RT (min) & Purity | NMR |
|---|---|---|---|---|
| 115 | 1-(4-(1H-pyrazol-4-yl)phenyl)-3-((2-methylbenzo[d]thiazol-6-yl)amino)pyrrolidin-2-one | 390.4 | E: 1.19, 97% F: 1.40, 95% | $^1$H NMR (500 MHz, DMSO-$d_6$) δ 8.05 (br. s., 2 H), 7.73-7.66 (m, 2 H), 7.63 (d, J = 8.9 Hz, 2 H), 7.60 (d, J = 8.9 Hz, 1 H), 7.22 (d, J = 1.8 Hz, 1 H), 6.91 (dd, J = 8.7, 2.0 Hz, 1 H), 4.44 (t, J = 9.0 Hz, 1 H), 3.94-3.72 (m, 2 H), 2.73-2.61 (m, 4 H), 2.00-1.82 (m, 1 H). |

Example 57

Preparation of 1-(4-(1H-pyrazol-4-yl)phenyl)-3-(benzylamino)pyrrolidin-2-one

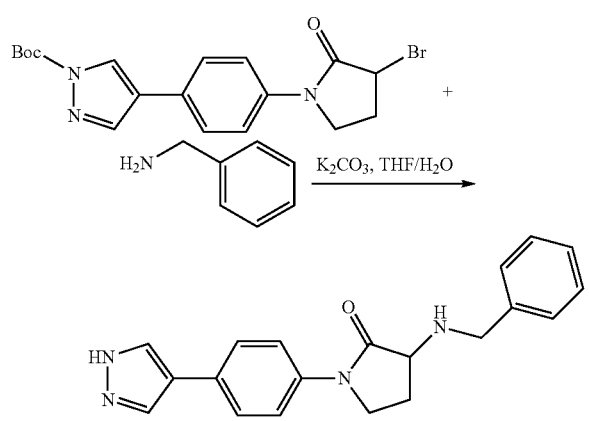

To a solution of Intermediate 2 (50 mg, 0.12 mmol) in THF (2.0 mL), were added benzylamine (19.8 mg, 0.185 mmol), $K_2CO_3$ (34.0 mg, 0.246 mmol) and water (0.2 mL). The reaction mixture was stirred at 90° C. in a microwave reactor for 1 h. The reaction mixture was concentrated and co-evaporated two times with toluene. The solid was dissolved in DCM and treated with TFA and allowed to stir at rt for 4 h. The mixture was concentrated, and the product was washed with hexanes, then purified by preparative LC/MS to afford Example 57 (14 mg, 33% yield). MS(ESI) m/z: 333.2 (M+H)$^+$; $^1$H NMR (400 MHz, DMSO-$d_6$) δ ppm 12.90 (s, 1H) 8.17 (s, 1H) 7.91 (s, 1H) 7.64-7.69 (m, 2H) 7.59-7.64 (m, 2H) 7.37-7.42 (m, 2H) 7.31-7.37 (m, 2H) 7.22-7.29 (m, 1H) 4.09 (q, J=5.27 Hz, 1H) 3.90 (d, J=1.82 Hz, 2H) 3.69-3.84 (m, 2H) 3.53 (t, J=8.75 Hz, 1H) 2.30-2.39 (m, 1H) 1.84 (dq, J=12.27, 9.11 Hz, 1H); HPLC RT=1.24 min, 96.15% (Method E), HPLC RT=1.83 min, 95.69% (Method F).

The following Examples in Table 3 were prepared using procedures similar to those used for the synthesis of Example 57.

TABLE 3

| Ex. | Structure and Name | LCMS (M + H)+ | HPLC Method, RT (min) & Purity | NMR |
|---|---|---|---|---|
| 58 | 1-(4-(1H-pyrazol-4-yl)phenyl)-3-(phenylamino)pyrrolidin-2-one | 319.2 | C: 1.866, 96.19% D: 1.967, 96.42% | $^1$H NMR (400 MHz, DMSO-$d_6$) δ ppm 12.91 (s, 1 H) 8.18 (s, 1 H) 7.92 (s, 1 H) 7.69-7.73 (m, 2 H) 7.62-7.67 (m, 2 H) 7.07-7.13 (m, 2 H) 6.73 (dd, J = 8.60, 0.94 Hz, 2 H) 6.56-6.61 (m, 1 H) 5.89 (d, J = 6.96 Hz, 1 H) 4.33-4.41 (m, 1 H) 3.81-3.88 (m, 2 H) 2.58-2.70 (m, 1 H) 1.91 (dq, J = 12.20, 9.40 Hz, 1 H). |
| 59 | 1-(4-(1H-pyrazol-4-yl)phenyl)-3-(phenethylamino)pyrrolidin-2-one, 2 TFA | 347.2 | C: 1.59, 95.64% D: 1.924, 95.44% | $^1$H NMR (400 MHz, DMSO-$d_6$) δ ppm 13.01 (s, 1 H) 9.31 (s, 1 H) 8.05 (s, 1 H) 7.65-7.71 (m, 4 H) 7.35-7.41 (m, 2 H) 7.26-7.34 (m, 3 H) 4.41 (dd, J = 10.35, 8.85 Hz, 1 H) 3.85-3.98 (m, 2 H) 3.37-3.45 (m, 2 H) 2.91-3.09 (m, 2 H) 2.55-2.64 (m, 1 H) 2.10-2.23 (m, 1 H). $^{19}$F NMR (376 MHz, DMSO-$d_6$) δ ppm −73.468 and −73.522. |

TABLE 3-continued

| Ex. | Structure and Name | LCMS (M + H)+ | HPLC Method, RT (min) & Purity | NMR |
|---|---|---|---|---|
| 60 | 1-(4-(1H-pyrazol-4-yl)phenyl)-3-(((R)-1-(3-methoxyphenyl)ethyl)amino)pyrrolidin-2-one, TFA | 377.3 | E: 0.850, 98.61% F: 1.404, 98.68% | $^1$H NMR (400 MHz, DMSO-$d_6$) δ ppm 12.91 (s, 1 H) 8.16 (s, 1 H) 7.90 (s, 1 H) 7.57-7.66 (m, 4 H) 7.25 (q, J = 8.01 Hz, 1 H) 6.93-7.01 (m, 2 H) 6.77-6.83 (m, 1 H) 4.20 (d, J = 6.40 Hz, 1 H) 3.76 (s, 3 H) 3.56-3.71 (m, 2 H) 2.29-2.38 (m, 1 H) 1.76-2.03 (m, 1 H) 1.59-1.71 (m, 1 H) 1.31 (dd, J = 13.05, 6.59 Hz, 3H). $^{19}$F NMR (376 MHz, DMSO-$d_6$) δ ppm −73.403. |
| 61 | 1-(4-(1H-pyrazol-4-yl)phenyl)-3-((3-fluorobenzyl)amino)pyrrolidin-2-one, TFA | 351.2 | E: 0.742, 98.15% F: 1.310, 96.53% | $^1$H NMR (400 MHz, DMSO-$d_6$) δ ppm 12.91 (s, 1 H) 8.17 (s, 1 H) 7.90 (s, 1 H) 7.59-7.69 (m, 4 H) 7.37 (td, J = 7.95, 6.18 Hz, 1 H) 7.20-7.26 (m, 2 H) 7.06 (td, J = 8.63, 1.88 Hz, 1 H) 3.91 (d, J = 3.64 Hz, 2 H) 3.69-3.83 (m, 2 H) 3.49 (t, J = 8.69 Hz, 1 H) 2.29-2.38 (m, 1 H) 1.82 (dq, J = 12.26, 9.05 Hz, 1 H).$^{19}$F NMR (376 MHz, DMSO-$d_6$) δ ppm −73.401 and −113.808. |
| 62 | 1-(4-(1H-pyrazol-4-yl)phenyl)-3-((3-fluorophenyl)amino)pyrrolidin-2-one | 337.2 | C: 2.249, 93.08% D: 2.259, 93.40% | $^1$H NMR (400 MHz, DMSO-$d_6$) δ ppm 12.98 (s, 1 H) 8.17 (s, 1 H) 7.91 (s, 1 H) 7.67-7.73 (m, 2 H) 7.61-7.65 (m, 2 H) 7.04-7.13 (m, 1 H) 6.48-6.56 (m, 2 H) 6.27-6.37 (m, 2 H) 4.41 (dt, J = 9.82, 7.73 Hz, 1 H) 3.83 (dd, J = 9.16, 5.77 Hz, 2 H) 2.56-2.65 (m, 1 H) 1.84-1.95 (m, 1 H). $^{19}$F NMR (376 MHz, DMSO-$d_6$) δ ppm −113.361. |
| 63 | 1-(4-(1H-pyrazol-4-yl)phenyl)-3-((3-methoxyphenyl)amino)pyrrolidin-2-one | 349.2 | C: 2.141, 96.66% D: 2.250, 97.41% | $^1$H NMR (400 MHz, DMSO-$d_6$) δ ppm 12.98 (s, 1 H) 8.17 (s, 1 H) 7.91 (s, 1 H) 7.67-7.72 (m, 2 H) 7.60-7.65 (m, 2 H) 6.98 (t, J = 8.00 Hz, 1 H) 6.27-6.33 (m, 2 H) 6.14-6.19 (m, 1 H) 5.91 (d, J = 7.03 Hz, 1 H) 4.36 (dt, J = 9.57, 7.73 Hz, 1 H) 3.80-3.87 (m, 2 H) 3.68 (s, 3 H) 2.56-2.64 (m, 1 H) 1.83-1.95 (m, 1 H). |
| 64 | 1-(4-(1H-pyrazol-4-yl)phenyl)-3-phenoxypyrrolidin-2-one | 320.0 | C: 1.986, 95.79% D: 2.016, 96.69% | $^1$H NMR (400 MHz, DMSO-$d_6$) δ ppm 12.90 (s, 1 H) 8.19 (s, 1 H) 7.93 (s, 1 H) 7.69-7.74 (m, 2 H) 7.63-7.68 (m, 2 H) 7.30-7.36 (m, 2 H) 7.06-7.11 (m, 2 H) 6.97-7.02 (m, 1 H) 5.26 (t, J = 8.00 Hz, 1 H) 3.82-3.95 (m, 2 H) 2.70-2.77 (m, 1 H) 2.10 (dq, J = 12.37, 8.57 Hz, 1 H). |

Example 65

N-(1-(4-(1H-Pyrazol-4-yl)phenyl)-2-oxopyrrolidin-3-yl)-3-methoxybenzamide

Example 65A

Preparation of N-(1-(4-bromophenyl)-2-oxopyrrolidin-3-yl)-3-methoxybenzamide

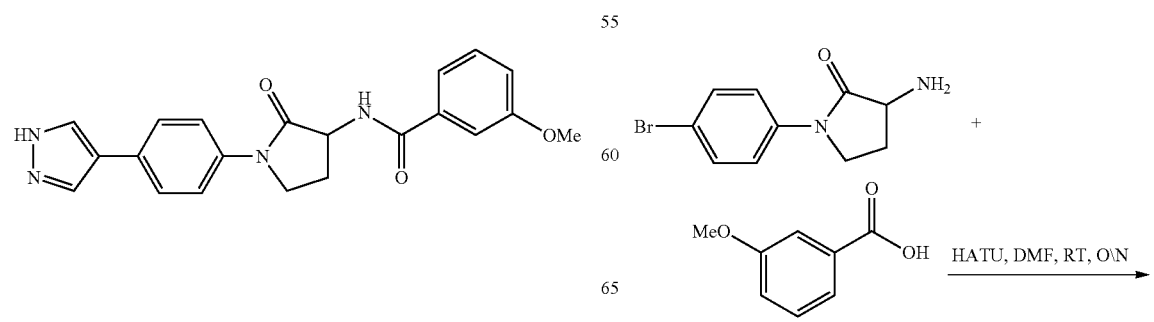

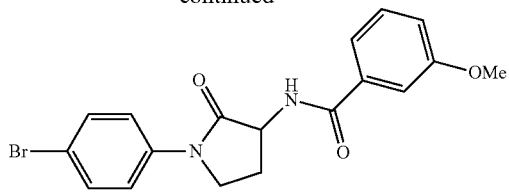

To a solution of Intermediate 1 (100 mg, 0.39 mmol) and 3-methoxybenzoic acid (71.6 mg, 0.47 mmol) in DMF (2 mL), were added TEA (0.273 mL, 1.96 mmol) and HATU (194 mg, 0.510 mmol). The mixture was stirred at rt for 14 h. The reaction mixture was diluted with ice-cold water and was stirred gently for 10 min. The precipitate was filtered and washed with water and hexanes to give Example 65A (120 mg, 73% yield) as a white solid. MS(ESI) m/z: 391.1 (M+H)$^+$; $^1$H NMR (300 MHz, DMSO-d$_6$) δ ppm 8.92 (d, J=7.93 Hz, 1H) 7.66-7.76 (m, 2H) 7.55-7.63 (m, 2H) 7.36-7.50 (m, 3H) 7.12 (ddd, J=8.03, 2.55, 1.13 Hz, 1H) 4.74-4.90 (m, 1H) 3.77-3.91 (m, 5H) 2.37-2.47 (m, 1H) 2.06-2.23 (m, 1H).

Example 65

To a solution of Example 4A (120 mg, 0.308 mmol) in DMF (3 mL), were added tert-butyl 4-(4,4,5,5-tetramethyl-1,3,2-dioxaborolan-2-yl)-1H-pyrazole-1-carboxylate (136 mg, 0.462 mmol), K$_2$CO$_3$ (128 mg, 0.925 mmol) and water (0.5 mL). The mixture was purged with nitrogen for 10 min and then was charged with 2nd generation XPhos precatalyst (14.6 mg, 0.018 mmol) and again purged with nitrogen for 10 min. The mixture was heated at 90° C. for 14 h, then was cooled to rt and diluted with water. The mixture was extracted with ethyl acetate. The combined organic phase was washed with water and brine, dried over Na$_2$SO$_4$, and concentrated. The residue was purified by preparative LC/MS to afford Example 65 (6 mg, 5% yield). MS(ESI) m/z: 377.2 (M+H)$^+$; $^1$H NMR (400 MHz, DMSO-d$_6$) δ ppm 12.92 (s, 1H) 8.90 (d, J=8.35 Hz, 1H) 8.18 (br. s., 1H) 7.92 (br. s., 1H) 7.67-7.73 (m, 2H) 7.60-7.66 (m, 2H) 7.38-7.51 (m, 3H) 7.12 (ddd, J=8.13, 2.60, 1.00 Hz, 1H) 4.85 (dt, J=10.27, 8.73 Hz, 1H) 3.86 (dd, J=9.54, 4.52 Hz, 2H) 3.82 (s, 3H) 2.39-2.46 (m, 1H) 2.08-2.21 (m, 1H), HPLC RT=0.963 min, 99.49% (Method E), HPLC RT=1.069 min, 99.69% (Method F).

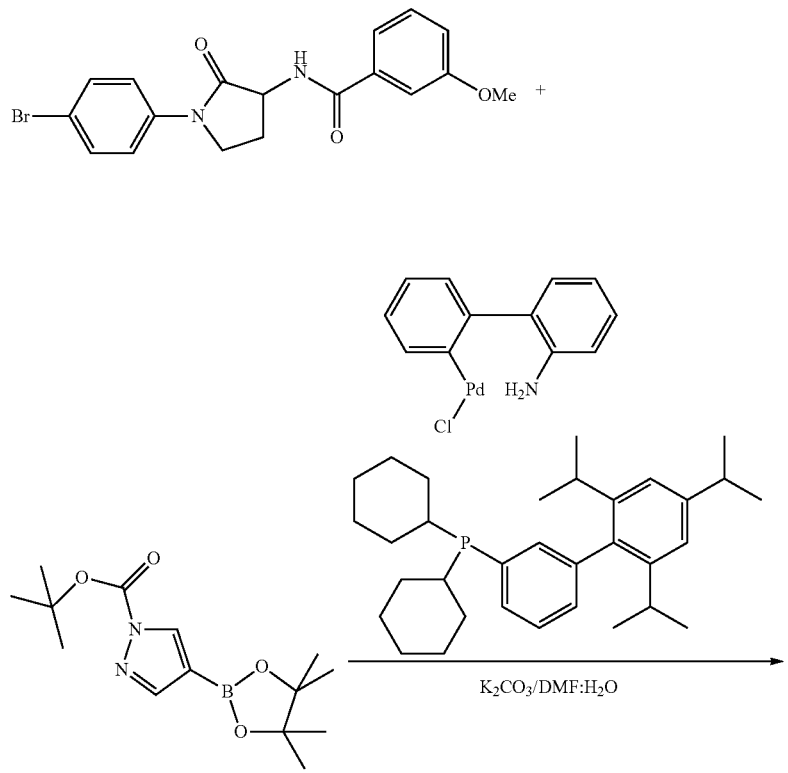

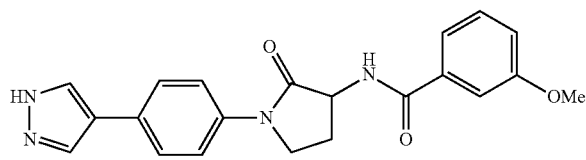 [SMILES: COc1cccc(C(=O)NC2CCN(c3ccc(-c4cn[nH]c4)cc3)C2=O)c1]

Example 66

3-((3-(Difluoromethoxy)phenyl)amino)-1-(3-methoxy-4-(1H-pyrazol-4-yl)phenyl)pyrrolidin-2-one

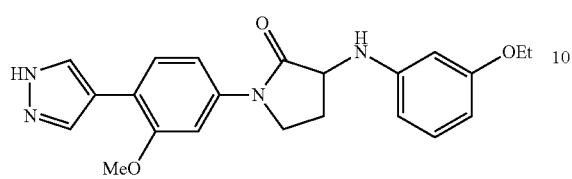

Example 66A

Preparation of 1-(4-bromo-3-methoxyphenyl)-3-((3-ethoxyphenyl)amino) pyrrolidin-2-one

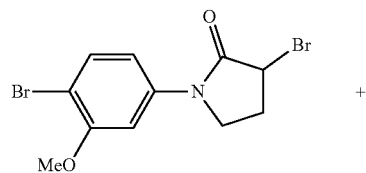

+

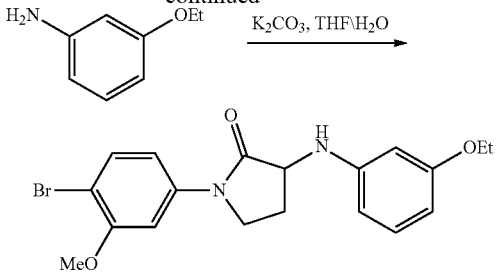

To a solution of Intermediate 4 (300 mg, 0.86 mmol) in THF (5.0 mL) was added 3-ethoxyaniline (177 mg, 1.29 mmol) and K₂CO₃ (297 mg, 2.15 mmol). The mixture was stirred at 100° C. for 14 h, then was cooled and partitioned between ethyl acetate and water. The ethyl acetate layer was washed with water and brine, dried over Na₂SO₄, and concentrated. The solid was purified by flash chromatography (0-50% EtOAc/Hex gradient) to obtain Example 66A (0.200 g, 52% yield) as a yellow solid. MS(ESI) m/z: 407.1 (M+H)⁺; ¹H NMR (300 MHz, DMSO-d₆) δ ppm 7.65 (d, J=2.27 Hz, 1H) 7.58 (d, J=8.69 Hz, 1H) 7.16 (dd, J=8.69, 2.64 Hz, 1H) 6.93-7.01 (m, 1H) 6.24-6.31 (m, 2H) 6.13-6.18 (m, 1H) 5.91 (d, J=7.18 Hz, 1H) 4.39 (dt, J=9.73, 7.79 Hz, 1H) 3.75-4.00 (m, 7H) 2.54-2.65 (m, 1H) 1.80-1.96 (m, 1H) 1.26-1.33 (t, J=5.1, 3 H).

Example 66

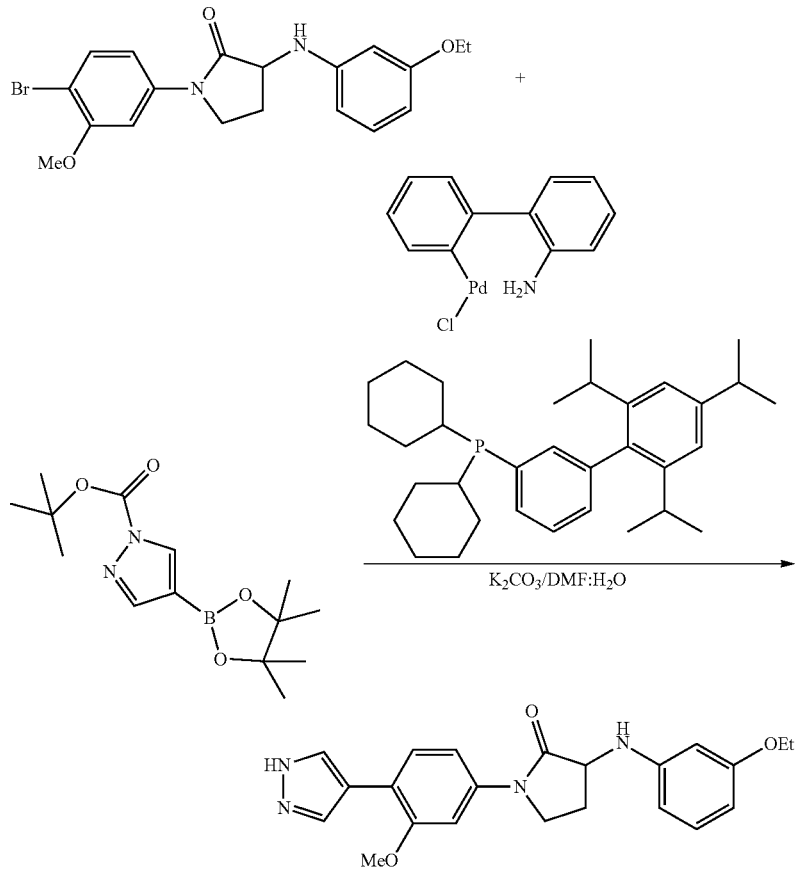

To a solution of Example 66A (120 mg, 0.281 mmol) in DMF (3 mL) were added tert-butyl 4-(4,4,5,5-tetramethyl-1,3,2-dioxaborolan-2-yl)-1H-pyrazole-1-carboxylate (124 mg, 0.421 mmol), $K_2CO_3$ (116 mg, 0.843 mmol) and water (0.5 mL). The reaction mixture was purged with nitrogen for 10 min and then charged with 2nd generation XPhos precatalyst (13.3 mg, 0.017 mmol) and again purged with nitrogen for 10 min. The reaction mixture was heated at 90° C. for 14 h. The reaction mixture was cooled and partitioned between with ethyl acetate and water. The organic phase was washed with brine, dried over $Na_2SO_4$, and concentrated. The product was purified by preparative LC/MS to afford Example 66 (70 mg, 58% yield) as a pale yellow solid. MS(ESI) m/z: 415.2 (M+H)$^+$; $^1$H NMR (400 MHz, DMSO-$d_6$) δ ppm 12.95 (br. s., 1H) 8.03 (br. s., 2H) 7.60-7.65 (m, 2H) 6.93-7.33 (m, 3H) 6.59 (dd, J=8.16, 1.63 Hz, 1H) 6.50 (t, J=2.20 Hz, 1H) 6.35 (dd, J=7.97, 1.95 Hz, 2H) 4.41-4.47 (m, 1H) 3.91 (s, 3H) 3.80-3.88 (m, 2H) 2.56-2.65 (m, 1H) 1.90 (dq, J=12.20, 9.51 Hz, 1H). $^{19}$F NMR (376 MHz, DMSO-$d_6$) δ ppm −80.908, HPLC RT=1.498 min, 97.24% (Method E), HPLC RT=1.541 min, 97.39% (Method F).

The following Examples in Table 4 were prepared using procedures similar to those used for the synthesis of Example 66.

TABLE 4

| Ex. | Structure and Name | LCMS (M + H)$^+$ | HPLC Method, RT (min) & Purity | NMR |
|---|---|---|---|---|
| 67 | 1-(3-methoxy-4-(1H-pyrazol-4-yl)phenyl)-3-(phenylamino)pyrrolidin-2-one | 349.2 | E: 1.323, 99.70%<br>F: 1.419, 97.54% | $^1$H NMR (400 MHz, DMSO-$d_6$) δ ppm 12.86 (br. s., 1 H) 8.09 (br. s., 1 H) 7.95 (br. s., 1 H) 7.63 (d, J = 6.34 Hz, 2 H) 7.16-7.21 (m, 1 H) 7.06-7.12 (m, 2 H) 6.72 (d, J = 7.72 Hz, 2 H) 6.58 (t, J = 7.28 Hz, 1 H) 5.90 (d, J = 7.03 Hz, 1 H) 4.39 (dt, J = 9.60, 7.78 Hz, 1 H) 3.80-3.89 (m, 5 H) 2.56-2.69 (m, 1 H) 1.90 (dq, J = 12.13, 9.47 Hz, 1 H). |
| 68 | 1-(3-methoxy-4-(1H-pyrazol-4-yl)phenyl)-3-((3-methoxyphenyl)amino)pyrrolidin-2-one | 379.3 | E: 1.344, 99.50%<br>F: 1.412, 99.16% | $^1$H NMR (400 MHz, DMSO-$d_6$) δ ppm 12.86 (br. s., 1 H) 8.09 (br. s., 1 H) 7.95 (br. s., 1 H) 7.59-7.65 (m, 2 H) 7.18 (dd, J = 8.44, 2.10 Hz, 1 H) 6.99 (t, J = 8.03 Hz, 1 H) 6.28-6.34 (m, 2 H) 6.14-6.19 (m, 1 H) 5.93 (d, J = 7.09 Hz, 1 H) 4.33-4.42 (m, 1 H) 3.87 (s, 5 H) 3.67 (s, 3 H) 2.60 (dtd, J = 14.27, 6.01, 6.01, 2.38 Hz, 1 H) 1.89 (dq, J = 12.13, 9.49 Hz, 1 H). |
| 69 | 3-((3-(difluoromethoxy)phenyl)amino)-1-(3-methoxy-4-(1H-pyrazol-4-yl)phenyl)pyrrolidin-2-one | 415.2 | E: 1.498, 97.66%<br>F: 1.541, 97.54% | $^1$H NMR (400 MHz, DMSO-$d_6$) δ ppm 12.95 (br. s., 1 H) 8.03 (br. s., 2 H) 7.60-7.65 (m, 2 H) 6.93-7.33 (m, 3 H) 6.59 (dd, J = 8.16, 1.63 Hz, 1 H) 6.50 (t, J = 2.20 Hz, 1 H) 6.35 (dd, J = 7.97, 1.95 Hz, 2 H) 4.41-4.47 (m, 1 H) 3.91 (s, 3 H) 3.80-3.88 (m, 2 H) 2.56-2.65 (m, 1 H) 1.90 (dq, J = 12.20, 9.51 Hz, 1 H). $^{19}$F NMR (376 MHz, DMSO-$d_6$) δ ppm −80.908. |
| 70 | 1-(3-methoxy-4-(1H-pyrazol-4-yl)phenyl)-3-((3-(trifluoromethoxy)phenyl)amino)pyrrolidin-2-one | 433.2 | E: 1.711, 99.58%<br>F: 1.757, 99.64% | $^1$H NMR (400 MHz, DMSO-$d_6$) δ ppm 12.87 (br. s., 1 H) 8.11 (br. s., 1 H) 7.95 (br. s., 1 H) 7.58-7.66 (m, 2 H) 7.15-7.22 (m, 2 H) 6.70-6.74 (m, 1 H) 6.67 (d, J = 0.69 Hz, 1 H) 6.43-6.52 (m, 2 H) 4.48 (dt, J = 9.98, 7.87 Hz, 1 H) 3.88 (s, 3 H) 3.80-3.85 (m, 2 H) 2.56-2.65 (m, 1 H) 1.85-1.97 (m, 1 H). $^{19}$F NMR (376 MHz, DMSO-$d_6$) δ ppm −57.237. |
| 71 | 3-((3-isopropoxyphenyl)amino)-1-(3-methoxy-4-(1H-pyrazol-4-yl)phenyl)pyrrolidin-2-one, TFA | 407.3 | E: 1.576, 98.96%<br>F: 1.647, 98.18% | $^1$H NMR (400 MHz, DMSO-$d_6$) δ ppm 8.03 (s, 2 H) 7.59-7.65 (m, 2 H) 7.18 (dd, J = 8.47, 2.13 Hz, 1 H) 6.96 (t, J = 8.25 Hz, 1 H) 6.25-6.30 (m, 2 H) 6.12-6.17 (m, 1 H) 4.51 (quin, J = 6.02 Hz, 1 H) 4.37 (dd, J = 9.91, 8.22 Hz, 1 H) 3.87 (s, 3 H) 3.80-3.85 (m, 2 H) 2.54-2.64 (m, 1 H) 1.88 (dq, J = 12.18, 9.43 Hz, 1 H) 1.25 (d, J = 6.0 Hz, 6 H). 19F NMR (376 MHz, DMSO-$d_6$) δ ppm −74.220. |

TABLE 4-continued

| Ex. | Structure and Name | LCMS (M + H)+ | HPLC Method, RT (min) & Purity | NMR |
|-----|--------------------|---------------|--------------------------------|-----|
| 72 | 3-((3-fluorophenyl)amino)-1-(3-methoxy-4-(1H-pyrazol-4-yl)phenyl)pyrrolidin-2-one | 367.2 | E: 1.436, 98.52% F: 1.487, 97.81% | $^1$H NMR (400 MHz, DMSO-$d_6$) δ ppm 12.86 (br. s., 1 H) 8.10 (br. s., 1 H) 7.95 (br. s., 1 H) 7.59-7.66 (m, 2 H) 7.18 (dd, J = 8.47, 2.13 Hz, 1 H) 7.05-7.13 (m, 1 H) 6.48-6.57 (m, 2 H) 6.28-6.37 (m, 2 H) 4.44 (dt, J = 9.87, 7.84 Hz, 1 H) 3.79-3.91 (m, 5 H) 2.57-2.66 (m, 1 H) 1.89 (dq, J = 12.19, 9.49 Hz, 1 H). $^{19}$F NMR (376 MHz, DMSO-$d_6$) δ ppm −113.356. |
| 73 | N-(3-((1-(3-methoxy-4-(1H-pyrazol-4-yl)phenyl)-2-oxopyrrolidin-3-yl)amino)phenyl)methanesulfonamide | 442.2 | A: 7.473, 95.32% B: 7.286, 95.61% | $^1$H NMR (400 MHz, DMSO-$d_6$) δ ppm 12.90 (s, 1 H) 9.46 (s, 1 H) 8.10 (s, 1 H) 7.95 (s, 1 H) 7.60-7.65 (m, 2 H) 7.18 (dd, J = 8.47, 2.13 Hz, 1 H) 7.03 (t, J = 8.03 Hz, 1 H) 6.60 (t, J = 2.01 Hz, 1 H) 6.46 (ddd, J = 17.96, 8.02, 1.51 Hz, 2 H) 6.10 (d, J = 7.15 Hz, 1 H) 4.30-4.38 (m, 1 H) 3.83-3.89 (m, 5 H) 2.95 (s, 3 H) 2.54-2.64 (m, 1 H) 1.87-1.98 (m, 1 H). |
| 74 | 1-(3-methoxy-4-(1H-pyrazol-4-yl)phenyl)-3-((3-methoxyphenyl)amino)pyrrolidin-2-one (Enantiomer-1) Enantiomer-I | 379.2 | A: 8.906, 98.08% B: 8.570, 98.85% | $^1$H NMR (400 MHz, DMSO-$d_6$) δ ppm 12.86 (s, 1 H) 8.11 (s, 1 H) 7.95 (br. s., 1 H) 7.63 (d, J = 11.11 Hz, 2 H) 7.18 (dd, J = 8.47, 2.13 Hz, 1 H) 6.99 (t, J = 8.03 Hz, 1 H) 6.27-6.34 (m, 2 H) 6.17 (dd, J = 8.03, 1.82 Hz, 1 H) 5.94 (d, J = 7.09 Hz, 1 H) 4.38 (dt, J = 9.71, 7.79 Hz, 1 H) 3.79-3.91 (m, 5 H) 3.68 (s, 3 H) 2.55-2.65 (m, 1 H) 1.89 (dq, J = 12.08, 9.40 Hz, 1 H). 132.92; 100% ee with Chiral HPLC RT = 9.08 min (Method VII), $[α]^{25.1}_D$ = +6.67 (c 0.03, MeOH). |
| 75 | 1-(3-methoxy-4-(1H-pyrazol-4-yl)phenyl)-3-((3-methoxyphenyl)amino)pyrrolidin-2-one (Enantiomer-2) Enantiomer-II | 379.2 | A: 8.897, 99.16% B: 8.677, 99.13% | $^1$H NMR (400 MHz, DMSO-$d_6$) δ ppm 12.86 (s, 1 H) 8.03 (s, 2 H) 7.63 (d, J = 11.04 Hz, 2 H) 7.18 (dd, J = 8.47, 2.13 Hz, 1 H) 6.99 (t, J = 8.00 Hz, 1 H) 6.27-6.34 (m, 2 H) 6.17 (dd, J = 8.06, 1.79 Hz, 1 H) 5.94 (d, J = 7.09 Hz, 1 H) 4.38 (dt, J = 9.62, 7.80 Hz, 1 H) 3.80-3.91 (m, 5 H) 3.68 (s, 3 H) 2.56-2.65 (m, 1 H) 1.83-1.95 (m, 1 H). 100% ee with Chiral HPLC RT = 13.06 min (Method IV), $[α]^{25.1}_D$ = −20.0 (c 0.03, MeOH). |

Example 76

Preparation of 1-(4-(2-aminopyridin-4-yl)phenyl)-3-((3-methoxyphenyl)amino) pyrrolidin-2-one (Enantiomer-1), and

Example 77

1-(4-(2-aminopyridin-4-yl)phenyl)-3-((3-methoxyphenyl)amino)pyrrolidin-2-one (Enantiomer-2)

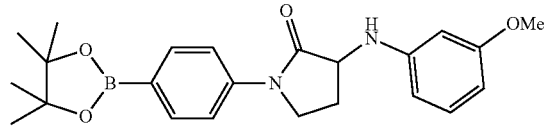

+

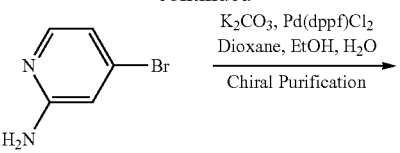

$\xrightarrow{\text{K}_2\text{CO}_3,\ \text{Pd(dppf)Cl}_2}_{\text{Dioxane, EtOH, H}_2\text{O}}$ Chiral Purification

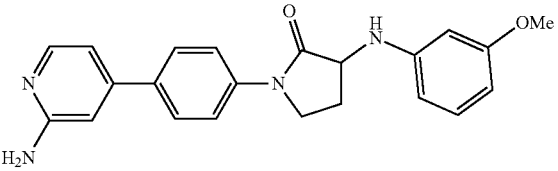

Enantomers-I and -II

To a solution of Intermediate 5 (300 mg, 0.735 mmol) and 4-bromopyridin-2-amine (191 mg, 1.10 mmol) in dioxane (8 mL) and ethanol (2 mL), were added $K_2CO_3$ (305 mg, 2.20 mmol) and water (1 mL). The reaction mixture was purged with nitrogen for 10 min, charged with PdCl$_2$(dppf)-CH$_2$Cl$_2$ Adduct (36.0 mg, 0.044 mmol), and again purged with nitrogen for 3 minutes. The mixture was heated at 90° C. for 14 h. The reaction was cooled, then diluted with ethyl acetate, washed with water and brine solution, dried over Na$_2$SO$_4$, and concentrated. The residue was purified by preparative HPLC to afford racemic product. Enantiomers were separated by Supercritical Fluid Chromatography [Column: CHIRALPAK® AD-H, 250×4.6 mm, 5µ; Co-solvent is 40% (0.20% DEA in IPA:ACN in 1:1)] to obtain Example 76 (26 mg, 9.3% yield), followed by Example 77 (34 mg, 12% yield) as a yellow solids.

Analytical data for Example 76: MS(ESI) m/z: 375.2 (M+H)$^+$; $^1$H NMR (400 MHz, DMSO-d$_6$) δ ppm 7.95 (d, J=5.33 Hz, 1H) 7.84 (d, J=8.78 Hz, 2H) 7.69 (d, J=8.85 Hz, 2H) 6.99 (t, J=8.00 Hz, 1H) 6.80 (dd, J=5.36, 1.47 Hz, 1H) 6.71 (s, 1H) 6.27-6.33 (m, 2H) 6.17 (dd, J=7.97, 1.95 Hz, 1H) 5.91-5.98 (m, 3H) 4.36-4.45 (m, 1H) 3.80-3.92 (m, 2H) 3.68 (s, 3H) 2.56-2.65 (m, 1H) 1.85-1.97 (m, 1H). HPLC RT=6.25 min, 98.86% (Method A), HPLC RT=7.53 min, 98.39% (Method B), 98.28% ee with chiral HPLC RT=6.64 min (Method I), [α]$^{24.9}_D$=−22.0 (c 0.1, THF).

Analytical data for Example 77: MS(ESI) m/z: 375.0 (M+H)$^+$; $^1$H NMR (400 MHz, DMSO-d$_6$) δ ppm 7.95 (d, J=5.40 Hz, 1H) 7.84 (d, J=8.78 Hz, 2H) 7.69 (d, J=8.78 Hz, 2H) 6.99 (t, J=7.97 Hz, 1H) 6.80 (dd, J=5.40, 1.51 Hz, 1H) 6.71 (s, 1H) 6.27-6.34 (m, 2H) 6.17 (dd, J=8.09, 1.82 Hz, 1H) 5.92-5.98 (m, 3H) 4.36-4.44 (m, 1H) 3.80-3.91 (m, 2H) 3.68 (s, 3H) 2.56-2.65 (m, 1H) 1.85-1.98 (m, 1H), HPLC RT=6.27 min, 98.92% (Method A), HPLC RT=7.55 min, 98.95% (Method B); 98.14% ee with HPLC RT=10.08 min (Method I), [α]$^{25.0}_D$=+8.0 (c 0.1, THF).

The following Examples in Table 5 were prepared using procedures similar to those used for the synthesis of Example 76.

TABLE 5

| Ex. | Structure and Name | LCMS (M + H)$^+$ | HPLC Method, RT (min) & Purity | NMR |
|---|---|---|---|---|
| 78 | 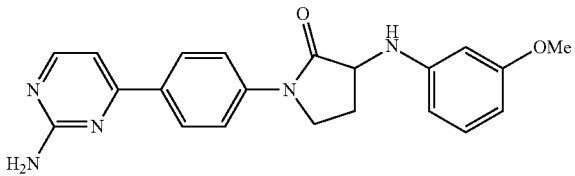<br>1-(4-(2-aminopyrimidin-4-yl)phenyl)-3-((3-methoxyphenyl)amino)pyrrolidin-2-one (Enantiomer-1) | 376.0 | H: 6.428, 96.17%<br>B: 7.463, 92.75% | $^1$H NMR (400 MHz, DMSO-d$_6$) δ ppm 8.29 (d, J = 5.21 Hz, 1 H) 8.12 (d, J = 8.91 Hz, 2 H) 7.86 (d, J = 8.85 Hz, 2 H) 7.13 (d, J = 5.21 Hz, 1 H) 6.99 (t, J = 8.00 Hz, 1 H) 6.63 (s, 2 H) 6.27-6.33 (m, 2 H) 6.17 (dd, J = 8.09, 1.88 Hz, 1 H) 5.96 (d, J = 7.28 Hz, 1 H) 4.37-4.45 (m, 1 H) 3.81-3.93 (m, 2 H) 3.68 (s, 3 H) 2.54-2.65 (m, 1 H) 1.86-1.97 (m, 1 H). 100% ee with HPLC RT = 6.65 min (Method II). |
| 79 | 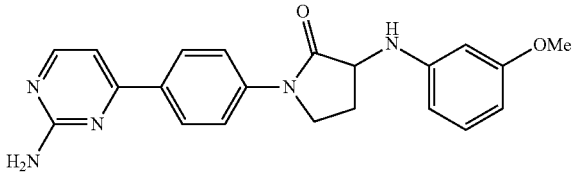<br>1-(4-(2-aminopyrimidin-4-yl)phenyl)-3-((3-methoxyphenyl)amino)pyrrolidin-2-one (Enantiomer-2) | 376.0 | H: 6.399, 96.99%<br>B: 7.459, 97.35% | $^1$H NMR (400 MHz, DMSO-d$_6$) δ ppm 8.29 (d, J = 5.27 Hz, 1 H) 8.12 (d, J = 8.85 Hz, 2 H) 7.86 (d, J = 8.91 Hz, 2 H) 7.13 (d, J = 5.27 Hz, 1 H) 6.99 (t, J = 8.00 Hz, 1 H) 6.63 (s, 2 H) 6.27-6.33 (m, 2 H) 6.17 (dd, J = 8.06, 2.10 Hz, 1 H) 5.96 (d, J = 7.15 Hz, 1 H) 4.37-4.45 (m, 1 H) 3.82-3.94 (m, 2 H) 3.68 (s, 3 H) 2.56-2.65 (m, 1 H) 1.86-1.98 (m, 1 H). 99.42% ee with HPLC RT = 9.24 min (Method II). |
| 80 | 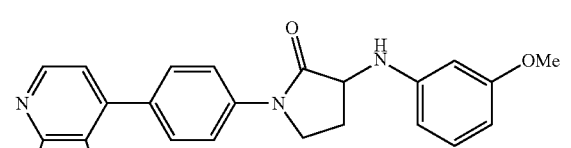<br>1-(4-(1H-pyrrolo[2,3-b]pyridin-4-yl)phenyl)-3-((3-methoxyphenyl)amino)pyrrolidin-2-one (Enantiomer-1) | 399.0 | H: 7.180, 96.71%<br>B: 8.113, 95.99% | $^1$H NMR (400 MHz, DMSO-d$_6$) δ ppm 11.78 (s, 1 H) 8.28 (d, J = 4.96 Hz, 1 H) 7.88-7.94 (m, 2 H) 7.81-7.86 (m, 2 H) 7.55 (t, J = 2.92 Hz, 1 H) 7.20 (d, J = 4.96 Hz, 1 H) 7.00 (t, J = 7.97 Hz, 1 H) 6.64 (dd, J = 3.26, 1.63 Hz, 1 H) 6.29-6.35 (m, 2 H) 6.15-6.20 (m, 1 H) 5.97 (d, J = 7.09 Hz, 1 H) 4.37-4.46 (m, 1 H) 3.84-3.94 (m, 2 H) 3.69 (s, 3 H) 2.57-2.65 (m, 1 H) 1.87-1.99 (m, 1 H). 100% ee with HPLC RT = 8.75 min (Method II). |

TABLE 5-continued

| Ex. | Structure and Name | LCMS (M + H)+ | HPLC Method, RT (min) & Purity | NMR |
|---|---|---|---|---|
| 81 | 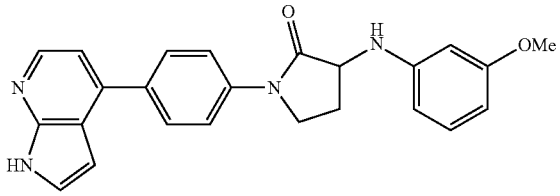

Enantiomer-II 1-(4-(1H-pyrrolo[2,3-b]pyridin-4-yl)phenyl)-3-((3-methoxyphenyl)amino)pyrrolidin-2-one (Enantiomer-2) | 399.0 | H: 7.140, 96.50% B: 8.121, 96.34% | $^1$H NMR (400 MHz, DMSO-d$_6$) δ ppm 11.79 (s, 1 H) 8.28 (d, J = 5.02 Hz, 1 H) 7.88-7.94 (m, 2 H) 7.81-7.86 (m, 2 H) 7.55 (t, J = 2.89 Hz, 1 H) 7.20 (d, J = 4.96 Hz, 1 H) 7.00 (t, J = 7.94 Hz, 1 H) 6.64 (dd, J = 3.36, 1.73 Hz, 1 H) 6.29-6.35 (m, 2 H) 6.16-6.21 (m, 1 H) 5.98 (d, J = 7.22 Hz, 1 H) 4.37-4.46 (m, 1 H) 3.86-3.93 (m, 2 H) 3.69 (s, 3 H) 2.58-2.66 (m, 1 H) 1.87-1.99 (m, 1 H). 99.30% ee with HPLC RT = 14.87 min (Method II). |

Example 82

Preparation of 1-(5-(1H-pyrazol-4-yl)pyridin-2-yl)-3-((3-fluoro-5-methoxyphenyl)amino)pyrrolidin-2-one

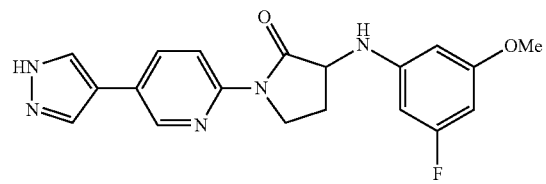 [SMILES: COc1cc(F)cc(NC2CCN(c3ccc(-c4cn[nH]c4)cn3)C2=O)c1]

Example 82A

Preparation of 1-(5-bromopyridin-2-yl)-3-((3-fluoro-5-methoxyphenyl)amino) pyrrolidin-2-one

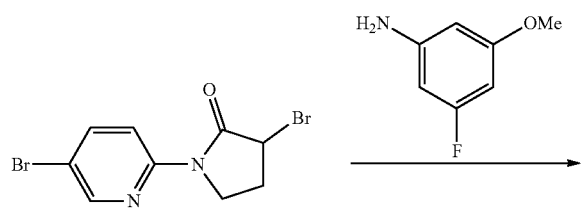

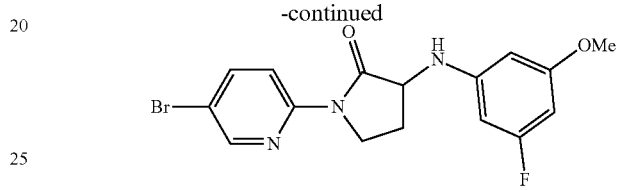

To a solution of Intermediate 9 (0.200 g, 0.625 mmol) in DMF (5 mL), was added K$_2$CO$_3$ (0.259 g, 1.88 mmol), followed by 3-fluoro-5-methoxyaniline (0.176 g, 1.25 mmol). The mixture was heated at 100° C. for 14 h. Water was added to the reaction mixture, which was extracted with EtOAc (2×). The combined organic phase was dried with Na$_2$SO$_4$, filtered and concentrated. The crude was purified by flash chromatography (0-15% EtOAc/pet. ether) to afford Example 82A (0.021 g, 0.055 mmol, 8.8% yield) as a white solid. MS(ESI) m/z: 380.3 (M+H)$^+$; $^1$H NMR (300 MHz, DMSO-d$_6$) δ=8.55 (d, J=2.3 Hz, 1H), 8.33-8.26 (m, 1H), 8.08 (dd, J=9.1, 2.6 Hz, 1H), 6.33 (d, J=7.9 Hz, 1H), 6.17-6.08 (m, 2H), 6.00 (dt, J=11.0, 2.3 Hz, 1H), 4.59-4.46 (m, 1H), 4.09 (t, J=8.9 Hz, 1H), 3.84-3.72 (m, 1H), 3.68 (s, 3H), 2.64-2.54 (m, 1H), 1.95-1.79 (m, 1H).

Example 82

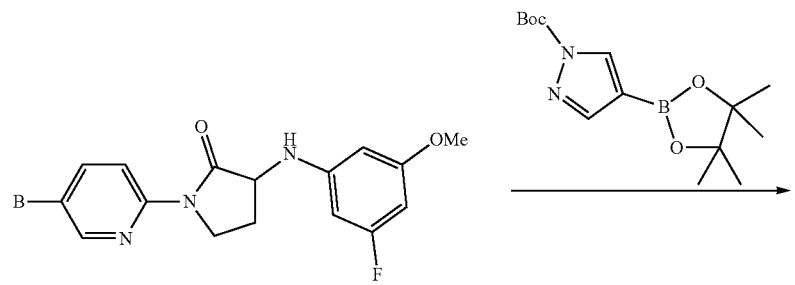

-continued

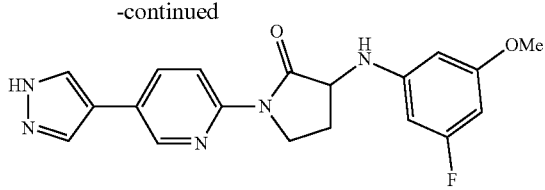

To a solution of Example 82A (0.021 g, 0.055 mmol) in DMF (1.4 mL) and water (0.2 mL), were added tert-butyl 4-(4,4,5,5-tetramethyl-1,3,2-dioxaborolan-2-yl)-1H-pyrazole-1-carboxylate (0.041 g, 0.138 mmol) and K$_2$CO$_3$ (0.023 g, 0.166 mmol). The reaction was degassed, then 2nd generation XPhos precatalyst (8.7 mg, 0.011 mmol) was added. The reaction was again degassed, then was heated at 100° C. overnight. The reaction mixture was filtered through CELITE®, and the filtrate was concentrated. The crude material was purified via preparative LC/MS to afford Example 82 (6 mg, 0.016 mmol, 29% yield) as a pale yellow solid. MS(ESI) m/z: 368.2; $^1$H NMR (400 MHz, DMSO-d$_6$) δ 13.04 (br. s., 1H), 8.71 (d, J=2.5 Hz, 1H), 8.32-8.24 (m, 2H), 8.07 (dd, J=2.3, 8.8 Hz, 1H), 7.99 (br. s., 1H), 6.32 (d, J=7.5 Hz, 1H), 6.17-6.09 (m, 2H), 6.00 (td, J=2.0, 11.0 Hz, 1H), 4.56-4.47 (m, 1H), 4.13 (t, J=9.3 Hz, 1H), 3.82 (dt, J=6.5, 10.3 Hz, 1H), 3.69 (s, 3H), 2.62-2.53 (m, 1H), 1.94-1.81 (m, 1H); $^{19}$F NMR (376 MHz, DMSO-d$_6$) δ −112.555.

The following Examples in Table 6 were prepared using procedures similar to those used for the synthesis of Example 82.

TABLE 6

| Ex. | Structure and Name | LCMS (M + H)$^+$ | HPLC Method, RT (min) & Purity | NMR |
|---|---|---|---|---|
| 83 | 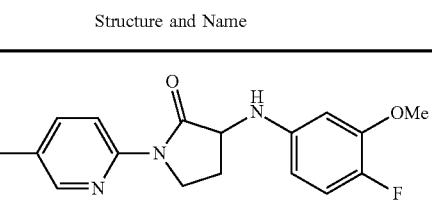 1-(5-(1H-pyrazol-4-yl)pyridin-2-yl)-3-((4-fluoro-3-methoxyphenyl)amino)pyrrolidin-2-one (Enantiomer 1) | 368.2 | A: 8.434, 97.74% B: 8.193, 98.75% | $^1$H NMR (400 MHz, DMSO-d$_6$) δ 13.04 (br. s., 1H), 8.71 (d, J = 2.0 Hz, 1H), 8.33-8.28 (m, 2H), 8.06 (dd, J = 2.3, 8.8 Hz, 2H), 6.95-6.87 (m, 1H), 6.53 (dd, J = 2.5, 7.5 Hz, 1H), 6.24-6.18 (m, 1H), 5.89 (d, J = 7.0 Hz, 1H), 4.51-4.41 (m, 1H), 4.14 (t, J = 9.0 Hz, 1H), 3.87-3.77 (m, 4H), 2.69-2.55 (m, 1H), 1.93-1.81 (m, 1H); $^{19}$F NMR (376 MHz, DMSO-d$_6$) δ −150.863; 96.76% ee with Chiral HPLC RT = 8.77 min (Method IV [α]$^{25}_D$ = +30.0 (c = 0.1, MeOH). |
| 84 | 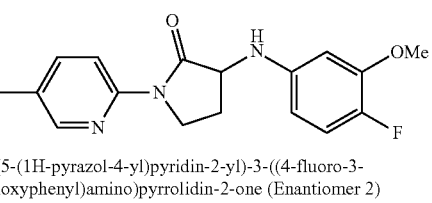 1-(5-(1H-pyrazol-4-yl)pyridin-2-yl)-3-((4-fluoro-3-methoxyphenyl)amino)pyrrolidin-2-one (Enantiomer 2) | 368.2 | A: 8.434, 9.81% B: 8.192, 98.73% | $^1$H NMR (400 MHz, DMSO-d$_6$) δ = 13.05 (br. s., 1H), 8.72 (d, J = 2.0 Hz, 1H), 8.35-8.26 (m, 2H), 8.11-7.96 (m, 2H), 7.00 (t, J = 8.0 Hz, 1H), 6.35-6.29 (m, 2H), 6.18 (d, J = 8.0 Hz, 1H), 5.98 (d, J = 7.5 Hz, 1H), 4.54-4.44 (m, 1H), 4.15 (t, J = 9.0 Hz, 1H), 3.90-3.79 (m, 1H), 3.69 (s, 3H), 2.59-2.54 (m, 1H), 1.94-1.83 (m,; 1H); 96.76% ee with Chiral HPLC RT = 10.00 min (Method IV [α]$^{25}_D$ = −33.6 (c = 0.1, MeOH). |
| 85 | 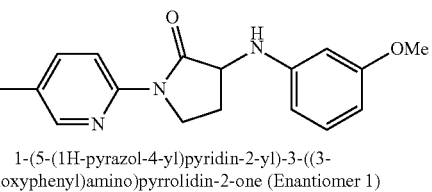 1-(5-(1H-pyrazol-4-yl)pyridin-2-yl)-3-((3-methoxyphenyl)amino)pyrrolidin-2-one (Enantiomer 1) | 350.2 | A: 8.220, 99.52% B: 7.913, 99.17% | $^1$H NMR (400 MHz, DMSO-d$_6$) δ ppm 12.84 (s, 1H), 8.04 (br. s., 2H), 7.67-7.59 (m, 2H), 7.17 (dd, J = 1.7, 8.5 Hz, 1H), 6.99 (t, J = 8.0 Hz, 1H), 6.35-6.27 (m, 2H), 6.20-6.15 (m, 1H), 5.93 (d, J = 7.1 Hz, 1H), 4.42-4.33 (m, 1H), 4.11 (q, J = 7.0 Hz, 2H), 3.90-3.79 (m, 2H), 3.68 (s, 3H), 2.65-2.55 (m, 1H), 1.95-1.84 (m, 1H), 1.44 (t, J = 6.9 Hz, 3H); 96.74% ee with Chiral HPLC RT = 10.33 min (Method IV), [α]$^{25}_D$ = +12.8 (c = 0.1, MeOH). |
| 86 | 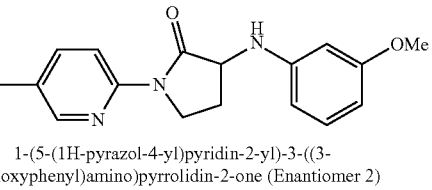 1-(5-(1H-pyrazol-4-yl)pyridin-2-yl)-3-((3-methoxyphenyl)amino)pyrrolidin-2-one (Enantiomer 2) | 350.2 | A: 8.235, 99.68% B: 7.941, 99.65% | $^1$H NMR $^1$H NMR (400 MHz, DMSO-d$_6$) δ = 13.05 (br. s., 1H), 8.72 (d, J = 2.5 Hz, 1H), 8.35-8.25 (m, 2H), 8.10-7.98 (m, 2H), 7.00 (t, J = 8.0 Hz, 1H), 6.35-6.27 (m, 2H), 6.20-6.15 (m, 1H), 5.98 (d, J = 7.5 Hz, 1H), 4.49 (td, J = 7.7, 10.2 Hz, 1H), 4.18-4.11 (m, 1H), 3.89-3.80 (m, 1H), 3.69 (s, 3H), 2.63-2.55 (m, 1H), 1.96-1.83 (m, 1H); 97.96% ee with Chiral HPLC RT = 14.11 min (Method IV), [α]$^{25}_D$ = −16.4 (c = 0.1, MeOH). |

TABLE 6-continued

| Ex. | Structure and Name | LCMS (M + H)+ | HPLC Method, RT (min) & Purity | NMR |
|---|---|---|---|---|
| 87 | 1-(5-(1H-pyrazol-4-yl)pyridin-2-yl)-3-((3-fluoro-5-methoxyphenyl)amino)pyrrolidin-2-one (Enantiomer 1) | 368.2 | A: 8.941, 99.16% B: 8.444, 99.61% | $^1$H NMR (400 MHz, DMSO-$d_6$) δ = 13.02 (br. s., 1H), 8.71 (d, J = 2.5 Hz, 1H), 8.30 (d, J = 8.5 Hz, 1H), 8.17-8.02 (m, 3H), 6.33 (d, J = 7.5 Hz, 1H), 6.17-6.09 (m, 2H), 6.00 (td, J = 2.2, 11.2 Hz, 1H), 4.56-4.47 (m, 1H), 4.18-4.09 (m, 1H), 3.87-3.77 (m, 1H), 3.69 (s, 3H), 2.61-2.53 (m, 1H), 1.93-1.80 (m, 1H); $^{19}$F NMR (376 MHz, DMSO-$d_6$) δ = −112.551; 98.56% ee with Chiral HPLC RT = 5.42 min (Method IV), $[α]^{25}_D$ = +40.0 (c = 0.1, MeOH). |
| 88 | 1-(5-(1H-pyrazol-4-yl)pyridin-2-yl)-3-((3-fluoro-5-methoxyphenyl)amino)pyrrolidin-2-one (Enantiomer 2) | 368.2 | A: 8.945, 98.78% B: 8.540, 98.28% | $^1$H NMR (400 MHz, DMSO-$d_6$) δ = 13.04 (br. s., 1H), 8.71 (d, J = 2.0 Hz, 1H), 8.32-8.24 (m, 2H), 8.10-7.96 (m, 2H), 6.33 (d, J = 7.5 Hz, 1H), 6.17-6.09 (m, 2H), 6.00 (td, J = 2.0, 11.0 Hz, 1H), 4.52 (td, J = 8.0, 10.0 Hz, 1H), 4.18-4.09 (m, 1H), 3.88-3.77 (m, 1H), 3.69 (s, 3H), 2.62-2.54 (m, 1H), 1.93-1.81 (m, 1H); $^{19}$F NMR (376 MHz, DMSO-$d_6$) δ = −112.551; 96.48% ee with Chiral HPLC RT = 9.43 min (Method IV), $[α]^{25}_D$ = −48.0 (c = 0.1, MeOH). |
| 89 | 1-(5-(1H-pyrazol-4-yl)pyridin-2-yl)-3-((3-fluoro-2-methoxyphenyl)amino)pyrrolidin-2-one (Enantiomer 1) | 368.0 | A: 9.216, 98.12% B: 8.780, 98.25% | $^1$H NMR (400 MHz, DMSO-$d_6$) δ = 13.03 (br. s., 1H), 8.71 (d, J = 2.0 Hz, 1H), 8.34-8.26 (m, 2H), 8.18-8.04 (m, 2H), 6.89 (dt, J = 6.0, 8.3 Hz, 1H), 6.61 (d, J = 8.0 Hz, 1H), 6.48 (ddd, J = 1.0, 8.5, 11.0 Hz, 1H), 5.66 (d, J = 8.0 Hz, 1H), 4.55 (td, J = 8.0, 10.5 Hz, 1H), 4.16 (t, J = 9.5 Hz, 1H), 3.87-3.80 (m, 1H), 3.79 (s, 3H), 2.62-2.56 (m, 1H), 2.11-1.99 (m, 1H); $^{19}$F NMR (376 MHz, DMSO-$d_6$) δ = −132.939; 99.48% ee with Chiral HPLC RT = 7.63 min (Method IV), $[α]^{25}_D$ = −16.0 (c = 0.1, MeOH). |
| 90 | 1-(5-(1H-pyrazol-4-yl)pyridin-2-yl)-3-((3-fluoro-2-methoxyphenyl)amino)pyrrolidin-2-one (Enantiomer 2) | 368.0 | A: 9.196, 96.97% B: 8.766, 97.33% | $^1$H NMR (400 MHz, DMSO-$d_6$) δ = 13.04 (br. s., 1H), 8.71 (d, J = 2.0 Hz, 1H), 8.34-8.24 (m, 2H), 8.10-7.95 (m, 2H), 6.93-6.85 (m, 1H), 6.61 (d, J = 8.5 Hz, 1H), 6.51-6.42 (m, 1H), 5.66 (d, J = 7.5 Hz, 1H), 4.60-4.50 (m, 1H), 4.16 (t, J = 9.8 Hz, 1H), 3.86-3.81 (m, 1H), 3.79 (s, 3H), 2.62-2.54 (m, 1H), 2.12-1.99 (m, 1H); $^{19}$F NMR (376 MHz, DMSO-$d_6$) δ = −132.939; 100% ee with Chiral HPLC RT = 10.22 min (Method IV), $[α]^{25}_D$ = +10.0 (c = 0.1, MeOH). |

Example 91

Preparation of 1-(4-(1H-pyrazol-4-yl)phenyl)-3-(3-fluorobenzyl)pyrrolidin-2-one

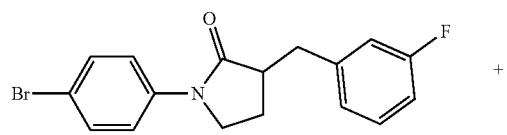

+

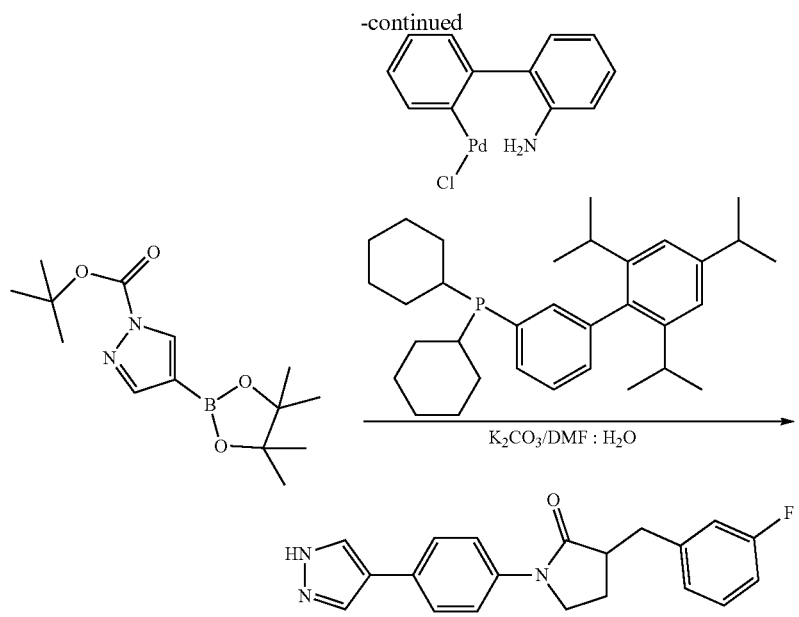

A mixture of Intermediate 11 (100 mg, 0.287 mmol), tert-butyl 4-(4,4,5,5-tetramethyl-1,3,2-dioxaborolan-2-yl)-1H-pyrazole-1-carboxylate (253 mg, 0.862 mmol) and potassium carbonate (159 mg, 1.15 mmol) in DMF (10 mL) and water (5 mL) was degassed with nitrogen, then 2nd generation XPhos precatalyst (22.6 mg, 0.029 mmol) was added. The mixture was stirred at 100° C. for 15 h. The reaction mixture was cooled to rt, filtered and concentrated. The crude product was purified by preparative HPLC to give Example 91 (12.5 mg, 0.037 mmol, 13% yield). MS(ESI) m/z: 336.2 (M+H)$^+$; $^1$H NMR (400 MHz, DMSO-d$_6$) δ ppm 12.88 (br. s., 1H), 8.15 (br. s., 1H), 7.89 (br. s., 1H), 7.68-7.56 (m, 4H), 7.38-7.30 (m, 1H), 7.18-7.10 (m, 2H), 7.08-6.99 (m, 1H), 3.81-3.63 (m, 2H), 3.16 (dd, J=4.5, 13.6 Hz, 1H), 3.03-2.88 (m, 1H), 2.80-2.69 (m, 1H), 2.13-2.00 (m, 1H), 1.83-1.70 (m, 1H); HPLC Method A: RT=9.54 min, 99.50% purity; HPLC Method B: RT=9.23 min, 99.31% purity.

The following Examples in Table 7 were prepared using procedures similar to those used for the synthesis of Example 91.

TABLE 7

| Ex. | Structure and Name | LCMS (M + H)$^+$ | HPLC Method, RT (min); Purity % | NMR |
|---|---|---|---|---|
| 92 | 1-(4-(1H-pyrazol-4-yl)phenyl)-3-benzylpyrrolidin-2-one | 318.2 | A: 9.54; 99.61 B: 8.90; 98.32 | $^1$H NMR (300 MHz, DMSO-d$_6$) δ ppm 12.91 (br. s., 1 H), 8.16 (br. s., 1 H), 7.90 (br. s., 1 H), 7.70-7.56 (m, 4 H), 7.36-7.17 (m, 5 H), 3.80-3.59 (m, 2 H), 3.13 (dd, J = 4.1, 13.5 Hz, 1 H), 2.93 (m, 1 H), 2.79-2.64 (m, 1 H), 2.09-2.00 (m, 1 H), 1.83-1.73 (m, 1H). |
| 93 | 1-(4-(1H-pyrazol-4-yl)phenyl)-3-(3-methoxybenzyl)pyrrolidin-2-one | 348.2 | A: 9.43; 99.91 B: 8.91; 99.45 | $^1$H NMR (400 MHz, DMSO-d$_6$) δ ppm 12.88 (br. s., 1H), 8.15 (br. s., 1 H), 7.89 (br. s., 1 H), 7.68-7.56 (m, 4 H), 7.24-7.17 (m, 1 H), 6.86-6.81 (m, 2 H), 6.80-6.75 (m, 1 H), 3.75 (s, 3 H), 3.73-3.60 (m, 2 H), 3.13 (dd, J = 4.0, 13.6 Hz, 1 H), 2.98-2.86 (m, 1 H), 2.72-2.64 (m, 1 H), 2.12-2.01 (m, 1 H), 1.83-1.69 (m, 1 H). |

TABLE 7-continued

| Ex. | Structure and Name | LCMS (M + H)+ | HPLC Method, RT (min); Purity % | NMR |
|---|---|---|---|---|
| 94 | 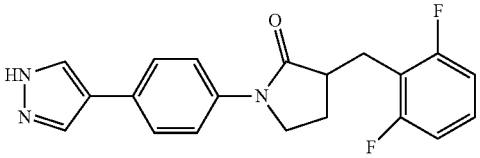 1-(4-(1H-pyrazol-4-yl)phenyl)-3-(2,6-difluorobenzyl)pyrrolidin-2-one | 354.2 | A: 9.72; 99.42 B: 9.29; 99.67 | $^1$H NMR (400 MHz, DMSO-$d_6$) δ ppm 12.90 (br. s., 1H), 8.16 (s, 1 H), 7.90 (s, 1 H), 7.69-7.58 (m, 4 H), 7.41-7.31 (m, 1 H), 7.14-7.06 (m, 2 H), 3.83-3.72 (m, 2 H), 3.21-3.14 (dd, J = 4.2, 9.4 Hz, 1 H), 2.88-2.82 (m, 1 H), 2.77-2.64 (m, 1 H), 2.16-2.07 (m, 1 H), 1.86-1.75 (m, 1 H); $^{19}$F NMR (376 MHz, DMSO-$d_6$) δ ppm −114.87 ppm. |
| 95 | 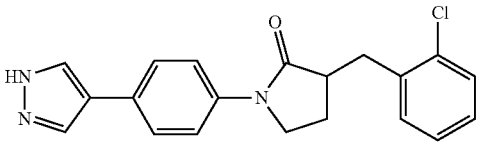 [SMILES: O=C1C(Cc2ccccc2Cl)CCN1c1ccc(-c2cn[nH]c2)cc1] 1-(4-(1H-pyrazol-4-yl)phenyl)-3-(2-chlorobenzyl)pyrrolidin-2-one | 352.2 | A: 10.05; 97.02 B: 9.90; 97.30 | $^1$H NMR (400 MHz, DMSO-$d_6$) δ ppm 12.89 (br. s., 1 H), 8.16 (br. s., 1 H), 7.90 (br. s., 1 H), 7.69-7.64 (m, 2 H), 7.64-7.58 (m, 2 H), 7.48-7.41 (m, 2 H), 7.35-7.24 (m, 2 H), 3.80-3.73 (m, 2 H), 3.36 (d, J = 4.3 Hz, 1 H), 3.06-2.94 (m, 1 H), 2.77 (dd, J = 10.2, 13.7 Hz, 1 H), 2.11-2.02 (m, 1 H), 1.89-1.74 (m, 1 H). |
| 96 | 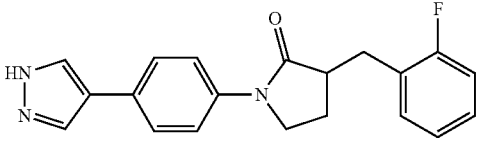 1-(4-(1H-pyrazol-4-yl)phenyl)-3-(2-fluorobenzyl)pyrrolidin-2-one | 336.2 | A: 9.57; 99.71 B: 9.14; 99.63 | $^1$H NMR (400 MHz, DMSO-$d_6$) δ ppm 12.90 (br. s., 1 H), 8.15 (br. s., 1 H), 7.90 (br. s., 1 H), 7.69-7.58 (m, 4 H), 7.39 (dt, J = 1.5, 7.7 Hz, 1 H), 7.33-7.26 (m, 1 H), 7.22-7.13 (m, 2 H), 3.80-3.69 (m, 2 H), 3.21 (dd, J = 4.1, 13.6 Hz, 1 H), 2.99-2.88 (m, 1 H), 2.70 (dd, J = 10.0, 13.7 Hz, 1 H), 2.15-2.03 (m, 1 H), 1.83-1.70 (m, 1 H); $^{19}$F NMR (376 MHz, DMSO-$d_6$) δ ppm −118.19 ppm. |
| 97 | 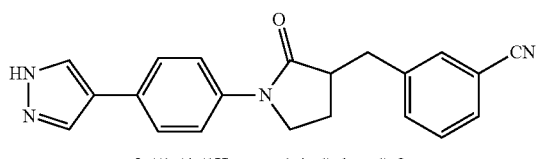 3-((1-(4-(1H-pyrazol-4-yl)phenyl)-2-oxopyrrolidin-3-yl)methyl)benzonitrile | 343.2 | C: 1.93; 98.53 D: 1.96; 98.79 | $^1$H NMR (400 MHz, DMSO-$d_6$) δ ppm 12.90 (br. s., 1 H), 8.16 (br. s., 1 H), 7.91 (br. s., 1 H), 7.79 (s, 1 H), 7.71 (d, J = 7.7 Hz, 1 H), 7.69-7.58 (m, 5 H), 7.57-7.50 (m, 1 H), 3.80-3.65 (m, 2 H), 3.24-3.15 (m, 1 H), 3.06-2.96 (m, 1 H), 2.85-2.74 (m, 1 H), 2.13-2.01 (m, 1 H), 1.85-1.70 (m, 1 H). |
| 98 | 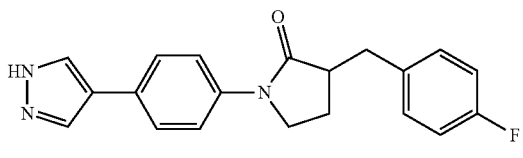 1-(4-(1H-pyrazol-4-yl)phenyl)-3-(4-fluorobenzyl)pyrrolidin-2-one | 336.2 | E: 1.54; 95.84 F: 1.56; 95.21 | $^1$H NMR (400 MHz, DMSO-$d_6$) δ ppm 12.91 (br. s., 1 H), 8.16 (br. s., 1 H), 7.90 (br. s., 1 H), 7.68-7.55 (m, 4 H), 7.36-7.27 (m, 2 H), 7.13 (t, J = 8.9 Hz, 2 H), 3.81-3.60 (m, 2 H), 3.11 (dd, J = 4.4, 13.6 Hz, 1 H), 2.99-2.86 (m, 1 H), 2.78-2.65 (m, 1 H), 2.14-2.01 (m, 1 H), 1.85-1.69 (m, 1 H); $^{19}$F NMR (376 MHz, DMSO-$d_6$) δ ppm −117.35 ppm. |
| 99 | 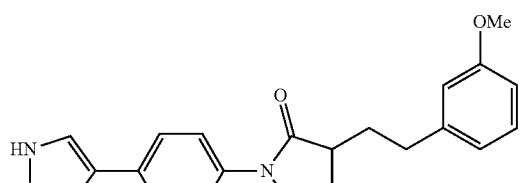 1-(4-(1H-pyrazol-4-yl)phenyl)-3-(3-methoxyphenethyl)pyrrolidin-2-one | 362.2 | C: 2.27; 95.02 D: 2.30; 96.25 | $^1$H NMR (400 MHz, DMSO-$d_6$) δ ppm 12.89 (br. s., 1 H), 8.15 (br. s., 1 H), 7.89 (br. s., 1 H), 7.68-7.57 (m, 4 H), 7.22 (t, J = 8.1 Hz, 1 H), 6.87-6.81 (m, 2 H), 6.80-6.74 (m, 1 H), 3.83-3.76 (m, 2 H), 3.75 (s, 3 H), 2.75-2.64 (m, 2 H), 2.59-2.54 (m, 1 H), 2.37-2.27 (m, 1 H), 2.14-2.03 (m, 1 H), 1.85-1.76 (m, 1 H), 1.72-1.60 (m, 1 H). |

TABLE 7-continued

| Ex. | Structure and Name | LCMS (M + H)+ | HPLC Method, RT (min); Purity % | NMR |
|---|---|---|---|---|
| 100 | 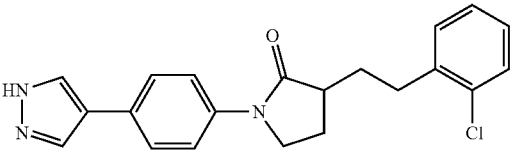<br>1-(4-(1H-pyrazol-4-yl)phenyl)-3-(2-chlorophenethyl)pyrrolidin-2-one | 366.2 | C: 2.49; 91.07<br>D: 2.51; 91.53 | $^1$H NMR (400 MHz, DMSO-d$_6$) δ ppm 12.90 (br. s., 1 H), 8.15 (br. s., 1 H), 7.89 (br. s., 1 H), 7.68-7.63 (m, 2 H), 7.62-7.58 (m, 2 H), 7.46-7.39 (m, 2 H), 7.34-7.22 (m, 2 H), 3.84-3.77 (m, 2 H), 2.83 (t, J = 8.0 Hz, 2 H), 2.64-2.55 (m, 1 H), 2.40-2.30 (m, 1 H), 2.17-2.04 (m, 1 H), 1.89-1.79 (m, 1 H), 1.72-1.61 (m, 1 H). |
| 101 | 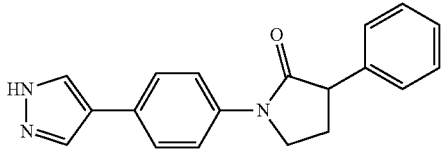<br>1-(4-(1H-pyrazol-4-yl)phenyl)-3-phenylpyrrolidin-2-one | 304.2 | A: 8.87; 95.35<br>B: 8.57; 93.77 | $^1$H NMR (400 MHz, DMSO-d$_6$) δ ppm 12.90 (br. s., 1 H), 8.20-7.80 (br. s., 2 H), 7.72-7.60 (m, 4 H), 7.40-7.24 (m, 5 H), 3.94 (m, 3 H), 2.63-2.53 (m, 1 H), 2.26-2.15 (m, 1 H). |
| 102 | 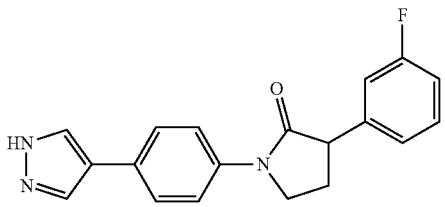 [SMILES: O=C1C(c2cccc(F)c2)CCN1c1ccc(-c2cn[nH]c2)cc1]<br>1-(4-(1H-pyrazol-4-yl)phenyl)-3-(3-fluorophenyl)pyrrolidin-2-one | 322.2 | E: 1.35; 98.65<br>F: 1.39; 98.68 | $^1$H NMR (400 MHz, DMSO-d$_6$) δ ppm 12.90 (br. s., 1 H), 8.16 (br. s., 1 H), 7.91 (br. s., 1 H), 7.72-7.67 (m, 2 H), 7.66-7.61 (m, 2 H), 7.46-7.37 (m, 1 H), 7.25-7.17 (m, 2 H), 7.16-7.09 (m, 1 H), 4.03-3.97 (t, J = 9.4 Hz, 1 H), 3.96-3.91 (m, 2 H), 2.63-2.55 (m, 1 H), 2.30-2.18 (m, 1 H), $^{19}$F NMR (376 MHz, DMSO-d$_6$) δ ppm −113.42 ppm. |
| 103 | 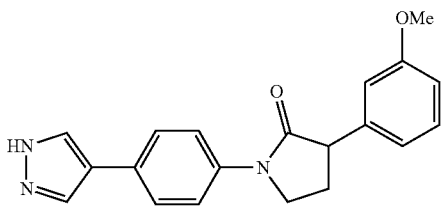 [SMILES: COc1cccc(C2CCN(c3ccc(-c4cn[nH]c4)cc3)C2=O)c1]<br>1-(4-(1H-pyrazol-4-yl)phenyl)-3-(3-methoxyphenyl)pyrrolidin-2-one | 334.2 | C: 2.02; 94.0<br>D: 2.05; 94.12 | $^1$H NMR (400 MHz, DMSO-d$_6$) δ ppm 12.91 (br. s., 1 H), 8.17 (br. s., 1 H), 7.91 (br. s., 1 H), 7.71-7.66 (m, 2 H), 7.65-7.60 (m, 2 H), 7.28 (t, J = 8.1 Hz, 1 H), 6.92-6.83 (m, 3 H), 3.97-3.88 (m, 3 H), 3.76 (s, 3 H), 2.62-2.53 (m, 1 H), 2.27-2.14 (m, 1 H). |
| 104 | 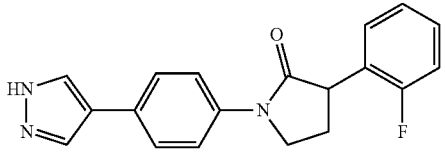 [SMILES: O=C1C(c2ccccc2F)CCN1c1ccc(-c2cn[nH]c2)cc1]<br>1-(4-(1H-pyrazol-4-yl)phenyl)-3-(2-fluorophenyl)pyrrolidin-2-one | 322.2 | C: 2.20; 97.04<br>D: 2.22; 94.78 | $^1$H NMR (400 MHz, DMSO-d$_6$) δ ppm 12.91 (br. s., 1 H), 8.17 (br. s., 1 H), 7.91 (br. s., 1 H), 7.71-7.60 (m, 4 H), 7.42-7.31 (m, 2 H), 7.25-7.17 (m, 2 H), 4.19-4.11 (m, 1 H), 3.99-3.90 (m, 2 H), 2.62-2.53 (m, 1 H), 2.24-2.11 (m, 1 H); $^{19}$F NMR (376 MHz, DMSO-d$_6$) δ ppm −117.42 ppm. |
| 105 | 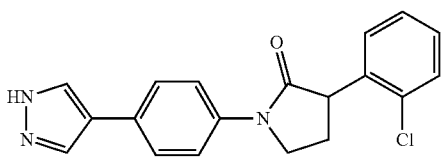 [SMILES: O=C1C(c2ccccc2Cl)CCN1c1ccc(-c2cn[nH]c2)cc1]<br>1-(4-(1H-pyrazol-4-yl)phenyl)-3-(2-chlorophenyl)pyrrolidin-2-one | 338.2 | E: 1.51; 94.39<br>F: 1.52; 94.16 | $^1$H NMR (400 MHz, DMSO-d$_6$) δ ppm 8.04 (br. s., 2 H), 7.73-7.60 (m, 4 H), 7.52-7.46 (m, 1 H), 7.42-7.29 (m, 3 H), 4.32 (t, J = 9.66 Hz, 1 H), 4.04-3.84 (m, 2 H), 2.64-2.54 (m, 1 H), 2.22-2.10 (m, 1 H). |

Example 108

1-(4-(1H-Pyrazol-4-yl)phenyl)-3-(3-methoxyphenoxy)pyrrolidin-2-one, TFA

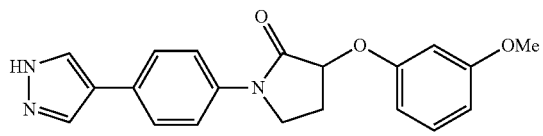 [SMILES: COc1cccc(OC2CCN(c3ccc(-c4cn[nH]c4)cc3)C2=O)c1]

Example 108A 1-(4-Bromophenyl)-3-(3-methoxyphenoxy)pyrrolidin-2-one

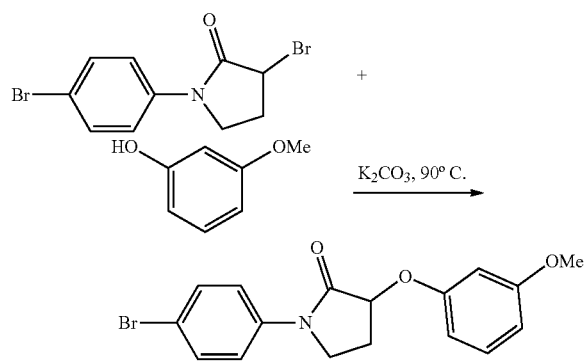

A mixture of Intermediate 1 (0.20 g, 0.627 mmol), K₂CO₃ (0.130 g, 0.940 mmol) and 3-methoxyphenol (0.389 g, 3.13 mmol) were heated at 90° C. overnight. The mixture was cooled to rt, then was partitioned between ethyl acetate and water. The organic phase was washed with water, 10% NaOH, water, and brine, dried over Na₂SO₄, and concentrated. The product was dissolved in DCM (2 mL) and precipitated by adding pet. ether. The precipitate was collected by filtration and dried to afford Example 108A as an off-white solid (175 mg, 73% yield). MS(ESI) m/z: 362.0 (M+H)⁺; ¹H NMR (300 MHz, DMSO-d₆) δ ppm 7.67-7.75 (m, 2H) 7.56-7.64 (m, 2H) 7.16-7.24 (m, 1H) 6.61-6.68 (m, 2H) 6.53-6.60 (m, 1H) 5.24 (t, J=8.12 Hz, 1H) 3.79-3.92 (m, 2H) 3.74 (s, 3H) 2.64-2.77 (m, 1H) 2.07 (dq, J=12.55, 8.55 Hz, 1H).

Example 108

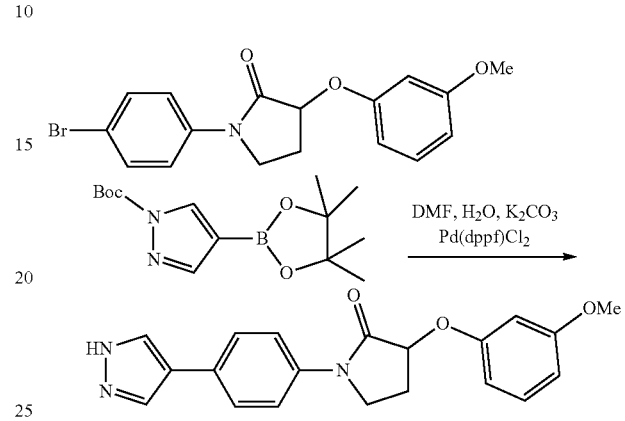

To a solution of Example 108A (100 mg, 0.276 mmol) in DMF (3 mL), was added K₂CO₃ (114 mg, 0.828 mmol) and water (0.5 mL). the mixture was purged with nitrogen for 10 minutes, and then charged with tert-butyl 4-(4,4,5,5-tetramethyl-1,3,2-dioxaborolan-2-yl)-1H-pyrazole-1-carboxylate (122 mg, 0.414 mmol) and 2nd generation XPhos precatalyst (13.0 mg, 0.017 mmol). The mixture was again purged nitrogen, then was heated at 90° C. overnight. The mixture was directly purified by preparative LCMS to afford Example 108 (10 mg, 0.021 mmol, 7.8% yield). MS(ESI) m/z: 350.2; ¹H NMR (400 MHz, DMSO-d₆) δ ppm 8.31 (s, 2H) 7.67-7.72 (m, 2H) 7.62-7.67 (m, 2H) 7.18-7.23 (m, 1H) 6.63-6.67 (m, 2H) 6.54-6.59 (m, 1H) 5.24 (t, J=7.97 Hz, 1H) 3.80-3.93 (m, 2H) 3.75 (s, 3H) 2.68-2.75 (m, 1H) 2.01-2.12 (m, 1H); HPLC Method C: RT=2.34 min, 99.3% purity; HPLC Method D: RT=2.34 min, 99.4% purity.

The following Examples in Table 8 were prepared using procedures similar to those used for the synthesis of Example 108.

TABLE 8

| Ex. | R | Name | LCMS (M + H)⁺ | HPLC Method, RT (min); Purity % | NMR |
|---|---|---|---|---|---|
| 109 | (3-methylphenoxy group) | 1-(4-(1H-pyrazol-4-yl)phenyl)-3-(m-tolyloxy)pyrrolidin-2-one | 334.2 | E: 1.50; 92.5 F: 1.53; 95.8 | ¹H NMR (400 MHz, DMSO-d₆) δ ppm 12.98 (s, 1 H) 8.31 (s, 2 H) 7.68-7.72 (m, 2 H) 7.62-7.66 (m, 2 H) 7.19 (t, J = 7.87 Hz, 1 H) 6.84-6.91 (m, 2 H) 6.80 (d, J = 7.53 Hz, 1 H) 5.21 (t, J = 8.00 Hz, 1 H) 3.82-3.90 (m, 2 H) 2.69-2.75 (m, 1 H) 2.28-2.30 (s, 3 H) 2.05-2.10 (m, 1 H). |

TABLE 8-continued

| Ex. | R | Name | LCMS (M + H)+ | HPLC Method, RT (min); Purity % | NMR |
|---|---|---|---|---|---|
| 110 | (2-chlorophenoxy) | 1-(4-(1H-pyrazol-4-yl)phenyl)-3-(2-chlorophenoxy)pyrrolidin-2-one | 354.2 | E: 1.51; 100 F: 1.54; 100 | ¹H NMR (400 MHz, DMSO-d₆) δ ppm 12.92 (s, 1 H) 8.18 (s, 1 H) 7.92 (br. s., 1 H) 7.68-7.74 (m, 2 H) 7.62-7.67 (m, 2 H) 7.45 (dd, J = 7.94, 1.54 Hz, 1 H) 7.36-7.41 (m, 1 H) 7.29-7.35 (m, 1 H) 7.01 (td, J = 7.61, 1.54 Hz, 1 H) 5.35 (t, J = 8.09 Hz, 1 H) 3.81-3.96 (m, 2 H) 2.65-2.77 (m, 1 H) 2.16 (dq, J = 12.53, 8.48 Hz, 1 H). |
| 111 | (2-fluoro-5-methoxyphenoxy) | 1-(4-(1H-pyrazol-4-yl)phenyl)-3-(2-fluoro-5-methoxyphenoxy)pyrrolidin-2-one | 368.2 | E: 1.42; 95.5 F: 1.43; 99.2 | ¹H NMR (400 MHz, DMSO-d₆) δ ppm 12.93 (s, 1 H) 8.20 (s, 1 H) 7.93 (s, 1 H) 7.62-7.73 (m, 4 H) 7.17 (dd, J = 11.17, 8.97 Hz, 1 H) 6.96 (dd, J = 7.15, 2.95 Hz, 1 H) 6.54 (dt, J = 8.94, 3.18 Hz, 1 H) 5.33 (t, J = 8.06 Hz, 1 H) 3.81-3.96 (m, 2 H) 3.75 (s, 3 H) 2.66-2.77 (m, 1 H) 2.15 (dq, J = 12.51, 8.50 Hz, 1 H). ¹⁹F NMR (376 MHz, DMSO-d₆) δ ppm −144.499. |
| 112 | (3-fluoro-5-methoxyphenoxy) | 1-(4-(1H-pyrazol-4-yl)phenyl)-3-(3-fluoro-5-methoxyphenoxy)pyrrolidin-2-one | 368.2 | E: 1.49; 98.9 F: 1.49; 94.0 | ¹H NMR (400 MHz, DMSO-d₆) δ ppm 12.92 (s, 1 H) 8.20 (s, 1 H) 7.93 (s, 1 H) 7.68-7.73 (m, 2 H) 7.63-7.68 (m, 2 H) 6.57 (dt, J = 10.93, 2.22 Hz, 1 H) 6.44-6.52 (m, 2 H) 5.30 (t, J = 8.06 Hz, 1 H) 3.80-3.95 (m, 2 H) 3.77 (s, 3 H) 2.70-2.77 (m, 1 H) 2.03-2.14 (m, 1 H); ¹⁹F NMR (376 MHz, DMSO-d₆) δ ppm −111.157. |
| 113 | (3-aminophenoxy) | 1-(4-(1H-pyrazol-4-yl)phenyl)-3-(3-aminophenoxy)pyrrolidin-2-one, TFA | 335.2 | E: 0.73; 98.2 F: 1.06; 97.9 | ¹H NMR (400 MHz, DMSO-d₆) δ ppm 8.06 (s, 2 H) 7.67-7.72 (m, 2 H) 7.62-7.67 (m, 2 H) 7.27 (t, J = 8.09 Hz, 1 H) 6.84 (dd, J = 8.16, 2.13 Hz, 1 H) 6.79 (t, J = 2.13 Hz, 1 H) 6.72 (dd, J = 7.87, 1.29 Hz, 1 H) 5.22 (t, J = 8.09 Hz, 1 H) 3.81-3.94 (m, 2 H) 2.66-2.75 (m, 1 H) 2.09 (dq, J = 12.70, 8.46 Hz, 1 H). |

Example 116

2-((1-(4-(1H-Pyrazol-4-yl)phenyl)-2-oxopyrrolidin-3-yl)amino)isonicotinonitrile

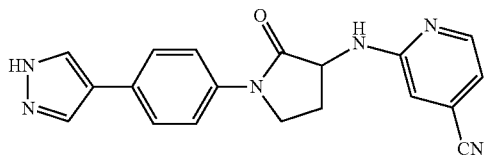 [SMILES: N#Cc1ccnc(NC2CCN(c3ccc(-c4cn[nH]c4)cc3)C2=O)c1]

Example 116A 2-((1-(4-Bromophenyl)-2-oxopyrrolidin-3-yl)amino)isonicotinonitrile

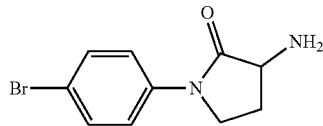

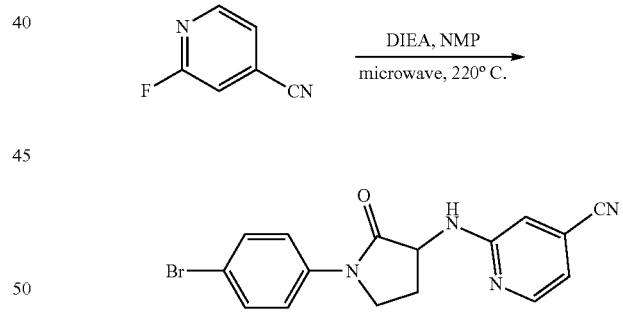

To a solution of Intermediate 4, TFA salt (50 mg, 0.135 mmol) in NMP (2 mL), were added 2-fluoroisonicotinonitrile (33.1 mg, 0.271 mmol) and DIEA (0.118 mL, 0.677 mmol). The reaction was heated in a microwave reactor at 220° C. for 30 min. The crude product was purified by preparative HPLC to afford Example 116A (48 mg, 0.134 mmol, 99% yield) as a white solid. MS(ESI) m/z: 356.9; ¹H NMR (400 MHz, chloroform-d) δ 10.19 (br. s., 1H), 7.96 (dd, J=6.2, 0.7 Hz, 1H), 7.58-7.46 (m, 4H), 7.41 (s, 1H), 6.90 (dd, J=6.2, 1.5 Hz, 1H), 4.63-4.37 (m, 1H), 4.03-3.80 (m, 2H), 2.78 (dddd, J=12.8, 8.8, 6.6, 2.6 Hz, 1H), 2.46 (dq, J=13.0, 9.0 Hz, 1H).

Example 116

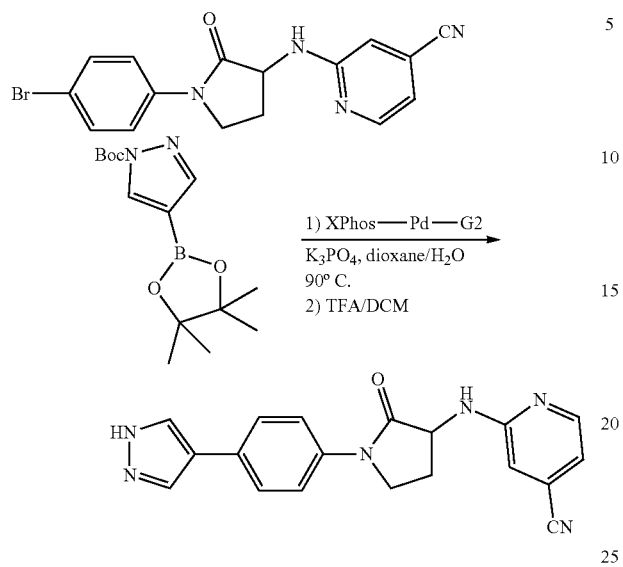

To a solution of Example 116A (20 mg, 0.056 mmol) in dioxane (1.5 mL) and water (0.3 mL), were added tert-butyl 4-(4,4,5,5-tetramethyl-1,3,2-dioxaborolan-2-yl)-1H-pyrazole-1-carboxylate (24.7 mg, 0.084 mmol), K$_3$PO$_4$ (59.4 mg, 0.280 mmol) and 2nd generation XPhos precatalyst (4.4 mg, 5.6 μmol). The reaction was stirred under N$_2$ at 90° C. for 1 h. The solvent was removed. The product was dissolved in DCM (1.5 mL) and TFA (0.5 mL) was added. After stirring at rt for 30 min, the solvent was removed. The crude product was purified by preparative HPLC to afford Example 116 (15.7 mg, 0.043 mmol, 77% yield). MS(ESI) m/z: 345.35; $^1$H NMR (500 MHz, DMSO-d$_6$) δ 8.18 (d, J=5.2 Hz, 1H), 8.09 (br. s., 2H), 7.72-7.66 (m, 2H), 7.66-7.60 (m, 2H), 7.54 (d, J=7.6 Hz, 1H), 7.16 (br. s., 1H), 6.98 (s, 1H), 6.87 (d, J=5.2 Hz, 1H), 4.96-4.76 (m, 1H), 3.95-3.76 (m, 2H), 2.14-1.91 (m, 1H); HPLC RT=1.08 min (Method E), HPLC RT=1.32 min (Method F).

Example 117

3-((3-Methoxy-2-methylphenyl)amino)-1-(6-methoxy-5-(1H-pyrazol-4-yl)pyridin-2-yl)pyrrolidin-2-one

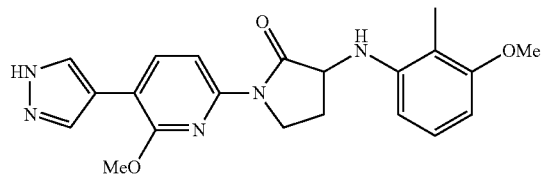 [SMILES: COc1cccc(NC2CCN(c3ccc(-c4cn[nH]c4)c(OC)n3)C2=O)c1C]

Example 117a

Preparation of 1-(5-bromo-6-methoxypyridin-2-yl)-3-((3-methoxy-2-methylphenyl)amino)pyrrolidin-2-one

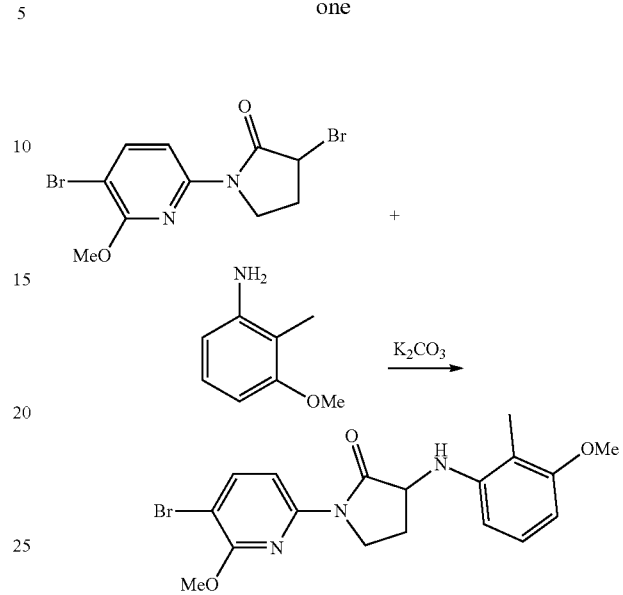

A solution of 3-bromo-1-(5-bromo-6-methoxypyridin-2-yl)pyrrolidin-2-one (50 mg, 0.143 mmol), 3-methoxy-2-methylaniline (98 mg, 0.714 mmol) and potassium carbonate (99 mg, 0.714 mmol) in THF (6 mL) and water (1.5 mL) was stirred at 95° C. for 24 h in a sealed tube. The mixture was cooled to RT, diluted with water (20 mL) and extracted with EtOAc (2×25 mL). The combined organic extracts were washed with 0.75 N HCl solution (2×25 mL), water and brine, dried over Na$_2$SO$_4$ and concentrated. The crude product was purified by flash chromatography (5-10% EtOAc in hexane gradient) to give 1-(5-bromo-6-methoxypyridin-2-yl)-3-((3-methoxy-2-methylphenyl) amino)pyrrolidin-2-one (26 mg, 44% yield) as an off-white solid. MS(ESI) m/z: 406.2 (M+H)$^+$; $^1$H NMR (400 MHz, DMSO-d$_6$) δ ppm 8.03 (d, J=8.5 Hz, 1H), 7.87 (d, J=8.4 Hz, 1H), 6.97 (t, J=8.3 Hz, 1H), 6.40 (d, J=8.5 Hz, 1H), 6.34 (d, J=8.0 Hz, 1H), 5.06 (d, J=7.5 Hz, 1H), 4.58-4.48 (m, 1H), 4.23-4.13 (m, 1H), 3.95 (s, 3H), 3.88-3.78 (m, 1H), 3.73 (s, 3H), 2.63-2.54 (m, 1H), 2.04-1.93 (m, 4H).

Example 117: Preparation of 3-((3-methoxy-2-methylphenyl)amino)-1-(6-methoxy-5-(1H-pyrazol-4-yl)pyridin-2-yl)pyrrolidin-2-one

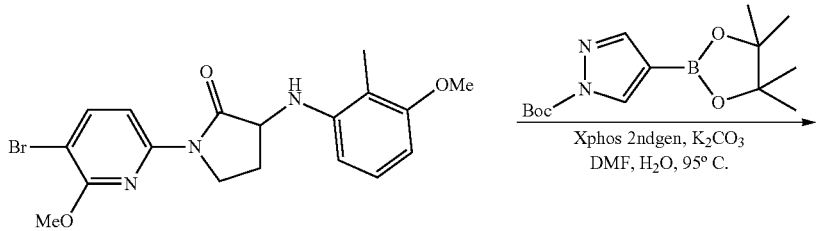

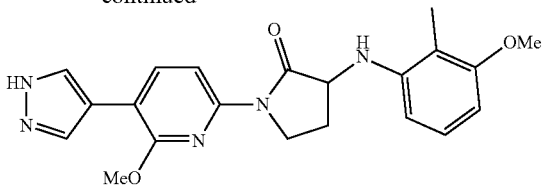

A solution of 1-(5-bromo-6-methoxypyridin-2-yl)-3-((3-methoxy-2-methylphenyl)amino)pyrrolidin-2-one (25 mg, 0.062 mmol), tert-butyl 4-(4,4,5,5-tetramethyl-1,3,2-dioxaborolan-2-yl)-1H-pyrazole-1-carboxylate (32.6 mg, 0.111 mmol) and potassium carbonate (29.8 mg, 0.215 mmol) in DMF (2 mL) and water (1 mL) was placed in a sealed tube. The reaction mixture was degassed with nitrogen, then 2nd generation XPhos precatalyst (7.26 mg, 9.23 μmol) was added. The reaction mixture heated at 95° C. for 5 h. Reaction mixture was cooled to RT and filtered. The filtrate was concentrated. Crude product was purified by preparative HPLC to give 3-((3-methoxy-2-methylphenyl)amino)-1-(6-methoxy-5-(1H-pyrazol-4-yl)pyridin-2-yl)pyrrolidin-2-one (12.7 mg, 52% yield). MS(ESI) m/z: 394.2 (M+H)$^+$; $^1$H NMR (400 MHz, DMSO-d$_6$) δ ppm 12.93 (br. s., 1H), 8.15 (br. s., 1H), 8.09 (d, J=8.3 Hz, 1H), 7.99 (br. s., 1H), 7.93 (d, J=8.3 Hz, 1H), 6.98 (t, J=8.2 Hz, 1H), 6.42 (d, J=8.1 Hz, 1H), 6.36 (d, J=8.1 Hz, 1H), 5.03 (d, J=7.1 Hz, 1H), 4.56-4.47 (m, 1H), 4.27-4.18 (m, 1H), 4.00 (s, 3H), 3.87 (dd, J=10.5, 3.9 Hz, 1H), 3.73 (s, 3H), 2.66-2.57 (m, 1H), 2.06-1.94 (m, 4H); HPLC: RT=2.04 min, 99.5% (Method E) and RT=2.08 min, 99.5% (Method F).

Example 118

1-(3'-Fluoro-2-methoxy-[3,4'-bipyridin]-6-yl)-3-((3-methoxyphenyl)amino) pyrrolidin-2-one

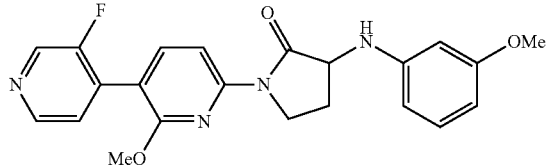 [SMILES: COc1cccc(NC2CCN(c3ccc(-c4ccncc4F)c(OC)n3)C2=O)c1]

Example 118a

Preparation of 1-(4-bromophenyl)-3-((6-methoxy-pyridin-2-yl)amino)pyrrolidin-2-one

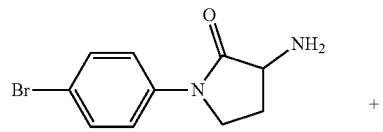

+

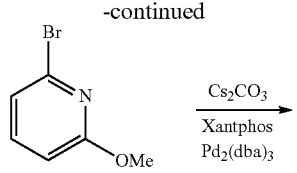

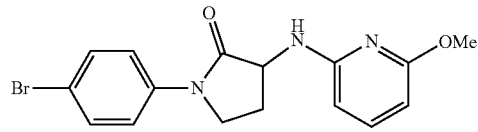

A solution of 3-amino-1-(4-bromophenyl)pyrrolidin-2-one (75 mg, 0.294 mmol), 2-bromo-6-methoxypyridine (111 mg, 0.588 mmol), cesium carbonate (287 mg, 0.882 mmol), 4,5-bis(diphenylphosphino)-9,9-dimethyxanthene (17.0 mg, 0.029 mmol) and tris(dibenzylideneacetone)dipalladium-chloroform adduct (15.2 mg, 0.015 mmol) in NMP (3.5 mL) was placed in a sealed tube. Reaction mixture was degassed with nitrogen, then stirred at 100° C. for 7 h. The reaction mixture was cooled to rt, diluted with water (60 mL) and extracted with EtOAc (2×50 mL). The combined organic extracts were washed with water and brine, dried over Na$_2$SO$_4$ and concentrated. The crude product was purified by flash chromatography (eluting with 10-20% EtOAc in hexane) to give 1-(4-bromophenyl)-3-((6-methoxypyridin-2-yl)amino)pyrrolidin-2-one (24 mg, 21% yield) as an off-white solid. MS(ESI) m/z: 362.2 (M+H)$^+$; $^1$H NMR (400 MHz, DMSO-d$_6$) δ ppm 7.74-7.67 (m, 2H), 7.61-7.53 (m, 2H), 7.34-7.28 (m, 1H), 7.03 (br. s., 1H), 6.11 (d, J=7.5 Hz, 1H), 5.89 (d, J=7.5 Hz, 1H), 4.63-4.55 (m, 1H), 3.86-3.78 (m, 2H), 3.60 (s, 3H), 3.32-3.23 (m, 1H), 2.29-2.24 (m, 1H).

Example 118: Preparation of 1-(3'-fluoro-2-methoxy-[3,4'-bipyridin]-6-yl)-3-((3-methoxyphenyl)amino)pyrrolidin-2-one

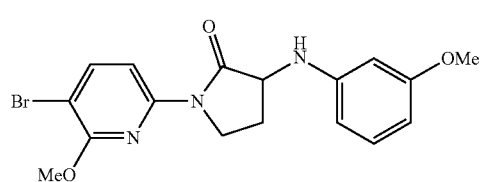

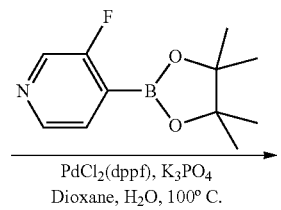

-continued

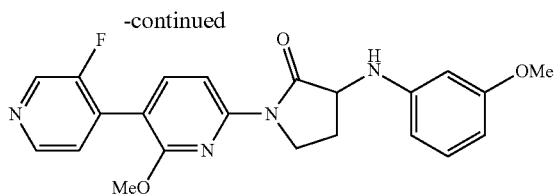

A solution of 1-(5-bromo-6-methoxypyridin-2-yl)-3-((3-methoxyphenyl)amino) pyrrolidin-2-one (50 mg, 0.127 mmol), 3-fluoropyridine-4-boronic acid pinacol ester (42.6 mg, 0.191 mmol) and potassium phosphate tribasic (67.6 mg, 0.319 mmol) in 1,4-dioxane (4 mL) and water (1.2 mL) was placed in a sealed tube. Reaction mixture was degassed with nitrogen, then PdCl$_2$(dppf)-CH$_2$Cl$_2$ adduct (12.5 mg, 0.015 mmol) was added. The reaction mixture stirred at 100° C. for 6 h, then was cooled to RT, diluted with water (30 mL) and extracted with EtOAc (2×25 mL). Combined organic extracts were washed with water and brine, dried over Na$_2$SO$_4$ and concentrated. The product was purified by preparative HPLC to give 1-(3'-fluoro-2-methoxy-[3,4'-bipyridin]-6-yl)-3-((3-methoxyphenyl)amino)pyrrolidin-2-one (27.6 mg, 53% yield). MS(ESI) m/z: 409.2 (M+H)$^+$; $^1$H NMR (400 MHz, DMSO-d$_6$) δ ppm 8.63 (d, J=2.0 Hz, 1H), 8.48 (dd, J=4.9, 1.0 Hz, 1H), 8.06-8.02 (m, 1H), 7.87 (dd, J=8.2, 0.9 Hz, 1H), 7.54 (dd, J=6.4, 4.9 Hz, 1H), 7.03-6.97 (m, 1H), 6.36-6.28 (m, 2H), 6.22-6.15 (m, 1H), 5.99 (d, J=7.3 Hz, 1H), 4.58-4.47 (m, 1H), 4.30-4.20 (m, 1H), 3.92 (s, 3H), 3.91-3.84 (m, 1H), 3.69 (s, 3H), 2.63-2.57 (m, 1H), 1.96-1.83 (m, 1H); $^{19}$F NMR (376 MHz, DMSO-d$_6$) δ ppm −129.17; HPLC: RT=1.82 min, 99.4% (Method E) and RT=1.74 min, 99.8% (Method F).

The following Examples in Table 9 were made by using the same procedure as shown in Examples 117 and 118.

TABLE 9

| Ex. | Structure and Name | Chirality | LCMS (M + H)+ | Chiral Purity | HPLC Method, RT (min) & Purity | $^1$H NMR |
|---|---|---|---|---|---|---|
| 119 | 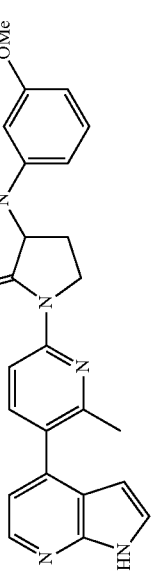<br>3-((3-methoxyphenyl)amino)-1-(6-methyl-5-(1H-pyrrolo[2,3-b]pyridin-4-yl)pyridin-2-yl)pyrrolidin-2-one (Ena-I) | Enantiomer-I | 414.20 | 100% ee (rt = 13.47 min), CHIRALPAK @ AS-H (250 × 4.6 mm), 5.0-μm particles; % CO$_2$: 70%, % Co-solvent: 30% (0.2% DEA in methanol), Total Flow: 3.0 g/min, Back Pressure: 100 bars, Temperature: 22° C., UV: 290 nm | I: 8.463, 99.576% J: 6.883, 99.606% | $^1$H NMR (400 MHz, DMSO-d$_6$) δ ppm = 11.81 (s, 1H), 8.31-8.27 (m, 2H), 7.80 (d, J = 8.5 Hz, 1H), 7.54-7.49 (m, 1H), 7.06-6.96 (m, 2H), 6.37-6.30 (m, 2H), 6.22-6.16 (m, 2H), 5.99 (d, J = 7.5 Hz, 1H), 4.55-4.46 (m, 1H), 4.22 (t, J = 9.0 Hz, 1H), 3.94-3.84 (m, 1H), 3.70 (s, 3H), 2.37 (s, 3H), 1.98-1.86 (m, 1H); SOR: $[α]^{25.3}_D$ = +16.0 (c 0.05, MeOH). |
| 120 | 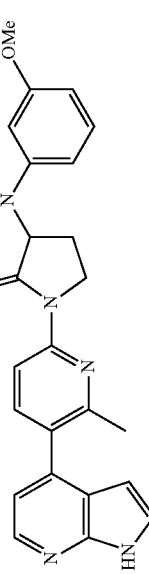<br>3-((3-methoxyphenyl)amino)-1-(6-methyl-5-(1H-pyrrolo[2,3-b]pyridin-4-yl)pyridin-2-yl)pyrrolidin-2-one (Ena-II) | Enantiomer-II | 414.20 | 100% ee (rt = 17.41 min), CHIRALPAK @ AS-H (250 × 4.6 mm), 5.0-μm particles; % CO$_2$: 70%, % Co-solvent: 30% (0.2% DEA in methanol), Total Flow: 3.0 121 g/min, Back Pressure: 100 bars, Temperature: 22° C., UV: 245 nm. | I: 7.874, 96.155% J: 8.323, 98.754% | $^1$H NMR (400 MHz, DMSO-d$_6$) δ ppm = 11.82 (br. s., 1H), 8.31-8.25 (m, 2H), 7.80 (d, J = 8.5 Hz, 1H), 7.52 (d, J = 3.5 Hz, 1H), 7.06-6.97 (m, 2H), 6.36-6.29 (m, 2H), 6.22-6.15 (m, 2H), 5.99 (d, J = 7.5 Hz, 1H), 4.55-4.43 (m, 1H), 4.23 (t, J = 9.0 Hz, 1H), 3.94-3.84 (m, 1H), 3.70 (s, 3H), 2.37 (s, 3H), 1.99-1.85 (m, 1H); SOR: $[α]^{24.7}_D$ = -32.0 (c 0.05, MeOH). |
| 121 | 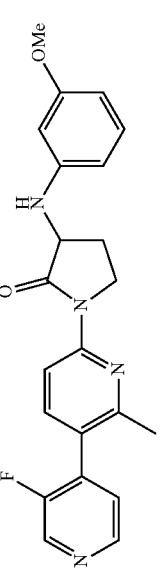<br>1-(3'-fluoro-2-methyl-[3,4'-bipyridin]-6-yl)-3-((3-methoxyphenyl)amino) pyrrolidin-2-one (Ena-II) | Enantiomer-II | 393.20 | 99.0544% ee (rt = 6.61 min), CHIRALPAK @ AS-H (250 × 4.6 mm), 5.0-μm particles; % CO$_2$: 80%, % Co-solvent: 20% (0.2% DEA in methanol), Total Flow: 3.0 g/min, Back Pressure: 100 bars, Temperature: 19.5° C., UV: 290 nm. | I: 15.643, 93.059% J: 15.823, 91.338% | $^1$H NMR (400 MHz, DMSO-d$_6$) δ ppm = 8.71 (d, J = 1.0 Hz, 1H), 8.55 (d, J = 4.0 Hz, 1H), 8.28 (d, J = 9.0 Hz, 1H), 7.79 (d, J = 8.5 Hz, 1H), 7.52 (dd, J = 6.5, 5.0 Hz, 1H), 7.00 (t, J = 8.0 Hz, 1H), 6.36-6.28 (m, 2H), 6.22-6.16 (m, 1H), 5.99 (d, J = 7.5 Hz, 1H), 4.55-4.45 (m, 1H), 4.20 (t, J = 9.3 Hz, 1H), 3.86 (td, J = 10.4, 6.8 Hz, 1H), 3.69 (s, 3H), 2.65-2.52 (m, 1H), 2.39-2.30 (m, 3H), 1.97-1.85 (m, 1H); F$^{19}$-NMR (400 MHz, DMSO-d$_6$): δ ppm -130.157; SOR: $[α]^{25.3}_D$ = -36.0 (c 0.05, MeOH). |

TABLE 9-continued

| Ex. | Structure and Name | Chirality | LCMS (M + H)+ | Chiral Purity | HPLC Method, RT (min) & Purity | $^1$H NMR |
|---|---|---|---|---|---|---|
| 122 | 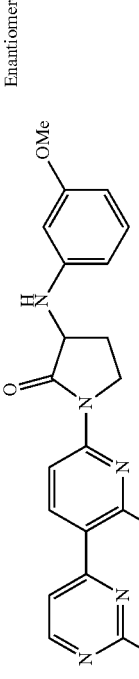<br>1-(5-(2-aminopyrimidin-4-yl)-6-methylpyridin-2-yl)-3-(3-methoxyphenyl)amino)pyrrolidin-2-one | Enantiomer-I | 391.20 | 100% ee (rt = 30.09 min), CHIRALPAK @ IC (250 × 4.6 mm), 5.0-μm particles; % CO$_2$: 60%, % Co-solvent: 40% (0.2% DEA in methanol), Total Flow: 4.0 g/min, Back Pressure: 100 bars, Temperature: 22.6° C., UV: 220 nm. | I: 6.235, 98.788% J: 7.854, 99.105% | $^1$H NMR (400 MHz, DMSO-d$_6$) δ ppm = 8.31 (d, J = 5.0 Hz, 1H), 8.25 (d, J = 8.5 Hz, 1H), 7.91 (d, J = 8.5 Hz, 1H), 7.00 (t, J = 8.0 Hz, 1H), 6.78 (d, J = 5.0 Hz, 1H), 6.71 (s, 2H), 6.35-6.28 (m, 2H), 6.22-6.15 (m, 1H), 5.97 (d, J = 7.5 Hz, 1H), 4.55-4.44 (m, 1H), 4.20 (t, J = 9.3 Hz, 1H), 3.85 (td, J = 10.3, 7.0 Hz, 1H), 3.69 (s, 3H), 2.61-2.55 (m, 4H), 1.97-1.83 (m, 1H); SOR: [α]$_D^{25.2}$ = −36.0 (c 0.05, MeOH). |
| 123 | 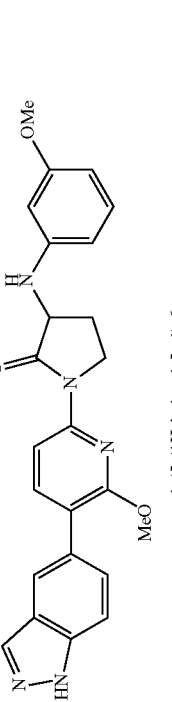<br>1-(5-(1H-indazol-5-yl)-6-methoxypyridin-2-yl)-3-(3-methoxyphenoxy)pyrrolidin-2-one (Ena-II) | Enantiomer-II | 431.20 | 100% ee (rt = 6.35 min), CHIRALPAK @ AS-H (250 × 4.6 mm), 5.0-μm particles; % CO$_2$: 60%, % Co-solvent: 40% (0.2% DEA in methanol), Total Flow: 3.0 g/min, Back Pressure: 100 bars, Temperature: 30° C., UV: 310 nm. | I: 18.717, 96.854% J: 16.939, 95.001% | $^1$H NMR (400 MHz, DMSO-d$_6$) δ ppm = 13.12 (br. s., 1H), 8.12 (s, 1H), 7.99 (d, J = 8.5 Hz, 1H), 7.93 (s, 1H), 7.91-7.87 (m, 1H), 7.62-7.52 (m, 2H), 7.23 (t, J = 8.3 Hz, 1H), 6.70-6.65 (m, 2H), 6.62-6.56 (m, 1H), 5.36 (s, 1H), 4.26 (t, J = 8.8 Hz, 2H), 3.99 (br. s., 4H), 3.76 (s, 3H), 2.76-2.70 (m, 1H), 2.09 (dd, J = 12.5, 8.5 Hz, 1H); SOR: [α]$_D^{25.1}$ = −24.0 (c 0.05, MeOH). |
| 124 | 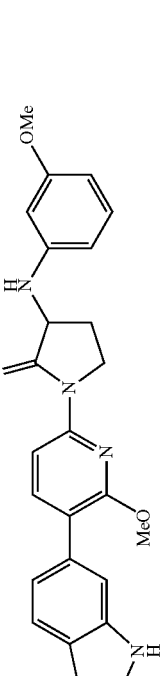<br>1-(5-(1H-indazol-6-yl)-6-methoxypyridin-2-yl)-3-(3-methoxyphenoxy)pyrrolidin-2-one (Ena-I) | Enantiomer-I | 431.20 | VII: 100% ee (rt = 6.650 min) | I: 17.356, 99.805% J: 17.932, 99.822% | $^1$H NMR (400 MHz, DMSO-d$_6$) δ ppm = 13.09 (s, 1H), 8.09 (s, 1H), 8.03-7.99 (m, 1H), 7.96-7.92 (m, 1H), 7.80 (d, J = 8.5 Hz, 1H), 7.71 (s, 1H), 7.31 (dd, J = 8.5, 1.5 Hz, 1H), 7.26-7.20 (m, 1H), 6.70-6.65 (m, 2H), 6.61-6.57 (m, 1H), 5.36 (t, J = 8.0 Hz, 1H), 4.27 (ddd, J = 11.2, 8.9, 2.5 Hz, 1H), 4.01-3.92 (m, 4H), 3.76 (s, 3H), 2.78-2.69 (m, 1H), 2.13-2.06 (m, 1H); SOR: [α]$_D^{25.0}$ = +28.0 (c 0.05, MeOH). |

TABLE 9-continued

| Ex. | Structure and Name | Chirality | LCMS (M + H)+ | Chiral Purity | HPLC Method, RT (min) & Purity | 1H NMR |
|---|---|---|---|---|---|---|
| 125 | 1-(5-(1H-indazol-6-yl)-6-methoxypyridin-2-yl)-3-(3-methoxyphenoxy)pyrrolidin-2-one (Ena-II) | Enantiomer-II | 431.20 | VII: 96.418% ee (rt = 7.572 min) | I: 17.36, 99.733% J: 17.95, 99.734% | 1H NMR (400 MHz, DMSO-d6) δ ppm = 13.09 (s, 1H), 8.09 (s, 1H), 8.03-7.99 (m, 1H), 7.96-7.91 (m, 1H), 7.80 (d, J = 8.5 Hz, 1H), 7.71 (s, 1H), 7.31 (dd, J = 8.5, 1.5 Hz, 1H), 7.27-7.20 (m, 1H), 6.71-6.65 (m, 2H), 6.62-6.57 (m, 1H), 5.36 (t, J = 8.0 Hz, 1H), 4.31-4.22 (m, 1H), 4.00-3.92 (m, 4H), 3.76 (s, 3H), 2.78-2.70 (m, 1H), 2.10 (dd, J = 12.3, 8.8 Hz, 1H); SOR: [α]$_D^{25.1}$ = −24.0 (c 0.05, MeOH). |
| 127 | 1-(2′-fluoro-2-methoxy-[3,4′-bipyridin]-6-yl)-3-((3-methoxyphenyl)amino)pyrrolidin-2-one | Racemate | 409.2 | | E: 2.30, 96.77% F: 2.35, 97.27% | 1H NMR (400 MHz, DMSO-d6) δ ppm 8.27 (d, J = 5.4 Hz, 1 H), 8.10 (d, J = 8.0 Hz, 1 H), 8.03 (d, J = 8.4 Hz, 1 H), 7.64 (d, J = 5.4 Hz, 1 H), 7.44 (s, 1 H), 6.99 (t, J = 7.9 Hz, 1 H), 6.34-6.27 (m, 2 H), 6.18 (d, J = 9.8 Hz, 1 H), 5.98 (d, J = 7.6 Hz, 1 H), 4.58-4.48 (m, 1 H), 4.30-4.20 (m, 1 H), 3.99 (s, 3 H), 3.94-3.84 (m, 1 H), 3.69 (s, 3 H), 2.63-2.54 (m, 1 H), 1.97-1.86 (m, 1 H), 19F NMR (376 MHz, DMSO-d6) δ ppm −69.14. |
| 128 | 1-(6-methoxy-5-(1H-pyrrolo[2,3-b]pyridin-4-yl)pyridin-2-yl)-3-((3-methoxyphenyl)amino)pyrrolidin-2-one | Racemate | 430.1 | | E: 1.79, 99.38% F: 1.48, 99.36% | 1H NMR (400 MHz, methanol-d4) δ ppm 8.34 (d, J = 5.9 Hz, 1 H), 8.19 (d, J = 8.3 Hz, 1 H), 8.04 (d, J = 8.1 Hz, 1 H), 7.61 (d, J = 3.7 Hz, 1 H), 7.57 (d, J = 5.9 Hz, 1 H), 7.13-7.04 (m, 1 H), 6.68 (d, J = 3.7 Hz, 1 H), 6.43-6.36 (m, 2 H), 6.31 (dd, J = 7.9, 2.3 Hz, 1 H), 4.50 (dd, J = 10.3, 8.3 Hz, 1H), 4.41 (t, J = 10.0 Hz, 1 H), 4.09-4.03 (m, 1 H), 4.02 (s, 3 H), 3.77 (s, 3 H), 2.81-2.70 (m, 1 H), 2.10-1.96 (m, 1 H), 19F NMR (400 MHz, methanol-d4) δ ppm −77.16. |

TABLE 9-continued
| Ex. | Structure and Name | Chirality | LCMS (M + H)+ | Chiral Purity | HPLC Method, RT (min) & Purity | 1H NMR |
|---|---|---|---|---|---|---|
| 129 | 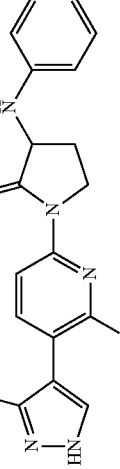<br>1-(6-methoxy-5-(3-methyl-1H-pyrazol-4-yl)pyridin-2-yl)-3-((3-methoxyphenyl)amino)pyrrolidin-2-one | Racemate | 394.1 | | E: 1.79, 99.87% F: 1.83, 99.89% | 1H NMR (400 MHz, DMSO-$d_6$) δ ppm 12.58 (br. s., 1 H), 7.91 (d, J = 8.1 Hz, 1 H), 7.85-7.50 (m, 2 H), 6.99 (t, J = 7.9 Hz, 1 H), 6.34-6.27 (m, 2 H), 6.17 (dd, J = 7.8, 2.2 Hz, 1 H), 5.95 (d, J = 7.3 Hz, 1 H), 4.52-4.41 (m, 1 H), 4.26-4.15 (m, 1 H), 3.91 (s, 3 H), 3.90-3.81 (m, 1 H), 3.68 (s, 3 H), 2.63-2.54 (m, 1 H), 2.23 (br. s., 3 H), 1.93-1.82 (m, 1 H). |

Example 130

5-(3-((3-Methoxyphenyl)amino)-2-oxopyrrolidin-1-yl)-2-(1H-pyrazol-4-yl)benzamide

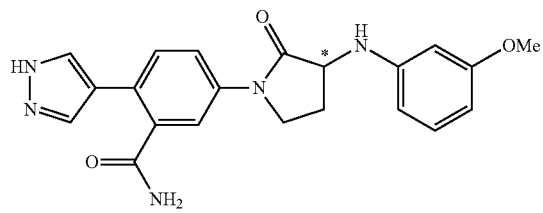 [SMILES: COc1cccc(NC2CCN(c3ccc(-c4cn[nH]c4)c(C(N)=O)c3)C2=O)c1]

Preparation of methyl 2-bromo-5-(3-bromo-2-oxopyrrolidin-1-yl)benzoate

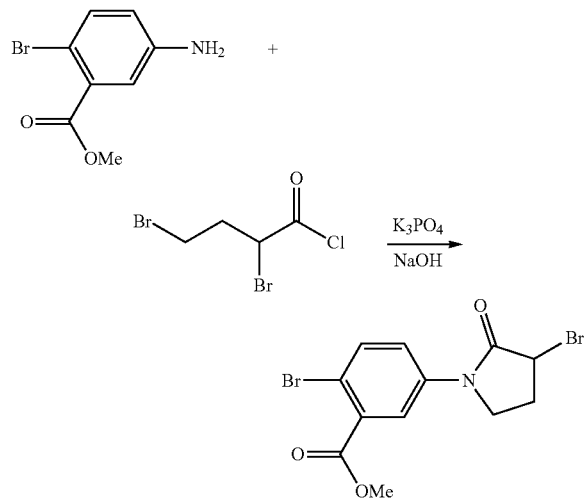

To a solution of methyl 5-amino-2-bromobenzoate (2.5 g, 10.9 mmol) and potassium phosphate tribasic (1.15 g, 5.43 mmol) in acetonitrile (100 mL) at 0° C., was added 2,4-dibromobutanoyl chloride (3.45 g, 13.0 mmol) dropwise. The reaction mixture was stirred at 5° C. to 10° C. for 3 h. The reaction mixture was diluted with water (150 mL) and extracted with EtOAc (2×150 mL). The combined organic extracts were washed with water and brine, dried over Na$_2$SO$_4$ and concentrated. The pale yellow oil was taken in DMF (60 mL) and cooled to 0° C. Potassium carbonate (6.01 g, 43.5 mmol) was added and the reaction mixture stirred at rt for 2 h. The reaction mixture was diluted with water (500 mL) and extracted with EtOAc (2×200 mL). The combined organic extracts were washed with water and brine, dried over Na$_2$SO$_4$ and concentrated. The crude product was purified by flash chromatography (eluting with 30-40% EtOAc in hexane) to give methyl 2-bromo-5-(3-bromo-2-oxopyrrolidin-1-yl)benzoate (3.4 g, 79% yield) as an off-white solid. MS(ESI) m/z: 378.4 (M+H)$^+$; $^1$H NMR (400 MHz, DMSO-d$_6$) δ ppm 8.15 (d, J=2.1 Hz, 1H), 7.83-7.75 (m, 2H), 4.93 (dd, J=3.9, 7.2 Hz, 1H), 4.00-3.91 (m, 2H), 3.88 (s, 3H), 2.83-2.71 (m, 1H), 2.40-2.30 (m, 1H).

Example 130b

Preparation of methyl 2-bromo-5-(3-((3-methoxyphenyl)amino)-2-oxopyrrolidin-1-yl)benzoate

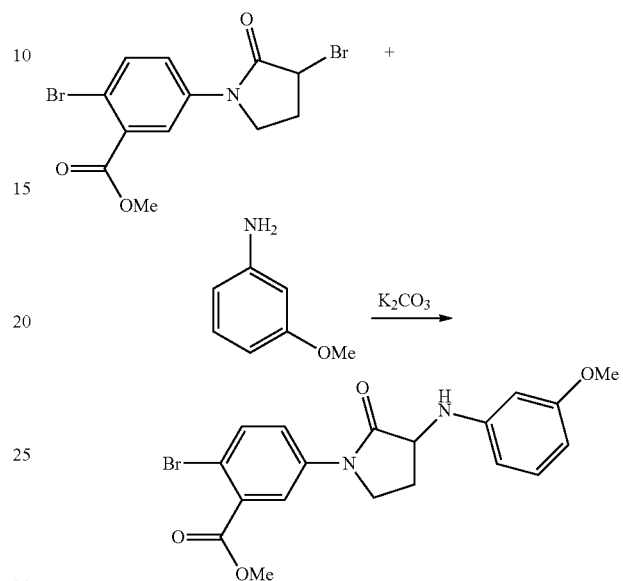

A solution of methyl 2-bromo-(3-bromo-2-oxopyrrolidin-1-yl)benzoate (2.5 g, 6.63 mmol), 3-methoxyaniline (2.04 g, 16.6 mmol) and potassium carbonate (2.75 g, 19.9 mmol) in DMF (20 mL) was heated at 95° C. for 15 h in a sealed tube. The reaction mixture was cooled to rt, diluted with water (250 mL) and extracted with EtOAc (2×250 mL). The combined organic extracts were washed with 0.75 N HCl solution (2×200 mL), water and brine, dried over Na$_2$SO$_4$ and concentrated to give methyl 2-bromo-5-(3-((3-methoxyphenyl)amino)-2-oxopyrrolidin-1-yl)benzoate (2.55 g, 89% yield) as a brown oil. MS(ESI) m/z: 421.2 (M+H)$^+$; $^1$H NMR (400 MHz, DMSO-d$_6$) δ ppm 8.20 (s, 1H), 7.77 (d, J=1.2 Hz, 2H), 6.98 (t, J=8.0 Hz, 1H), 6.32-6.25 (m, 2H), 6.17 (dd, J=1.9, 8.0 Hz, 1H), 5.95 (d, J=7.3 Hz, 1H), 4.46-4.35 (m, 1H), 3.87 (s, 3H), 3.86-3.78 (m, 2H), 3.67 (s, 3H), 2.57-2.53 (2.04, 1 H), 1.95-1.85 (mmol), 1H).

Example 130c

Preparation of tert-butyl 4-(2-(methoxycarbonyl)-4-(3-((3-methoxyphenyl)amino)-2-oxopyrrolidin-1-yl)phenyl)-1H-pyrazole-1-carboxylate

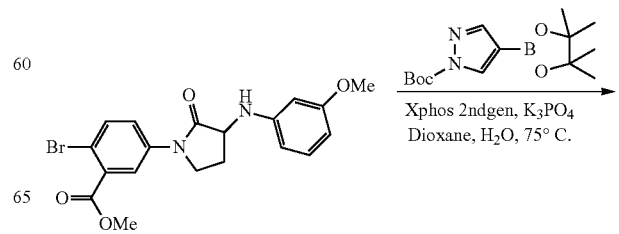

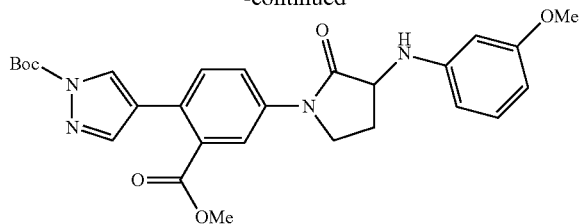

A solution of methyl 2-bromo-5-(3-((3-methoxyphenyl)amino)-2-oxopyrrolidin-1-yl)benzoate (0.5 g, 1.19 mmol), tert-butyl 4-(4,4,5,5-tetramethyl-1,3,2-dioxaborolan-2-yl)-1H-pyrazole-1-carboxylate (0.526 g, 1.79 mmol) and potassium phosphate tribasic (0.633 g, 2.98 mmol) in 1,4-dioxane (15 mL) and water (0.2 mL) was degassed with nitrogen. 2nd generation XPhos precatalyst (0.056 g, 0.072 mmol) was added and the reaction mixture heated at 75° C. for 2 h. The reaction mixture was cooled to rt, diluted with water (150 mL) and extracted with EtOAc (2×200 mL). The combined organic extracts were washed with water and brine, dried over Na$_2$SO$_4$ and concentrated to give the crude. The crude product was purified by flash chromatography (eluting with 50-60% EtOAc in hexane) to give tert-butyl 4-(2-(methoxycarbonyl)-4-(3-((3-methoxyphenyl) amino)-2-oxopyrrolidin-1-yl)phenyl)-1H-pyrazole-1-carboxylate (0.52 g, 85% yield) as an off-white solid. MS(ESI) m/z: 507.4 (M+H)$^+$; $^1$H NMR (300 MHz, DMSO-d$_6$) δ ppm 8.39 (d, J=0.7 Hz, 1H), 8.19 (d, J=2.3 Hz, 1H), 7.91-7.85 (m, 2H), 7.62 (d, J=8.6 Hz, 1H), 7.03-6.95 (m, 1H), 6.34-6.27 (m, 2H), 6.20-6.15 (m, 1H), 5.97 (d, J=7.2 Hz, 1H), 4.47-4.37 (m, 1H), 3.92-3.83 (m, 2H), 3.78 (s, 3H), 3.68 (s, 3H), 2.62-2.55 (m, 1H), 1.97-1.87 (m, 1H), 1.60 (s, 9H).

Example 130

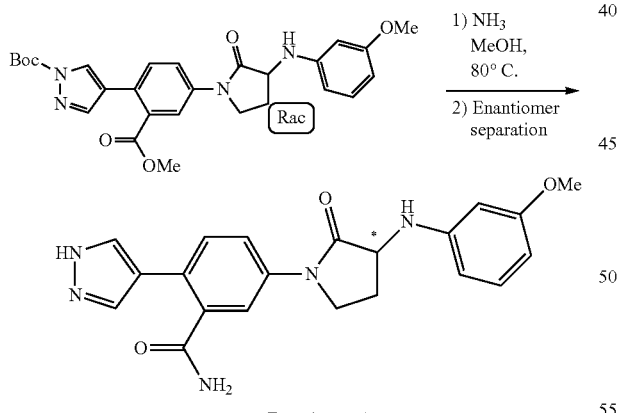

A solution of tert-butyl-4-(2-(methoxycarbonyl)-4-(3-((3-methoxyphenyl)amino)-2-oxopyrrolidin-1-yl)phenyl)-1H-pyrazole-1-carboxylate (0.2 g, 0.395 mmol) in methanol (12 mL) was placed in a sealed tube. The solution was cooled to −50° C. and ammonia in MeOH (4 mL, 0.395 mmol) was added. The reaction mixture was heated at 80° C. for 42 h, then was cooled to rt. The solvent was evaporated. The crude product was purified by flash chromatography (eluting with 7-9% methanol in chloroform) to give 100 mg of the product as racemate. The enantiomers were separated by preparative Supercritical Fluid Chromatography [CHIRALCEL® OD-H (250×21 mm), 5, Co-solvent is 45% (0.25% DEA in methanol)] to afford enantiomer 1 (Example 130) (6.5 mg, 4% yield) as an off-white solid; MS(ESI) m/z: 392.2 (M+H)$^+$; $^1$H NMR (400 MHz, DMSO-d$_6$) δ ppm 12.74 (br. s., 1H), 7.84 (s, 2H), 7.77-7.66 (m, 3H), 7.55 (d, J=8.5 Hz, 1H), 7.47 (s, 1H), 6.99 (t, J=8.0 Hz, 1H), 6.34-6.28 (m, 2H), 6.17 (dd, J=2.0, 7.7 Hz, 1H), 5.95 (d, J=7.1 Hz, 1H), 4.43-4.35 (m, 1H), 3.90-3.79 (m, 2H), 3.68 (s, 3H), 2.66-2.55 (m, 1H), 1.97-1.84 (m, 1H). Chiral HPLC RT=4.79 min, purity=100% (100% ee).

Example 132

1-(4-Methoxy-5-(1H-pyrazol-4-yl)pyrimidin-2-yl)-3-((3-methoxyphenyl)amino) pyrrolidin-2-one

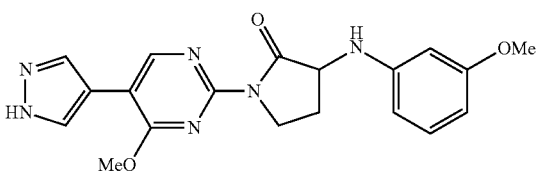 [SMILES: COc1cccc(NC2CCN(c3ncc(-c4cn[nH]c4)c(OC)n3)C2=O)c1]

Example 132a

Preparation of 3-bromo-1-(5-bromo-4-methoxypyrimidin-2-yl)pyrrolidin-2-one

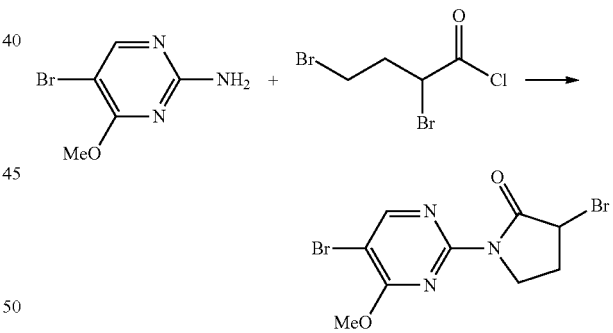

To a solution of 5-bromo-4-methoxypyrimidin-2-amine (1.5 g, 7.35 mmol) and Et$_3$N (1.13 mL, 8.09 mmol) in DCM (50 mL) at 0° C., 2,4-dibromobutanoyl chloride (2.138 g, 8.09 mmol) was added dropwise over 10 min. The cold bath was removed and the reaction mass was stirred at rt for 2 h. The reaction mixture was evaporated to dryness and K$_2$CO$_3$ (1.32 g, 9.56 mmol) in water (10 mL) was added. The mixture was heated to 100° C. for 1 h, then was cooled and was diluted with ethyl acetate (100 mL). The organic phase was washed with brine, dried over Na$_2$SO$_4$, filtered and concentrated to give crude 3-bromo-1-(5-bromo-4-methoxypyrimidin-2-yl)pyrrolidin-2-one (350 mg) as a yellow semi-solid. MS(ESI) m/z: 350.2 (M+H)$^+$. The product obtained was taken to next step without further purification.

Example 132b

Preparation of 1-(5-bromo-4-methoxypyrimidin-2-yl)-3-((3-methoxyphenyl)amino)pyrrolidin-2-one

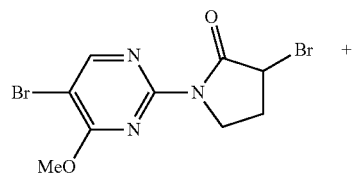

To the stirred solution of 3-bromo-1-(5-bromo-4-methoxypyrimidin-2-yl)pyrrolidin-2-one (300 mg, 0.291 mmol) and 3-methoxyaniline (143 mg, 1.16 mmol) in a mixture of THF (3 mL) and water (3 mL), was added K₂CO₃ (201 mg, 1.45 mmol). The reaction mixture was heated to 90° C. for 12 h, then was cooled to rt and extracted with ethyl acetate (10 mL). The organic layer was separated, dried over sodium sulphate and concentrated to afford crude 1-(5-bromo-4-methoxypyrimidin-2-yl)-3-((3-methoxyphenyl)amino)pyrrolidin-2-one (200 mg) as yellow semi-solid. MS(ESI) m/z: 393.1 (M+H)⁺. The product obtained was taken to next step without purification.

Example 132: Preparation of 1-(4-methoxy-5-(1H-pyrazol-4-yl)pyrimidin-2-yl)-3-((3-methoxyphenyl)amino) pyrrolidin-2-one

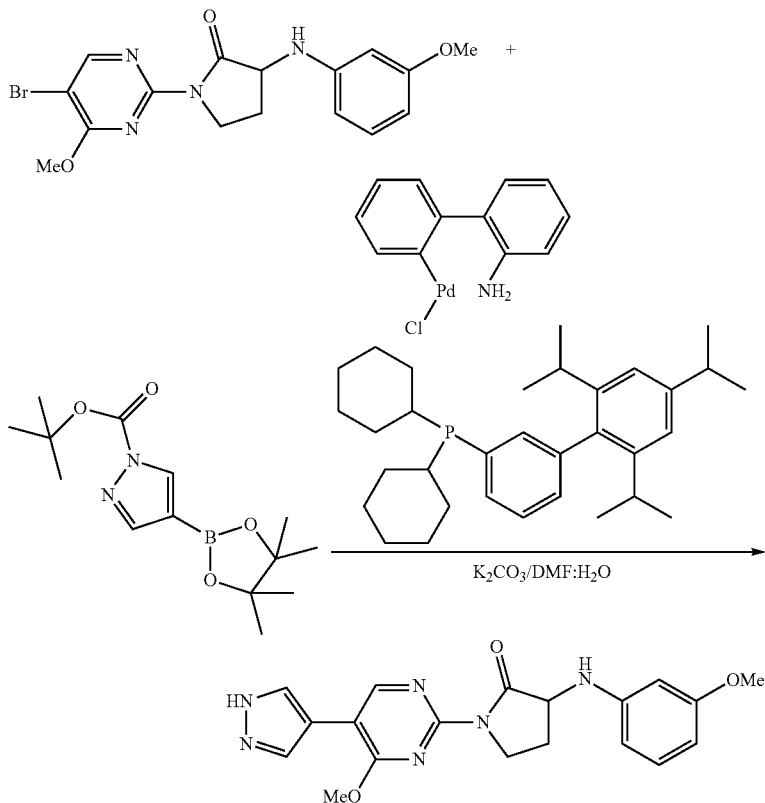

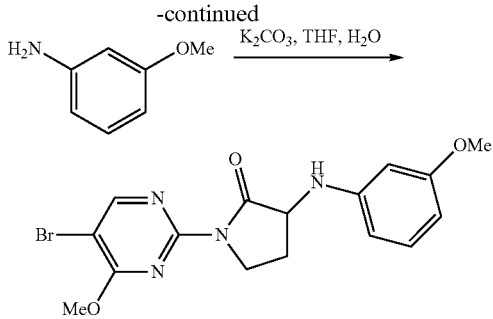

To a solution of 1-(5-bromo-4-methoxypyrimidin-2-yl)-3-((3-methoxyphenyl) amino)pyrrolidin-2-one (200 mg, 0.071 mmol) in DMF (4 mL) were added K₂CO₃ (9.84 mg, 0.071 mmol) and water (1 mL). The mixture was purged with nitrogen for 10 min and then charged with tert-butyl 4-(4,4,5,5-tetramethyl-1,3,2-dioxaborolan-2-yl)-1H-pyrazole-1-carboxylate (20.9 mg, 0.071 mmol) and 2nd generation XPhos precatalyst (56.0 mg, 0.071 mmol). The reaction mixture was purged with nitrogen for 10 min, then was heated at 95° C. for 4 h. The reaction mixture was cooled, diluted with water and extracted with ethyl acetate. The combined ethyl acetate layers were washed with water and brine, dried over Na₂SO₄, filtered and concentrated. The residue was purified by preparative HPLC with the following conditions: Waters XBridge C18, 19×150 mm, 5 µm; Guard Column: Waters XBridge C18, 19×10 mm, 5 µm;

Mobile Phase A: 5:95 acetonitrile:water with 10 mM NH₄OAc; Mobile Phase B: 95:5 acetonitrile:water with 10 mM NH₄OAc; Gradient: 10-35% B over 25 minutes and 5 minutes hold at 100% B; Flow: 15 ml/min. Fractions containing the desired product were concentrated to afford 1-(4-methoxy-5-(1H-pyrazol-4-yl)pyrimidin-2-yl)-3-((3-methoxyphenyl)amino) pyrrolidin-2-one (6 mg, 22% yield) as a pale yellow solid. MS(ESI) m/z: 381.2 (M+H)⁺; ¹H NMR (400 MHz, DMSO-d₆) δ ppm 12.99 (bs, 1H) 8.76-8.84 (m, 1H) 8.01-8.25 (m, 2H) 6.95-7.03 (m, 1H) 6.26-6.35 (m, 2H) 6.14-6.20 (m, 1H) 5.89-6.00 (m, 1H) 4.38-4.47 (m, 1H) 4.06 (s, 3H) 3.80-3.95 (m, 2H) 3.68 (s, 3H) 1.80-1.95 (m, 2H). HPLC RT=1.50 min, 100% (Method E), 1.35 min, 95.8% (Method F).

Example 133

(3R,4S)-1-(4-(1H-Pyrazol-4-yl)phenyl)-4-(hydroxymethyl)-3-((3-methoxyphenyl)amino) pyrrolidin-2-one

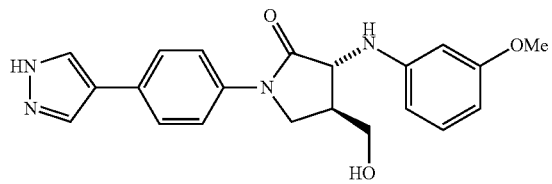 [SMILES: COc1cccc(N[C@H]2C(=O)N(c3ccc(-c4cn[nH]c4)cc3)C[C@@H]2CO)c1]

Example 133a

Preparation of 1-(4-bromophenyl)-4-(((tert-butyldimethylsilyl)oxy)methyl)-3-((3-methoxyphenyl)amino)pyrrolidin-2-one

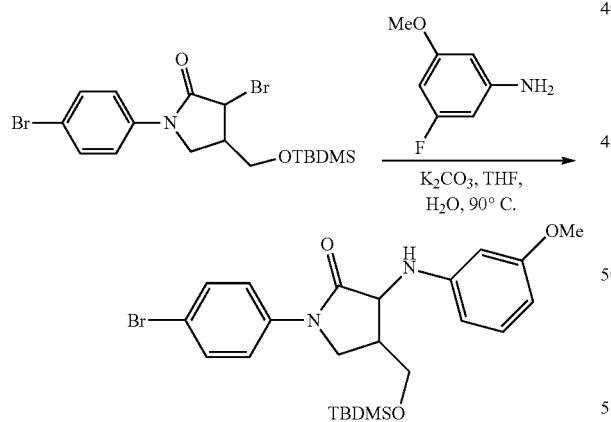

A solution of 3-bromo-1-(4-bromophenyl)-4-(((tert-butyldimethylsilyl)oxy) methyl)pyrrolidin-2-one (0.720 g, 1.55 mmol) and 3-methoxyaniline (0.522 mL, 4.66 mmol) in THF (25 mL) was added potassium carbonate (0.644 g, 4.66 mmol) and water (2.0 mL). The reaction mixture was heated at 90° C. for 2 days in a sealed tube. The reaction mixture was diluted with ethyl acetate, washed with water and brine solution, dried over Na₂SO₄, filtered and concentrated. The resultant oil was dissolved in DCM and precipitated by adding hexanes. The resultant solid was collected by filtration and washed with hexane to obtain 1-(4-bromophenyl)-4-(((tert-butyldimethylsilyl)oxy)methyl)-3-((3-methoxyphenyl)amino)pyrrolidin-2-one (0.300 g, 0.590 mmol, 38% yield). MS(ESI) m/z: 381.2 (M+H)⁺; ¹H NMR (400 MHz, DMSO-d₆) δ ppm 7.69 (d, J=9.04 Hz, 2H) 7.59 (d, J=9.04 Hz, 2H) 6.96 (t, J=8.28 Hz, 1H) 6.22-6.30 (m, 2H) 6.12-6.20 (m, 1H) 6.03 (d, J=8.53 Hz, 1H) 4.24 (t, J=8.78 Hz, 1H) 3.85-3.92 (m, 1H) 3.80 (d, J=3.51 Hz, 2H) 3.67 (s, 3H) 3.61 (t, J=9.04 Hz, 1H) 0.88 (s, 9H) 0.05 (d, J=3.40 Hz, 6H).

Example 133b

Preparation of (3R,4S)-1-(4-bromophenyl)-4-(hydroxymethyl)-3-((3-methoxyphenyl) amino)pyrrolidin-2-one and (3S,4R)-1-(4-bromophenyl)-4-(hydroxymethyl)-3-((3-methoxyphenyl)amino) pyrrolidin-2-one

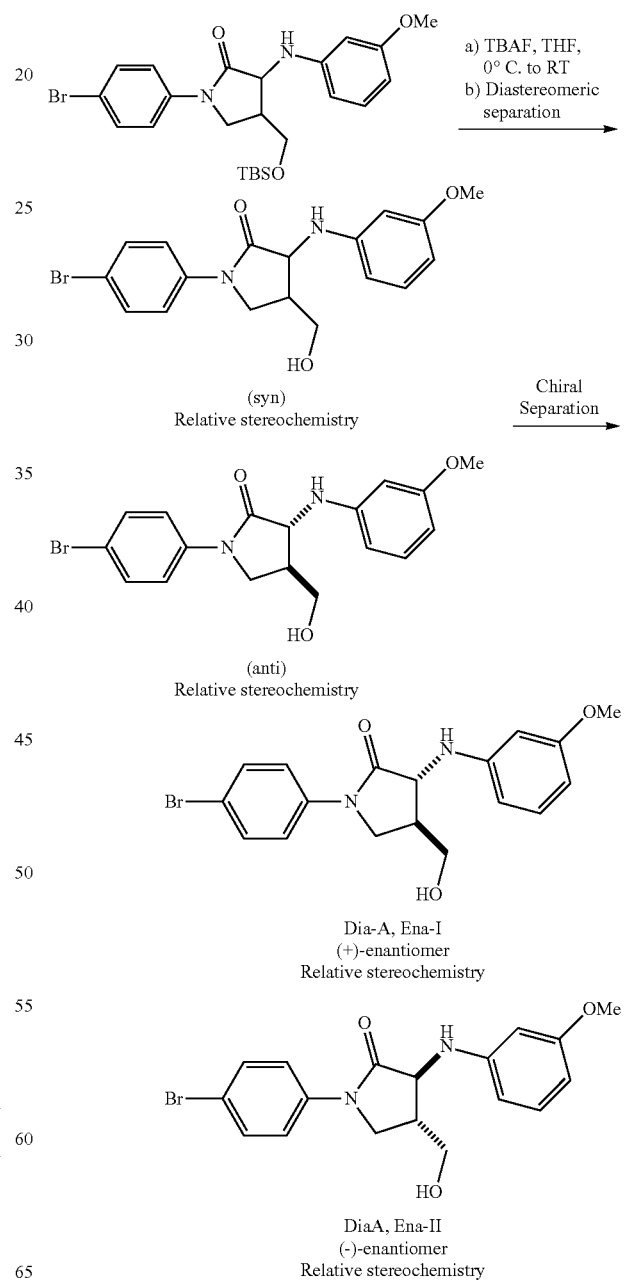

To a solution of 1-(4-bromophenyl)-4-(((tert-butyldimethylsilyl)oxy)methyl)-3-((3-methoxyphenyl)amino)pyrrolidin-2-one (0.300 g, 0.593 mmol) in THF (15 mL) at 0° C., was added dropwise 1.0 M solution of TBAF (1.780 mL, 1.780 mmol) in THF. The reaction mixture was then allowed to warm to rt and stir for 2 h. The reaction mixture was quenched with water and the phases were separated. The aqueous phase was extracted with EtOAC (3×). The combined organic extracts were washed with brine, dried over $Na_2SO_4$ and concentrated to afford the mixture of diastereomers. The diastereomers were separated by preparative HPLC to afford the syn and anti diastereomers in the ratio of 95:5 (anti: syn).

The anti diastereomer was subjected to chiral separation using chiral SFC method (Column: Lux Cellulose-4 (250× 4.6 mm), 5 t, 60% $CO_2$; 40% (0.2% DEA in MeOH); 250 nm UV: Flow rate: 70 g/min; Temperature: 35° C.; Enantiomer-1: RT=6.50 and Enantiomer-2: RT=9.50).

Obtained separated enantiomers as fractions which were concentrated and lyophilized to obtain (3R,4S)-1-(4-bromophenyl)-4-(hydroxymethyl)-3-((3-methoxyphenyl) amino)pyrrolidin-2-one (0.070 g, 0.165 mmol, 27.7% yield). MS(ESI) m/z: 393.1 (M+H)$^+$; $^1$H NMR (400 MHz, DMSO-$d_6$) δ ppm 7.71-7.65 (m, 2H), 7.60-7.55 (m, 2H), 6.99-6.92 (m, 1H), 6.31-6.24 (m, 2H), 6.18-6.12 (m, 1H), 6.01 (d, J=8.0 Hz, 1H), 4.94 (t, J=5.0 Hz, 1H), 4.26-4.19 (m, 1H), 3.90-3.82 (m, 1H), 3.70-3.55 (m, 4H); 100% ee (RT: 5.85), determined by chiral SFC analysis, Column: Lux Cellulose-4 (250×4.6 mm), 5μ, Mobile Phase: 0.2% DEA in MeOH with Co-solvent $CO_2$ 40%]; $[α]^{25.1}_D$=+88.0 (c 0.05, DMSO) and (3S,4R)-1-(4-bromophenyl)-4-(hydroxymethyl)-3-((3-methoxyphenyl)amino)pyrrolidin-2-one (0.065 g, 0.130 mmol, 22% yield). MS(ESI) m/z: 393.1 (M+H)$^+$; $^1$H NMR (400 MHz, DMSO-$d_6$) δ ppm 7.72-7.64 (m, 2H), 7.62-7.53 (m, 2H), 6.95 (t, J=7.7 Hz, 1H), 6.31-6.23 (m, 2H), 6.18-6.11 (m, 1H), 6.02 (d, J=7.9 Hz, 1H), 4.95 (s, 1H), 4.23 (t, J=9.3 Hz, 1H), 3.91-3.80 (m, 1H), 3.71-3.53 (m, 4H); 99% ee (RT: 9.90), determined by chiral SFC analysis, Column: Lux Cellulose-4 (250×4.6 mm), 5μ, Mobile Phase: 0.2% DEA in MeOH with Co-solvent $CO_2$ 40%]; $[α]^{25.1}_D$=-92.0 (c 0.05, DMSO).

Example 133: Preparation of (3R,4S)-1-(4-(1H-pyrazol-4-yl)phenyl)-4-(hydroxymethyl)-3-((3-methoxyphenyl)amino)pyrrolidin-2-one

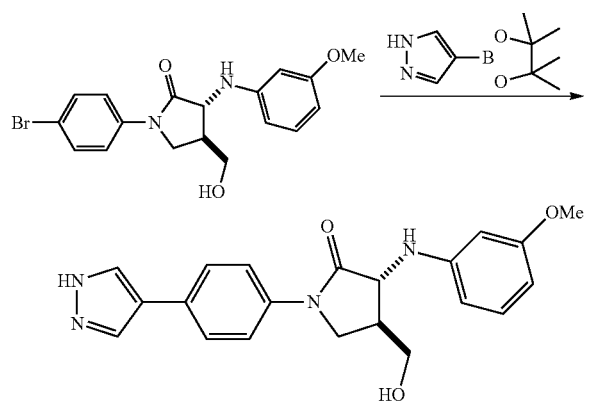

To a solution of (3R,4S)-1-(4-bromophenyl)-4-(hydroxymethyl)-3-((3-methoxyphenyl)amino)pyrrolidin-2-one (0.060 g, 0.153 mmol) in Dioxane (3 mL), was added 1-Boc-pyrazole-4-boronic acid pinacol ester (0.054 g, 0.184 mmol), potassium phosphate tribasic (0.065 g, 0.307 mmol) and water (0.6 mL). The reaction mixture was bubbled with nitrogen for 5 min. 2nd generation XPhos precatalyst (7.2 mg, 9.2 μmol) was added to the reaction mixture and was again bubbled with nitrogen for 5 min. The reaction mixture was heated at 70° C. for 3 h. Reaction mixture was cooled to rt, diluted with EtOAc, and washed with water and brine, dried over $Na_2SO_4$ and concentrated. The crude product was dissolved in DCM (3 mL), and TFA (0.1 mL) was added. The reaction mixture was stirred for overnight at rt. The solvent was evaporated in vacuo to afford a gummy product which was purified by preparative HPLC to afford (3R,4S)-1-(4-(1H-pyrazol-4-yl)phenyl)-4-(hydroxymethyl)-3-((3-methoxyphenyl)amino)pyrrolidin-2-one (7.7 mg, 95%). MS(ESI) m/z: 379.2 (M+H)$^+$; $^1$H NMR (400 MHz, DMSO-$d_6$) δ ppm 12.90 (br. s., 1H) 8.16 (s, 1H) 7.90 (br. s., 1H) 7.68 (d, J=8.80 Hz, 2H) 7.62 (d, J=9.05 Hz, 2H) 6.95 (t, J=7.95 Hz, 1H) 6.25-6.31 (m, 2H) 6.14 (d, J=8.31 Hz, 1H) 6.00 (d, J=8.56 Hz, 1H) 4.93 (t, J=4.89 Hz, 1H) 4.22 (t, J=8.93 Hz, 1H) 3.87 (t, J=9.05 Hz, 1H) 3.65-3.69 (m, 1H) 3.66 (s, 3H) 3.55-3.65 (m, 2H); 100% ee (RT: 4.03), determined by chiral SFC analysis, Column: CHIRALCEL® OJ-H (250×4.6 mm), 5μ, Mobile Phase: 0.2% DEA in MeOH with Co-solvent $CO_2$ 40%]; $[α]^{25.1}_D$=+27.2 (c 0.05, DMSO).

Example 134

1-(6-Methoxy-5-(1H-pyrazol-4-yl)pyrazin-2-yl)-3-((3-methoxyphenyl)amino) pyrrolidin-2-one

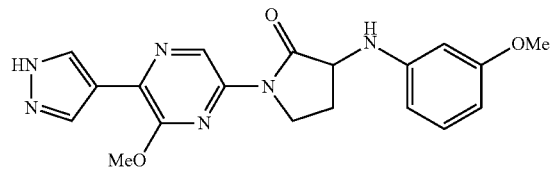 [SMILES: COc1cccc(NC2CCN(c3cnc(-c4cn[nH]c4)c(OC)n3)C2=O)c1]

Example 134a

Preparation of 3-bromo-1-(5-bromo-6-methoxypyrazine-2-yl)pyrrolidin-2-one

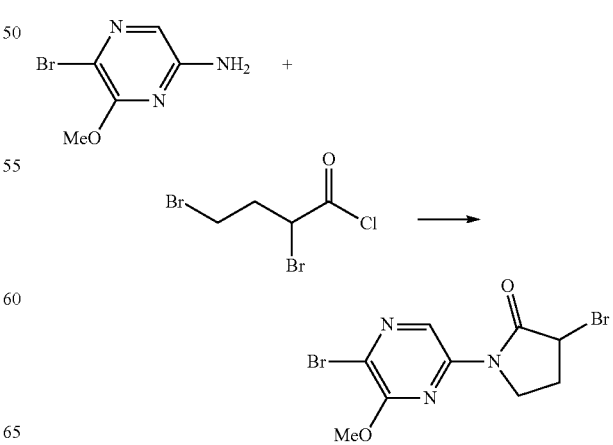

To a stirred solution of 5-bromo-6-methoxypyrazine-2-amine (300 mg, 1.47 mmol) and Et₃N (266 µl, 1.91 mmol) in THF (2 mL) at −10° C., 2,4-dibromobutyryl chloride (233 µl, 1.76 mmol) in THF (1 mL) was added dropwise. The reaction mixture was stirred at 0° C. for 2 h. NaH (176 mg, 4.41 mmol) was added portionwise over 10 min. The mixture was stirred at 0° C. for 20 min, then was quenched with ice water (20 mL) and extracted with ethyl acetate (20 mL). The organic phase was dried over Na₂SO₄, filtered and concentrated to give 3-bromo-1-(5-bromo-6-methoxypyrazine-2-yl)pyrrolidin-2-one (100 mg, 19% yield) as red semi-solid, which was taken to the next step without further purification. MS(ESI) m/z: 351.9 (M+H)⁺.

Example 134b

Preparation of 1-(5-bromo-6-methoxypyrazine-2-yl)-3-((3-methoxyphenyl)amino)pyrrolidin-2-one

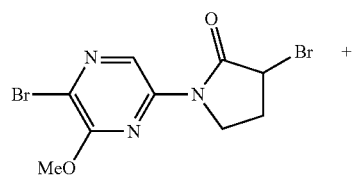

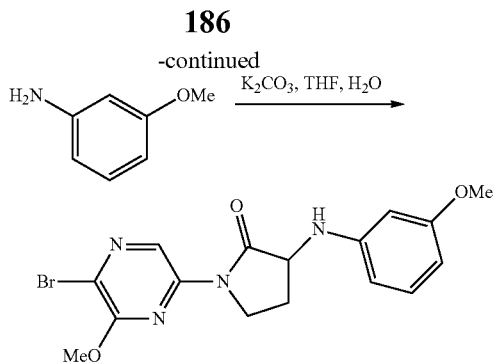

To a stirred solution of 3-bromo-1-(5-bromo-6-methoxypyrazine-2-yl)pyrrolidin-2-one (100 mg, 0.285 mmol) and 3-methoxyaniline (140 mg, 1.14 mmol) in a mixture of THF (2 mL) and water (2 mL), was added K₂CO₃ (197 mg, 1.43 mmol). The reaction mixture was heated at 90° C. for 12 h. The reaction mixture was cooled to rt and extracted with ethyl acetate (10 mL). The organic layer was separated, dried over sodium sulphate and concentrated under reduced pressure to afford 1-(5-bromo-6-methoxypyrazine-2-yl)-3-((3-methoxyphenyl)amino)pyrrolidin-2-one (100 mg, 89% yield) as yellow semi-solid, which was taken to next step without further purification. MS(ESI) m/z: 395.0 (M+H)⁺.

Example 134: Preparation of 1-(6-methoxy-5-(1H-pyrazol-4-yl)pyrazin-2-yl)-3-((3-methoxyphenyl)amino)pyrrolidin-2-one

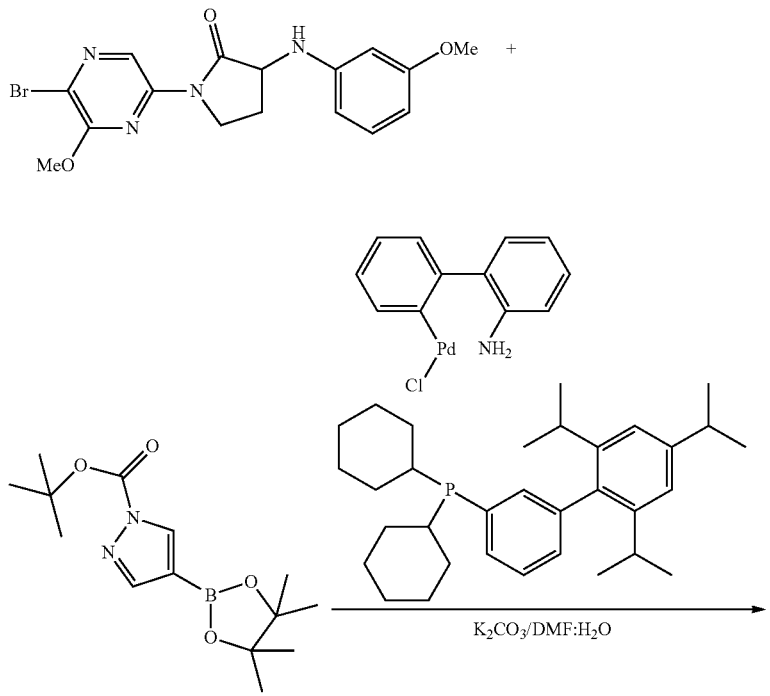

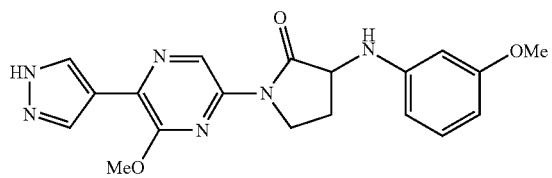

A solution of 1-(5-bromo-6-methoxypyrazine-2-yl)-3-((3-methoxyphenyl)amino) pyrrolidin-2-one (100 mg, 0.254 mmol), tert-butyl 4-(4,4,5,5-tetramethyl-1,3,2-dioxaborolan-2-yl)-1H-pyrazole-1-carboxylate (82 mg, 0.28 mmol) and $K_2CO_3$ (105 mg, 0.763 mmol) in DMF (3 mL) and water (0.5 mL), was bubbled with Ar for 5 min. 2nd generation XPhos precatalyst (20.0 mg, 0.025 mmol) was added, then the mixture was heated at 95° C. for 4 h. The reaction mixture was cooled, diluted with water, and extracted with ethyl acetate. The combined ethyl acetate layers were washed with water and brine solution, dried over $Na_2SO_4$, filtered and concentrated. The residue was purified by preparative HPLC to afford 1-(6-methoxy-5-(1H-pyrazol-4-yl)pyrazin-2-yl)-3-((3-methoxyphenyl)amino)pyrrolidin-2-one (37.2 mg, 38% yield) as a pale yellow solid. MS(ESI) m/z: 381.2 $(M+H)^+$; $^1H$ NMR (400 MHz, DMSO-$d_6$) δ ppm 13.15 (br. s, 1H) 9.08 (s, 1H) 8.31 (s, 1H) 8.12 (s, 1H) 7.00 (t, J=8.07 Hz, 1H) 6.28-6.36 (m, 2H) 6.19 (dd, J=8.44, 2.08 Hz, 1H) 6.01 (d, J=7.58 Hz, 1H) 4.48-4.59 (m, 1H) 4.16 (t, J=9.05 Hz, 1H) 4.07 (s, 3H) 3.85 (td, J=10.33, 6.72 Hz, 1H) 3.69 (s, 3H) 2.61 (dd, J=12.72, 6.36 Hz, 1H) 1.88-2.03 (m, 1H). HPLC RT=1.47 min, 99.0% (Method E), 1.67 min, 100% (Method F).

The following Examples in Table 10 were made by using the same procedure as shown in Examples 130-134.

TABLE 10

| Ex. | Structure and Name | Chirality | LCMS (M+H)+ | Chiral Purity | HPLC Method, RT (min) & Purity | 1H NMR |
|---|---|---|---|---|---|---|
| 135 | 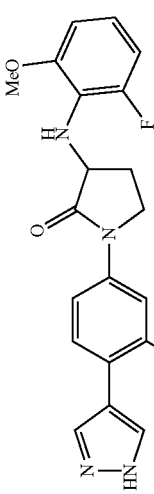<br>3-((2-fluoro-6-methoxyphenyl)amino)-1-(3-methoxy-4-(1H-pyrazol-4-yl)phenyl)pyrrolidin-2-one | Enantiomer-I | 396.90 | 100% ee (rt-6.94), CHIRALCEL @ AS-H (250 × 4.6 mm), 5.0-μm particles; % CO2: 70%, % Co-solvent: 30% (0.2% DEA in MeOH), Total Flow: 3.0 g/min, Back Pressure: 100 bars, Temperature: 25.2° C., UV: 266 nm. | I: 9.61, 98.47%<br>J: 8.93, 99.4% | 1H NMR (400 MHz, DMSO-d6) δ = 12.86 (br. s., 1H), 8.10 (br. s., 1H), 7.94 (br. s., 1H), 7.65-7.59 (m, 2H), 7.15 (dd, J = 8.5, 2.0 Hz, 1H), 6.79-6.67 (m, 3H), 4.94 (dd, J = 7.8, 2.3 Hz, 1H), 4.47 (dt, J = 10.5, 8.0 Hz, 1H), 3.87-3.75 (m, 8H), 2.59-2.54 (m, 1H), 2.13-2.00 (m, 1H); F19-NMR (400 MHz, DMSO-d6): δ ppm -129.745; SOR: [α]D24.8 = +24.0 (c 0.05, DMSO). |
| 136 | 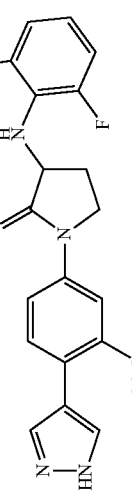<br>3-((2-fluoro-6-methoxyphenyl)amino)-1-(3-methoxy-4-(1H-pyrazol-4-yl)phenyl)pyrrolidin-2-one | Enantiomer-II | 397.00 | 96.76% ee (rt-8.81), CHIRALCEL @ AS-H (250 × 4.6 mm), 5.0-μm particles; % CO2: 70%, % Co-solvent: 30% (0.2% DEA in MeOH), Total Flow: 3.0 g/min, Back Pressure: 100 bars, Temperature: 25.7° C., UV: 266 nm. | I: 9.60, 98.18%<br>J: 8.95, 99.12% | 1H NMR (400 MHz, DMSO-d6) δ = 12.84 (br. s., 1H), 8.02 (br. s., 2H), 7.66-7.56 (m, 2H), 7.15 (dd, J = 8.5, 2.0 Hz, 1H), 6.80-6.67 (m, 3H), 4.94 (dd, J = 7.8, 2.3 Hz, 1H), 4.48 (dt, J = 10.9, 8.1 Hz, 1H), 3.92-3.75 (m, 8H), 2.61-2.58 (m, 1H), 2.13-1.99 (m, 1H); F19-NMR (400 MHz, DMSO-d6): δ ppm -129.745; [α]D24.8 = -44.0 (c 0.05, DMSO). |
| 137 | 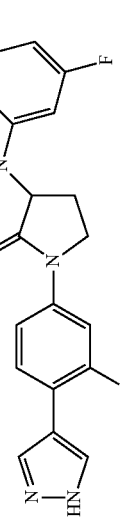<br>3-((3-fluoro-5-methoxyphenyl)amino)-1-(3-methoxy-4-(1H-pyrazol-4-yl)phenyl)pyrrolidin-2-one | Enantiomer-I | 396.90 | 100% ee (rt-5.27), CHIRALCEL @ OD-H (250 × 4.6 mm), 5.0-μm particles; % CO2: 60%, % Co-solvent: 40% (0.2% DEA in MeOH), Total Flow: 4.0 g/min, Back Pressure: 100 bars, Temperature: 25.5° C., UV: 268 nm. | I: 9.62, 99.33%<br>J: 9.03, 99.6% | 1H NMR (400 MHz, DMSO-d6) δ = 12.85 (br. s., 1H), 8.03 (br. s., 2H), 7.71-7.56 (m, 2H), 7.18 (dd, J = 8.5, 2.0 Hz, 1H), 6.31 (s, 1H), 6.19-6.07 (m, 2H), 6.00 (dt, J = 11.2, 2.2 Hz, 1H), 4.43 (dt, J = 9.8, 7.9 Hz, 1H), 3.94-3.77 (m, 5H), 3.69 (s, 3H), 2.71-2.56 (m, 1H), 1.97-1.74 (m, 1H); F19-NMR (400 MHz, DMSO-d6): δ ppm -112.564; SOR: [α]D24.8 = +36.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 138 | 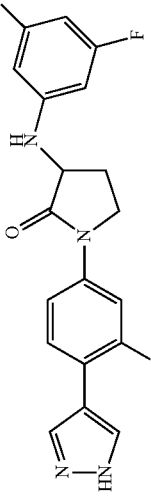<br>3-((3-fluoro-5-methoxyphenyl)amino)-1-(3-methoxy-4-(1H-pyrazol-4-yl)phenyl)pyrrolidin-2-one | Enantiomer-II | 397.20 | 98.74% ee (rt-10.52), CHIRALCEL @ OD-H (250 × 4.6 mm), 5.0-µm particles; % $CO_2$: 60%, % Co-solvent: 40% (0.2% DEA in MeOH), Total Flow: 4.0 g/min, Back Pressure: 100 bars, Temperature: 25.8° C., UV: 268 nm. | I: 9.53, 98.2%<br>J: 9.02, 98.5% | 1H NMR (400 MHz, DMSO-$d_6$) δ = 12.70 (br. s., 1H), 8.03 (s, 2H), 7.66-7.58 (m, 2H), 7.18 (dd, J = 8.3, 2.3 Hz, 1H), 6.30 (d, J = 7.5 Hz, 1H), 6.18-6.09 (m, 2H), 6.00 (dt, J = 11.0, 2.3 Hz, 1H), 4.43 (dt, J = 9.9, 7.8 Hz, 1H), 3.92-3.78 (m, 5H), 3.69 (s, 3H), 2.70-2.55 (m, 1H), 2.01-1.79 (m, 1H); F19-NMR (400 MHz, DMSO-$d_6$): δ ppm −112.565; SOR: $[α]_D^{24.7}$ = −48.0 (c 0.05, DMSO). |
| 139 | 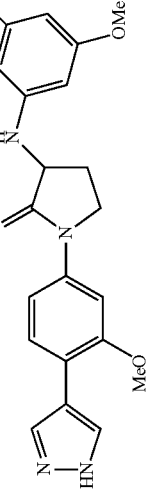<br>3-((3,5-dimethoxyphenyl)amino)-1-(3-methoxy-4-(1H-pyrazol-4-yl)phenyl)pyrrolidin-2-one | Enantiomer-I | 409.00 | 99.0868% ee (rt-8.35), CHIRALPAK @ IC (250 × 4.6 mm), 5.0-µm particles; % $CO_2$: 60%, % Co-solvent: 40% (0.2% DEA in IPA:ACN (1:1)), Total Flow: 4.0 g/min, Back Pressure: 99 bars, Temperature: 24.7° C., UV: 269 nm. | I: 8.75, 96.8%<br>J: 8.82, 97.2% | 1H NMR (400 MHz DMSO-$d_6$) δ = 12.86 (br. s., 1H), 8.08 (br. s., 2H), 7.66-7.58 (m, 2H), 7.19 (dd, J = 8.5, 2.0 Hz, 1H), 5.97-5.90 (m, 3H), 5.79 (t, J = 2.0 Hz, 1H), 4.43-4.32 (m, 1H), 3.91-3.81 (m, 5H), 3.67 (s, 6H), 2.70-2.54 (m, 1H), 1.95-1.82 (m, 1H); SOR: $[α]_D^{24.9}$ = +16.0 (c 0.05, DMSO). |
| 140 | 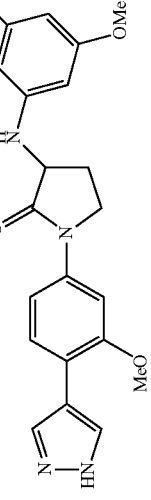<br>3-((3,5-dimethoxyphenyl)amino)-1-(3-methoxy-4-(1H-pyrazol-4-yl)phenyl)pyrrolidin-2-one | Enantiomer-II | 409.10 | 95.621% ee (rt-10.49), CHIRALPAK @ IC (250 × 4.6 mm), 5.0-µm particles; % $CO_2$: 60%, % Co-solvent: 40% (0.2% DEA in IPA:ACN (1:1)), Total Flow: 4.0 g/min, Back Pressure: 100 bars, Temperature: 24.9° C., UV: 269 nm. | I: 8.74, 97.4%<br>J: 8.83, 98.0% | 1H NMR (400 MHz DMSO-$d_6$) δ = 8.03 (s, 2H), 7.67-7.60 (m, 2H), 7.19 (dd, J = 8.5, 2.0 Hz, 1H), 5.98-5.90 (m, 3H), 5.81-5.75 (m, 1H), 4.43-4.34 (m, 1H), 3.95-3.80 (m, 5H), 3.67 (s, 6H), 2.60 (d, J = 5.5 Hz, 1H), 1.95-1.82 (m, 1H); SOR: $[α]_D^{24.9}$ = −36.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 141 | 3-(((3-fluoro-4-methoxyphenyl)amino)-1-(3-methoxy-4-(1H-pyrazol-4-yl)phenyl) pyrrolidin-2-one | Enantiomer-I | 397.10 | 100% ee (rt-11.28), WHELK-O1 @ (R,R) (250 × 4.6 mm), 5.0-μm particles; % CO₂; 60%, % Co-solvent: 40% (0.2% DEA in IPA:ACN (1:1)), Total Flow: 4.0 g/min, Back Pressure: 100 bars, Temperature: 24° C., UV: 275 nm. | I: 8.74, 96.2% J: 9.64, 99.0% | ¹H NMR (400 MHz DMSO-d₆) δ ppm = 12.86 (br. s., 1H), 8.11 (br. s., 1H), 8.00-7.88 (m, 1H), 7.66-7.56 (m, 2H), 7.18 (dd, J = 8.3, 2.3 Hz, 1H), 6.97-6.89 (m, 1H), 6.63 (dd, J = 14.1, 2.5 Hz, 1H), 6.47 (dd, J = 9.0, 1.5 Hz, 1H), 5.85 (d, J = 7.0 Hz, 1H), 4.33 (dt, J = 9.5, 7.5 Hz, 1H), 3.94-3.78 (m, 5H), 3.72 (s, 3H), 2.61 (dt, J = 12.0, 6.0 Hz, 1H), 1.93-1.77 (m, 1H); F¹⁹-NMR (400 MHz, DMSO-d₆): δ ppm −134.266; SOR: $[\alpha]_D^{25.1}$ = +52.0 (c 0.05, DMSO). |
| 142 | 3-(((3-fluoro-4-methoxyphenyl)amino)-1-(3-methoxy-4-(1H-pyrazol-4-yl)phenyl) pyrrolidin-2-one | Enantiomer-II | 396.90 | 99.2688% ee (rt-19.40), WHELK-O1 @ (R,R) (250 × 4.6 mm), 5.0-μm particles; % CO₂; 60%, % Co-solvent: 40% (0.2% DEA in IPA:CAN (1:1)), Total Flow: 4.0 g/min, Back Pressure: 99 bars, Temperature: 24° C., UV: 275 nm. | I: 8.79, 97.0% J: 8.65, 98.7% | ¹H NMR (400 MHz DMSO-d₆) δ ppm = 12.85 (br. s., 1H), 8.03 (br. s., 2H), 7.68-7.56 (m, 2H), 7.18 (dd, J = 8.3, 2.3 Hz, 1H), 6.98-6.87 (m, 1H), 6.63 (dd, J = 14.1, 2.5 Hz, 1H), 6.48 (d, J = 9.0 Hz, 1H), 5.84 (d, J = 7.0 Hz, 1H), 4.33 (dd, J = 17.6, 8.0 Hz, 1H), 3.90-3.78 (m, 5H), 3.72 (s, 3H), 2.72-2.55 (m, 1H), 1.94-1.78 (m, 1H); F¹⁹-NMR (400 MHz, DMSO-d₆): δ ppm −134.264; SOR: $[\alpha]_D^{25.1}$ = −56.0 (c 0.05, DMSO). |
| 143 | 3-((4-fluoro-2-methoxyphenyl)amino)-1-(3-methoxy-4-(1H-pyrazol-4-yl)phenyl) pyrrolidin-2-one | Enantiomer-II | 396.90 | 100% ee (rt-5.41), Column: CHIRALCEL @ OD-H (250 × 4.6 mm), 5.0-μm particles; % CO₂: 60%, % Co-solvent: 40% (0.2% DEA in methanol), Total Flow: 4.0 g/min, Back Pressure: 103 bars, Temperature: 24° C., UV: 267 nm. | I: 8.79, 96.1% J: 8.92, 99.0% | ¹H NMR (400 MHz, DMSO-d₆) δ ppm = 12.79 (br. s., 1H), 8.03 (s, 2H), 7.67-7.57 (m, 2H), 7.19 (dd, J = 8.5, 2.0 Hz, 1H), 6.82 (dd, J = 10.5, 2.5 Hz, 1H), 6.72-6.57 (m, 2H), 4.99 (d, J = 5.5 Hz, 1H), 4.27 (ddd, J = 10.5, 8.0, 5.0 Hz, 1H), 3.94-3.85 (m, 5H), 3.84 (s, 3H), 2.76-2.64 (m, 1H), 2.02-1.87 (m, 1H); F¹⁹-NMR (400 MHz, DMSO-d₆): δ ppm −125.956; SOR:$[\alpha]_D^{25.0}$ = +8.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 144 | 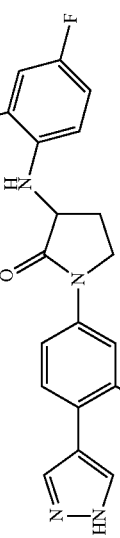<br>3-((4-fluoro-2-methoxyphenyl)amino)-1-(3-methoxy-4-(1H-pyrazol-4-yl)phenyl)pyrrolidin-2-one | Enantiomer-II | 397.10 | 94.7824% ee (rt-6.79), CHIRALCEL ® OD-H (250 × 4.6 mm), 5.0-μm particles; % CO2: 60%, % Co-solvent: 40% (0.2% DEA in methanol), Total Flow: 4.0 g/min, Back Pressure: 100 bars, Temperature: 23.9° C., UV: 267 nm. | I: 9.62, 94.8% J: 9.28, 98.9% | 1H NMR (400 MHz, DMSO-d6) δ ppm = 12.76 (br. s., 1H), 8.03 (s, 2H), 7.67-7.59 (m, 2H), 7.22-7.16 (m, 1H), 6.82 (dd, J = 10.5, 2.5 Hz, 1H), 6.73-6.58 (m, 2H), 4.99 (d, J = 5.0 Hz, 1H), 4.27 (ddd, J = 10.3, 8.0, 5.3 Hz, 1H), 3.94-3.85 (m, 5H), 3.84 (s, 3H), 2.76-2.63 (m, 1H), 2.03-1.87 (m, 1H); F19-NMR (400 MHz, DMSO-d6): δ ppm −125.958; SOR: $[\alpha]_D^{25.3}$ = −20.0 (c 0.05, DMSO). |
| 145 | 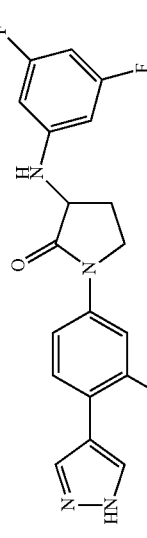<br>3-((3,5-difluorophenyl)amino)-1-(3-methoxy-4-(1H-pyrazol-4-yl)phenyl)pyrrolidin-2-one | Enantiomer-I | 385.10 | 100% ee (rt-6.31), Column: WHELK-O1 ® (R,R) (250 × 4.6 mm), 5.0-μm particles; % CO2: 60%, % Co-solvent: 40% (0.2% DEA in IPA:ACN (1:1)), Total Flow: 4.0 g/min, Back Pressure: 101 bars, Temperature: 23.7° C., UV: 274 nm. | I: 9.79, 94.7% J: 9.33, 95.8% | 1H NMR (400 MHz, DMSO-d6) δ ppm = 12.86 (br. s., 1H), 8.20-7.86 (m, 2H), 7.67-7.55 (m, 2H), 7.18 (dd, J = 8.5, 2.0 Hz, 1H), 6.68 (d, J = 7.5 Hz, 1H), 6.39 (dd, J = 10.8, 2.3 Hz, 2H), 6.28 (tt, J = 9.5, 2.3 Hz, 1H), 4.48 (dt, J = 9.8, 7.9 Hz, 1H), 3.94-3.70 (m, 5H), 2.70-2.57 (m, 1H), 1.96-1.81 (m, 1H); F19-NMR (400 MHz, DMSO-d6): δ ppm −110.944; SOR: $[\alpha]_D^{25.3}$ = +76.0 (c 0.05, DMSO). |
| 146 | 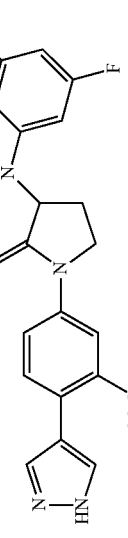<br>3-((3,5-difluorophenyl)amino)-1-(3-methoxy-4-(1H-pyrazol-4-yl)phenyl)pyrrolidin-2-one | Enantiomer-II | 384.90 | 97.4364% ee (rt-8.0), WHELK-O1 ® (R,R) (250 × 4.6 mm), 5.0-μm particles; % CO2: 60%, % Co-solvent: 40% (0.2% DEA in IPA:ACN (1:1)), Total Flow: 4.0 g/min, Back Pressure: 97 bars, Temperature: 23.8° C., UV: 274 nm. | I: 9.79, 95.1% J: 9.40, 99.2% | 1H NMR (400 MHz DMSO-d6) δ ppm = 12.80 (br. s., 1H), 8.03 (s, 2H), 7.67-7.57 (m, 2H), 7.18 (dd, J = 8.5, 2.0 Hz, 1H), 6.68 (d, J = 7.5 Hz, 1H), 6.39 (dd, J = 10.8, 2.3 Hz, 2H), 6.28 (tt, J = 9.5, 2.3 Hz, 1H), 4.48 (dt, J = 10.0, 7.8 Hz, 1H), 3.93-3.78 (m, 5H), 2.70-2.56 (m, 1H), 1.97-1.79 (m, 1H); F19-NMR (400 MHz, DMSO-d6): δ ppm −110.944; SOR: $[\alpha]_D^{24.9}$ = −112.00 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 147 | 3-((2-fluoro-5-methoxyphenyl)amino)-1-(3-methoxy-4-(1H-pyrazol-4-yl)phenyl) pyrrolidin-2-one | Enantiomer-I | 397.20 | 100% ee (rt-6.53), Column: WHELK-O1 ® (R,R) (250 × 4.6 mm), 5.0-μm particles; % CO$_2$; 60%, % Co-solvent: 40% (0.2% DEA in methanol), Total Flow: 4.0 g/min, Back Pressure: 100 bars, Temperature: 24.1° C., UV: 272 nm. | I: 9.39, 98.6%<br>J: 8.89, 98.9% | 1H NMR (400 MHz DMSO-d$_6$) δ 12.85 (br. s., 1H), 8.10 (br. s., 1H), 7.94 (br. s., 1H), 7.67-7.57 (m, 2H), 7.18 (dd, J = 8.4, 2.1 Hz, 1H), 6.95 (dd, 1 = 11.5, 8.8 Hz, 1H), 6.46 (dd, J = 7.5, 2.8 Hz, 1H), 6.13 (dt, J = 8.8, 3.1 Hz, 1H), 5.76-5.58 (m, 1H), 4.59-4.43 (m, 1H), 3.95-3.78 (m, 5H), 3.68 (s, 3H), 2.63-2.53 (m, 1H), 2.17-1.94 (m, 1H); F$^{19}$-NMR (400 MHz, DMSO-d$_6$): δ ppm −144.171; SOR: [α]$_D^{25.0}$ = +72.0 (c 0.05, MeOH). |
| 148 | 3-((5-fluoro-2-methoxyphenyl)amino)-1-(3-methoxy-4-(1H-pyrazol-4-yl)phenyl) pyrrolidin-2-one | Enantiomer-II | 397.20 | 100% ee (rt-5.78), CHIRALPAK ® IC (250 × 4.6 mm), 5.0-μm particles; % CO$_2$; 60%, % Co-solvent: 40% (0.2% DEA in methanol), Total Flow: 4.0 g/min, Back Pressure: 101 bars, Temperature: 24.3° C., UV: 271 nm. | I: 9.77, 98.3%<br>J: 9.26, 98.6% | 1H NMR (400 MHz DMSO-d$_6$) δ ppm = 12.85 (br. s., 1H), 8.10 (br. s., 1H), 7.94 (br. s., 1H), 7.68-7.57 (m, 2H), 7.18 (dd, J = 8.4, 2.1 Hz, 1H), 6.80 (dd, J = 8.8, 5.3 Hz, 1H), 6.57 (dd, J = 11.3, 2.8 Hz, 1H), 6.36 (td, J = 8.7, 3.0 Hz, 1H), 5.42 (d, J = 5.3 Hz, 1H), 4.47-4.29 (m, 1H), 3.93-3.82 (m, 5H), 3.80 (s, 3H), 2.74-2.62 (m, 1H), 2.08-1.92 (m, 1H); F$^{19}$-NMR (400 MHz, DMSO-d$_6$): δ ppm −122.075; SOR: [α]$_D^{24.8}$ = +4.0 (c 0.05, MeOH). |
| 149 | 3-((2-fluoro-5-methoxyphenyl)amino)-1-(3-methoxy-4-(1H-pyrazol-4-yl)phenyl) pyrrolidin-2-one | Enantiomer-II | 397.20 | 100% ee (rt-12.44), Column: WHELK-O1 ® (R,R) (250 × 4.6 mm), 5.0-μm particles; % CO$_2$; 60%, % Co-solvent: 40% (0.2% DEA in methanol), Total Flow: 4.0 g/min, Back Pressure: 100 bars, Temperature: 24.1° C., UV: 272 nm. | I: 9.39, 96.0%<br>J: 8.87, 95.2% | 1H NMR (400 MHz, DMSO-d$_6$) δ = 12.85 (br. s., 1H), 8.10 (br. s., 1H), 7.95 (br. s., 1H), 7.74-7.51 (m, 2H), 7.18 (dd, J = 8.5, 2.0 Hz, 1H), 6.96 (dd, J = 11.5, 8.8 Hz, 1H), 6.47 (dd, J = 7.5, 2.8 Hz, 1H), 6.14 (dt, J = 8.8, 3.3 Hz, 1H), 5.72-5.59 (m, 1H), 4.58-4.46 (m, 1H), 3.98-3.79 (m, 5H), 3.69 (s, 3H), 2.63-2.56 (m, 1H), 2.15-1.99 (m, 1H); F$^{19}$-NMR (400 MHz, DMSO-d$_6$): δ ppm −144.176; SOR: [α]$_D^{25.1}$ = −72.0 (c 0.05, MeOH). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 150 | 3-((3-fluoro-2-methoxyphenyl)amino)-1-(3-methoxy-4-(1H-pyrazol-4-yl)phenyl)pyrrolidin-2-one | Enantiomer-I | 397.20 | 100% ee (rt-8.23), CHIRALPAK @ AS-H (250 × 4.6 mm), 5.0-μm particles; % CO₂: 70%, % Co-solvent: 30% (0.2% DEA in methanol), Total Flow: 3.0 g/min, Back Pressure: 100 bars, Temperature: 24.3° C., UV: 269 nm. | I: 9.71, 98.9%, J: 8.860, 99.4% | ¹H NMR (400 MHz, DMSO-d₆) δ ppm = 12.84 (br. s., 1H), 8.18-7.86 (m, 2H), 7.68-7.57 (m, 2H), 7.19 (dd, J = 8.4, 2.1 Hz, 1H), 6.89 (td, J = 8.2, 6.1 Hz, 1H), 6.61 (d, J = 8.3 Hz, 1H), 6.48 (ddd, J = 11.0, 8.3, 1.3 Hz, 1H), 5.59 (d, J = 7.0 Hz, 1H), 4.44 (dt, J = 10.1, 7.7 Hz, 1H), 3.94-3.82 (m, 5H), 3.80 (d, J = 0.8 Hz, 3H), 2.72-2.56 (m, 1H), 2.14-1.96 (m, 1H); F¹⁹-NMR (400 MHz, DMSO-d₆): δ ppm −132.938; SOR:[α]²⁵·⁰_D = −8.0 (c 0.05, MeOH). |
| 151 | 3-((3-fluoro-2-methoxyphenyl)amino)-1-(3-methoxy-4-(1H-pyrazol-4-yl)phenyl)pyrrolidin-2-one | Enantiomer-II | 396.90 | 95.764% ee (rt-10.11), CHIRALPAK @ AS-H (250 × 4.6 mm), 5.0-μm particles; % CO₂: 70%, % Co-solvent: 30% (0.2% DEA in methanol), Total Flow: 3.0 g/min, Back Pressure: 100 bars, Temperature: 23.4° C., UV: 269 nm. | I: 9.73, 88.9%, J: 9.16, 92.7% | ¹H NMR (400 MHz, DMSO-d₆) δ ppm = 12.77 (br. s., 1H), 8.02 (s, 2H), 7.63 (d, J = 8.3 Hz, 2H), 7.20 (s, 1H), 6.89 (td, J = 8.3, 6.3 Hz, 1H), 6.61 (d, J = 8.3 Hz, 1H), 6.48 (ddd, J = 11.0, 8.3, 1.3 Hz, 1H), 5.59 (d, J = 7.0 Hz, 1H), 4.48-4.39 (m, 1H), 3.96-3.83 (m, 5H), 3.80 (d, J = 0.8 Hz, 3H), 2.65-2.58 (m, 1H), 2.12-1.93 (m, 1H); F¹⁹-NMR (400 MHz, DMSO-d₆): δ ppm −132.939; SOR:[α]²⁵·⁰_D = +8.0 (c 0.05, MeOH). |
| 152 | 3-((2-fluoro-4-methoxyphenyl)amino)-1-(3-methoxy-4-(1H-pyrazol-4-yl)phenyl)pyrrolidin-2-one | Enantiomer-I | 397.20 | 99.0304% ee (rt-4.26), CHIRALPAK @ AS-H (250 × 4.6 mm), 5.0-μm particles; % CO₂: 60%, % Co-solvent: 40% (0.2% DEA in methanol), Total Flow: 3.0 g/min, Back Pressure: 99 bars, Temperature: 23.5° C., UV: 269 nm. | I: 9.17, 96.1%, J: 9.44, 96.0% | ¹H NMR (400 MHz, DMSO-d₆) δ ppm = 12.85 (br. s., 1H), 8.02 (br. s., 2H), 7.62 (dd, J = 5.3, 3.3 Hz, 2H), 7.17 (dd, J = 8.4, 2.1 Hz, 1H), 6.92-6.83 (m, 1H), 6.78 (dd, J = 13.3, 2.8 Hz, 1H), 6.62 (dd, J = 8.7, 2.1 Hz, 1H), 5.16 (d, J = 5.5 Hz, 1H), 4.43-4.29 (m, 1H), 3.92-3.77 (m, 5H), 3.68 (s, 3H), 2.63-2.54 (m, 1H), 2.10-1.94 (m, 1H); F¹⁹-NMR (400 MHz, DMSO-d₆): δ ppm −131.065; SOR:[α]²⁵·¹_D = +28.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 153 | 3-((2-fluoro-4-methoxyphenyl)amino)-1-(3-methoxy-4-(1H-pyrazol-4-yl)phenyl) pyrrolidin-2-one | Enantiomer-II | 397.20 | 98.0254% ee (rt-5.73), CHIRALPAK ® AS-H (250 × 4.6 mm), 5.0-μm particles; % $CO_2$: 60%, % Co-solvent: 40% (0.2% DEA in methanol), Total Flow: 3.0 g/min, Back Pressure: 99 bars, Temperature: 23.3° C., UV: 269 nm. | I: 9.17, 95.1% J: 9.74, 97.9% | 1H NMR (400 MHz, DMSO-$d_6$) δ ppm = 12.81 (br. s., 1H), 8.02 (br. s., 2H), 7.62 (dd, J = 5.1, 3.1 Hz, 2H), 7.17 (dd, J = 8.5, 2.0 Hz, 1H), 6.92-6.83 (m, 1H), 6.78 (dd, J = 13.3, 2.8 Hz, 1H), 6.62 (dd, J = 9.0, 2.0 Hz, 1H), 5.16 (d, J = 5.5 Hz, 1H), 4.41-4.31 (m, 1H), 3.92-3.78 (m, 5H), 3.68 (s, 3H), 2.63-2.54 (m, 1H), 2.09-1.94 (m, 1H); $F^{19}$-NMR (400 MHz, DMSO-$d_6$): δ ppm −131.067; SOR:$[α]^{25.0}_D$ = −64.0 (c 0.05, DMSO). |
| 154 | 3-((4-fluoro-3-methoxyphenyl)amino)-1-(3-methoxy-4-(1H-pyrazol-4-yl)phenyl) pyrrolidin-2-one | Enantiomer-I | 397.20 | 100% ee (rt-10.23), Column: CHIRALPAK ® AS-H (250 × 4.6 mm), 5.0-μm particles; % $CO_2$: 70%, % Co-solvent: 30% (0.2% DEA in methanol), Total Flow: 3.0 g/min, Back Pressure: 100 bars, Temperature: 23.3° C., UV: 269 nm. | I: 8.90, 91.3% J: 8.32, 93.4% | 1H NMR (400 MHz, DMSO-$d_6$) δ ppm = 8.02 (s, 2H), 7.68-7.55 (m, 2H), 7.18 (dd, J = 8.5, 2.0 Hz, 1H), 6.91 (dd, J = 11.5, 8.8 Hz, 1H), 6.53 (dd, J = 7.5, 2.5 Hz, 1H), 6.21 (dt, J = 8.7, 3.0 Hz, 1H), 5.84 (d, J = 7.0 Hz, 1H), 4.44-4.30 (m, 1H), 3.93-3.81 (m, 5H), 3.80-3.73 (m, 3H), 2.61 (d, J = 5.8 Hz, 1H), 1.97-1.76 (m, 1H); $F^{19}$-NMR (400 MHz, DMSO-$d_6$): δ ppm −150.858; SOR: $[α]^{25.1}_D$ = +16.0 (c 0.05, DMSO). |
| 155 | 3-((4-fluoro-3-methoxyphenyl)amino)-1-(3-methoxy-4-(1H-pyrazol-4-yl)phenyl) pyrrolidin-2-one | Enantiomer-II | 397.20 | 88.8136% ee (rt-12.26), CHIRALPAK ® AS-H (250 × 4.6 mm), 5.0-μm particles; % $CO_2$: 70%, % Co-solvent: 30% (0.2% DEA in methanol), Total Flow: 3.0 g/min, Back Pressure: 100 bars, Temperature: 23.3° C., UV: 269 nm. | I: 8.90, 89.9% J: 8.26, 94.4% | 1H NMR (400 MHz, DMSO-$d_6$) δ ppm = 8.02 (s, 2H), 7.67-7.53 (m, 2H), 7.18 (dd, J = 8.4, 2.1 Hz, 1H), 6.91 (dd, J = 11.5, 8.8 Hz, 1H), 6.53 (dd, J = 7.5, 2.5 Hz, 1H), 6.21 (dt, J = 8.8, 3.0 Hz, 1H), 5.84 (d, J = 7.0 Hz, 1H), 4.44-4.30 (m, 1H), 3.95-3.81 (m, 5H), 3.77 (s, 3H), 2.62 (br. s., 1H), 2.00-1.79 (m, 1H); $F^{19}$-NMR (400 MHz, DMSO-$d_6$): δ ppm −150.856; SOR: $[α]^{25.1}_D$ = −20.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 156 | 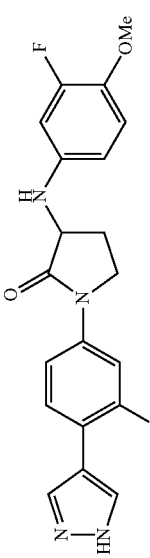<br>1-(3-chloro-4-(1H-pyrazol-4-yl)phenyl)-3-(((3-fluoro-4-methoxyphenyl)amino) pyrrolidin-2-one | Enantiomer-I | 401.00 | 99.0504% ee (rt-8.72), CHIRALCEL ® OJ-H (250 × 4.6 mm), 5.0-μm particles; % $CO_2$: 60%, % Co-solvent: 40% (0.2% DEA in methanol), Total Flow: 3.0 g/min, Back Pressure: 100 bars, Temperature: 30° C., UV: 269 nm. | I: 9.54, 97.0% J: 9.07, 96.0% | 1H NMR (400 MHz DMSO-d6) δ ppm = 13.14-12.95 (m, 1H), 8.16 (br. s., 1H), 8.01-7.93 (m, 1H), 7.90 (br. s., 1H), 7.65 (d, J = 1.5 Hz, 2H), 6.98-6.87 (m, 1H), 6.62 (dd, J = 14.1, 2.5 Hz, 1H), 6.51-6.41 (m, 1H), 5.84 (d, J = 7.0 Hz, 1H), 4.40-4.27 (m, 1H), 3.92-3.76 (m, 2H), 3.72 (s, 3H), 2.65-2.53 (m, 1H), 1.98-1.81 (m, 1H); $F^{19}$-NMR (400 MHz, DMSO-d6): δ ppm −134.223; SOR: $[α]_D^{24.7}$ = −36.0 (c 0.05, MeOH). |
| 157 | 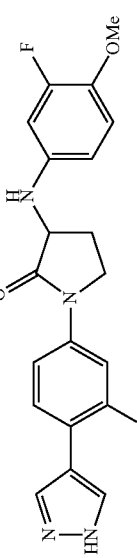<br>1-(3-chloro-4-(1H-pyrazol-4-yl)phenyl)-3-(((3-fluoro-4-methoxyphenyl)amino) pyrrolidin-2-one | Enantiomer-II | 399.00 | 88.3946% ee (rt-9.36), CHIRALCEL ® OJ-H (250 × 4.6 mm), 5.0-μm particles; % $CO_2$: 60%, % Co-solvent: 40% (0.2% DEA in methanol), Total Flow: 3.0 g/min, Back Pressure: 100 bars, Temperature: 30° C., UV: 270 nm. | I: 9.40, 95.5% J: 9.28, 94.8% | 1H NMR (400 MHz, DMSO-d6) δ ppm = 13.07 (br. s., 1H), 8.16 (br. s., 1H), 7.98-7.94 (m, 1H), 7.90 (br. s., 1H), 7.65 (d, J = 1.5 Hz, 2H), 6.97-6.89 (m, 1H), 6.62 (dd, J = 14.1, 2.5 Hz, 1H), 6.52-6.43 (m, 1H), 5.84 (d, J = 7.0 Hz, 1H), 4.39-4.30 (m, 1H), 3.91-3.76 (m, 2H), 3.72 (s, 3H), 2.63-2.54 (m, 1H), 1.95-1.82 (m, 1H); $F^{19}$-NMR (400 MHz, DMSO-d6): δ ppm −134.223; SOR: $[α]_D^{25.0}$ = +20.0 (c 0.05, MeOH). |
| 158 | 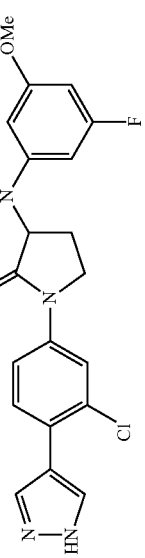<br>1-(3-chloro-4-(1H-pyrazol-4-yl)phenyl)-3-(((3-fluoro-5-methoxyphenyl)amino) pyrrolidin-2-one | Enantiomer-I | 401.00 | 99.5806% ee (rt-8.81), CHIRALPAK ® IC (250 × 4.6 mm), 5.0-μm particles; % $CO_2$: 60%, % Co-solvent: 40% (0.2% DEA in methanol), Total Flow: 3.0 g/min, Back Pressure: 100 bars, Temperature: 30° C., UV: 269 nm. | I: 10.24, 96.8% J: 9.98, 95.8% | 1H NMR (400 MHz, DMSO-d6) δ ppm = 13.06 (br. s., 1H), 8.16 (br. s., 1H), 7.97 (t, J = 1.3 Hz, 1H), 7.91 (br. s., 1H), 7.65 (d, J = 1.5 Hz, 2H), 6.81 (dd, J = 10.8, 2.8 Hz, 1H), 6.70-6.57 (m, 2H), 5.01 (d, J = 6.0 Hz, 1H), 4.35-4.26 (m, 1H), 3.91-3.79 (m, 5H), 2.64-2.54 (m, 1H), 2.04-1.88 (m, 1H); $F^{19}$-NMR (400 MHz, DMSO-d6): δ ppm −125.986; SOR: $[α]_D^{25.1}$ = −12.0 (c 0.05, MeOH). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 159 | 1-(3-chloro-4-(1H-pyrazol-4-yl)phenyl)-3-(((3-fluoro-5-methoxyphenyl)amino)pyrrolidin-2-one | Enantiomer-II | 401.00 | 99.2354% ee (rt-12), CHIRALPAK @ IC (250 × 4.6 mm), 5.0-μm particles; % $CO_2$; 60%, % Co-solvent: 40% (0.2% DEA in methanol), Total Flow: 3.0 g/min, Back Pressure: 100 bars, Temperature: 30° C., UV: 269 nm. | I: 10.33, 95.1% J: 9.77, 96.3% | 1H NMR (400 MHz, DMSO-d6) δ ppm = 13.07 (br. s., 1H), 8.17 (br. s., 1H), 8.00-7.96 (m, 1H), 7.90 (br. s., 1H), 7.65 (d, J = 1.0 Hz, 2H), 6.81 (dd, J = 10.8, 2.8 Hz, 1H), 6.72-6.56 (m, 2H), 5.01 (d, J = 5.5 Hz, 1H), 4.36-4.25 (m, 1H), 3.91-3.78 (m, 5H), 2.63-2.54 (m,1H), 2.04-1.88 (m, 1H); F19-NMR (400 MHz, DMSO-d6): δ ppm −125.986; SOR: $[\alpha]^{24.7}_D$ = +16.0 (c 0.05, MeOH). |
| 160 | 1-(3-chloro-4-(1H-pyrazol-4-yl)phenyl)-3-(((4-fluoro-3-methoxyphenyl)amino)pyrrolidin-2-one | Enantiomer-I | 401.00 | 100% ee (rt-11.49), CHIRALPAK @ IC (250 × 4.6 mm), 5.0-μm particles; % $CO_2$; 60%, % Co-solvent: 40% (0.2% DEA in methanol), Total Flow: 4.0 g/min, Back Pressure: 100 bars, Temperature: 30° C., UV: 270 nm. | I: 9.74, 99.1% J: 9.20, 99.1% | 1H NMR (400 MHz DMSO-d6) 0 ppm = 13.34 (br. s., 1H), 8.43 (br. s., 1H), 8.23 (t, J = 1.3 Hz, 1H), 8.17 (br. s., 1H), 7.91 (d, J = 1.2 Hz, 2H), 7.18 (dd, J = 11.5, 8.8 Hz, 1H), 6.78 (dd, J = 7.6, 2.7 Hz, 1H), 6.46 (dt, J = 8.6, 3.2 Hz, 1H), 6.13 (d, J = 7.1 Hz, 1H), 4.65 (dt, J = 9.5, 7.8 Hz, 1H), 4.17-3.98 (m, 5H), 2.91-2.82 (m, 1H), 2.22-2.07 (m, 1H); F19-NMR (400 MHz, DMSO-d6): δ ppm −150.815; SOR: $[\alpha]^{25.1}_D$ = −44.0 (c 0.05, DMSO). |
| 161 | 1-(3-chloro-4-(1H-pyrazol-4-yl)phenyl)-3-(((4-fluoro-3-methoxyphenyl)amino)pyrrolidin-2-one | Enantiomer-II | 401.00 | 98.0722% ee (rt-13.82), CHIRALPAK @ IC (250 × 4.6 mm), 5.0-μm particles; % $CO_2$; 60%, % Co-solvent: 40% (0.2% DEA in methanol), Total Flow: 4.0 g/min, Back Pressure: 100 bars, Temperature: 30° C., UV: 270 nm. | I: 9.74, 99.1% J: 9.20, 99.0% | 1H NMR (400 MHz, DMSO-d6) δ ppm = 13.33 (br. s., 1H), 8.43 (br. s., 1H), 8.23 (t, J = 1.3 Hz, 1H), 8.17 (br. s., 1H), 7.91 (d, J = 1.2 Hz, 2H), 7.18 (dd, J = 11.5, 8.8 Hz, 1H), 6.78 (dd, J = 7.6, 2.7 Hz, 1H), 6.46 (dt, J = 8.7, 3.1 Hz, 1H), 6.13 (d, J = 7.3 Hz, 1H), 4.65 (dt, J = 9.7, 7.6 Hz, 1H), 4.18-4.00 (m, 5H), 2.91-2.81 (m, 1H), 2.21-2.08 (m, 1H); F19-NMR (400 MHz, DMSO-d6): δ ppm −150.815. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 162 | 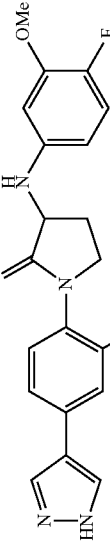 1-(2-chloro-4-(1H-pyrazol-4-yl)phenyl)-3-((4-fluoro-3-methoxyphenyl)amino)pyrrolidin-2-one | Enantiomer-I | 401.20 | 100% ee (rt-6.69), CHIRALPAK ® IA (250 × 4.6 mm), 5.0-μm particles; % CO$_2$; 60%, % Co-solvent: 40% (0.2% DEA in methanol), Total Flow: 4.0 g/min, Back Pressure: 100 bars, Temperature: 30° C., UV: 260 nm. | I: 9.24, 99.9%, J: 8.82, 99.8% | 1H NMR (400 MHz, DMSO-d$_6$) 0 ppm = 13.05 (br. s., 1H), 8.32 (br. s., 1H), 8.02 (br. s., 1H), 7.85 (d, J = 2.0 Hz, 1H), 7.72-7.63 (m, 1H), 7.40 (d, J = 8.0 Hz, 1H), 6.92 (dd, J = 11.5, 9.0 Hz, 1H), 6.56 (dd, J = 7.5, 2.5 Hz, 1H), 6.23 (dt, J = 8.7, 3.2 Hz, 1H), 5.82 (d, J = 6.5 Hz, 1H), 4.26 (s, 1H), 3.81-3.61 (m, 5H), 2.71-2.58 (m, 1H), 2.04-1.90 (m, 1H); 19F-NMR (400 MHz, DMSO-d$_6$): δ ppm −150.819; SOR: [α]$_D^{24.9}$ = −60.0 (c 0.05, DMSO). |
| 163 | 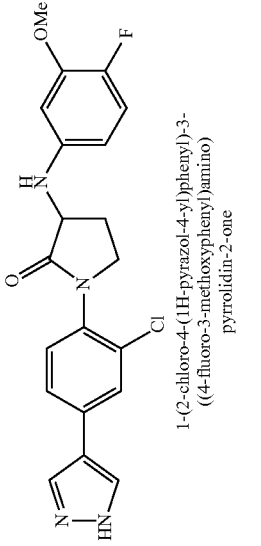 1-(2-chloro-4-(1H-pyrazol-4-yl)phenyl)-3-((4-fluoro-3-methoxyphenyl)amino)pyrrolidin-2-one | Enantiomer-II | 401.20 | 99.2868% ee (rt-11.2), CHIRALPAK ® IA (250 × 4.6 mm), 5.0-μm particles; % CO$_2$; 60%, % Co-solvent: 40% (0.2% DEA in methanol), Total Flow: 4.0 g/min, Back Pressure: 100 bars, Temperature: 30° C., UV: 260 nm. | I: 9.24, 99.7%, J: 8.82, 99.5% | 1H NMR (400 MHz DMSO-d$_6$) δ ppm = 13.05 (br. s., 1H), 8.32 (br. s., 1H), 8.02 (br. s., 1H), 7.85 (d, J = 2.0 Hz, 1H), 7.67 (dd, J = 8.0, 2.0 Hz, 1H), 7.40 (d, J = 8.0 Hz, 1H), 6.92 (dd, J = 11.5,9.0 Hz, 1H), 6.56 (dd, J = 7.5, 2.5 Hz, 1H), 6.23 (dt, J = 8.7, 3.2 Hz, 1H), 5.82 (d, J = 6.5 Hz, 1H), 4.35-4.22 (m, 1H), 3.82-3.58 (m, 5H), 2.75-2.55 (m, 1H), 2.06-1.86 (m, 1H); F$^{19}$-NMR (400 MHz, DMSO-d6) δ ppm −150.819; SOR: [α]$_D^{24.9}$ = +40.0 (c 0.05, DMSO). |
| 164 | 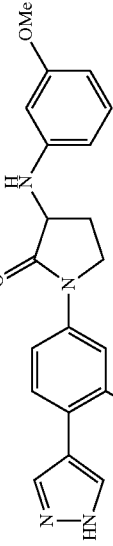 1-(3-chloro-4-(1H-pyrazol-4-yl)phenyl)-3-((3-methoxyphenyl)amino)pyrrolidin-2-one | Enantiomer-I | 383.20 | 100% ee (rt-7.27), CHIRALCEL ® OJ-H (250 × 4.6 mm), 5.0-μm particles; % CO$_2$: 60%, % Co-solvent: 40% (0.2% DEA in methanol), Total Flow: 4.0 g/min, Back Pressure: 100 bars, Temperature: 30° C., UV: 270 nm. | I: 9.80, 96.1%, J: 9.17, 94.9% | 1H NMR (400 MHz DMSO-d$_6$) δ ppm = 13.06 (s, 1H), 8.17 (br. s., 1H), 7.97 (t, J = 1.3 Hz, 1H), 7.91 (br. s., 1H), 7.66 (d, J = 1.5 Hz, 2H), 7.03-6.95 (m, 1H), 6.34-6.25 (m, 2H), 6.18 (dd, J = 7.8, 2.8 Hz, 1H), 5.94 (d, J = 7.5 Hz, 1H), 4.45-4.34 (m, 1H), 3.93-3.77 (m, 2H), 3.69 (s, 3H), 2.60 (d, J = 11.5 Hz, 1H), 1.98-1.85 (m, 1H); SOR: [α]$_D^{25.1}$ = −68.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 165 | 1-(3-chloro-4-(1H-pyrazol-4-yl)phenyl)-3-((3-methoxyphenyl)amino)pyrrolidin-2-one | Enantiomer-II | 383.20 | 94.1896% ee (rt-8.97), CHIRALCEL ® OJ-H (250 × 4.6 mm), 5.0-μm particles; % CO₂: 60%, % Co-solvent: 40% (0.2% DEA in methanol), Total Flow: 4.0 g/min, Back Pressure: 100 bars, Temperature: 30° C., UV: 270 nm. | I: 9.81, 97.7% J: 9.18, 96.9% | ¹H NMR (400 MHz, DMSO-d₆) δ ppm = 13.07 (br. s., 1H), 8.17 (br. s., 1H), 7.97 (t, J = 1.3 Hz, 1H), 7.91 (br. s., 1H), 7.71-7.61 (m, 2H), 6.99 (t, J = 8.0 Hz, 1H), 6.34-6.27 (m, 2H), 6.22-6.15 (m, 1H), 5.94 (d, J = 7.0 Hz, 1H), 4.46-4.35 (m, 1H), 3.93-3.77 (m, 2H), 3.69 (s, 3H), 2.65-2.56 (m, 1H), 1.98-1.78 (m, 1H); SOR: [α]²⁵·⁰_D = +48.0 (c 0.05, DMSO). |
| 166 | 1-(2-chloro-4-(1H-pyrazol-4-yl)phenyl)-3-((3-methoxyphenyl)amino)pyrrolidin-2-one | Enantiomer-I | 383.20 | 100% ee (rt-10.00 min), CHIRALPAK ® IA (250 × 4.6 mm), 5.0-μm particles; % CO₂: 60%, % Co-solvent: 40% (0.2% DEA in methanol), Total Flow: 4.0 g/min, Back Pressure: 100 bars, Temperature: 30° C., UV: 260 nm. | I: 9.27, 99.5% J: 8.75, 98.0% | ¹H NMR (400 MHz, DMSO-d₆) δ ppm = 13.31 (br. s., 1H), 8.57 (br. s., 1H), 8.28 (br. s., 1H), 8.11 (d, J = 2.0 Hz, 1H), 7.93 (dd, J = 8.3, 2.0 Hz, 1H), 7.66 (d, J = 8.1 Hz, 1H), 7.25 (t, J = 8.1 Hz, 1H), 6.63-6.55 (m, 2H), 6.43 (ddd, J = 8.1, 2.3, 0.9 Hz, 1H), 6.16 (d, J = 6.8 Hz, 1H), 4.60-4.52 (m, 1H), 4.03-3.88 (m, 5H), 2.90-2.80 (m, 1H), 2.33-2.18 (m, 1H); SOR: [α]²⁵·³_D = −68.0 (c 0.05, DMSO). |
| 167 | 1-(2-chloro-4-(1H-pyrazol-4-yl)phenyl)-3-((3-methoxyphenyl)amino)pyrrolidin-2-one | Enantiomer-II | 383.20 | 100% ee (rt-12.86), CHIRALPAK ® IA (250 × 4.6 mm), 5.0-μm particles; % CO₂: 60%, % Co-solvent: 40% (0.2% DEA in methanol), Total Flow: 4.0 g/min, Back Pressure: 100 bars, Temperature: 30° C., UV: 260 nm. | I: 9.27, 99.5% J: 8.75, 99.3% | ¹H NMR (400 MHz, DMSO-d₆) δ ppm = 13.30 (br. s., 1H), 8.67-8.42 (m, 1H), 8.32 (br. s., 1H), 8.11 (d, J = 2.0 Hz, 1H), 7.93 (dd, J = 8.2, 2.1 Hz, 1H), 7.66 (d, J = 8.1 Hz, 1H), 7.28-7.21 (m, 1H), 6.62-6.55 (m, 2H), 6.43 (ddd, J = 8.1, 2.3, 0.9 Hz, 1H), 6.16 (d, J = 6.6 Hz, 1H), 4.62-4.51 (m, 1H), 4.02-3.88 (m, 5H), 2.91-2.80 (m, 1H), 2.32-2.19 (m, 1H); SOR: [α]²⁵·⁰_D = +76.0 (c 0.05, DMSO). |
| 168 | 1-(2-chloro-4-(1H-pyrazol-4-yl)phenyl)-3-(((3-fluoro-5-methoxyphenyl)amino)pyrrolidin-2-one | Enantiomer-I | 401.00 | 100% ee (rt-6.73), CHIRALPAK ® IA (250 × 4.6 mm), 5.0-μm particles; % CO₂: 60%, % Co-solvent: 40% (0.2% DEA in methanol), Total Flow: 4.0 g/min, Back Pressure: 100 bars, Temperature: 30° C., UV: 260 nm. | I: 9.74, 97.6% J: 9.26, 99.9% | ¹H NMR (400 MHz, DMSO-d₆) δ ppm = 13.05 (br. s., 1H), 8.44-7.92 (m, 2H), 7.85 (d, J = 1.8 Hz, 1H), 7.67 (dd, J = 8.2, 1.9 Hz, 1H), 7.39 (d, J = 8.3 Hz, 1H), 6.30 (d, J = 7.0 Hz, 1H), 6.19-6.11 (m, 2H), 6.00 (dt, J = 11.0, 2.3 Hz, 1H), 4.34 (dt, J = 9.5, 7.7 Hz, 1H), 3.77-3.60 (m, 5H), 2.64-2.58 (m, 1H), 1.98 (dq, J = 12.1, 9.4 Hz, 1H); F¹⁹-NMR (400 MHz, DMSO-d₆): δ ppm −112.559; SOR: [α]²⁵·³_D = −64.0 (c 0.05, DMSO). |

TABLE 10-continued

| Ex. | Structure and Name | Chirality | LCMS (M+H)+ | Chiral Purity | HPLC Method, RT (min) & Purity | ¹H NMR |
|---|---|---|---|---|---|---|
| 169 | 1-(2-chloro-4-(1H-pyrazol-4-yl)phenyl)-3-((3-fluoro-5-methoxyphenyl)amino)pyrrolidin-2-one | Enantiomer-II | 401.20 | 100% ee (rt-10.73), CHIRALPAK @ IA (250 × 4.6 mm), 5.0-μm particles; % CO₂: 60%, % Co-solvent: 40% (0.2% DEA in methanol), Total Flow: 4.0 g/min, Back Pressure: 100 bars, Temperature: 30° C., UV: 260 nm. | I: 9.71, 97.7% J: 9.13, 98.2% | ¹H NMR (400 MHz, DMSO-d₆) δ ppm = 8.18 (br. s., 2H), 7.85 (d, J = 2.0 Hz, 1H), 7.67 (dd, J = 8.0, 2.0 Hz, 1H), 7.40 (d, J = 8.5 Hz, 1H), 6.36-6.22 (m, 1H), 6.20-6.11 (m, 2H), 6.00 (dt, J = 11.3, 2.1 Hz, 1H), 4.40-4.29 (m, 1H), 3.77-3.63 (m, 5H), 2.63 (d, J = 7.0 Hz, 1H), 2.06-1.92 (m, 1H); F¹⁹-NMR (400 MHz, DMSO-d₆): δ ppm −112.571; SOR: [α]₍D₎²⁵·³ = +48.0 (c 0.05, DMSO). |
| 170 | 1-(6-methoxy-5-(1H-pyrazol-4-yl)pyridin-2-yl)-3-(3-methoxyphenoxy)pyrrolidin-2-one | Enantiomer-I | 381.10 | 100% ee (rt = 6.1 min), CHIRALPAK @ AS-H (250 × 4.6 mm), 5.0-μm particles; % CO₂: 75%, % Co-solvent: 25% (0.2% DEA in methanol), Total Flow: 3.0 g/min, Back Pressure: 100 bars, Temperature: 20.6° C., UV: 310 nm. | I: 14.51, 98.9% J: 15.35, 97.6% | ¹H NMR (400 MHz, DMSO-d₆) δ ppm = 12.96 (br. s., 1H), 8.17 (br. s., 1H), 8.11 (d, J = 8.0 Hz, 1H), 8.01 (br. s., 1H), 7.94-7.88 (m, 1H), 7.27-7.18 (m, 1H), 6.69-6.63 (m, 2H), 6.61-6.56 (m, 1H), 5.33 (t, J = 8.3 Hz, 1H), 4.22 (ddd, J = 11.2, 8.9, 2.5 Hz, 1H), 4.01 (s, 3H), 3.92 (ddd, J = 10.9, 8.7, 7.0 Hz, 1H), 3.76 (s, 3H), 2.76-2.65 (m, 1H), 2.08 (dd, J = 12.5, 8.5 Hz, 1H); SOR: [α]₍D₎²⁵·⁰ = +28.0 (c 0.05, MeOH). |
| 171 | 1-(6-methoxy-5-(1H-pyrazol-4-yl)pyridin-2-yl)-3-(3-methoxyphenoxy)pyrrolidin-2-one | Enantiomer-II | 381.40 | 99.2602% ee (rt = 7.72 min), CHIRALPAK @ AS-H (250 × 4.6 mm), 5.0-μm particles; % CO₂: 75%, % Co-solvent: 25% (0.2% DEA in methanol), Total Flow: 3.0 g/min, Back Pressure: 100 bars, Temperature: 20.5° C., UV: 310 nm. | I: 8.88, 96.6% J: 9.88, 96.3% | ¹H NMR (400 MHz, DMSO-d₆) δ ppm = 12.97 (br. s., 1H), 8.24-8.14 (m, 1H), 8.11 (d, J = 8.5 Hz, 1H), 8.05 (br. s., 1H), 7.91 (d, J = 8.5 Hz, 1H), 7.26-7.19 (m, 1H), 6.70-6.63 (m, 2H), 6.61-6.56 (m, 1H), 5.33 (t, J = 8.3 Hz, 1H), 4.22 (ddd, J = 11.0, 8.8, 2.8 Hz, 1H), 4.01 (s, 3H), 3.97-3.88 (m, 1H), 3.76 (s, 3H), 2.75-2.65 (m, 1H), 2.08 (dq, J = 12.5, 8.7 Hz, 1H); SOR: [α]₍D₎²⁵·⁰ = −28.0 (c 0.05, MeOH). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 172 | 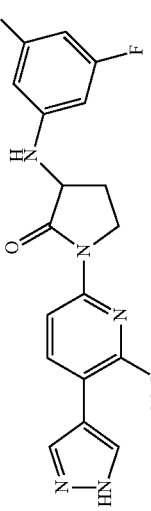<br>3-(3-fluoro-5-methoxyphenoxy)-1-(6-methoxy-5-(1H-pyrazol-4-yl)pyridin-2-yl)pyrrolidin-2-one | Enantiomer-I | 399.20 | 100% ee (rt = 4.9 min), CHIRALPAK @ AS-H (250 × 4.6 mm), 5.0-µm particles; % CO₂: 75%, % Co-solvent: 25% (0.2% DEA in methanol), Total Flow: 3.0 g/min, Back Pressure: 100 bars, Temperature: 20.7° C., UV: 305 nm. | I: 17.47, 97.9% J: 16.19, 95.9% | ¹H NMR (400 MHz, DMSO-d₆) δ ppm = 12.96 (br. s., 1H), 8.17 (br. s., 1H), 8.11 (d, J = 8.0 Hz, 1H), 8.01 (br. s., 1H), 7.90 (d, J = 8.0 Hz, 1H), 6.57 (dt, J = 10.9, 2.1 Hz, 1H), 6.53-6.44 (m, 2H), 5.38 (t, J = 8.3 Hz, 1H), 4.27-4.17 (m, 1H), 4.01 (s, 3H), 3.96-3.86 (m, 1H), 3.77 (s, 3H), 2.78-2.65 (m, 1H), 2.15-2.03 (m, 1H); SOR: [α]²⁴·⁸_D = +40.0 (c 0.05, MeOH). |
| 173 | 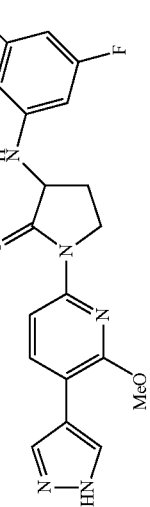<br>3-(3-fluoro-5-methoxyphenoxy)-1-(6-methoxy-5-(1H-pyrazol-4-yl)pyridin-2-yl)pyrrolidin-2-one | Enantiomer-II | 399.10 | 100% ee (rt = 5.86 min), CHIRALPAK @ AS-H (250 × 4.6 mm), 5.0-µm particles; % CO₂: 75%, % Co-solvent: 25% (0.2% DEA in methanol), Total Flow: 3.0 g/min, Back Pressure: 100 bars, Temperature: 20.6° C., UV: 305 nm. | I: 15.56, 95.1% J: 16.21, 95.5% | ¹H NMR (400 MHz, DMSO-d₆) δ ppm = 12.94 (br. s., 1H), 8.14-8.05 (m, 3H), 7.90 (d, J = 8.5 Hz, 1H), 6.57 (dt, J = 10.9, 2.1 Hz, 1H), 6.53-6.43 (m, 2H), 5.38 (t, J = 8.3 Hz, 1H), 4.22 (t, J = 8.5 Hz, 1H), 4.01 (s, 3H), 3.91 (dt, J = 11.2, 8.2 Hz, 1H), 3.77 (s, 3H), 2.78-2.65 (m, 1H), 2.15-2.01 (m, 1H); SOR: [α]²⁴·⁸_D = −48.0 (c 0.05, MeOH). |
| 175 | 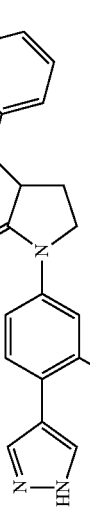<br>1-(3-(difluoromethyl)-4-(1H-pyrazol-4-yl)phenyl)-3-((3-methoxyphenyl)amino) pyrrolidin-2-one | Enantiomer-I | 399.1 | 98.44% ee (RT = 7.23 min), [Method: Column: CHIRALCEL @ AS-H (250 × 4.6 mm), 5µ, Mobile Phase: 0.2% DEA in methanol, CO₂ Flow Rate: 3.0 g/min, Co-solvent flow rate; 1.0 g/min, % Co-solvent: 25% (0.2% DEA in MeOH), Total Flow: 4.0 g/min, BackPressure: 100 bars, Temperature: 23.8° C., UV: 256 nm]. | I: 9.50, 99.3% J: 9.14, 99.2% | ¹H NMR (400 MHz, DMSO-d₆) δ ppm 13.15 (br. s., 1H), 8.15 (d, J = 2.5 Hz, 1H), 7.86-7.76 (m, 3H), 7.56 (d, J = 8.5 Hz, 1H), 7.18-6.87 (dd, J = 7.8, 2.3 Hz, 1H), 6.17 (m, 2H), 6.34-6.27 (m, 2H), 5.96 (d, J = 7.0 Hz, 1H), 4.46-4.37 (m, 1H), 3.93-3.82 (m, 2H), 3.68 (s, 3H), 2.66-2.54 (m, 1H), 1.97-1.86 (m, 1H), ¹⁹F NMR (376 MHz, DMSO-d₆) δ ppm −109.25 ppm; SOR: [α]²⁴·⁸_D = +20.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 176 | 1-(3-(difluoromethyl)-4-(1H-pyrazol-4-yl)phenyl)-3-((3-methoxyphenyl)amino)pyrrolidin-2-one | Enantiomer-II | 399.0 | 98.66% ee (RT = 9.56 min), [Method: Column: CHIRALCEL ® AS-H (250 × 4.6 mm), 5μ, Mobile Phase: 0.2% DEA in methanol, CO₂ Flow Rate: 3.0 g/min, Co-solvent flow rate: 1.0 g/min, % Co-solvent: 25% (0.2% DEA in MeOH), Total Flow: 4.0 g/min, BackPressure: 100 bars, Temperature: 23.6° C., UV: 256 nm]. | I: 9.49, 99.8% J: 9.25, 99.8% | ¹H NMR (400 MHz, DMSO-d₆) δ ppm 13.15 (br. s., 1H), 8.15 (d, J = 2.0 Hz, 1H), 7.87-7.75 (m, 3H), 7.56 (d, J = 8.5 Hz, 1H), 7.17-6.87 (m, 2H), 6.34-6.27 (m, 2H), 6.17 (dd, J = 8.0,1.5 Hz, 1H), 5.96 (d, J = 7.5 Hz, 1H), 4.46-4.37 (m, 1H), 3.92-3.83 (m, 2H), 3.68 (s, 3H), 2.64-2.54 (m, 1H), 1.97-1.87 (m, 1H), ¹⁹F NMR (376 MHz, DMSO-d₆) δ ppm −109.25 ppm, SOR: [α]$_D^{25.0}$ = −64.0 (c 0.05, DMSO). |
| 177 | 1-(3-(difluoromethyl)-4-(1H-pyrazol-4-yl)phenyl)-3-((3-fluoro-5-methoxyphenyl)amino)pyrrolidin-2-one | Enantiomer-I | 416.9 | 100% ee (RT = 8.57 min), [Method: Column: WHELK-O1 ® (R,R) (250 × 4.6 mm), 5μ, Mobile Phase: 0.2% DEA in methanol, CO₂ Flow Rate: 2.4 g/min, Co-solvent flow rate; 1.6 g/min, % Co-solvent: 40% (0.2% DEA in MeOH), Total Flow: 4.0 g/min, Back Pressure: 100 bars, Temperature: 23.7° C., UV: 259 nm]. | I: 9.87, 99.4% J: 10.93, 99.5% | ¹H NMR (400 MHz, DMSO-d₆) δ ppm 13.09 (br. s., 1H), 8.14 (d, J = 2.0 Hz, 1H), 7.84-7.75 (m, 3H), 7.56 (d, J = 8.5 Hz, 1H), 7.17-6.86 (m, 1H), 6.33 (d, J = 7.5 Hz, 1H), 6.17-6.10 (m, 2H), 6.00 (dt, J = 11.0, 2.0 Hz, 1H), 4.50-4.41 (m, 1H), 3.93-3.82 (m, 2H), 3.69 (s, 3H), 2.65-2.55 (m, 1H), 1.98-1.84 (m, 1H), ¹⁹F NMR (376 MHz, DMSO-d₆) δ ppm −109.26, −112.53 ppm, SOR: [α]$_D^{25.1}$ = +28.0 (c 0.05, DMSO). |
| 178 | 1-(3-(difluoromethyl)-4-(1H-pyrazol-4-yl)phenyl)-3-((3-fluoro-5-methoxyphenyl)amino)pyrrolidin-2-one | Enantiomer-II | 416.9 | 100% ee (RT = 10.82), [Method: Column: WHELK-O1 ® (R,R) (250 × 4.6 mm), 5μ, Mobile Phase: 0.2% DEA in methanol, CO₂ Flow Rate: 2.4 g/min, Co-solvent flow rate; 1.6 g/min, % Co-solvent: 40% (0.2% DEA in MeOH), Total Flow: 4.0 g/min, Back Pressure: 100 bars, Temperature: 23.7° C., UV: 259 nm]. | I: 9.87, 98.3% J: 9.61, 98.5% | ¹H NMR (400 MHz, DMSO-d₆) δ ppm 13.11 (br. s., 1H), 8.14 (d, J = 2.2 Hz, 1H), 7.85-7.75 (m, 3H), 7.56 (d, J = 8.5 Hz, 1H), 7.16-6.87 (m, 1H), 6.32 (d, J = 7.5 Hz, 1H), 6.16-6.10 (m, 2H), 6.00 (dt, J = 11.0, 2.0 Hz, 1H), 4.50-4.41 (m, 1H), 3.93-3.81 (m, 2H), 3.69 (s, 3H), 2.66-2.55 (m, 1H), 1.99-1.83 (m, 1H), ¹⁹F NMR (376 MHz, DMSO-d₆) δ ppm −109.26, −112.54 ppm, SOR: [α]$_D^{25.0}$ = −32.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 179 | 1-(3-(difluoromethyl)-4-(1H-pyrazol-4-yl)phenyl)-3-((4-fluoro-3-methoxyphenyl) amino)pyrrolidin-2-one | Enantiomer-I | 416.9 | 98.72% ee (RT = 8.14 min), [Method: Column: WHELK-O1 @ (R,R) (250 × 4.6 mm), 5μ, Mobile Phase: 0.2% DEA in methanol, CO₂ Flow Rate: 2.4 g/min, Co-solvent flow rate; 1.6 g/min, % Co-solvent: 40% (0.2% DEA in MeOH), Total Flow: 4.0 g/min, Back Pressure: 101 bars, Temperature: 24.6° C., UV: 263 nm]. | I: 9.45, 98.6% J: 9.68, 97.7% | ¹H NMR (400 MHz, DMSO-d₆) δ ppm 13.15 (br. s., 1H), 8.15 (d, J = 2.5 Hz, 1H), 7.97-7.53 (m, 4H), 7.17-6.94 (m, 1H), 6.90 (dd, J = 12.3, 3.3 Hz, 1H), 6.53 (dd, J = 7.5, 2.5 Hz, 1H), 6.21 (dt, J = 8.7, 3.2 Hz, 1H), 5.88 (d, J = 7.5 Hz, 1H), 4.45-4.35 (m, 1H), 3.95-3.82 (m, 2H), 3.77 (s, 3H), 2.65-2.56 (m, 1H), 1.98-1.86 (m, 1H), ¹⁹F NMR (376 MHz, DMSO-d₆) δ ppm -109.13, -150.83 ppm. SOR: [α]$_D^{25.2}$ = +32.0 (c 0.05, DMSO). |
| 180 | 1-(3-(difluoromethyl)-4-(1H-pyrazol-4-yl)phenyl)-3-((4-fluoro-3-methoxyphenyl) amino)pyrrolidin-2-one | Enantiomer-II | 416.9 | 98.08% ee (RT = 11.13 min), [Method: Column: WHELK-O1 @ (R,R) (250 × 4.6 mm), 5μ, Mobile Phase: 0.2% DEA in methanol, CO₂ Flow Rate: 2.4 g/min, Co-solvent flow rate; 1.6 g/min, % Co-solvent: 40% (0.2% DEA in MeOH), Total Flow: 4.0 g/min, Back Pressure: 100 bars, Temperature: 24.8° C., UV: 263 nm]. | I: 9.45, 97.8% J: 9.44, 97.9% | ¹H NMR (400 MHz, DMSO-d₆) δ ppm 13.15 (br. s., 1H), 8.15 (d, J = 2.0 Hz, 1H), 7.98-7.53 (m, 4H), 7.17-6.94 (m, 1H), 6.93-6.87 (m, 1H), 6.53 (dd, J = 7.5, 2.5 Hz, 1H), 6.21 (dt, J = 9.0, 3.0 Hz, 1H), 5.88 (d, J = 7.0 Hz, 1H), 4.46-4.35 (m, 1H), 3.94-3.82 (m, 2H), 3.77 (s, 3H), 2.65-2.56 (m, 1H), 1.96-1.85 (m, 1H), ¹⁹F NMR (376 MHz, DMSO-d₆) δ ppm -109.13, -150.83 ppm, SOR: [α]$_D^{25.1}$ = -44.1 (c 0.05, DMSO). |
| 181 | 3-((4-fluoro-3-methoxyphenyl)amino)-1-(3-(methoxymethyl)-4-(1H-pyrazol-4-yl)phenyl)pyrrolidin-2-one | Enantiomer-I | 411.2 | 100% ee (RT = 12.98 min), [Method: Column: CHIRALPAK @ IA (250 × 4.6 mm), 5μ, Mobile Phase: 0.2% DEA in methanol, CO₂ Flow Rate: 1.8 g/min, Co-solvent flow rate; 1.2 g/min, % Co-solvent: 40% (0.2% DEA in MeOH), Total Flow: 3.0 g/min, Back Pressure: 100 bars, Temperature: 23.8° C., UV: 220 nm]. | I: 9.48, 98.8% J: 9.25, 99.9% | ¹H NMR (400 MHz, DMSO-d₆) δ ppm 12.98 (br. s., 1H), 7.86-7.77 (m, 3H), 7.66 (dd, J = 8.3, 2.3 Hz, 1H), 7.47 (d, J = 8.0 Hz, 1H), 6.91 (dd, J = 11.5, 8.5 Hz, 1H), 6.53 (dd, J = 7.5, 3.0 Hz, 1H), 6.26-6.15 (m, 1H), 5.86 (d, J = 7.0 Hz, 1H), 4.42 (s, 2H), 4.40-4.31 (m, 1H), 3.88-3.80 (m, 2H), 3.76 (s, 3H), 3.34 (s, 3H), 2.66-2.57 (m, 1H), 1.98-1.82 (m, 1H), ¹⁹F NMR (376 MHz, DMSO-d₆) δ ppm -150.89 ppm, SOR: [α]$_D^{24.9}$ = +36.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 182 | 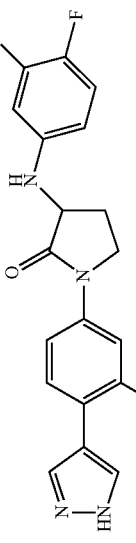<br>3-((4-fluoro-3-methoxyphenyl)amino)-1-(3-(methoxymethyl)-4-(1H-pyrazol-4-yl)phenyl)pyrrolidin-2-one | Enantiomer-II | 411.2 | 98.42% ee (RT = 18.38), [Method: Column: CHIRALPAK ® IA (250 × 4.6 mm), 5μ, Mobile Phase: 0.2% DEA in methanol, CO2 Flow Rate: 1.8 g/min, Co-solvent flow rate: 1.2 g/min, % Co-solvent: 40% (0.2% DEA in MeOH), Total Flow: 3.0 g/min, Back Pressure: 100 bars, Temperature: 24.0° C., UV: 220 nm]. | I: 8.93, 97.7%; J: 8.48, 98.7% | 1H NMR (400 MHz, DMSO-d6) δ ppm 12.99 (br. s., 1H), 7.97-7.86 (m, 1H), 7.80 (d, J = 2.0 Hz, 1H), 7.75-7.70 (m, 1H), 7.68-7.64 (m, 1H), 7.48 (d, J = 8.5 Hz, 1H), 6.91 (dd, J = 11.5,9.0 Hz, 1H), 6.53 (dd, J = 7.8, 2.8 Hz, 1H), 6.25-6.17 (m, 1H), 5.86 (d, J = 6.5 Hz, 1H), 4.42 (s, 2H), 4.40-4.31 (m, 1H), 3.89-3.80 (m, 2H), 3.76 (s, 3H), 3.34 (s, 3H), 2.65-2.57 (m, 1H), 1.98-1.83 (m, 1H), 19F NMR (376 MHz, DMSO-d6) δ ppm −150.90 ppm. SOR: [α]$_D^{25.9}$ = −40.0 (c 0.05, DMSO). |
| 183 | 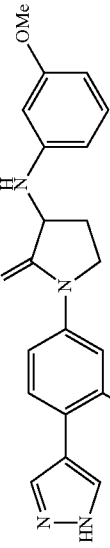<br>1-(3-(methoxymethyl)-4-(1H-pyrazol-4-yl)phenyl)-3-((3-methoxyphenyl)amino)pyrrolidin-2-one | Enantiomer-I | 393.2 | 100% ee (RT = 13.78 min), [Method: Column: CHIRALPAK ® IA (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 24.6° C., UV: 262 nm]. | I: 8.84, 95.7%; J: 8.35, 97.6% | 1H NMR (400 MHz, DMSO-d6) δ ppm 12.99 (br. s., 1H), 7.97-7.86 (m, 1H), 7.80 (d, J = 2.5 Hz, 1H), 7.76-7.70 (m, 1H), 7.66 (dd, J = 8.3, 2.3 Hz, 1H), 7.48 (d, J = 8.5 Hz, 1H), 6.98 (t, J = 8.0 Hz, 1H), 6.34-6.27 (m, 2H), 6.17 (dt, J = 8.0, 1.3 Hz, 1H), 5.94 (d, J = 7.5 Hz, 1H), 4.42 (s, 2H), 4.41-4.33 (m, 1H), 3.88-3.80 (m, 2H), 3.68 (s, 3H), 3.34 (s, 3H), 2.66-2.57 (m, 1H), 1.98-1.83 (m, 1H), SOR: [α]$_D^{24.7}$ = +40.0 (c 0.05, DMSO). |
| 184 | 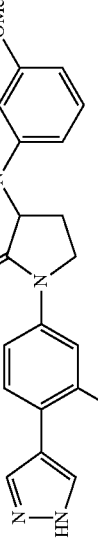<br>1-(3-(methoxymethyl)-4-(1H-pyrazol-4-yl)phenyl)-3-((3-methoxyphenyl)amino)pyrrolidin-2-one | Enantiomer-II | 393.2 | 96.28% ee (RT = 20.68 min), [Method: Column: CHIRALPAK ® IA (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 24.9° C., UV: 275 nm]. | I: 8.84, 99.0%; J: 8.35, 98.7% | 1H NMR (400 MHz, DMSO-d6) δ ppm 12.99 (br. s., 1H), 7.96-7.78 (m, 3H), 7.66 (dd, J = 8.3, 2.3 Hz, 1H), 7.48 (d, J = 8.5 Hz, 1H), 6.98 (t, J = 8.0 Hz, 1H), 6.35-6.27 (m, 2H), 6.17 (dt, J = 8.0, 1.3 Hz, 1H), 5.94 (d, J = 7.0 Hz, 1H), 4.42 (s, 2H), 4.41-4.31 (m, 1H), 3.90-3.79 (m, 2H), 3.68 (s, 3H), 3.34 (s,3H), 2.66-2.56 (m, 1H), 1.99-1.84 (m, 1H), SOR: [α]$_D^{24.8}$ = −32.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 185 | 3-((3-fluoro-5-methoxyphenyl)amino)-1-(3-(methoxymethyl)-4-(1H-pyrazol-4-yl)phenyl)pyrrolidin-2-one | Enantiomer-I | 411.2 | 100% ee (RT = 5.39 min), [Method: Column: CHIRALCEL ® OD-H (250 × 4.6 mm), 5μ, Mobile Phase: 0.2% DEA in methanol, CO2 Flow Rate: 1.8 g/min, Co-solvent flow rate: 1.2 g/min, % Co-solvent: 40% (0.2% DEA in MeOH), Total Flow: 3.0 g/min, BackPressure: 100 bars, Temperature: 30.0° C., UV: 260 nm]. | I: 8.75, 99.6% J: 9.05, 99.5% | 1H NMR (400 MHz, DMSO-d6) δ ppm 12.89 (br. s., 1H), 7.85-7.78 (m, 3H), 7.65 (dd, J = 8.5, 2.5 Hz, 1 H), 7.47 (d, J = 8.5 Hz, 1H), 6.29 (d, J = 7.5 Hz, 1H), 6.17-6.10 (m, 2H), 6.03-5.96 (m, 1H), 4.47-4.37 (m, 3 H), 3.89-3.79 (m, 2H), 3.69 (s, 3 H), 3.34 (s, 3H), 2.66-2.54 (m, 1 H), 1.93-1.82 (m, 1H), 19F NMR (376 MHz, DMSO-d6) δ ppm −112.57 ppm, SOR: [α]D25.0 = +32.0 (c 0.05, DMSO). |
| 186 | 3-((3-fluoro-5-methoxyphenyl)amino)-1-(3-(methoxymethyl)-4-(1H-pyrazol-4-yl)phenyl)pyrrolidin-2-one | Enantiomer-II | 411.2 | 100% ee (RT = 8.8 min), [Method: Column: CHIRALCEL ® OD-H (250 × 4.6 mm), 5μ, Mobile Phase: 0.2% DEA in methanol, CO2 Flow Rate: 1.8 g/min, Co-solvent flow rate: 1.2 g/min, % Co-solvent: 40% (0.2% DEA in MeOH), Total Flow: 3.0 g/min, BackPressure: 100 bars, Temperature: 30.0° C., UV: 260 nm]. | I: 8.74, 99.1% J: 9.05, 99.4% | 1H NMR (400 MHz, DMSO-d6) δ ppm 12.94 (br. s., 1H), 7.85-7.77 (m, 3H), 7.65 (dd, J = 8.5, 2.5 Hz, 1 H), 7.47 (d, J = 8.0 Hz, 1H), 6.29 (d, J = 7.0 Hz, 1H), 6.17-6.10 (m, 2H), 6.03-5.96 (m, 1H), 4.46-4.37 (m, 3 H), 3.88-3.80 (m, 2H), 3.69 (s, 3 H), 3.34 (s, 3H), 2.66-2.54 (m, 1 H), 1.94-1.83 (m, 1H), 19F NMR (376 MHz, DMSO-d6) δ ppm −112.57 ppm, SOR: [α]D25.0 = −44.0 (c 0.05, DMSO). |
| 187 | 1-(3-(hydroxymethyl)-4-(1H-pyrazol-4-yl)phenyl)-3-((3-methoxyphenyl)amino)pyrrolidin-2-one | Racemate | 379.2 | | I: 7.85, 97.0% J: 7.46, 97.2% | 1H NMR (400 MHz, DMSO-d6) δ ppm 12.95 (br. s., 1H), 8.00-7.89 (br. s., 1H), 7.81 (d, J = 2.5 Hz, 1H), 7.79-7.70 (br. s., 1H), 7.65 (dd, J = 8.5, 2.5 Hz, 1H), 7.43 (d, J = 8.0 Hz, 1H), 6.99 (t, J = 7.8 Hz, 1H), 6.35-6.28 (m, 2H), 6.20-6.15 (m, 1H), 5.92 (d, J = 7.0 Hz, 1H), 5.25 (t, J = 5.3 Hz, 1H), 4.53 (d, J = 5.0 Hz, 2H), 4.43-4.31 (m, 1H), 3.87-3.81 (m, 2 H), 3.68 (s, 3H), 2.66-2.56 (m, 1 H), 1.95-1.82 (m, 1H). |

| Ex. | Structure and Name | Chirality | LCMS (M+H)+ | Chiral Purity | HPLC Method, RT (min) & Purity | 1H NMR |
|---|---|---|---|---|---|---|
| 188 | 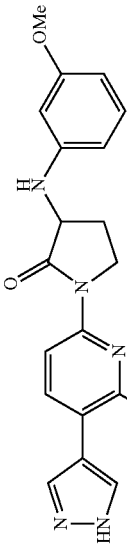 3-((3-methoxyphenyl)amino)-1-(6-methyl-5-(1H-pyrazol-4-yl)pyridin-2-yl)pyrrolidin-2-one | Enantiomer-I | 364.2 | 100% ee (RT = 9.18 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH) Total Flow: 4.0 g/min, Back Pressure: 101 bars, Temperature: 22.1° C., UV: 254 nm]. | I: 8.40, 97.5% J: 8.34, 98.3% | 1H NMR (400 MHz, DMSO-d6) δ ppm 13.00 (br. s., 1H), 8.15 (d, J = 8.5 Hz, 1H), 7.91 (br. s., 2H), 7.84 (d, J = 8.5 Hz, 1H), 6.98 (t, J = 8.0 Hz, 1 H), 6.35-6.27 (m, 2H), 6.21-6.14 (m, 1H), 5.94 (d, J = 7.5 Hz, 1H), 4.53-4.40 (m, 1H), 4.21-4.11 (m, 1 H), 3.89-3.77 (m, 1H), 3.68 (s, 3H), 2.62-2.55 (m, 4H), 1.92-1.79 (m, 1 H), SOR: [α]25.0D = +56.0 (c 0.05, DMSO). |
| 189 | 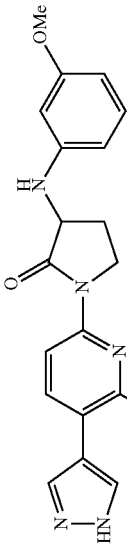 3-((3-methoxyphenyl)amino)-1-(6-methyl-5-(1H-pyrazol-4-yl)pyridin-2-yl)pyrrolidin-2-one | Enantiomer-II | 364.2 | 100% ee (RT = 13.74 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH) Total Flow: 4.0 g/min, Back Pressure: 97 bars, Temperature: 22.5° C., UV: 291 nm]. | I: 8.40, 98.1% J: 8.34, 97.4% | 1H NMR (400 MHz, DMSO-d6) δ ppm 13.01 (br. s., 1H), 8.15 (d, J = 8.5 Hz, 1H), 7.91 (br. s., 2H), 7.85 (d, J = 8.5 Hz, 1H), 7.01-6.95 (m, 1H), 6.35-6.26 (m, 2H), 6.17 (dd, J = 7.8, 1.8 Hz, 1H), 5.96 (d, J = 7.5 Hz, 1H), 4.51-4.40 (m, 1H), 4.21-4.12 (m, 1 H), 3.89-3.77 (m, 1H), 3.68 (s, 3 H), 2.62-2.55 (m, 4H), 1.93-1.79 (m, 1H), SOR: [α]25.0D = −56.0 (c 0.05, DMSO). |
| 190 | 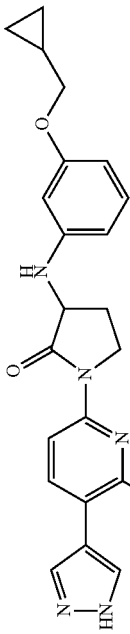 3-((3-(cyclopropylmethoxy)phenyl) amino)-1-(6-methyl-5-(1H-pyrazol-4-yl)pyridin-2-yl)pyrrolidin-2-one | Enantiomer-II | 404.2 | 100% ee (RT = 10.97 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH) Total Flow: 4.0 g/min, Back Pressure: 100 bars, Temperature: 30.0° C., UV: 254 nm]. | I: 10.27, 97.8% J: 9.20, 98.9% | 1H NMR (400 MHz, DMSO-d6) δ ppm 12.99 (br. s., 1H), 8.15 (d, J = 8.5 Hz, 1H), 7.91 (s, 2H), 7.85 (d, J = 8.5 Hz, 1H), 6.96 (t, J = 8.3 Hz, 1H), 6.33-6.26 (m, 2H), 6.18-6.11 (m, 1H), 5.92 (d, J = 7.0 Hz, 1H), 4.51-4.41 (m, 1H), 4.22-4.09 (m, 1H), 3.82 (td, J = 10.4, 6.8 Hz, 1H), 3.72 (d, J = 7.0 Hz, 2H), 2.62-2.55 (m, 4H), 1.93-1.81 (m, 1H), 1.22-1.13 (m, 1 H), 0.59-0.50 (m, 2H), 0.32-0.24 (m, 2H), SOR: [α]25.2D = +44.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 191 | 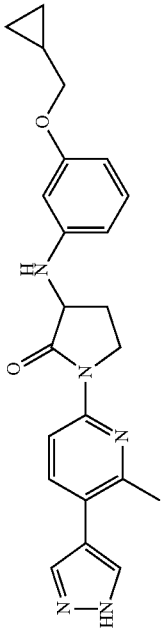<br>3-((3-(cyclopropylmethoxy)phenyl)amino)-1-(6-methyl-5-(1H-pyrazol-4-yl)pyridin-2-yl)pyrrolidin-2-one | Enantiomer-II | 404.2 | 100% ee (RT = 16.28 min), [Method: Column: Lux Cellulose-4 (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 254 nm]. | I: 10.28, 98.8% J: 9.19, 99.5% | 1H NMR (400 MHz, DMSO-d$_6$) δ ppm 13.01 (br. s., 1H), 8.15 (d, J = 8.5 Hz, 1H), 7.91 (s, 2H), 7.85 (d, J = 8.5 Hz, 1H), 6.96 (t, J = 8.3 Hz, 1H), 6.32-6.26 (m, 2H), 6.17-6.12 (m, 1H), 5.92 (d, J = 7.0 Hz, 1H), 4.51-4.41 (m, 1H), 4.21-4.10 (m, 1H), 3.82 (td, J = 10.4, 6.8 Hz, 1H), 3.72 (d, J = 6.5 Hz, 2H), 2.62-2.55 (m, 4H), 1.92-1.80 (m, 1H), 1.25-1.14 (m, 1H), 0.59-0.51 (m, 2H), 0.33-0.25 (m, 2H), SOR: [α]$_D^{25.0}$ = −68.0 (c 0.05, DMSO). |
| 192 | 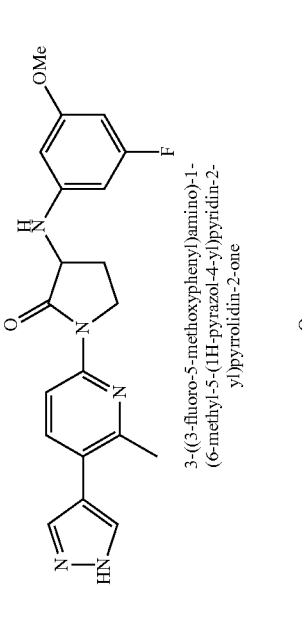<br>3-((3-fluoro-5-methoxyphenyl)amino)-1-(6-methyl-5-(1H-pyrazol-4-yl)pyridin-2-yl)pyrrolidin-2-one | Enantiomer-I | 382.2 | 100% ee (RT = 6.16 min), [Method: Column: Lux Cellulose-4 (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 250 nm]. | I: 9.56, 99.1% J: 8.59, 99.0% | 1H NMR (400 MHz, DMSO-d$_6$) δ ppm 13.02 (br. s., 1H), 8.14 (dd, J = 8.6, 0.5 Hz, 1H), 7.92 (br. s., 2H), 7.86 (d, J = 8.6 Hz, 1H), 6.33 (d, J = 7.6 Hz, 1H), 6.19-6.10 (m, 2H), 6.01 (dt, J = 11.2, 2.2 Hz, 1H), 4.57-4.44 (m, 1H), 4.23-4.12 (m, 1H), 3.84-3.72 (m, 1H), 3.70 (s, 3H), 2.63-2.54 (m, 4H), 1.93-1.81 (m, 1H), 19F NMR (376 MHz, DMSO-d$_6$) δ ppm −112.55 ppm, SOR: [α]$_D^{24.9}$ = +60.0 (c 0.05, DMSO). |
| 193 | 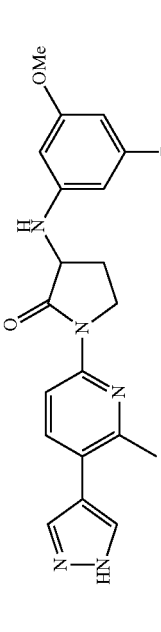<br>3-((3-fluoro-5-methoxyphenyl)amino)-1-(6-methyl-5-(1H-pyrazol-4-yl)pyridin-2-yl)pyrrolidin-2-one | Enantiomer-II | 382.2 | 98.44% ee (RT = 7.58 min), [Method: Column: Lux Cellulose-4 (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 250 nm]. | I: 9.56, 97.5% J: 8.58, 97.7% | 1H NMR (400 MHz, DMSO-d$_6$) δ ppm 13.04 (br. s., 1H), 8.14 (dd, J = 8.6, 0.5 Hz, 1H), 7.91 (br. s., 2H), 7.85 (d, J = 8.6 Hz, 1H), 6.32 (d, J = 7.3 Hz, 1H), 6.17-6.09 (m, 2H), 6.00 (dt, J = 11.2, 2.2 Hz, 1H), 4.56-4.45 (m, 1H), 4.22-4.08 (m, 1H), 3.85-3.73 (m, 1H), 3.69 (s, 3H), 2.62-2.53 (m, 4H), 1.92-1.78 (m, 1H), 19F NMR (376 MHz, DMSO-d$_6$) δ ppm −112.55 ppm, SOR: [α]$_D^{25.0}$ = −72.0 (c 0.05, DMSO). |

| Ex. | Structure and Name | Chirality | LCMS (M+H)+ | Chiral Purity | HPLC Method, RT (min) & Purity | $^1$H NMR |
|---|---|---|---|---|---|---|
| 194 | 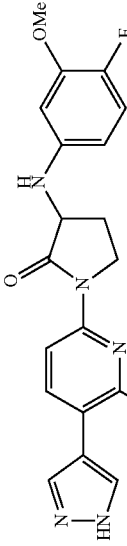<br>3-((4-fluoro-3-methoxyphenyl)amino)-1-(6-methyl-5-(1H-pyrazol-4-yl)pyridin-2-yl)pyrrolidin-2-one | Enantiomer-I | 382.2 | 100% ee (RT = 7.28 min), [Method: Column: Lux Cellulose-4 (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 254 nm]. | I: 8.76, 99.6% J: 8.34, 99.6% | $^1$H NMR (400 MHz, DMSO-d$_6$) δ ppm 13.03 (br. s., 1H), 8.14 (d, J = 8.5 Hz, 1H), 7.91 (s, 2H), 7.85 (d, J = 8.5 Hz, 1H), 6.91 (dd, J = 11.5, 9.0 Hz, 1H), 6.53 (dd, J = 7.5, 2.5 Hz, 1H), 6.26-6.16 (m, 1H), 5.88 (d, J = 7.5 Hz, 1H), 4.50-4.40 (m, 1H), 4.22-4.12 (m, 1H), 3.87-3.78 (m, 1H), 3.76 (s, 3H), 2.62-2.57 (m, 1H), 2.56 (s, 3H), 1.94-1.79 (m, 1H). $^{19}$F NMR (376 MHz, DMSO-d$_6$) δ ppm −150.86 ppm, SOR: [α]$_D^{25.0}$ = +48.0 (c 0.05, DMSO). |
| 195 | 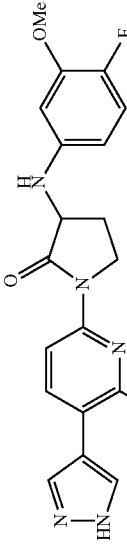<br>3-((4-fluoro-3-methoxyphenyl)amino)-1-(6-methyl-5-(1H-pyrazol-4-yl)pyridin-2-yl)pyrrolidin-2-one | Enantiomer-II | 382.2 | 100% ee (RT = 9.49 min), [Method: Column: Lux Cellulose-4 (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 254 nm]. | I: 8.91, 98.9% J: 8.31, 99.4% | $^1$H NMR (400 MHz, DMSO-d$_6$) δ ppm 12.88 (br. s., 1H), 8.14 (d, J = 8.5 Hz, 1H), 7.91 (s, 2H), 7.84 (d, J = 8.5 Hz, 1H), 6.91 (dd, J = 11.5, 9.0 Hz, 1H), 6.53 (dd, J = 7.5, 2.5 Hz, 1H), 6.25-6.16 (m, 1H), 5.87 (d, J = 7.5 Hz, 1H), 4.49-4.40 (m, 1H), 4.22-4.13 (m, 1H), 3.87-3.78 (m, 1H), 3.77 (s, 3H), 2.63-2.57 (m, 1H), 2.56 (s, 3H), 1.94-1.80 (m, 1H). $^{19}$F NMR (376 MHz, DMSO-d$_6$) δ ppm −150.83 ppm, SOR: [α]$_D^{25.1}$ = −60.0 (c 0.05, DMSO). |
| 196 | 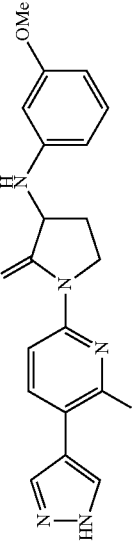<br>1-(6-methoxy-5-(1H-pyrazol-4-yl)pyridin-2-yl)-3-((3-methoxyphenyl)amino)pyrrolidin-2-one | Enantiomer-I | 380.2 | 94.5% ee (RT = 12.65 min), [Method: Column: Lux Cellulose-4 (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 220 nm]. | I: 10.08, 96.0% J: 9.26, 96.8% | $^1$H NMR (400 MHz, DMSO-d$_6$) δ ppm 12.72 (br. s., 1H), 8.10-8.05 (m, 3H), 7.90 (d, J = 8.0 Hz, 1H), 6.99 (t, J = 8.0 Hz, 1H), 6.33-6.27 (m, 2H), 6.20-6.15 (m, 1H), 5.94 (d, J = 7.0 Hz, 1H), 4.51-4.43 (m, 1H), 4.25-4.16 (m, 1H), 4.00 (s, 3H), 3.91-3.79 (m, 1H), 3.68 (s, 3H), 2.62-2.54 (m, 1H), 1.94-1.80 (m, 1H), SOR: [α]$_D^{25.1}$ = +48.0 (c 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 197 | 1-(6-methoxy-5-(1H-pyrazol-4-yl)pyridin-2-yl)-3-((3-methoxyphenyl)amino)pyrrolidin-2-one | Enantiomer-II | 380.2 | 94.5% ee (RT = 15.75 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 220 nm]. | I: 10.07, 99.3% J: 9.26, 96.1% | 1H NMR (400 MHz, DMSO-d6) δ ppm 8.12-8.04 (m, 3H), 7.90 (d, J = 8.5 Hz, 1H), 6.99 (t, J = 7.8 Hz, 1H), 6.35-6.27 (m, 2H), 6.20-6.14 (m, 1H), 5.95 (d, J = 7.0 Hz, 1H), 4.51-4.42 (m, 1H), 4.26-4.16 (m, 1H), 4.00 (s, 3H), 3.92-3.79 (m, 1H), 3.68 (s, 3H), 2.62-2.54 (m, 1H), 1.93-1.81 (m, 1H), SOR: [α]D24.9 = −68.0 (c 0.1, DMSO). |
| 198 | 3-((3-fluoro-5-methoxyphenyl)amino)-1-(6-methoxy-5-(1H-pyrazol-4-yl)pyridin-2-yl)pyrrolidin-2-one | Enantiomer-I | 398.2 | 97.78% ee (RT = 10.09 min), [Method: Column: CHIRALPAK ® IA (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 311 nm]. | I: 10.50, 95.8% J: 9.71, 95.8% | 1H NMR (400 MHz, DMSO-d6) δ ppm 12.85 (br. s., 1H), 8.12-8.05 (m, 3H), 7.89 (d, J = 8.0 Hz, 1H), 6.31 (d, J = 7.5 Hz, 1H), 6.17-6.10 (m, 2H), 6.03-5.97 (m, 1H), 4.54-4.47 (m, 1H), 4.25-4.17 (m, 1H), 4.00 (s, 3H), 3.91-3.80 (m, 1H), 3.69 (s, 3H), 2.61-2.54 (m, 1H), 1.92-1.81 (m, 1H), 19F NMR (376 MHz, DMSO-d6) δ ppm −112.54, SOR: [α]D24.9 = +50.0 (c 0.1, DMSO). |
| 199 | 3-((3-fluoro-5-methoxyphenyl)amino)-1-(6-methoxy-5-(1H-pyrazol-4-yl)pyridin-2-yl)pyrrolidin-2-one | Enantiomer-II | 398.2 | 96.78% ee (RT = 15.38 min), [Method: Column: CHIRALPAK ® IA (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 311 nm]. | I: 10.51, 95.9% J: 9.71, 95.4% | 1H NMR (400 MHz, DMSO-d6) δ ppm 12.77 (br. s., 1H), 8.12-8.05 (m, 3H), 7.89 (d, J = 8.0 Hz, 1H), 6.31 (d, J = 7.0 Hz, 1H), 6.17-6.10 (m, 2H), 6.03-5.97 (m, 1H), 4.55-4.47 (m, 1H), 4.26-4.16 (m, 1H), 4.00 (s, 3H), 3.89-3.81 (m, 1H), 3.69 (s, 3H), 2.61-2.54 (m, 1H), 1.93-1.81 (m, 1H), 19F NMR (376 MHz, DMSO-d6) δ ppm −112.54, SOR: [α]D25.0 = −28.0 (c 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 200 | 3-((3-methoxyphenyl)amino)-1-(4-methyl-5-(1H-pyrazol-4-yl)pyridin-2-yl)pyrrolidin-2-one | Racemate | 364.2 | | I: 8.01, 97.4% J: 7.60, 98.5% | 1H NMR (400 MHz, DMSO-d6) δ ppm 13.09 (br. s., 1H), 8.41 (s, 1H), 8.21 (s, 1H), 8.10-7.78 (m, 2H), 6.98 (t, J = 8.1 Hz, 1H), 6.36-6.27 (m, 2H), 6.17 (ddd, J = 8.2, 2.3, 0.7 Hz, 1H), 5.94 (d, J = 7.3 Hz, 1H), 4.52-4.42 (m, 1H), 4.16-4.08 (m, 1H), 3.88-3.78 (m, 1H), 3.68 (s, 3H), 2.61-2.54 (m, 1H), 2.41 (s, 3H), 1.94-1.82 (m, 1H). |
| 201 | 3-((3-(difluoromethoxy)phenyl)amino)-1-(6-methyl-5-(1H-pyrazol-4-yl)pyridin-2-yl)pyrrolidin-2-one | Enantiomer-I | 400.2 | 100% ee (RT = 3.47 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 249 nm]. | I: 9.68, 98.9% J: 9.13, 98.0% | 1H NMR (400 MHz, methanol-d4) δ ppm 8.19 (d, J = 8.0 Hz, 1H), 7.85 (br. s., 2H), 7.78 (d, J = 8.5 Hz, 1H), 7.15 (t, J = 8.0 Hz, 1H), 6.95-6.53 (m, 3H), 6.44 (dd, J = 7.8, 2.8 Hz, 1H), 4.48 (dd, J = 10.5, 8.0 Hz, 1H), 4.34-4.27 (m, 1H), 4.00-3.90 (m, 1H), 2.77-2.68 (m, 1H), 2.60 (s, 3H), 2.04-1.93 (m, 1H), 19F NMR (400 MHz, methanol-d4) δ ppm -82.47 ppm, SOR: [α]$_D^{24.9}$ = +66.0 (c 0.1, DMSO). |
| 202 | 3-((3-(difluoromethoxy)phenyl)amino)-1-(6-methyl-5-(1H-pyrazol-4-yl)pyridin-2-yl)pyrrolidin-2-one | Enantiomer-II | 400.2 | 98.62% ee (RT = 4.76 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 249 nm]. | I: 9.68, 98.3% J: 9.13, 98.5% | 1H NMR (400 MHz, methanol-d4) δ ppm 8.19 (d, J = 8.5 Hz, 1H), 7.85 (br. s., 2H), 7.78 (d, J = 8.0 Hz, 1H), 7.15 (t, J = 8.0 Hz, 1H), 6.95-6.53 (m, 3H), 6.44 (dd, J = 7.8, 2.8 Hz, 1H), 4.48 (dd, J = 10.3, 8.3 Hz, 1H), 4.34-4.25 (m, 1H), 4.00-3.90 (m, 1H), 2.76-2.67 (m, 1H), 2.58 (s, 3H), 2.05-1.93 (m, 1H), 19F NMR (400 MHz, methanol-d4) δ ppm -82.47 ppm, SOR: [α]$_D^{25.2}$ = -88.0 (c 0.1, DMSO). |

| Ex. | Structure and Name | Chirality | LCMS (M+H)+ | Chiral Purity | HPLC Method, RT (min) & Purity | 1H NMR |
|---|---|---|---|---|---|---|
| 203 | 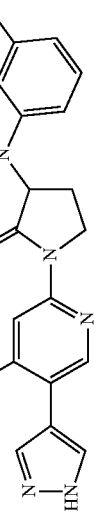<br>1-(4-ethyl-5-(1H-pyrazol-4-yl)pyridin-2-yl)-3-((3-methoxyphenyl)amino)pyrrolidin-2-one | Enantiomer-I | 378.2 | 100% ee (RT = 6.49 min), [Method: Column: CHIRALCEL ® OJ-H (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 25% (0.2% DEA in MeOH), Total Flow: 4.0 g/min, BackPressure: 100 bars, Temperature: 30.0° C., UV: 250 nm]. | I: 9.02, 99.2% J: 8.52, 99.7% | $^1$H NMR (400 MHz, DMSO-d$_6$) δ ppm 13.08 (br. s., 1H), 8.34 (s, 1H), 8.29 (s, 1H), 7.87 (br. s., 2H), 6.99 (t, J = 8.0 Hz, 1H), 6.36-6.28 (m, 2 H), 6.17 (dd, J = 7.1, 1.2 Hz, 1H), 5.95 (d, J = 7.5 Hz, 1H), 4.53-4.43 (m, 1 H), 4.17-4.08 (m, 1H), 3.89-3.78 (m, 1H), 3.68 (s, 3H), 2.74 (q, J = 7.5 Hz, 2H), 2.63-2.54 (m, 1H), 1.96-1.83 (m, 1H), 1.14 (t, J = 7.5 Hz, 3H), SOR: [α]$^{25.3}_D$ = −54.0 (c 0.1, DMSO). |
| 204 | 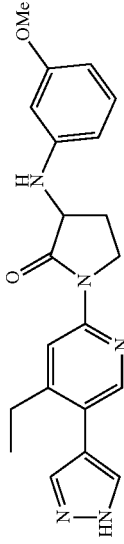<br>1-(4-ethyl-5-(1H-pyrazol-4-yl)pyridin-2-yl)-3-((3-methoxyphenyl)amino)pyrrolidin-2-one | Enantiomer-II | 378.2 | 100% ee (RT = 10.22 min), [Method: Column: CHIRALCEL ® OJ-H (250 × 4.6 mm), 5μ, Mobile Phase: 0.2% DEA in methanol, CO$_2$ Flow Rate: 2.4 g/min, Co-solvent flow rate: 1.6 g/min, % Co-solvent: 25% (0.2% DEA in MeOH), Total Flow: 4.0 g/min, BackPressure: 100 bars, Temperature: 30.0° C., UV: 250 nm]. | I: 9.03, 98.7% J: 8.52, 99.6% | $^1$H NMR (400 MHz, DMSO-d$_6$) δ ppm 13.09 (br. s., 1H), 8.34 (s, 1H), 8.29 (s, 1H), 7.86 (br. s., 2H) 6.99 (t, J = 8.1 Hz, 1H), 6.35-6.27 (m, 2H), 6.17 (dd, J = 7.1, 1.2 Hz, 1H), 5.95 (d, J = 7.3 Hz, 1H), 4.53-4.43 (m, 1H), 4.20-4.08 (m, 1H), 3.88-3.77 (m, 1 H), 3.68 (s, 3H), 2.74 (q, J = 7.5 Hz, 2 H), 2.61-2.54 (m, 1H), 1.95-1.83 (m, 1H), 1.14 (t, J = 7.5 Hz, 3H), SOR: [α]$^{25.3}_D$ = +54.0 (c 0.1, DMSO). |
| 205 | 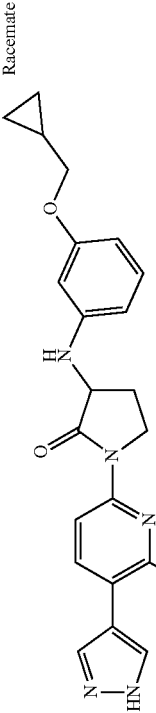<br>3-((3-(cyclopropylmethoxy)phenyl)amino)-1-(6-methoxy-5-(1H-pyrazol-4-yl)pyridin-2-yl)pyrrolidin-2-one | Racemate | 420.2 | | K: 18.01, 97.1% L: 16.46, 98.2% | $^1$H NMR (400 MHz, DMSO-d$_6$) δ ppm 12.94 (br. s., 1H), 8.14 (br. s., 1 H), 8.08 (d, J = 8.4 Hz, 1H), 7.99 (br. s., 1H), 7.90 (d, J = 8.5 Hz, 1H), 6.96 (t, J = 8.3 Hz, 1H), 6.33-6.25 (m, 2 H), 6.18-6.12 (m, 1H), 5.91 (d, J = 7.5 Hz, 1H), 4.53-4.42 (m, 1H), 4.20 (t, J = 9.0 Hz, 1H), 4.00 (s, 3H), 3.90-3.79 (m, 1H), 3.73 (d, J = 7.0 Hz, 2H), 2.63-2.54 (m, 1H), 1.94-1.82 (m, 1H), 1.26-1.13 (m, 1H), 0.59-0.51 (m, 2H), 0.32-0.24 (m, 2 H). |

| Ex. | Structure and Name | Chirality | LCMS (M+H)+ | Chiral Purity | HPLC Method, RT (min) & Purity | ¹H NMR |
|---|---|---|---|---|---|---|
| 206 | 3-((3-(cyclopropylmethoxy)phenyl)amino)-1-(4-methyl-5-(1H-pyrazol-4-yl)pyridin-2-yl)pyrrolidin-2-one | Enantiomer-I | 404.2 | 100% ee (RT = 7.68 min), [Method: Column: Lux Cellulose-4 (250 × 4.6 mm), 5μ, Mobile Phase: 0.2% DEA in methanol, CO₂ Flow Rate: 2.4 g/min, Co-solvent flow rate: 1.6 g/min, % Co-solvent: 40% (0.2% DEA in MeOH), Total Flow: 4.0 g/min, Back Pressure: 100 bars, Temperature: 30.0° C., UV: 259 nm]. | I: 9.47, 97.1% J: 8.93, 98.1% | ¹H NMR (400 MHz, DMSO-d₆) δ ppm 13.08 (br. s., 1H), 8.41 (s, 1H), 8.21 (s, 1H), 7.93 (br. s., 2H), 6.96 (t, J = 8.3 Hz, 1H), 6.33-6.25 (m, 2 H), 6.18-6.11 (m, 1H), 5.90 (d, J = 7.0 Hz, 1H), 4.52-4.39 (m, 1H), 4.18-4.07 (m, 1H), 3.82 (td, J = 10.3, 6.5 Hz, 1H), 3.73 (d, J = 7.0 Hz, 2H), 2.63-2.53 (m, 1H), 2.41 (s, 3H), 1.95-1.81 (m, 1H), 1.27-1.12 (m, 1 H), 0.59-0.50 (m, 2H), 0.34-0.25 (m, 2H), SOR: [α]$_D^{25.3}$ = +44.0 (c 0.1, DMSO). |
| 207 | 3-((4-fluoro-3-methoxyphenyl)amino)-1-(6-methoxy-5-(1H-pyrazol-4-yl)pyridin-2-yl)pyrrolidin-2-one | Enantiomer-II | 398.2 | 100% ee (RT = 4.79 min), [Method: Column: CHIRALPAK ® IA (250 × 4.6 mm), 5μ, Mobile Phase: 0.2% DEA in methanol, % Co-solvent: 30% (0.2% DEA in MeOH), Total Flow: 3.0 g/min, Back Pressure: 100 bars, Temperature: 30.0° C., UV: 219 nm] | I: 9.86, 99.1% J: 9.37, 99.4% | ¹H NMR (400 MHz, DMSO-d₆) δ ppm 12.95 (br. s., 1H), 8.12-8.04 (m, 3H), 7.90 (d, J = 8.5 Hz, 1H), 6.91 (dd, J = 11.5, 8.5 Hz, 1H), 6.53 (dd, J = 7.5, 3.0 Hz, 1H), 6.24-6.17 (m, 1H), 5.87 (d, J = 7.5 Hz, 1H), 4.50-4.40 (m, 1H), 4.26-4.16 (m, 1 H), 4.00 (s, 3H), 3.91-3.81 (m, 1 H), 3.76 (s, 3H), 2.63-2.53 (m, 1 H), 1.93-1.80 (m, 1H), ¹⁹F NMR (376 MHz, DMSO-d₆) δ ppm -150.80, SOR: [α]$_D^{25.2}$ = +56.0 (c 0.1,DMSO) |
| 208 | 3-((4-fluoro-3-methoxyphenyl)amino)-1-(6-methoxy-5-(1H-pyrazol-4-yl)pyridin-2-yl)pyrrolidin-2-one | Enantiomer-II | 398.2 | 97.50% ee (RT = 6.22 min), [Method: Column: CHIRALPAK ® IA (250 × 4.6 mm), 5μ, Mobile Phase: 0.2% DEA in methanol, % Co-solvent: 30% (0.2% DEA in MeOH), Total Flow: 3.0 g/min, Back Pressure: 100 bars, Temperature: 30.0° C., UV: 219 nm] | I: 9.85, 99.5% J: 9.36, 99.6% | ¹H NMR (400 MHz, DMSO-d₆) δ ppm 12.89 (br. s., 1H), 8.12-8.03 (m, 3H), 7.90 (d, J = 8.5 Hz, 1H), 6.91 (dd, J = 11.5, 8.5 Hz, 1H), 6.53 (dd, J = 7.5, 3.0 Hz, 1H), 6.25-6.17 (m, 1H), 5.87 (d, J = 7.0 Hz, 1H), 4.50-4.41 (m, 1H), 4.27-4.16 (m, 1 H), 4.00 (m, 3H), 3.91-3.80 (m, 1 H), 3.76 (s, 3H), 2.64-2.53 (m, 1 H), 1.94-1.81 (m, 1H), ¹⁹F NMR (376 MHz, DMSO-d₆) δ ppm -150.80, SOR: [α]$_D^{25.0}$ = -56.0 (c 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 209 | 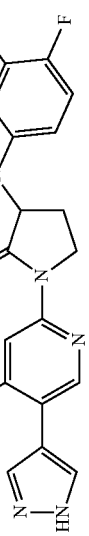<br>3-((4-fluoro-3-methoxyphenyl)amino)-1-(4-methyl-5-(1H-pyrazol-4-yl)pyridin-2-yl)pyrrolidin-2-one | Enantiomer-I | 382.2 | 97.50% ee (RT = 4.1 min), [Method: Column: CHIRALPAK ® IA (250 × 4.6 mm), 5μ, Mobile Phase: 0.2% DEA in methanol, % Co-solvent: 30% (0.2% DEA in MeOH), Total Flow: 3.0 g/min, Back Pressure: 100 bars, Temperature: 30.0° C., UV: 260 nm] | I: 8.09, 98.6% J: 7.72, 97.4% | 1H NMR (400 MHz, DMSO-d6) δ ppm 13.05 (br. s., 1H), 8.41 (s, 1H), 8.21 (s, 1H), 7.93 (br. s., 2H), 6.91 (dd, J = 11.5, 9.0 Hz, 1H), 6.53 (dd, J = 7.5, 2.5 Hz, 1H), 6.26-6.16 (m, 1H), 5.87 (d, J = 7.0 Hz, 1H), 4.50-4.41 (m, 1H), 4.18-4.09 (m, 1H), 3.87-3.80 (m, 1H), 3.77 (s, 3H), 2.63-2.54 (m, 1H), 2.41 (s, 3H), 1.97-1.81 (m, 1H). 19F NMR (376 MHz, DMSO-d6) δ ppm -150.81, SOR: [α]D24.9 = +58.0 (c 0.1, DMSO). |
| 210 | 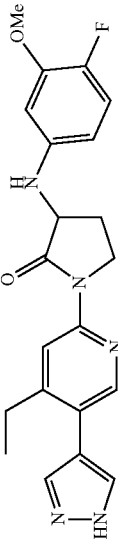<br>1-(4-ethyl-5-(1H-pyrazol-4-yl)pyridin-2-yl)-3-((4-fluoro-3-methoxyphenyl)amino) pyrrolidin-2-one | Enantiomer-I | 396.2 | 98.66% ee (RT = 3.67 min), [Method: Column: CHIRALPAK ® IA (250 × 4.6 mm), 5μ, Mobile Phase: 0.2% DEA in methanol, % Co-solvent: 25% (0.2% DEA in MeOH), Total Flow: 4.0 g/min, Back Pressure: 100 bars, Temperature: 30.0° C., UV: 254 nm] | I: 8.69, 98.7% J: 8.23, 98.5% | 1H NMR (400 MHz, DMSO-d6) δ ppm 13.04 (br. s., 1H), 8.35 (s, 1H), 8.29 (s, 1H), 7.87 (s, 2H), 6.21 (dd, J = 11.5, 9.0 Hz, 1H), 6.53 (dd, J = 7.5, 3.0 Hz, 1H), 6.22 (dt, J = 8.5, 3.0 Hz, 1H), 5.87 (d, J = 7.0 Hz, 1H), 4.51-4.41 (m, 1H), 4.17-4.09 (m, 1H), 3.88-3.79 (m, 1H), 3.77 (s, 3H), 2.74 (q, J = 7.5 Hz, 2H), 2.62-2.54 (m, 1H), 1.95-1.82 (m, 1H), 1.14 (t, J = 7.3 Hz, 3H). 19F NMR (376 MHz, DMSO-d6) δ ppm -150.82, SOR: [α]D25.0 = +76.0 (c 0.1, DMSO). |
| 211 | 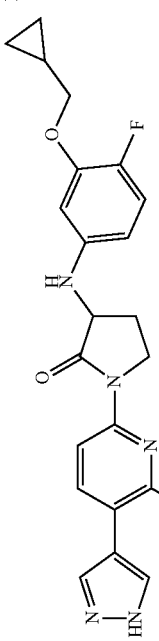<br>3-((3-(cyclopropylmethoxy)-4-fluorophenyl)amino)-1-(6-ethyl-5-(1H-pyrazol-4-yl)pyridin-2-yl)pyrrolidin-2-one | Enantiomer-I | 436.2 | 100% ee (RT = 6.6 min), [Method: Column: CHIRALPAK ® IA (250 × 4.6 mm), 5μ, Mobile Phase: 0.2% DEA in methanol, % Co-solvent: 40% (0.2% DEA in MeOH), Total Flow: 4.0 g/min, Back Pressure: 100 bars, Temperature: 30.0° C., UV: 251 nm] | K: 17.53, 98.7% L: 15.88, 94.7% | 1H NMR (400 MHz, DMSO-d6) δ ppm 12.93 (br. s., 1H), 8.12 (d, J = 8.5 Hz, 1H), 7.84 (s, 2H), 7.78 (d, J = 8.5 Hz, 1H), 6.91 (dd, J = 11.5, 9.0 Hz, 1H), 6.50 (dd, J = 7.3, 2.8 Hz, 1H), 6.25-6.16 (m, 1H), 5.82 (d, J = 7.0 Hz, 1H), 4.49-4.38 (m, 1H), 4.18 (t, J = 9.3 Hz, 1H), 3.89-3.82 (m, 1H), 3.81 (d, J = 7.0 Hz, 2H), 2.85 (q, J = 7.4 Hz, 2H), 2.61-2.54 (m, 1H), 1.94-1.81 (m, 1H), 1.28-1.17 (m, 4H), 0.63-0.53 (m, 2H), 0.35-0.26 (m, 2H). 19F NMR (376 MHz, DMSO-d6) δ ppm -149.84, SOR: [α]D25.1 = +24.0 (c 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 212 | 3-((3-(cyclopropylmethoxy)-4-fluorophenyl)amino)-1-(6-ethyl-5-(1H-pyrazol-4-yl)pyridin-2-yl)pyrrolidin-2-one | Enantiomer-II | 436.2 | 96.28% ee (RT = 8.6 min), [Method: Column: CHIRALPAK @ IA (250 × 4.6 mm), 5μ, Mobile Phase: 0.2% DEA in methanol, % Co-solvent: 40% (0.2% DEA in MeOH), Total Flow: 4.0 g/min, Back Pressure: 100 bars, Temperature: 30.0° C., UV: 251 nm]. | K: 16.90, 94.6% L: 15.87, 95.6% | 1H NMR (400 MHz, DMSO-d6) δ ppm 13.05 (br. s., 1H), 8.12 (d, J = 8.5 Hz, 1H), 7.84 (br. s., 2H), 7.78 (d, J = 8.5 Hz, 1H), 6.91 (dd, J = 11.5, 9.0 Hz, 1H), 6.50 (dd, J = 7.3, 2.8 Hz, 1H), 6.26-6.15 (m, 1H), 5.83 (d, J = 7.5 Hz, 1H), 4.48-4.38 (m, 1H), 4.18 (t, J = 9.0 Hz, 1H), 3.88-3.82 (m, 1H), 3.81 (d, J = 7.0 Hz, 2H), 2.85 (q, J = 7.4 Hz, 2H), 2.62-2.54 (m, 1H), 1.93-1.81 (m, 1H), 1.28-1.18 (m, 4H), 0.61-0.49 (m, 2H), 0.36-0.26 (m, 2H), 19F NMR (376 MHz, DMSO-d6) δ ppm -149.84, SOR: [α]D25.0 = -42.0 (c 0.1, DMSO). |
| 213 | 3-((3-(cyclopropylmethoxy)-4-fluorophenyl)amino)-1-(4-ethyl-5-(1H-pyrazol-4-yl)pyridin-2-yl)pyrrolidin-2-one | Racemate | 436.2 | | E: 2.03, 98.7% F: 1.83, 98.8% | 1H NMR (400 MHz, DMSO-d6) δ ppm 8.37-8.26 (m, 2H), 7.86 (s, 2H), 7.25-6.97 (m, 1H), 6.91 (dd, J = 11.5, 8.8 Hz, 1H), 6.49 (dd, J = 7.6, 2.7 Hz, 1H), 6.25-6.18 (m, 1H), 4.45 (dd, J = 10.0, 8.1 Hz, 1H), 4.17-4.06 (m, 1H), 3.91-3.77 (m, 3H), 2.74 (q, J = 7.5 Hz, 2H), 2.62-2.53 (m, 1H), 1.91-1.78 (m, 1H), 1.28-1.17 (m, 1H), 1.14 (t, J = 7.5 Hz, 3H), 0.61-0.52 (m, 2H), 0.38-0.27 (m, 2H), 19F NMR (376 MHz, DMSO-d6) δ ppm -74.44, -149.80. |
| 214 | 3-((3-(cyclopropylmethoxy)phenyl)amino)-1-(6-methoxy-5-(1H-pyrazol-4-yl)pyridin-2-yl)pyrrolidin-2-one | Enantiomer-I | 420.2 | 100% ee (RT = 9.9 min), [Method: Column: CHIRALCEL @ OJ-H (250 × 4.6 mm), 5μ, Mobile Phase: 0.2% DEA in methanol, % Co-solvent: 30% (0.2% DEA in MeOH), Total Flow: 4.0 g/min, Back Pressure: 100 bars, Temperature: 30.0° C., UV: 311 nm]. | K: 18.63, 98.7% L: 16.42, 99.0% | 1H NMR (400 MHz, DMSO-d6) δ ppm 12.95 (br. s., 1H), 8.12-8.05 (m, 3H), 7.91 (d, J = 8.0 Hz, 1H), 6.96 (t, J = 8.3 Hz, 1H), 6.32-6.27 (m, 2H), 6.18-6.12 (m, 1H), 5.92 (d, J = 7.0 Hz, 1H), 4.51-4.43 (m, 1H), 4.24-4.17 (m, 1H), 4.00 (s, 3H), 3.91-3.80 (m, 1H), 3.73 (d, J = 7.0 Hz, 2H), 2.61-2.54 (m, 1H), 1.95-1.81 (m, 1H), 1.23-1.16 (m, 1H), 0.58-0.52 (m, 2H), 0.32-0.26 (m, 2H), SOR: [α]D25.1 = -52.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 215 | 3-((3-(cyclopropylmethoxy)phenyl)amino)-1-(6-methoxy-5-(1H-pyrazol-4-yl)pyridin-2-yl)pyrrolidin-2-one | Enantiomer-II | 420.2 | 100% ee (RT = 11.55 min), [Method: Column: CHIRALCEL ® OJ-H (250 × 4.6 mm), 5μ, Mobile Phase: 0.2% DEA in methanol, % Co-solvent: 30% (0.2% DEA in MeOH), Total Flow: 4.0 g/min, Back Pressure: 100 bars, Temperature: 30.0° C., UV: 215 nm]. | K: 13.50, 98.8%, L: 16.27, 99.9% | 1H NMR (400 MHz, DMSO-d6) δ ppm 12.93 (br. s., 1H), 8.12-8.04 (m, 3H), 7.90 (d, J = 8.5 Hz, 1H), 6.96 (t, J = 8.3 Hz, 1H), 6.33-6.26 (m, 2H), 6.18-6.12 (m, 1H), 5.91 (d, J = 7.5 Hz, 1H), 4.54-4.41 (m, 1H), 4.23-4.16 (m, 1H), 4.00 (s, 3H), 3.91-3.79 (m, 1H), 3.73 (d, J = 7.0 Hz, 2H), 2.62-2.54 (m, 1H), 1.95-1.80 (m, 1H), 1.24-1.13 (m, 1H), 0.59-0.51 (m, 2H), 0.34-0.25 (m, 2H), SOR: [α]$_D^{25.1}$ = +54.0 (c 0.1, DMSO |
| 216 | 3-((3-(cyclopropylmethoxy)-4-fluorophenyl)amino)-1-(6-methoxy-5-(1H-pyrazol-4-yl)pyridin-2-yl)pyrrolidin-2-one | Enantiomer-I | 438.2 | 100% ee (RT = 16.21 min), [Method: Column: CHIRALPAK ® IC (250 × 4.6 mm), 5μ, Mobile Phase: 0.2% DEA in methanol, % Co-solvent: 40% (0.2% DEA in MeOH), Total Flow: 4.0 g/min, Back Pressure: 101 bars, Temperature: 20.2° C., UV: 309 nm]. | K: 17.61, 96.7%, L: 16.35, 96.6% | 1H NMR (400 MHz, DMSO-d6) δ ppm 12.95 (br. s., 1H), 8.12-8.02 (m, 3H), 7.89 (d, J = 8.4 Hz, 1H), 6.92 (dd, J = 11.5, 8.5 Hz, 1H), 6.49 (dd, J = 7.5, 2.5 Hz, 1H), 6.25-6.15 (m, 1H), 5.84 (d, J = 7.0 Hz, 1H), 4.49-4.39 (m, 1H), 4.25-4.14 (m, 1H), 3.99 (s, 3H), 3.91-3.83 (m, 1H), 3.80 (d, J = 7.0 Hz, 2H), 2.62-2.53 (m, 1H), 1.95-1.78 (m, 1H), 1.30-1.16 (m, 1H), 0.63-0.52 (m, 2H), 0.36-0.25 (m, 2H), 19F NMR (376 MHz, DMSO-d6) δ ppm −149.85, SOR: [α]$_D^{20.1}$ = +384.8 (c 0.05, DMSO). |
| 217 | 3-((3-(cyclopropylmethoxy)-4-fluorophenyl)amino)-1-(6-methoxy-5-(1H-pyrazol-4-yl)pyridin-2-yl)pyrrolidin-2-one | Enantiomer-II | 438.2 | 100% ee (RT = 22.0 min), [Method: Column: CHIRALPAK ® IC (250 × 4.6 mm), 5μ, Mobile Phase: 0.2% DEA in methanol, % Co-solvent: 40% (0.2% DEA in MeOH), Total Flow: 4.0 g/min, Back Pressure: 98 bars, Temperature: 20.2° C., UV: 308 nm]. | K: 17.61, 96.5%, L: 16.32, 96.3% | 1H NMR (400 MHz, DMSO-d6) δ ppm 12.78 (br. s., 1H), 8.12-8.02 (m, 3H), 7.89 (d, J = 8.5 Hz, 1H), 6.91 (dd, J = 11.5, 8.5 Hz, 1H), 6.49 (dd, J = 7.5, 2.5 Hz, 1H), 6.20 (dt, J = 5.6, 2.9 Hz, 1H), 5.84 (d, J = 7.0 Hz, 1H), 4.52-4.38 (m, 1H), 4.26-4.13 (m, 1H), 3.99 (s, 3H), 3.90-3.83 (m, 1H), 3.80 (d, J = 7.0 Hz, 2H), 2.62-2.54 (m, 1H), 1.94-1.79 (m, 1H), 1.29-1.16 (m, 1H), 0.61-0.50 (m, 2H), 0.36-0.23 (m, 2H), 19F NMR (376 MHz, DMSO-d6) δ ppm −149.86, SOR: [α]$_D^{25.7}$ = −612.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 218 | 3-((3-ethoxyphenyl)amino)-1-(6-methoxy-5-(1H-pyrazol-4-yl)pyridin-2-yl)pyrrolidin-2-one | Enantiomer-I | 394.2 | 97.12% ee (RT = 16.54 min), [Method: Column: CHIRALPAK ® IC (250 × 4.6 mm), 5μ, Mobile Phase: 0.2% DEA in methanol, % Co-solvent: 40% (0.2% DEA in MeOH), Total Flow: 4.0 g/min, Back Pressure: 100 bars, Temperature: 30.0° C., UV: 310 nm]. | I: 10.55, 98.8% J: 9.73, 99.3% | 1H NMR (400 MHz, DMSO-d6) δ ppm 12.90 (br. s., 1H), 8.13-8.04 (m, 3H), 7.91 (d, J = 8.4 Hz, 1H), 6.97 (t, J = 8.0 Hz, 1H), 6.35-6.24 (m, 2H), 6.20-6.11 (m, 1H), 5.92 (d, J = 7.5 Hz, 1H), 4.51-4.40 (m, 1H), 4.26-4.14 (m, 1H), 4.01 (s, 3H), 3.94 (q, J = 7.1 Hz, 2H), 3.89-3.79 (m, 1H), 2.63-2.53 (m, 1H), 1.96-1.80 (m, 1H), 1.30 (t, J = 7.2 Hz, 3H), SOR: [α]$_D^{26.1}$ = +40.0 (c 0.05, DMSO). |
| 219 | 3-((3-ethoxyphenyl)amino)-1-(6-methoxy-5-(1H-pyrazol-4-yl)pyridin-2-yl)pyrrolidin-2-one | Enantiomer-II | 394.2 | 96.68% ee (RT = 22.42 min), [Method: Column: CHIRALPAK ® IC (250 × 4.6 mm), 5μ, Mobile Phase: 0.2% DEA in methanol, % Co-solvent: 40% (0.2% DEA in MeOH), Total Flow: 4.0 g/min, Back Pressure: 100 bars, Temperature: 30.0° C., UV: 310 nm]. | I: 10.98, 99.7% J: 9.72, 99.7% | 1H NMR (400 MHz, DMSO-d6) δ ppm 12.92 (br. s., 1H), 8.14-8.03 (m, 3H), 7.92 (d, J = 8.0 Hz, 1H), 6.97 (t, J = 8.0 Hz, 1H), 6.34-6.26 (m, 2H), 6.20-6.12 (m, 1H), 5.92 (d, J = 7.0 Hz, 1H), 4.53-4.41 (m, 1H), 4.27-4.15 (m, 1H), 4.00 (s, 3H), 3.96 (q, J = 7.2 Hz, 2H), 3.90-3.82 (m, 1H), 2.63-2.55 (m, 1H), 1.94-1.80 (m, 1H), 1.31 (t, J = 7.2 Hz, 3H), SOR: [α]$_D^{25.8}$ = −84.0 (c 0.05, DMSO). |
| 220 | 3-((3-(difluoromethoxy)phenyl)amino)-1-(6-methoxy-5-(1H-pyrazol-4-yl)pyridin-2-yl)pyrrolidin-2-one | Enantiomer-I | 416.2 | 100% ee (RT = 5.29 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 101 bars, Temperature: 21.4° C., UV: 311 nm]. | K: 15.37, 98.4% L: 16.15, 97.7% | 1H NMR (400 MHz, DMSO-d6) δ ppm 12.93 (br. s., 1H), 8.15-8.02 (m, 3H), 7.90 (d, J = 8.1 Hz, 1H), 7.33-6.92 (m, 2H), 6.58 (dd, J = 7.9, 1.8 Hz, 1H), 6.50 (t, J = 2.2 Hz, 1H), 6.35 (dd, J = 8.1, 2.0 Hz, 1H), 6.30 (d, J = 7.6 Hz, 1H), 4.59-4.49 (m, 1H), 4.26-4.17 (m, 1H), 4.00 (s, 3H), 3.91-3.80 (m, 1H), 2.63-2.56 (m, 1H), 1.96-1.83 (m, 1H), 19F NMR (376 MHz, DMSO-d6) δ ppm −80.91, SOR: [α]$_D^{25.3}$ = −44.8 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 221 | 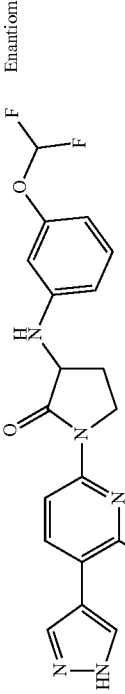<br>3-((3-(difluoromethoxy)phenyl)amino)-1-(6-methoxy-5-(1H-pyrazol-4-yl)pyridin-2-yl)pyrrolidin-2-one | Enantiomer-II | 416.2 | 95.80% ee (RT = 7.61 min), [Method: Column: Lux Cellulose-4 (250 × 4.6 mm), 5μ, Mobile Phase: 0.2% DEA in methanol, CO2 Flow Rate: 2.4 g/min, Co-solvent flow rate: 1.6 g/min, % Co-solvent: 40% (0.2% DEA in MeOH), Total Flow: 4.0 g/min, Back Pressure: 98 bars, Temperature: 21.2° C., UV: 310 nm]. | K: 15.37, 95.8% L: 16.15, 94.6% | 1H NMR (400 MHz, DMSO-d6) δ ppm 12.93 (br. s., 1H), 8.15-8.02 (m, 3H), 7.90 (d, J = 8.1 Hz, 1H), 7.33-6.92 (m, 2H), 6.58 (dd, J = 7.9, 1.8 Hz, 1H), 6.50 (t, J = 2.2 Hz, 1H), 6.35 (dd, J = 8.1, 2.0 Hz, 1H), 6.30 (d, J = 7.6 Hz, 1H), 4.59-4.49 (m, 1H), 4.26-4.17 (m, 1H), 4.00 (s, 3H), 3.91-3.80 (m, 1H), 2.63-2.56 (m, 1H), 1.96-1.83 (m, 1H), 19F NMR (376 MHz, DMSO-d6) δ ppm −80.91, SOR: [α]$_D^{25.3}$ = −44.8 (c 0.05, DMSO). |
| 223 | 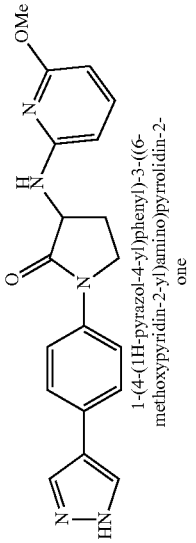<br>1-(4-(1H-pyrazol-4-yl)phenyl)-3-((6-methoxypyridin-2-yl)amino)pyrrolidin-2-one | Racemate | 350.2 | | E: 1.49, 100% F: 2.08, 100% | 1H NMR (400 MHz, chloroform-d) δ ppm 7.86 (s, 2H), 7.75-7.70 (m, 2H), 7.58-7.52 (m, 2H), 7.38 (t, J = 7.9 Hz, 1H), 6.16-6.09 (m, 2H), 5.12 (br. s., 1H), 4.58-4.51 (m, 1H), 3.97-3.88 (m, 2H), 3.87 (s, 3H), 3.04-2.93 (m, 1H), 2.20-2.08 (m, 1H). |
| 224 | 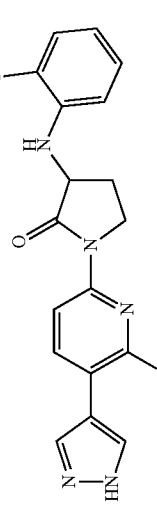<br>3-((2-fluorophenyl)amino)-1-(6-methoxy-5-(1H-pyrazol-4-yl)pyridin-2-yl)pyrrolidin-2-one | Racemate | 368.1 | | E: 1.96, 100% F: 1.92, 100% | 1H NMR (400 MHz, DMSO-d6) δ ppm 12.94 (br. s., 1H), 8.15 (s, 1H), 8.08 (d, J = 8.3 Hz, 1H), 7.99 (s, 1H), 7.90 (d, J = 8.3 Hz, 1H), 7.09-6.88 (m, 3H), 6.66-6.56 (m, 1H), 5.68 (dd, J = 7.8, 2.4 Hz, 1H), 4.64-4.54 (m, 1H), 4.27-4.18 (m, 1H), 4.00 (s, 3H), 3.90-3.79 (m, 1H), 2.60-2.54 (m, 1H), 2.14-1.99 (m, 1H), 19F NMR (376 MHz, DMSO-d6) δ ppm−134.29. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 225 | 3-(2H-benzo[b][1,4]oxazin-4(3H)-yl)-1-(6-methoxy-5-(1H-pyrazol-4-yl)pyridin-2-yl)pyrrolidin-2-one | Racemate | 392.2 | | E: 1.94, 100%<br>F: 1.89, 100% | 1H NMR (400 MHz, DMSO-d6) δ ppm 12.94 (br. s., 1H), 8.15 (s, 1H), 8.09 (d, J = 8.0 Hz, 1H), 7.99 (s, 1H), 7.93 (d, J = 8.0 Hz, 1H), 6.87 (d, J = 7.5 Hz, 1H), 6.80-6.69 (m, 2H), 6.61-6.53 (m, 1H), 5.15-5.07 (m, 1H), 4.30-4.18 (m, 3H), 4.00 (s, 3H), 3.92-3.83 (m, 1H), 3.29-3.18 (m, 2H), 2.45-2.35 (m, 1H), 2.18-2.06 (m, 1H). |
| 226 | 3-(4-((1H-pyrazol-4-yl)phenyl)-3-(pyrazin-2-ylamino)pyrrolidin-2-one | Racemate | 321.2 | | E: 1.18, 100%<br>F: 1.09, 100% | 1H NMR (400 MHz, chloroform-d) δ ppm 8.06 (s, 1H), 8.02 (br. s., 1H), 7.92-7.86 (m, 3H), 7.71 (d, J = 8.5 Hz, 2H), 7.59-7.51 (m, 2H), 5.32 (br. s., 1H), 4.66-4.57 (m, 1H), 3.98-3.86 (m, 2H), 3.10-2.98 (m, 1H), 2.11-1.97 (m, 1H). |
| 227 | 1-(4-((1H-pyrazol-4-yl)phenyl)-3-(pyrimidin-5-ylamino)pyrrolidin-2-one | Racemate +E99:E102 | 321.2 | | E: 1.05, 100%<br>F: 0.89, 100% | 1H NMR (400 MHz, DMSO-d6) δ ppm 12.90 (br. s., 1H), 8.43 (s, 1H), 8.27 (s, 2H), 8.17 (br. s., 1H), 7.91 (br. s., 1H), 7.72-7.66 (m, 2H), 7.66-7.60 (m, 2H), 6.49 (d, J = 7.6 Hz, 1H), 4.61-4.52 (m, 1H), 3.91-3.79 (m, 2H), 2.66-2.58 (m, 1H), 2.03-1.90 (m, 1H). |
| 228 | 3-(3,4-dihydroquinoxalin-1(2H)-yl)-1-(6-methoxy-5-(1H-pyrazol-4-yl)pyridin-2-yl)pyrrolidin-2-one | Racemate | 391.3 | | E: 1.49, 99.6%<br>F: 1.04, 100% | 1H NMR (400 MHz, DMSO-d6) δ ppm 12.95 (br. s., 1H), 8.15 (br. s., 1H), 8.08 (d, J = 8.1 Hz, 1H), 8.00 (br. s., 1H), 7.94 (d, J = 8.3 Hz, 1H), 6.62 (d, J = 7.8 Hz, 1H), 6.49-6.39 (m, 3H), 5.53 (br. s., 1H), 5.00-4.93 (m, 1H), 4.23 (t, J = 9.4 Hz, 1H), 4.00 (s, 3H), 3.93-3.84 (m, 1H), 3.30-3.08 (m, 4H), 2.39-2.31 (m, 1H), 2.11-2.04 (m, 1H). |

| Ex. | Structure and Name | Chirality | LCMS (M+H)+ | Chiral Purity | HPLC Method, RT (min) & Purity | 1H NMR |
|---|---|---|---|---|---|---|
| 229 | 3-(2H-benzo[b][1,4]oxazin-4(3H)-yl)-1-(6-methoxy-5-(1H-pyrazol-4-yl)pyridin-2-yl)pyrrolidin-2-one (Enantiomer-1) | Enantiomer-I | 392.2 | 100% ee (RT = 2.29 min), [Method: Column: CHIRALPAK @ AS-H (250 × 4.6 mm), 5μ, Mobile Phase: 0.2% DEA in methanol, % Co-solvent: 40% (0.2% DEA in MeOH), Total Flow: 4.0 g/min, Back Pressure: 100 bars, Temperature: 30.0° C., UV: 310 nm]. | I: 8.78, 96.4% J: 9.97, 95.4% | 1H NMR (400 MHz, DMSO-d6) δ ppm 12.88 (br. s., 1H), 8.11-8.04 (m, 3H), 7.93 (d, J = 8.0 Hz, 1H), 6.87 (d, J = 7.5 Hz, 1H), 6.81-6.68 (m, 2H), 6.62-6.53 (m, 1H), 5.15-5.04 (m, 1H), 4.30-4.16 (m, 3H), 4.00 (s, 3H), 3.92-3.81 (m, 1H), 3.26-3.18 (m, 2H), 2.44-2.35 (m, 1 H), 2.20-2.09 (m, 1H). |
| 230 | 3-(2H-benzo[b][1,4]oxazin-4(3H)-yl)-1-(6-methoxy-5-(1H-pyrazol-4-yl)pyridin-2-yl)pyrrolidin-2-one | Enantiomer-II | 392.2 | 100% ee (RT = 4.21 min), [Method: Column: CHIRALPAK @ AS-H (250 × 4.6 mm), 5μ, Mobile Phase: 0.2% DEA in methanol, % Co-solvent: 40% (0.2% DEA in MeOH), Total Flow: 4.0 g/min, Back Pressure: 100 bars, Temperature: 30.0° C., UV: 310 nm]. | I: 8.78, 95.6% J: 9.93, 95.2% | 1H NMR (400 MHz, DMSO-d6) δ ppm 12.91 (br. s., 1H), 8.12-8.02 (m, 3H), 7.93 (d, J = 8.0 Hz, 1H), 6.87 (d, J = 7.6 Hz, 1H), 6.80-6.68 (m, 2H), 6.62-6.53 (m, 1H), 5.15-5.05 (m, 1H), 4.30-4.15 (m, 3H), 4.00 (s, 3H), 3.91-3.80(m, 1H), 3.26-3.19 (m, 2H), 2.43-2.34 (m, 1 H), 2.19-2.09 (m, 1H). |
| 231 | 1-(4-(1H-pyrazol-4-yl)phenyl)-3-((3-(difluoromethoxy)phenyl)amino)pyrrolidin-2-one | Enantiomer-I | 385.20 | 100% ee (rt-21.294), determined by [Method: Column: CHIRALPAK @ IC(250 × 4.6 mm), 5μ, Mobile Phase: n-Hexane:EtOH (80:20), 0.2% DEA in Flow: 1.0 ml/min]. | I: 9.60, 98.8% J: 9.32, 98.8% | 1H NMR (400 MHz, DMSO-d6) δ ppm 12.98 (s, 1H) 8.04 (s, 2H) 7.67-7.73 (m, 2H) 7.61-7.66 (m, 2H) 6.94-7.34 (m, 2H) 6.58 (dd, J = 8.13. 1.79 Hz, 1H) 6.50 (t, J = 2.10 Hz, 1 H 6.35 (dd, J = 7.87, 1.98 Hz, 1H) 6.29 (d, J = 7.34 Hz, 1H) 4.38-4.46 (m, 1 H) 3.80-3.87 (m, 2H) 2.56-2.65 (m, 1H) 1.83-1.96 (m, 1H). 19F NMR (376 MHz, DMSO-d6) δ ppm −80.905. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 232 | 1-(4-(1H-pyrazol-4-yl)phenyl)-3-((3-(difluoromethoxy)phenyl)amino)pyrrolidin-2-one | Enantiomer-II | 385.20 | 97.286% ee (rt-28.935), determined by [Method: Column: CHIRALPAK. ® IC(250 × 4.6 mm), 5μ, Mobile Phase: 0.2% DEA in n-Hexane:EtOH (80:20), Flow: 1.0 ml/min]. | M: 9.63, 99.4%, J: 9.31, 96.7% | 1H NMR (400 MHz, DMSO-d6) δ ppm 12.98 (s, 1H) 8.05 (s, 2H) 7.67-7.72 (m, 2H) 7.61-7.66 (m, 2H) 6.94-7.34 (m, 2H) 6.58 (dd, J = 8.19. 1.66 Hz, 1H) 6.50 (t, J = 2.13 Hz, 1H) 6.35 (dd, J = 7.87, 1.91 Hz, 1H) 6.29 (d, J = 7.28 Hz, 1H) 4.38-4.46 (m, 1H) 3.80-3.86 (m, 2H) 2.56-2.65 (m, 1H) 1.84-1.96 (m, 1H). 19F NMR (376 MHz, DMSO-d6) δ ppm −80.905. |
| 233 | 1-(4-(1H-pyrazol-4-yl)phenyl)-3-((3-(cyclopropylmethoxy)phenyl)amino)pyrrolidin-2-one | Enantiomer-I | 389.20 | 96.66% ee (rt-10.67), [Method: Column: CHIRALPAK ® AS-H (250 × 4.6 mm), 5μ, Mobile Phase: 0.2% DEA in methanol, CO2 Flow Rate: 1.0 g/min, Co-solvent flow rate: 1.0 g/min, % Co-solvent: 35% (0.2% DEA in MeOH), Total Flow: 2.0 g/min, Back Pressure: 150 bars, Temperature: 30.0° C., UV: 240 nm]. | I: 10.23, 97.6%, L: 15.06, 97.8% | 1H NMR (400 MHz, DMSO-d6) δ ppm 8.05 (br. s., 2H) 7.68-7.75 (m, 2H) 7.61-7.67 (m, 2H) 6.97 (t, J = 8.28 Hz, 1H) 6.27-6.34 (m, 2H) 6.12-6.19 (m, 1H) 4.37 (dd, J = 9.79. 8.28 Hz, 1H) 3.80-3.89 (m, 2H) 3.74 (d, J = 7.03 Hz, 2H) 2.57-2.65 (m, 1H) 1.82-1.96 (m, 1H) 1.13-1.26 (m, 1H) 0.51-0.60 (m, 2H) 0.26-0.33 (m, 2H). [α]25.1D = −32.0 (c 0.1, DMSO). |
| 235 | 1-(4-(1H-pyrazol-4-yl)phenyl)-3-((3-(cyclopropylmethoxy)phenyl)amino)pyrrolidin-2-one | Enantiomer-II | 389.20 | 96.24% ee (rt-13.18). [Method: Column: CHIRALPAK ® AS-H (250 × 4.6 mm), 5μ, Mobile Phase: 0.2% DEA in methanol, CO2 Flow Rate: 1.0 g/min, Co-solvent flow rate: 1.0 g/min, % Co-solvent: 35% (0.2% DEA in MeOH), Total Flow: 2.0 g/min, Back Pressure: 150 bars, Temperature: 30.0° C., UV: 240 nm]. | I: 10.24, 98.9%, J: 9.62, 99.1% | 1H NMR (400 MHz, DMSO-d6) δ ppm 8.05 (br. s., 2H) 7.67-7.74 (m, 2H) 7.59-7.66 (m, 2H) 6.97 (t, J = 8.28 Hz, 1H) 6.26-6.33 (m, 2H) 6.11-6.18 (m, 1H) 4.37 (dd, J = 9.79. 8.28 Hz, 1H) 3.79-3.88 (m, 2H) 3.74 (d, J = 7.03 Hz, 2H) 2.56-2.65 (m, 1H) 1.82-1.95 (m, 1H) 1.13-1.25 (m, 1H) 0.51-0.59 (m, 2H) 0.26-0.33 (m, 2H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 237 | 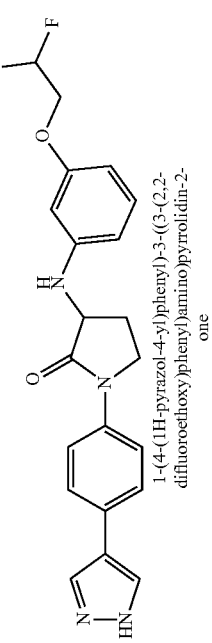 1-(4-(1H-pyrazol-4-yl)phenyl)-3-((3-(2,2-difluoroethoxy)phenyl)amino)pyrrolidin-2-one | Enantiomer-I | 399.20 | 100% ee (rt-5.64) [Method: Column: CHIRALPAK @ IC (250 × 4.6 mm), 5μ, Mobile Phase: 0.2% DEA in methanol. CO$_2$ Flow Rate: 2.4 g/min, % Co-solvent: 40% (0.2% DEA in MeOH), Total Flow: 4.0 g/min, Back Pressure: 100 bars, Temperature: 24.3° C., UV: 270 nm]. | I: 9.48, 98.8% J: 9.25, 99.9% | 1H NMR (400 MHz, DMSO-d$_6$) δ ppm 12.98 (s, 1H) 8.05 (s, 2H) 7.68-7.73 (m, 2H) 7.60-7.66 (m, 2H) 7.01 (t, J = 8.06 Hz, 1H) 6.33-6.40 (m, 3H) 6.20-6.25 (m, 1H) 6.01 (d, J = 7.15 Hz, 1H) 4.40 (dt, J = 9.65, 7.76 Hz, 1H) 4.22 (td, J = 14.70, 3.67 Hz, 2H) 3.78-3.87 (m, 2H) 2.56-2.66 (m, 1H) 1.81-1.94 (m, 1H). 19F NMR (376 MHz, DMSO-d$_6$) δ ppm −125.591. [α]$_D^{25.0}$ = +12.0 (c 0.1, MeOH). |
| 238 | 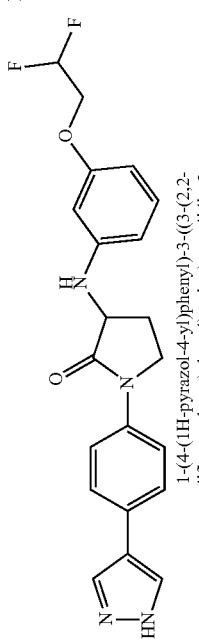 1-(4-(1H-pyrazol-4-yl)phenyl)-3-((3-(2,2-difluoroethoxy)phenyl)amino)pyrrolidin-2-one | Enantiomer-II | 399.20 | 99.0% ee (rt-7.2), [Method: Column: CHIRALPAK @ IC (250 × 4.6 mm), 5μ, Mobile Phase: 0.2% DEA in methanol. CO$_2$ Flow Rate: 2.4 g/min, % Co-solvent: 40% (0.2% DEA in MeOH), Total Flow: 4.0 g/min, Back Pressure: 99 bars, Temperature: 24.1° C., UV: 270 nm]. | I: 9.47, 99.0% J: 9.24, 99.9% | 1H NMR (400 MHz, DMSO-d$_6$) δ ppm 8.05 (s, 2H) 7.67-7.73 (m, 2 H) 7.60-7.66 (m, 2H) 7.01 (t, J = 8.06 Hz, 1H) 6.33-6.40 (m, 3H) 6.20-6.25 (m, 1H) 6.01 (d, J = 7.15 Hz, 1H) 4.40 (dt, J = 9.63, 7.80 Hz, 1H) 4.22 (td, J = 14.71, 3.64 Hz, 2H) 3.80-3.86 (m, 2H) 2.56-2.65 (m, 1H) 1.82-1.94 (m, 1H). 19F NMR (376 MHz, DMSO-d$_6$) δ ppm −125.591. [α]$_D^{24.7}$ = −12.0 (c 0.1, MeOH). |
| 239 | 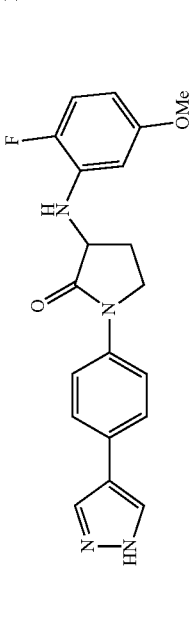 1-(4-(1H-pyrazol-4-yl)phenyl)-3-((2-fluoro-5-methoxyphenyl)amino)pyrrolidin-2-one | Enantiomer-II | 366.90 | 100% ee (rt-29.42), [Method: Column: CHIRALPAK @ IA (250 × 4.6 mm), 5μ, Mobile Phase: 0.2% DEA in methanol. CO$_2$ Flow Rate: 1.8 g/min. Co-solvent flow rate; 1.2 g/min, % Co-solvent: 40% (0.2% DEA in MeOH), Total Flow: 4.0 g/min, Back Pressure: 100 bars, Temperature: 23.3° C., UV: 270 nm]. | I: 9.11, 97.4% J: 9.07, 97.3% | 1H NMR (400 MHz, DMSO-d$_6$) δ ppm 12.92 (br. s., 1H) 8.18 (br. s., 1 H) 7.92 (br. s., 1H) 7.67-7.73 (m, 2 H) 7.61-7.66 (m, 2H) 6.95 (dd, J = 11.61, 8.78 Hz, 1H) 6.45 (dd, J = 7.56, 2.85 Hz, 1H)6.13(dt, J = 8.74, 3.19 Hz, 1H) 5.68 (dd, J = 7.84, 2.07 Hz, 1H) 4.44-4.53 (m, 1H) 3.79-3.86 (m, 2H) 3.68 (s, 3 H) 2.53-2.60 (m, 1H) 1.99-2.11 (m, 1H). 19F NMR (376 MHz, DMSO-d$_6$) δ ppm −144.171. [α]$_D^{24.9}$ = −100.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 240 | 1-(4-(1H-pyrazol-4-yl)phenyl)-3-((2-fluoro-5-methoxyphenyl)amino)pyrrolidin-2-one | Enantiomer-I | 367.20 | 100% ee (rt-26.49), [Method: Column: CHIRALPAK ® IA (250 × 4.6 mm), 5μ, Mobile Phase: 0.2% DEA in methanol. CO₂ Flow Rate: 1.8 g/min. Co-solvent flow rate; 1.2 g/min, % Co-solvent: 40% (0.2% DEA in MeOH), Total Flow: 3.0 g/min, Back Pressure: 95 bars, Temperature: 23.5° C., UV: 274 nm]. | I: 9.25, 99.7% J: 9.03, 99.9% | ¹H NMR (400 MHz, DMSO-d₆) δ ppm 12.90 (br. s., 1H) 8.17 (br. s., 1 H) 7.91 (br. s., 1H) 7.61-7.70 (m, 4 H) 6.95 (dd, J = 11.79, 8.78 Hz, 1H) 6.45 (dd, J = 7.53, 2.76 Hz, 1H) 6.13 (dt, J = 8.66, 3.20 Hz, 1H) 5.65 (d, J = 7.78 Hz, 1H) 4.42-4.53 (m, 1H) 3.76-3.89 (m, 2H) 3.68 (s, 3H) 2.54-2.60 (m, 1H) 1.99-2.12 (m, 1 H). ¹⁹F NMR (376 MHz, DMSO-d₆) δ ppm −144.176. [α]$_D^{25.2}$ = +104.0 (c 0.05, DMSO). |
| 241 | 1-(3-ethyl-4-(1H-pyrazol-4-yl)phenyl)-3-(((4-fluoro-3-methoxyphenyl)amino) pyrrolidin-2-one | Enantiomer-I | 395.20 | 100% ee (rt-8.18), [Method: Column: CHIRALPAK ® IC (250 × 4.6 mm), 5μ, Mobile Phase: 0.2% DEA in methanol, CO₂ Flow Rate: 2.4 g/min, Co-solvent flow rate; 1.6 g/min, % Co-solvent: 40% (0.2% DEA in MeOH), Total Flow: 4.0 g/min, Back Pressure: 100 bars, Temperature: 23.5° C., UV: 260 nm]. | I: 9.86, 99.6% J: 9.19, 99.7% | ¹H NMR (400 MHz, DMSO-d₆) δ ppm 12.90 (br. s., 1H) 7.76 (s, 2H) 7.64 (d, J = 2.01 Hz, 1H) 7.52 (dd, J = 8.53, 2.51 Hz, 1H) 7.33 (d, J = 8.53 Hz, 1H) 6.91 (dd, J = 11.55, 9.04 Hz, 1H) 6.54 (dd, J = 7.53, 3.01 Hz, 1H) 6.21 (dt, J = 8.66, 3.20 Hz, 1H) 5.84 (d, J = 6.53 Hz, 1H) 4.30-4.39 (m, 1 H) 3.81-3.87 (m, 2H) 3.77 (s, 3H) 2.68-2.75 (m, 2H) 2.62 (td, J = 8.03, 4.02 Hz, 1H) 1.82-1.95 (m, 1H) 1.14 (t, J = 7.55 Hz, 3H). ¹⁹F NMR (376 MHz, DMSO-d₆) δ ppm −150.869. [α]$_D^{24.7}$ = −4.0 (c 0.05, methanol). |
| 242 | 1-(3-ethyl-4-(1H-pyrazol-4-yl)phenyl)-3-(((4-fluoro-3-methoxyphenyl)amino) pyrrolidin-2-one | Enantiomer-I | 395.20 | 99.10% ee (rt-9.96), [Method: Column: CHIRALPAK ® IC (250 × 4.6 mm), 5μ, Mobile Phase: 0.2% DEA in methanol. CO₂ Flow Rate: 2.4 g/min, Co-solvent flow rate; 1.6 g/min, % Co-solvent: 40% (0.2% DEA in MeOH), Total Flow: 4.0 g/min, Back Pressure: 100 bars, Temperature: 23.5° C., UV: 260 nm]. | I: 9.86, 98.4% J: 9.18, 99.6% | ¹H NMR (400 MHz, DMSO-d₆) δ ppm 12.80 (br. s., 1H) 7.77 (s, 2H) 7.65 (d, J = 2.01 Hz, 1H) 7.53 (dd, J = 8.28, 2.26 Hz, 1H) 7.34 (d, J = 8.53 Hz, 1H) 6.92 (dd, J = 11.55, 9.04 Hz, 1H) 6.54 (dd, J = 7.53, 2.51 Hz, 1H) 6.22 (dt, J = 8.66, 3.20 Hz, 1H) 5.86 (d, J = 7.03 Hz, 1H) 4.31-4.41 (m, 1 H) 3.84 (dd, J = 9.79, 4.27 Hz, 2H) 3.77 (s, 3H) 2.72 (q, J = 7.53 Hz, 2H) 2.62 (td, J = 8.03, 4.02 Hz, 1H) 1.82-1.95 (m, 1H) 1.10-1.19 (t, J = 7.55 Hz, 3H). ¹⁹F NMR (376 MHz, DMSO-d₆) δ ppm −150.915. [α]$_D^{24.7}$ = +12.0 (c 0.05, methanol). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 243 | 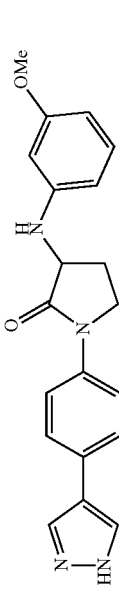<br>1-(3-ethyl-4-(1H-pyrazol-4-yl)phenyl)-3-((3-methoxyphenyl)amino)pyrrolidin-2-one | Enantiomer-I | 377.20 | 100% ee (rt-5.25), [Method: Column: CHIRALCEL ® AS-H (250 × 4.6 mm), 5μ, Mobile Phase: 0.2% DEA in methanol, CO2 Flow Rate: 2.4 g/min, Co-solvent flow rate: 1.6 g/min, % Co-solvent: 25% (0.2% DEA in MeOH), Total Flow: 4.0 g/min, Back Pressure: 100 bars, Temperature: 30.0° C., UV: 260 nm]. | K: 15.43, 99.5% L: 13.97, 98.8% | 1H NMR (300 MHz, DMSO-d6) δ ppm 12.92 (br. s., 1H) 7.76 (s, 2H) 7.65 (d, J = 2.27 Hz, 1H) 7.53 (dd, J = 8.50, 2.46 Hz, 1H) 7.33 (d, J = 8.69 Hz, 1H) 6.94-7.04 (m, 1H) 6.26-6.35 (m, 2H) 6.13-6.21 (m, 1H) 5.93 (d, J = 6.80 Hz, 1H) 4.31-4.42 (m, 1H) 3.84 (dd, J = 9.07, 4.15 Hz, 2H) 3.68 (s, 3H) 2.71 (q, J = 7.55 Hz, 2H) 2.56-2.65 (m, 1H) 1.89 (dd, J = 11.71, 9.82 Hz, 1H) 1.14 (t, J = 7.55 Hz, 3H). [α]$_D^{25.0}$ = +32.0 (c 0.05, DMSO) |
| 244 | 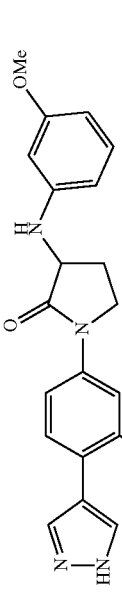<br>1-(3-ethyl-4-(1H-pyrazol-4-yl)phenyl)-3-((3-methoxyphenyl)amino)pyrrolidin-2-one | Enantiomer-II | 377.20 | 100% ee (rt-6.88), [Method: Column: CHIRALCEL ® AS-H (250 × 4.6 mm), 5μ, Mobile Phase: 0.2% DEA in methanol, CO2 Flow Rate: 2.4 g/min, Co-solvent flow rate: 1.6 g/min, % Co-solvent: 25% (0.2% DEA in MeOH), Total Flow: 4.0 g/min, Back Pressure: 100 bars, Temperature: 30.0° C., UV: 260 nm]. | K: 15.39, 94.5% L: 13.96, 95.8% | 1H NMR (300 MHz, DMSO-d6) δ ppm 12.93 (br. s., 1H) 7.76 (s, 2H) 7.65 (d, J = 2.27 Hz, 1H) 7.53 (dd, J = 8.31, 2.27 Hz, 1H) 7.33 (d, J = 8.69 Hz, 1H) 6.94-7.04 (m, 1H) 6.25-6.38 (m, 2H) 6.13-6.21 (m, 1H) 5.93 (d, J = 7.18 Hz, 1H) 4.29-4.42 (m, 1H) 3.84 (dd, J = 9.25, 4.34 Hz, 2H) 3.68 (s, 3H) 2.71 (q, J = 7.30 Hz, 2H) 2.58-2.64 (m, 1H) 1.80-1.99 (m, 1H) 1.14 (t, J = 7.55 Hz, 3H). [α]$_D^{24.8}$ = −44.0 (c 0.05, DMSO). |
| 245 | 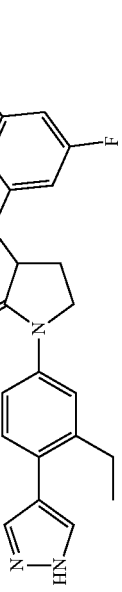<br>1-(3-ethyl-4-(1H-pyrazol-4-yl)phenyl)-3-((3-fluoro-5-methoxyphenyl)amino)pyrrolidin-2-one | Enantiomer-I | 395.20 | 99.81% ee (rt-8.35). [Method: Column: CHIRALCEL ® AS-H (250 × 4.6 mm), 5μ, Mobile Phase: 0.2% DEA in methanol, CO2 Flow Rate: 1.0 g/min, Co-solvent flow rate: 1.0 g/min, % Co-solvent: 25% (0.2% DEA in MeOH), Total Flow: 4.0 g/min, Back Pressure: 100 bars, Temperature: 25.0° C., UV: 256 nm]. | I: 10.38, 98.9% J: 9.56, 99.2% | 1H NMR (400 MHz, DMSO-d6) δ ppm 12.81 (br. s., 1H) 7.76 (s, 2H) 7.64 (d, J = 2.51 Hz, 1H) 7.52 (dd, J = 8.28, 2.26 Hz, 1H) 7.33 (d, J = 8.53 Hz, 1H) 6.29 (d, J = 7.53 Hz, 1H) 6.10-6.17 (m, 2H) 6.00 (dt, J = 11.04, 2.26 Hz, 1H) 4.40 (dt, J = 9.66, 7.72 Hz, 1H) 3.79-3.86 (m, 2H) 3.69 (s, 3H) 2.68-2.75 (q, 2H) 2.56-2.65 (m, 1H) 1.88 (dq, J = 12.24, 9.47 Hz, 1H) 1.14 (t, J = 7.53 Hz, 3H). 19F NMR (376 MHz, DMSO-d6) δ ppm −112.565. [α]$_D^{25.3}$ = +16.0 (c 0.05, methanol |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 246 | 1-(3-ethyl-4-(1H-pyrazol-4-yl)phenyl)-3-((3-fluoro-5-methoxyphenyl)amino)pyrrolidin-2-one | Enantiomer-II | 395.20 | 98.34% ee (rt-12.19), [Method: Column: CHIRALCEL® AS-H (250 × 4.6 mm), 5μ, Mobile Phase: 0.2% DEA in methanol, CO2 Flow Rate: 1.0 g/min, Co-solvent flow rate: 1.0 g/min, % Co-solvent: 25% (0.2% DEA in MeOH), Total Flow: 4.0 g/min, Back Pressure: 100 bars, Temperature: 25.0° C., UV: 256 nm]. | I: 10.37, 99.2%, J: 9.57, 99.0% | 1H NMR (400 MHz, DMSO-d6) δ ppm 12.81 (br. s., 1H) 7.76 (s, 2H) 7.64 (d, J = 2.51 Hz, 1H) 7.52 (dd, J = 8.28, 2.26 Hz, 1H) 7.33 (d, J = 8.53 Hz, 1H) 6.29 (d, J = 7.53 Hz, 1H) 6.10-6.18 (m, 2H) 6.00 (dt, J = 11.04, 2.26 Hz, 1H) 4.40 (dt, J = 9.66, 7.72 Hz, 1H) 3.80-3.86 (m, 2H) 3.69 (s, 3H) 2.71 (q, J = 7.53 Hz, 2H) 2.57-2.65 (m, 1H) 1.88 (dq, J = 12.24, 9.47 Hz, 1H) 1.14 (t, J = 7.53 Hz, 3H). 19F NMR (376 MHz, DMSO-d6) δ ppm −112.576. [α]D24.9 = −16.0 (c 0.05, methanol). |
| 247 | 3-((3-(cyclopropylmethoxy)phenyl)amino)-1-(3-ethyl-4-(1H-pyrazol-4-yl)phenyl)pyrrolidin-2-one | Enantiomer-I | 417.20 | 100% ee (rt-2.59), [Method: Column: CHIRALCEL® AS-H (250 × 4.6 mm), 5μ, Mobile Phase: 0.2% DEA in methanol, CO2 Flow Rate: 1.0 g/min, Co-solvent flow rate: 1.0 g/min, % Co-solvent: 40% (0.2% DEA in MeOH), Total Flow: 4.0 g/min, Back Pressure: 100 bars, Temperature: 30.0° C., UV: 260 nm]. | K: 17.94, 96.5%, L: 16.19, 97.1% | 1H NMR (300 MHz, DMSO-d6) δ ppm 12.84 (br. s., 1H) 7.76 (s, 2H) 7.65 (d, J = 2.27 Hz, 1H) 7.53 (dd, J = 8.31, 2.27 Hz, 1H) 7.33 (d, J = 8.31 Hz, 1H) 6.96 (t, J = 8.31 Hz, 1H) 6.26-6.33 (m, 2H) 6.10-6.18 (m, 1H) 5.89 (d, J = 6.80 Hz, 1H) 4.31-4.41 (m, 1H) 3.84 (dd, J = 9.25, 4.34 Hz, 2 H) 3.73 (d, J = 6.80 Hz, 2H) 2.71 (q, J = 7.68 Hz, 2H) 2.61 (m, 1H) 1.82-1.96 (m, 1H) 1.08-1.25 (m, 4H) 0.51-0.59 (m, 2H) 0.29 (q, J = 4.78 Hz, 2H). [α]D25.0 = +40 (c 0.05, DMSO |
| 248 | 3-((3-(cyclopropylmethoxy)phenyl)amino)-1-(3-ethyl-4-(1H-pyrazol-4-yl)phenyl)pyrrolidin-2-one | Enantiomer-II | 417.20 | 100% ee (rt-3.28), [Method: Column: CHIRALCEL® AS-H (250 × 4.6 mm), 5μ, Mobile Phase: 0.2% DEA in methanol, CO2 Flow Rate: 1.0 g/min, Co-solvent flow rate: 1.0 g/min, % Co-solvent: 40% (0.2% DEA in MeOH), Total Flow: 4.0 g/min, Back Pressure: 100 bars, Temperature: 30.0° C., UV: 260 nm]. | K: 17.95, 95.4%, L: 16.10, 95.6% | 1H NMR (300 MHz, DMSO-d6) δ ppm 12.69 (s, 1H) 7.76 (s, 2H) 7.65 (d, J = 2.27 Hz, 1H) 7.53 (dd, J = 8.69 Hz, 1 H) 6.96 (t, J = 8.12 Hz, 1H) 6.26-6.34 (m, 2H) 6.15 (d, J = 9.07 Hz, 1 H) 5.89 (d, J = 6.80 Hz, 1H) 4.29-4.42 (m, 1H) 3.84 (dd, J = 9.25, 4.34 Hz, 2H) 3.73 (d, J = 7.18Hz, 2H) 2.66-2.77 (m, 3H) 1.82-1.93 (m, 1 H) 1.09-1.23 (m, 4H) 0.50-0.60 (m, 2H) 0.25-0.34 (m, 2H). [α]D25.0 = −40.0 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 249 | 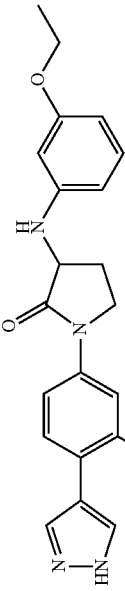<br>3-((3-ethoxyphenyl)amino)-1-(3-methoxy-4-(1H-pyrazol-4-yl)phenyl)pyrrolidin-2-one | Enantiomer-I | 393.20 | 98.44% ee (rt-13.37). [Method: Column: CHIRALPAK @ IC (250 × 4.6 mm), 5μ, Mobile Phase: 0.2% DEA in methanol. CO$_2$ Flow Rate: 1.0 g/min, Co-solvent flow rate; 1.0 g/min, % Co-solvent: 40% (0.2% DEA in MeOH). Total Flow: 4.0 g/min, Back Pressure: 100 bars, Temperature: 30.0° C., UV: 260 nm]. | I: 9.74, 98.5% J: 9.16, 99.7% | 1H NMR (400 MHz, DMSO-d$_6$) δ ppm 12.83 (br. s., 1H) 8.03 (s, 2H) 7.63 (d, J = 10.27 Hz, 2H) 7.19 (dd, J = 8.3 1, 2.20 Hz, 1H) 6.97 (t, J = 8.07 Hz, 1H) 6.27-6.35 (m, 2H) 6.16 (dd, J = 8.07, 1.47 Hz, 1H) 5.89 (d, J = 6.85 Hz, 1H) 4.38 (dt, J = 9.72, 7.61 Hz, 1H) 3.95 (q, J = 7.09 Hz, 2H) 3.79-3.90 (m, δH) 2.57-2.65 (m, 1H) 1.82-1.96 (m, 1H) 1.30 (t, J = 6.97 Hz, 3H). [α]$_D^{24.9}$ = +28.0 (c 0.05. DMSO). |
| 250 | 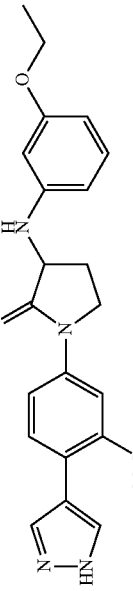<br>3-((3-ethoxyphenyl)amino)-1-(3-methoxy-4-(1H-pyrazol-4-yl)phenyl)pyrrolidin-2-one | Enantiomer-II | 393.20 | 96.08% ee (rt-15.17), [Method: Column: CHIRALPAK @ IC (250 × 4.6 mm), 5μ, Mobile Phase: 0.2% DEA in methanol. CO$_2$ Flow Rate: 1.0 g/min, Co-solvent flow rate; 1.0 g/min, % Co-solvent: 40% (0.2% DEA in MeOH). Total Flow: 4.0 g/min, Back Pressure: 100 bars, Temperature: 30.0° C., UV: 260 nm]. | I: 9.74, 97.4% J: 9.16, 97.9% | 1H NMR (400 MHz, DMSO-d$_6$) δ ppm 12.85 (br. s., 1H) 8.09 (br. s., 1H) 7.94 (br. s., 1H) 7.58-7.66 (m, 2H) 7.18 (dd, J = 8.31, 2.20 Hz, 1H) 6.97 (t, J = 8.07 Hz, 1H) 6.25-6.33 (m, 2H) 6.16 (dd, J = 7.70, 2.08 Hz, 1H) 5.89 (d, J = 6.85 Hz, 1H) 4.37 (dt, J = 9.66, 7.64 Hz, 1H) 3.95 (q, J = 7.09 Hz, 2H) 3.77-3.89 (m, δH) 2.56-2.64 (m, 1H) 1.82-1.95 (m, 1H) 1.30 (t, J = 6.97 Hz, 3H). [α]$_D^{25.0}$ = −40.0 (c 0.05, DMSO). |
| 251 | 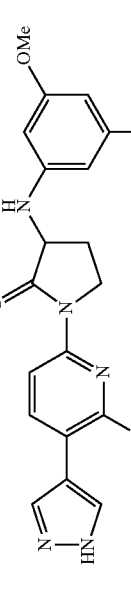<br>3-(3-fluoro-5-methoxyphenyl)amino)-1-(6-(methylamino)-5-(1H-pyrazol-4-yl)pyridin-2-yl)pyrrolidin-2-one | Enantiomer-I | 397.20 | 96.98% ee (rt-4.67 min), [Method: Column: CHIRALPAK @ AS-H (250 × 4.6 mm), 5μ, Mobile Phase: 0.2% DEA in methanol. CO$_2$ Flow Rate: 1.0 g/min, Co-solvent flow rate: 1.0 g/min, % Co-solvent: 30% (0.2% DEA in MeOH). Total Flow: 3.0 g/min, Back Pressure: 100 bars. Temperature: 30.0° C., UV: 220 nm]. | E: 1.29, 100.0% F: 1.63, 100.0% | 1H NMR (400 MHz, DMSO-d$_6$) δ ppm 13.00 (br. s., 1H) 7.95 (br. s., 1H) 7.73 (br. s., 1H) 7.44-7.52 (m, 2H) 6.29 (d, J = 7.34 Hz, 1H) 6.08-6.17 (m, 2H) 6.00 (dt, J = 11.00, 2.20 Hz, 1H) 5.85 (d, J = 4.65 Hz, 1H) 4.41-4.51 (m, 1H) 4.16-4.25 (m, 1H) 3.77-3.88 (m, 1H) 3.69 (s, 3H) 2.84 (d, J = 4.65 Hz, 3H) 2.54-2.61 (m, 1H) 1.75-1.90 (m, 1H). 19F NMR (376 MHz, methanol-d4) d ppm −112.570. [α]$_D^{25.8}$ = +24.0 (c 0.05, DMSO). |

| Ex. | Structure and Name | Chirality | LCMS (M+H)+ | Chiral Purity | HPLC Method, RT (min) & Purity | ¹H NMR |
|---|---|---|---|---|---|---|
| 252 | 3-((3-fluoro-5-methoxyphenyl)amino)-1-(6-(methylamino)-5-(1H-pyrazol-4-yl)pyridin-2-yl)pyrrolidin-2-one | Enantiomer-II | 397.20 | 93.34% ee (rt-5.41 min). [Method: Column: CHIRALPAK @ AS-H (250 × 4.6 mm), 5μ, Mobile Phase: 0.2% DEA in methanol, CO₂ Flow Rate: 1.0 g/min, Co-solvent flow rate: 1.0 g/min, % Co-solvent: 30% (0.2% DEA in MeOH), Total Flow: 3.0 g/min, Back Pressure: 100 bars, Temperature: 30.0° C., UV: 220 nm]. | E: 1.28, 100.0% F: 1.62, 100.0% | ¹H NMR (400 MHz, DMSO-d₆) δ ppm 13.03 (s, 1H) 7.86 (s, 2H) 7.43-7.54 (m, 2H) 6.29 (d, J = 7.34 Hz, 1H) 6.08-6.17 (m, 2H) 5.99 (dt, J = 11.13, 2.26 Hz, 1H) 5.85 (d, J = 4.65 Hz, 1H) 4.41-4.52 (m, 1H) 4.14-4.24 (m, 1H) 3.75-3.87 (m, 1H) 3.69 (s, 3H) 2.84 (d, J = 4.65 Hz, 3H) 2.53-2.61 (m, 1H) 1.75-1.84 (m, 1H). ¹⁹F NMR (376 MHz, methanol-d4) d ppm −112.570. [α]$_D^{25.8}$ = −95.200 (c 0.05, DMSO). |
| 253 | 3-((3-methoxyphenyl)amino)-1-(6-(methylamino)-5-(1H-pyrazol-4-yl)pyridin-2-yl)pyrrolidin-2-one | Enantiomer-I | 379.20 | 92.38% ee (rt-3.31 min). [Method: Column: CHIRALPAK @ AS-H (250 × 4.6 mm), 5μ, Mobile Phase: 0.2% DEA in methanol, CO₂ Flow Rate: 1.0 g/min, Co-solvent flow rate: 1.0 g/min, % Co-solvent: 40% (0.2% DEA in MeOH), Total Flow: 3.0 g/min, Back Pressure: 100 bars, Temperature: 30.0° C., UV: 240 nm]. | E: 1.03, 99.3% F: 1.54, 100% | 1N NMR (400 MHz DMSO-d₆) δ ppm 13.01 (br. s., 1H) 7.95 (br. s., 1H) 7.76 (br. s., 1H) 7.49 (q, J = 8.07 Hz, 2H) 6.94-7.02 (m, 1H) 6.26-6.34 (m, 2H) 6.17 (dd, J = 7.83, 1.96 Hz, 1H) 5.92 (d, J = 7.34 Hz, 1H) 5.80-5.89 (m, 1H) 4.42 (dt, J = 9.96, 7.73 Hz, 1H) 4.20 (t, J = 9.29 Hz, 1H) 3.83 (td, J = 10.52, 6.85 Hz, 1H) 3.68 (s, 3H) 2.85 (d, J = 4.40 Hz, 3H) 2.54-2.61 (m, 1H) 1.78-1.90 (m, 1H). |
| 254 | 3-((3-methoxyphenyl)amino)-1-(6-(methylamino)-5-(1H-pyrazol-4-yl)pyridin-2-yl)pyrrolidin-2-one | Enantiomer-II | 379.20 | 96.34% cc (rt-3.97 min). [Method: Column: CHIRALPAK @ AS-H (250 × 4.6 mm), 5μ, Mobile Phase: 0.2% DEA in methanol, CO₂ Flow Rate: 1.0 g/min, Co-solvent flow rate: 1.0 g/min, % Co-solvent: 40% (0.2% DEA in MeOH), Total Flow: 3.0 g/min, Back Pressure: 100 bars, Temperature: 30.0° C., UV: 240 nm]. | E: 1.17, 98.5% F: 1.55, 94.7% | ¹H NMR (400 MHz DMSO-d₆) δ ppm 13.01 (br. s., 1H) 7.85 (br. s., 2H) 7.49 (q, J = 8.03 Hz, 2H) 6.97-7.02 (m, 1H) 6.26-6.36 (m, 2H) 6.17 (dd, J = 7.78, 2.76 Hz, 1H) 5.91 (br. s., 1H) 5.85 (d, J = 4.52 Hz, 1H) 4.42 (br. s., 1H) 4.15-4.26 (m, 1H) 3.76-3.92 (m, 1H) 3.64-3.70 (m, 3H) 2.84 (d, J = 4.02 Hz, 3H) 2.54-2.61 (m, 1H) 1.78-1.91 (m, 1H). |

TABLE 10-continued

| Ex. | Structure and Name | Chirality | LCMS (M+H)⁺ | Chiral Purity | HPLC Method, RT (min) & Purity | ¹H NMR |
|---|---|---|---|---|---|---|
| 255 | 3-(benzo[d][1,3]dioxol-5-ylamino)-1-(6-methoxy-5-(1H-pyrazol-4-yl)pyridin-2-yl)pyrrolidin-2-one | Racemate | 394.3 | | D: 1.67, 97.7% | ¹H NMR (400 MHz, DMSO-d₆) δ ppm 12.96 (br. s., 1H) 6.69 (d, J = 8.03 Hz, 1H) 6.46 (d, J = 2.01 Hz, 1H) 6.16 (dd, J = 8.28, 2.26 Hz, 1H) 5.86 (s, 2H) 5.69 (d, J = 7.03 Hz, 1H) 4.38 (dt, J = 10.04, 7.53 Hz, 1H) 4.15-4.25 (m, 1H) 4.00 (s, 3H) 3.86 (td, J = 10.42, 6.78 Hz, 1H) 2.58-2.65 (m, 1H) 1.78-1.94 (m, 1H). |
| 256 | 3-((2,3-dihydrobenzo[b][1,4]dioxin-6-yl)amino)-1-(6-methoxy-5-(1H-pyrazol-4-yl)pyridin-2-yl)pyrrolidin-2-one | Racemate | 408.3 | | D: 1.57, 98.3% | ¹H NMR (400 MHz, DMSO-d₆) δ ppm 13.21 (br. s., 1H) 8.41 (br. s., 1H) 8.35 (d, J = 8.31 Hz, 1H) 8.25 (br. s., 1H) 8.17 (d, J = 8.07 Hz, 1H) 6.87 (d, J = 8.31 Hz, 1H) 6.45-6.57 (m, 2H) 5.81 (d, J = 7.09 Hz, 1H) 4.54-4.65 (m, 1H) 4.40-4.51 (m, 3H) 4.34, 4.40 (m, 2H) 4.26 (s, 3H) 4.11 (td, J = 10.33, 6.97 Hz, 1H) 2.80-2.87 (m, 1H) 2.01-2.17 (m, 1H). |
| 257 | 3-((1-(6-methoxy-5-(1H-pyrazol-4-yl)pyridin-2-yl)-2-oxopyrrolidin-3-yl)amino)benzonitrile | Racemate | 375.3 | | D: 1.61, 97.6% | ¹H NMR (400 MHz, DMSO-d₆) δ ppm 13.21 (br. s., 1H) 8.42 (s, 1H) 8.35 (d, J = 8.31 Hz, 1H) 8.26 (s, 1H) 8.15 (d, J = 8.07 Hz, 1H) 7.50-7.59 (m, 1H) 7.33-7.38 (m, 1H) 7.27-7.33 (m, 1H) 7.24 (dt, J = 7.64, 1.07 Hz, 1H) 6.82 (d, J = 7.83 Hz, 1H) 4.88 (dt, J = 10.33, 7.92 Hz, 1H) 4.43-4.55 (m, 1H) 4.27 (s, 3H) 4.12 (td, J = 10.52, 6.85 Hz, 1H) 2.83-2.91 (m, 1H) 2.09-2.24 (m, 1H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 258 | 3-((1-(6-methoxy-5-(1H-pyrazol-4-yl)pyridin-2-yl)-2-oxopyrrolidin-3-yl)amino)benzamide | Racemate | 393.2 | | C: 1.09, 99.6% | 1H NMR (400 MHz, DMSO-d6) δ ppm 13.21 (br. s., 1H) 8.40 (br. s., 1H) 8.35 (d, J = 8.31 Hz, 1H) 8.20-8.32 (m, 1H) 8.13-8.20(m, 1H) 8.04 (br. s., 1H) 7.44-7.52 (m, 2H) 7.38-7.44 (m, 1H) 7.28-7.38 (m, 1H) 7.12 (dd, J = 8.07, 1.47 Hz, 1H) 6.39 (d, J = 7.58 Hz, 1H) 4.82 (dt, J = 10.27, 7.83 Hz, 1H) 4.44-4.54 (m, 1H) 4.27 (s, 3H) 4.14 (td, J = 10.45, 6.72 Hz, 1H) 2.82-2.91 (m, 1H) 2.10-2.24 (m, 1H). |
| 259 | 3-(benzo[d]thiazol-6-ylamino)-1-(6-methoxy-5-(1H-pyrazol-4-yl)pyridin-2-yl)pyrrolidin-2-one | Racemate | 407.2 | | C: 1.40, 93.8% | 1H NMR (400 MHz, DMSO-d6) δ ppm 13.21 (br. s., 1H) 9.21 (s, 1H) 8.41 (br. s., 1H) 8.36 (d, J = 8.31 Hz, 1H) 8.27 (d, J = 8.31 Hz, 1H) 8.18 (d, J = 8.07 Hz, 1H) 8.05 (d, J = 8.80 Hz, 1H) 7.59 (d, J = 2.45 Hz, 1H) 7.26 (dd, J = 8.93, 2.32 Hz, 1H) 6.62 (d, J = 7.34 Hz, 1H) 4.85 (dt, J = 9.90, 7.89 Hz, 1H) 4.47-4.57 (m, 1H) 4.27 (s, 3H) 4.15 (td, J = 10.45, 6.72 Hz, 1H) 2.88-2.93 (m, 1H) 2.11-2.28 (m, 1H). |
| 260 | N-(3-((1-(6-methoxy-5-(1H-pyrazol-4-yl)pyridin-2-yl)-2-oxopyrrolidin-3-yl)amino)phenyl)acetamide | Racemate | 407.3 | | D: 1.28, 96.4% | 1H NMR (400 MHz, DMSO-d6) δ ppm 9.94 (s, 1H) 8.28-8.41 (m, 3H) 8.18 (d, J = 8.07 Hz, 1H) 7.29 (s, 1H) 7.21-7.27 (m, 1H) 7.05 (d, J = 8.07 Hz, 1H) 6.68 (dd, J = 8.07, 1.71 Hz, 1H) 4.66 (t, J = 9.17 Hz, 1H) 4.44-4.52 (m, 1H) 4.26 (s, 3H) 4.14 (td, J = 10.33, 6.72 Hz, 1H) 2.81-2.88 (m, 2H) 2.24-2.33 (m, 3H) 2.11-2.23 (m, 1H). |
| 261 | 3-((2-chloro-5-methoxyphenyl)amino)-1-(6-methoxy-5-(1H-pyrazol-4-yl)pyridin-2-yl)pyrrolidin-2-one | Racemate | 414.2 | | C: 1.93, 97.7% | 1H NMR (400 MHz, DMSO-d6) δ ppm 13.21 (br. s., 1H) 8.36 (d, J = 8.07 Hz, 2H) 8.28 (br. s., 1H) 8.18 (d, J = 8.07 Hz, 1H) 7.45 (d, J = 8.56 Hz, 1H) 6.71 (d, J = 2.69 Hz, 1H) 6.53 (dd, J = 8.68, 2.81 Hz, 1H) 5.79 (d, J = 7.09 Hz, 1H) 4.90 (dt, J = 10.52, 7.83 Hz, 1H) 4.50 (t, J = 9.54 Hz, 1H) 4.27 (s, 3H) 4.12 (td, J = 10.58, 6.72 Hz, 1H) 3.98 (s, 3H) 2.88 (dt, J = 11.49, 7.46 Hz, 1H) 2.25-2.38 (m, 1H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 262 | 1-(6-methoxy-5-(1H-pyrazol-4-yl)pyridin-2-yl)-3-((3-(oxazol-5-yl)phenyl)amino)pyrrolidin-2-one | Racemate | 417.2 | | D: 1.58, 97.9% | 1H NMR (400 MHz, DMSO-d6) δ ppm 13.21 (br. s., 1H) 8.66 (s, 1H) 8.35 (d, J = 8.31 Hz, 3H) 8.17 (d, J = 8.31 Hz, 1H) 7.83 (s, 1H) 7.41-7.51 (m, 1H) 7.34 (t, J = 1.83 Hz, 1H) 7.22 (d, J = 8.07 Hz, 1H) 7.00 (dd, J = 7.95, 1.83 Hz, 1H) 6.48 (d, J = 7.58 Hz, 1H) 4.86 (dt, J = 10.09, 7.92 Hz, 1 H) 4.43-4.54 (m, 1H) 4.27 (s, 3H) 4.15 (td, J = 10.33, 6.72 Hz, 1H) 2.84-2.92 (m, 1H) 2.13-2.26 (m, 1H). |
| 263 | 3-((2,2-dioxido-1,3-dihydrobenzo[c]thiophen-5-yl)amino)-1-(6-methoxy-5-(1H-pyrazol-4-yl)pyridin-2-yl)pyrrolidin-2-one | Racemate | 440.2 | | D: 1.33, 95.6% | 1H NMR (400 MHz, DMSO-d6) δ ppm 13.21 (br. s., 1H) 8.41 (br. s., 1 H) 8.35 (d, J = 8.31 Hz, 1H) 8.25 (br. s., 1H) 8.17 (d, J = 8.07 Hz, 1H) 7.35 (d, J = 8.31 Hz, 1H) 6.91-7.02 (m, 2 H) 6.48 (d, J = 7.58 Hz, 1H) 4.72-4.83 (m, 1H) 4.62 (s, 2H) 4.56 (s, 2 H) 4.40-4.52 (m, 1H) 4.26 (s, 3H) 4.13 (td, J = 10.45, 6.72 Hz, 1H) 2.83-2.91 (m, 1H) 2.08-2.24 (m, 1H). |
| 264 | 1-(6-methoxy-5-(1H-pyrazol-4-yl)pyridin-2-yl)-3-((3-(morpholinosulfonyl)phenyl)amino)pyrrolidin-2-one | Racemate | 499.3 | | D: 1.52, 96.6% | 1H NMR (400 MHz, DMSO-d6) δ ppm 13.21 (br. s., 1H) 8.41 (br. s., 1 H) 8.35 (d, J = 8.31 Hz, 1H) 8.26 (br. s., 1H) 8.15 (d, J = 8.07 Hz, 1H) 7.58-7.67 (m, 1H) 7.25-7.35 (m, 2H) 7.16 (dt, J = 7.21, 0.92 Hz, 1H) 6.91 (d, J = 7.58 Hz, 1H) 4.89 (dt, J = 10.09, 8.04 Hz, 1H) 4.43-4.54 (m, 1H) 4.27 (s, 3H) 4.08-4.20 (m, 1H) 3.83-3.97 (m, 4H) 3.06-3.19 (m, 4H) 2.80-2.90 (m, 1H) 2.14-2.29 (m, 1 H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 265 | N-(3-((1-(6-methoxy-5-(1H-pyrazol-4-yl)pyridin-2-yl)-2-oxopyrrolidin-3-yl)amino)phenyl)methanesulfonamide | Racemate | 443.2 | | C: 1.31, 98.4% | 1H NMR (400 MHz, DMSO-d6) δ ppm 13.24 (s, 1H) 9.72 (s, 1H) 8.35 (d, J = 8.07 Hz, 3H) 8.17 (d, J = 8.31 Hz, 1H) 7.47 (s, 1H) 7.35 (s, 1H) 7.29 (t, J = 8.07 Hz, 1H) 7.22 (s, 1H) 6.86 (t, J = 2.20 Hz, 1H) 6.71 (dd, J = 7.46, 1.59 Hz, 1H) 6.74 (dd, J = 7.95, 1.83 Hz, 1H) 6.38 (br. s., 1H) 4.70 (br. s., 1H) 4.43-4.53 (m, 1H) 4.26 (s, 3H) 4.09-4.20 (m, 1H) 3.22 (s, 3H) 2.81-2.89 (m, 1H) 2.09-2.25 (m, 1H). |
| 266 | 3-((3-(1H-tetrazol-5-yl)phenyl)amino)-1-(6-methoxy-5-(1H-pyrazol-4-yl)pyridin-2-yl)pyrrolidin-2-one | Racemate | 418.3 | | C: 1.12, 97.8% | 1H NMR (400 MHz, DMSO-d6) δ ppm 13.25 (br. s., 1H) 8.45 (s, 1H) 8.39 (d, J = 8.07 Hz, 1H) 8.28 (s, 1H) 8.10 (d, J = 8.31 Hz, 1H) 7.60 (t, J = 1.71 Hz, 1H) 7.39-7.52 (m, 2H) 6.93-7.00 (m, 1H) 6.64 (dd, J = 10.03, 9.05 Hz, 1H) 5.66 (s, 2H) 4.66-4.76 (m, 1H) 4.36 (td, J = 10.03, 7.34 Hz, 1H) 4.23-4.31 (m, 3H) 3.13-3.25 (m, 1H) 2.98-3.06 (m, 1H). |
| 267 | 3-((3-isopropoxyphenyl)amino)-1-(6-methoxy-5-(1H-pyrazol-4-yl)pyridin-2-yl)pyrrolidin-2-one | Racemate | 408.3 | | D: 1.92, 97.9% | 1H NMR (400 MHz, DMSO-d6) δ ppm 13.21 (br. s., 1H) 8.41 (br. s., 1H) 8.35 (d, J = 8.31 Hz, 1H) 8.26 (br. s., 1H) 8.17 (d, J = 8.31 Hz, 1H) 7.17-7.27 (m, 1H) 6.47-6.59 (m, 2H) 6.37-6.46 (m, 1H) 6.17 (d, J = 7.34 Hz, 1H) 4.66-4.82 (m, 2H) 4.42-4.52 (m, 1H) 4.21-4.31 (m, 3H) 4.12 (td, J = 10.39, 6.85 Hz, 1H) 2.80-2.89 (m, 1H) 2.06-2.21 (m, 1H) 1.45-1.55 (m, δH). |

| Ex. | Structure and Name | Chirality | LCMS (M+H)+ | Chiral Purity | HPLC Method, RT (min) & Purity | 1H NMR |
|---|---|---|---|---|---|---|
| 268 | 3-((1-(6-methoxy-5-(1H-pyrazol-4-yl)pyridin-2-yl)-2-oxopyrrolidin-3-yl)amino)benzenesulfonamide | Racemate | 429.2 | | D: 1.21, 99.2% | 1H NMR (400 MHz, DMSO-d6) δ ppm 8.34 (t, J = 8.56 Hz, 7H) 8.17 (d, J = 8.07 Hz, 1H) 8.12 (d, J = 8.31 Hz, 1H) 7.50-7.57 (m, 1H) 7.44-7.49 (m, 1H) 7.43 (t, J = 2.08 Hz, 1H) 7.26-7.34 (m, 2H) 7.21-7.26 (m, 1H) 7.17 (dd, J = 7.95, 2.08 Hz, 1H) 6.98-7.05 (m, 1H) 6.75 (d, J = 7.83 Hz, 1H) 5.83 (s, 2H) 4.80-4.88 (m, 2H) 4.51 (dd, J = 11.37, 3.06 Hz, 2H) 4.31-4.36 (m, 2H) 4.27 (s, 4H) 4.21 (s, 4H) 4.11-4.18 (m, 4H) 3.96 (dd, J = 10.39, 4.03 Hz, δH) 2.84 (br. s., 2H) 2.38 (s, 1H) 2.20 (d, J = 9.54 Hz, 1H) 2.14 (s, 15H) 1.93-2.03 (m, 1 H). |
| 269 | 3-((4-(tert-butyl)thiazol-2-yl)amino)-1-(6-methoxy-5-(1H-pyrazol-4-yl)pyridin-2-yl)pyrrolidin-2-one | Racemate | 413.3 | | C: 1.26, 94.9% | 1H NMR (400 MHz, DMSO-d6) δ ppm 8.28-8.42 (m, 3H) 8.14 (d, J = 8.07 Hz, 1H) 6.52 (br. s., 1H) 4.87 (br. s., 2H) 4.50 (t, J = 9.29 Hz, 2H) 4.26 (s, 4H) 4.16 (td, J = 10.15, 7.34 Hz, 2H) 2.34-2.46 (m, 1H) 1.43 (s, 9H). |
| 270 | 3-((1,3-dimethyl-1H-pyrazol-5-yl)amino)-1-(6-methoxy-5-(1H-pyrazol-4-yl)pyridin-2-yl)pyrrolidin-2-one | Racemate | 368.3 | | C: 0.88, 97.9% | 1H NMR (400 MHz, DMSO-d6) δ ppm 12.96 (br. s., 1H) 8.16 (s, 1H) 8.10 (d, J = 8.03 Hz, 1H) 8.00 (br. s., 1H) 7.92 (d, J = 8.53 Hz, 1H) 5.79 (d, J = 8.03 Hz, 1H) 5.24 (s, 1H) 4.15-4.33 (m, 2H) 3.96-4.05 (m, 3H) 3.83 (td, J = 10.29, 7.03 Hz, 1H) 3.48 (s, 3H) 1.87-2.02 (m, 4H). |

TABLE 10-continued

| Ex. | Structure and Name | Chirality | LCMS (M+H)+ | Chiral Purity | HPLC Method, RT (min) & Purity | ¹H NMR |
|---|---|---|---|---|---|---|
| 271 | 3-((1,5-dimethyl-1H-pyrazol-3-yl)amino)-1-(6-methoxy-5-(1H-pyrazol-4-yl)pyridin-2-yl)pyrrolidin-2-one | Racemate | 368.3 | | C: 0.97, 98.6% | ¹H NMR (400 MHz, DMSO-d₆) δ ppm 13.20 (br. s., 1H) 8.40 (s, 1H) 8.33 (d, J = 8.07 Hz, 1H) 8.25 (s, 1H) 8.17 (d, J = 8.31 Hz, 1H) 5.53-5.67 (m, 2H) 4.51-4.63 (m, 1H) 4.44 (t, J = 9.29 Hz, 1H) 4.25 (s, 3H) 4.07 (td, J = 10.52, 6.85 Hz, 1H) 3.75 (s, 3H) 2.38 (s, 3H) 2.12-2.24 (m, 1H). |
| 272 | 3-((1-isopropyl-1H-pyrazol-4-yl)amino)-1-(6-methoxy-5-(1H-pyrazol-4-yl)pyridin-2-yl)pyrrolidin-2-one | Racemate | 382.2 | | D: 1.25, 95.3% | ¹H NMR (400 MHz, DMSO-d₆) δ ppm 13.21 (br. s., 1H) 8.41 (br. s., 1 H) 8.34 (d, J = 8.07 Hz, 1H) 8.25 (br. s., 1H) 8.17 (d, J = 8.31 Hz, 1H) 7.50 (s, 1H) 7.31 (d, J = 0.73 Hz, 1H) 5.01 (d, J = 5.62 Hz, 1H) 4.59 (dt, J = 13.39, 6.63 Hz, 1H) 4.38-4.48 (m, 1H) 4.20-4.31 (m, 4H) 4.02-4.15 (m, 1H) 2.07-2.20 (m, 1H) 1.62 (d, J = 6.85 Hz, 6H). |
| 273 | 1-(6-methoxy-5-(1H-pyrazol-4-yl)pyridin-2-yl)-3-morpholinopyrrolidin-2-one | Racemate | 344.2 | | A: 1.15, 98.0% | ¹H NMR (400 MHz, DMSO-d₆) δ ppm 12.95 (br. s., 1H) 8.15 (s, 1H) 8.05-8.10 (m, 1H) 7.99 (s, 1H) 7.91 (d, J = 8.53 Hz, 1H) 4.07-4.15 (m, 1 H) 3.98 (s, 3H) 3.75-3.84 (m, 1H) 3.67 (t, J = 9.04 Hz, 1H) 3.60 (t, J = 4.77 Hz, 4H) 2.83-2.92 (m, 2H) 2.15-2.25 (m, 1H) 2.01-2.09 (m, 1 H). |
| 274 | 1-(6-methoxy-5-(1H-pyrazol-4-yl)pyridin-2-yl)-3-((R)-3-methylmorpholino)pyrrolidin-2-one | Racemate | 358.2 | | A: 1.45, 97.0% | ¹H NMR (400 MHz, DMSO-d₆) δ ppm 12.95 (br. s., 1H) 8.15 (s, 1H) 8.07 (d, J = 8.03 Hz, 1H) 7.99 (s, 1H) 7.92 (d, J = 8.03 Hz, 1H) 4.08-4.19 (m, 2H) 3.98 (s, 3H) 3.76-3.86 (m, 1H) 3.62-3.75 (m, 2H) 3.50 (t, J = 9.29 Hz, 1H) 3.14 (t, J = 10.04 Hz, 1H) 1.97-2.19 (m, 2H) 0.97 (d, J = 6.02 Hz, 3H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 275 | 3-(2,6-dimethylmorpholino)-1-(6-methoxy-5-(1H-pyrazol-4-yl)pyridin-2-yl)pyrrolidin-2-one | Racemate | 372.2 | | A: 1.58, 98.2% | 1H NMR (400 MHz, DMSO-d6) δ ppm 12.95 (br. s., 1H) 8.15 (s, 1H) 8.07 (d, J = 8.03 Hz, 1H) 7.99 (s, 1H) 7.91 (d, J = 8.03 Hz, 1H) 4.10 (t, J = 9.04 Hz, 1H) 3.98 (s, 3H) 3.76-3.85 (m, 1H) 3.68 (t, J = 9.04 Hz, 1H) 3.56 (d, J = 8.03 Hz, 2H) 2.94 (d, J = 10.54 Hz, 1H) 2.64 (d, J = 10.54 Hz, 1H) 2.39 (t, J = 10.54 Hz, 1H) 2.13-2.24 (m, 1H) 1.96-2.09 (m, 2H) 1.24 (s, 1H) 1.06 (d, J = 5.02 Hz, 6H). |
| 276 | 3-(4-(dimethylamino)piperidin-1-yl)-1-(6-methoxy-5-(1H-pyrazol-4-yl)pyridin-2-yl)pyrrolidin-2-one | Racemate | 385.3 | | A: 0.84, 95.8% | 1H NMR (400 MHz, chloroform-d) δ ppm 7.56-7.66 (m, 2H) 7.44-7.55 (m, 2H) 6.58 (d, J = 8.53 Hz, 1H) 6.49 (d, J = 2.51 Hz, 1H) 6.36-6.45 (m, 1H) 4.74 (br. s., 1H) 4.07 (dd, J = 9.79, 7.78 Hz, 1H) 3.80-3.90 (m, 5H) 3.77 (s, 3H) 2.82 (dddd, J = 12.49, 8.09, 6.02, 2.01 Hz, 1H) 2.00-2.15 (m, 1H). |
| 277 | 3-(3,4-dihydroisoquinolin-2(1H)-yl)-1-(6-methoxy-5-(1H-pyrazol-4-yl)pyridin-2-yl)pyrrolidin-2-one | Racemate | 390.3 | | A: 1.79, 96.3% | 1H NMR (400 MHz, DMSO-d6) δ ppm 12.96 (br. s., 1H) 8.16 (s, 1H) 8.08 (d, J = 8.03 Hz, 1H) 8.00 (s, 1H) 7.94 (d, J = 8.03 Hz, 1H) 7.02-7.19 (m, 6H) 4.18 (t, J = 9.29 Hz, 1H) 4.06 (d, J = 14.56 Hz, 1H) 4.00 (s, 4H) 3.93 (t, J = 9.04 Hz, 1H) 3.81-3.89 (m, 1H) 3.75 (d, J = 15.06 Hz, 1H) 3.06-3.17 (m, 1H) 2.83 (br. s., 3H) 2.28 (d, J = 9.04 Hz, 3H) 2.11-2.21 (m, 1H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 278 | 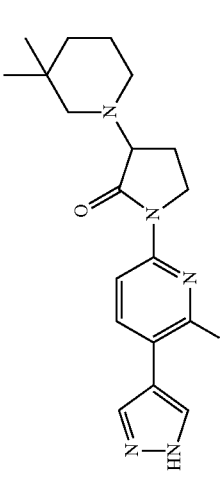<br>3-(3,3-dimethylpiperidin-1-yl)-1-(6-methoxy-5-(1H-pyrazol-4-yl)pyridin-2-yl)pyrrolidin-2-one | Racemate | 370.3 | | A: 2.02, 97.9% | 1H NMR (400 MHz, DMSO-d6) δ ppm 12.95 (br. s., 1H) 8.14 (br. s., 1 H) 8.06 (d, J = 8.53 Hz, 1H) 7.99 (br. s., 1H) 7.92 (d, J = 8.53 Hz, 1H) 4.05-4.14 (m, 1H) 3.98 (s, 3H) 3.74-3.82 (m, 1H) 3.68 (t, J = 9.04 Hz, 1H) 2.75-2.80 (m, 1H) 2.43 (d, J = 11.04 Hz, 3H) 2.12-2.22 (m, 2H) 1.94-2.04 (m, 1H) 1.53 (br. s., 2H) 1.18-1.26 (m, 3H) 0.93 (s, 6H). |
| 279 | 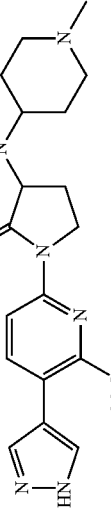<br>1-(6-methoxy-5-(1H-pyrazol-4-yl)pyridin-2-yl)-3-(methyl(1-methylpiperidin-4-yl)amino)pyrrolidin-2-one | Racemate | 385.3 | | A: 0.88, 93.2% | |
| 280 | 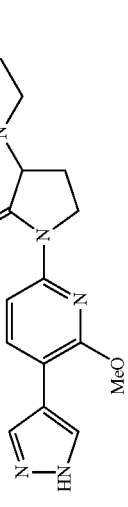<br>3-(1,1-dioxidothiomorpholino)-1-(6-methoxy-5-(1H-pyrazol-4-yl)pyridin-2-yl)pyrrolidin-2-one | Racemate | 392.1 | | A: 1.26, 95.7% | 1H NMR (400 MHz, DMSO-d6) δ ppm 8.08 (d, J = 8.53 Hz, 3H) 7.91 (d, J = 8.03 Hz, 1H) 3.12 (br. s., 4H) 3.06 (s, 2H) 2.27 (s, 1H) 2.05 (s, 1 H) 1.24 (s, 3H) 0.86 (s, 1H). |

| Ex. | Structure and Name | Chirality | LCMS (M+H)+ | Chiral Purity | HPLC Method, RT (min) & Purity | 1H NMR |
|---|---|---|---|---|---|---|
| 281 | 3-(2,3-dihydro-1H-pyrrolo[2,3-b]pyridin-1-yl)-1-(6-methoxy-5-(1H-pyrazol-4-yl)pyridin-2-yl)pyrrolidin-2-one | Racemate | 377.2 | | B: 0.85, 98.4% | 1H NMR (400 MHz, DMSO-d6) δ ppm 12.96 (br. s., 1H) 8.16 (br. s., 1H) 8.08 (d, J = 8.03 Hz, 1H) 8.00 (br. s., 1H) 7.90 (d, J = 8.03 Hz, 1H) 7.75 (d, J = 5.02 Hz, 1H) 7.30 (d, J = 6.02 Hz, 1H) 6.43-6.53 (m, 1H) 5.16 (t, J = 10.04 Hz, 1H) 4.22-4.31 (m, 1H) 4.01 (s, 3H) 3.84-3.91 (m, 1H) 3.65 (d, J = 7.53 Hz, 1H) 3.43 (d, J = 8.53 Hz, 1H) 3.01 (d, J = 8.53 Hz, 2H) 2.26-2.32 (m, 2H). |
| 282 | 3-(4,4-difluoropiperidin-1-yl)-1-(6-methoxy-5-(1H-pyrazol-4-yl)pyridin-2-yl)pyrrolidin-2-one hydrochloride | Racemate | 378.1 | | B: 1.13, 98.8% | 1H NMR (400 MHz, DMSO-d6) δ ppm 12.95 (br. s., 1H) 8.15 (s, 1H) 8.07 (d, J = 8.53 Hz, 1H) 7.99 (s, 1H) 7.91 (d, J = 8.53 Hz, 1H) 4.13 (t, J = 9.04 Hz, 1H) 3.95-4.02 (m, 3H) 3.74-3.89 (m, 2H) 2.98 (dt, J = 11.67, 5.46 Hz, 2H) 2.65 (d, J = 5.52 Hz, 1H) 2.16-2.27 (m, 1H) 1.88-2.09 (m, 8H). |
| 283 | 3-(3-fluoropiperidin-1-yl)-1-(6-methoxy-5-(1H-pyrazol-4-yl)pyridin-2-yl)pyrrolidin-2-one hydrochloride | Racemate | 360.1 | | B: 0.97, 96.3% | 1H NMR (400 MHz, DMSO-d6) δ ppm 12.95 (br. s., 1H) 8.15 (s, 1H) 8.07 (d, J = 8.03 Hz, 1H) 7.99 (s, 1H) 7.92 (dd, J = 8.03, 2.51 Hz, 1H) 4.69 (br. s., 1H) 4.58 (br. s., 1H) 4.05-4.17 (m, 1H) 3.98 (s, 3H) 3.72-3.84 (m, 2H) 2.78-2.89 (m, 1H) 2.73 (br. s., 1H) 2.42 (br. s., 2H) 2.18 (br. s., 1H) 1.99-2.10 (m, 1H) 1.83 (br. s., 1H) 1.71 (br. s., 1H) 1.52 (d, J = 13.55 Hz, 2H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 284 | 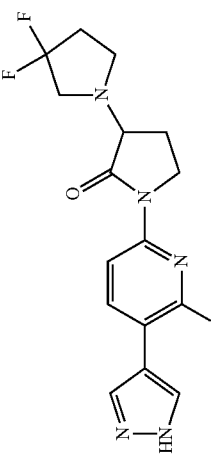<br>3,3-difluoro-1'-(6-methoxy-5-(1H-pyrazol-4-yl)pyridin-2-yl)-[1,3'-bipyrrolidin]-2'-one hydrochloride | Racemate | 364.2 | | A: 1.46, 95.3% | 1H NMR (400 MHz, DMSO-d6) δ ppm 12.96 (br. s., 1H) 8.12 (s, 1H) 8.08 (d, J = 8.03 Hz, 1H) 8.00 (br. s., 1H) 7.88 (d, J = 8.53 Hz, 1H) 4.07-4.18 (m, 1H) 3.95-4.02 (m, 3H) 3.77-3.87 (m, 1H) 3.60-3.68 (m, 1H) 3.40-3.47 (m, 1H) 3.05-3.15 (m, 1H) 3.00 (dd, J = 15.06, 11.04 Hz, 1H) 2.84-2.92 (m, 1H) 2.27 (td, J = 15.44, 7.78 Hz, 3H) 2.02 (dd, J = 12.30, 9.79 Hz, 1H). |
| 285 | 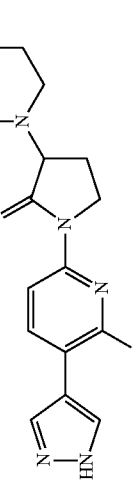<br>1-(6-methoxy-5-(1H-pyrazol-4-yl)pyridin-2-yl)-3-(4-(trifluoromethyl)piperidin-1-yl)pyrrolidin-2-one hydrochloride | Racemate | 410.2 | | A: 1.97, 98.7% | 1H NMR (400 MHz, DMSO-d6) δ ppm 12.95 (br. s., 1H) 8.15 (s, 1H) 8.07 (d, J = 8.03 Hz, 1H) 7.99 (s, 1H) 7.92 (d, J = 8.53 Hz, 1H) 4.11 (t, J = 8.78 Hz, 2H) 3.98 (s, 3H) 3.69-3.86 (m, 2H) 3.10 (d, J = 11.04 Hz, 1H) 2.86 (d, J = 9.04 Hz, 1H) 2.29 (s, 2H) 2.19 (d, J = 9.54 Hz, 1H) 1.97-2.08 (m, 1H) 1.80 (br. s., 2H) 1.37-1.53 (m, 2H). |
| 286 | 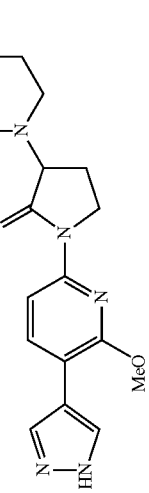<br>1-(6-methoxy-5-(1H-pyrazol-4-yl)pyridin-2-yl)-3-(4-(methylsulfonyl)piperazin-1-yl)pyrrolidin-2-one | Racemate | 421.2 | | A: 1.45, 96.1% | 1H NMR (400 MHz, DMSO-d6) δ ppm 12.95 (br. s., 1H) 8.15 (s, 1H) 8.08 (d, J = 8.03 Hz, 1H) 7.99 (s, 1H) 7.91 (d, J = 8.03 Hz, 1H) 6.54 (s, 2H) 6.30 (s, 1H) 4.09-4.17 (m, 1H) 3.98 (S, 3H) 3.76-3.84 (m, 2H) 3.13 (t, J = 5.02 Hz, 4H) 2.93-3.00 (m, 2H) 2.89 (s, 3H) 2.61-2.66 (m, 2H) 2.16-2.25 (m, 1H) 2.05 (dd, J = 12.55, 9.54 Hz, 1H). |

| Ex. | Structure and Name | Chirality | LCMS (M+H)+ | Chiral Purity | HPLC Method, RT (min) & Purity | ¹H NMR |
|---|---|---|---|---|---|---|
| 287 | 1-(6-methoxy-5-(1H-pyrazol-4-yl)pyridin-2-yl)-3-(4-(4-methoxyphenyl)piperazin-1-yl)pyrrolidin-2-one dihydrochloride | Racemate | 449.3 | | A: 1.63, 99.0% | ¹H NMR (400 MHz, DMSO-d₆) δ ppm 12.95 (br. s., 1H) 8.15 (s, 1H) 8.08 (d, J = 8.53 Hz, 1H) 7.99 (br. s., 1H) 7.93 (d, J = 8.03 Hz, 1H) 6.90 (d, J = 9.54 Hz, 2H) 6.82 (d, J = 9.04 Hz, 2H) 4.13 (br. s., 1H) 3.99 (s, 3H) 3.83 (d, J = 11.04 Hz, 1H) 3.75 (t, J = 9.04 Hz, 1H) 3.69 (s, 3H) 2.94-3.10 (m, 6H) 2.26 (s, 1H) 2.10 (d, J = 8.53 Hz, 1H). |
| 288 | 3-(4-(4-hydroxyphenyl)piperazin-1-yl)-1-(6-methoxy-5-(1H-pyrazol-4-yl)pyridin-2-yl)pyrrolidin-2-one | Racemate | 435.2 | | A: 1.24, 96.5% | ¹H NMR (400 MHz, DMSO-d₆) δ ppm 12.97 (br. s., 1H) 8.81 (s, 1H) 7.97-8.23 (m, 3H) 7.89-7.96 (m, 1H) 6.74-6.85 (m, 2H) 6.60-6.73 (m, 2H) 4.08-4.18 (m, 1H) 3.95-4.02 (m, 3H) 3.77-3.86 (m, 1H) 3.74 (t, J = 9.04 Hz, 1H) 2.92-3.06 (m, 6H) 2.63-2.67 (m, 1H) 2.16-2.29 (m, 1H) 2.00-2.14 (m, 1H) 1.91 (s, 1H). |
| 289 | 3-(4-(hydroxymethyl)piperidin-1-yl)-1-(6-methoxy-5-(1H-pyrazol-4-yl)pyridin-2-yl)pyrrolidin-2-one | Racemate | 372.2 | | A: 1.29, 98.9% | ¹H NMR (400 MHz, DMSO-d₆) δ ppm 12.95 (br. s., 1H) 8.15 (s, 1H) 8.06 (d, J = 8.53 Hz, 1H) 7.99 (s, 1H) 7.92 (d, J = 8.03 Hz, 1H) 7.01 (br. s., 1H) 6.53 (s, 1H) 6.30 (s, 1H) 4.41 (t, J = 5.52 Hz, 1H) 4.10 (t, J = 8.53 Hz, 1H) 3.98 (s, 3H) 3.25 (t, J = 5.77 Hz, 2H) 2.99 (d, J = 11.55 Hz, 1H) 2.75 (d, J = 11.55 Hz, 1H) 2.56-2.64 (m, 2H) 2.11-2.29 (m, 2H) 1.94-2.10 (m, 1H) 1.64 (br. s., 2H) 1.34 (br. s., 1H) 1.12 (t, J = 12.30 Hz, 2H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 290 | (3S)-3-fluoro-1'-(6-methoxy-5-(1H-pyrazol-4-yl)pyridin-2-yl)-[1,3'-bipyrrolidin]-2'-one hydrochloride | Racemate | 346.2 | | A: 1.49, 97.5% | 1H NMR (400 MHz, DMSO-d6) δ ppm 12.95 (br. s., 1H) 8.15 (br. s., 1 H) 8.07 (d, J = 8.53 Hz, 1H) 7.99 (br. s., 1H) 7.89 (d, J = 8.03 Hz, 1H) 5.30 (d, J = 6.02 Hz, 1H) 5.16 (d, J = 6.53 Hz, 1H) 4.05-4.19 (m, 1H) 3.98 (s, 3H) 3.77-3.91 (m, 1H) 3.52-3.65 (m, 1H) 3.06-3.21 (m, 1H) 2.85-2.99 (m, 1H) 2.69-2.84 (m, 1H) 2.56-2.63 (m, 1H) 2.21-2.32 (m, 1 H) 1.91-2.19 (m, 2H) 1.88 (br. s., 1 H). |
| 291 | 1-(6-methoxy-5-(1H-pyrazol-4-yl)pyridin-2-yl)-3-(4-methoxypiperidin-1-yl)pyrrolidin-2-one hydrochloride | Racemate | 372.2 | | A: 1.51, 98.7% | 1H NMR (400 MHz, DMSO-d6) δ ppm 12.95 (br. s., 1H) 8.15 (br. s., 1 H) 8.07 (d, J = 8.03 Hz, 1H) 7.99 (br. s., 1H) 7.91 (d, J = 8.03 Hz, 1H) 4.10 (t, J = 8.78 Hz, 1H) 3.98 (s, 3H) 3.75-3.85 (m, 1H) 3.71 (t, J = 9.04 Hz, 1 H) 3.23 (s, 3H) 3.12-3.20 (m, 1H) 2.92-3.06 (m, 1H) 2.68-2.76 (m, 2 H) 2.23-2.34 (m, 1H) 2.10-2.22 (m, 1H) 1.94-2.07 (m, 1H) 1.85 (d, J = 10.54 Hz, 2H) 1.42 (dd, J = 8.78. 4.27 Hz, 2H). |
| 292 | 1-(1-(6-methoxy-5-(1H-pyrazol-4-yl)pyridin-2-yl)-2-oxopyrrolidin-3-yl)piperidin-4-one hydrochloridehydrate | Racemate | 356.1 | | B: 1.34, 96.5% | 1H NMR (400 MHz, DMSO-d6) δ ppm 12.96 (br. s., 1H) 8.15 (s, 1H) 8.08 (d, J = 8.03 Hz, 1H) 7.99 (s, 1H) 7.92 (d, J = 8.53 Hz, 1H)4.14(t, J = 9.04 Hz, 1H) 3.98 (s, 3H) 3.93 (t, J = 9.29 Hz, 1H) 3.74-3.86 (m, 1H) 3.15 (dd, J = 11.55, 6.02 Hz, 2H) 2.78-2.92 (m, 2H) 2.38 (t, J = 6.02 Hz, 4 H) 2.19-2.30 (m, 1H) 2.02-2.14 (m, 1H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 293 | (3R)-3-(dimethylamino)-1'-(6-methoxy-5-(1H-pyrazol-4-yl)pyridin-2-yl)-[1,3'-bipyrrolidin]-2'-one | Racemate | 371.2 | | B: 0.79, 98.2% | 1H NMR (400 MHz, DMSO-d6) δ ppm 12.94 (br. s., 1H) 8.07 (d, J = 8.03 Hz, 3H) 7.84-7.93 (m, 1H) 4.12 (t, J = 9.29 Hz, 1H) 3.98 (s, 3H) 3.74 3.88 (m, 1H) 3.56 (td, J = 8.78, 4.02 Hz, 1H) 3.14 (t, J = 8.03 Hz, 1H) 2.84-3.05 (m, 2H) 2.69-2.74 (m, 1H) 2.30 (br. s., 4H) 2.20-2.26 (m, 1H) 1.93-2.07 (m, 2H) 1.92 (s, 1H) 1.69 (d, J = 5.02 Hz, 1H). |
| 294 | N-((3S)-1'-(6-methoxy-5-(1H-pyrazol-4-yl)pyridin-2-yl)-2'-oxo-[1,3'-bipyrrolidin]-3-yl)acetamide | Racemate | 385.2 | | B: 0.90, 98.3% | 1H NMR (400 MHz, DMSO-d6) δ ppm 12.95 (br. s., 1H) 8.15 (s, 1H) 8.07 (d, J = 8.03 Hz, 1H) 7.93-8.03 (m, 2H) 7.89 (d, J = 8.53 Hz, 1H) 4.07 4.24 (m, 2H) 3.98 (s, 3H) 3.83 (d, J = 8.53 Hz, 1H) 3.46-3.60 (m, 1H) 2.99-3.15 (m, 1H) 2.81 (d, J = 6.53 Hz, 2H) 2.45 (d, J = 9.04 Hz, 1H) 2.25 (br. s., 1H) 1.92-2.14 (m, 2H) 1.71-1.85 (m, 3H) 1.56 (br. s., 1H). |
| 295 | (3S)-3-hydroxy-1'-(6-methoxy-5-(1H-pyrazol-4-yl)pyridin-2-yl)-[1,3'-bipyrrolidin]-2'-one | Racemate | 344.2 | | A: 1.18, 95.8% | 1H NMR (400 MHz, DMSO-d6) δ ppm 12.95 (s, 1H) 8.15 (s, 1H) 8.07 (d, J = 8.03 Hz, 1H) 7.99 (s, 1H) 7.89 (d, J = 8.03 Hz, 1H) 4.71 (dd, J = 8.53, 5.02 Hz, 1H) 4.21 (br. s., 1H) 4.08 4.14 (m, 1H) 3.98 (s, 3H) 3.84 (s, 1H) 3.51 (s, 1H) 2.76 (s, 2H) 2.23 (br. s., 2H) 1.90-2.06 (m, 3H) 1.56 (d, J = 15.06 Hz, 1H). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 296 | 3-(4-fluoropiperidin-1-yl)-1-(6-methoxy-5-(1H-pyrazol-4-yl)pyridin-2-yl)pyrrolidin-2-one hydrochloride | Racemate | 360.2 | | B: 0.88, 98.9% | 1H NMR (400 MHz, DMSO-d6) δ ppm 12.95 (br. s., 1H) 8.15 (s, 1H) 8.07 (d, J = 8.03 Hz, 1H) 7.99 (s, 1H) 7.92 (d, J = 8 03 Hz, 1H) 4.75 (br. s., 1H) 4.62 (br. s., 1H) 4.07 4.16 (m. 1H) 3.98 (s, 3H) 3.71-3.83(m.2 H) 2.98 (br. s., 1H) 2.78 (br. s., 2H) 2.44 (br. s., 2H) 2.18(br. s., 1H) 1.96-2.08 (m, 1H) 1.89 (br. s., 2H) 1.72 (br. s., 2H). |
| 297 | 1-(6-(1H-pyrazol-4-yl)pyridin-3-yl)-3-((3-methoxyphenyl)amino)pyrrolidin-2-one | Enantiomer-I | 349.80 | RT = 4.17 min, ee = 99.58%; Co-solvent: 0.2% DEA in methanol, Column: CHIRALCEL @ AS-H (250 × 4.6 mm), 5μ, Sample Well: P2: 1A, Column Temperature: 25, Total Flow: 4, CO2 Flow Rate: 2.4, Co-solvent Flow Rate: 1.6, Co-solvent %: 40, Back Pressure: 102, absorbance at 245 nm. | M: 11.20, 97.7% N: 12.11, 98.0% | 1H NMR (400 MHz, DMSO-d6) δ = 13.05 (br. s., 1H), 8.86 (d, J = 2.0 Hz, 1H), 8.37-8.06 (m, 3H), 7.78-7.67 (m, 1H), 6.99 (t, J = 8.0 Hz, 1H), 6.35-6.25 (m, 2H), 6.23-6.12 (m, 1H), 5.96 (d, J = 7.0 Hz, 1H), 4.40 (td, J = 7.7, 9.7 Hz, 1H), 3.93-3.79 (m, 2H), 3.68 (s, 3H), 2.69-2.57 (m, 1H), 2.00-1.84 (m, 1H); [α]$_D^{25.1}$ = −50.0 (c = 0.1, DMSO). |
| 298 | 1-(6-(1H-pyrazol-4-yl)pyridin-3-yl)-3-((3-methoxyphenyl)amino)pyrrolidin-2-one | Enantiomer-II | 350.20 | RT = 5.3 min, ee = 98.76%; Co-solvent: 0.2% DEA in methanol, Column: CHIRALCEL @ AS-H (250 × 4.6 mm), 5μ, Sample Well: P2: 2A, Column Temperature: 25.4, Total Flow: 4, CO2 Flow Rate: 2.4, Co-solvent Flow Rate: 1.6, Co-solvent %: 40, Back Pressure: 99, absorbance at 245 nm. | M: 11.21, 99.7% N: 12.13, 99.6% | 1H NMR (400 MHz, DMSO-d6) δ = 13.03 (br. s., 1H), 8.86 (d, J = 2.5 Hz, 1H), 8.21-8.06 (m, 3H), 7.73 (d, J = 8.5 Hz, 1H), 6.99 (t, J = 8.0 Hz, 1H), 6.35-6.24 (m, 2H), 6.22-6.12 (m, 1H), 5.96 (d, J = 7.0 Hz, 1H), 4.46-4.33 (m, 1H), 3.94-3.79 (m, 2H), 3.68 (s, 3H), 2.69-2.56 (m, 1H), 2.00-1.84 (m, 1H); [α]$_D^{25.2}$ = +42.0 (c = 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 299 | 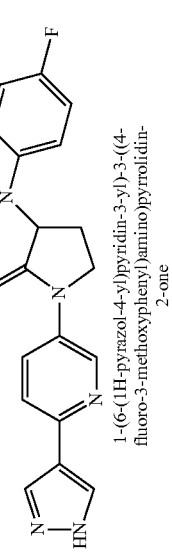<br>1-(6-(1H-pyrazol-4-yl)pyridin-3-yl)-3-((4-fluoro-3-methoxyphenyl)amino)pyrrolidin-2-one | Enantiomer-I | 368.00 | RT = 3.75 min, ee = 100%; Co-solvent: 0.2% DEA in methanol, Column: CHIRALCEL ® AS-H (250 × 4.6 mm), 5μ, Sample Well: P2: 3A, Column Temperature: 24.6, Total Flow: 4, CO2 Flow Rate: 2.4, Co-solvent Flow Rate: 1.6, Co-solvent %: 40, Back Pressure: 97, absorbance at 271 nm. | M: 11.70, 97.0%<br>N: 12.57, 98.4% | 1H NMR (400 MHz, DMSO-d6) δ = 13.02 (br. s., 1H), 8.86 (d, J = 2.5 Hz, 1H), 8.24-8.04 (m, 3H), 7.73 (d, J = 8.5 Hz, 1H), 6.92 (dd, J = 9.0, 11.5 Hz, 1H), 6.53 (dd, J = 2.5, 7.5 Hz, 1H), 6.25-6.15 (m, 1H), 5.88 (d, J = 7.0 Hz, 1H), 4.45-4.31 (m, 1H), 3.94-3.80 (m, 2H), 3.77 (s, 3H), 2.70-2.58 (m, 1H), 1.99-1.83 (m, 1H); 19F NMR (400 MHz, DMSO-d6) δ = −150.827; [α]25.2 D = −28.400 (c = 0.1, DMSO). |
| 300 | 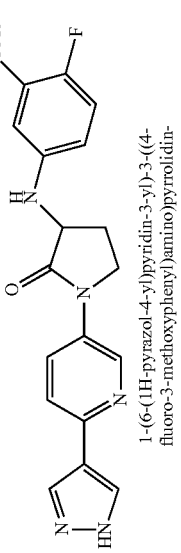<br>1-(6-(1H-pyrazol-4-yl)pyridin-3-yl)-3-((4-fluoro-3-methoxyphenyl)amino)pyrrolidin-2-one | Enantiomer-II | 368.00 | RT = 5.88 min, ee = 99.36%; Co-solvent: 0.2% DEA in methanol, Column: CHIRALCEL ® AS-H (250 × 4.6 mm), 5μ, Sample Well: P2: 4A, Column Temperature: 25.2, Total Flow: 4, CO2 Flow Rate: 2.4, Co-solvent Flow Rate: 1.6, Co-solvent %: 40, Back Pressure: 97, absorbance at 271 nm. | M: 11.70, 97.0%<br>N: 12.57, 98.4% | 1H NMR (400 MHz, DMSO-d6) δ = 13.05 (br. s., 1H), 8.85 (d, J = 3.0 Hz, 1H), 8.26-8.03 (m, 3H), 7.73 (d, J = 8.5 Hz, 1H), 6.97-6.86 (m, 1H), 6.53 (dd, J = 2.5, 7.5 Hz, 1H), 6.21 (td, J = 3.0, 9.0 Hz, 1H), 5.88 (d, J = 7.0 Hz, 1H), 4.39 (dd, J = 7.7, 9.7 Hz, 1H), 3.93-3.79 (m, 2H), 3.77 (s, 3H), 2.70-2.57 (m, 1H), 1.98-1.84 (m, 1H); 19F NMR (400 MHz, DMSO-d6) δ = −150.824; [α]24.9 D = +62.0 (c = 0.1, DMSO). |
| 301 | 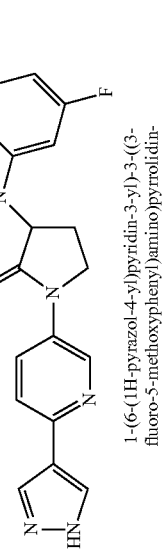<br>1-(6-(1H-pyrazol-4-yl)pyridin-3-yl)-3-((3-fluoro-5-methoxyphenyl)amino)pyrrolidin-2-one | Enantiomer-I | 367.90 | RT = 5.8 min, ee = 98.82%; Co-solvent: 0.2% DEA in methanol, Column: CHIRALCEL ® OD-H (4.6 × 250 mm), 5μ, Sample Well: P2: 5A, Column Temperature: 24.8, Total Flow: 4, CO2 Flow Rate: 2.4, Co-solvent Flow Rate: 1.6, Co-solvent %: 40, Back Pressure: 104, absorbance at 271 nm. | M: 12.73, 99.6%<br>N: 13.51, 99.3% | 1H NMR (400 MHz, DMSO-d6) δ = 13.04 (br. s., 1H), 8.85 (d, J = 2.5 Hz, 1H), 8.32-8.03 (m, 3H), 7.73 (d, J = 8.5 Hz, 1H), 6.32 (d, J = 7.5 Hz, 1H), 6.18-6.07 (m, 2H), 6.05-5.94 (m, 1H), 4.52-4.37 (m, 1H), 3.94-3.77 (m, 2H), 3.73-3.64 (m, 3H), 2.69-2.58 (m, 1H), 1.99-1.85 (m, 1H); 19F NMR (400 MHz, DMSO-d6) δ = −112.517; [α]25 D = +49.200 (c = 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 302 | 1-(6-(1H-pyrazol-4-yl)pyridin-3-yl)-3-((3-fluoro-5-methoxyphenyl)amino)pyrrolidin-2-one | Enantiomer-II | 367.90 | RT = 9.89 min, ee = 98.12%; Co-solvent: 0.2% DEA in methanol, Column: CHIRALCEL @ OD-H (4.6 × 250 mm), 5µ, Sample Well: P2: 6A, Column Temperature: 24.8, Column Flow: 4, CO₂ Flow Rate: 2.4, Co-solvent Flow Rate: 1.6, Co-solvent %: 40, Back Pressure: 104, absorbance at 271 nm. | M: 12.73, 99.7% N: 13.5, 99.6% | $^1$H NMR (400 MHz, DMSO-d$_6$) δ = 13.05 (br. s., 1H), 8.85 (d, J = 2.0 Hz, 1H), 8.25-8.03 (m, 3H), 7.73 (d, J = 9.0 Hz, 1H), 6.32 (d, J = 7.5 Hz, 1H), 6.18-6.07 (m, 2H), 6.00 (td, J = 2.3, 11.0 Hz, 1H), 4.50-4.37 (m, 1H), 3.93-3.78 (m, 2H), 3.69 (s, 3H), 2.70-2.57(m, 1H), 1.99-1.87 (m, 1H); $^{19}$F NMR (400 MHz, DMSO-d6) δ = -112.522; [α]$_D^{25.1}$ = -54.800 (c = 0.1, DMSO). |
| 303 | 1-(5-(1H-pyrazol-4-yl)pyridin-2-yl)-3-((2-fluoro-5-methoxyphenyl)amino)pyrrolidin-2-one | Enantiomer-II | 367.80 | RT = 6.36 min, ee = 99.74%; Co-solvent: 0.2% DEA in methanol, Column: CHIRALPAK @ IC (250 × 4.6 mm), 5µ, Sample Well: P1: ID, Column Temperature: 24.6, Total Flow: 4, CO₂ Flow Rate: 2.4, Co-solvent Flow Rate: 1.6, Co-solvent %: 40, Back Pressure: 100, absorbance at 265 nm. | I: 8.94, 98.4%; J: 8.28, 98.8% | $^1$H NMR (400 MHz, DMSO-d$_6$) δ = 12.95 (br. s., 1H), 8.71 (d, J = 2.0 Hz, 1H), 8.31-8.29 (m, 1H), 8.17-7.96 (m, 3H), 6.95 (dd, J = 11.5, 8.5 Hz, 1H), 6.46 (dd, J = 7.5, 3.0 Hz, 1H), 6.13 (dt, J = 8.9, 3.1 Hz, 1H), 5.73 (d, J = 6.0 Hz, 1H), 4.67-4.52 (m, 1H), 4.22-4.04 (m, 1H), 3.82 (td, J = 10.3, 6.5 Hz, 1H), 3.68 (s, 3H), 2.63-2.54 (m, 1H), 2.14-1.96 (m, 1H); $^{19}$F NMR (400 MHz, DMSO-d$_6$) δ = -144.137; [α]$_D^{25}$ = +82.0 (c = 0.1, DMSO). |
| 304 | 1-(5-(1H-pyrazol-4-yl)pyridin-2-yl)-3-((2-fluoro-5-methoxyphenyl)amino)pyrrolidin-2-one | Enantiomer-II | 367.80 | RT = 8.07 min, ee = 99.26%; Co-solvent: 0.2% DEA in methanol, Column: CHIRALPAK @ IC (250 × 4.6 mm), 5µ, Sample Well: P1: 2D, Column Temperature: 24.6, Total Flow: 4, CO₂ Flow Rate: 2.4, Co-solvent Flow Rate: 1.6, Co-solvent %: 40, Back Pressure: 100, absorbance at 265 nm. | I: 8.94, 98.4%; J: 8.28, 98.8% | $^1$H NMR (400 MHz, DMSO-d$_6$) δ = 13.04 (br. s., 1H), 8.71 (d, J = 2.0 Hz, 1H), 8.37-8.21 (m, 2H), 8.11-7.93 (m, 2H), 6.95 (dd, J = 11.5, 8.5 Hz, 1H), 6.46 (dd, J = 7.5, 3.0 Hz, 1H), 6.13 (dt, J = 8.9, 3.1 Hz, 1H), 5.73 (dd, J = 8.3, 2.3 Hz, 1H), 4.68-4.52 (m, 1H), 4.14 (t, J = 9.3 Hz, 1H), 3.89-3.74 (m, 1H), 3.68 (s, 3H), 2.63-2.54 (m, 1H), 2.14-1.98 (m, 1H); 9F $^1$H NMR (400 MHz, DMSO-d$_6$) δ = -144.137; [α]$_D^{25}$ = -368.400 (c = 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 305 | 1-(2,3-difluoro-4-(1H-pyrazol-4-yl)phenyl)-3-((3-methoxyphenyl)amino)pyrrolidin-2-one | Enantiomer-I | 385.20 | RT = 10.0 min, ee = 99.68%; Co-solvent: 0.2% DEA in methanol, Column: CHIRALPAK ® AS-H (250 × 4.6 mm), 5μ, Sample Well: P1: 1C, Column Temperature: 24.2, Total Flow: 3, CO2 Flow Rate: 2.1, Co-solvent Flow Rate: 0.9, Co-solvent %: 30, Back Pressure: 99, absorbance at 260 nm. | I: 9.27, 99.1% J: 8.75, 99.3% | 1H NMR (400 MHz, DMSO-d6) δ = 13.22 (br. s., 1H), 8.12 (br. s., 2H), 7.62 (td, J = 8.3, 2.0 Hz, 1H), 7.34 (ddd, J = 8.8, 7.0, 1.8 Hz, 1H), 6.99 (t, J = 8.0 Hz, 1H), 6.36-6.25 (m, 2H), 6.22-6.12 (m, 1H), 5.96 (d, J = 7.0 Hz, 1H), 4.37 (dt, J = 9.7, 7.7 Hz, 1H), 3.92-3.73 (m, 2H), 3.69 (s, 3H), 2.72-2.57 (m, 1H), 2.09-1.91 (m, 1H); 19F NMR (400 MHz, DMSO-d6) δ = −140.035, −143.530; [α]$^{25}_D$ = +34.0 (c = 0.1, DMSO) |
| 306 | 1-(2,3-difluoro-4-(1H-pyrazol-4-yl)phenyl)-3-((3-methoxyphenyl)amino)pyrrolidin-2-one | Enantiomer-II | 385.20 | RT = 11.53 min, ee = 99.44%; Co-solvent: 0.2% DEA in methanol, Column: CHIRALPAK ® AS-H (250 × 4.6 mm), 5μ, Sample Well: P1: 2C, Column Temperature: 24.3, Total Flow: 3, CO2 Flow Rate: 2.1, Co-solvent Flow Rate: 0.9, Co-solvent %: 30, Back Pressure: 99, absorbance at 260 nm. | I: 9.26, 99.2% J: 8.24, 99.5% | 1H NMR (400 MHz, DMSO-d6) δ = 13.22 (br. s., 1H), 8.12 (br. s., 2H), 7.62 (td, J = 8.0, 2.0 Hz, 1H), 7.34 (ddd, J = 8.7, 6.9, 2.0 Hz, 1H), 6.99 (t, J = 8.0 Hz, 1H), 6.38-6.27 (m, 2H), 6.21-6.12 (m, 1H), 5.96 (d, J = 7.0 Hz, 1H), 4.37 (dt, J = 9.7, 7.7 Hz, 1H), 3.93-3.73 (m, 2H), 3.69 (s, 3H), 2.71-2.58 (m, 1H), 2.09-1.91 (m, 1H); 19F NMR (400 MHz, DMSO-d6) δ = −140.035, −143.530; [α]$^{25.1}_D$ = −40.800 (c = 0.1, DMSO). |
| 307 | 1-(2,3-difluoro-4-(1H-pyrazol-4-yl)phenyl)-3-((4-fluoro-3-methoxyphenyl)aminopyrrolidin-2-one | Enantiomer-I | 403.20 | RT = 6.60 min, ee = 100%; Co-solvent: 0.2% DEA in methanol, Column: CHIRALPAK ® IA (250 × 4.6 mm), 5μ, Sample Well: P1: 3C, Column Temperature: 24.2, Total Flow: 4, CO2 Flow Rate: 2.4, Co-solvent Flow Rate: 1.6, Co-solvent %: 40, Back Pressure: 100, absorbance at 259 nm. | I: 9.29, 99.6% J: 8.31, 97.6% | 1H NMR (400 MHz, DMSO-d6) δ = 13.21 (br. s., 1H), 8.12 (d, J = 1.5 Hz, 2H), 7.61 (ddd, J = 8.7, 7.7, 1.8 Hz, 1H), 7.38-7.27 (m, 1H), 6.92 (dd, J = 11.5, 8.5 Hz, 1H), 6.55 (dd, J = 7.5, 2.5 Hz, 1H), 6.23 (dt, J = 8.7, 3.2 Hz, 1H), 5.88 (d, J = 7.0 Hz, 1H), 4.36 (dt, J = 9.3, 7.7 Hz, 1H), 3.91-3.72 (m, 5H), 2.71-2.58 (m, 1H), 2.06-1.91 (m, 1H); 19F NMR (400 MHz, DMSO-d6) δ = −140.037, −143.538, −150.790; [α]$^{25.1}_D$ = −60.400 (c = 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 308 | 1-(2,3-difluoro-4-(1H-pyrazol-4-yl)phenyl)-3-((4-fluoro-3-methoxyphenyl)amino)pyrrolidin-2-one | Enantiomer-II | 403.20 | RT = 8.87 min; ee = 98.06%; Co-solvent: 0.2% DEA in methanol, Column: CHIRALPAK ® IA (250 × 4.6 mm), 5μ, Sample Well: P1: 4C, Column Temperature: 24.1, Total Flow: 4, CO2 Flow Rate: 2.4, Co-solvent Flow Rate: 1.6, Co-solvent %: 40, Back Pressure: 100, absorbance at 259 nm. | I: 9.26, 99.2% J: 8.24, 99.5% | 1H NMR (400 MHz, DMSO-d6) δ = 13.21 (br. s., 1H), 8.12 (d, J = 1.5 Hz, 2H), 7.66-7.56 (m, 1H), 7.34 (ddd, J = 8.8, 7.0, 1.8 Hz, 1H), 6.92 (dd, J = 11.5, 8.5 Hz, 1H), 6.55 (dd, J = 7.5, 2.5 Hz, 1H), 6.27-6.17 (m, 1H), 5.88 (d, J = 7.0 Hz, 1H), 4.36 (dt, J = 9.3, 7.7 Hz, 1H), 3.90-3.72 (m, 5H), 2.70-2.58 (m, 1H), 2.06-1.90 (m, 1H); 19F NMR (400 MHz, DMSO-d6) δ = −140.035, −143.534, −150.789; [α]D25.1 = +20.0 (c = 0.1, DMSO). |
| 309 | 1-(2,3-difluoro-4-(1H-pyrazol-4-yl)phenyl)-3-((3-fluoro-5-methoxyphenyl)amino)pyrrolidin-2-one | Enantiomer-I | 403.20 | RT = 3.81 min; ee = 100% Co-solvent: 0.2% DEA in methanol, Column: CHIRALCEL ® OD-H (250 × 4.6 mm), 5μ, Sample Well: P1: 5C, Column Temperature: 24.1, Total Flow: 4, CO2 Flow Rate: 2.4, Co-solvent Flow Rate: 1.6, Co-solvent %: 40, Back Pressure: 100, absorbance at 257 nm. | I: 9.744, 99.6% J: 8.68, 99.2% | 1H NMR (400 MHz, DMSO-d6) δ = 13.21 (br. s., 1H), 8.12 (s, 2H), 7.67-7.56 (m, 1H), 7.33 (ddd, J = 8.8, 7.3, 2.0 Hz, 1H), 6.33 (d, J = 7.5 Hz, 1H), 6.19-6.10 (m, 2H), 6.01 (dt, J = 11.3, 2.1 Hz, 1H), 4.47-4.34 (m, 1H),3.91-3.65 (m, 5H), 2.72-2.58 (m, 1H), 2.07-1.89 (m, 1H); 19F NMR (400 MHz, DMSO-d6) δ = −112.539, −140.010, −143.539; [α]D24.7 = +40.0 (c = 0.1, DMSO). |
| 310 | 1-(2,3-difluoro-4-(1H-pyrazol-4-yl)phenyl)-3-((3-fluoro-5-methoxyphenyl)amino)pyrrolidin-2-one | Enantiomer-II | 403.20 | RT = 14.63 min, ee = 98.4%; Co-solvent: 0.2% DEA in methanol, Column: CHIRALCEL ® OD-H (250 × 4.6 mm), 5μ, Sample Well: P1: 6C, Column Temperature: 24.2, Total Flow: 4, CO2 Flow Rate: 2.4, Co-solvent Flow Rate: 1.6, Co-solvent %: 40, Back Pressure: 100, absorbance at 257 nm. | I: 9.76, 99.6% J: 8.70, 99.7% | 11 1H NMR (400 MHz, DMSO-d6) δ = 13.23 (br. s., 1H), 8.12 (s, 2H), 7.62 (td, J = 8.2, 1.8 Hz, 1H), 7.38-7.27 (m, 1H), 6.34 (s, 1H), 6.21-6.09 (m, 2H), 6.05-5.94 (m, 1H), 4.41 (dt, J = 9.9, 7.6 Hz, 1H), 3.90-3.65 (m, 5H), 2.71-2.57 (m, 1H), 2.06-1.89 (m, 1H); 19F NMR (400 MHz, DMSO-d6) δ = −112.539, −140.016, −143.539; [α]D25 = −48.400 (c = 0.1, DMSO). |

| Ex. | Structure and Name | Chirality | LCMS (M+H)+ | Chiral Purity | HPLC Method, RT (min) & Purity | 1H NMR |
|---|---|---|---|---|---|---|
| 311 | 1-(3,5-difluoro-4-(1H-pyrazol-4-yl)phenyl)-3-((3-methoxyphenyl)amino)pyrrolidin-2-one | Enantiomer-I | 385.20 | RT = 8.84 min, ee = 100%; Co-solvent: 0.2% DEA in methanol, Column: CHIRALCEL ® OD-H (250 × 4.6 mm), 5μ, Sample Well: P2: 1C, Column Temperature: 23, Total Flow: 4, CO₂ Flow Rate: 2.4, Co-solvent Flow Rate: 1.6, Co-solvent %: 40, Back Pressure:97, absorbance at 273 nm. | I: 9.82, 98.9% J: 9.28, 99.0% | 1H NMR (400 MHz, DMSO-d₆) δ = 13.22 (br. s., 1H), 8.00 (br. s., 2H), 7.69-7.55 (m, 2H), 6.99 (t, J = 8.0 Hz, 1H), 6.34-6.25 (m, 2H), 6.21-6.13 (m, 1H), 5.95 (d, J = 7.0 Hz, 1H), 4.44 (dt, J = 10.0, 7.8 Hz, 1H), 3.94-3.73 (m, 2H), 3.68 (s, 3H), 2.65-2.54 (m, 1H), 1.99-1.82 (m, 1H); 19F NMR (400 MHz, DMSO-d₆) δ = -110.763; [α]²⁵_D = +48.0 (c = 0.05, DMSO) |
| 312 | 1-(3,5-difluoro-4-(1H-pyrazol-4-yl)phenyl)-3-((3-methoxyphenyl)amino)pyrrolidin-2-one | Enantiomer-II | 385.20 | RT = 14.80 min, ee = 98.42%; Co-solvent: 0.2% DEA in methanol, Column: CHIRALCEL ® OD-H (250 × 4.6 mm), 5μ, Sample Well: P2: 2C, Column Temperature: 23, Total Flow: 4, CO₂ Flow Rate: 2.4, Co-solvent Flow Rate: 1.6, Co-solvent %: 40, Back Pressure: 99, absorbance at 273 nm. | I: 10.00, 98.9% J: 9.29, 97.4% | 1H NMR (400 MHz, DMSO-d₆) δ = 13.22 (br. s., 1H), 8.01 (br. s., 2H), 7.68-7.57 (m, 2H), 7.04-6.93 (m, 1H), 6.35-6.25 (m, 2H), 6.21-6.13 (m, 1H), 5.95 (d, J = 7.5 Hz, 1H), 4.44 (dt, J = 9.9, 7.8 Hz, 1H), 3.93-3.73 (m, 2H), 3.68 (s, 3H), 2.64-2.55 (m, 1H), 1.98-1.83 (m, 1H); 19F NMR (400 MHz, DMSO-d₆) δ = -110.763; [α]²⁵_D = -40.0 (c = 0.05, DMSO). |
| 313 | 1-(6-ethyl-5-(1H-pyrazol-4-yl)pyridin-2-yl)-3-((3-methoxyphenyl)amino)pyrrolidin-2-one | Enantiomer-I | 378.20 | RT = 9.62 min, ee = 100%: Co-solvent: 0.2% DEA in methanol, Column: CHIRALPAK ® IA (250 × 4.6 mm), 5μ, Sample Well: 12A, Column Temperature: 30, Total Flow: 4, Co-solvent %: 40, Back Pressure: 100, absorbance at 250 nm. | I: 9.40, 99.6% J: 8.76, 98.7% | 1H NMR (400 MHz, DMSO-d₆) δ = 13.04 (br. s., 1H), 8.14 (d, J = 8.5 Hz, 1H), 7.79 (d, J = 8.5 Hz, 3H), 6.99 (t, J = 8.0 Hz, 1H), 6.37-6.26 (m, 2H), 6.21-6.12 (m, 1H), 5.95 (d, J = 7.5 Hz, 1H), 4.47 (dt, J = 10.0, 7.8 Hz, 1H), 4.19 (ddd, J = 10.9, 8.9, 1.8 Hz, 1H), 3.86 (td, J = 10.4, 6.8 Hz, 1H), 3.71-3.63 (m, 3H), 2.91-2.80 (m, 2H), 2.64-2.54(111, 1H), 1.96-1.81 (m, 1H), 1.23 (t, J = 7.5 Hz, 3H); [α]²⁵·³_D = +48.0 (c = 0.1, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 314 | <br>1-(6-ethyl-5-(1H-pyrazol-4-yl)pyridin-2-yl)-3-((3-methoxyphenyl)amino)pyrrolidin-2-one | Enantiomer-II | 378.20 | RT = 14.67 min; ee = 98.80%; Co-solvent: 0.2% DEA in methanol, Column: CHIRALPAK ® IA (250 × 4.6 mm), 5μ, Sample Well: 13A, Column Temperature: 30, Total Flow: 4, Co-solvent %: 30, Back Pressure: 100, absorbance at 250 nm. | I: 9.40, 98.8% J: 8.76, 99.0% | 1H NMR (400 MHz, DMSO-d6) δ = 13.04 (br. s., 1H), 8.14 (d, J = 8.5 Hz, 1H), 7.94-7.72 (m, 3H), 7.04-6.93 (m, 1H), 6.36-6.25 (m, 2H), 6.20-6.13 (m, 1H), 5.95 (d, J = 7.5 Hz, 1H), 4.47 (dt, J = 10.0, 7.5 Hz, 1H), 4.26-4.12 (m, 1H), 3.91-3.78 (m, 1H), 3.68 (s, 3H), 2.92-2.80 (m, 2H), 2.64-2.53 (m, 1H), 1.96-1.78 (m, 1H), 1.23 (t, J = 7.5 Hz, 3H); [α]$_D^{25.2}$ = −66.0 (c = 0.1, DMSO). |
| 315 | <br>1-(6-ethyl-5-(1H-pyrazol-4-yl)pyridin-2-yl)-3-((3-fluoro-5-methoxyphenyl)amino)pyrrolidin-2-one | Enantiomer-I | 396.20 | RT = 12.44 min; ee = 100%; Co-solvent: 0.2% DEA in methanol, Column: CHIRALPAK ® AD-H (250 × 4.6 mm), 5μ, Sample Well: 15E, Column Temperature: 30, Total Flow: 4, Co-solvent %: 40, Back Pressure: 100, absorbance at 250 nm. | I: 10.37, 97.0% J: 9.21, 97.4% | 1H NMR (400 MHz, DMSO-d6) δ = 13.05 (br. s., 1H), 8.13 (d, J = 8.5 Hz, 1H), 7.98 (s, 1H), 7.82-7.76 (m, 1H), 7.72 (s, 1H), 6.32 (d, J = 8.0 Hz, 1H), 6.17-6.10 (m, 2H), 6.00 (dt, J = 11.0, 2.0 Hz, 1H), 4.51 (dt, J = 10.2, 8.0 Hz, 1H), 4.24-4.15 (m, 1H), 3.89-3.79 (m, 1H), 3.69 (s, 3H), 2.86 (q, J = 7.5 Hz, 2H), 2.63-2.54 (m, 1H), 1.93-1.80 (m, 1H), 1.23 (t, J = 7.5 Hz, 3H); 19F NMR (400 MHz, DMSO-d6) 5 = −112.551; [α]$_D^{25.2}$ = +92.0 (c = 0.05, DMSO). |
| 316 | 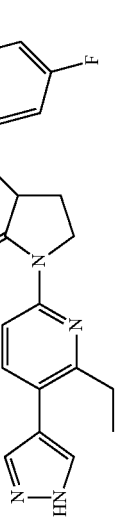<br>1-(6-ethyl-5-(1H-pyrazol-4-yl)pyridin-2-yl)-3-((3-fluoro-5-methoxyphenyl)amino)pyrrolidin-2-one | Enantiomer-II | 396.20 | RT = 24.66 min; ee = 100%; Co-solvent: 0.2% DEA in methanol, Column: CHIRALPAK ® AD-H (250 × 4.6 mm), 5μ, Sample Well: 16E, Column Temperature: 30, Total Flow: 4, Co-solvent %: 40, Back Pressure: 100, absorbance at 250 nm. | I: 10.3, 96.9% J: 9.21, 96.9% | 1H NMR (400 MHz, DMSO-d6) δ = 13.05 (br. s., 1H), 8.13 (d, J = 8.5 Hz, 1H), 7.98 (s, 1H), 7.82-7.76 (m, 1H), 7.72 (s, 1H), 6.32 (d, J = 7.5 Hz, 1H), 6.18-6.10 (m, 2H), 6.00 (dt, J = 11.2, 2.2 Hz, 1H), 4.51 (dt, J = 9.9, 7.8 Hz, 1H), 4.23-4.14 (m, 1H), 3.89-3.80 (m, 1H), 3.69 (s, 3H), 2.86 (q, J = 7.5 Hz, 2H), 2.63-2.54 (m, 1H), 1.93-1.81 (m, 1H), 1.23 (t, J = 7.5 Hz, 3H); 19F NMR (400 MHz, DMSO-d6) 5 = −112.551; [α]$_D^{25.1}$ = −56.0(c = 0.05, DMSO). |

| Ex. | Structure and Name | Chirality | LCMS (M+H)⁺ | Chiral Purity | HPLC Method, RT (min) & Purity | ¹H NMR |
|---|---|---|---|---|---|---|
| 317 | 1-(6-ethyl-5-(1H-pyrazol-4-yl)pyridin-2-yl)-3-((4-fluoro-3-methoxyphenyl)amino) pyrrolidin-2-one | Enantiomer-I | 396.20 | RT = 7.18 min, ee = 100%; Co-solvent: 0.2% DEA in methanol, Column: CHIRALPAK ® IA (250 × 4.6 mm), 5μ, Sample Well: 11D, Column Temperature: 30, Total Flow: 4, Back solvent %: 40, Co-Pressure: 100, absorbance at 254 nm. | I: 9.42, 98.9% J: 9.21, 96.9% | ¹H NMR (400 MHz, DMSO-d₆) δ = 13.04 (br. s., 1H), 8.14 (d, J = 8.5 Hz, 1H), 8.01-7.71 (m, 3H), 6.92 (dd, J = 11.5, 8.5 Hz, 1H), 6.54 (dd, J = 7.5, 3.0 Hz, 1H), 6.21 (dt, J = 8.8, 3.1 Hz, 1H), 5.87 (d, J = 7.0 Hz, 1H), 4.45 (dt, J = 9.8, 7.7 Hz, 1H), 4.26-4.13 (m, 1H), 3.92-3.81 (m, 1H), 3.77 (s, 3H), 2.92-2.79 (m, 2H), 2.65-2.54 (m, 1H), 1.95-1.80 (m, 1H), 1.23 (t, J = 7.5 Hz, 3H); ¹⁹F NMR (400 MHz, DMSO-d₆) δ = −150.863; [α]$_D^{24.9}$ = +54.0 (c = 0.1, DMSO). |
| 318 | 1-(6-ethyl-5-(1H-pyrazol-4-yl)pyridin-2-yl)-3-((4-fluoro-3-methoxyphenyl)amino) pyrrolidin-2-one | Enantiomer-II | 396.20 | RT = 12.77 min, ee = 99.29%; Co-solvent: 0.2% DEA in methanol, Column: CHIRALPAK ® IA (250 × 4.6 mm), 5μ, Sample Well: 12D, Column Temperature: 30, Total Flow: 4, Back solvent %: 40, Co-Pressure: 100, absorbance at 254 nm. | I: 9.42, 98.0% J: 9.21, 97.8% | ¹H NMR (400 MHz, DMSO-d₆) δ = 13.04 (br. s., 1H), 8.14 (d, J = 8.5 Hz, 1H), 8.01-7.70 (m, 3H), 6.92 (dd, J = 11.5, 8.5 Hz, 1H), 6.54 (dd, J = 7.5, 3.0 Hz, 1H), 6.21 (dt, J = 8.7, 3.2 Hz, 1H), 5.87 (d, J = 7.0 Hz, 1H), 4.51-4.38 (m, 1H), 4.25-4.12 (m, 1H), 3.92-3.80 (m, 1H), 3.77 (s, 3H), 2.91-2.80 (m, 2H), 2.65-2.55 (m, 1H), 1.96-1.81 (m, 1H), 1.23 (t, J = 7.5 Hz, 3H); ¹⁹F NMR (400 MHz, DMSO-d₆) δ = −150.829; [α]$_D^{25.1}$ = −48.0 (c = 0.1, DMSO). |
| 319 | 1-(5-(1H-pyrazol-4-yl)pyridin-2-yl)-3-((3-(cyclopropylmethoxy)phenyl)amino) pyrrolidin-2-one | Enantiomer-I | 390.20 | RT = 14.02 min, ee = 100%; Co-solvent: 0.2% DEA in methanol, Column: CHIRALPAK ® IC (250 × 4.6 mm), 5μ, Sample Well: 17C, Column Temperature: 30, Total Flow: 4, Back solvent %: 40, Co-Pressure: 100, absorbance at 270 nm. | I: 9.58, 97.2% J: 9.33, 98.4% | ¹H NMR (400 MHz, DMSO-d₆) δ = 13.02 (br. s., 1H), 8.70 (dd, J = 2.5, 1.0 Hz, 1H), 8.33-8.28 (m, 1H), 8.13 (br. s., 2H), 8.09-8.03 (m, 1H), 6.99-6.92 (m, 1H), 6.32-6.26 (m, 2H), 6.17-6.12 (m, 1H), 5.92 (d, J = 7.0 Hz, 1H), 4.47 (dt, J = 10.0, 7.8 Hz, 1H), 4.17-4.09 (m, 1H), 3.83 (td, J = 10.3, 7.0 Hz, 1H), 3.73 (d, J = 7.0 Hz, 2H), 2.62-2.54 (m, 1H), 1.94-1.82 (m, 1H), 1.25-1.15 (m, 1H), 0.58-0.51 (m, 2H), 0.32-0.26 (m, 2H); [α]$_D^{25}$ = +44.0 (c = 0.05, DMSO). |

TABLE 10-continued

| Ex. | Structure and Name | Chirality | LCMS (M+H)+ | Chiral Purity | HPLC Method, RT (min) & Purity | ¹H NMR |
|---|---|---|---|---|---|---|
| 320 | 1-(5-(1H-pyrazol-4-yl)pyridin-2-yl)-3-((3-(cyclopropylmethoxy)phenyl)amino)pyrrolidin-2-one | Enantiomer-II | 390.20 | RT = 18.34 min, ee = 98.82%; Co-solvent: 0.2% DEA in methanol, Column: CHIRALPAK ® IC (250 × 4.6 mm), 5μ, Sample Well: 18C, Column Temperature: 30, Total Flow: 4, Co-solvent %: 40, Back Pressure: 100, absorbance at 270 nm. | I: 9.57, 99.9%; J: 9.34, 99.0% | ¹H NMR (400 MHz, DMSO-d₆) δ = 12.97 (br. s., 1H), 8.70 (d, J = 2.5 Hz, 1H), 8.33-8.27 (m, 1H), 8.13 (s, 2H), 8.06 (dd, J = 9.0, 2.5 Hz, 1H), 7.00-6.91 (m, 1H), 6.33-6.24 (m, 2H), 6.18-6.11 (m, 1H), 5.91 (d, J = 7.0 Hz, 1H), 4.52-4.42 (m, 1H), 4.18-4.08 (m, 1H), 3.83 (td, J = 10.3, 7.0 Hz, 1H), 3.73 (d, J = 7.0 Hz, 2H), 2.62-2.53 (m, 1H), 1.95-1.80 (m, 1H), 1.25-1.12 (m, 1H), 0.58-0.50 (m, 2H), 0.32-0.26 (m, 2H); [α]²⁵·¹_D = −88.0 (c = 0.05, DMSO). |
| 321 | 1-(5-(1H-pyrazol-4-yl)pyridin-2-yl)-3-((3-(difluoromethoxy)phenyl)amino)pyrrolidin-2-one | Enantiomer-I | 386.20 | RT = 5.57 min, ee = 100%; Co-solvent: 0.2% DEA in methanol, Column: CHIRALPAK ® IC (250 × 4.6 mm), 5μ, Sample Well: 16A, Column Temperature: 30, Total Flow: 4, Co-solvent %: 40, Back Pressure: 100, absorbance at 270 nm. | I: 9.25, 99.2%; J: 8.75, 96.8% | ¹H NMR (400 MHz, DMSO-d₆) δ = 12.97 (br. s., 1H), 8.71 (dd, J = 2.5, 1.0 Hz, 1H), 8.30 (d, J = 8.0 Hz, 1H), 8.13 (s, 2H), 8.06 (dd, J = 9.0, 2.5 Hz, 1H), 7.35-6.90 (m, 2H), 6.59 (dd, J = 7.8, 1.8 Hz, 1H), 6.51 (t, J = 2.3 Hz, 1H), 6.39-6.25 (m, 2H), 4.58-4.47 (m, 1H), 4.19-4.08 (m, 1H), 3.84 (td, J = 10.3, 7.0 Hz, 1H), 1.96-1.82 (m, 1H); ¹⁹F NMR (400 MHz, DMSO-d₆) δ = −80.916; [α]²⁵·¹_D = +124.0 (c = 0.05, DMSO). |
| 322 | 1-(5-(1H-pyrazol-4-yl)pyridin-2-yl)-3-((3-(difluoromethoxy)phenyl)amino)pyrrolidin-2-one | Enantiomer-II | 386.20 | RT = 7.77 min, ee = 99.48; Co-solvent: 0.2% DEA in methanol, Column: CHIRALPAK ® IC (250 × 4.6 mm), 5μ, Sample Well: 17A, Column Temperature: 30, Total Flow: 4, Co-solvent %: 40, Back Pressure: 100, absorbance at 270 nm. | I: 9.21, 98.7%; J: 8.75, 99.3% | ¹H NMR (400 MHz, DMSO-d₆) δ = 13.00 (br. s., 1H), 8.71 (d, J = 2.5 Hz, 1H), 8.34-8.26 (m, 1H), 8.13 (s, 2H), 8.06 (dd, J = 8.8, 2.3 Hz, 1H), 7.34-6.91 (m, 2H), 6.59 (dd, J = 8.3, 1.8 Hz, 1H), 6.51 (t, J = 2.3 Hz, 1H), 6.39-6.25 (m, 2H), 4.53 (dt, J = 10.0, 7.8 Hz, 1H), 4.20-4.10 (m, 1H), 3.84 (td, J = 10.3, 6.5 Hz, 1H), 2.63-2.53 (m, 1H), 1.90 (dq, J = 12.2, 9.6 Hz, 1H); ¹⁹F NMR (400 MHz, DMSO-d₆) 5 = −80.907; [α]²⁵·¹_D = −56.0 (c = 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 323 | (3S,4R)-1-(4-(1H-pyrazol-4-yl)phenyl)-4-(hydroxymethyl)-3-((3-methoxyphenyl)amino)pyrrolidin-2-one | Enantiomer | 379.20 | RT = 3.27, 100% ee determined by chiral SFC analysis, Column: CHIRALCEL® OJ-H (250 × 4.6 mm), 5μ, Mobile Phase: 0.2% DEA in MeOH with Co-solvent CO2 40%. | E: 1.35, 99.3% F: 1.29, 98.2% | 1H NMR (400 MHz, DMSO-d6) δ ppm 12.90 (br. s., 1H) 8.17 (s, 1H) 7.91 (br. s., 1H) 7.68 (m, J = 8.80 Hz, 2H) 7.63 (m, J = 8.80 Hz, 2H) 6.96 (t, J = 8.07 Hz, 1H) 6.25-6.33 (m, 2H) 6.11-6.19 (m, 1H) 6.01 (d, J = 8.07 Hz, 1H) 4.94 (t, J = 4.89 Hz, 1H) 4.23 (t, J = 8.93 Hz, 1H) 3.83-3.93 (m, 1H) 3.65-3.69 (m, 1H) 3.67 (s, 3H) 3.55-3.66 (m, 2H); [α]25.1D = −108.0 (c 0.05, DMSO). |
| 324 | 2-((1-(4-(1H-pyrazol-4-yl)phenyl)-2-oxopyrrolidin-3-yl)amino)-4-methoxybenzamide | Racemate | 392.20 | | E: 1.31, 97.6% F: 1.35, 98.0% | 1H NMR (400 MHz, DMSO-d6) δ ppm 12.91 (br. s., 1H) 8.88 (d, J = 5.62 Hz, 1H) 8.18 (s, 1H) 7.92 (br. s., 1H) 7.70 (d, J = 8.56 Hz, 2H) 7.54-7.66 (m, 4H) 6.99 (s, 1H) 6.29 (s, 1H) 6.12-6.23 (m, 1H) 4.39-4.54 (m, 1H) 3.85 (d, J = 9.05 Hz, 2H) 3.77 (s, 3H) 2.76 (br. s., 1H) 1.72-1.95 (m, 1H). |
| 325 | 1-(4-(1H-pyrazol-4-yl)phenyl)-3-((3-methoxy-2-methylphenyl)amino)pyrrolidin-2-one | Enantiomer-I | 363.20 | RT = 8.13 min, ee = 98.01%; Column: CHIRALCEL® OJ-H (250 × 4.6 mm), 5μ, Mobile Phase: 0.2% DEA in MeOH with Co-solvent CO2 40%. | I: 14.48, 99.8% J: 13.86, 98.8% | 1H NMR (400 MHz, DMSO-d6) δ ppm 12.72 (br. s., 1H) 8.05 (s, 2H) 7.73 (m, J = 9.04 Hz, 2H) 7.64 (m, J = 8.53 Hz, 2H) 6.99 (t, J = 8.28 Hz, 1H) 6.42 (d, J = 8.03 Hz, 1H) 6.36 (d, J = 8.03 Hz, 1H) 4.98 (d, J = 6.53 Hz, 1H) 4.32-4.46 (m, 1H) 3.85 (dd, J = 9.54, 4.02 Hz, 2H) 3.74 (s, 3H) 2.60-2.73 (m, 2H) 1.91-2.07 (m, 4H); [α]25.1D = +4.0 (c 0.05, DMSO). |
| 326 | 1-(4-(1H-pyrazol-4-yl)phenyl)-3-((3-methoxy-2-methylphenyl)amino)pyrrolidin-2-one | Enantiomer-II | 363.20 | RT = 14.25 min, ee = 97.19%; CHIRALCEL® OJ-H (250 × 4.6 mm), 5μ, Mobile Phase: 0.2% DEA in MeOH with Co-solvent CO2 40%. | I: 14.48, 99.9% J: 13.85, 99.9% | 1H NMR (400 MHz, DMSO-d6) δ ppm 8.05 (s, 2H) 7.73 (d, J = 8.53 Hz, 2H) 7.64 (d, J = 8.53 Hz, 2H) 6.99 (t, J = 8.28 Hz, 1H) 6.42 (d, J = 8.03 Hz, 1H) 6.36 (d, J = 8.03 Hz, 1H) 4.98 (d, J = 6.53 Hz, 1H) 4.40 (dd, J = 17.07, 8.03 Hz, 2H) 3.85 (dd, J = 9.79, 4.27 Hz, 2H) 3.74 (s, 3H) 2.61-2.71 (m, 2H) 1.94-2.04 (m, 4H); [α]25.1D = −8.0 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 327 | 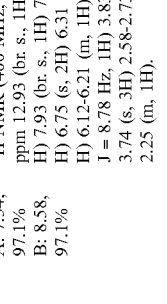<br>1-(4-(1H-pyrazol-4-yl)phenyl)-2-oxopyrrolidin-3-yl 2-amino-4-methoxybenzoate | Racemate | 393.20 | | A: 7.54, 97.1%<br>B: 8.58, 97.1% | 1H NMR (400 MHz, DMSO-d6) δ ppm 12.93 (br. s., 1H) 8.18 (br. s., 1H) 7.93 (br. s., 1H) 7.54-7.78 (m, 5H) 6.75 (s, 2H) 6.31 (d, J = 2.51 Hz, 1H) 6.12-6.21 (m, 1H) 5.67 (t, J = 8.78 Hz, 1H) 3.83-3.97 (m, 2H) 3.74 (s, 3H) 2.58-2.73 (m, 1H) 2.03-2.25 (m, 1H). |
| 328 | <br>1-(2-fluoro-4-(1H-pyrazol-4-yl)phenyl)-3-((3-methoxyphenyl)amino)pyrrolidin-2-one | Enantiomer-I | 367.2 | ee 100%, RT 8.11 min.s, Method Name; CO2 3.0_40 Colvent_100.met, Injection Volume - 10 mL, Co-solvent; 0.2% DEA in IPA:ACN (1:1), Column; CHIRALPAK ® IA (250 × 4.6 mm), 5μ, Sample Well; P1: 1A, Column Temperature; 24.2, Total Flow; 3, CO2 Flow Rate: 1.8, Co-solvent Flow Rate: 1.2, Co-solvent %; 40, Back Pressure; 99. | B: 8.27, 99.9%<br>A: 8.87, 96.9% | 1H NMR (400 MHz DMSO-d6) δ ppm 13.02 (br. s., 1H) 8.29 (br. s., 1H) 8.00 (br. s., 1H) 7.61 (dd, J = 12.39, 1.79 Hz, 1H) 7.50 (d, J = 1.82 Hz, 1H) 7.45 (d, J = 8.16 Hz, 1H) 6.95-7.02 (m, 1H) 6.28-6.35 (m,2H) 6.18 (d, J = 1.76 Hz, 1H) 5.93 (d, J = 6.96 Hz, 1H) 4.27-4.38 (m, 1H) 3.76-3.85 (m,2H) 3.71 (s, 3H) 2.57-2.69 (m, 1H) 1.90-2.03 (m, 1H). 19F NMR (376 MHz, DMSO-d6) δ ppm –119.98. |
| 329 | 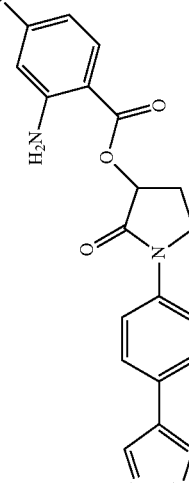<br>1-(2-fluoro-4-(1H-pyrazol-4-yl)phenyl)-3-((3-methoxyphenyl)amino)pyrrolidin-2-one | Enantiomer-II | 366.8 | ee 99.32%,RT 10.84 min.s, Method Name; CO2 3.0_40 Colvent_100.met, Injection Volume - 10 mL, Co-solvent; 0.2% DEA in IPA:ACN (1:1), Column; CHIRALPAK ® IA (250 × 4.6 mm), 5μ, Sample Well; P1: 1A, Column Temperature; 24.2, Total Flow; 3, CO2 Flow Rate: 1.8, Co-solvent Flow Rate: 1.2, Co-solvent %; 40, Back Pressure; 99. | B: 8.23, 98.6%<br>A: 8.88, 99.2% | 1H NMR (400 MHz, DMSO-d6) δ ppm 13.02 (br. s., 1H) 8.29 (s, 1H) 8.00 (s, 1H) 7.61 (dd, J = 12.39, 1.79 Hz, 1H) 7.52 (d, J = 1.88 Hz, 1H) 7.41-7.47 (m, 1H) 6.98 (d, J = 16.06 Hz, 1H). 19F NMR (376 MHz, DMSO-d6) δ ppm –119.99. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 330 | 3-((4-fluoro-3-methoxyphenyl)amino)-1-(2-fluoro-4-(1H-pyrazol-4-yl)phenyl)pyrrolidin-2-one | Enantiomer-I | 384.80 | ee 97.84%, RT 5.38 mins, Method Name; CO2 3.0_40 Colvent_100.met, Injection Volume - 10 mL, Co-solvent: 0.2% DEA in IPA:ACN (1:1), Column; CHIRALPAK @ IA (250 × 4.6 mm), 5μ, Sample Well; P1: 5A, Column Temperature; 24.7, Total Flow; 3, CO2 Flow Rate: 1.8, Co-solvent Flow Rate: 1.2, Co-solvent %; 40, Back Pressure; 99. | B: 8.59, 96.5% A: 8.92, 97.8% | 1H NMR (400 MHz, DMSO-d6) δ ppm 13.02 (br. s., 1H) 8.29 (br. s., 1 H) 8.00 (br. s., 1H) 7.61 (dd, J = 12.39, 1.79 Hz, 1H) 7.52 (d, J = 1.88 Hz, 1H) 7.44 (s, 1H) 6.88-6.95 (m, 1H) 6.54 (dd, J = 7.53, 2.64 Hz, 1H) 6.22 (dt, J = 8.69, 3.09 Hz, 1 H) 5.85 (d, J = 6.78 Hz, 1H) 4.27-4.36 (m, 1H) 3.78-3.84 (m, 1H) 3.77 (s, 3H) 3.68-3.75 (m, 1H) 2.59-2.69 (m, 1H) 1.90-2.02. 19F NMR (376 MHz, DMSO-d6) δ ppm −120.001, −150.887 (m, 1H). |
| 331 | 3-((4-fluoro-3-methoxyphenyl)amino)-1-(2-fluoro-4-(1H-pyrazol-4-yl)phenyl)pyrrolidin-2-one | Enantiomer-II | 384.90 | RT 9.02 mins, ee 100%. Method Name; CO2 3.0_40 Colvent_100.met, Injection Volume - 10 mL, Co-solvent: 0.2% DEA in IPA:ACN (1:1), Column; CHIRALPAK @ IA (250 × 4.6 mm), 5μ, Sample Well; P1: 5A, Column Temperature; 24.7, Total Flow; 3, CO2 Flow Rate: 1.8, Co-solvent Flow Rate: 1.2, Co-solvent %; 40, Back Pressure; 99. | B: 8.59, 97.1% A: 8.59, 96.4% | 1H NMR (400 MHz, DMSO-d6) δ ppm 13.03 (s, 1H) 8.29 (br. s., 1H) 8.00 (br. s., 1H) 7.61 (dd, J = 12.36, 1.76 Hz, 1H) 7.51 (m, J = 1.88 Hz, 1 H) 7.41-7.47 (m, 1H) 6.87-6.96 (m, 1H) 6.54 (dd, J = 7.59, 2.64 Hz, 1 H) 6.22 (dt, J = 8.69, 3.09 Hz, 1H) 5.85 (d, J = 6.84 Hz, 1H) 4.26-4.36 (m, 1H) 3.78-3.84 (m, 1H) 3.77 (s, 3H) 3.69-3.75 (m, 1H) 2.59-2.69 (m, 1H) 1.89-2.02 (m, 1H). 19F NMR (376 MHz, DMSO-d6) δ ppm −120.004, −150.877. |
| 332 | 3-((4-fluoro-3-methoxyphenyl)amino)-1-(3-fluoro-4-(1H-pyrazol-4-yl)phenyl)pyrrolidin-2-one | Enantiomer-I | 384.90 | RT 9.94 mins, ee 99.24%. Method Name; CO2 3.0_30 Colvent_100.met, Injection Volume - 10 mL, Co-solvent: 0.2% DEA in methanol, Column; CHIRALCEL @ AS-H (250 × 4.6 mm), 5μ, Sample Well; P1: 7A, Column Temperature; 24.4, Total Flow; 4, CO2 Flow Rate: 2.1, Co-solvent Flow Rate: 0.9, Co-solvent %; 30, Back Pressure; 100. | B: 9.00, 98.4% A: 9.37, 97.7% | 1H NMR (400 MHz DMSO-d6) δ ppm 13.08 (br. s., 1H) 7.90-8.20 (br. s., 2H) 7.77-7.80(m, 2H) 7.52 (dd, J = 8.63, 2.16 Hz, 1H) 6.88-6.95 (m, 1H) 6.53 (dd, J = 7.53, 2.64 Hz, 1H) 6.20 (dt, J = 8.67, 3.13 Hz, 1H) 5.87 (d, J = 7.09 Hz, 1H) 4.35-4.44 (m, 1 H) 3.79-3.91 (m, 2H) 3.77 (s, 3H) 2.56-2.65 (m, 1H) 1.83-1.95 (m, 1 H). 19F NMR (376 MHz, DMSO-d6) δ ppm−113.574,-150.824. |

TABLE 10-continued

| Ex. | Structure and Name | Chirality | LCMS (M+H)⁺ | Chiral Purity | HPLC Method, RT (min) & Purity | ¹H NMR |
|---|---|---|---|---|---|---|
| 333 | 3-((4-fluoro-3-methoxyphenyl)amino)-1-(3-fluoro-4-(1H-pyrazol-4-yl)phenyl)pyrrolidin-2-one | Enantiomer-II | 384.90 | RT 12.41 min.s, ee 96.64%. Method Name; CO₂ 3.0_30 Colvent_100.met, Injection Volume - 10 mL, Co-solvent; 0.2% DEA in methanol, Column; CHIRALCEL @ AS-H (250 × 4.6 mm), 5μ, Sample Well; P1: 7A, Column Temperature; 24.4, Total Flow; 4, CO₂ Flow Rate: 2.1, Co-solvent Flow Rate: 0.9, Co-solvent %; 30, Back Pressure; 100. | B: 8.98, 97.5% A: 9.36, 97.7% | ¹H NMR (400 MHz, DMSO-d₆) δ ppm 13.07 (br. s., 1H) 8.15 (br. s., 1H) 7.93 (s, 1H) 7.73-7.80 (m, 2H) 7.52 (dd, J = 8.66, 2.20 Hz, 1H) 6.88-6.95 (m, 1H) 6.53 (dd, J = 7.56, 2.67 Hz, 1H) 6.20 (dt, J = 8.71, 3.08 Hz, 1H) 5.86 (d, J = 7.15 Hz, 1H) 4.35-4.44 (m, 1H) 3.78-3.91 (m, 2H) 3.77 (s, 3H) 2.56-2.65 (m, 1H) 1.83-1.96 (m, 1H). ¹⁹F NMR (376 MHz, DMSO-d₆) δ ppm −113.575, −150.823. |
| 334 | 1-(3-fluoro-4-(1H-pyrazol-4-yl)phenyl)-3-((2-fluoro-5-methoxyphenyl)amino)pyrrolidin-2-one | Enantiomer-I | 384.80 | RT 10.51 min.s, ee 96.4%. Method Name; CO₂ 4.0_40 Colvent_100.met, Injection Volume - 10 mL, Co-solvent; 0.2% DEA in methanol, Column; WHELK-O1 @ (R,R) (250 × 4.6 mm), 5μ, Sample Well; P1: 1B, Column Temperature; 24.3, Total Flow; 4, CO₂ Flow Rate: 2.4, Co-solvent Flow Rate: 1.6, Co-solvent %; 40, Back Pressure; 100. | B: 9.34, 94.3% A: 9.85, 95.5% | ¹H NMR (400 MHz DMSO-d₆) δ ppm 13.01 (br. s., 1H) 8.04 (bs, 2H) 7.73-7.80 (m, 2H) 7.52 (dd, J = 8.60, 2.20 Hz, 1H) 6.92-6.98 (m, 1H) 6.45 (dd, J = 7.53, 2.89 Hz, 1H) 6.13 (dt, J = 8.75, 3.22 Hz, 1H) 5.71 (dd, J = 8.09, 2.26 Hz, 1H) 4.49-4.57 (m, 1H) 3.76-3.91 (m, 2H) 3.68 (s, 3H) 2.01-2.13 (m, 1H). ¹⁹F NMR (376 MHz, DMSO-d₆) δ ppm −113.579, −144.121. |
| 335 | 1-(3-fluoro-4-(1H-pyrazol-4-yl)phenyl)-3-((2-fluoro-5-methoxyphenyl)amino)pyrrolidin-2-one | Enantiomer-II | 384.90 | RT 18.51 min.s, ee 95.4%. Method Name; CO₂ 4.0_40 Colvent_100.met, Injection Volume - 10 mL, Co-solvent; 0.2% DEA in methanol, Column; WHELK-O1 @ (R,R) (250 × 4.6 mm), 5μ, Sample Well; P1: 1B, Column Temperature; 24.3, Total Flow; 4, CO₂ Flow Rate: 2.4, Co-solvent Flow Rate: 1.6, Co-solvent %; 40, Back Pressure; 100. | B: 9.32, 93.9% A: 9.86, 97.0% | ¹H NMR (400 MHz DMSO-d₆) δ ppm 13.04 (br. s., 1H) 7.98-8.10 (m, 2H) 7.72-7.80 (m, 2H) 7.52 (dd, J = 8.66, 2.20 Hz, 1H) 6.90-7.00 (m, 1H) 6.45 (dd, J = 7.56, 2.92 Hz, 1H) 6.13 (dt, J = 8.74, 3.19 Hz, 1H) 5.71 (dd, J = 8.06, 2.23 Hz, 1H) 4.47-4.59 (m, 1H) 3.75-3.92 (m, 2H) 3.68 (s, 3H) 1.99-2.13 (m, 1H). ¹⁹F NMR (376 MHz, DMSO-d₆) δ ppm −113.579, −144.121. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 336 | 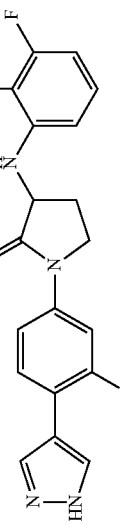<br>3-((3-fluoro-2-methoxyphenyl)amino)-1-(3-fluoro-4-(1H-pyrazol-4-yl)phenyl)pyrrolidin-2-one | Enantiomer-I | 385.20 | RT 6.2 min.s, ee 100%. Method Name; CO2 4.0_40 Colvent_100.met, Injection Volume - 10 mL, Co-solvent; 0.2% DEA in methanol Column; CHIRALPAK @ IC (250 × 4.6 mm), 5µ, Sample Well; P1: 2A, Column Temperature; 25.0, Total Flow; 4, CO2 Flow Rate: 2.4, Co-solvent Flow Rate: 1.6, Co-solvent %; 40, Back Pressure; 100. | B: 13.19, 92.2%<br>A: 9.40, 89.9% | 1H NMR (400 MHz, DMSO-d6) δ ppm 13.10 (bs, 1H) 8.20 (bs, 1H) 7.92 (bs, 1H) 7.74-7.81 (m, 2H) 7.53 (dd, J = 8.66, 2.26 Hz, 1H) 6.85-6.93 (m, 1H), 6.57-6.65 (m, 1H) 6.48 (ddd, J = 11.01, 8.31, 1.25 Hz, 1 H) 5.64 (d, J = 7.28 Hz, 1H) 4.42-4.52 (m, 1H) 3.80-3.91 (m, 2H) 3.79 (s, 3H) 2.56-2.65 (m, 1H) 1.98-2.14 (m, 1H). 19F NMR (376 MHz, DMSO-d6) δ ppm -113.569, -132.920. |
| 337 | 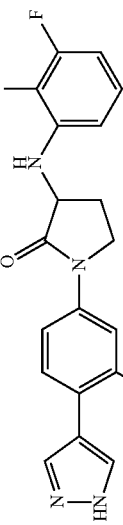<br>3-((3-fluoro-2-methoxyphenyl)amino)-1-(3-fluoro-4-(1H-pyrazol-4-yl)phenyl)pyrrolidin-2-one | Enantiomer-II | 384.90 | RT 8.53 min.s, ee 99.44%. Method Name; CO2 4.0_40 Colvent_100.met, Injection Volume - 10 mL, Co-solvent; 0.2% DEA in methanol Column; CHIRALPAK @ IC (250 × 4.6 mm), 5µ, Sample Well; P1: 2A, Column Temperature; 25.0, Total Flow; 4, CO2 Flow Rate: 2.4, Co-solvent Flow Rate: 1.6, Co-solvent %; 40, Back Pressure; 100. | B: 13.20, 91.4%<br>A: 10.03, 89.7% | 1H NMR (400 MHz, DMSO-d6) δ ppm 13.10 (bs, 1H) 8.22 (s, 1H) 7.90 (s, 1H) 7.73-7.81 (m, 2H) 7.53 (dd, J = 8.60, 2.20 Hz, 1H) 6.86-6.93 (m, 1H) 6.60 (d, J = 8.41 Hz, 1H) 6.48 (ddd, J = 11.00, 8.33, 1.32 Hz, 1 H) 5.64 (d, J = 7.34 Hz, 1H) 4.43-4.52 (m, 1H) 3.82-3.92 (m, 2H) 3.79 (s, 3H) 2.56-2.66 (m, 1H) 1.99-2.13 (m, 1H). 19F NMR (376 MHz, DMSO-d6) δ ppm -113.569, -139.920. |
| 338 | 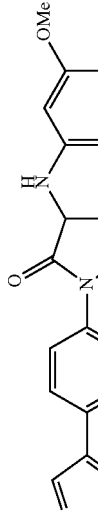<br>1-(2-fluoro-4-(1H-pyrazol-4-yl)phenyl)-3-(((3-fluoro-5-methoxyphenyl)amino)pyrrolidin-2-one | Enantiomer-I | 384.90 | RT 4.24 min.s, ee 100%. Method Name; CO2 4.0_40 Colvent_100.met, Injection Volume - 10 mL, Co-solvent; 0.2% DEA in IPA:ACN (1:1) Column; CHIRALPAK @ IA (250 × 4.6 mm), 5µ, Sample Well; P1: 3B, Column Temperature; 24.6, Total Flow; 4, CO2 Flow Rate: 2.4, Co-solvent Flow Rate: 1.6, Co-solvent %; 40, Back Pressure; 104. | B: 9.03, 96.3%<br>A: 9.40, 98.4% | 1H NMR (400 MHz, DMSO-d6) δ ppm 13.01 (br. s., 1H) 8.28 (br. s., 1 H) 8.00 (br. s., 1H) 7.61 (dd, J = 12.39, 1.85 Hz, 1H) 7.52 (d, J = 1.88 Hz, 1H) 7.40-7.46 (m, 1H) 6.31 (d, J = 7.15 Hz, 1H) 6.13 (d, J = 2.20 Hz, 2H) 5.99 (dt, J = 11.11, 2.20 Hz, 1H) 4.32-4.41 (m, 1H) 3.70-3.83 (m, 2H) 3.69 (s, 3H) 2.57-2.66 (m, 1H) 1.89-2.02 (m, 1 H). 19F NMR (376 MHz, DMSO-d6) δ ppm -112.561, -120.001. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 339 | 1-(2-fluoro-4-(1H-pyrazol-4-yl)phenyl)-3-(((3-fluoro-5-methoxyphenyl)amino)pyrrolidin-2-one | Enantiomer-II | 384.90 | RT 7.1 min.s, ee 100%. Method Name; CO2 4.0_40 Covent_100.met, Injection Volume - 10 mL, Co-solvent: 0.2% DEA in IPA:ACN (1:1) Column; CHIRALPAK @ IA (250 × 4.6 mm), 5μ, Sample Well; P1: 3B, Column Temperature: 24.6, Total Flow; 4, CO2 Flow Rate: 2.4, Co-solvent %; 40, Back Pressure; 104. | B: 9.03, 95.4% A: 9.40, 95.7% | 1H NMR (400 MHz, DMSO-d6) δ ppm 13.01 (br. s., 1H) 8.28 (br. s., 1 H) 8.00 (br. s., 1H) 7.61 (dd, J = 12.33, 1.85 Hz, 1H) 7.51 (m, J = 1.88 Hz, 1H) 7.40-7.46 (m, 1H) 6.30 (d, J = 7.15 Hz, 1H) 6.10-6.18 (m, 2H) 5.99 (dt, J = 11.12, 2.19 Hz, 1 H) 4.32-4.41 (m, 1H) 3.70-3.83 (m, 2H) 3.69 (s, 4H) 2.57-2.66 (m. 1H) 1.89-2.02 (m, 1H). 19F NMR (376 MHz, DMSO-d6) δ ppm −112.561, −120.002. |
| 340 | 1-(2-fluoro-4-(1H-pyrazol-4-yl)phenyl)-3-(((2-fluoro-5-methoxyphenyl)amino)pyrrolidin-2-one | Enantiomer-II | 385.00 | RT 9.84 min.s, ee 100%. Method Name; CO2 3.0_30 Covent_100.met Injection Volume - 10 mL, Co-solvent: 0.2% DEA in IPA:ACN (1:1) Column; CHIRALPAK @ IA (250 × 4.6 mm), 5μ, Sample Well; P1: 5B, Column Temperature: 24.4, Total Flow; 3, CO2 Flow Rate: 2.1, Co-solvent %; 30, Back Pressure; 100. | B: 8.91, 95.6% A: 9.33, 96.0% | 1H NMR (400 MHz, DMSO-d6) δ ppm 13.02 (br. s., 1H) 8.28 (br. s., 1 H) 8.00 (br. s., 1H) 7.61 (dd, J = 12.42, 1.82 Hz, 1H) 7.52 (d, J = 1.88 Hz, 1H) 7.42-7.47 (m, 1H) 6.92-6.98 (m, 1H) 6.46 (dd, J = 7.53, 2.89 Hz, 1H) 6.13 (dt, J = 8.77, 3.18 Hz, 1H) 5.67 (dd, J = 7.62, 2.29 Hz, 1 H) 4.40-4.50 (m, 1H) 3.70-3.85 (m, 2H) 3.69 (s, 3H) 2.54-2.62 (m, 1H) 2.09-2.21 (m, 1H). 19F NMR (376 MHz, DMSO-d6) δ ppm −119.994, −144.098. |
| 341 | 1-(2-fluoro-4-(1H-pyrazol-4-yl)phenyl)-3-(((2-fluoro-5-methoxyphenyl)amino)pyrrolidin-2-one | Enantiomer-II | 384.90 | RT 11.85 min.s, ee 97.46%. Method Name; CO2 3.0_30 Covent_100.met Injection Volume - 10 mL, Co-solvent: 0.2% DEA in IPA:ACN (1:1) Column; CHIRALPAK @ IA (250 × 4.6 mm), 5μ, Sample Well; P1: 5B, Column Temperature: 24.4, Total Flow; 3, CO2 Flow Rate: 2.1, Co-solvent %; 30, Back Pressure; 100. | B: 8.89, 98.0% A: 9.3, 98.8% | 1H NMR (400 MHz, DMSO-d6) δ ppm 13.02 (s, 1H) 8.28 (s, 1H) 8.00 (s, 1H) 7.61 (dd, J = 12.45, 1.79 Hz, 1 H) 7.49-7.53 (m, 1H) 7.41-7.47 (m, 1H) 6.88-6.99 (m, 1H) 6.46 (dd, J = 7.53, 2.95 Hz, 1H) 6.13 (dt, J = 8.77, 3.18 Hz, 1H) 5.67 (dd, J = 7.65, 2.26 Hz, 1H) 4.39-4.50 (m, 1H) 3.71-3.85 (m, 2H) 3.69 (s, 3 H) 2.53-2.61 (m, 1H) 2.09-2.22 (m, 1H). 19F NMR (376 MHz, DMSO-d6) δ ppm −119.991, −144.096. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 342 | 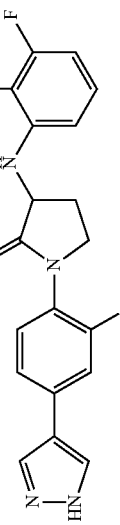<br>3-((3-fluoro-2-methoxyphenyl)amino)-1-(2-fluoro-4-(1H-pyrazol-4-yl)phenyl)pyrrolidin-2-one | Enantiomer-I | 384.90 | RT 6.26 mins, ee 97.84%. Method Name; CO₂ 4.0_40 Colvent_100.met, Injection Volume - 10 mL, Co-solvent; 0.2% DEA in methanol, Column: CHIRALCEL @ OJ-H (4.6 × 250 mm), 5µ, Sample Well; P1: 1F, Column Temperature; 25.2, Total Flow; 4, CO₂ Flow Rate: 2.4, Co-solvent Flow Rate: 1.6, Co-solvent %; 40, Back Pressure; 100. | B: 9.23, 95.4% A: 9.67, 95.8% | 1H NMR (400 MHz, DMSO-d₆) δ ppm 13.00 (bs, 1H) 8.14 (s, 2H) 7.61 (dd, J = 12.45, 1.73 Hz, 1H) 7.50 (d, J = 1.82 Hz, 1H) 7.46 (m, J = 7.91 Hz, 1H) 6.90 (td, J = 8.25, 6.21 Hz, 1 H) 6.62 (d, J = 8.35 Hz, 1H) 6.48 (ddd, J = 11.04, 8.35, 1.32 Hz, 1H) 5.57 (d, J = 6.96 Hz, 1H) 4.34-4.44 (m, 1H) 3.80-3.86 (m, 1H) 3.79 (m. 3H) 3.69-3.76 (m, 1H) 2.57-2.69 (m, 1H) 2.07-2.20 (m, 1H). 19F NMR (376 MHz, DMSO-d₆) δ ppm -120.072, -132.905. |
| 343 | 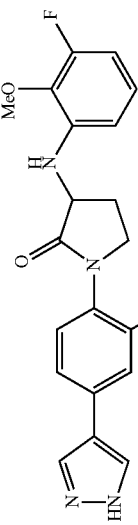<br>3-((3-fluoro-2-methoxyphenyl)amino)-1-(2-fluoro-4-(1H-pyrazol-4-yl)phenyl)pyrrolidin-2-one | Enantiomer-II | 384.90 | RT 11.86 mins, ee 97.34%. Method Name; CO₂ 4.0_40 Colvent_100.met, Injection Volume - 10 mL, Co-solvent; 0.2% DEA in methanol, Column: CHIRALCEL @ OJ-H (4.6 × 250 mm), 5µ, Sample Well; P1: 1F, Column Temperature; 25.2, Total Flow; 4, CO₂ Flow Rate: 2.4, Co-solvent Flow Rate: 1.6, Co-solvent %; 40, Back Pressure; 100. | B: 9.223, 94.97% A: 9.647, 93.97% | 1H NMR (400 MHz, DMSO-d₆) δ ppm 13.01 (s, 1H) 8.14 (br. s., 2H) 7.61 (dd, J = 12.45, 1.73 Hz, 1H) 7.51 (m, J = 1.82 Hz, 1H) 7.44-7.49 (m, 1 H) 6.86-6.94 (m, 1H) 6.62 (d, J = 8.41 Hz, 1H) 6.48 (ddd, J = 11.04, 8.31,1.35 Hz, 1H) 5.57 (d, J = 6.96 Hz, 1H) 4.34-4.44 (m, 1H) 3.80-3.86 (m, 1H) 3.79 (s, 3H) 3.69-3.76 (m, 1H) 2.59-2.66 (m, 1H) 2.07-2.19 (m, 1H). 19F NMR (376 MHz, DMSO-d₆) δ ppm -120.065, -132.904. |
| 344 | 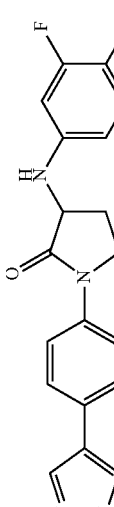<br>1-(2-fluoro-4-(1H-pyrazol-4-yl)phenyl)-3-(((3-fluoro-4-methoxyphenyl)amino)pyrrolidin-2-one | Enantiomer-I | 384.90 | RT 4.79 mins, ee 100%. Method Name; CO₂ 4.0_40 Colvent_100.met, Injection Volume - 10 mL, Co-solvent; 0.2% DEA in IPA:ACN (1:1), Column; CHIRALPAK @ IA (250 × 4.6 mm), 5µ, Sample Well; P1: 1c, Column Temperature; 24.5, Total Flow; 4, CO₂ Flow Rate: 2.4, Co-solvent Flow Rate: 1.6, Co-solvent %; 40, Back Pressure; 99. | B: 8.45, 92.0% A: 8.74, 91.7% | 1H NMR (400 MHz, DMSO-d₆) δ ppm 13.02 (br. s., 1H) 8.28 (br. s., 1 H) 8.00 (br. s., 1H) 7.61 (dd, J = 12.39, 1.79 Hz, 1H) 7.48-7.53 (m, 1H) 7.43 (m, J = 8.16 Hz, 1H) 6.90-6.97 (m, 1H) 6.63 (dd, J = 14.18, 2.70 Hz, 1H) 6.45-6.50 (m, 1H) 5.84 (d, J = 6.71 Hz, 1H) 4.23-4.31 (m, 1H) 3.74-3.84 (m, 2 H) 3.72 (s, 3H) 2.57-2.69 (m, 1H) 1.88-2.00 (m, 1H). 19F NMR (376 MHz, DMSO-d₆) δ ppm -120.01, -134.25 |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 345 | 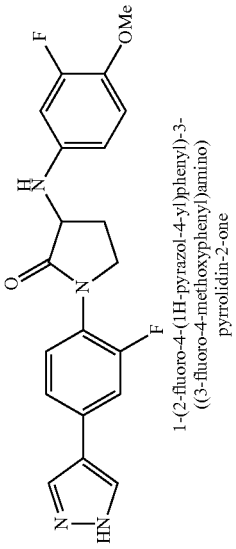<br>1-(2-fluoro-4-(1H-pyrazol-4-yl)phenyl)-3-(((3-fluoro-4-methoxyphenyl)amino)pyrrolidin-2-one | Enantiomer-II | 384.90 | RT 7.12 min.s, ee 99.562%. Method Name; CO2 4.0_40 Colvent_100.met, Injection Volume - 10 mL, Co-solvent; 0.2% DEA in IPA:ACN (1:1), Column; CHIRALPAK @ IA (250 × 4.6 mm), 5µ, Sample Well; P1: 1c, Column Temperature; 24.5, Total Flow; 4, CO2 Flow Rate: 2.4, Co-solvent Flow Rate: 1.6, Co-solvent %; 40, Back Pressure; 99. | B: 8.44, 98.0% A: 8.75, 98.3% | 1H NMR (400 MHz, DMSO-d6) δ ppm 13.02 (br. s., 1H) 8.28 (br. s., 1 H) 8.00 (br. s., 1H) 7.61 (dd, J = 12.36, 1.82 Hz, 1H) 7.51 (m, J = 1.82 Hz, 1H) 7.40-7.46 (m, 1H) 6.93 (m, J = 9.04 Hz, 1H) 6.63 (dd, J = 14.18, 2.70 Hz, 1H) 6.45-6.51 (m, 1H) 5.84 (d, J = 6.84 Hz, 1H) 4.23-4.31 (m, 1H) 3.74-3.83 (m, 2 H) 3.72 (s, 3H) 2.58-2.69 (m, 1H) 1.87-2.01 (m, 1H). 19F NMR (376 MHz, DMSO-d6) δ ppm −120.009, −134.251. |
| 346 | 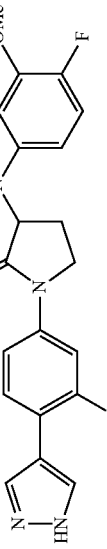<br>1-(3-(2-(dimethylamino)ethoxy)-4-(1H-pyrazol-4-yl)phenyl)-3-((4-fluoro-3-methoxyphenyl)amino)pyrrolidin-2-one | Racemate | 454.3. | | E: 1.16, 97.7 % F: 1.06, 98.4% | 1H NMR (400 MHz, DMSO-d6) δ ppm 12.5 (bs, 1H) 8.11(bs,2H) 7.64 (d, J = 8.47 Hz, 1H) 7.58 (d, J = 2.07 Hz, 1H) 7.21 (dd, J = 8.47, 2.07 Hz, 1H) 6.92 (dd, J = 11.55, 8.72 Hz, 1H) 6.53 (dd, J = 7.59, 2.64 Hz, 1 H) 6.21 (dt, J = 8.75, 3.06 Hz, 1H) 5.85 (d, J = 6.96 Hz, 1H) 4.31-4.41 (m, 1H) 4.12 (m, 2H) 3.81-3.91 (m, 2H) 3.77 (s, 3H) 2.73 (m, 2H) 2.25 (s, 6H) 1.83-1.90 (m,2H). 19F NMR (376 MHz, DMSO-d6) δ ppm −150.888. |

| Ex. | Structure and Name | Chirality | LCMS (M+H)+ | Chiral Purity | HPLC Method, RT (min) & Purity | 1H NMR |
|---|---|---|---|---|---|---|
| 347 | 1-(3-(2-(dimethylamino)ethoxy)-4-(1H-pyrazol-4-yl)phenyl)-3-((4-fluoro-3-methoxyphenyl)amino)pyrrolidin-2-one | Racemate | 436.30 | | E: 1.132, 94.1% F: 1.036, 97.4% | 1H NMR (400 MHz, DMSO-d6) δ ppm 8.11 (s, 2H) 7.64 (d, J = 8.47 Hz, 1H) 7.59 (d, J = 2.07 Hz, 1H) 7.21 (dd, J = 8.47, 2.07 Hz, 1H) 6.99 (m,1 H) 6.31 (m, 2H) 6.17 (dd, J = 7.72, 2.01 Hz, 1H) 5.93 (d, J = 7.09 Hz, 1 H) 4.33-4.42 (m, 1H) 4.12 (m,2H) 3.79-3.91 (m, 2H) 3.68 (s, 3H) 2.73 (m, 1H) 2.64-2.69 (m, 1H) 2.25 (s, 6H) 1.88-1.92 (m, 2H). |
| 348 | 1-(4-(1H-pyrazol-4-yl)-3-(2,2,2-trifluoro-1-hydroxyethyl)phenyl)-3-((3-methoxyphenyl)amino)pyrrolidin-2-one | Racemate | 447.20 | | B: 8.85, 98.5% A: 9.05, 98.4% | 1H NMR (400 MHz, DMSO-d6) δ ppm 13.2 (bs,1H) 8.08 (dd J = 12.30, 1.63 Hz, 1H) 7.64-7.72 (m, 3H) 7.35-7.39 (m, 1H) 6.99 (t, J = 8.00 Hz, 1H) 6.8 (bs,1H) 6.27-6.34 (m, 2 H) 6.14-6.20 (m, 1H) 5.95 (t, J = 6.34 Hz, 1H) 5.21-5.27 (m, 1H) 4.34-4.45 (m, 1H) 3.80-3.88 (m, 2 H) 3.68 (s, 3H) 2.57-2.65 (m, 1H) 1.88-1.95 (m, 1H). 19F NMR (376 MHz, DMSO-d6) δ ppm −75.195. |
| 349 | 1-(2,5-difluoro-4-(1H-pyrazol-4-yl)phenyl)-3-((4-fluoro-3-methoxyphenyl)amino)pyrrolidin-2-one | Enantiomer-II | 403.20 | 10.51 min.s, ee; 100%. Method Name; CO2 4.0_40 Colvent_100.met, Injection Volume - 10 mL, Co-solvent; 0.2% DEA in methanol, Column: CHIRALCEL ® OD-H (250 × 4.6 mm), 5µ, Sample Well; 24A: 1B, Column Temperature; 30, Total Flow; 4, CO2 Flow Rate: 2.4, Co-solvent Flow Rate: 1.6 Co-solvent %; 30, Back Pressure; 100. | B: 8.82, 98.8% A: 9.45, 98.5% | 1H NMR (400 MHz, DMSO-d6) δ ppm 13.18 (br. s., 1H) 8.25 (br. s., 1 H) 8.01 (br. s., 1H) 7.78 (dd, J = 11.80, 6.96 Hz, 1H) 7.49 (dd, J = 11.61, 6.53 Hz, 1H) 6.92 (dd, J = 11.51, 8.75 Hz, 1H) 6.54 (dd, J = 7.59, 2.64 Hz, 1H) 6.22 (dt. J = 8.66, 3.11 Hz, 1H) 5.86 (d, J = 6.90 Hz, 1H) 4.28-4.38 (m, 1H) 3.79-3.87 (m, 2H) 3.78 (s, 3H) 2.59-2.66 (m, 1H) 1.91-2.02 (m, 1H). 19F NMR (376 MHz, DMSO-d6) δ ppm −119.02, −124.48, −150.78. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 350 | 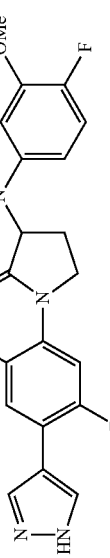<br>1-(2,5-difluoro-4-(1H-pyrazol-4-yl)phenyl)-3-((4-fluoro-3-methoxyphenyl)amino)pyrrolidin-2-one | Enantiomer-I | 403.20 | 8.12 min.s, ee 97.78%. Method Name; CO2 4.0_40 Colvent_100.met, Injection Volume - 10 mL, Co-solvent: 0.2% DEA in methanol, Column: CHIRALCEL ® OD-H (250 × 4.6 mm), 5µ, Sample Well; 25A: 1B, Column Temperature; 30, Total Flow; 4, CO2 Flow Rate: 2.4, Co-solvent Flow Rate: 1.6 Co-solvent %; 30, Back Pressure; 100. | B: 8.83, 97.3%<br>A: 9.45, 97.3% | 1H NMR (400 MHz, DMSO-d6) δ ppm 13.18 (br. s., 1H) 7.80-8.25 (br. s., 2H) 7.78 (dd, J = 11.76, 6.93 Hz, 1 H) 7.49 (dd, J = 11.51. 8.75 Hz, 1H) 6.92 (dd, J = 7.53, 2.64 Hz, 1H) 6.22 (dt, J = 8.64, 3.11 Hz, 1H) 5.86 (d, J = 6.90 Hz, 1H) 4.28-4.37 (m, 1H) 3.78-3.87 (m, 2H) 3.78 (s, 3H) 2.59-2.66 (m, 1H) 1.92-2.03 (m, 1H). 19F NMR (376 MHz, DMSO-d6) δ ppm -119.02, -124.48, -150.78. |
| 351 | 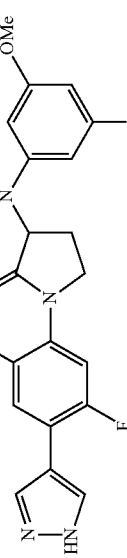<br>1-(2,5-difluoro-4-(1H-pyrazol-4-yl)phenyl)-3-((3-fluoro-5-methoxyphenyl)amino)pyrrolidin-2-one | Enantiomer-I | 403.20 | RT 3.13 min.s, ee 100%. Method Name; CO2 4.0_40 Colvent_100.met, Injection Volume - 10 mL, Co-solvent: 0.2% DEA in methanol, Column: CHIRALCEL ® OD-H (250 × 4.6 mm), 5µ, Sample Well; 26A: 1B, Column Temperature; 30, Total Flow; 4, CO2 Flow Rate: 2.4, Co-solvent Flow Rate: 1.6 Co-solvent %; 40, Back Pressure; 100. | B: 9.205, 96.9%<br>A: 9.886, 97.0% | 1H NMR (400 MHz, DMSO-d6) δ ppm 13.18 (br. s., 1H) 8.25 (br. s., 1 H) 8.01 (br. s., 1H) 7.78 (dd, J = 11.80, 6.90 Hz, 1H) 7.48 (dd, J = 11.58. 6.49 Hz, 1H) 6.30 (d, J = 7.15 Hz, 1H) 6.10-6.18 (m, 2H) 6.00 (dt, J = 11.12, 2.22 Hz, 1H) 4.34-4.43 (m, 1H) 3.73-3.86 (m, 2H) 3.70 (s, 3H) 2.58-2.66 (m, 1H) 1.87-2.03 (m, 1H). 19F NMR (376 MHz, DMSO-d6) δ ppm -112.54, -119.005, -124.48. |
| 352 | 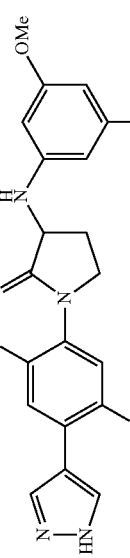<br>1-(2,5-difluoro-4-(1H-pyrazol-4-yl)phenyl)-3-((3-fluoro-5-methoxyphenyl)amino)pyrrolidin-2-one | Enantiomer-II | 403.20 | RT 8.107 min.s, ee 99.48%. Method Name; CO2 4.0_40 Colvent_100.met, Injection Volume - 10 mL, Co-solvent: 0.2% DEA in methanol, Column: CHIRALCEL ® OD-H (250 × 4.6 mm), 5µ, Sample Well; 27A: 1B, Column Temperature; 30, Total Flow; 4, Co-solvent Flow Rate: 1.6 Co-solvent %; 40, Back Pressure; 100. | B: 9.19, 97.0%<br>A: 9.87, 98.0% | 1H NMR (400 MHz, DMSO-d6) δ ppm 13.18 (br. s., 1H) 8.25 (br. s., 1 H) 8.01 (br. s., 1H) 7.78 (dd, J = 11.73, 6.90 Hz, 1H) 7.48 (dd, J = 11.55, 6.53 Hz, 1H) 6.30 (d, J = 7.34 Hz, 1H) 6.15-6.18 (m, 1H) 6.13 (s, 1H) 6.00 (dt, J = 11.12, 2.19 Hz, 1H) 4.33-4.43 (m, 1H) 3.73-3.86 (m, 2H) 3.70 (s, 3H) 2.58-2.66 (m, 1H) 1.90-2.02 (m, 1H). 19F NMR (376 MHz, DMSO-d6) δ ppm -112.54, -119.0, -124.75. |

| Ex. | Structure and Name | Chirality | LCMS (M+H)+ | Chiral Purity | HPLC Method, RT (min) & Purity | $^1$H NMR |
|---|---|---|---|---|---|---|
| 353 | 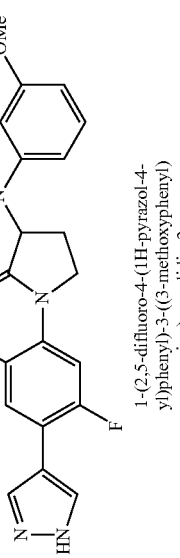<br>1-(2,5-difluoro-4-(1H-pyrazol-4-yl)phenyl)-3-((3-methoxyphenyl)amino)pyrrolidin-2-one | Enantiomer-I | 385.20 | RT 6.43 min.s, ee 100%. Method Name; CO$_2$ 4.0_40 Colvent_100.met, Injection Volume - 10 mL, Co-solvent; 0.2% DEA in methanol, Column: CHIRALCEL @ OD-H (250 × 4.6 mm), 5μ, Sample Well; 28A: 1B, Column Temperature; 30, Total Flow; 4. CO$_2$ Flow Rate: 2,4, Co-solvent %; 40, Back Pressure; 100. | B: 8.72, 98.6% A: 9.36, 98.3% | $^1$H NMR (400 MHz, DMSO-d$_6$) δ ppm 13.18 (br. s., 1H) 8.13 (br. s., 2 H) 7.78 (dd, J = 11.83, 6.93 Hz, 1H) 7.49 (dd, J = 11.58, 6.49 Hz, 1H) 6.99 (t, J = 8.03 Hz, 1H) 6.31 (m, 2H) 6.16-6.21 (m, 1H) 5.94 (d, J = 7.09 Hz, 1 H) 4.30-4.39 (m, 1H) 3.73-3.87 (m, 2H) 3.69 (s,3H) 2.57-2.66 (m, 1H) 1.90-2.04 (m, 1H). $^{19}$F NMR (376 MHz, DMSO-d$_6$) δ ppm −119.03, −124.48. |
| 354 | 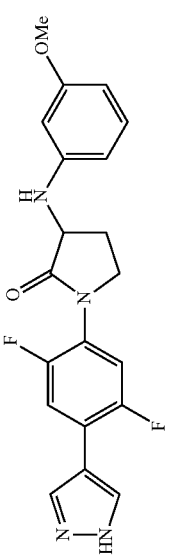<br>1-(2,5-difluoro-4-(1H-pyrazol-4-yl)phenyl)-3-((3-methoxyphenyl)amino)pyrrolidin-2-one | Enantiomer-II | 385.20 | RT 14.89 min.s, ee 100%. Method Name; CO$_2$ 4.0_40 Colvent_100.met, Injection Volume - 10 mL, Co-solvent; 0.2% DEA in methanol, Column: CHIRALCEL @ OD-H (250 × 4.6 mm), 5μ, Sample Well; 21B: Column Temperature; 30, Total Flow; 4. Co-solvent %; 40, Back Pressure; 100. | B: 8.73, 99.6% A: 9.36, 99.7% | $^1$H NMR (400 MHz, DMSO-d$_6$) δ ppm 13.18 (br. s., 1H) 8.24 (s, 1H) 8.01 (br. s., 1H) 7.77 (dd, J = 11.83, 7.00 Hz, 1H) 7.48 (dd, J = 11.61, 6.53 Hz, 1H) 6.99 (t, J = 7.97 Hz, 1H) 6.28-6.34 (m, 2H) 6.15-6.19 (m, 1H) 5.93 (d, J = 7.03 Hz, 1H) 4.30-4.38 (m, 1H) 3.72-3.86 (m, 2H) 3.68 (s, 3H) 2.56-2.65 (m, 1H) 1.91-2.03 (m, 1H). $^{19}$F NMR (376 MHz, DMSO-d$_6$) δ ppm −73.41, −119.05, 124.48. |
| 355 | 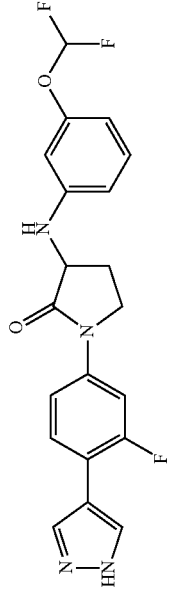<br>3-(3-(difluoromethoxy)phenyl)amino)-1-(3-fluoro-4-(1H-pyrazol-4-yl)phenyl) pyrrolidin-2-one | Enantiomer-I | 403.20 | RT 5.62 min.s, ee 98.46%. Method Name; CO$_2$ 4.0_40 Colvent_100.met, Injection Volume - 10 mL, Co-solvent; 0.2% DEA in methanol, Column: CHIRALCEL @ OD-H (250 × 4.6 mm), 5μ, Sample Well; 25C: Column Temperature; 30, Total Flow; 4. Co-solvent %; 30, Back Pressure; 100. | B: 9.42, 97.7% A: 10.0, 97.9% | $^1$H NMR (300 MHz, DMSO-d$_6$) δ ppm 13.18 (br. s., 1H) 8.13 (br. s., 2 H) 7.71-7.81 (m, 2H) 7.52 (dd, J = 8.55, 1.79 Hz, 1H) 6.89-7.39 (m, 2H) 6.89 (s, 1H) 6.58 (d, J = 8.22 Hz, 1H) 6.50 (s, 1H) 6.35 (d, J = 8.12 Hz,1 H) 6.30 (s, 1H) 3.87 (d, J = 7.88 Hz, 2 H) 2.54-2.66 (m, 1H) 1.86-1.96 (m, 1H). $^{19}$F NMR (376 MHz, DMSO-d$_6$) δ ppm −80.91, −113.57. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 356 | 3-((3-(difluoromethoxy)phenyl)amino)-1-(3-fluoro-4-(1H-pyrazol-4-yl)phenyl)pyrrolidin-2-one | Enantiomer-II | 403.20 | RT 7.58 min.s, ee 95.06%. Method Name: CO2_4.0_40 Co-solvent_100.met, Injection Volume - 10 mL, Co-solvent: 0.2% DEA in methanol, Column: CHIRALPAK @ IC (250 × 4.6 mm), 5μ, Sample Well; 26c: Column Temperature; 30, Total Flow; 4, Co-solvent %; 30, Back Pressure; 100. | B: 9.43, 97.8%, A: 9.99, 98.4% | 1H NMR (400 MHz, DMSO-d6) δ ppm 13.18 (br. s., 1H) 8.13 (br. s., 1H) 7.93 (br. s., 1H) 7.76-7.81 (m, 1H) 7.74 (d, J = 1.98 Hz, 1H) 7.54 (d, J = 1.79 Hz, 1H) 6.81-7.51 (m, 2H) 6.48-6.52 (m, 1H) 6.35 (d, J = 6.37 Hz, 1H) 6.30 (m, 2H) 4.41-4.52 (m, 1H) 3.85 (m, 2H) 2.56 (m, 1H) 1.81-1.99 (m, 1H). 19F NMR (376 MHz, DMSO-d6) δ ppm −80.91, −113.57. |
| 357 | 1-(3-fluoro-5-(1H-pyrazol-4-yl)pyridin-2-yl)-3-((3-methoxyphenyl)amino)pyrrolidin-2-one | Enantiomer-I | 368.20 | RT 9.42 min.s, ee 100%. Method Name: CO2_4.0_40 Co-solvent_100.met, Injection Volume - 10 mL, Co-solvent: 0.2% DEA in methanol, Column: Lux Cellulose-21 (250 × 4.6 mm), 5μ, Sample Well; 11f: Column Temperature; 30, Total Flow; 4, Co-solvent %; 30, Back Pressure; 100. | B: 7.70, 94.8%, A: 8.13, 97.1% | 1H NMR (400 MHz, methanol-d4) δ ppm 8.46-8.51 (m, 1H) 8.00-8.22(bs, 2H) 7.86 (dd, J = 10.86, 1.88 Hz, 1H) 6.91-6.96 (m, 1H) 6.25-6.30 (m, 2H) 6.15-6.20 (m, 1H) 4.30-4.36 (m, 1H) 3.86-3.92 (m,2H) 3.65 (s, 3H) 2.91-2.98 (m, 1H) 2.63-2.73 (m, 2H) 1.99-2.11 (m, 1H). 19F NMR (376 MHz, DMSO-d6) δ ppm −124.614. |
| 358 | 1-(3-fluoro-5-(1H-pyrazol-4-yl)pyridin-2-yl)-3-((3-methoxyphenyl)amino)pyrrolidin-2-one | Enantiomer-II | 368.20 | RT 11.52 min.s, ee 96.75%. Method Name: CO2_4.0_40 Co-solvent_100.met, Injection Volume - 10 mL, Co-solvent: 0.2% DEA in methanol, Column: Lux Cellulose-21 (250 × 4.6 mm), 5μ, Sample Well; 11f: Column Temperature; 30, Total Flow; 4, Co-solvent %; 30, Back Pressure; 100. | B: 14.58, 5.4%, A: 15.53, 97.2% | 1H NMR (400 MHz, methanol-d4) δ ppm 8.61 (dd, J = 1.85, 0.85 Hz, 1H) 8.00-8.22(bs, 2H) 7.98 (dd, J = 10.92, 1.94 Hz, 1H) 7.06 (t, J = 8.19 Hz, 1H) 6.37-6.42 (m, 2H) 6.30 (ddd, J = 8.14, 2.31, 0.85 Hz, 1H) 4.42-4.48 (m, 1H) 3.98-4.04 (m, 2H) 3.77 (s, 3H) 2.76-2.85 (m, 2H) 2.12-2.24 (m, 2H). 19F NMR (376 MHz, DMSO-d6) δ ppm −124.62. |
| 359 | 1-(3-fluoro-5-(1H-pyrazol-4-yl)pyridin-2-yl)-3-((3-fluoro-5-methoxyphenyl)amino)pyrrolidin-2-one | Enantiomer-I | 386.20 | RT 7.28 min.s, ee; 100%. Method Name: CO2_4.0_40 Co-solvent_100.met, Injection Volume - 10 mL, Co-solvent: 0.2% DEA in methanol, Column: CHIRALPAK @ IC (250 × 4.6 mm), 5μ, Sample Well; 13F: Column Temperature; 30, Total Flow; 4, Co-solvent %; 30, Back Pressure; 100. | B:15.91, 99.5%, A: 16.92, 98.7% | 1H NMR (400 MHz, methanol-d4) δ ppm 8.60 (dd, J = 1.91, 0.85 Hz, 1H) 8.24 (s, 1H) 8.05 (s, 1H) 7.98 (dd, J = 10.89, 1.91 Hz, 1H) 6.15-6.19 (m, 1H) 6.13 (t, J = 2.13 Hz, 1H) 6.01 (dt, J = 10.92, 2.20 Hz, 1H) 4.46 (dd, J = 10.10, 8.22 Hz, 1H) 3.98-4.04 (m, 2H) 3.76 (s,3H) 2.75-2.84 (m, 1H) 2.10-2.22 (m, 1H). 19F NMR (376 MHz, DMSO-d6) δ ppm −114.54, −124.61. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 360 | 1-(3-fluoro-5-(1H-pyrazol-4-yl)pyridin-2-yl)-3-((3-fluoro-5-methoxyphenyl)amino)pyrrolidin-2-one | Enantiomer-II | 386.20 | RT 8.47 mins, ee 94.26%. Method Name; CO2 4.0_40 Colvent_100.met, Injection Volume - 10 mL, Co-solvent; 0.2% DEA in methanol, Column: CHIRALPAK ® IC (250 × 4.6 mm), 5μ, Sample Well; 14F: Column Temperature; 30, Total Flow; 4, Co-solvent %; 30. | B: 15.98, 98.1%. A: 16.88, 98.8% | 1H NMR (400 MHz, methanol-d4) δ ppm 8.60 (dd, J = 1.91, 0.85 Hz, 1H) 8.24 (br. s., 1H) 8.06 (br. s., 1H) 7.98 (dd, J = 10.92, 1.94 Hz, 1H) 6.15-6.19 (m, 1H) 6.13 (t, J = 2.10 Hz, 1H) 6.01 (dt, J = 10.92, 2.20 Hz, 1H) 4.43-4.49 (m, 1H) 3.98-4.04 (m, 2H) 3.76 (s, 3H) 2.74-2.84 (m, 1H) 2.11-2.22 (m, 1H). 19F NMR (376 MHz, DMSO-d6) δ ppm −114.54, −124.61. |
| 361 | 3-((3-(cyclopropylmethoxy)phenyl)amino)-1-(3-fluoro-4-(1H-pyrazol-4-yl)phenyl)pyrrolidin-2-one | Enantiomer-I | 407.20 | RT 13.26 mins, ee 100%. Method Name; CO2 4.0_40 Colvent_100.met, Injection Volume - 10 mL, Co-solvent; 0.2% DEA in methanol, Column: CHIRALPAK ® IC (250 × 4.6 mm), 5μ, Sample Well; 15F : Column Temperature; 30, Total Flow; 4, Co-solvent %; 30, Back Pressure; 100. | B: 15.98, 97.9%. A: 10.56, 99.5% | 1H NMR (400 MHz, methanol-d4) δ ppm 7.99-8.10 (bs, 2H) 7.78 (d, J = 2.26 Hz, 1H) 7.70-7.76 (m, 1H) 7.49 (dd, J = 8.50, 2.23 Hz, 1H) 7.05 (t, J = 8.16 Hz, 1H) 6.34-6.40 (m, 2H) 6.28 (ddd, J = 8.14, 2.27, 0.82 Hz, 1H) 4.40 (dd, J = 10.10, 8.22 Hz, 1H) 3.91-3.97 (m, 2H) 3.79 (d, J = 6.84 Hz, 2H) 2.71-2.81 (m, 1H) 1.98-2.10 (m, 1H) 1.18-1.29 (m, 1H) 0.58-0.64 (m, 2H) 0.32-0.37 (m, 2H). 19F NMR (376 MHz, DMSO-d6) δ ppm −115.26. |
| 362 | 3-((3-(cyclopropylmethoxy)phenyl)amino)-1-(3-fluoro-4-(1H-pyrazol-4-yl)phenyl)pyrrolidin-2-one | Enantiomer-II | 407.20 | RT 15.52 mins, ee 96.94%. Method Name; CO2 4.0_40 Colvent_100.met, Injection Volume - 10 mL, Co-solvent; 0.2% DEA in methanol, Column: CHIRALPAK ® IC (250 × 4.6 mm), 5μ, Sample Well; 16F: Column Temperature; 30, Total Flow; 4, Co-solvent %; 30, Back Pressure; 100. | B: 10.54, 99.7%. A: 9.99, 98.4% | 1H NMR (400 MHz, methanol-d4) δ ppm 7.99-8.10 (bs, 2H) 7.69-7.80 (m, 2H) 7.49 (dd, J = 8.41, 2.20 Hz, 1H) 7.05 (t, J = 8.13 Hz, 1H) 6.35-6.40 (m, 2H) 6.28 (ddd, J = 8.14, 2.24, 0.85 Hz, 1H) 4.40 (dd, J = 10.10, 8.16 Hz, 1H) 3.90-3.96 (m, 2H) 3.79 (d, J = 6.84 Hz, 2H) 2.72-2.81 (m, 1H) 1.99-2.10 (m, 1H) 1.20-1.30 (m, 1H) 0.58-0.64 (m, 2H) 0.31-0.37 (m, 2H). 19F NMR (376 MHz, DMSO-d6) δ ppm −115.26. |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 363 | 1-(3-cyclopropyl-4-(1H-pyrazol-4-yl)phenyl)-3-((3-methoxyphenyl)amino)pyrrolidin-2-one | Enantiomer-I | 389.20 | RT 11.61 min.s, ee = 100%. Method Name; CO₂ 4.0_40 Colvent_100.met, Injection Volume - 10 mL, Co-solvent; 0.2% DEA in methanol. Column: CHIRALCEL ® OJ-H (250 × 4.6 mm), 5µ, Sample Well; 26C: Column Temperature; 30, Total Flow; 4. Co-solvent %; 25, Back Pressure; 100. | B: 9.56, 99.1% A: 10.06, 99.8% | 1H NMR (400 MHz, DMSO-d₆) δ ppm 12.9 (bs, 1H) 8.17 (br. s., 1H) 7.68 (m, 3H) 7.25 (t, J = 8.01 Hz, 1H) 6.53-6.59 (m, 2H) 6.43 (ddd, J = 8.10, 2.29, 0.73 Hz, 1H) 6.17 (d, J = 6.97 Hz, 1H) 4.57-4.65 (m, 1H) 4.08 (dd, J = 9.23, 4.40 Hz, 2H) 3.94 (s, 3H) 2.81-2.90 (m, 1H) 2.30-2.39 (m, 1H) 2.07-2.20 (m, 1H) 1.18-1.25 (m, 2H) 0.88-0.96 (m, 2H). |
| 364 | 3-((2-fluoro-5-methoxyphenyl)amino)-1-(3-methyl-4-(1H-pyrazol-4-yl)phenyl)pyrrolidin-2-one | Enantiomer-II | 381.20 | RT = 10.78 min, ee = 100%; Column: CHIRALCEL ® AS-H (250 × 4.6 mm), 5µ, Mobile Phase: CO₂:60% with % Co-solvent: 40% (0.2% DEA in methanol). Flow Rate: 4 ml/min, UV: 264 nm. | A: 9.70, 97.9% B: 9.17, 95.3% | 1H NMR (400 MHz, DMSO-d₆) δ ppm 12.96 (br. s., 1H) 7.58(br. s., 2H) 7.55-7.61 (m, 2H) 7.39-7.45 (m, 1H) 6.91-6.99 (m, 1H) 6.46 (dd, J = 7.56, 2.92 Hz, 1H) 6.14 (dt, J = 8.75, 3.18 Hz, 1H) 5.65 (dd, J = 7.62, 2.16 Hz, 1H) 4.48 (dt, J = 10.01, 8.11 Hz, 1H) 3.79-3.88 (m, 2H) 3.69 (s, 3H) 2.54-2.63 (m, 1H) 2.40 (s, 3H) 2.01-2.12 (m, 1H); 19F NMR (376 MHz, DMSO-d₆) δ ppm −144.171; [α]$_D^{25.3}$ = −24.00 (c 0.1, MeOH). |
| 365 | 3-((3-fluoro-5-methoxyphenyl)amino)-1-(3-methyl-4-(1H-pyrazol-4-yl)phenyl)pyrrolidin-2-one | Enantiomer-II | 381.20 | RT = 8.32 min, ee = 100%; :CHIRALCEL ® AS-H (250 × 4.6 mm), 5µ, Mobile Phase: CO₂:65% with % Co-solvent: 35% (0.2% DEA in methanol), Flow Rate: 3 ml/min, UV: 259 nm. | A: 9.02, 98.1% B: 8.64, 95.8% | 1H NMR (400 MHz, DMSO-d₆) δ ppm 12.35 (br. s., 1H) 7.83(br. s., 2H) 7.53-7.62 (m, 2H) 7.42 (d, J = 8.16 Hz, 1H) 6.90-6.94 (m, 1H) 6.63 (dd, J = 14.18, 2.70 Hz, 1H) 6.47 (dt, J = 8.85, 1.35 Hz, 1H) 5.84 (d, J = 6.84 Hz, 1H) 4.26-4.33 (m, 1H) 3.79-3.83 (m, 2H) 3.71 (s, 3H) 2.61 (dtd, J = 14.32, 5.87, 5.87, 2.73 Hz, 1H) 2.38 (s, 3H) 1.80-1.90 (m, 1H). |

| Ex. | Structure and Name | Chirality | LCMS (M+H)+ | Chiral Purity | HPLC Method, RT (min) & Purity | 1H NMR |
|---|---|---|---|---|---|---|
| 366 | 3-((3,5-dimethoxyphenyl)amino)-1-(3-methyl-4-(1H-pyrazol-4-yl)phenyl)pyrrolidin-2-one | Enantiomer-I | 393.20 | RT = 4.17 min, ee = 100%; :CHIRALCEL @ AS-H (250 × 4.6 mm), 5μ, Mobile Phase: CO$_2$:60% with % Co-solvent: 40% (0.2% DEA in methanol), Flow Rate: 4 ml/min, UV: 260 nm. | A: 9.12, 96.9%; B: 8.76, 97.9% | $^1$H NMR (400 MHz, DMSO-d$_6$) δ ppm 12.92 (br. s., 1H) 7.90 (br s., 2H) 7.55-7.59 (m, 2H) 7.42 (d, J = 8.16 Hz, 1H) 5.90-5.93 (m, 3H) 5.75-5.81 (m, 1H) 4.30-4.40 (m, 1H) 3.78-3.87 (m, 2H) 3.66 (s, 6H) 2.56-2.65 (m, 1H) 2.40 (s, 3H) 1.88 (dq, J = 12.15, 9.42 Hz, 1H); [α]$^{25.1}_D$ = −6.00 (c 0.1, THF). |
| 367 | 1-(4-(1H-pyrazol-4-yl)-3-(trifluoromethyl)phenyl)-3-((3-methoxyphenyl)amino)pyrrolidin-2-one | Enantiomer-II | 417.20 | RT = 12.46 min, ee = 100%; Column: WHELK-O1 @ (R,R) (250 × 4.6 mm), 5μ, Mobile Phase: CO$_2$:60% with % Co-solvent: 40% (0.2% DEA in methanol:IPA 1:1) Flow Rate: 4 ml/min, UV: 259 nm. | A: 10.03, 99.5%; B: 9.23, 97.6% | $^1$H NMR (400 MHz, DMSO-d$_6$) δ ppm 13.12 (br.s, 1H) 8.32 (d, J = 2.32 Hz, 1H) 7.84 (dd, J = 8.53, 2.26 Hz, 1H) 7.76 (br.s, 2H) 7.57 (d, J = 8.53 Hz, 1H) 6.99 (t, J = 8.03 Hz, 1H) 6.26-6.35 (m, 2H) 6.18 (dd, J = 7.78, 2.01 Hz, 1H) 5.98 (d, J = 7.34 Hz, 1H) 4.43 (dt, J = 9.87, 7.84 Hz, 1H) 3.83-3.96 (m, 2H) 3.68 (s, 3H) 2.57-2.69 (m, 1H) 1.92 (dq, J = 12.24, 9.43 Hz, 1H); $^{19}$F NMR (376 MHz, DMSO-d$_6$) δ ppm −57.328; [α]$^{25}_D$ = +36.00 (c 0.05 DMSO). |
| 368 | 1-(4-(1H-pyrazol-4-yl)-3-(trifluoromethyl)phenyl)-3-((3-methoxyphenyl)amino)pyrrolidin-2-one | Enantiomer-II | 417.20 | RT 16.17 min, ee = 100%; Column: WHELK-O1 @ (R,R) (250 × 4.6 mm), 5μ, Mobile Phase: CO$_2$:60% with % Co-solvent: 40% (0.2% DEA in methanol:IPA 1:1) Flow Rate: 4 ml/min, UV: 259 nm. | A: 9.93, 97.8%; B: 9.34, 98.2% | $^1$H NMR (400 MHz, DMSO-d$_6$) δ ppm 13.13 (br.s, 1H) 8.33 (d, J = 2.32 Hz, 1H) 7.85 (dd, J = 8.53, 2.26 Hz, 1H) 7.76 (br.s, 2H) 7.58 (d, J = 8.53 Hz, 1H) 7.00 (t, J = 8.03 Hz, 1H) 6.26-6.37 (m, 2H) 6.15-6.21 (m, 1H) 5.99 (d, J = 7.34 Hz, 1H) 4.44 (dt, J = 9.84, 7.88 Hz, 1H) 3.83-3.97 (m, 2H) 3.68 (s, 3H) 2.58-2.66 (m, 1H) 1.93 (dq, J = 12.25, 9.49 Hz, 1H); $^{19}$F NMR (376 MHz, DMSO-d$_6$) δ ppm −57.328; [α]$^{25.1}_D$ = −72.00 (c 0.05, DMSO). |

TABLE 10-continued

| Ex. | Structure and Name | Chirality | LCMS (M+H)+ | Chiral Purity | HPLC Method, RT (min) & Purity | ¹H NMR |
|---|---|---|---|---|---|---|
| 369 | 1-(4-((1H-pyrazol-4-yl)-3-(trifluoromethyl)phenyl)-3-((3-fluoro-5-methoxyphenyl)amino)pyrrolidin-2-one | Enantiomer-I | 434.90 | RT = 8.14 min, ee = 100%; Column: WHELK-O1 @ (R,R) (250 × 4.6 mm), 5μ, Mobile Phase: CO$_2$:60% with % Co-solvent: 40% (0.2% DEA in methanol:IPA 1:1) Flow Rate: 4 ml/min, UV: 259 nm. | M: 16.61, 97.6%, N: 14.21, 96.9% | ¹H NMR (400 MHz, DMSO-d$_6$) δ ppm 13.13 (br.s, 1H) 8.32 (d, J = 2.32 Hz, 1H) 7.94 (br.s, 1H) 7.84 (dd, J = 8.53, 2.32 Hz, 1H) 7.76 (br.s, 1H) 7.58 (d, J = 8.53 Hz, 1H) 6.35 (d, J = 7.47 Hz, 1H) 6.10-6.17 (m, 2H) 6.01 (dt, J = 11.12, 2.19 Hz, 1H) 4.48 (dt, J = 9.98, 7.97 Hz, 1H) 3.82-3.95 (m, 2H) 3.70 (s, 3H) 2.58-2.67 (m, 1H) 1.85-1.99 (m, 1H); ¹⁹F NMR (376 MHz, DMSO-d$_6$) δ ppm −57.336, −112.517; [α]$_D^{25}$ = +36.00 (c 0.05, DMSO) |
| 370 | 1-(4-((1H-pyrazol-4-yl)-3-(trifluoromethyl)phenyl)-3-((3-fluoro-5-methoxyphenyl)amino)pyrrolidin-2-one | Enantiomer-II | 434.90 | RT = 9.94 min, ee = 100%; Column: WHELK-O1 @ (R,R) (250 × 4.6 mm), 5μ, Mobile Phase: CO$_2$:60% with % Co-solvent: 40% (0.2% DEA in methanol:IPA 1:1) Flow Rate: 4 ml/min, UV: 259 nm. | A: 9.93, 98.0%, B: 9.34, 98.3% | ¹H NMR (400 MHz, DMSO-d$_6$) δ ppm 13.11 (br.s, 1H) 8.32 (d, J = 2.32 Hz, 1H) 7.90 (br.s, 1H) 7.84 (dd, J = 8.60, 2.26 Hz, 1H) 7.64 (br.s, 1H) 7.58 (d, J = 8.53 Hz, 1H) 6.34 (d, J = 7.34 Hz, 1H) 6.10-6.17 (m, 2H) 6.01 (dt, J = 11.17, 2.20 Hz, 1H) 4.47 (dt, J = 10.02, 7.91 Hz, 1H) 3.81-3.96 (m, 2H) 3.70 (s, 3H) 2.58-2.66 (m, 1H) 1.84-1.98 (m, 1H); ¹⁹F NMR (376 MHz, DMSO-d$_6$) δ ppm −57.336, −112.517; [α]$_D^{25}$ = −40.00 (c 0.05, DMSO). |
| 371 | 1-(4-((1H-pyrazol-4-yl)-3-(trifluoromethyl)phenyl)-3-((4-fluoro-3-methoxyphenyl)amino)pyrrolidin-2-one | Enantiomer-I | 435.00 | RT 7.83 min, ee = 100%; Column: WHELK-O1 @ (R,R) (250 × 4.6 mm), 5μ, Mobile Phase: CO$_2$:60% with % Co-solvent: 40% (0.2% DEA in methanol:IPA 1:1) Flow Rate: 4 ml/min, UV: 259 nm. | A: 10.06, 98.2%, B: 9.47, 97.7% | ¹H NMR (400 MHz, DMSO-d$_6$) δ ppm 13.10 (br.s, 1H) 8.32 (d, J = 2.26 Hz, 1H) 7.86 (br.s, 1H) 7.85 (dd, J = 8.50, 2.29 Hz, 1H) 7.71 (br.s, 1H) 7.58 (d, J = 8.53 Hz, 1H) 6.93 (dd, J = 11.55, 8.72 Hz, 1H) 6.53 (dd, J = 7.53, 2.64 Hz, 1H) 6.22 (dt, J = 8.71, 3.11 Hz, 1H) 5.90 (d, J = 7.22 Hz, 1H) 4.42 (dt, J = 9.74, 7.84 Hz, 1 H) 3.84-3.95 (m, 2H) 3.76 (s, 3H) 2.58-2.66 (m, 1H) 1.92 (dq, J = 12.31, 9.47 Hz, 1H); ¹⁹F NMR (376 MHz, DMSO-d$_6$) δ ppm −57.325, −150.796; [α]$_D^{25.1}$ = +16.00 (c 0.05, DMSO). |

TABLE 10-continued

| Ex. | Structure and Name | Chirality | LCMS (M+H)+ | Chiral Purity | HPLC Method, RT (min) & Purity | ¹H NMR |
|---|---|---|---|---|---|---|
| 372 | 1-(4-(1H-pyrazol-4-yl)-3-(trifluoromethyl)phenyl)-3-((4-fluoro-3-methoxyphenyl)amino)pyrrolidin-2-one | Enantiomer-II | 435.20 | RT = 4.25 min, ee = 100%; Column: CHIRALPAK® IC (250 × 4.6 mm), 5μ, Mobile Phase: CO$_2$:60% with % Co-solvent: 40% (0.2% DEA in methanol), Flow Rate: 4 ml/min, UV: 259 nm. | M: 9.78, 97.6% N: 9.57, 98.2% | ¹H NMR (400 MHz, DMSO-d$_6$) δ ppm 13.11 (br.s, 1H) 8.33 (d, J = 2.32 Hz, 1H) 7.90 (br.s, 1H) 7.84 (dd, J = 8.50, 2.29 Hz, 1H) 7.62 (br.s, 1H) 7.58 (d, J = 8.53 Hz, 1H) 6.96 (dd, J = 11.67, 8.78 Hz, 1H) 6.46 (dd, J = 7.53, 2.95 Hz, 1H) 6.14 (dt, J = 8.75, 3.18 Hz, 1H) 5.76 (dd, J = 8.19, 2.23 Hz, 1H) 4.51-4.62 (m, 1H) 3.81-3.96 (m, 2H) 3.76 (s, 3H) 2.54-2.63 (m, 1H) 2.03-2.16 (m, 1H); ¹⁹F NMR (376 MHz, DMSO-d$_6$) δ ppm −52.325, −150.799; [α]$_D^{25}$ = −44.00 (c 0.05, DMSO). |
| 373 | 1-(4-(1H-pyrazol-4-yl)-3-(trifluoromethyl)phenyl)-3-((2-fluoro-5-methoxyphenyl)amino)pyrrolidin-2-one | Enantiomer-II | 434.90 | RT = 12.26 min, ee = 95.71%; Column: WHELK-O1® (R,R) (250 × 4.6 mm), 5μ, Mobile Phase: CO$_2$:60% with % Co-solvent: 40% (0.2% DEA in methanol:IPA (1:1) Flow Rate: 4 ml/min. | M: 17.03, 98.9% N: 14.16, 99.3% | ¹H NMR (400 MHz, DMSO-d$_6$) δ ppm 12.98 (br.s, 1H) 8.33 (d, J = 2.32 Hz, 1H) 7.84 (dd, J = 8.53, 2.26 Hz, 1 H) 7.77 (br. s, 2H) 7.58 (d, J = 8.47 Hz, 1H) 6.96 (dd, J = 11.67, 8.78 Hz, 1H) 6.46 (dd, J = 7.53, 2.95 Hz, 1H) 6.14 (dt, J = 8.77, 3.21 Hz, 1H) 5.76 (dd, J = 8.13, 2.23 Hz, 1H) 4.52-4.62 (m, 1H) 3.82-3.96 (m, 2H) 3.69 (s, 3H) 2.56-2.62 (m, 1H) 2.05-2.17 (m, 1H); ¹⁹F NMR (376 MHz, DMSO-d$_6$) δ ppm −57.320, −144.091; [α]$_D^{25.3}$ = −96.00 (c 0.05, DMSO). |
| 374 | 5-(3-((3-fluoro-5-methoxyphenyl)amino)-2-oxopyrrolidin-1-yl)-2-(1H-pyrazol-4-yl)benzonitrile | Enantiomer-I | 392.20 | RT = 9.06 min, ee = 100%; Column: CHIRALPAK® IC (250 × 4.6 mm), 5μ, Mobile Phase: CO$_2$:60% with % Co-solvent: 40% (0.1% NH$_4$OH in methanol). Flow Rate: 4 ml/min, UV: 270 nm. | A: 9.64, 99.9% B: 9.03, 99.8% | ¹H NMR (400 MHz, DMSO-d$_6$) δ ppm 13.20 (br. s., 1H) 8.16 (br. s., 2 H) 8.15 (d, J = 2.38 Hz, 1H) 8.07 (dd, J = 8.82, 2.48 Hz, 1H) 7.79 (d, J = 8.85 Hz, 1H) 6.32 (d, J = 7.47 Hz, 1H) 6.08-6.17 (m, 2H) 6.00 (dt, J = 11.17, 2.20 Hz, 1H) 4.46 (dt, J = 9.98, 7.91 Hz, 1H) 3.76-3.94 (m, 2H) 3.69 (s, 3H) 2.55-2.70 (m, 1H) 1.90 (dq, J = 12.17, 9.52 Hz, 1H); ¹⁹F NMR (376 MHz, DMSO-d$_6$) δ ppm −112.511; [α]$_D^{25.2}$ = +60.00 (c 0.05, DMSO). |

| Ex. | Structure and Name | Chirality | LCMS (M+H)+ | Chiral Purity | HPLC Method, RT (min) & Purity | 1H NMR |
|---|---|---|---|---|---|---|
| 375 | 5-(3-((3-fluoro-5-methoxyphenyl)amino)-2-oxopyrrolidin-1-yl)-2-(1H-pyrazol-4-yl)benzonitrile | Enantiomer-II | 392.20 | RT 11.09 min, ee = 98.65%; Column: CHIRALPAK® IC (250 × 4.6 mm), 5μ, Mobile Phase: CO₂:60% with % Co-solvent: 40% (0.1% NH₄OH in methanol). Flow Rate: 4 ml/min, UV: 270 nm. | A: 9.62, 99.5% B: 9.03, 99.4% | ¹H NMR (400 MHz, DMSO-d₆) δ ppm 13.22 (br. s., 1H) 8.16 (br. s., 2 H) 8.15 (d, J = 2.38 Hz, 1H) 8.07 (dd, J = 8.82, 2.48 Hz, 1H) 7.76-7.83 (m, 1H) 6.32 (d, J = 7.47 Hz, 1H) 6.09-6.17 (m, 2H) 6.00 (dt, J = 11.11, 2.20 Hz, 1H) 4.46 (dt, J = 9.99, 7.93 Hz, 1 H) 3.78-3.95 (m, 2H) 3.69 (s, 3H) 2.56-2.65 (m, 1H) 1.90 (dq, J = 12.25, 9.49 Hz, 1H); ¹⁹F NMR (376 MHz, DMSO-d₆) δ ppm −112.507; [α]²⁵_D = −60.00 (c 0.05, DMSO). |
| 376 | 5-(3-((3-fluoro-2-methoxyphenyl)amino)-2-oxopyrrolidin-1-yl)-2-(1H-pyrazol-4-yl)benzonitrile (Ena-II) | Enantiomer-II | 392.20 | RT-12.18 min, ee - 98.67%; Column: CHIRALPAK® AD-H (250 × 4.6 mm), 5μ, Mobile Phase: CO₂:60% with % Co-solvent: 40% (0.1% NH₄OH in methanol), Flow Rate: 4 ml/min, UV: 275 nm. | A: 9.94, 99.5% B: 9.27, 98.8% | ¹H NMR (400 MHz, DMSO-d₆) δ ppm 13.23 (br. s., 1H) 8.13-8.19 (m, 3H) 8.08 (dd, J = 8.85, 2.45 Hz, 1 H) 7.80 (d, J = 8.78 Hz, 1H) 6.89 (td, J = 8.28, 6.21 Hz, 1H) 6.61 (d, J = 8.41 Hz, 1H) 6.48 (ddd, J = 11.01, 8.35, 1.35 Hz, 1H) 5.66 (d, J = 7.59 Hz, 1 H) 4.49 (dt, J = 10.40, 8.01 Hz, 1H) 3.81-3.94 (m, 2H) 3.78 (s, 3H) 2.57-2.65 (m, 1H) 2.00-2.15 (m, 1H); ¹⁹F NMR (376 MHz, DMSO-d₆) δ ppm −132.905; [α]²⁵_D = −12.00 (c 0.05, DMSO). |
| 377 | 5-(3-((3-methoxyphenyl)amino)-2-oxopyrrolidin-1-yl)-2-(1H-pyrazol-4-yl)benzonitrile | Enantiomer-I | 374.20 | RT = 21.73 min, ee = 100%; Column: CHIRALPAK® IC (250 × 4.6 mm), 5μ, Mobile Phase: CO₂:60% with % Co-solvent: 40% (0.1% NH₄OH in methanol), Flow Rate: 4 ml/min, UV: 275 nm. | A: 9.06, 98.5% B: 8.55, 99.5% | ¹H NMR (400 MHz DMSO-d₆) δ ppm 13.24 (br. s., 1H) 8.13-8.19 (m, 3H) 8.07 (dd, J = 8.82, 2.48 Hz, 1H) 7.79 (d, J = 8.78 Hz, 1H) 6.99 (t, J = 8.00 Hz, 1H) 6.26-6.33 (m, 2H) 6.17 (ddd, J = 8.13, 2.32, 0.78 Hz, 1H) 5.96 (d, J = 7.34 Hz, 1H) 4.42 (dt, J = 9.77, 7.88 Hz, 1H) 3.78-3.94 (m, 2H) 3.68 (s, 3H) 2.56-2.65 (m, 1 H) 1.91 (dq, J = 12.24, 9.45 Hz, 1H); [α]²⁵_D = +444.00 (c 0.05, DMSO). |

TABLE 10-continued

| Ex. | Structure and Name | Chirality | LCMS (M+H)+ | Chiral Purity | HPLC Method, RT (min) & Purity | 1H NMR |
|---|---|---|---|---|---|---|
| 378 | 5-(3-((3-methoxyphenyl)amino)-2-oxopyrrolidin-1-yl)-2-(1H-pyrazol-4-yl)benzonitrile | Enantiomer-II | 374.20 | RT = 28.84 min, ee = 97.78%; Column: CHIRALPAK ® IC (250 × 4.6 mm), 5μ, Mobile Phase: CO$_2$:60% with % Co-solvent: 40% (0.1%NH$_4$OH in methanol), Flow Rate: 4 ml/min, UV: 275 nm. | A: 9.06, 96.1%; B: 8.56, 100% | 1H NMR (400 MHz DMSO-d$_6$) δ ppm 13.25 (br. s., 1H) 8.13-8.19 (m, 3H) 8.07 (dd, J = 8.85, 2.45 Hz, 1 H) 7.76-7.82 (m, 1H) 6.99 (t, J = 8.00 Hz, 1H) 6.26-6.34 (m, 2H) 6.17 (ddd, J = 8.13, 2.26, 0.78 Hz, 1H) 5.96 (d, J = 7.34 Hz, 1H) 4.42 (dt, J = 9.77, 7.91 Hz, 1H) 3.79-3.95 (m, 2H) 3.68 (s, 3H) 2.56-2.65 (m, 1 H) 1.91 (dq, J = 12.24, 9.43 Hz, 1H); [α]$_D^{25}$ = −32.00 (c 0.05, DMSO). |
| 379 | 5-(3-((4-fluoro-3-methoxyphenyl)amino)-2-oxopyrrolidin-1-yl)-2-(1H-pyrazol-4-yl)benzonitrile | Enantiomer-I | 392.20 | RT = 12.72 min, ee = 100%; Column: CHIRALPAK ® AD-H (250 × 4.6 mm), 5μ, Mobile Phase: CO$_2$:60% with % Co-solvent: 40% (0.1% NH$_4$OH in methanol), Flow Rate: 4 ml/min, UV: 275 nm. | A: 9.15, 99.6%; B: 8.66, 99.9% | 1H NMR (400 MHz DMSO-d$_6$) δ ppm 13.25 (br. s., 1H) 8.12-8.19 (m, 3H) 8.07 (dd, J = 8.82, 2.48 Hz, 1 H) 7.76-7.82 (m, 1H) 6.91 (dd, J = 11.51, 8.75 Hz, 1H) 6.52 (dd, J = 7.53, 2.64 Hz, 1H) 6.20 (dt, J = 8.66, 3.11 Hz, 1H) 5.88 (d, J = 7.15 Hz, 1H) 4.41 (dt, J = 9.68, 7.84 Hz, 1 H) 3.79-3.95 (m, 2H) 3.76 (s, 3H) 2.57-2.69 (m, 1H) 1.91 (dq, J = 12.31, 9.45 Hz, 1H); 19F NMR (376 MHz, DMSO-d$_6$) δ ppm −150.770;[α]$_D^{25}$ = +48.00 (c 0.05, DMSO). |
| 380 | 5-(3-((4-fluoro-3-methoxyphenyl)amino)-2-oxopyrrolidin-1-yl)-2-(1H-pyrazol-4-yl)benzonitrile | Enantiomer-II | 392.20 | RT = 26.61 min, ee = 99.32%; Column: CHIRALPAK ® AD-H (250 × 4.6 mm), 5μ, Mobile Phase: CO$_2$:60% with % Co-solvent: 40% (0.1% NH$_4$OH in methanol), Flow Rate: 4 ml/min, UV: 275 nm. | A: 9.15, 98.2%; B: 8.64, 97.1% | 1H NMR (400 MHz DMSO-d$_6$) δ ppm 13.25 (br. s., 1H) 8.12-8.19 (m, 3H) 8.07 (dd, J = 8.85, 2.45 Hz, 1 H) 7.79 (d, J = 8.78 Hz, 1H) 6.91 (dd, J = 11.51, 8.75 Hz, 1H) 6.52 (dd, J = 7.59, 2.64 Hz, 1H) 6.20 (dt, J = 8.67, 3.13 Hz, 1H) 5.88 (d, J = 7.15 Hz, 1H) 4.41 (dt, J = 9.71, 7.82 Hz, 1 H) 3.80-3.95 (m, 2H) 3.76 (s, 3H) 2.57-2.65 (m, 1H) 1.92 (dq, J = 12.31, 9.45 Hz, 1H); 19F NMR (376 MHz, DMSO-d$_6$) δ ppm −150.771; [α]$_D^{25}$ = −40.00 (c 0.05, DMSO). |

Example 383

(R)-1-(4-(1H-Pyrazol-4-yl)phenyl)-3-((3-methoxyphenyl)amino)pyrrolidin-2-one

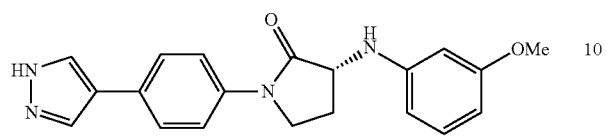

Example 383: Preparation of (R)-1-(4-(1H-pyrazol-4-yl)phenyl)-3-((3-methoxyphenyl) amino)pyrrolidin-2-one

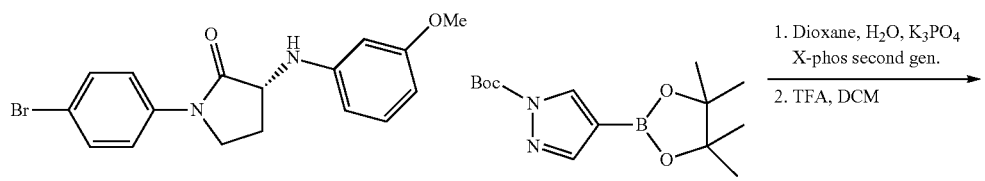

Example 383a

Preparation of (R)-1-(4-bromophenyl)-3-((3-methoxyphenyl)amino)pyrrolidin-2-one

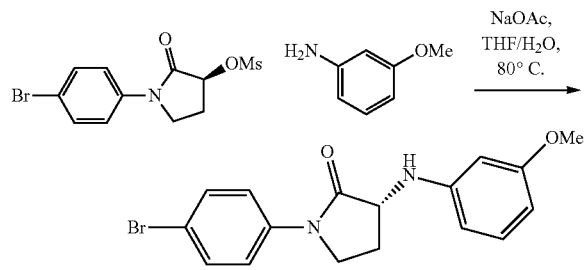

To a solution of (S)-1-(4-bromophenyl)-2-oxopyrrolidin-3-yl methanesulfonate (190 mg, 0.569 mmol) in THF (4 mL), was added 3-methoxyaniline (140 mg, 1.137 mmol), sodium acetate trihydrate (232 mg, 1.71 mmol) and water (4 mL). The reaction mixture was heated at 80° C. overnight. The reaction mixture was cooled to rt, diluted with ethyl acetate, washed with water, 0.75 N HCl and brine, dried over Na$_2$SO$_4$, filtered and concentrated to give brown gummy solid, which was purified by flash chromatography (0-100% EtOAc/hexane) to afford (R)-1-(4-bromophenyl)-3-((3-methoxyphenyl)amino)pyrrolidin-2-one (80 mg, 63%) as white solid. MS(ESI) m/z: 362.8 (M+H)$^+$; $^1$H NMR (400 MHz, DMSO-d$_6$) δ ppm 7.65-7.75 (m, 2H) 7.54-7.62 (m, 2H) 6.98 (t, J=8.03 Hz, 1H) 6.25-6.33 (m, 2H) 6.13-6.20 (m, 1H) 5.93 (d, J=7.53 Hz, 1H) 4.38 (dt, J=9.66, 7.72 Hz, 1H) 3.75-3.87 (m, 2H) 3.68 (s, 3H) 2.53-2.64 (m, 1H) 1.82-1.96 (m, 1H); 100% ee (rt=9.62) [Method: Column: CHIRALCEL® OJ-H (250×4.6 mm), 5μ; Mobile Phase: 0.2% DEA in methanol]; [α]$^{20.9}_D$=+4.0 (c 0.05, MeOH).

To a solution of (R)-1-(4-bromophenyl)-3-((3-methoxyphenyl)amino)pyrrolidin-2-one (75 mg, 0.208 mmol) in dioxane (6 mL) was added tert-butyl 4-(4,4,5,5-tetramethyl-1,3,2-dioxaborolan-2-yl)-1H-pyrazole-1-carboxylate (92 mg, 0.311 mmol), potassium phosphate tribasic (88 mg, 0.415 mmol) and water (1 mL). The mixture was bubbled with N$_2$ for 10 minutes, then 2nd generation XPhos precatalyst (9.8 mg, 0.012 mmol) was added. The mixture was bubbled with N$_2$ for 10 minutes, then the reaction mixture heated at 70° C. for 2.5 h. The reaction was cooled to rt and diluted with ethyl acetate, washed with water and brine, dried over Na$_2$SO$_4$, filtered and concentrated. The crude solid was dissolved in DCM (10 mL), then TFA (0.2 mL, 2.60 mmol) was added and the mixture was stirred at rt for 3 h. The solvents were removed in vacuo. The crude product was purified by preparative HPLC to afford (R)-1-(4-(1H-pyrazol-4-yl)phenyl)-3-((3-methoxyphenyl)amino)pyrrolidin-2-one (25 mg, 34%) as a white solid. MS(ESI) m/z: 349.2 (M+H)$^+$; $^1$H NMR (400 MHz, DMSO-d$_6$) δ ppm 12.92 (br. s., 1H) 8.17 (br. s., 1H) 7.92 (br. s., 1H) 7.60-7.71 (m, 4H) 6.99 (t, J=8.03 Hz, 1H) 6.26-6.34 (m, 2H) 6.17 (dd, J=7.53, 2.01 Hz, 1H) 5.93 (d, J=7.03 Hz, 1H) 4.32-4.41 (m, 1H) 3.80-3.87 (m, 2H) 3.68 (s, 3H) 2.56-2.65 (m, 1H) 1.82-1.95 (m, 1H); HPLC: RT=10.31 min, 98.2% (Method A) and RT=8.46 min, 97.0% (Method B); 98.6% ee (RT=5.59) [CHIRALCEL® AS-H (250×4.6 mm), 5μ, Mobile Phase: 0.2% DEA in MeOH, CO$_2$ Flow Rate: 2.1 ml/min]; [α]$^{24.8}_D$=+4.0 (c 0.05, MeOH).

The following Examples in Table 11 were made by using the same procedure as show in Example 383.

TABLE 11

| Ex. | Structure and Name | LCMS (M + H)+ | HPLC Method, RT (min) & Purity | 1H NMR |
|---|---|---|---|---|
| 384 | (R)-1-(4-(1H-pyrazol-4-yl)phenyl)-3-((2,4-dimethoxyphenyl)amino)pyrrolidin-2-one | 379.1 | C: 1.40, 96.0% | 1H NMR (400 MHz, DMSO-d6) δ ppm 12.91 (br. s., 1 H) 8.18 (br. s., 1 H) 7.94 (d, J = 2.51 Hz, 1 H) 7.67-7.76 (m, 2 H) 7.54-7.67 (m, 2 H) 6.63 (d, J = 9.04 Hz, 1 H) 6.48-6.57 (m, 1 H) 6.40 (dd, J = 8.53, 2.51 Hz, 1 H) 4.75 (d, J = 4.02 Hz, 1 H) 4.08-4.21 (m, 1 H) 3.82-3.89 (m, 2 H) 3.81 (s, 3 H) 3.69 (s, 3 H) 2.72 (td, J = 7.91, 3.76 Hz, 1 H) 1.81-1.99 (m, 1 H). |
| 385 | (R)-1-(4-(1H-pyrazol-4-yl)phenyl)-3-((2,3-dimethoxyphenyl)amino)pyrrolidin-2-one | 379.1 | D: 1.40, 99.0% | 1H NMR (400 MHz, DMSO-d6) δ ppm 12.91 (br. s., 1 H) 8.17 (br. s., 1 H) 7.91 (br. s., 1 H) 7.71 (m, J = 8.78 Hz, 2 H) 7.63 (m, J = 8.78 Hz, 2 H) 6.86 (t, J = 8.16 Hz, 1 H) 6.42 (d, J = 7.53 Hz, 1 H) 6.37 (dd, J = 8.28, 1.00 Hz, 1 H) 5.29 (d, J = 6.27 Hz, 1 H) 4.24-4.39 (m, 1 H) 3.84 (dd, J = 9.66, 4.14 Hz, 2 H) 3.73-3.78 (m, 3 H) 3.65-3.72 (m, 3 H) 2.61-2.66 (m, 1 H) 1.91-2.06 (m, 1 H). |
| 386 | (R)-1-(4-(1H-pyrazol-4-yl)phenyl)-3-(benzo[d][1,3]dioxol-4-ylamino)pyrrolidin-2-one | 363.2 | D: 1.31, 95.7% | 1H NMR (400 MHz, DMSO-d6) δ ppm 12.90 (br. s., 1 H) 8.17 (br. s., 1 H) 7.91 (br. s., 1 H) 7.66-7.75 (m, 2 H) 7.54-7.66 (m, 2 H) 6.67 (d, J = 8.53 Hz, 1 H) 6.45 (d, J = 2.26 Hz, 1 H) 6.15 (dd, J = 8.53, 2.26 Hz, 1 H) 5.85 (s, 2 H) 5.63 (d, J = 6.52 Hz, 1 H) 4.17-4.31 (m, 1 H) 3.69-3.88 (m, 2 H) 2.56-2.64 (m, 1 H) 1.85 (dq, J = 12.23, 9.31 Hz, 1 H). |
| 387 | (R)-3-((1-(4-(1H-pyrazol-4-yl)phenyl)-2-oxopyrrolidin-3-yl)amino)benzonitrile | 344.2 | D: 1.33, 98.2% | 1H NMR (400 MHz, DMSO-d6) δ ppm 12.91 (br. s., 1 H) 8.17 (br. s., 1 H) 7.91 (br. s., 1 H) 7.65-7.74 (m, 2 H) 7.56-7.65 (m, 2 H) 7.21-7.32 (m, 1 H) 7.06-7.11 (m, 1 H) 7.04 (dd, J = 8.41, 1.63 Hz, 1 H) 6.97 (d, J = 7.52 Hz, 1 H) 6.53 (d, J = 7.53 Hz, 1 H) 4.50 (dt, J = 9.98, 7.81 Hz, 1 H) 3.73-3.94 (m, 2 H) 2.57-2.65 (m, 1 H) 1.81-1.98 (m, 1 H). |
| 388 | 3-((1-(4-(1H-pyrazol-4-yl)phenyl)-2-oxopyrrolidin-3-yl)amino)benzamide | 362.3 | C: 0.91, 98.6% | 1H NMR (400 MHz, DMSO-d6) δ ppm 12.90 (br. s., 1 H) 8.17 (br. s., 1 H) 7.91 (br. s., 1 H) 7.76 (m, J = 8.78 Hz, 2 H) 7.70 (m, J = 8.78 Hz, 2 H) 7.63 (m, J = 8.78 Hz, 2 H) 7.17-7.25 (m, 2 H) 7.14 (t, J = 7.78 Hz, 1 H) 7.08 (d, J = 7.53 Hz, 1 H) 6.86 (dd, J = 8.03, 1.51 Hz, 1 H) 6.08 (d, J = 7.28 Hz, 1 H) 4.37-4.52 (m, 1 H) 3.78-3.93 (m, 2 H) 2.62 (tt, J = 7.75, 3.92 Hz, 1 H) 1.84-1.98 (m, 1 H). |
| 389 | (R)-1-(4-(1H-pyrazol-4-yl)phenyl)-3-((3,4-dimethoxyphenyl)amino)pyrrolidin-2-one | 379.3 | D: 1.22, 98.5% | 1H NMR (400 MHz, DMSO-d6) δ ppm 12.91 (br. s., 1 H) 8.17 (br. s., 1 H) 7.91 (br. s., 1 H) 7.66-7.76 (m, 2 H) 7.53-7.66 (m, 2 H) 6.73 (d, J = 8.53 Hz, 1 H) 6.45 (d, J = 2.76 Hz, 1 H) 6.20 (dd, J = 8.78, 2.51 Hz, 1 H) 5.51 (d, J = 6.78 Hz, 1 H) 4.20-4.35 (m, 1 H) 3.76-3.91 (m, 2 H) 3.70 (s, 3 H) 3.64 (s, 3 H) 2.56-2.65 (m, 1 H) 1.88 (dq, J = 12.14, 9.34 Hz, 1 H). |
| 390 | (R)-1-(4-(1H-pyrazol-4-yl)phenyl)-3-((3-(dimethylamino)phenyl)amino)pyrrolidin-2-one | 362.3 | D: 1.47, 95.7% | 1H NMR (400 MHz, DMSO-d6) δ ppm 12.91 (br. s., 1 H) 8.16 (br. s., 1 H) 7.93 (br. s., 1 H) 7.70 (m, J = 8.78 Hz, 2 H) 7.63 (m, J = 8.78 Hz, 2 H) 6.90 (t, J = 8.03 Hz, 1 H) 5.91-6.19 (m, 3 H) 5.62 (d, J = 6.02 Hz, 1 H) 4.26-4.43 (m, 1 H) 3.84 (dd, J = 9.16, 4.64 Hz, 2 H) 2.84 (s, 6 H) 2.60 (ddt, J = 12.27, 8.19, 4.33, 4.33 Hz, 1 H) 1.90 (dq, J = 12.11, 9.35 Hz, 1 H). |
| 391 | N-(3-((1-(4-(1H-pyrazol-4-yl)phenyl)-2-oxopyrrolidin-3-yl)amino)phenyl)acetamide | 376.2 | C: 1.25, 97.7% | 1H NMR (400 MHz, DMSO-d6) δ ppm 12.90 (br. s., 1 H) 9.67 (s, 1 H) 8.17 (br. s., 1 H) 7.92 (br. s., 1 H) 7.67-7.78 (m, 2 H) 7.54-7.67 (m, 2 H) 7.01-7.07 (m, 1 H) 6.91-7.01 (m, 1 H) 6.79 (d, J = 8.03 Hz, 1 H) 6.42 (dd, J = 8.03, 1.51 Hz, 1 H) 5.91 (d, J = 7.03 Hz, 1 H) 4.21-4.37 (m, 1 H) 3.85 (dd, J = 9.41, 4.39 Hz, 2 H) 2.56-2.65 (m, 1 H) 2.01 (s, 3 H) 1.84-1.97 (m, 1 H). |
| 392 | (R)-1-(4-(1H-pyrazol-4-yl)phenyl)-3-((2,2-dioxido-1,3-dihydrobenzo[c]thiophen-5-yl)amino)pyrrolidin-2-one | 409.2 | C: 1.09, 97.1% | 1H NMR (400 MHz, DMSO-d6) δ ppm 12.91 (br. s., 1 H) 8.16 (br. s., 1 H) 7.92 (br. s., 1 H) 7.70 (m, J = 8.78 Hz, 2 H) 7.63 (m, J = 8.78 Hz, 2 H) 7.09 (d, J = 8.28 |

TABLE 11-continued

| Ex. | Structure and Name | LCMS (M + H)+ | HPLC Method, RT (min) & Purity | 1H NMR |
|---|---|---|---|---|
| | | | | Hz, 1 H) 6.65-6.79 (m, 2 H) 6.19 (d, J = 7.03 Hz, 1 H) 4.38-4.45 (m, 1 H) 4.33-4.38 (m, 2 H) 4.30 (s, 2 H) 3.76-3.92 (m, 2 H) 2.58-2.65 (m, 1 H) 1.83-1.98 (m, 1 H). |
| 393 | 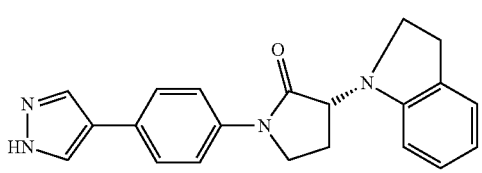 (R)-1-(4-(1H-pyrazol-4-yl)phenyl)-3-(indolin-1-yl)pyrrolidin-2-one | 345.2 | C: 1.77, 94.5% | 1H NMR (400 MHz, DMSO-d6) δ ppm 12.91 (br. s., 1 H) 8.17 (br. s., 1 H) 7.92 (br. s., 1 H) 7.66-7.75 (m, 2 H) 7.58-7.66 (m, 2 H) 7.04 (d, J = 6.78 Hz, 1 H) 6.97 (t, J = 7.65 Hz, 1 H) 6.51-6.64 (m, 2 H) 4.76 (dd, J = 10.29, 8.78 Hz, 1 H) 3.77-3.93 (m, 2 H) 3.47-3.58 (m, 1 H) 3.34-3.41 (m, 1 H) 2.87-3.02 (m, 2 H) 2.34-2.42 (m, 1 H) 2.09-2.22 (m, 1H). |
| 394 | 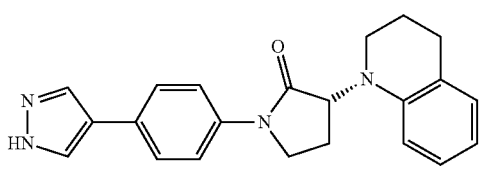 (R)-1-(4-(1H-pyrazol-4-yl)phenyl)-3-(3,4-dihydroquinolin-1(2H)-yl)pyrrolidin-2-one | 359.3 | D: 1.64, 98.4% | 1H NMR (400 MHz, DMSO-d6) δ ppm 12.91 (br. s., 1 H) 8.17 (br. s., 1 H) 7.91 (br. s., 1 H) 7.67-7.74 (m, 2 H) 7.51-7.67 (m, 2 H) 6.85-7.06 (m, 2 H) 6.75 (d, J = 8.28 Hz, 1 H) 6.53 (t, J = 7.28 Hz, 1 H) 4.95 (t, J = 9.54 Hz, 1 H) 3.74-3.94 (m, 2 H) 3.07-3.23 (m, 2 H) 2.67-2.75 (m, 2 H) 2.34-2.44 (m, 1 H) 2.06-2.23 (m, 1 H) 1.73-2.02 (m, 2 H) 1.36 (s, 1 H). |
| 395 | 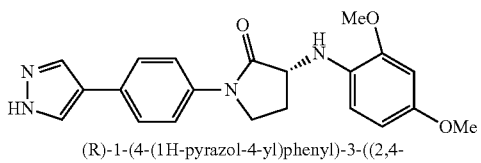 (R)-1-(4-(1H-pyrazol-4-yl)phenyl)-3-((2,4-dimethoxyphenyl)amino)pyrrolidin-2-one | 379.3 | D:, 1.44, 91.9% | 1H NMR (400 MHz, DMSO-d6) δ ppm 12.92 (br. s., 1 H) 8.17 (br. s., 2 H) 7.89 (s, 1 H) 7.93 (s, 1 H) 7.79-7.85 (m, 1 H) 7.67-7.76 (m, 3 H) 7.57-7.67 (m, 2 H) 6.63 (d, J = 9.04 Hz, 1 H) 6.51-6.57 (m, 1 H) 6.40 (dd, J = 8.53, 2.51 Hz, 1 H) 4.74 (d, J = 4.52 Hz, 1 H) 4.50 (d, J = 2.51 Hz, 1 H) 4.10-4.22 (m, 1 H) 3.89 (s, 1 H) 3.82-3.87 (m, 2 H) 3.81 (s, 3 H) 3.75 (s, 1 H) 3.69 (s, 3 H) 2.69-2.76 (m, 1 H) 1.83-1.99 (m, 1 H) 1.19-1.30 (m, 2 H). |
| 396 | 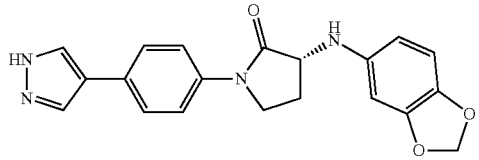 [SMILES: O=C1[C@H](Nc2ccc3c(c2)OCO3)CCN1c1ccc(-c2cn[nH]c2)cc1] (R)-1-(4-(1H-pyrazol-4-yl)phenyl)-3-(benzo[d][1,3]dioxol-5-ylamino)pyrrolidin-2-one | 363.1 | C: 1.15, 96.6% | 1H NMR (400 MHz, DMSO-d6) δ ppm 12.91 (br. s., 1 H) 8.17 (br. s., 1 H) 7.91 (br. s., 1 H) 7.67-7.72 (m, 2 H) 7.57-7.67 (m, 2 H) 6.68 (d, J = 8.53 Hz, 1 H) 6.45 (d, J = 2.51 Hz, 1 H) 6.15 (dd, J = 8.28, 2.26 Hz, 1 H) 5.85 (s, 2 H) 5.63 (d, J = 7.03 Hz, 1 H) 4.19-4.32 (m, 1 H) 3.74-3.88 (m, 2 H) 2.61 (dd, J = 3.51, 2.01 Hz, 1 H) 1.81-1.93 (m, 1 H) 1.24 (s, 2 H) |

What is claimed is:

1. A compound according to Formula (I):

$$(I)$$

or an enantiomer, a diastereomer, a stereoisomer, a tautomer, or a pharmaceutically acceptable salt thereof, wherein Ring A is independently selected from $J_1$, $J_2$, $J_3$, and $J_4$ are independently selected from N, $CR_3$ and $CR_4$; provided no more than two of $J_1$, $J_2$, $J_3$, and $J_4$ are N;

K is independently selected from the group consisting of N, $CR_1$ and $CR_2$;

L is $NR_6(CR_7R_7)_m$;

$R_1$ is independently selected from the group consisting of H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$ is independently selected from the group consisting of H, F, Cl, Br, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from the group consisting of H, F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)k(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from the group consisting of H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is independently selected from the group consisting of H, =O, $C_{1-4}$alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_6$ is independently selected from the group consisting of H and $C_{1-4}$alkyl substituted with 0-4 $R_e$;

$R_7$ is independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$; alternatively, $R_7$ and $R_7$ form =O;

$R_8$ is independently selected from the group consisting of $C_{3-6}$ cycloalkyl, heterocyclyl, aryl and heteroaryl, each substituted with 0-5 $R_9$;

alternatively, when m is zero, $R_8$ and $R_6$ together with the nitrogen atom to which they are both attached form a heterocyclic ring substituted with 0-5 $R_9$;

$R_9$ is independently selected from the group consisting of H, =O, F, Cl, Br, $C_{1-4}$alkyl, $C_{2-4}$alkenyl, $C_{2-4}$alkynyl, nitro, —$(CR_dR_d)_rS(O)_pR_c$, —$(CR_dR_d)_rS(O)_pNR_aR_a$, —$(CR_dR_d)_rNR_aS(O)_pR_c$, —$(CR_dR_d)_rOR_b$, —$(CR_dR_d)_rCN$, —$(CR_dR_d)_rNR_aR_a$, —$(CR_dR_d)_rNR_aC(=O)R_b$, —$(CR_dR_d)_rNR_aC(=O)NR_aR_a$, —$(CR_dR_d)_rNR_aC(=O)OR_b$, —$(CR_dR_d)_rC(=O)OR_b$, —$(CR_dR_d)_rC(=O)NR_aR_a$, —$(CR_dR_d)_rC(=O)R_b$, —$(CR_dR_d)_rOC(=O)R_b$, —$(CR_dR_d)_rOC(=O)NR_aR_a$, —$(CR_dR_d)_r$-cycloalkyl, —$(CR_dR_d)_r$-heterocyclyl, —$(CR_dR_d)_r$-aryl, and —$(CR_dR_d)_r$-heteroaryl, wherein said alkyl, cycloalkyl, heterocyclyl, aryl, or heteroaryl is substituted with 0-4 $R_e$;

$R_a$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from the group consisting of H and $C_{1-4}$alkyl substituted with 0-5 $R_e$;

$R_e$, at each occurrence, is independently selected from the group consisting of $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$—$C_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O) NR$_f$R$_f$ and —(CH$_2$)$_r$NR$_f$R$_f$;

$R_f$, at each occurrence, is independently selected from the group consisting of H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

m is independently selected from zero, 1, and 2;

p, at each occurrence, is independently selected from zero, 1, and 2; and r, at each occurrence, is independently selected from zero, 1, 2, 3, and 4.

2. The compound of claim 1 or an enantiomer, a diastereomer, a stereoisomer, a tautomer, or a pharmaceutically acceptable salt thereof, wherein $R_1$ is independently selected from the group consisting of H, F, Cl, Br, OH, CN, NR$_a$R$_a$, —OC$_{1-4}$ alkyl substituted with 0-3 $R_e$, and $C_{1-4}$ alkyl substituted with 0-3 $R_e$;

$R_2$ is independently selected from the group consisting of H, F, Cl, Br, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$NR$_a$S(O)$_p$NR$_a$R$_a$, and —(CH$_2$)$_r$NR$_a$S(O)$_p$R$_c$;

$R_3$ is independently selected from the group consisting of H, F, Cl, Br, CN, $C_{1-4}$ alkyl substituted with 0-3 $R_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$N-R$_a$C(=O)R$_b$, —(CH$_2$)$_r$OC(=O)NR$_a$R$_a$, —(CH$_2$)$_r$N-R$_a$C(=O)NR$_a$R$_a$, —(CH$_2$)$_r$C(=O)OR$_b$, —(CH$_2$)$_r$S (O)$_p$NR$_a$R$_a$, —(CH$_2$)$_r$—$C_{3-6}$ carbocyclyl substituted with 0-3 $R_e$, and —(CH$_2$)$_r$-heterocyclyl substituted with 0-3 $R_e$;

$R_4$ is independently selected from the group consisting of H, F, Cl, Br, OH, CN, and $C_{1-4}$ alkyl substituted with 0-3 $R_e$;

$R_5$ is independently selected from the group consisting of H, =O, $C_{1-4}$alkyl substituted with 0-4 $R_e$, —(CH$_2$)$_r$OR$_b$, C(=O)R$_b$, and —C(=O)OR$_b$;

$R_6$ is independently selected from the group consisting of H and $C_{1-4}$alkyl substituted with 0-4 $R_e$;

$R_7$ is independently selected from the group consisting of H, $C_{1-4}$alkyl substituted with 0-4 $R_e$, —(CH$_2$)$_r$OR$_b$, —(CH$_2$)$_r$C(=O)R$_b$, —(CH$_2$)$_r$NR$_a$C(=O)R$_b$, —(CH$_2$)$_r$C(=O)OR$_b$, (CH$_2$)$_r$-$C_{3-6}$ carbocyclyl substituted with 0-3 $R_e$, and —(CH$_2$)$_r$-heterocyclyl substituted with 0-3 $R_e$;

$R_8$ is independently selected from the group consisting of

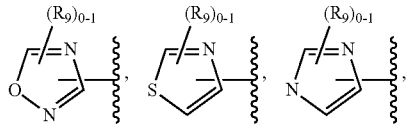

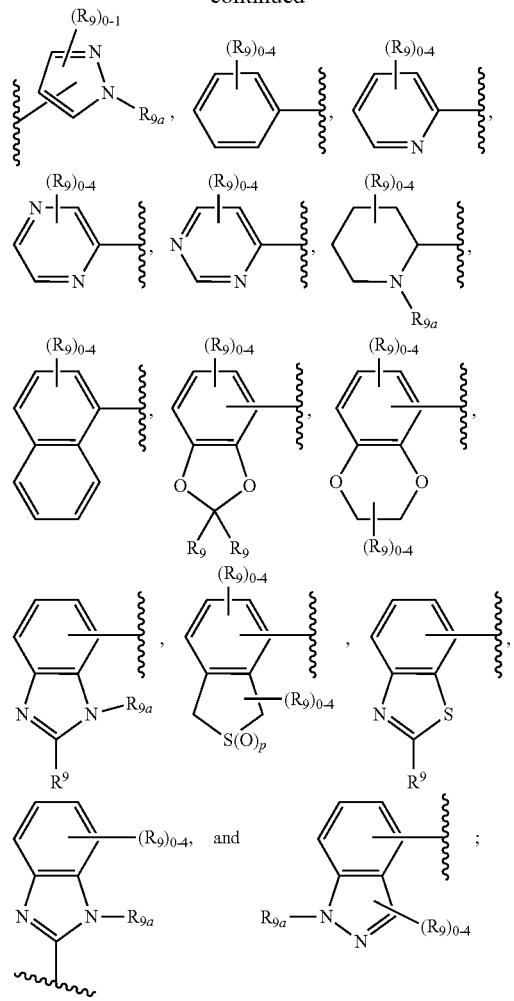

$R_9$ is independently selected from the group consisting of H, =O, F, Cl, Br, $C_{1-4}$alkyl, $C_{2-4}$alkenyl, $C_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C (=O)R$_b$, —(CHR$_d$)$_r$NR$_a$C(=O)NR$_a$R$_a$, —(CHR$_d$)$_r$N-R$_a$C(=O)OR$_b$, —(CHR$_d$)$_r$C(=O)OR$_b$, —(CHR$_d$)$_r$C (=O)NR$_a$R$_a$, —(CHR$_d$)$_r$OC(=O)NR$_a$R$_a$, —(CHR$_d$)$_r$C(=O)R$_b$, —(CHR$_d$)$_r$ OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 $R_e$;

$R_{9a}$ is independently selected from the group consisting of H, $C_{1-4}$ alkyl, —S(O)$_p$R$_c$, —S(O)$_p$NR$_a$R$_a$, —C(=O) OR$_b$, —(CH$_2$)$_r$C(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_a$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_e$, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_a$, at each occurrence, is independently selected from the group consisting of H and $C_{1-4}$alkyl substituted with 0-5 $R_e$;

$R_e$, at each occurrence, is independently selected from the group consisting of $C_{1-6}$ alkyl substituted with 0-5 $R_f$, $C_{2-6}$ alkenyl, Cab alkynyl, —(CH$_2$)$_r$—$C_{3-6}$ cycloalkyl, —(CH$_2$)$_r$—$C_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

3. The compound of claim 2, having Formula (II):

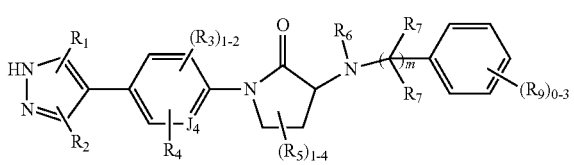

(II)

or an enantiomer, a diastereomer, a stereoisomer, a tautomer, or a pharmaceutically acceptable salt thereof, wherein $J_4$ is independently selected from the group consisting of N and CR$_4$;

$R_1$ is independently selected from the group consisting of H, F, Cl, Br, CN, NR$_a$R$_a$, and $C_{1-4}$alkyl substituted with 0-4 $R_e$;

$R_2$ is independently selected from the group consisting of H, F, Cl, Br, OH, CN, NR$_a$R$_a$, and $C_{1-4}$alkyl substituted with 0-4 $R_e$;

$R_3$ is independently selected from the group consisting of H, F, Cl, Br, CN, $C_{1-4}$ alkyl substituted with 0-3 $R_e$, —(CH$_2$)$_r$OR$_b$, —NR$_a$R$_a$, C(=O)NR$_a$R$_a$, and $C_{3-6}$ cycloalkyl substituted with 0-3 $R_e$;

$R_4$ is independently selected from the group consisting of H, F, Cl, Br, OH, CN, OC$_{1-4}$ alkyl substituted with 0-3 $R_e$, and $C_{1-4}$ alkyl substituted with 0-3 $R_e$;

$R_5$ is independently selected from the group consisting of H, =O, $C_{1-4}$alkyl substituted with 0-4 $R_e$, —(CH$_2$)$_r$OR$_b$, C(=O)R$_b$, and —C(=O)OR$_b$;

$R_6$ is independently selected from the group consisting of H and $C_{1-4}$alkyl substituted with 0-4 $R_e$;

$R_7$ is independently selected from H, $C_{1-4}$alkyl substituted with 0-4 $R_e$, and —(CH$_2$)$_r$OR$_b$;

alternatively, $R_7$ and $R_7$ form =O;

$R_9$ is independently selected from the group consisting of F, Cl, Br, $C_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$C(=O)OR$_b$, —(CH$_2$)$_r$C(=O)NR$_a$R$_a$, —(CH$_2$)$_r$OC(=O)NR$_a$R$_a$, —(CH$_2$)$_r$C(=O)R$_b$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_a$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_e$, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from the group consisting of $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$—$C_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

m is independently selected from zero, 1, and 2;

p, at each occurrence, is independently selected from zero, 1, and 2; and r, at each occurrence, is independently selected from zero, 1, 2, 3, and 4.

4. The compound of claim 3, having Formula (III):

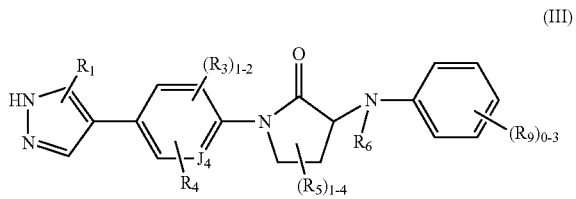

(III)

or an enantiomer, a diastereomer, a stereoisomer, a tautomer, or a pharmaceutically acceptable salt thereof, wherein $J_4$ is independently selected from the group consisting of N and CR$_4$;

$R_1$ is independently selected from the group consisting of H, F, Cl, Br, CN, NR$_a$R$_a$, and $C_{1-4}$alkyl substituted with 0-4 $R_e$;

R₃ is independently selected from the group consisting of H, F, Cl, Br, CN, $C_{1-4}$ alkyl substituted with 0-3 $R_e$, —$(CH_2)_rOR_b$, —$NR_aR_a$, $C(=O)NR_aR_a$, and $C_{3-6}$ cycloalkyl substituted with 0-3 $R_e$;

R₄ is independently selected from H, F, Cl, Br, OH, CN, $OC_{1-4}$ alkyl substituted with 0-3 $R_e$, and $C_{1-4}$ alkyl substituted with 0-3 $R_e$;

R₅ is independently selected from the group consisting of H, =O, $C_{1-4}$alkyl substituted with 0-4 $R_e$, —$(CH_2)_rOR_b$, $C(=O)R_b$, and —$C(=O)OR_b$;

R₆ is independently selected from the group consisting of H and $C_{1-4}$alkyl substituted with 0-4 $R_e$;

R₉ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rN-R_aC(=O)NR_aR_a$, —$(CH_2)_rNR_aC(=O)OR_b$, —$(CH_2)_rC(=O)OR_b$, —$(CH_2)_rC(=O)NR_aR_a$, —$(CH_2)_rOC(=O)NR_aR_a$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

R_a, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

R_b, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

R_c, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

R_e, at each occurrence, is independently selected from the group consisting of $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

R_f, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

5. The compound of claim 4, or enantiomer, a diastereomer, a stereoisomer, a tautomer, or a pharmaceutically acceptable salt thereof, wherein R₁ is independently selected from the group consisting of H and $C_{1-4}$alkyl;

R₃ is independently selected from the group consisting of H, F, Cl, CN, $C_{1-3}$ alkyl substituted with 0-3 $R_e$, —$OC_{1-3}$ alkyl substituted with 0-3 $R_e$, $NR_aR_a$, $C(=O)NR_aR_a$, and $C_{3-6}$ cycloalkyl;

R₅ is independently selected from the group consisting of H, =O, $C_{1-4}$alkyl substituted with 0-4 $R_e$, —$(CH_2)_rOR_b$, $C(=O)R_b$, and —$C(=O)OR_b$;

R₆ is H;

R₉ is independently selected from the group consisting of F, Cl, $C_{1-4}$ alkyl, —$OR_b$, CN, $S(O)_pNR_aR_a$, $NHS(O)_pR_c$, $NR_aR_a$, $C(=O)NR_aR_a$, $NR_aC(=O)R_b$, $C_{3-6}$ cycloalkyl, and heterocyclyl, wherein said alkyl, cycloalkyl, or heterocyclyl is substituted with 0-4 $R_e$;

R_a, at each occurrence, is independently selected from the group consisting of H and $C_{1-6}$ alkyl substituted with 0-5 $R_e$; or $R_a$ and $R_a$ together with the nitrogen atom to which they are both attached form a heterocyclic ring substituted with 0-5 $R_e$;

R_b, at each occurrence, is independently selected from the group consisting of H, $C_{1-6}$ alkyl substituted with 0-5 $R_e$, $C_{3-6}$ cycloalkyl substituted with 0-5 $R_e$, and —$(CH_2)_r$-heterocyclyl substituted with 0-5 $R_e$;

R_c, at each occurrence, is independently selected from the group consisting of $C_{1-6}$ alkyl substituted with 0-5 $R_e$;

R_e, at each occurrence, is independently selected from the group consisting of $C_{1-6}$ alkyl substituted with 0-5 $R_f$, F, Cl, Br, CN, $NO_2$, =O, $CO_2H$, OH, and $OC_{1-4}$alkyl; and r, at each occurrence, is independently selected from zero, 1, 2, and 3.

6. The compound of claim 2, having Formula (VI):

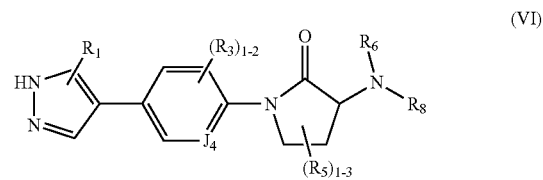

(VI)

or an enantiomer, a diastereomer, a stereoisomer, a tautomer, or a pharmaceutically acceptable salt thereof, wherein J₄ is independently selected from the group consisting of N and $CR_4$;

R₁ is independently selected from the group consisting of H, F, Cl, Br, CN, $NR_aR_a$, and $C_{1-4}$alkyl substituted with 0-4 $R_e$;

R₃ is independently selected from the group consisting of H, F, CN, $C_{1-4}$ alkyl substituted with 0-3 $R_e$, and —$OR_b$;

R₄ is independently selected from the group consisting of H, F, Cl, Br, OH, CN, $OC_{1-4}$ alkyl substituted with 0-3 $R_e$, and $C_{1-4}$ alkyl substituted with 0-3 $R_e$;

R₅ is independently selected from the group consisting of H, =O, $C_{1-4}$alkyl substituted with 0-4 $R_e$, —$(CH_2)_rOR_b$, $C(=O)R_b$, and —$C(=O)OR_b$;

R₆ and R₈ together with the nitrogen atom to which they are both attached form a heterocyclic ring substituted with 0-5 $R_9$;

R₉ is independently selected from the group consisting of H, =O, F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

R_a, at each occurrence, is independently selected from the group consisting of H, $C_{1-6}$ alkyl substituted with 0-5

$R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from the group consisting of $C_{1-6}$ alkyl substituted with 0-5 $R_f$, $C_{2-6}$ alkenyl, Cab alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

7. The compound of claim 6, or an enantiomer, a diastereomer, a stereoisomer, a tautomer, or a pharmaceutically acceptable salt thereof, wherein $R_6$ and $R_8$ together with the nitrogen atom to which they are both attached form a heterocyclic ring substituted with 0-5 $R_9$, wherein the heterocyclic ring is selected from the group consisting of

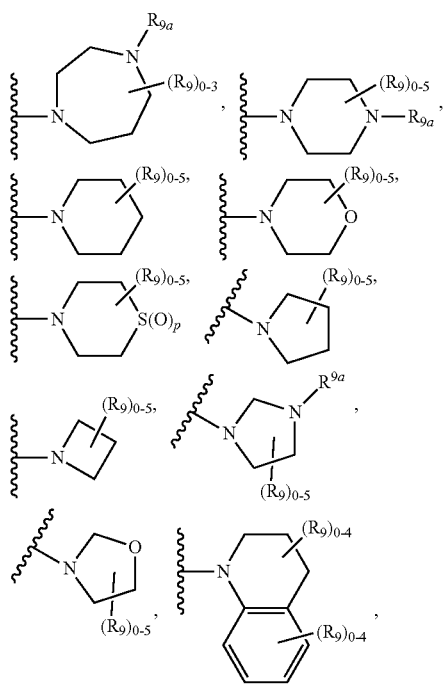

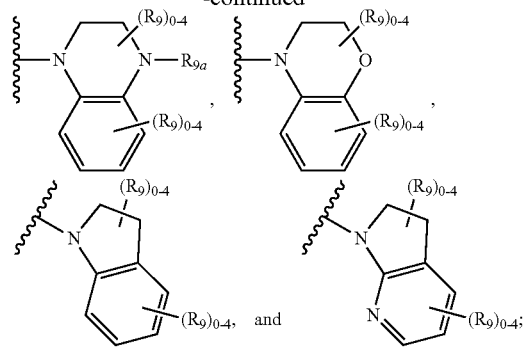

$R_9$ is independently selected from the group consisting of H, =O, F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_{9a}$ is independently selected from the group consisting of H, $C_{1-4}$ alkyl, —$S(O)_pR_c$, —$S(O)_pNR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_e$, at each occurrence, is independently selected from the group consisting of $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

8. The compound of claim 2, having Formula (VII):

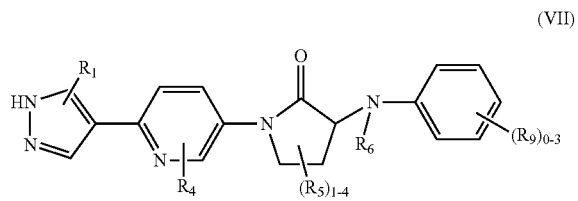

(VII)

or an enantiomer, a diastereomer, a stereoisomer, a tautomer, or a pharmaceutically acceptable salt thereof, wherein $R_1$ is independently selected from the group consisting of H, F, Cl, Br, CN, $NR_aR_a$, and $C_{1-4}$alkyl substituted with 0-4 $R_e$;

$R_4$ is independently selected from the group consisting of H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from the group consisting of H, =O, $C_{1-4}$alkyl substituted with 0-4 $R_e$, —$(CH_2)_r OR_b$, $C(=O)R_b$, and —$C(=O)OR_b$;

$R_6$ is independently selected from the group consisting of H and $C_{1-4}$alkyl substituted with 0-4 $R_e$;

$R_9$ is independently selected from the group consisting of F, Cl, Br, $C_{1-4}$ alkyl, nitro, —$(CH_2)_r S(O)_p R_c$, —$(CH_2)_r S(O)_p NR_a R_a$, —$(CH_2)_r NR_a S(O)_p R_c$, —$(CH_2)_r OR_b$, —$(CH_2)_r CN$, —$(CH_2)_r NR_a R_a$, —$(CH_2)_r NR_a C(=O)R_b$, —$(CH_2)_r NR_a C(=O)NR_a R_a$, —$(CH_2)_r NR_a C(=O)OR_b$, —$(CH_2)_r C(=O)OR_b$, —$(CH_2)_r C(=O)NR_a R_a$, —$(CH_2)_r OC(=O)NR_a R_a$, —$(CH_2)_r C(=O)R_b$, —$(CH_2)_r OC(=O)R_b$, —$(CH_2)_r C(=O)NR_a R_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from the group consisting of $C_{1-6}$ alkyl substituted with 0-5 $R_f$, $C_{2-6}$ alkenyl, Cab alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r OR_f$, $S(O)_p R_f$, $S(O)_p NR_f R_f$, and —$(CH_2)_r NR_f R_f$;

$R_f$, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

9. The compound of claim 2, having Formula (VIII):

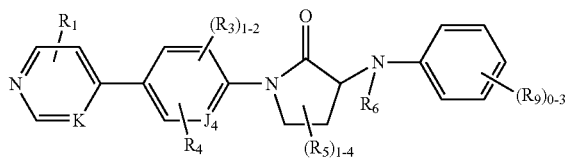

(VIII)

or an enantiomer, a diastereomer, a stereoisomer, a tautomer, or a pharmaceutically acceptable salt thereof, wherein $J_4$ is independently selected from the group consisting of N and $CR_4$;

K is independently selected from the group consisting of N and $CR_1$;

$R_1$ is independently selected from the group consisting of H, F, Cl, Br, CN, $NR_a R_a$, and $C_{1-4}$alkyl substituted with 0-4 $R_e$;

$R_3$ is independently selected from the group consisting of H, F, Cl, Br, CN, $C_{1-4}$ alkyl substituted with 0-3 $R_e$, and —$(CH_2)_r OR_b$;

$R_4$ is independently selected from the group consisting of H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from the group consisting of H, =O, $C_{1-4}$alkyl substituted with 0-4 $R_e$, —$(CH_2)_r OR_b$, $C(=O)R_b$, and —$C(=O)OR_b$;

$R_6$ is independently selected from the group consisting of H and $C_{1-4}$alkyl substituted with 0-4 $R_e$;

$R_9$ is independently selected from the group consisting of F, Cl, Br, $C_{1-4}$ alkyl, nitro, —$(CH_2)_r S(O)_p R_c$, —$(CH_2)_r S(O)_p NR_a R_a$, —$(CH_2)_r NR_a S(O)_p R_c$, —$(CH_2)_r OR_b$, —$(CH_2)_r CN$, —$(CH_2)_r NR_a R_a$, —$(CH_2)_r NR_a C(=O)R_b$, —$(CH_2)_r NR_a C(=O)NR_a R_a$, —$(CH_2)_r NR_a C(=O)OR_b$, —$(CH_2)_r C(=O)OR_b$, —$(CH_2)_r C(=O)NR_a R_a$, —$(CH_2)_r OC(=O)NR_a R_a$, —$(CH_2)_r C(=O)R_b$, —$(CH_2)_r OC(=O)R_b$, —$(CH_2)_r C(=O)NR_a R_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from the group consisting of $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r OR_f$, $S(O)_p R_f$, $S(O)_p NR_f R_f$, and —$(CH_2)_r NR_f R_f$;

$R_f$, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

10. The compound of claim 2, having Formula (IX):

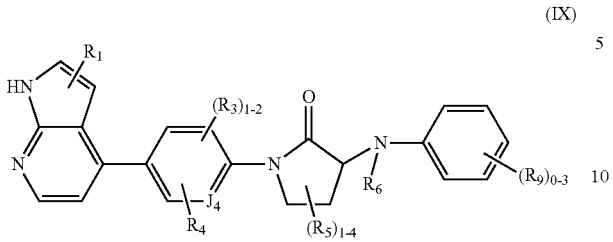

(IX)

or an enantiomer, a diastereomer, a stereoisomer, a tautomer, or a pharmaceutically acceptable salt thereof, wherein $J_4$ is independently selected from the group consisting of N and $CR_4$;

$R_1$ is independently selected from the group consisting of H, F, Cl, Br, CN, $NR_aR_a$, and $C_{1-4}$alkyl substituted with 0-4 $R_e$;

$R_3$ is independently selected from the group consisting of H, F, Cl, Br, CN, $C_{1-4}$ alkyl substituted with 0-3 $R_e$, and —$(CH_2)_rOR_b$;

$R_4$ is independently selected from the group consisting of H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from the group consisting of H, =O, $C_{1-4}$alkyl substituted with 0-4 $R_e$, —$(CH_2)_rOR_b$, $C(=O)R_b$, and —$C(=O)OR_b$;

$R_6$ is independently selected from the group consisting of H and $C_{1-4}$alkyl substituted with 0-4 $R_e$;

$R_9$ is independently selected from the group consisting of F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rC(=O)OR_b$, —$(CH_2)_rC(=O)NR_aR_a$, —$(CH_2)_rOC(=O)NR_aR_a$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from the group consisting of $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from the group consisting of $C_{1-6}$ alkyl substituted with 0-5 $R_f$, $C_{2-6}$ alkenyl, Cab alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from the group consisting of H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

11. The compound of claim 2, having Formula (X):

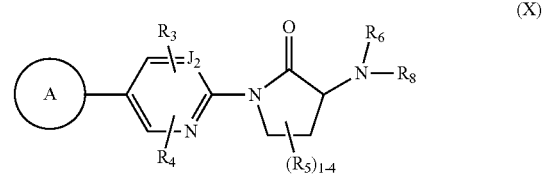

(X)

or an enantiomer, a diastereomer, a stereoisomer, a tautomer, or a pharmaceutically acceptable salt thereof, wherein $J_2$ is independently selected from the group consisting of N, $CR_3$ and $CR_4$;

Ring A is independently selected from

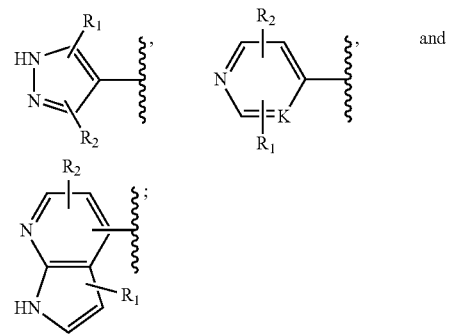

and

K is independently selected from the group consisting of N, $CR_1$, and $CR_2$;

$R_1$ is independently selected from the group consisting of H, F, Cl, Br, CN, $NR_aR_a$, and $C_{1-4}$alkyl substituted with 0-4 $R_e$;

$R_2$ is independently selected from the group consisting of H, F, Cl, Br, OH, CN, $NR_aR_a$, and $C_{1-4}$alkyl substituted with 0-4 $R_e$;

$R_3$ is independently selected from the group consisting of H, F, Cl, Br, CN, $C_{1-4}$ alkyl substituted with 0-3 $R_e$, —$(CH_2)_rOR_b$, —$NR_aR_a$, $C(=O)NR_aR_a$, and $C_{3-6}$ cycloalkyl substituted with 0-3 $R_e$;

$R_4$ is independently selected from the group consisting of H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from the group consisting of H, =O, $C_{1-4}$alkyl substituted with 0-4 $R_e$, —$(CH_2)_rOR_b$, $C(=O)R_b$, and —$C(=O)OR_b$;

$R_6$ is H;

$R_8$ is independently selected from the group consisting of

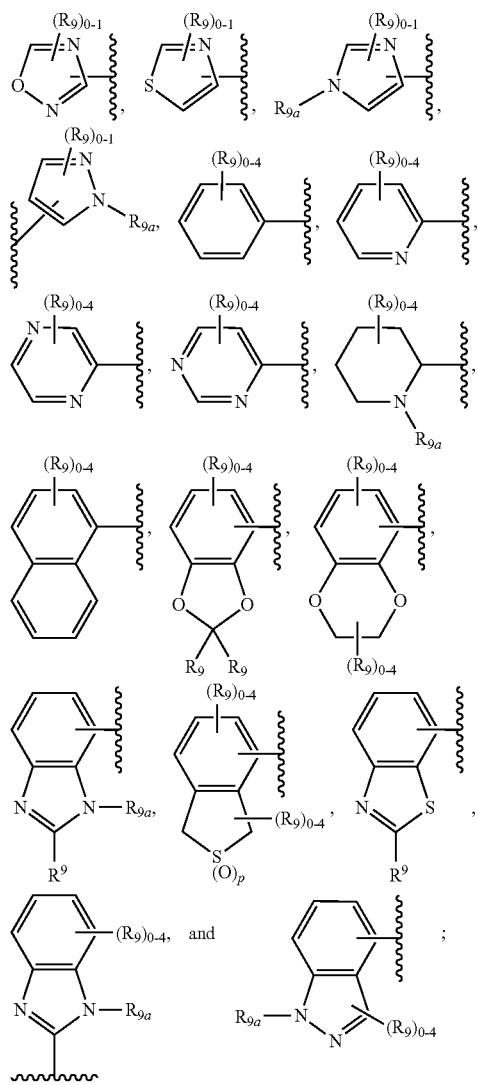

or $R_6$ and $R_8$ together with the nitrogen atom to which they are both attached form a heterocyclic ring substituted with 0-5 $R_9$, wherein the heterocyclic ring is selected from the group consisting of

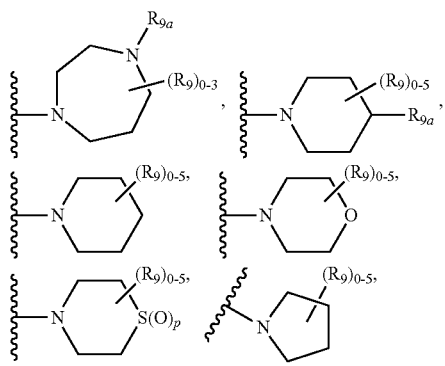

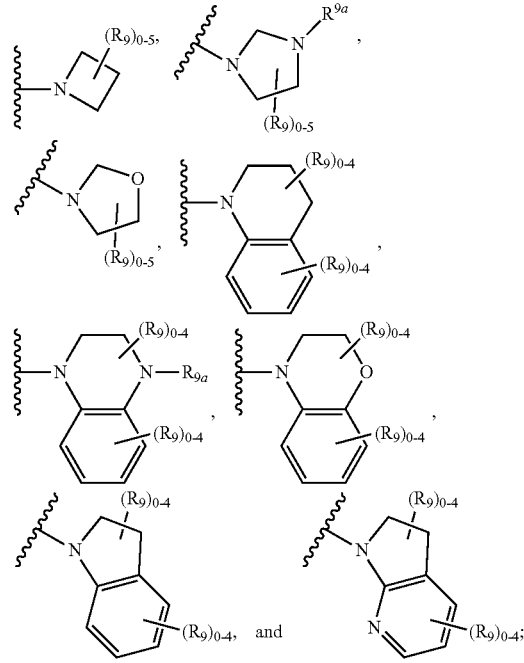

$R_9$ is independently selected from the group consisting of H, F, Cl, $C_{1-4}$ alkyl, $-OR_b$, CN, $S(O)_pNR_aR_a$, NHS$(O)_pR_c$, $NR_aR_a$, $C(=O)NR_aR_a$, $NR_aC(=O)R_b$, $C_{3-6}$ cycloalkyl, and heterocyclyl, wherein said alkyl, cycloalkyl, or heterocyclyl is substituted with 0-4 $R_e$;

$R_{9a}$ is independently selected from the group consisting of H, $C_{1-4}$ alkyl, $-S(O)_pR_c$, $-S(O)_pNR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from the group consisting of H and $C_{1-6}$ alkyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from the group consisting of H, $C_{1-6}$ alkyl substituted with 0-5 $R_e$, $-(CH_2)_r-C_{3-6}$ cycloalkyl substituted with 0-5 $R_e$, and $-(CH_2)_r$-heterocyclyl substituted with 0-5 $R_e$;

$R_c$, at each occurrence, is independently selected from the group consisting of $C_{1-6}$ alkyl substituted with 0-5 $R_e$;

$R_e$, at each occurrence, is independently selected from the group consisting of $C_{1-6}$ alkyl substituted with 0-5 $R_f$, F, Cl, Br, CN, $NO_2$, $=O$, $CO_2H$, OH, and $OC_{1-4}$alkyl; and r, at each occurrence, is independently selected from zero, 1, 2, and 3.

12. A pharmaceutical composition comprising one or more compounds according to claim 1 and a pharmaceutically acceptable carrier or diluent.

13. A method for treatment of a disorder associated with aberrant Rho kinase activity selected from the group consisting of a cardiovascular disorder, a smooth muscle related disorder, a fibrotic disease, an inflammatory disease, a neuropathic disorder, an oncologic disorder, and an autoimmune disorder, comprising administering to a patient in need thereof a therapeutically effective amount of the pharmaceutical composition of claim 12.

14. The method of claim 13, wherein said cardiovascular disorder is selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension.

\* \* \* \* \*